US009128101B2

(12) United States Patent
Halbert et al.

(10) Patent No.: US 9,128,101 B2
(45) Date of Patent: Sep. 8, 2015

(54) BIOMARKERS FOR THERANOSTICS

(75) Inventors: David D. Halbert, Colleyville, TX (US); Christine Kuslich, Paradise Valley, AZ (US); George Poste, Cave Creek, AZ (US); Michael Klass, Oro Valley, AZ (US); David Spetzler, Scottsdale, AZ (US); Traci Pawlowski, Laguna Niguel, CA (US); Andrea Tasinato, Gimel (CH); Daniel Holterman, Phoenix, AZ (US)

(73) Assignee: Caris Life Sciences Switzerland Holdings GmbH, Basel (CH)

( * ) Notice: Subject to any disclaimer, the term of this patent is extended or adjusted under 35 U.S.C. 154(b) by 0 days.

(21) Appl. No.: 13/581,795

(22) PCT Filed: Mar. 1, 2011
(Under 37 CFR 1.47)

(86) PCT No.: PCT/US2011/026750
§ 371 (c)(1),
(2), (4) Date: Mar. 12, 2013

(87) PCT Pub. No.: WO2011/109440
PCT Pub. Date: Sep. 9, 2011

(65) Prior Publication Data

US 2013/0287772 A1 Oct. 31, 2013

Related U.S. Application Data

(60) Provisional application No. 61/274,124, filed on Mar. 1, 2010, provisional application No. 61/357,517, filed on Jun. 22, 2010, provisional application No. 61/364,785, filed on Jul. 15, 2010.

(51) Int. Cl.

| | |
|---|---|
| ***G01N 33/53*** | (2006.01) |
| ***G01N 33/68*** | (2006.01) |
| ***C12Q 1/68*** | (2006.01) |
| ***G01N 33/574*** | (2006.01) |

(52) U.S. Cl.
CPC .......... *G01N 33/6893* (2013.01); *C12Q 1/6883* (2013.01); *G01N 33/57484* (2013.01); *G01N 33/6872* (2013.01); *C12Q 2600/106* (2013.01); *C12Q 2600/112* (2013.01); *C12Q 2600/136* (2013.01); *C12Q 2600/158* (2013.01); *C12Q 2600/178* (2013.01); *G01N 2333/705* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 4,275,149 | A | 6/1981 | Litman |
| 4,448,765 | A | 5/1984 | Ash |
| 4,551,435 | A | 11/1985 | Liberti |
| 4,714,556 | A | 12/1987 | Ambrus |
| 4,725,550 | A | 2/1988 | Perucho |
| 4,737,456 | A | 4/1988 | Weng |
| 4,741,446 | A | 5/1988 | Miller |
| 4,787,974 | A | 11/1988 | Ambrus |
| 4,795,698 | A | 1/1989 | Owen |
| 4,877,867 | A | 10/1989 | Shalitin |
| 4,925,788 | A | 5/1990 | Liberti |
| 4,957,859 | A | 9/1990 | Bizub |
| 4,991,104 | A | 2/1991 | Miller |
| 5,026,650 | A | 6/1991 | Schwarz |
| 5,089,181 | A | 2/1992 | Hauser |
| 5,104,802 | A | 4/1992 | Rhodes |
| 5,108,933 | A | 4/1992 | Liberti |
| 5,153,131 | A | 10/1992 | Wolf |
| 5,153,133 | A | 10/1992 | Schwarz |
| 5,158,871 | A | 10/1992 | Rossomando |
| 5,186,827 | A | 2/1993 | Liberti |
| 5,200,084 | A | 4/1993 | Liberti |
| 5,210,040 | A | 5/1993 | Jou |
| 5,242,974 | A | 9/1993 | Holmes |
| 5,270,163 | A | 12/1993 | Gold |
| 5,376,252 | A | 12/1994 | Ekstrom |
| 5,384,261 | A | 1/1995 | Winkler |
| 5,405,783 | A | 4/1995 | Pirrung |
| 5,412,087 | A | 5/1995 | McGall |
| 5,424,186 | A | 6/1995 | Fodor |
| 5,429,807 | A | 7/1995 | Matson |

(Continued)

FOREIGN PATENT DOCUMENTS

| | | | |
|---|---|---|---|
| CA | 2453198 | A1 | 7/2005 |
| EP | 0527905 | B1 | 11/1995 |

(Continued)

OTHER PUBLICATIONS

Geuze et al (J. Cell Biol, 1988, 107(6 Pt2): Abstract).*

(Continued)

*Primary Examiner* — Sean Aeder
(74) *Attorney, Agent, or Firm* — Ramin Akhavan

(57) ABSTRACT

Biomarkers can be assessed for diagnostic, therapy-related or prognostic methods to identify phenotypes, such as a condition or disease, or the stage or progression of a disease. Circulating biomarkers from a bodily fluid can be used in profiling of physiological states or determining phenotypes. These include nucleic acids, protein, and circulating structures such as vesicles. Biomarkers can be used for theranostic purposes to select candidate treatment regimens for diseases, conditions, disease stages, and stages of a condition, and can also be used to determine treatment efficacy. The biomarkers can be circulating biomarkers, including vesicles and microRNA.

21 Claims, 195 Drawing Sheets

(56) References Cited

U.S. PATENT DOCUMENTS

| | | | |
|---|---|---|---|
| 5,436,327 | A | 7/1995 | Southern |
| 5,437,998 | A | 8/1995 | Schwarz |
| 5,445,934 | A | 8/1995 | Fodor |
| 5,459,073 | A | 10/1995 | Ryan |
| 5,466,574 | A | 11/1995 | Liberti |
| 5,472,672 | A | 12/1995 | Brennan |
| 5,486,359 | A | 1/1996 | Caplan |
| 5,496,699 | A | 3/1996 | Sorenson |
| 5,512,332 | A | 4/1996 | Liberti |
| 5,523,228 | A | 6/1996 | Ingram |
| 5,527,681 | A | 6/1996 | Holmes |
| 5,529,756 | A | 6/1996 | Brennan |
| 5,532,128 | A | 7/1996 | Eggers |
| 5,538,848 | A | 7/1996 | Livak |
| 5,545,531 | A | 8/1996 | Rava |
| 5,554,501 | A | 9/1996 | Coassin |
| 5,556,752 | A | 9/1996 | Lockhart |
| 5,561,071 | A | 10/1996 | Hollenberg |
| 5,571,639 | A | 11/1996 | Hubbell |
| 5,593,839 | A | 1/1997 | Hubbell |
| 5,597,531 | A | 1/1997 | Liberti |
| 5,599,695 | A | 2/1997 | Pease |
| 5,610,281 | A | 3/1997 | Brenner |
| 5,624,711 | A | 4/1997 | Sundberg |
| 5,658,734 | A | 8/1997 | Brock |
| 5,665,594 | A | 9/1997 | Schwarz |
| 5,693,473 | A | 12/1997 | Shattuck-Eidens |
| 5,698,271 | A | 12/1997 | Liberti |
| 5,700,637 | A | 12/1997 | Southern |
| 5,702,941 | A | 12/1997 | Schwarz |
| 5,710,001 | A | 1/1998 | Skolnick |
| 5,723,591 | A | 3/1998 | Livak |
| 5,736,330 | A | 4/1998 | Fulton |
| 5,747,282 | A | 5/1998 | Skolnick |
| 5,753,441 | A | 5/1998 | Skolnick |
| 5,804,375 | A | 9/1998 | Gelfanc |
| 5,837,492 | A | 11/1998 | Tavtigian |
| 5,849,517 | A | 12/1998 | Ryan |
| 5,876,930 | A | 3/1999 | Livak |
| 5,895,748 | A | 4/1999 | Johnson |
| 5,906,744 | A | 5/1999 | Carroll |
| 5,985,153 | A | 11/1999 | Dolan |
| 5,993,665 | A | 11/1999 | Terstappen |
| 5,997,866 | A | 12/1999 | Johnson |
| 5,998,151 | A | 12/1999 | Johnston |
| 6,004,755 | A | 12/1999 | Wang |
| 6,030,775 | A | 2/2000 | Yang |
| 6,030,787 | A | 2/2000 | Livak |
| 6,033,857 | A | 3/2000 | Tavtigian |
| 6,040,338 | A | 3/2000 | Sartorelli |
| 6,057,107 | A | 5/2000 | Fulton |
| 6,090,546 | A | 7/2000 | Breivik |
| 6,117,674 | A | 9/2000 | Goodwin |
| 6,118,910 | A | 9/2000 | Chang |
| 6,120,856 | A | 9/2000 | Liberti |
| 6,124,104 | A | 9/2000 | Tavtigian |
| 6,136,182 | A | 10/2000 | Dolan |
| 6,143,496 | A | 11/2000 | Brown |
| 6,144,616 | A | 11/2000 | Suzuki |
| 6,150,514 | A | 11/2000 | Swensen |
| 6,207,805 | B1 | 3/2001 | Weiner |
| 6,216,671 | B1 | 4/2001 | Sawert |
| 6,218,114 | B1 | 4/2001 | Peck |
| 6,218,122 | B1 | 4/2001 | Friend |
| 6,221,620 | B1 | 4/2001 | Johnston |
| 6,250,128 | B1 | 6/2001 | Ando |
| 6,258,569 | B1 | 7/2001 | Livak |
| 6,262,242 | B1 | 7/2001 | Steck |
| 6,269,957 | B1 | 8/2001 | Bowers |
| 6,271,002 | B1 | 8/2001 | Linsley |
| 6,291,184 | B1 | 9/2001 | Gold |
| 6,300,080 | B1 | 10/2001 | Brenner |
| 6,329,179 | B1 | 12/2001 | Kopreski |
| 6,329,209 | B1 | 12/2001 | Wagner |
| 6,357,601 | B1 | 3/2002 | Bowers |
| 6,365,362 | B1 | 4/2002 | Terstappen |
| 6,365,418 | B1 | 4/2002 | Wagner |
| 6,376,190 | B1 | 4/2002 | Gold |
| 6,406,870 | B2 | 6/2002 | Brenner |
| 6,406,921 | B1 | 6/2002 | Wagner |
| 6,408,878 | B2 | 6/2002 | Unger |
| 6,416,987 | B1 | 7/2002 | Liu-Chen |
| 6,446,706 | B1 | 9/2002 | Rosenfeld |
| 6,458,539 | B1 | 10/2002 | Gold |
| 6,475,808 | B1 | 11/2002 | Wagner |
| 6,475,809 | B1 | 11/2002 | Wagner |
| 6,482,594 | B2 | 11/2002 | Gold |
| 6,482,795 | B1 | 11/2002 | Steck |
| 6,494,555 | B1 | 12/2002 | Ishikawa |
| 6,501,245 | B2 | 12/2002 | Okuda |
| 6,512,096 | B2 | 1/2003 | Weiner |
| 6,528,057 | B1 | 3/2003 | Ambrus |
| 6,551,843 | B1 | 4/2003 | Rao |
| 6,586,177 | B1 | 7/2003 | Shuber |
| 6,599,331 | B2 | 7/2003 | Chandler |
| 6,601,270 | B2 | 8/2003 | Eckhardt |
| 6,620,627 | B1 | 9/2003 | Liberti |
| 6,623,526 | B1 | 9/2003 | Lloyd |
| 6,623,982 | B1 | 9/2003 | Liberti |
| 6,645,432 | B1 | 11/2003 | Anderson |
| 6,645,731 | B2 | 11/2003 | Terstappen |
| 6,649,359 | B2 | 11/2003 | Mutter |
| 6,653,129 | B1 | 11/2003 | Bander |
| 6,660,159 | B1 | 12/2003 | Terstappen |
| 6,683,455 | B2 | 1/2004 | Ebbels |
| 6,685,911 | B1 | 2/2004 | Zitvogel |
| 6,691,333 | B1 | 2/2004 | Krist |
| 6,692,916 | B2 | 2/2004 | Bevilacqua |
| 6,719,868 | B1 | 4/2004 | Schueller |
| 6,754,010 | B2 | 6/2004 | Takeshita |
| 6,773,812 | B2 | 8/2004 | Chandler |
| 6,790,366 | B2 | 9/2004 | Terstappen |
| 6,793,753 | B2 | 9/2004 | Unger |
| 6,812,023 | B1 | 11/2004 | Lamparski |
| 6,837,946 | B2 | 1/2005 | Beswick |
| 6,861,259 | B2 | 3/2005 | Columbus |
| 6,890,426 | B2 | 5/2005 | Terstappen |
| 6,899,137 | B2 | 5/2005 | Unger |
| 6,899,863 | B1 | 5/2005 | Dhellin |
| 6,911,201 | B1 | 6/2005 | Merchav |
| 6,916,634 | B2 | 7/2005 | Kopreski |
| 6,929,030 | B2 | 8/2005 | Unger |
| 6,939,671 | B2 | 9/2005 | Kopreski |
| 6,960,439 | B2 | 11/2005 | Bevilacqua |
| 6,964,850 | B2 | 11/2005 | Bevilacqua |
| 7,011,794 | B2 | 3/2006 | Kagan |
| 7,029,676 | B2 | 4/2006 | Brenner |
| 7,049,059 | B2 | 5/2006 | Danenberg |
| 7,074,586 | B1 | 7/2006 | Cheronis |
| 7,081,340 | B2 | 7/2006 | Baker |
| 7,089,168 | B2 | 8/2006 | Maimon |
| 7,118,661 | B2 | 10/2006 | Surh |
| 7,118,910 | B2 | 10/2006 | Unger |
| 7,125,711 | B2 | 10/2006 | Pugia |
| 7,129,040 | B2 | 10/2006 | Steck |
| 7,135,147 | B2 | 11/2006 | Cox |
| 7,138,062 | B2 | 11/2006 | Yin |
| 7,141,978 | B2 | 11/2006 | Peck |
| 7,154,219 | B2 | 12/2006 | Hamada |
| 7,163,789 | B2 | 1/2007 | Chen |
| 7,189,368 | B2 | 3/2007 | Andersson |
| 7,189,580 | B2 | 3/2007 | Beebe |
| 7,189,581 | B2 | 3/2007 | Beebe |
| 7,195,986 | B1 | 3/2007 | Bousse |
| 7,198,923 | B1 | 4/2007 | Abrignani |
| 7,201,881 | B2 | 4/2007 | Cox |
| 7,217,795 | B2 | 5/2007 | Steck |
| 7,226,429 | B2 | 6/2007 | Tullis |
| 7,229,538 | B2 | 6/2007 | Tseng |
| 7,232,653 | B1 | 6/2007 | Austrup |
| 7,233,865 | B2 | 6/2007 | Chien |
| 7,238,255 | B2 | 7/2007 | Derand |
| 7,238,324 | B2 | 7/2007 | Ko |
| 7,250,496 | B2 | 7/2007 | Bentwich |

(56) References Cited

U.S. PATENT DOCUMENTS

| | | | |
|---|---|---|---|
| 7,250,497 | B2 | 7/2007 | Scholl |
| 7,253,003 | B2 | 8/2007 | Beebe |
| 7,258,837 | B2 | 8/2007 | Yager |
| 7,261,824 | B2 | 8/2007 | Schlautmann |
| 7,267,950 | B2 | 9/2007 | Belly |
| 7,274,316 | B2 | 9/2007 | Moore |
| 7,282,350 | B2 | 10/2007 | Rao |
| 7,314,721 | B2 | 1/2008 | Gure |
| 7,319,007 | B2 | 1/2008 | Cybulski |
| 7,323,140 | B2 | 1/2008 | Handique |
| 7,329,391 | B2 | 2/2008 | Cox |
| 7,332,288 | B2 | 2/2008 | Terstappen |
| 7,338,637 | B2 | 3/2008 | Pease |
| 7,351,380 | B2 | 4/2008 | Simmons |
| 7,351,584 | B2 | 4/2008 | Silber |
| 7,351,592 | B2 | 4/2008 | Storek |
| 7,357,864 | B2 | 4/2008 | Takada |
| 7,381,471 | B2 | 6/2008 | Augustine |
| 7,390,463 | B2 | 6/2008 | He |
| 7,399,600 | B2 | 7/2008 | Carr |
| 7,399,632 | B2 | 7/2008 | Simmons |
| 7,402,229 | B2 | 7/2008 | Sibbett |
| 7,411,184 | B2 | 8/2008 | Sarrut |
| 7,413,709 | B2 | 8/2008 | Roitman |
| 7,415,359 | B2 | 8/2008 | Hill |
| 7,419,639 | B2 | 9/2008 | Osterfeld |
| 7,419,822 | B2 | 9/2008 | Jeon |
| 7,422,669 | B2 | 9/2008 | Jacobson |
| 7,422,725 | B2 | 9/2008 | Kimizuka |
| 7,431,887 | B2 | 10/2008 | Storek |
| 7,445,844 | B2 | 11/2008 | Chandler |
| 7,449,096 | B2 | 11/2008 | Berndt |
| 7,452,509 | B2 | 11/2008 | Cox |
| 7,452,713 | B2 | 11/2008 | Barlocchi |
| 7,462,489 | B2 | 12/2008 | Ley |
| 7,467,928 | B2 | 12/2008 | Fakunle |
| 7,485,214 | B2 | 2/2009 | Palmieri |
| 7,488,596 | B2 | 2/2009 | Lee |
| 7,518,726 | B2 | 4/2009 | Rulison |
| 7,526,387 | B2 | 4/2009 | Baker |
| 7,541,578 | B2 | 6/2009 | Weng |
| 7,544,506 | B2 | 6/2009 | Breidford |
| 7,552,741 | B2 | 6/2009 | Yamada |
| 7,560,226 | B2 | 7/2009 | Christopherson |
| 7,568,399 | B2 | 8/2009 | Sparks |
| 7,575,722 | B2 | 8/2009 | Arnold |
| 7,579,136 | B2 | 8/2009 | Shim |
| 7,581,429 | B2 | 9/2009 | Sparks |
| 7,591,936 | B2 | 9/2009 | Sarrut |
| 7,592,441 | B2 | 9/2009 | Bentwich |
| 7,593,913 | B2 | 9/2009 | Wang |
| 7,625,573 | B2 | 12/2009 | Zitvogel |
| 7,640,947 | B2 | 1/2010 | Fernandes |
| 7,642,348 | B2 | 1/2010 | Bentwich |
| 7,655,479 | B2 | 2/2010 | Zhukov |
| 7,666,361 | B2 | 2/2010 | McBride |
| 7,670,840 | B2 | 3/2010 | Croce |
| 7,704,735 | B2 | 4/2010 | Facer |
| 7,745,150 | B2 | 6/2010 | Liang |
| 7,750,124 | B2 | 7/2010 | Gurney |
| 7,751,053 | B2 | 7/2010 | Carr |
| 7,888,035 | B2 | 2/2011 | Klass |
| 7,897,356 | B2 | 3/2011 | Klass |
| 7,955,802 | B2 | 6/2011 | Whitman |
| 8,008,019 | B2 | 8/2011 | Merante |
| 8,021,847 | B2 | 9/2011 | Pietrzkowski |
| 8,048,418 | B2 | 11/2011 | Noguera-Troise |
| 8,124,015 | B2 | 2/2012 | Diercks |
| 8,192,954 | B2 | 6/2012 | Klass |
| 8,211,653 | B2 | 7/2012 | Klass |
| 8,278,059 | B2 | 10/2012 | Klass |
| 2001/0018189 | A1 | 8/2001 | Brenner |
| 2002/0106684 | A1 | 8/2002 | Kopreski |
| 2002/0150966 | A1 | 10/2002 | Muraca |
| 2002/0192724 | A1 | 12/2002 | Brenner |
| 2003/0036077 | A1 | 2/2003 | Chenchik |
| 2003/0061687 | A1 | 4/2003 | Hansen |
| 2003/0068642 | A1 | 4/2003 | Urnovitz |
| 2003/0118997 | A1 | 6/2003 | Bejanin |
| 2003/0194734 | A1 | 10/2003 | Jatkoe |
| 2004/0005596 | A1 | 1/2004 | Li |
| 2004/0028692 | A1 | 2/2004 | Zitvogel |
| 2004/0038207 | A1 | 2/2004 | Orntoft |
| 2004/0088116 | A1 | 5/2004 | Khalil |
| 2004/0096915 | A1 | 5/2004 | Diamandis |
| 2004/0152112 | A1 | 8/2004 | Croce |
| 2004/0191817 | A1 | 9/2004 | Scott |
| 2004/0197314 | A1 | 10/2004 | Delcayre |
| 2004/0214184 | A1 | 10/2004 | Skubitz |
| 2004/0219568 | A1 | 11/2004 | Bevilacqua |
| 2004/0224322 | A1 | 11/2004 | Bevilacqua |
| 2004/0224337 | A1 | 11/2004 | Foehr |
| 2004/0243354 | A1 | 12/2004 | Periwal |
| 2005/0059024 | A1 | 3/2005 | Conrad |
| 2005/0060101 | A1 | 3/2005 | Bevilacqua |
| 2005/0064470 | A1 | 3/2005 | Rana |
| 2005/0084421 | A1 | 4/2005 | Unger |
| 2005/0084913 | A1 | 4/2005 | Punnonen |
| 2005/0112882 | A1 | 5/2005 | Unger |
| 2005/0124071 | A1 | 6/2005 | Kraus |
| 2005/0129581 | A1 | 6/2005 | McBride |
| 2005/0145496 | A1 | 7/2005 | Goodsaid |
| 2005/0152908 | A1 | 7/2005 | Liew |
| 2005/0158708 | A1 | 7/2005 | Alroy |
| 2005/0159378 | A1 | 7/2005 | McSwiggen |
| 2005/0176137 | A1 | 8/2005 | Merchav |
| 2005/0176143 | A1 | 8/2005 | Merchav |
| 2005/0180958 | A1 | 8/2005 | Merchav |
| 2005/0181504 | A1 | 8/2005 | Merchav |
| 2005/0201901 | A1 | 9/2005 | Grossman |
| 2005/0208510 | A1 | 9/2005 | Latham |
| 2005/0214173 | A1 | 9/2005 | Facer |
| 2005/0221398 | A1 | 10/2005 | Jacquemier |
| 2005/0222399 | A1 | 10/2005 | Bentwich |
| 2005/0244880 | A1 | 11/2005 | Kallioniemi |
| 2005/0250148 | A1 | 11/2005 | Bevilacqua |
| 2005/0252773 | A1 | 11/2005 | McBride |
| 2005/0260646 | A1 | 11/2005 | Baker |
| 2005/0277121 | A1 | 12/2005 | Pasloske |
| 2005/0287543 | A1 | 12/2005 | Yu |
| 2005/0287610 | A1 | 12/2005 | Clements |
| 2006/0003465 | A1 | 1/2006 | Zhukov |
| 2006/0006067 | A1 | 1/2006 | Unger |
| 2006/0116321 | A1 | 6/2006 | Robbins |
| 2006/0211000 | A1 | 9/2006 | Sorge |
| 2006/0222637 | A1 | 10/2006 | Bamdad |
| 2006/0222654 | A1 | 10/2006 | Delcayre |
| 2006/0275844 | A1 | 12/2006 | Linke |
| 2007/0003965 | A1 | 1/2007 | Ramsay |
| 2007/0004044 | A1 | 1/2007 | Ramsay |
| 2007/0009966 | A1 | 1/2007 | Pommer |
| 2007/0042380 | A1 | 2/2007 | Bentwich |
| 2007/0042405 | A1 | 2/2007 | Lokshin |
| 2007/0042982 | A1 | 2/2007 | Bentwich |
| 2007/0054333 | A1 | 3/2007 | Steck |
| 2007/0059765 | A1 | 3/2007 | Wang |
| 2007/0065845 | A1 | 3/2007 | Baker |
| 2007/0071762 | A1 | 3/2007 | Ts'o |
| 2007/0077553 | A1 | 4/2007 | Bentwich |
| 2007/0104738 | A1 | 5/2007 | Tatischeff |
| 2007/0134687 | A1 | 6/2007 | Georges |
| 2007/0141589 | A1 | 6/2007 | Baker |
| 2007/0161004 | A1 | 7/2007 | Brown |
| 2007/0172857 | A1 | 7/2007 | Daito |
| 2007/0172900 | A1 | 7/2007 | Cahill |
| 2007/0178445 | A1 | 8/2007 | Eshleman |
| 2007/0191273 | A1 | 8/2007 | Ambati |
| 2007/0196835 | A1 | 8/2007 | Bankaitis-Davis |
| 2007/0203333 | A1 | 8/2007 | McSwiggen |
| 2007/0207489 | A1 | 9/2007 | Pestano |
| 2007/0224208 | A1 | 9/2007 | Guo |
| 2007/0238118 | A1 | 10/2007 | Goldrick |
| 2007/0243552 | A1 | 10/2007 | Williams |
| 2007/0254295 | A1 | 11/2007 | Harvey |

(56) References Cited

U.S. PATENT DOCUMENTS

2007/0292878 A1 12/2007 Raymond
2007/0298118 A1 12/2007 Lotvall
2008/0004233 A1 1/2008 Malafa
2008/0014146 A1 1/2008 Von Hoff
2008/0014598 A1 1/2008 Wiederhold
2008/0064049 A1 3/2008 Clarke
2008/0070243 A1 3/2008 Bevilacqua
2008/0085524 A1 4/2008 Lois
2008/0096768 A1 4/2008 Laird
2008/0132694 A1 6/2008 Himmelreich
2008/0160517 A1 7/2008 Danenberg
2008/0182239 A1 7/2008 Mullinax
2008/0183395 A1 7/2008 Bevilacqua
2008/0208784 A1 8/2008 Hill
2008/0213280 A1 9/2008 Benyunes
2008/0213907 A1 9/2008 Lomnytska
2008/0220422 A1 9/2008 Shoemaker
2008/0227655 A1 9/2008 Bevilacqua
2008/0233573 A1 9/2008 Storm
2008/0241126 A1 10/2008 Better
2008/0242622 A1 10/2008 Lowe
2008/0254481 A1 10/2008 Love
2008/0261258 A1 10/2008 Smith
2008/0261908 A1 10/2008 Croce
2008/0268429 A1 10/2008 Pietrzkowski
2008/0293055 A1 11/2008 Freeman
2008/0306017 A1 12/2008 Croce
2008/0312199 A1 12/2008 Glinsky
2008/0318210 A1 12/2008 Bentwich
2008/0318223 A1 12/2008 Scholl
2008/0318224 A1 12/2008 Scholl
2008/0318230 A1 12/2008 Agus
2009/0004687 A1 1/2009 Mansfield
2009/0011428 A1 1/2009 Nam
2009/0017012 A1 1/2009 Bepler
2009/0061422 A1 3/2009 Linke
2009/0061454 A1 3/2009 Brody
2009/0075267 A1 3/2009 Siena
2009/0092983 A1 4/2009 Birnbaum
2009/0098538 A1 4/2009 Glinsky
2009/0098553 A1 4/2009 Guilford
2009/0098554 A1 4/2009 Ge
2009/0104649 A1 4/2009 Garovic
2009/0111121 A1 4/2009 Des Rosiers
2009/0118175 A1 5/2009 Macina
2009/0130125 A1 5/2009 Loibner
2009/0148460 A1 6/2009 Delcayre
2009/0155798 A1 6/2009 Ring
2009/0170715 A1 7/2009 Glinsky
2009/0181406 A1 7/2009 Ridder
2009/0197255 A1 8/2009 Cybulski
2009/0203533 A1 8/2009 Munnes
2009/0215642 A1 8/2009 Knudson
2009/0220944 A1 9/2009 Fais
2009/0226887 A1 9/2009 Brisson
2009/0226902 A1 9/2009 Drexhage
2009/0226937 A1 9/2009 Liang
2009/0232766 A1 9/2009 Wang
2009/0233279 A1 9/2009 Glinskii
2009/0233297 A1 9/2009 Mambo
2009/0239246 A1 9/2009 Pemberton
2009/0246199 A1 10/2009 Noguera-Troise
2009/0246289 A1 10/2009 Superko
2009/0258379 A1 10/2009 Klein
2009/0258436 A1 10/2009 Hornbeck
2009/0264508 A1 10/2009 Sullenger
2009/0280490 A1 11/2009 Baker
2009/0280493 A1 11/2009 Wirtz
2009/0291932 A1 11/2009 White
2009/0311702 A1 12/2009 Shak
2010/0010073 A1 1/2010 Thum
2010/0048681 A1 2/2010 Croce
2010/0055723 A1 3/2010 Smalley
2010/0055724 A1 3/2010 Taylor
2010/0062450 A1 3/2010 Arber
2010/0069298 A1 3/2010 Penny et al.
2010/0086956 A1 4/2010 Newman
2010/0092524 A1 4/2010 Taylor
2010/0113290 A1 5/2010 Klass
2010/0173788 A1 7/2010 Goncalves
2010/0184034 A1 7/2010 Bankaitis-Davis
2010/0184046 A1 7/2010 Klass
2010/0196426 A1 8/2010 Skog
2010/0196889 A1 8/2010 Bankaitis-Davis
2010/0203529 A1 8/2010 Kuslich
2010/0203566 A1 8/2010 Liang
2010/0209915 A1 8/2010 Bankaitis-Davis
2010/0216137 A1 8/2010 Bankaitis-Davis
2010/0222230 A1 9/2010 Iliopoulos
2010/0233691 A1 9/2010 Bankaitis-Davis
2010/0248225 A1 9/2010 Bankaitis-Davis
2010/0248290 A1 9/2010 Lam
2010/0255470 A1 10/2010 Bankaitis-Davis
2010/0256464 A1 10/2010 Love
2010/0267574 A1 10/2010 You
2010/0285458 A1 11/2010 Bankaitis-Davis
2010/0298151 A1 11/2010 Taylor
2010/0304989 A1 12/2010 Von Hoff
2010/0330558 A1 12/2010 Bankaitis-Davis
2010/0330683 A1 12/2010 Des Rosiers
2011/0003704 A1 1/2011 Skog
2011/0008808 A1 1/2011 Pemberton
2011/0097717 A1 4/2011 Bankaitis-Davis
2011/0151460 A1 6/2011 Klass
2011/0166030 A1 7/2011 Wang
2011/0177054 A1 7/2011 Gibbings
2012/0164628 A1 6/2012 Duffin

FOREIGN PATENT DOCUMENTS

EP 1065378 B1 4/2002
EP 1260520 A2 11/2002
EP 1394272 B1 3/2006
EP 0785216 B2 6/2006
EP 1278825 B1 6/2006
EP 1751311 A2 2/2007
EP 1777301 A2 4/2007
EP 1784501 A2 5/2007
EP 1947194 A1 7/2008
EP 0705902 B2 8/2008
EP 1668152 B1 8/2008
EP 1983002 A2 10/2008
EP 2000543 A2 12/2008
EP 2036990 A1 3/2009
EP 0699754 B2 8/2009
EP 0705903 B2 8/2009
EP 2105511 A1 9/2009
EP 1648498 B1 3/2010
EP 2316972 A1 5/2011
GB 2327497 A 1/1999
GB 2465088 B 7/2012
GB 2463401 B 1/2014
WO WO9322684 A1 11/1993
WO WO9422018 A1 9/1994
WO WO9529693 A1 11/1995
WO WO9637630 A1 11/1996
WO WO9735589 A1 10/1997
WO WO9833907 A1 8/1998
WO WO0123550 A2 4/2001
WO WO0136601 A1 5/2001
WO WO0164248 A1 9/2001
WO WO0164751 A2 9/2001
WO WO03044166 A2 5/2003
WO WO03063690 A2 8/2003
WO WO03075741 A2 9/2003
WO WO03075957 A1 9/2003
WO WO03076603 A2 9/2003
WO WO03078662 A1 9/2003
WO WO03094859 A2 11/2003
WO WO2004014292 A2 2/2004
WO WO2004022097 A1 3/2004
WO WO2004066957 A2 8/2004
WO WO2004073319 A2 8/2004
WO WO2004091375 A2 10/2004

(56) References Cited

FOREIGN PATENT DOCUMENTS

| | | | |
|---|---|---|---|
| WO | WO2004091510 | A2 | 10/2004 |
| WO | WO2004092343 | A2 | 10/2004 |
| WO | WO2005000207 | A2 | 1/2005 |
| WO | WO2005009217 | A2 | 2/2005 |
| WO | WO2005009363 | A2 | 2/2005 |
| WO | WO2005012350 | A2 | 2/2005 |
| WO | WO2005016381 | A2 | 2/2005 |
| WO | WO2005037233 | A2 | 4/2005 |
| WO | WO2005039382 | A2 | 5/2005 |
| WO | WO2005048917 | A2 | 6/2005 |
| WO | WO2005051307 | A2 | 6/2005 |
| WO | WO2005054512 | A2 | 6/2005 |
| WO | WO2005055948 | A2 | 6/2005 |
| WO | WO2005056766 | A2 | 6/2005 |
| WO | WO2005067391 | A2 | 7/2005 |
| WO | WO2005067460 | A2 | 7/2005 |
| WO | WO2005078124 | A2 | 8/2005 |
| WO | WO2005100606 | A2 | 10/2005 |
| WO | WO2005111211 | A2 | 11/2005 |
| WO | WO2005116250 | A2 | 12/2005 |
| WO | WO2005117967 | A2 | 12/2005 |
| WO | WO2005118806 | A2 | 12/2005 |
| WO | WO2005118875 | A2 | 12/2005 |
| WO | WO2005121369 | A2 | 12/2005 |
| WO | WO2006004910 | A2 | 1/2006 |
| WO | WO2006007529 | A2 | 1/2006 |
| WO | WO2006023403 | A2 | 3/2006 |
| WO | WO2006023420 | A2 | 3/2006 |
| WO | WO2006033020 | A2 | 3/2006 |
| WO | WO2006045110 | A2 | 4/2006 |
| WO | WO2006047637 | A1 | 5/2006 |
| WO | WO2006047638 | A2 | 5/2006 |
| WO | WO2006047639 | A2 | 5/2006 |
| WO | WO2006050166 | A2 | 5/2006 |
| WO | WO2006054991 | A1 | 5/2006 |
| WO | WO2006066965 | A2 | 6/2006 |
| WO | WO2006087233 | A2 | 8/2006 |
| WO | WO2006126040 | A1 | 11/2006 |
| WO | WO2007001868 | A1 | 1/2007 |
| WO | WO2007030642 | A2 | 3/2007 |
| WO | WO2007059300 | A2 | 5/2007 |
| WO | WO2007073499 | A2 | 6/2007 |
| WO | WO2007075706 | A2 | 7/2007 |
| WO | WO2007081140 | A1 | 7/2007 |
| WO | WO2007084253 | A2 | 7/2007 |
| WO | WO2007088537 | A2 | 8/2007 |
| WO | WO2007092772 | A2 | 8/2007 |
| WO | WO2007103261 | A2 | 9/2007 |
| WO | WO2007103572 | A2 | 9/2007 |
| WO | WO2007103808 | A2 | 9/2007 |
| WO | WO2007109321 | A2 | 9/2007 |
| WO | WO2007114896 | A2 | 10/2007 |
| WO | WO2007126386 | A1 | 11/2007 |
| WO | WO2007127848 | A1 | 11/2007 |
| WO | WO2008008284 | A2 | 1/2008 |
| WO | WO2008021483 | A2 | 2/2008 |
| WO | WO2008028926 | A2 | 3/2008 |
| WO | WO2008042941 | A2 | 4/2008 |
| WO | WO2008046911 | A2 | 4/2008 |
| WO | WO2008057305 | A2 | 5/2008 |
| WO | WO2008061104 | A2 | 5/2008 |
| WO | WO2008063414 | A2 | 5/2008 |
| WO | WO2008065378 | A2 | 6/2008 |
| WO | WO2008065384 | A2 | 6/2008 |
| WO | WO2008069881 | A2 | 6/2008 |
| WO | WO2008070042 | A2 | 6/2008 |
| WO | WO2008070137 | A2 | 6/2008 |
| WO | WO2008076447 | A2 | 6/2008 |
| WO | WO2008079269 | A2 | 7/2008 |
| WO | WO2008082730 | A2 | 7/2008 |
| WO | WO2008099280 | A2 | 8/2008 |
| WO | WO2008108986 | A2 | 9/2008 |
| WO | WO2008112283 | A2 | 9/2008 |
| WO | WO2008114011 | A2 | 9/2008 |
| WO | WO2008115419 | A2 | 9/2008 |
| WO | WO2008117278 | A2 | 10/2008 |
| WO | WO2008121132 | A2 | 10/2008 |
| WO | WO2008121615 | A2 | 10/2008 |
| WO | WO2008123866 | A2 | 10/2008 |
| WO | WO2008123867 | A1 | 10/2008 |
| WO | WO2008137835 | A2 | 11/2008 |
| WO | WO2008137838 | A2 | 11/2008 |
| WO | WO2008138578 | A2 | 11/2008 |
| WO | WO2008143639 | A2 | 11/2008 |
| WO | WO2008151004 | A1 | 12/2008 |
| WO | WO2008157490 | A1 | 12/2008 |
| WO | WO2009002931 | A2 | 12/2008 |
| WO | WO2009015357 | A1 | 1/2009 |
| WO | WO2009018386 | A1 | 2/2009 |
| WO | WO2009019215 | A1 | 2/2009 |
| WO | WO2009021322 | A1 | 2/2009 |
| WO | WO2009027703 | A2 | 3/2009 |
| WO | WO2009036236 | A1 | 3/2009 |
| WO | WO2009052573 | A1 | 4/2009 |
| WO | WO2009058379 | A2 | 5/2009 |
| WO | WO2009058893 | A2 | 5/2009 |
| WO | WO2009061297 | A1 | 5/2009 |
| WO | WO2009070642 | A1 | 6/2009 |
| WO | WO2009070653 | A1 | 6/2009 |
| WO | WO2009074988 | A1 | 6/2009 |
| WO | WO2009090268 | A1 | 7/2009 |
| WO | WO2009092011 | A1 | 7/2009 |
| WO | WO2009092386 | A2 | 7/2009 |
| WO | WO2009097136 | A1 | 8/2009 |
| WO | WO2009097325 | A1 | 8/2009 |
| WO | WO2009100029 | A1 | 8/2009 |
| WO | WO2009103542 | A1 | 8/2009 |
| WO | WO2009103790 | A2 | 8/2009 |
| WO | WO2009105223 | A1 | 8/2009 |
| WO | WO2009108860 | A2 | 9/2009 |
| WO | WO2009118204 | A2 | 10/2009 |
| WO | WO2009124251 | A1 | 10/2009 |
| WO | WO2009126160 | A1 | 10/2009 |
| WO | WO2009134944 | A2 | 11/2009 |
| WO | WO2009147519 | A1 | 12/2009 |
| WO | WO2009155505 | A2 | 12/2009 |
| WO | WO2009158513 | A1 | 12/2009 |
| WO | WO2010006048 | A2 | 1/2010 |
| WO | WO2010032059 | A2 | 3/2010 |
| WO | WO2010032060 | A1 | 3/2010 |
| WO | WO2010032061 | A1 | 3/2010 |
| WO | WO2010033773 | A2 | 3/2010 |
| WO | WO2010041060 | A1 | 4/2010 |
| WO | WO2010056337 | A2 | 5/2010 |
| WO | WO2010056337 | A3 | 5/2010 |
| WO | WO2010056993 | A2 | 5/2010 |
| WO | WO2010062763 | A1 | 6/2010 |
| WO | WO2010065765 | A2 | 6/2010 |
| WO | WO2010065968 | A1 | 6/2010 |
| WO | WO2010070276 | A1 | 6/2010 |
| WO | WO2010072410 | A2 | 7/2010 |
| WO | WO2010080702 | A2 | 7/2010 |
| WO | WO2010093465 | A1 | 8/2010 |
| WO | WO2010121238 | A2 | 10/2010 |
| WO | WO2010141862 | A2 | 12/2010 |
| WO | WO2011056688 | A2 | 5/2011 |
| WO | WO2011066589 | A1 | 6/2011 |
| WO | WO2011088226 | A2 | 7/2011 |
| WO | WO2011088226 | A3 | 7/2011 |
| WO | WO2011109440 | A1 | 9/2011 |
| WO | WO2011127219 | A1 | 10/2011 |
| WO | WO2012006476 | A2 | 1/2012 |
| WO | WO2012024543 | A1 | 2/2012 |
| WO | WO2012092336 | A2 | 7/2012 |
| WO | WO2012115885 | A1 | 8/2012 |
| WO | WO2012170711 | A1 | 12/2012 |
| WO | WO2012170715 | A1 | 12/2012 |
| WO | WO2012174282 | A2 | 12/2012 |
| WO | WO2012174282 | A3 | 12/2012 |
| WO | WO2013022995 | A2 | 2/2013 |
| WO | WO2013022995 | A3 | 2/2013 |

OTHER PUBLICATIONS

Wang et al (Clinical Cancer Research, 2007, 13(8): 2354-2361).*
Mears et al (Proteomics, 2004, 4(12): 4019-4031).*

(56) References Cited

OTHER PUBLICATIONS

Ariztia et al (99th AACR Annual meeting, 2008, Abstract #4560).*
Tockman et al (Cancer Res., 1992, 52:2711s-2718s).*
Hoorn et al (Nephrology, 2005, 10: 283-290).*
Hunter et al (PLOS One, 2008, 3(11): 1-11).*
Taylor et al (Gynecologic Oncology, 2008, 110(1): 13-21).*
Abe et al. Preparation of recombinant MK-1/Ep-CAM and establishment of an ELISA system for determining soluble MK-1/Ep-CAM levels in sera of cancer patients. (Journal of Immunological Methods, 2002, 270: 227-233).
Al-Nedawi et al. Intercellular transfer of the oncogenic receptor EGFRvIII by microvesicles derived from tumour cells. Nat Cell Biol. May 2008; 10(5): 619-24.
Al-Nedawi et al. Microvesicles: messengers and mediators of tumor progression. Cell Cycle. Jul. 1, 2009; 8(13) 2014-8. Epub Jul. 11, 2009.
Alymani et al. Predictive biomarkers for personalised anti-cancer drug use: Discovery to clinical implementation. European Journal of Cancer. 2010; 46(5): 869-879.
Ambs et al: "Genomic profiling of MicroRNA and messenger RNA reveals deregulated MicroRNA expression in prostate cancer", Cancer Research, vol. 68. No. 15, Aug. 1, 2008. pp. 6162-6170.
Andre et al. Exosomes for cancer immunotherapy, Annals of Oncology, 2004, 15 (Supplement 4): iv141-iv144.
Andre et al. Malignant effusions and immunogenic tumour-derived exosomes. Lancet. Jul. 27, 2002; 360(9329): 295-305.
Andre et al. Tumor-derived exosomes: a new source of tumor rejection antigens. Vaccine 20, 2002: A28-A31.
Andreasen et al. β-Amyloid(Aβ) protein in cerebrospinal fluid as a biomarker for Alzheimer's disease. Peptides. 2002; 23:1205-1214.
Aporntewan et al., Hypomethylation of Intragenic LINE-1 Represses Transcription in Cancer Cells through AGO2, PLoS ONE 6(3): e17934 (2011).
Ariztia et al. Differential cross-reactivity of membrane derived vesicles determines the invasive potential of mesothelioma, breast and ovarian cancer, 99th AACR Annual Meeting, Apr. 12, 2008 abstract.
Arroyo et al., Argonaute2 complexes carry a population of circulating microRNAs independent of vesicles in human plasma, Proc Natl Acad Sci U S A. Mar. 22, 2011;108(12):5003-8. doi: 10.1073/pnas. 1019055108. Epub Mar. 7, 2011.
Arroyo et al., Argonaute2 complexes carry a population of circulating microRNAs independent of vesicles in human plasma, Proc Natl Acad Sci U S A. Mar. 22, 2011;108(12):5003-8. doi: 10.1073/pnas. 1019055108. Epub Mar. 7, 2011. Supplement.
Baj-Krzyworzeka et al. Tumour-derived microvesicles carry several surface determinants and mRNA of tumour cells and transfer some of these determinants to monocytes. Cancer Immunol Immunother. Jul. 2006; 55(7): 808-18. Epub Nov. 9, 2005.
Bandres et al: "Identification by Real-time PCR of 13 mature microRNAs differentially expressed in colorectal cancer and non-tumoral tissues", Molecular Cancer, vol. 5, No. 1, Jul. 19, 2006, p. 29.
Bansard et al. Can rheumatoid arthritis responsiveness to methotrexate and biologics be predicted? Rheumatology. 2009; 48(9): 1021-1028.
Barbarotto et al. "MicroRNAs and cancer: Profile, profile, profile" Int J Cancer (2008) 122:969-977.
Bard et al. Proteomic analysis of exosomes isolated from human malignant pleural effusions. Am J Respir Cell Mol Biol. Jul. 2004; 31(1): 114-21. Epub Feb. 19, 2004.
Bartel. MicroRNAs: genomics, biogenesis, mechanism, and function. Cell. Jan. 23, 2004; 116(2): 281-97.
Baxevanis, Antibody-based cancer therapy. Expert Opin Drug Discov. Apr. 2008;3(4):441-52.
Becker, R. Biomarkers in Atrial Fibrillation: Investigating Biologic Plausibility, Cause, and Effect. Journal of Thrombosis and Thrombolysis. 2005;19(1):71-75.
Berek et al. Biologic and immunologic therapies for ovarian cancer. J Clin Oncol. May 15, 2003; 21(10 Suppl):168s-174s.
Blower et al. MicroRNAs modulate the chemosensitivity of tumor cells. Mol Cancer Ther. Jan. 2008; 7(1): 1-9.
Bohler et al. Endometriosis markers: Immunologic alterations as diagnostic indicators for endometriosis. Reproductive Sciences. 2007; 14(6): 595-604.
Bracken et al., Global analysis of the mammalian RNA degradome reveals widespread miRNA-dependent and miRNA-independent endonucleolytic cleavage, Nucleic Acids Research, 2011, 1-11.
Bracken et al., Global analysis of the mammalian RNA degradome reveals widespread miRNA-dependent and miRNA-independent endonucleolytic cleavage, Nucleic Acids Research, 2011, 1-11 Supplement.
Brase et al., Circulating miRNAs are correlated with tumor progression in prostate cancer. Int J Cancer. Feb. 1, 2011;128(3):608-16.
Brawer et al. Measurement of complexed PSA improves specificity for early detection of prostate cancer. Urology. Sep. 1998;52(3):372-8.
Brown et al. Activation of SPARC expression in reactive stroma associated with human epithelial ovarian cancer. Gynecologic Oncology. 1999; 75(1): 25-33.
Bryant et al: Changes in circulating microRNA levels associated with prostate cancer, British Journal of Cancer, vol. 186, No. 4, Feb. 14, 2012, pp. 768-774.
Budman et al. Biomarkers for detection and surveillance of bladder cancer. Can Urol Assoc J. Jun. 2008;2(3):212-21.
Burroughs et al., Deep-sequencing of human argonaute-associated small RNAs provides insight into miRNA sorting and reveals argonaute association with RNA fragments of diverse origin, RNA Biology 8:1, 158-177; 2011.
Burroughs et al., Deep-sequencing of human argonaute-associated small RNAs provides insight into miRNA sorting and reveals argonaute association with RNA fragments of diverse origin, RNA Biology 8:1, 158-177; 2011 Supplement.
Caby et al. Exosomal-like vesicles are present in human blood plasma. International Immunology. Jul. 2005; 17(7):879-887.
Calin et al. Frequent deletions and down-regulation of micro-RNA genes miR15 and miR16 at 13q14 in chronic lymphocytic leukemia. Proc Natl Acad Sci USA. Nov. 26, 2002; 99(24):15524-9.
Calin et al. MicroRNA signatures in human cancers. Nature Rev Cancer. Nov. 2006; 6(11):857-66.
Calin et al. MicroRNA-cancer connection: the beginning of a new tale. Cancer Res. Aug. 1, 2006; 66(15): 7390-4.
Carr et al. Circulating membrane vesicles in leukemic blood. Cancer Res. Nov. 1985; 45(11 Pt 2): 5944-51.
Castellana et al., Membrane microvesicles: Macromessengers in cancer disease and progression, Thrombosis Res 125 Suppl, 2 (2010) 584-588.
Castelletti et al., Apical transport and folding of prostate-specific membrane antigen occurs independent of glycan processing. J Biol Chem. Feb. 10, 2006;281(6):3505-12. Epub Oct. 12, 2005.
Ceccarini et al. Biochemical and NMR studies on structure and release conditions of RNA-containing vesicles shed by human colon adenocarcinoma cells, Int. J. Cancer: 44, 1989: 714-21.
Chen et al. "Characterization of microRNAs in serum: a novel class of biomarkers for diagnosis of cancer and other diseases" Cell Research (2008) 18: 997-1006.
Chen et al. Microfluidic isolation and transcriptome analysis of serum microvesicles. Lab Chip, 2010, DOI: 10.1039/b916199f. First published on the web Dec. 8, 2009.
Cheruvanky. Rapid isolation of urinary exosomal biomarkers using a nanomembrane ultrafiltration concentrator. Am J Physiol Renal Physiol. 2007; 292(5): F1657-1661.
Choi et al. Proteomic Analysis of Microvesicles Derived from Human Colorectal Cancer Cells. Journal of Proteome Research. 2007; 6(12): 4646-4655.
Chromy et al. Proteomic Analysis of Human Serum by Two-Dimensional Differential Gel Electrophoresis after Depletion of High-Abundant Proteins. J Proteome Res. 2004; 3:1120-1127.
Cifuentes, et al. A Novel miRNA Processing Pathway Independent of Dicer Requires Argonaute2 Catalytic Activity, Science 328, 1694 (2010).
Clarke et al. Molecular mechanisms of metastasis in prostate cancer. Asian Journal of Andrology. 2009; 11: 57-67.

(56) References Cited

OTHER PUBLICATIONS

Clayton et al. Analysis of Antigen Presenting Cell Derived Exosomes, Based on Immuno-Magnetic Isolation and Flow Cytometry. J Immunol Methods. 2001;1: 247 (1-2): 163-74.
Clayton et al. Exosomes in tumour immunity. Curr Oncol, 2009; 16(3): 46-9.
Clayton et al., Analysis of antigen presenting cell derived exosomes, based on immuno-magnetic isolation and flow cytometry, Journal of Immunological Methods 247 (2001) 163-174.
Coate et al. Molecular predictive and prognostic markers in non-small-cell lung cancer. The Lancet Oncology. 2009; 10(10): 1001-1010.
Cocucci et al. Shedding microvesicles: artifacts no more. Trends Cell Biol. 2009; 19(2): 43-51.
Cummings et al. Disease-modifying therapies for Alzheimer disease: Challenges to early intervention. Neurology. Oct. 16, 2007;69(16):1622-34.
Cummins et al. Implications of micro-RNA profiling for cancer diagnosis. Oncogene. Oct. 9, 2006; 25(46): 6220-7. Review.
Cummins et al: "The colorectal microRNAome", Proc Natl Acad Sci USA, vol. 103, No. 10, Mar. 7, 2006, pp. 3687-3692.
Da Cunha et al. Bioinformatics construction of the human cell surfaceome. Proc Natl Acad Sci USA Sep. 2009, vol. 106, No. 39, pp. 16752-16757.
Datta et al. Sensitive detection of occult breast cancer by the reverse-transcriptase polymerase chain reaction. J Clin Oncol. Mar. 1994; 12(3): 475-82.
De Cecco et al. Gene expression profiling of advanced ovarian cancer: characterization of a molecular signature involving fibroblast growth factor 2. Oncogene. Oct. 21, 2004; 23(49): 8171-83.
De Gassart et al. Lipid raft-associated protein sorting in exosomes. Blood. Dec. 15, 2003;102(13):4336-44. Epub Jul. 24, 2003.
Demilito et al. Surrogate markers as a guide to evaluate response to antiretroviral therapy. Curr Med Chem. Mar. 2003;10(5):349-65.
Denzel et al. MMP7 is a target of the tumour-associated antigen EpCAM. Int J Exp Pathol. Oct. 2012;93(5):341-53.
Deras et al. PCA3: a molecular urine assay for predicting prostate biopsy outcome. J Urol. 2008; 179: 1587-1592.
Di Vizio et al. Oncosome formation in prostate cancer: association with a region of frequent chromosomal deletion in metastatic disease. Cancer Res. 2009; 69: 5601-5609.
Ding, GW182 family proteins are crucial for microRNA-mediated gene silencing, Trends Cell Biol. Aug. 2007;17(8):411-6. Epub Sep. 4, 2007.
Dolo et al. Membrane vesicles shed into the extracellular medium by human breast carcinoma cells carry tumor-associated surface antigens. Clin Exp Metastasis. Jul. 1995; 13(4): 277-86.
Draghici et al. Epitomics: Serum Screening for the Early Detection of Cancer on Microarrays Using Complex Panels of Tumor Antigens. Expert Rev Mol Diagn. Sep. 2005;5(5):735-43.
D'Souza et al. A strategy for blood biomarker amplification and localization using ultrasound. Proc Natl Acad Sci U S A. Oct. 6, 2009; 106(40): 17152-7.
Dusing et al. ACE inhibitors, angiotensin receptor blockers and direct renin inhibitors in combination: a review of their role after the ONTARGET trial. Current Medical Research and Opinion. Sep. 2009; 25(9): 2287-2301.
Dutt et al. Drug-sensitive FGFR2 mutations in endometrial carcinoma. Proc Natl Acad Sci U S A. Jun. 24, 2008; 105(25): 8713-7.
El-Hefnawy et al. Characterization of Amplifiable, Circulating RNA in Plasma and Its Potential as a Tool for Cancer Diagnostics. Clinical Chemistry. 2004; 50(3):564-573.
Emery et al. Evidence-based review of biologic markers as indicators of disease progression and remission in rheumatoid arthritis. Rheumatology International. Jul. 2007; 27(9):793-806.
Escola et al. Selective enrichment of tetraspan proteins on the internal vesicles of multivesicular endosomes and on exosomes secreted by human B-lymphocytes. J Biol Chem. Aug. 7, 1998; 273(32): 20121-7.
Esquela-Kerscher et al. Oncomirs—microRNAs with a role in cancer. Nature Rev Cancer. Apr. 2006; 6(4): 259-69.
Feigin, A. Evidence from Biomarkers and Surrogate Endpoints. NeuroRX. Jul. 2004; 1(3): 323-330.
Fevrier et al. Exosomes: endosomal-derived vesicles shipping extracellular messages. Current Opinion in Cell Biology. 2004, 16: 415-21.
Fingleton et al: "A rat monoclonal antibody that recognizes pro and active MMP-7 indicates polarized expression in vivo", Hybridoma, vol. 26, No. 1, Feb. 1, 2007, pp. 22-27.
Flavin et al. Potentially important microRNA cluster on chromosome 17p13.1 in primary peritoneal carcinoma. Mod Pathol. Feb. 2009;22(2): 197-205.
Fowler et al. Predictive Value of Biochemical Markers in Stroke. Journal of Neuroscience Nursing. Feb. 2007; 39(1): 58-60.
Garcia et al. Extracellular plasma RNA from colon cancer patients is confined in a vesicle-like structure and is mRNA-enriched. RNA. 2008; 14:1424-1432.
Gaur et al. Characterization of microRNA expression levels and their biological correlates in human cancer cell lines. Cancer Res. Mar. 15, 2007; 67(6): 2456-68.
Geuze et al. Sorting of mannose 6-phosphate receptors and lysosomal membrane proteins in endocytic vesicles. J Cell Biol. Dec. 1988; 107(6 Pt 2): 2491-501.
Gibbings et al. Multi vesicular bodies associate with components of miRNA effector complexes and modulate miRNA activity. Nat Cell Biol. 2009; 11(9): 1143-9.
Graner et al. Proteomic and immunologic analyses of brain tumor exosomes. DD. FASEB J. 2009; 23(5): 1541-57.
Greenbaum et al. Comparing protein abundance and mRNA expression levels on a genomic scale. Genome Biol. 2003; 4(9): 117. (8 pages).
Groskopf et al., APTIMA PCA3 Molecular Urine Test: Development of a Method to Aid in the Diagnosis of Prostate Cancer Clinical Chemistry 52:6 1089-1095 (2006).
Gu et al. Identification and characterization of microRNAs from the bovine adipose tissue and mammary gland. FEBS Lett. Mar. 6, 2007; 581(5): 981-8.
Haese et al. "Clinical utility of the PCA3 urine assay in European men scheduled for repeat biopsy" Eur Urol; vol. 54, pp. 1081-1088 (2008).
Halperin et al. Biomarkers for evaluation of clinical efficacy of multipotential neuroprotective drugs for Alzheimer's and Parkinson's diseases neurotherapeutics. Jan. 2009; 6(1):128-140.
Hansen et al. Fibroblast growth factor receptor 2, gain-of-function mutations, and tumourigenesis: investigating a potential link. J Pathol. Sep. 2005; 207(1): 27-31.
Hansen: "Lipid Rafts Exist as Stable Cholesterol-independent Microdomains in the Brush Border Membrane of Enterocytes", Journal of Biological Chemistry, vol. 276, No. 34, Jun. 1, 2001, pp. 32338-32344.
Hegmans et al. Proteomic Analysis of Exosomes Secreted by Human Mesothelioma Cells. The American Journal of Pathology. 2004; 164(5): 1807-1815.
Heijnen et al. Activation platelets release two types of membrane vesicles: microvesicles by surface shedding and exosomes derived from exocytosis of multivesicular bodies and alpha granules. Blood. Dec. 1, 1999; 94(11): 3791-9.
Hemler. Tetraspanin proteins mediate cellular penetration, invasion, and fusion events and define a novel type of membrane microdomain. Annu. Rev. Cell Dev. Biol. 2003. 19: 397-422.
Hoorn et al. Prospects for urinary proteomics: exosomes as a source of urinary biomarkers. Nephrology. 2005; 10(3): 283-90.
Horoszewicz et al. Monoclonal antibodies to a new antigenic marker in epithelial prostatic cells and serum of prostatic cancer patients. Anticancer Res. Sep.-Oct. 1987; 7(5B): 927-35. (Abstract).
Hu et al. Loss of heterozygosity of M6P/IGF2R gene is an early event in the development of prostate cancer. Prostate Cancer Prostatic Dis. 2006; 9(1): 62-7.
Huber et al. Human colorectal cancer cells induce T-cell death through release of proapoptotic microvesicles: role in immune escape. Gastroenterology. Jun. 2005; 128(7): 1796-804.

(56) References Cited

OTHER PUBLICATIONS

Hubert et al. STEAP: a prostate-specific cell-surface antigen highly expressed in human prostate tumors. Proc Natl Acad Sci U S A. Dec. 7, 1999; 96(25): 14523-8.
Hunter et al. Detection of microRNA expression in human peripheral blood microvesicles. PLoS ONE. 2008; 3(11): e3694.
Iero et al. Tumour-released exosomes and their implications in cancer immunity. Cell Death Differ. Jan. 2008; 15(1): 80-8.
Ii et al: Role of matrix metalloproteinase-7 (matrilysin) in human cancer invasion, apoptosis, growth, and angiogenesis, Experimental Biology and Medicine, vol. 231, No. 1, Jan. 2006, pp. 20-27.
Infante et al. Peritumoral fibroblast SPARC expression and patient outcome with resectable pancreatic adenocarcinoma. J Clin Oncol. Jan. 20, 2007; 25(3): 319-25.
Iorio et al. MicroRNA gene expression deregulation in human breast cancer. Cancer Res. Aug. 15, 2005; 65(16): 7065-70.
Iorio et al. MicroRNA signatures in human ovarian cancer. Cancer Res. Sep. 15, 2007; 67(18): 8699-707.
Jang et al. Mutations in fibroblast growth factor receptor 2 and fibroblast growth factor receptor 3 genes associated with human gastric and colorectal cancers. Cancer Res. May 1, 2001; 61(9): 3541-3.
Janowska-Wieczorek et al. Microvesicles derived from activated platelets induce metastasis and angiogenesis in lung cancer. Int. J. Cancer, 2005; 113(5): 752-760.
Jansen et al. Exosomal secretion of cytoplasmic prostate cancer xenograft-derived proteins. Mol Cell Proteomics. Jun. 2009; 8(6): 1192-205. Epub Feb. 9, 2009.
Johnstone et al. Vesicle formation during reticulocyte maturation. Vesicle formation during reticulocyte maturation. Association of plasma membrane activities with released vesicles (exosomes). J Biol Chern., 1987; 262(19): 9412-20.
Kampoli et al. Biomarkers of premature atherosclerosis. Trends in Molecular Medicine. Jul. 2009; 15(7): 323-332.
Keller et al., Exosomes: From biogenesis and secretion to biological function, Immunol. Lett. 107 (2): 102-8 (2006).
Kesimer et al. Characterization of exosome-like vesicles released from human tracheobronchial ciliated epithelium: a possible role in innate defense. FASEB J. Jun. 2009; 23(6): 1858-68.
Khalil A. Biomarker discovery: A proteomic approach for brain cancer profiling. Cancer Sci. 2007; 98(2): 201-213.
Khambata-Ford et al. Expression of epiregulin and amphiregulin and K-ras mutation status predict disease control in metastatic colorectal cancer patients treated with cetuximab. Journal of Clinical Oncology. 2007; 25(22): 3230-3237.
Kilpelainen et al. False-Positive Screening Results in the Finnish Prostate Cancer Screening Trial. Br J Cancer. 2010; 102: 469-474.
Kim et al. The multiplex bead array approach to identifying serum biomarkers associated with breast cancer. Breast Cancer Res. 2009; 11 (2):R22.
Koga et al. Purification, characterization and biological significance of tumor-derived exosomes. Anticancer Res. Nov.-Dec. 2005; 25(6A): 3703-8.
Kopreski et al. Detection of tumor messenger RNA in the serum of patients with malignant melanoma. Clin Cancer Res. Aug. 1999; 5(8): 1961-5.
Kristiansen et al.,Tumour biological aspects of CD24, a mucin-like adhesion molecule, Journal of Molecular Histology 35: 255-262, 2004.
Kushner et al. 2009 Focused Updates: ACC/AHA Guidelines for the Management of Patients With ST-Elevation Myocardial Infarction (Updating the 2004 Guideline and 2007 Focused Update) and ACC/AHA/SCAI Guidelines on Percutaneous Coronary Intervention (Updating the 2005 Guideline and 2007 Focused Update) J Am Coll Cardiol. 2009; 54: 2205-2241.
Kuslich et al. Plasma exosomes are a robust biosignature for prostate cancer. Abstract. AACR 2010 Annual Meeting. Apr. 18, 2010.
Lamparski et al. Production and characterization of clinical grade exosomes derived from dendritic cells. Journal of immunological Methods. 270, 2002: 211-26.
Landewe R. Predictive markers in rapidly progressing rheumatoid arthritis. The Journal of Rheumatology. Nov. 1, 2007; 80: 8-15.
Lanoix J et al: “Secretory vesicle analysis for discovery of low abundance plasma biomarkers” Expert Opinion on Medical Diagnostics, vol. 2, No. 5, May 1, 2008, pp. 475-485.
Larsson et al., Antiprostasome antibodies: possible serum markers for prostate cancer metastasizing liability. Urol Oncol. May-Jun. 2006;24(3):195-200.
Laulagnier et al. Characterization of exosome subpopulations from RBL-2H3 cells using fluorescent lipids. Blood Cells, Molecules, and Diseases. 2005; 35: 116-121.
Lee et al. Silencing by small RNAs is linked to endosomal trafficking. Nature Cell Biol. 2009; 11(9): 1150-6.
Lehmann et al. Senescence-Associated Exosome Release from Human Prostate Cancer Cells. Cancer Research. 2008; 68(19): 7864-7871.
Li et al. “Expression of MicroRNAs in prostate cancer and its significance” Clin Oncol Cancer Res; vol. 6, pp. 21-28 (2009).
Li et al. [Separation and identification of the exosomes derived from a mouse hepatoma carcinoma cell line (H22) and initial investigation of their protein composition]. Zhonghua Gan Zang Bing Za Zhi. Jun. 2007; 15(6): 437-40. (Abstract in English only). Original article in Chinese.
Li et al. Claudin-containing exosomes in the peripheral circulation of women with ovarian cancer. BMC Cancer. 2009; 9:244.
Liu L et al: ‘Detection of circulating cancer cells in lung cancer patients with a panel of marker genes’, Biochemical and Biophysical Research Communications, vol. 372, No. 4, pp. 756-760, (2008).
Llorente, Caveolin-1 and MAL are located on prostasomes secreted by the prostate cancer PC-3 cell line, Journal of Cell Science 117: 5343 (2004).
Lodes et al. Detection of cancer with serum miRNAs on an oligonucleotide microarray. PLoS One. Jul. 14, 2009; 4(7): e6229.
Logozzi et al. High levels of exosomes expressing CD63 and caveolin-1 in plasma of melanoma patients. PLoS One. 2009; 4(4): e5219. (10 pages).
Lu et al. Identification of extracellular delta-catenin accumulation for prostate cancer detection. Prostate. Mar. 1, 2009; 69(4): 411-8.
Lu et al. MicroRNA expression profiles classify human cancers. Nature. 2005; 435:834-838.
Lu et al., A Gene Expression Signature Predicts Survival of Patients with Stage I Non-Small Cell Lung Cancer. Plos Med, Dec. 2006, vol. 3, No. 12; pp. 2229-2243.
Ludwig et al. Biomarkers in cancer staging, prognosis and treatment selection. Nat Rev Cancer. Nov. 2005;5(11):845-56.
Maisel, A.S. Cardiovascular and renal surrogate markers in the clinical management of hypertension. Cardiovascular Drugs and Therapy. Aug. 2009; 23(4): 317-326.
Mandel et al. Gene and protein signatures in sporadic Parkinson’s disease and a novel genetic model of PD. Parkinsonism & Related Disorders. 2007; 13:S242-S247.
Martens-Uzunova et al., Diagnostic and prognostic signatures from the small non-coding RNA transcriptone in prostate cancer. Oncogene (2011) 1-14.
Martin-Ventura et al. Biomarkers in cardiovascular medicine. Revista Española de Cardiología (English Edition). Jun. 2009; 62(6): 677-688.
Mears et al. Proteomic analysis of melanoma-derived exosomes by two-dimensional polyacrylamide gel electrophoresis and mass spectrometry. Proteomics. Dec. 2004; 4(12): 4019-31.
Menon et al. Recent developments in ovarian cancer screening. Curr Opin Obstet Gynecol. Feb. 2000; 12(1): 39-42.
Mettlin et al. Relative sensitivity and specificity of serum prostate specific antigen (PSA) level compared with age-referenced PSA, PSA density, and PSA change. Data from the American Cancer Society National Prostate Cancer Detection Project. (Cancer, vol. 74, No. 5, p. 1615-1620, 1994).
Millimaggi et al. Tumor Vesicle-Associated CD147 Modulates the Angiogenic. Capability of Endothelial Cells. Neoplasia. 2007; 9(4): 349-357.
Miska. How microRNAs control cell division, differentiation, and death. Curr Opin Genet Dev. Oct. 2005; 15(5): 563-8.

(56) References Cited

OTHER PUBLICATIONS

Mitchell et al. Can urinary exosomes act as treatment response markers in prostate cancer? Journal of Translational Medicine. 2009; 7(4).
Mitchell et al. Circulating microRNAs as stable blood-based markers for cancer detection. Proc Natl Acad Sci USA. Jul. 29, 2008; 105(30): 10513-8.
Mitchell et al., Circulating microRNAs as stable blood-based markers for cancer detection, Proc Nat'l Acad Sci USA 105:10513-10518 (Jul. 29, 2008) Supplement.
Monleon et al. Differential secretion of fas ligand- or APO2 ligand/TNF-related apoptosis-inducing ligand-carrying microvesicles during activation-induced death of human t cells. The Journal of Immunology. 2001; 167: 6736-44.
Moreno et al. Detection of hematogenous micrometastasis in patients with prostate cancer. Cancer Res. Nov. 1, 1992; 52(21): 6110-2.
Mothe et al. Virological, immune and host genetics markers in the control of HIV infection. Disease Markers. 2009: 27(3-4): 105-120.
Nakanishi et al. PCA3 molecular urine assay correlates with prostate cancer tumor volume: implication in selecting candidates for active surveillance. J Urol. May 2008;179(5): 1804-10.
Nilsson et al. E4, a new monoclonal antibody identifying a human prostatic cell surface antigen. Cancer Biother Radiopharm. 1997; 12: 395-403.
Nomura et al. Assessment of an ELISA kit for platelet-derived microparticles by joint research at many institutes in Japan. J Atheroscler Thromb. 2009; 16(6): 878-87.
Oakman et al. The role of topoisomerase IIα and HER-2 in predicting sensitivity to anthracyclines in breast cancer patients. Cancer Treatment Reviews. 2009; 35(8): 662-667.
Olver et al. (2007). "Proteomic Analysis of Secreted Exosomes," Chapter 7 in Subcellular Proteomics: From Cell Deconstruction to System Reconstruction Subcellular Biochemistty. Bertrand et a l ( eds. ), Springer. vol. 43, Section 2, pp. 99-131.
Ouyang et al. "A duplex quantitative polymerase chain reaction assay based on quantification . . . " J Urol; vol. 181, pp. 2508-2514 (2009).
Palacio et al. Anti-endometrial autoantibodies in women with a diagnosis of infertility. American Journal of Reproductive Immunology. vol. 38, Nr. 2, Aug. 1997, pp. 100-105.
Pan et al. Electron microscopic evidence for externalization of the transferrin receptor in vesicular form in sheep reticulocytes. J Cell Biol., 1985; 101(3): 942-8.
Pan et al. Fate of the transferrin receptor during maturation of sheep reticulocytes in vitro: selective externalization of the receptor. RM. Cell. 1983; 33(3): 967-78.
Pang et al. MicroRNAs and Prostate Cancer. ABBS 2010; 42(6): 363-369.
Panici P et al: "Predictive value of multiple tumor marker assays in second-look procedures for ovarian cancer", Gynecologic Oncology, vol. 35, No. 3, Dec. 1, 1989, pp. 286-289.
Pauley et al., Formation of GW bodies is a consequence of microRNA genesis, EMBO Rep. Sep. 2006;7(9):904-10. Epub Aug. 11, 2006.
Pawlowski et al. Identification and characterization of exosome subpopulations to provide the foundation for a novel exosome-based cancer diagnostic platform. Abstract. AACR 2010 Annual Meeting. Apr. 20, 2010.
Pepe et al. (Journal of the National Cancer Institute, vol. 93, No. 14, p. 1054-1061, 2001).
Pereira et al. Cardiovascular pharmacogenomics and individualized drug therapy. Nature Reviews Cardiology. Oct. 2009; 6:632-638.
Piccin et al., Circulating microparticles: pathophysiology and clinical implications. Blood Reviews (2007) 21, 157-171.
Pisitkun et al. Identification and proteomic profiling of exosomes in human urine. Proc Nat'l Acad Sci USA. 2004; 101(36):13368-13373.
Pollock et al. Frequent activating FGFR2 mutations in endometrial carcinomas parallel germline mutations associated with craniosynostosis and skeletal dysplasia syndromes. Oncogene. Nov. 1, 2007; 26(50): 7158-62.
Porkka, K. P. et al. "MicroRNA Expression Profiling in Prostate Cancer" Cancer Res. Jul. 2007, vol. 67, No. 13, pp. 6130-6135.
Rabinowits et al. Exosomal microRNA: a diagnostic marker for lung cancer. Clin Lung Cancer, 2009: 10(1):42-6.
Rajendran et al. Alzheimer's disease beta-amyloid peptides are released in association with exosomes. Proc Natl Acad Sci U S A. Jul. 25, 2006; 103(30): 11172-7.
Rakha et al. Combinatorial biomarker expression in breast cancer. Breast Cancer Res Treat. Apr. 2010;120(2):293-308.
Raposo et al. Accumulation of major histocompatibility complex class II molecules in mast cell secretory granules and their release upon degranulation. Mol Biol Cell. Dec. 1997; 8(12): 2631-45.
Ratajczak et al. Embryonic stem cell-derived microvesicles reprogram hematopoietic progenitors: Evidence for horizontal transfer of mRNA and protein delivery. Leukemia. May 2006; 20(5): 847-56.
Ratajczak et al. Membrane-derived microvesicles: important and underappreciated mediators of cell-to-cell communication. Leukemia. Sep. 2006; 20(9): 1487-95.
Resnick et al. The detection of differentially expressed microRNAs from the serum of ovarian cancer patients using a novel real-time PCR platform. Gynecol Oncol. Jan. 2009; 112(1):55-9.
Rokhlin et al. 5E10: a prostate-specific surface-reactive monoclonal antibody. Cancer Lett. Sep. 25, 1998; 131(2): 129-36.
Rugo H. S. New treatments for metastatic breast cancer: mechanisms of action of nanoparticle albumin-bound taxanes. Commun Oncol 2008; 5 (suppl 4): 8-12.
Runz et al. Malignant ascites-derived exosomes of ovarian carcinoma patients contain CD24 and EpCAM. Gynecol Oncol. Dec. 2007; 107(3): 563-71.
Rupp et al. Loss of EpCAM expression in breast cancer derived serum exosomes: Role of proteolytic cleavage. Gynecol Oncol. Aug. 2011;122(2):437-46.
Sabapatha et al. Specific isolation of placenta-derived exosomes from the circulation of pregnant women and their immunoregulatory consequences. Am J Reprod Immunol. Nov.-Dec. 2006; 56 (5-6):345-55.
Safranek et al: Expression of MMP-7, MMP-9, TIMP-1 and TIMP-2 mRNA in Lung Tissue of Patients with Non-small Cell Lung Cancer (NSCLC) and Benign Pulmonary Disease, Anticancer Research, Jul. 1, 2009, pp. 2513-2518.
Sankaranarayanan et al. Worldwide burden of gynaecological cancer: the size of the problem. Best Pract Res Clin Obstet Gynaecol. Apr. 2006; 20(2): 207-25.
Savelieva and Camm. Anti-arrhythmic drug therapy for atrial fibrillation: current anti-arrhythmic drugs, investigational agents, and innovative approaches. Europace. 2008; 10(6): 647-665.
Schiera et al. Neurons produce FGF2 and VEGF and secrete them at least in part by shedding extracellular vesicles. J. Cell Mol. Med. 2007; 11(6): 1384-1394.
Schorey et al. Exosome function: from tumor immunology to pathogen biology. Traffic. 2008; 9(6): 871-881.
Seliger et al., Association of HLA class I antigen abnormalities with disease progression and early recurrence in prostate cancer. Cancer Immunol Immunother. Apr. 2010;59(4):529-40.
Seligson et al. Epithelial cell adhesion molecule (KSA) expression: pathobiology and its role as an independent predictor of survival in renal cell carcinoma. Clin Cancer Res. Apr. 15, 2004; 10(8): 2659-69.
Selth et al: Circulating microRNAs: macro-utility as markers of prostate cancer?, Endocrine Related Cancer, vol. 19, No. 4, Apr. 5, 2012, pp. R99-R113.
Shabason J et al: "The Profile of Glioma Microvesicles After Irradiation", International Journal of Radiation, vol. 78, No. 3, Nov. 1, 2010, p. S130.
Shedden et al. Expulsion of small molecules in vesicles shed by cancer cells: association with gene expression and chemosensitivity profiles. Cancer Res. Aug. 1, 2003; 63(15): 4331-7.
Sheldon et al., New mechanism for Notch signaling to endothelium at a distance by Delta-like 4 incorporation into exosomes, Blood, Sep. 30, 2010 vol. 116, No. 13.
Siegfried et al. Distinct patterns of expression of keratinocyte growth factor and its receptor in endometrial carcinoma. Cancer. Mar. 15, 1997; 79(6): 1166-71.
Simak et al. Cell membrane microparticles in blood and blood products: potentially pathogenic agents and diagnostic markers. Transfusion Medicine Reviews. 2006; 20(1): 1-26.

(56) References Cited

OTHER PUBLICATIONS

Simpson et al. Exosomes: proteomic insights and diagnostic potential. Expert Rev Proteomics. Jun. 2009; 6(3): 267-83.
Simpson et al. Proteomic profiling of exosomes: current perspectives. Proteomics. Oct. 2008; 8(19): 4083-99.
Siva et al. "Molecular assays for the detection of microRNAs in prostate cancer" Mol Cancer; vol. 8, pp. 17 (2009).
Skog et al. Glioblastoma microvesicles transport RNA and proteins that promote tumour growth and provide diagnostic biomarkers. Nature Cell Biology. 2008; 10:1470-1476.
Spetzler et al. Plasma exomome-based biosignatures: A novel method for early diagnosis of colorectal cancer. Abstract. AACR 2010 Annual Meeting. Apr. 19, 2010.
Staubach et al. Proteomics of MUC1-containing lipid rafts from plasma membranes and exosomes of human breast carcinoma cells MCF-7. Proteomics. 2009; 9(10): 2820-35.
Sun et al. The role of microRNA-221 and microRNA-222 in androgen-independent prostate cancer cell lines, Cancer Res; vol. 69, pp. 3356-3363 (2009).
Sung et al. Tumor microenvironment promotes cancer progression, metastasis, and therapeutic resistance. Curr Probl Cancer. 2007; 31(2): 36-100.
Szarvas et al. Matrix metalloproteinases and their clinical relevance in urinary bladder cancer. Nat. Rev. Urol. 2011; 8: 241-254.
Taylor and Black. Neoplastic and developmental importance of shed plasma membrane fragments. Amer. Zool. (1986) 26:511-514.
Taylor et al. Binding of specific peroxidase-labeled antibody to placental-type phosphatase on tumor-derived membrane fragments. Cancer Res. Nov. 1980; 40(11): 4064-9.
Taylor et al. Characterization of humoral responses of ovarian cancer patients: antibody subclasses and antigenic components. Gynecol Oncol. Feb. 2010;116(2):213-21.
Taylor et al. Identification of antigenic components recognized by membrane-bound antibodies from ovarian cancer patients. American Journal of Reproductive Immunology, vol. 6, No. 4, Dec. 1, 1984, pp. 179-184, Munksgaard International Publishers, Copenhagen, DK.
Taylor et al. Isolation of plasma membrane fragments from cultured murine melanoma cells. Biochem Biophys Res Commun. Jun. 15, 1983; 113(2): 470-6.
Taylor et al. MicroRNA signatures of tumor-derived exosomes as diagnostic biomarkers of ovarian cancer. Gynecol Oncol. Jul. 2008; 110(1): 13-21.
Taylor et al. Patient-derived tumor-reactive antibodies as diagnostic markers for ovarian cancer. Gynecol Oncol. 2009 Oct;115(1):112-20.
Taylor et al. Pregnancy-associated exosomes and their modulation of T cell signaling. J Immunol. Feb. 1, 2006; 176(3): 1534-42.
Taylor et al. Pregnancy-linked suppression of TcR signaling pathways by a circulating factor absent in recurrent spontaneous pregnancy loss (RPL). Mol Immunol Apr. 2006; 43(11): 1872-80.
Taylor et al. Quantitation of peroxidiseantibody binding to membrane fragments using column chromatography. Anal Biochem. Sep. 15, 1979; 98(1): 53-9.
Taylor et al. Shed membrane fragment-associated markers for endometrial and ovarian cancers. Gynecol Oncol. Mar. 2002; 84(3): 443-8.
Taylor et al. Shedding of plasma membrane fragments. Neoplastic and developmental importance. Dev Biol (NY 1985). 1986; 3:33-57.
Taylor et al. Tumour-derived exosomes and their role in cancer-associated T-cell signalling defects. Br J Cancer. Jan. 31, 2005; 92(2): 305-11.
Thal et al. The role of biomarkers in clinical trials for alzheimer disease. Alzheimer Dis Assoc Disord. 2006; 20(1): 6-15.
Thery et al. Exosomes: composition, biogenesis and function. Nature Rev. Immunol., 2002; 2(8): 569-79.
Thery et al. Membrane vesicles as conveyors of immune responses. Nat Rev Immunol Aug. 2009; 9(8):581-93. Epub Jun. 5, 2009.
Thomas et al. Biomarkers in peripheral arterial disease trends in cardiovascular medicine.Trends Cardiovasc Med. Jul. 2009;19(5):147-51.
Thomas et al. Differential expression of osteonectin/SPARC during human prostate cancer progression. Clin Cancer Res. Mar. 2000; 6(3):1140-9.
Tockman et al. Considerations in bringing a cancer biomarker to clinical application. Cancer Res. May 1, 1992; 52(9 Suppl): 2711s-2718s.
Tong et al. MicroRNA profile analysis of human prostate cancers. Cancer Gene Ther. Mar. 2009; 16(3): 206-16.
Trubey et al. Quantitation of HLA class II protein incorporated into human immunodeficiency type 1 virions purified by anti-CD45 immunoaffinity depletion of microvesicles. Journal of Virology. Dec. 2003: 12699-709; available at http://jvi.asm.org, accessed Dec. 17, 2011.
Turchinovich et al., Characterization of extracellular circulating microRNA, Nucleic Acids Res. Sep. 1, 2011;39(16):7223-33. Epub May 24, 2011.
Valadi et al. Exosome-mediated transfer of mRNAs and microRNAs is a novel mechanism of genetic exchange between cells. Nature Cell Biology. 2007; 9(6): 654-659.
Valenti et al. Human tumor-released microvesicles promote the differentiation of myeloid cells with transforming growth factor-beta-mediated suppressive activity on T lymphocytes. Cancer Res 2006; 66: 9290-8.
Van Doormaal et al. Cell-derived microvesicles and cancer. Neth J Med. 2009; 67(7): 266-73.
van Gils et al. "Molecular PCA3 diagnostics on prostatic fluid" The Prostate; vol. 67, pp. 881-887 (2007).
van Gils et al. Detailed analysis of histopathological parameters in radical prostatectomy specimens and PCA3 urine test results. The Prostate; vol. 68, pp. 1215-1222 (2008).
Venneker and Asghar, CD59: a molecule involved in antigen presentation as well as downregulation of membrane attack complex, Exp Clin Immunogenet. 1992;9(1):33-47.
Vickers et al., MicroRNAs are transported in plasma and delivered to recipient cells by high-density lipoproteins, Nat Cell Biol 2011 13:423-33, Epub Mar. 20, 2011.
Wang et al. Down-regulation of CD9 expression during prostate carcinoma progression is associated with CD9 mRNA modifications. Clin Cancer Res. Apr. 15, 2007; 13(8): 2354-61.
Wang et al., Export of microRNAs and microRNA-protective protein by mammalian cells. Nucleic Acids Res. 38:7248-59. Epub Jul. 7, 2010.
Watkins et al. Increased levels of SPARC (osteonectin) in human breast cancer tissues and its association with clinical outcomes. Prostaglandins Leukot Essent Fatty Acids. Apr. 2005; 72(4): 267-72.
Wieczorek et al. Diagnostic and Prognostic Value of RNA-Proteolipid in Sera of Patients with Malignant Disorders following Therapy: First Clinical Evaluation of a Novel Tumor Marker. Cancer Res. Dec. 1, 1987;47(23):6407-12.
Wieczorek et al. Isolation and characterization of an RNA—proteolipid complex associated with the malignant state in humans. Proc. Natl. Acad. Sci. 1985; 82: 3455-3459.
Written Opinion of the International Searching Authority for Int'l Patent Publication WO2010056337, mailed Jul. 21, 2010.
Written Opinion of the International Searching Authority for Int'l Patent Publication WO2011066589, mailed Jan. 4, 2011.
Written Opinion of the International Searching Authority for Int'l Patent Publication WO2011088226, mailed Jul. 20, 2011.
Written Opinion of the International Searching Authority for Int'l Patent Publication WO2011109440, mailed May 17, 2011.
Written Opinion of the International Searching Authority for Int'l Patent Publication WO2011127219, mailed Jun. 28, 2011.
Written Opinion of the International Searching Authority for Int'l Patent Publication WO2012024543, mailed Jan. 10, 2012.
Written Opinion of the International Searching Authority for Int'l Patent Publication WO2012115885, mailed Jun. 14, 2012.
Written Opinion of the International Searching Authority for Int'l Patent Publication WO2012170711, mailed Aug. 10, 2012.
Written Opinion of the International Searching Authority for Int'l Patent Publication WO2012174282, mailed Dec. 4, 2012.
Written Opinion of the International Searching Authority for Int'l Patent Publication WO2013022995, mailed Feb. 6, 2013.

(56) References Cited

OTHER PUBLICATIONS

Wysoczynsk et al. Lung cancer secreted microvesicles: underappreciated modulators of microenvironment in expanding tumors. Int. J. Cancer. 2009; 125(7): 1595-603.
Yang et al. MicroRNA expression profiling in human ovarian cancer: miR-214 induces cell survival and cisplatin resistance by targeting PTEN. Cancer Res. Jan. 15, 2008; 68(2): 425-33.
Yu et al. The regulation of exosome secretion: a novel function of the p53 protein. Cancer Res. May 1, 2006; 66(9): 4795-801.
Zhang et al. MicroRNAs exhibit high frequency genomic alterations in human cancer. Proc Natl Acad Sci U S A. Jun. 13, 2006; 103(24): 9136-41.
Zhang et al., An Array-Based Analysis of Micro RNA Expression Comparing Matched Frozen and Formalin-Fixed Paraffin-Embedded Human Tissue Samples, J Mol Diag 10:513-519 (Oct. 2, 2008).
Zhang et al., An Array-Based Analysis of Micro RNA Expression Comparing Matched Frozen and Formalin-Fixed Paraffin-Embedded Human Tissue Samples, J Mol Diag 10:513-519 (Oct. 2, 2008) Supplement.
Zhang et al., microRNAs as oncogenes and tumor suppressors, Developmental Biology 302 (2007) 1-12.
Ariztia et al. Differential cross-reactivity of membrane derived vesicles determines the invasive potential of mesothelioma, breast and ovarian cancer. 99th AACR Annual Meeting, Apr. 12, 2008. (Abstract retrieved from the Internet.).
Clarke et al. Molecular mechanisms of metastasis in prostate cancer. Asian Journal of Andrology. 2009; 11:57-67.
Denzel et al. MMP7 is a target of the tumour-associated antigen EpCAM. Int J. Exp. Path. 2012; 93: 341-353.
Escaff et al. Study of matrix metalloproteinases and their inhibitors in prostate cancer. British Journal of Cancer. 2010; 102(5): 922-929.
Fingleton et al. A rat monoclonal antibody that recognizes pro- and active MMP-7 indicates polarized express in vivo. Hybridoma. 2007; 26(1): 22-27.
Keller et al. Exosomes: From biogenesis and secretion to biological function. Immunology Letters. 2006; 107: 102-108.
Masanori et al. Role of matrix metalloproteinase-7 (matrilysin) in human cancer invasion, apoptosis, growth, and angiogenesis. Experimental Biology and Medicine. 2006; 231(1): 20-27.
Office action dated Sep. 2, 2013 for EP application No. 11751233.5.
Office action dated Jan. 13, 2014 for Chinese application No. 201180022248.2 (translation at pp. 10-19).
Office action dated Apr. 23, 2014 for EP application No. 11751233.5.
Office action dated Sep. 4, 2014 for Japanese application No. 2012-556185 (translation at pp. 4-6).
Office action dated Oct. 10, 2014 for Chinese application No. 201180022248.2 (translation at pp. 7-12).
Rabinowits et al. Exosomal microRNA: A diagnostic marker for lung cancer. Clin Lung Cancer. 2009; 10(1): 42-46.
Rupp et al. Loss of EpCAM expression in breast cancer derived serum exosomes: Role of proteolytic cleavage. Gynecologic Oncology. 2011; 102: 437-446.
Safranek et al. Expression of MMP-7, MMP-9, TIMP-1 and TIMP-2 mRNA in lung tissue of patients with non-small cell lung cancer (NSCLC) and benign pulmonary disease, (2009).
Shabason et al. The profile of glioma microvesicles after irradiation. Int Journal of Radiation. 2010; 78(3): S130 (Abstract).
Sung et al. Tumor microenvironment promotes cancer progression, metastasis, and therapeutic resistance. Curr Probl Cancer . 2007; 31(2): 36-100.
Szarvas et al. Matrix metalloproteinases and their clinical relevance in urinary bladder cancer. Nature Review Urology. 2011; 6: 241-254.

* cited by examiner

FIG. 1a

| Cancer Lineage, Group Comparison, Disease State | Antigens | References |
|---|---|---|
| **Breast** | BCA-225 | Cerani et al., 1985 |
| **Breast** | BCA-225 | Mesa-Tejada et al., 1988 |
| **Breast** | BCA-225 | Loy et al., 1991 |
| **Breast** | BCA-225 | Ma et al., 1993 |
| **Breast** | hsp70 | Wolfers et al. 2001 Nat Med 793: 297 |
| **Breast** | MART-1 | Wolfers et al. 2001 Nat Med 793: 297 |
| **Breast** | ER | Oldenhuis CN et al., Eur J Cancer. 2008 May;44(7):946-53. Epub 2008 Apr 7; Payne SJ et al., Histopathology. 2008 Jan;52(1):82-90 |
| **Breast** | Class III b-tubulin | Galmarini CM et al., Clin Cancer Res. 2008 Jul 15;14(14):4511-6 |
| **Breast** | VEGFA | Linderholm BK et al., Cancer Res. 2001 Mar 1;61(5):2256-60 |
| **Breast** | HER2/neu (for Her2+BC) | De Laurentiis M et al., Ann Oncol. 2005 May;16 Suppl 4:iv7-13. |
| **Breast** | GPR30 | Filardo EJ et al., Steroids. 2008 Oct;73(9-10):870-3. |
| **Breast** | ErbB4(JM) isoform | Määttä JA et al., Mol Biol Cell. 2006 Jan;17(1):67-79. |
| **Breast** | MPR8 | Bera TK et al., Molecular Medicine 7(8): 509-516, 2001 |
| **Breast** | MISIIR | Jamie N Bakkum-Gamez et al., Gynecologic oncology (Gynecol Oncol) Vol. 108 Issue 1 Pg. 141-8 |
| **Ovarian** | CA125 (0C125)# | Bast et al., 1981 |
| **Ovarian** | CA125 | Dabawat S, et al., 1983 |
| **Ovarian** | CA125 | Davis H et al., 1986 |
| **Ovarian** | CA125 | Nouwen E, et al., 1986 |
| **Ovarian** | CA125 | Quirk J, et al., 1988 |
| **Ovarian** | CA-125 | Fukazawa I et al., 1988 |
| **Ovarian** | VEGFA | Osada R et al., Hum Pathol. 2006 Nov;37(11):1414-25. |
| **Ovarian** | VEGFR2 | Chen BY et al., Zhonghua Zhong Liu Za Zhi. 2005 Jan;27(1):33-7 |
| **Ovarian** | HER2 | Steffensen KD et al., Int J Oncol. 2008 Jul;33(1):195-204 |
| **Ovarian** | MISIIR | Jamie N Bakkum-Gamez et al., Gynecologic oncology (Gynecol Oncol) Vol. 108 Issue 1 Pq. 141-8 |
| **Lung** | CYFRA 21-1 | Kulpa J, et al., C Clin Chem 48: 1931-1937 (2002) |
| **Lung** | TPA-M | Kulpa J, et al., *supra.* |
| **Lung** | TPS | Kulpa J, et al., *supra.* |
| **Lung** | CEA | Kulpa J, et al., *supra.* |
| **Lung** | SCC-Ag | Kulpa J, et al., *supra.* |
| **Lung** | XAGE-1b | Kikuchi et al., Cancer Immunity, 8:13 (2008) |
| **Lung** | HLA class I | Kikuchi et al., *supra.* |
| **Lung** | TA-MUC1 | Kuemmel et al., Lung Cancer Jun 6, 2008 |
| **Lung** | KRAS | Zhang Z et al., Cancer Biol Ther. 2006 Nov;5(11):1481-6 |
| **Lung** | hENT1 | Oguri T et al., Cancer Lett. 2007 Oct 18;256(1):112-9. |
| **Lung** | kinin B1 receptor | Chee J et al., Biol Chem. 2008 Sep;389(9):1225-33. |

FIG. 1b

| Cancer Lineage, Group Comparison, Disease State | Antigens | References |
|---|---|---|
| **Lung** | kinin B2 receptor | Chee J et al., Biol Chem. 2008 Sep;389(9):1225-33. |
| **Lung** | TSC403 | Ozaki K et al., CANCER RESEARCH 58, 3499-3503, August 15, 1998 |
| **Lung** | HTI56 | Dobbs LG et al., JHC Volume 47(2): 129-137, 1999 |
| **Lung** | DC-LAMP | Salaun B et al., American Journal of Pathology. 2004;164:861-871 |
| **Colon** | CEA | Park et al., 2002 |
| **Colon** | MUC2 | Park et al., 2002 |
| **Colon** | GPA33 | Huber et al., 2005 |
| **Colon** | CEACAM5 | Huber et al., 2005 |
| **Colon** | ENFB1 | Huber et al., 2006 |
| **Colon** | CCSA-3 | Leman et al., 2007 |
| **Colon** | CCSA-4 | Leman et al., 2008 |
| **Colon** | ADAM 10 | Choi et al., 2007, J Ethnopharmacol 110(1): 49-55. |
| **Colon** | CD44 | Choi et al., 2007, J Ethnopharmacol 110(1): 49-55. |
| **Colon** | NG2 | Choi et al., 2007, J Ethnopharmacol 110(1): 49-55. |
| **Colon** | ephrin-B1 | Choi et al., 2007, J Ethnopharmacol 110(1): 49-55. |
| **Colon** | plakoglobin | Choi et al., 2007, J Ethnopharmacol 110(1): 49-55. |
| **Colon** | galectin-4 | Choi et al., 2007, J Ethnopharmacol 110(1): 49-55. |
| **Colon** | RACK1 | Choi et al., 2007, J Ethnopharmacol 110(1): 49-55 |
| **Colon** | tetraspanin-8 | Choi et al., 2007, J Ethnopharmacol 110(1): 49-55 |
| **Colon** | FasL | Choi et al., 2007, J Ethnopharmacol 110(1): 49-55 |
| **Colon** | A33 | Choi et al., 2007, J Ethnopharmacol 110(1): 49-55 |
| **Colon** | CEA | Choi et al., 2007, J Ethnopharmacol 110(1): 49-55 |
| **Colon** | EGFR | Choi et al., 2007, J Ethnopharmacol 110(1): 49-55 |
| **Colon** | dipeptidase 1 | Choi et al., 2007, J Ethnopharmacol 110(1): 49-55 |
| **Colon** | PTEN | Frattini et al., 2007 |
| **Colon** | Na(+)-dependent glucose transporter | Wang Y et al., Pediatr Res. 1994 Oct;36(4):514-21. |
| **Colon** | UDP-glucuronosyltransferase 1A | Gong QH et al., Pharmacogenetics 11:357-368(2001). |
| **Benign Prostatic Hyperplasia** | KIA1 | Ueda T, et al., 1996 |
| **Benign Prostatic Hyperplasia** | Intact Fibronectin | Janković MM, Kosanović MM, Dis Markers. 2008;25(1):49-58. |
| **Prostate** | PSA | Nurmikko P et al., 2000 |
| **Prostate** | TMPRSS2 | Wilson S et al., Biochem J. 2005 Jun 15;388(Pt 3):967-72. |
| **Prostate** | FASLG | Huber et al., 2005, Gastroenterol Nurs 28(6): 510-1. |
| **Prostate** | TNFSF10 | Huber et al., 2005, Gastroenterol Nurs 28(6): 510-1 |
| **Prostate** | PSMA | Pinto JT et al., Clin Cancer Res. 1996 Sep;2(9):1445-51. |
| **Prostate** | NGEP | Das S et al., Cancer Res. 2007 Feb 15;67 (4):1594-1601 |
| **Prostate** | IL-7R1 | Haudenschild DR et al., Prostate. 2006 Sep 1;66(12):1268-74. |

FIG. 1c

| Cancer Lineage, Group Comparison, Disease State | Antigens | References |
|---|---|---|
| **Prostate** | CSCR4 | Chinni SR et al., Mol Cancer Res. 2008 Mar;6(3):446-57. |
| **Prostate** | CysLT1R | Matsuyama M et al., Oncol Rep. 2007 Jul;18(1):99-104. |
| **Prostate** | TRPM8 | Bidaux G et al., J Clin Invest. 2007 Jun;117(6):1647-57. |
| **Prostate** | Kv1.3 | Prevarskaya N et al., Cell Death Differ. 2007 Jul;14(7):1295-304. |
| **Prostate** | TRPV6 | Prevarskaya N et al., Cell Death Differ. 2007 Jul;14(7):1295-304. |
| **Prostate** | TRPM8 | Prevarskaya N et al., Cell Death Differ. 2007 Jul;14(7):1295-304. |
| **Prostate** | PSGR | Xu LL et al., Cancer Res. 2000 Dec 1;60(23):6568-72. |
| **Prostate** | MISIIR | Bakkum-Gamez J.N. et al., Gynecol Oncol Vol. 108 Issue 1 Pg. 141-8 |
| **Melanoma** | TYRP1 | Mears et al., 2004 |
| **Melanoma** | SILV | Mears et al., 2004 |
| **Melanoma** | MLANA | Mears et al., 2004 |
| **Melanoma** | MCAM | Mears et al., 2004 |
| **Melanoma** | CD63 | Azorsa et al. 1991 |
| **Melanoma** | CD63 | Barrio et al. 1998 |
| **Melanoma** | CD63 | Demetrick et al., 1992 |
| **Melanoma** | CD63 | Mete et al., 2005 |
| **Melanoma** | CD63 | Kwon et al., 2007 |
| **Melanoma** | Alix | Mears et al., 2004, Proteomics 4(12): 4019-31. |
| **Melanoma** | hsp70 | Mears et al., 2004, Proteomics 4(12): 4019-31 |
| **Melanoma** | moesin | Mears et al., 2004, Proteomics 4(12): 4019-31. |
| **Melanoma** | p120 catenin | Mears et al., 2004, Proteomics 4(12): 4019-31 |
| **Melanoma** | PGRL | Mears et al., 2004, Proteomics 4(12): 4019-31 |
| **Melanoma** | syntaxin-binding protein 1 & 2 | Mears et al., 2004, Proteomics 4(12): 4019-31 |
| **Melanoma** | DUSP1 | |
| **Brain** | PRMT8 | Lee et al., 2005 |
| **Brain** | BDNF | Binder and Scharfman, 2004 |
| **Brain** | EGFR | Hicke et al., J. Biol. Chem. 276, 48644-48654, 2001; Daniels et al., PNAS 100, 15416-15421, 2003 |
| **Brain** | DPPX | Kim et al., J. Biochem, 2001, Vol. 129, No. 2 289-295 |
| **Brain** | Elk | Lhotak V et al., MOLECULAR AND CELLULAR BIOLOGY, May 1991, p. 2496-2502 |
| **Brain** | Densin-180 | Apperson ML et al., Journal of Neuroscience Volume 16, Number 21, Issue of November 1, 1996 pp. 6839-6852 |
| **Brain** | BAI2 | Shiratsuchi T et al., Cytogenet Cell Genet. 1997;79(1-2):103-8. |
| **Brain** | BAI3 | Shiratsuchi T et al., Cytogenet Cell Genet. 1997;79(1-2):103-8. |
| **Psoriasis** | flt-1 | Detmar M, et al., 1994 |
| **Psoriasis** | VPF receptors | Detmar M, et al., 1994 |
| **Psoriasis** | kdr | Detmar M, et al., 1994 |
| **CVD** | FATP6 | Gimeno RE et al., J Biol Chem. 2003 May 2;278(18):16039-44. |
| **Hematological malignancies** | CD44 | Liu J and Jiang G, II Mol Immunol. 2006 Oct;3(5):359-65. |

FIG. 1d

| Cancer Lineage, Group Comparison, Disease State | Antigens | References |
|---|---|---|
| **Hematological malignancies** | CD58 | Kroger N, et al., 1997 |
| **Hematological malignancies** | CD31 | Kroger N, et al., 1998 |
| **Hematological malignancies** | CD11a | Kroger N, et al., 1999 |
| **Hematological malignancies** | CD49d | Kroger N, et al., 2000 |
| **Hematological malignancies** | GARP | Wang R et al., PLoS ONE. 2008 Jul 16;3(7):e2705. |
| **Hematological malignancies** | BTS | Suenaga T et al., Eur J Immunol. 2007 Nov;37(11):3197-207. |
| **Hematological malignancies** | Raftlin | Saeki K et al., The EMBO Journal (2003) 22, 3015-3026 |
| **Hepatocellular Carcinoma** | HBxAg | Wang W, et al., 1991 |
| **Hepatocellular Carcinoma** | HBsAg | Wang W, et al., 1991 |
| **Hepatocellular Carcinoma** | NLT | Simonson GD et al., Journal of Cell Science 107, 1065-1072 (1994) |
| **Cervical Cancer** | MCT-1 | Pinheiro C, et al., 2008 |
| **Cervical Cancer** | MCT-2 | Pinheiro C, et al., 2008 |
| **Cervical Cancer** | MCT-4 | Pinheiro C, et al., 2008 |
| **Head and Neck Cancer** | EGFR | Sheikh Ali MA et al., Cancer Sci. 2008 Aug;99(8):1589-94 |
| **Head and Neck Cancer** | EphB4 | Yavrouian EJ et al., Arch Otolaryngol Head Neck Surg. 2008 Sep;134(9):985-91. |
| **Head and Neck Cancer** | EphrinB2 | Yavrouian EJ et al., Arch Otolaryngol Head Neck Surg. 2008 Sep;134(9):985-91. |
| **Endometrial Cancer** | AlphaV Beta6 integrin | Hecht JL et al., Appl Immunohistochem Mol Morphol. 2008 Aug 11. |
| **Autoimmune Disease** | Tim-2 | Chakravarti S, et al., 2005 |
| **Irritable Bowel Disease** | Il-16 | Seegert D, et al., 2001 |
| **Irritable Bowel Disease** | 5-HT | Kerckhoffs AP et al., Neurogastroenterol Motil. 2008 Aug;20(8):900-7. |
| **Irritable Bowel Disease** | Il-1beta | Seegert D, et al., 2001 |
| **Irritable Bowel Disease** | Il-12 | Seegert D, et al., 2001 |
| **Irritable Bowel Disease** | TNF-alpha | Seegert D, et al., 2001 |
| **Irritable Bowel Disease** | interferon gamma | Seegert D, et al., 2001 |

FIG. 1e

| Cancer Lineage, Group Comparison, Disease State | Antigens | References |
|---|---|---|
| **Irritable Bowel Disease** | Il-6 | Seegert D, et al., 2001 |
| **Irritable Bowel Disease** | Rantes | Seegert D, et al., 2001 |
| **Irritable Bowel Disease** | MCP-1 | Seegert D, et al., 2001 |
| **Diabetes** | IL-6 | Pradhan A, et al., 2001 |
| **Diabetes** | CRP | Pradhan A, et al., 2001 |
| **Diabetes** | RBP4 | Lee SJ et al., Anal Chem. 2008 Apr 15;80(8):2867-73. |
| **Barrett's Esophagus** | p53 | Hamelin R, et al., 1994 |
| **Barrett's Esophagus** | MUC1 | Burjonrappa SC et al., Indian J Cancer. 2007 Jan-Mar;44(1):1-5. |
| **Barrett's Esophagus** | MUC6 | Glickman JN et al., Am J Surg Pathol. 2003 Oct;27(10):1357-65 |
| **Fibromyalgia** | neopterin | Bonaccorso S, et al., 1997 |
| **Fibromyalgia** | gp130 | Maes M et al., 1999 |
| **Stroke** | S-100 | Missler U, et al., 1997 |
| **Stroke** | Neuron specific enolase | Missler U, et al., 1997 |
| **Stroke** | PARK7 | Allard L, et al., 2005 |
| **Stroke** | NDKA | Allard L, et al., 2005 |
| **Stroke** | ApoC-I | Allard L, et al., 2005 |
| **Stroke** | ApoC-III | Allard L, et al., 2003 |
| **Stroke** | SAA | Allard L, et al., 2003 |
| **Stroke** | AT-III fragment | Allard L, et al., 2003 |
| **Stroke** | Lp-PLA2 | http://www.doctorslounge.com/neurology/news/stroke_lp-pla2_crp.shtml; Gorelick PB, Am J Cardiol. 2008 Jun 16;101(12A):34F-40F |
| **Stroke** | hs-CRP | http://www.doctorslounge.com/neurology/news/stroke_lp-pla2_crp.shtml |
| **Multiple Sclerosis** | B7 | Ferrante P, et al., 1998 |
| **Multiple Sclerosis** | B7-2 | Ferrante P, et al., 1998 |
| **Multiple Sclerosis** | CD-95(fas) | Ferrante P, et al., 1998 |
| **Multiple Sclerosis** | Apo-1/Fas | Ferrante P, et al., 1998 |
| **Parkinsons Disease** | PARK2 | Shimura H, eat al., 2000 |
| **Parkinsons Disease** | Ceruloplasmin | Shi M et al., Neurobiol Dis. 2008 Sep 26. |
| **Parkinsons Disease** | VDBP | Zhang et al., 2008 Am. J. Clin. Pathol. 129, 526-9., |
| **Parkinsons Disease** | tau | Zhang et al., 2008 Am. J. Clin. Pathol. 129, 526-9; Mollenhauer B et al., Dement Geriatr Cogn Disord; 2006;22(3):200-8; Davidsson P and Sjögren M, Dis Markers. 2005;21(2):81-92. |
| **Parkinsons Disease** | DJ-1 | Waragai et al., 2007 Neurosci. Lett. 425, 18-22 & Waragai et at 2006 Biochem. Biophys. Res. Commun. 345, 967-72 |
| **Rheumatic Disease** | Citrulinated fibrin a-chain | Skriner et al., 2006 |
| **Rheumatic Disease** | CD5 antigen-like fibrinogen fragment D | Skriner et al., 2006 |

FIG. 1f

| Cancer Lineage, Group Comparison, Disease State | Antigens | References |
|---|---|---|
| **Rheumatic Disease** | CD5 antigen-like fibrinogen fragment B | Skriner et al., 2006 |
| **Rheumatic Disease** | TNFalpha | Anderson AK et al., Arthritis Res Ther. 2008;10(2):204. Epub 2008 Mar 14. |
| **Alzheimers Disease** | APP695 | Rebeck G, et al., 2001 |
| **Alzheimers Disease** | APP751 | Rebeck G, et al., 2001 |
| **Alzheimers Disease** | APP770 | Rebeck G, et al., 2001 |
| **Alzheimers Disease** | BACE1 | Hebert SS et al., 2008. Proc Natl Acad Sci U.S.A., 105(17): 6415-20 |
| **Alzheimers Disease** | Cystatin C | Simonsen et al., 2008 Neurobiol. Aging. 29, 961-8 |
| **Alzheimers Disease** | Amyloid Beta | Simonsen et al., 2008 Neurobiol. Aging. 29, 961-8 |
| **Alzheimers Disease** | t-Tau | Simonsen et al., 2008 Neurobiol. Aging. 29, 961-8 |
| **Alzheimers Disease** | Complement factor H | Hye et al., 2006 Brain. 129, 3042-50 |
| **Alzheimers Disease** | alpha-2-macroglobulin | Hye et al., 2006 Brain. 129, 3042-50 |
| **Alzheimers Disease** | APOE4 | Albert MS, Proc Natl Acad Sci U S A. 1996 Nov 26;93(24):13547-51. |
| **Prion Diseases** | PrPSc | Takemura K et al., Exp Biol Med (Maywood) Feb;231(2)204-14, 2006 |
| **Prion Diseases** | 14-3-3 zeta | Kubler E et at , British Medical Bulletin 66:267-279, 2003 |
| **Prion Diseases** | S-100 | Kubler E et al , British Medical Bulletin 66:267-279, 2003 |
| **Prion Diseases** | AQP-4 | Kubler E et al , British Medical Bulletin 66:267-279, 2003 |
| **Chronic Neuropathic Pain** | Chemokine receptor (CCR2/4) | White FA et al., Proc Natl Acad Sci U S A. 2007 Dec 18;104(51):20151-8 |
| **Peripheral Neuropathic Pain** | OX42 (rodent) | Blackbeard J et al., J Neurosci Methods. 2007 Aug 30;164(2):207-17 |
| **Peripheral Neuropathic Pain** | ED9 (rodent) | Blackbeard J et al., J Neurosci Methods. 2007 Aug 30;164(2):207-17 |
| **Schizophrenia** | ATP5B | Altar CA, Neuropsychopharmacology. 2008 Oct 15. |
| **Schizophrenia** | ATP5H | Altar CA, Neuropsychopharmacology. 2008 Oct 15. |
| **Schizophrenia** | ATP6V1B | Altar CA, Neuropsychopharmacology. 2008 Oct 15. |
| **Schizophrenia** | DNM1 | Altar CA, Neuropsychopharmacology. 2008 Oct 15. |
| **GIST** | PDGFRA | Yang J et al., ncer. 2008 Oct 1;113(7):1532-43 |
| **GIST** | c-kit | Yang J et al., ncer. 2008 Oct 1;113(7):1532-43 |
| **GIST** | NHE-3 | Kulaksiz H et al., Cell Tissue Res. 2001 Mar;303(3):337-43. |
| **Renal Cell Carcinoma** | HIF1alpha | Rathmell WK, Chen S, Expert Rev Anticancer Ther. 2008 Jan;8(1):63-73. |
| **Renal Cell Carcinoma** | VEGF | Rathmell WK, Chen S, Expert Rev Anticancer Ther. 2008 Jan;8(1):63-74. |
| **Renal Cell Carcinoma** | PDGFRA | Rathmell WK, Chen S, Expert Rev Anticancer Ther. 2008 Jan;8(1):63-74. |
| **Cirrhosis** | NLT | Simonson GD et al., Journal of Cell Science 107,1065-1072 (1994) |
| **Cirrhosis** | HBsAg | Wang, W. et al., 1991 |
| **Esophageal cancer** | CaSR | Justinich CJ et al., Am J Physiol Gastrointest Liver Physiol. 2008 Jan;294(1):G120-9. |

FIG. 1g

| Cancer Lineage, Group Comparison, Disease State | Antigens | References |
|---|---|---|
| **Influenza** | Hemmaglutanin | Verma RK and Jain Amita, FEMS Immunol Med Microbiol 51 (2007) 453-461 |
| **Influenza** | Neurominidase | Verma RK and Jain Amita, *supra.* |
| **TB** | Antigen 60 | Verma RK and Jain Amita, *supra.* |
| **TB** | HSP antigen | Verma RK and Jain Amita, *supra.* |
| **TB** | Lipoarabinoman nan antigen | Verma RK and Jain Amita, *supra.* |
| **TB** | Antigen of acylated trehalose family | Verma RK and Jain Amita, *supra.* |
| **TB** | DAT antigen | Verma RK and Jain Amita, *supra.* |
| **TB** | Sulfolipid antigen | Verma RK and Jain Amita, *supra.* |
| **TB** | TAT antigen | Verma RK and Jain Amita, *supra.* |
| **TB** | Trehalose 6,6-dimycolate (cord-factor) antigen | Verma RK and Jain Amita, *supra.* |
| **HIV** | Gp41 | Phogat S et al., J Intern Med. 2007 July ; 262(1): 26-43. |
| **HIV** | gp120 | Phogat S et al., J Intern Med. 2007 July ; 262(1): 26-43. |
| **Autism** | VIP | Nelson KB et al Annals of Neurology 2001, 49:597-606.. |
| **Autism** | PACAP | Nelson KB et al Annals of Neurology 2001, 49:597-606. |
| **Autism** | CGRP | Nelson KB et al Annals of Neurology 2001, 49:597-606. |
| **Autism** | NT3 | Nelson KB et al Annals of Neurology 2001, 49:597-606. |
| **Asthma** | YKL-40 | Scot, I., Thorax 2008;63:365, A New Biomarker in Asthma |
| **Asthma** | S-nitrosothiols | Holgate, ST., Lancet. 1998 May 2;351(9112):1317-9. |
| **Asthma** | SCCA2 | Izuhara, K., Allergol Int. 2006 Dec ;55 (4):361-7. |
| **Asthma** | PAI | Izuhara, K., Allergol Int. 2006 Dec ;55 (4):361-7. |
| **Asthma** | amphiregulin | Izuhara, K., Allergol Int. 2006 Dec ;55 (4):361-7. |
| **Asthma** | Periostin | Izuhara, K., Allergol Int. 2006 Dec ;55 (4):361-7. |
| **Lupus** | TNFR | Suh CH and Kim HA, Expert Rev Mol Diagn. 2008 Mar;8(2):189-98 |
| **Vulnerable plaque** | Alpha v Beta 3 integrin | Burtea C et al., Cardiovasc Res. 2008 Apr 1;78(1):148-57. |
| **Vulnerable plaque** | MMP9 | Blankenberg S et al., 2003 Circulation 107:1579-1585. |

FIG. 2a

| Cancer Lineage, Group Comparison, Other Significant Disease State | Binding Agents | Select Reference(s) |
|---|---|---|
| **Breast** | Herceptin (Trastuzumab) | Adams GP, Weiner LM, Nat Biotechnol. 2005 Sep;23(9):1147-57. |
| **Breast** | CCND1 PNA | Tian et al , NAR 24(5-7):1085-91, 2005; Tian et al., Ann NY Acad Sci 1059, 106-44, 2005 |
| **Breast** | MYC PNA | Tian et at , NAR 24(5-7):1085-91, 2005; Tian et al., Ann NY Acad Sci 1059, 106-44, 2005 |
| **Breast** | IGF-1 PNA | Tian et al , J. of Nucl Med 48(10), 1699-707, 20007 |
| **Breast** | MYC PNA | Tian et al., Bioconjug Chem 16)1)70-9, 2005 |
| **Breast** | SC4 aptamer (Ku) | Zhang et al. 2004 |
| **Breast** | All-7 aptamer (ERB2) | Kunz et al., MolecularCancer Research(4) 983998, 2006 |
| **Breast** | Galectin -3 binding agent | Cancer Invest 26(6)615-23, 2008 |
| **Breast** | mucin-type O-glycans binding agent | Cancer Invest 26(6)615-23, 2008 |
| **Breast** | L-PHA binding agent | Abbott et al., J Proteome Res 7(4)1470-80, 2008 |
| **Breast** | Galectin-9 binding agent | Yamaguchi et al., Breast J 5(2), 2006 |
| **Breast** | ER | Payne SJ et al., Histopathology. 2008 Jan;52(1):82-90. |
| **Breast** | PR | Payne SJ et al., Histopathology. 2008 Jan;52(1):82-90. |
| **Ovarian** | (90)Y-muHMFG1 binding agent | Oei et al 2008 |
| **Ovarian** | OC125 (anti-CA125 antibody) | Matsuoka et al 1987 |
| **Ovarian** | monoclonal antibodies (HMFG1, HMFG2, H317, and H17E2), Hu2PLAP | Kosmas et al , Oncology 55 (5),435-446, 1998 |
| **Lung** | SCLC specific aptamer HCA 12 | Chen et at , Chem Med Chem (3)991-1001, 2008 |
| **Lung** | SCLC specific aptamer HCC03 | Chen et al , Chem Med Chem (3)991-1001, 2008 |
| **Lung** | SCLC specific aptamer HCH07 | Chen et al , Chem Med Chem (3)991-1001, 2008 |
| **Lung** | SCLC specific aptamer HCH01 | Chen et at , Chem Med Chem (3)991-1001, 2008 |
| **Lung** | A-p50 aptamer (NF-KB) | Mi et al., Mol Ther 16(1)66-73, 2008 |
| **Lung** | Cetuximab | Rossi A et al., Rev Recent Clin Trials. 2008 Sep;3(3):217-27 |
| **Lung** | Panitumumab | Rossi A et al., Rev Recent Clin Trials. 2008 Sep;3(3):217-27 |
| **Lung** | Bevacizumab | Gettinger S et al., Semin Respir Crit Care Med. 2008 Jun;29(3):291-301 |
| **Lung** | L19 antibody | Pedretti et al., Lung Cancer Sep 15, 2008 |
| **Lung** | F16 antibody | Pedretti et al., Lung Cancer Sep 15, 2008 |
| **Lung** | anti-CD45 (anti-ICAM-1 antibody, aka UV3) | Brooks et al., Int J Cancer 2438(10)2438-45, 2008 |
| **Lung** | L2G7 Ab (anti-HGF antibody) | Stabile et al., Mol Cancer Ther 7(7)1913-22, 2008 |
| **Colon** | angiopoietin 2 specific aptamer | Sarraf-Yazdi et al., J SURG Res 146(1)16-23, 2008. |

FIG. 2b

| Cancer Lineage, Group Comparison, Other Significant Disease State | Binding Agents | Select Reference(s) |
|---|---|---|
| **Colon** | beta-catenin aptamer | Lee et al., Cancer Research 66(21)10560-6, 2006. |
| **Colon** | TCF1 aptamer | Choi et al., Mol Caner Therapy (9)2428-34, 2006. |
| **Colon** | anti-Derlin1 antibody | Ran et al., Clin Cancer Res 14(206538-45, 2008 |
| **Colon** | anti-RAGE antibody | Turovskaya et al., Carcinogenesis 29(10)2035-2043, 2008. |
| **Colon** | monoclonal antibody gb3.1 | Turovskaya et al., Carcinogenesis 29(10)2035-2043, 2008. |
| **Colon** | Galectin-3 binding agent | Greco et al., Glycobiology 14(9)783-92, 2004. |
| **Colon** | Cetuximab | Giuliani F, Colucci G et al., Int J Biol Markers. 2007 Jan-Mar;22(1 Suppl 4):S62-70 |
| **Colon** | Panitumumab | Chua YJ, Cunningham D, Clin Colorectal Cancer. 2005 Nov;5 Suppl 2:S81-8. |
| **Colon** | Matuzumab | Chua YJ, Cunningham D, Clin Colorectal Cancer. 2005 Nov;5 Suppl 2:S81-8. |
| **Colon** | Bevacizumab | Majer M et al., Anticancer Agents Med Chem. 2007 Sep;7(5):492-503 |
| **Colon** | Mac-2 binding agent | Lotz MM et al., Proc Natl Acad Sci U S A. 1993 90(18): 8319-23, "Mitogen-activated protein kinases p42mapk and p44mapk are required for fibroblast proliferation." |
| **Adenoma versus CRC** | Complement C3 | Qui et al , J of Proteome Res 7(4)1693-1703, 2008 |
| **Adenoma versus CRC** | histidine-rich glycoprotein binding agent | Qui et al , J of Proteome Res 7(4)1693-1703, 2008 |
| **Adenoma versus CRC** | kininogen-1 binding agent | Qui et al , J of Proteome Res 7(4)1693-1703, 2008 |
| **Adenoma versus CRC** | Galectin-3 binding agent | Schoeppner HL et al., Cancer. 1995 Jun 15;75(12):2818-26. |
| **Adenoma with low grade versus high grade dysplasia** | Galectin-3 binding agent | Schoeppner HL et al., Cancer. 1995 Jun 15;75(12):2818-26. |
| **CRC versus normal** | anti-ODC monoclonal antibody | Hu HY et al., World J Gastroenterol. 2005 Apr 21;11(15):2244-8. |
| **CRC versus normal** | anti-CEA monoclonal antibody | Zhang HZ et al., Cancer Res. 1989 Oct 15;49(20):5766-73. |
| **CRC versus normal** | Mac-2 binding agent | Lotz MM et al., Proc Natl Acad Sci U S A. 1993 Apr 15;90(8):3466-70. |
| **Prostate** | PSA binding agent | Nurmikko P et al., 2000, Clin Chem 46(10): 1610-8. |
| **Prostate** | PSMA binding agent | Aggarwal S et al., Cancer Res. 2006 Sep 15;66(18):9171-7. |
| **Prostate** | TMPRSS2 binding agent | Wilson S et al., Biochem J. 2005 Jun 15;388(Pt 3):967-72. |
| **Prostate** | monoclonal antibody 5D4 | Sawant et al., J Drug Target 16(7)601-4, 2008. |
| **Prostate** | XPSM-A9 | Lupold et al., Cancer Research 62(14): 4029-4033, 2002. |
| **Prostate** | XPSM-A10 | Lupold et al., Cancer Research 62(14): 4029-4033, 2002. |
| **Prostate** | Galectin-3 binding agent | Califice et al., Int J Oncol 25(4)983-92, 2004 |
| **Prostate** | E-selectin binding agent | Bhaskar et al., Cancer Research 63(19(6387-94, 2003. |

FIG. 2c

| Cancer Lineage, Group Comparison, Other Significant Disease State | Binding Agents | Select Reference(s) |
|---|---|---|
| **Prostate** | Galectin-1 binding agent | van den Brule et al., J Pathology 193(1)80-7, 2001 |
| **Prostate** | E4 (IgG2a kappa) | Nilsson S et al., Cancer Biother Radiopharm. 1997 Dec;12(6):395-403. |
| **Melanoma** | Tremelimumab (anti-CTLA4 antibody) | Camacho LH, Expert Opin Investig Drugs 17(3)371-85, 2008. |
| **Melanoma** | 1pilimumumab (anti-CTLA4 antibody) | Lens M et al., Recent Patents Anticancer Drug Discovery Jun3(2)105-13, 2008. |
| **Melanoma** | CTLA-4 aptamers | Santulli-Marotto et al., Cancer Research 63(21)7483-9, 2003. |
| **Melanoma** | STAT-3 peptide aptamers | Nagel Wolfrum et al., Molecular Cancer Research 2:170-182, 2004 |
| **Melanoma** | Galectin-1 binding agent | Mathieu et al., J Invest Dermatol 127(10)2399-410, 2007, Le Mercier et al., J Neuropathol Exp Neurol. 67(5)456-69, 2008. |
| **Melanoma** | Galectin-3 binding agent | Prieto et al., Clin Cancer Res 12(22)6709-15, 2006; Vereecken et al., Arch Dermatol Res 296(8)353-8, 2005 |
| **Melanoma** | PNA | Dore et al., Pigment Cell Res 7(6)461-4, 1994. |
| **Pancreatic** | H38-15 (HGF aptamer) | Saito T and Tomida M, DNA Cell Biol. 2005 Oct;24(10):624-33. |
| **Pancreatic** | H38-21(HGF aptamer) | Saito T and Tomida M, DNA Cell Biol. 2005 Oct;24(10):624-33. |
| **Pancreatic** | Matuzumab | Kleepspeies A et al., Clin Cancer Res. 2008 Sep 1;14(17):5426-36 |
| **Pancreatic** | Cetuximanb | Burris H 3rd et al., Oncologist. 2008 Mar;13(3):289-98. |
| **Pancreatic** | Bevacizumab | Burris H 3rd et al., Oncologist. 2008 Mar;13(3):289-98. |
| **Brain** | aptamer 111.1 (pigpen) | Blank Met al., JBC May 11; 276(19)16464-8, 2001 |
| **Brain** | TTA1 (Tenascin-C ) aptamer | Hicke et al., J. Biol. Chem. 276, 48644-48654, 2001; Daniels et al., PNAS 100, 15416-15421, 2003 |
| **Psoriasis** | E-selectin binding agent | Rottman JB et al., Lab Invest. 2001 Mar;81(3):335-47. |
| **Psoriasis** | ICAM-1 binding agent | Rottman JB et al., Lab Invest. 2001 Mar;81(3):335-47. |
| **Psoriasis** | VLA-4 binding agent | Rottman JB et al., Lab Invest. 2001 Mar;81(3):335-47. |
| **Psoriasis** | VCAM-1 binding agent | Rottman JB et al., Lab Invest. 2001 Mar;81(3):335-47. |
| **Psoriasis** | alphaEbeta7 binding agent | Rottman JB et al., Lab Invest. 2001 Mar;81(3):335-47. |
| **Cardiovascular Disease** | RB007 (factor IXA aptamer) | Chan MY et al., Circulation. 2008 Jun 3;117(22):2865-74. Epub 2008 May 27 |
| **Cardiovascular Disease** | ARC1779 (anti VWF) aptamer | Gilbert JC et al., Circulation. 2007 Dec 4;116(23):2678-86. Epub 2007 Nov 19 |
| **Cardiovascular Disease** | LOX1 binding agent | Dunn S et al., Biochem J. 2008 Jan 15;409(2):349-55. |
| **Hematological malignancies** | anti-CD20 | Ravandi F et al., Clin Cancer Res. 2003 Feb;9(2):535. |
| **Hematological malignancies** | anti-CD52 | Ravandi F et al., Clin Cancer Res. 2003 Feb;9(2):535. |
| **B-Cell Chronic Lymphocytic Leukemias** | Rituximab | Robak T, Leuk Lymphoma. 2004 Feb;45(2):205-19. |

FIG. 2d

| Cancer Lineage, Group Comparison, Other Significant Disease State | Binding Agents | Select Reference(s) |
|---|---|---|
| B-Cell Chronic Lymphocytic Leukemias | Alemtuzumab | Robak T, Leuk Lymphoma. 2004 Feb;45(2):205-19. |
| B-Cell Chronic Lymphocytic Leukemias | Apt48 (BCL6) | Chattopadhyay et al 2006, J Assoc Physicians India 54: 547. |
| B-Cell Chronic Lymphocytic Leukemias | R0-60 aptamer | Wu CC et al., Hum Gene Ther. 2003 Jun 10;14(9):849-60. |
| B-Cell Chronic Lymphocytic Leukemias | D-R15-8 aptamer | Wu CC et al., Hum Gene Ther. 2003 Jun 10;14(9):849-60. |
| B-cell lymphoma | Ibritumomab | Cheson BD, Leonard JP, N Engl J Med. 2008 Aug 7;359(6):613-26. |
| B-cell lymphoma | Tositumomab | Cheson BD, Leonard JP, *supra.* |
| B-cell lymphoma | Anti-CD20 Antibodies | Cheson BD, Leonard JP, *supra.* |
| B-cell lymphoma | Alemtuzumab | Cheson BD, Leonard JP, *supra.* |
| B-cell lymphoma | Galiximab | Cheson BD, Leonard JP, *supra.* |
| B-cell lymphoma | Anti-CD40 Antibodies | Cheson BD, Leonard JP, *supra.* |
| B-cell lymphoma | Epratuzumab | Cheson BD, Leonard JP, *supra.*. |
| B-cell lymphoma | Lumiliximab | Cheson BD, Leonard JP, *supra.* |
| B-cell lymphoma | Monoclonal antibody Hu1D10 | Cheson BD, Leonard JP, *supra.* |
| B-cell lymphoma-DLBCL | Galectin-3 binding agent | D'Haene N et al., Int J Immunopathol Pharmacol. 2005 Jul-Sep;18(3):431-43. |
| B-cell lymphoma | Apt48 | Chattopadhyay A et al., Oncogene. 2006 Apr 6;25(15):2223-33. |
| Burkitt's lymphoma | TD05 aptamer | Mallikaratchy P et al., Mol Cell Proteomics Dec; 6(12)2230-8, 2007. |
| Burkitt's lymphoma | IgM monoclonal antibody (38-13) | Wiels J et al., Cancer Res. 1984 Jan;44(1):129- 33. |
| Cervical Cancer | Galectin-9 binding agent | Liang et al., Clin Oncol 134(8)899-907, 2008. |
| Cervical Cancer | HPVE7 aptamer | Nauenburg S et al., FASEB J. 2001 Mar;15(3):592-4. Epub 2001 Jan 19. |
| Endometrial Cancer | Galectin-1 binding agent | Mylonas I et al., Anticancer Res. 2007 JulAug;27(4A):1975-80. |
| Head and Neck Cancer | (111)In-cMAb U36 | Sandstrom K et al., Tumour Biol. 2008;29(3):137-44. |
| Head and Neck Cancer | anti-LOXL4 antibody | Weise JB et al., Eur J Cancer. 2008 Jun;44(9):1323-31. |
| Head and Neck Cancer | U36 monoclonal antibody | Verel I et al., Int J Cancer. 2002 May 20;99(3):396-402. |
| Head and Neck Cancer | BIWA-1 monoclonal antibody | Verel I et al., Int J Cancer. 2002 May 20;99(3):396-402. |

FIG. 2e

| Cancer Lineage, Group Comparison, Other Significant Disease State | Binding Agents | Select Reference(s) |
|---|---|---|
| **Head and Neck Cancer** | BIWA-2 monoclonal antibody | Verel I et al., Int J Cancer. 2002 May 20;99(3):396-402. |
| **Head and Neck Cancer** | BIWA-4 monoclonal antibody | Verel I et al., Int J Cancer. 2002 May 20;99(3):396-402. |
| **Head and Neck Cancer** | BIWA-8 monoclonal antibody | Verel I et al., Int J Cancer. 2002 May 20;99(3):396-402. |
| **Irritable Bowel Disease** | ACCA (anti-glycan antibody) | Li X et al., World J Gastroenterol. 2008 Sep 7;14(33):5115-24. |
| **Irritable Bowel Disease** | ALCA(anti-glycan antibody) | Li X et al., World J Gastroenterol. 2008 Sep 7;14(33):5115-24. |
| **Irritable Bowel Disease** | AMCA (anti-glycan antibody) | Li X et al., World J Gastroenterol. 2008 Sep 7;14(33):5115-24. |
| **Diabetes** | RBP4 aptamer | Lee SJ et al., Anal Chem. 2008 Apr 15;80(8):2867-73. |
| **Fibromyalgia** | L-selectin binding agent | Macedo JA et al., J Neuroimmunol. 2007 Aug;188(1-2):159-66,. |
| **Multiple Sclerosis** | Natalizumab (Tysabri) | Goodin DS et al., Neurology. 2008 Sep 2;71(10):766-73. |
| **Rheumatic Disease** | Rituximab (anti-CD20 antibody) | Anderson AK et al., Arthritis Res Ther. 2008;10(2):204. Epub 2008 Mar 14. |
| **Rheumatic Disease** | Keliximab (anti-CD4 antibody) | Anderson AK et al., Arthritis Res Ther. 2008;10(2):204. Epub 2008 Mar 14. |
| **Alzheimers Disease** | TH14-BACE1 aptamers | Rentmeister A et al., RNA. 2006 Sep;12(9):1650-60. Epub 2006 Aug 3 |
| **Alzheimers Disease** | S10-BACE1 aptamers | Rentmeister A et al., RNA. 2006 Sep;12(9):1650-60. Epub 2006 Aug 3 |
| **Alzheimers Disease** | anti-Abeta monoclonal antibody | Geylis V et al., Autoimmun Rev. 2006 Jan;5(1):33-9. Epub 2005 Aug 1. Review. |
| **Alzheimers Disease** | Bapineuzumab (AAB-001) - Elan | Hock C et al., Neuron. 2003 May 22;38(4):54754 |
| **Alzheimers Disease** | LY2062430 (anti-amyloid beta Ab)-Eli Lilly | Irena Melnikova, Nature Reviews Drug Discovery 6, 341-342 (May 2007) |
| **Alzheimers Disease** | BACE1-Anti sense | Faghihi MA et al., Nat Med. 2008 Jul;14(7):723- 30. Epub 2008 Jun 29 |
| **Prion Diseases** | rhuPrP© aptamer | Takemura K et al., Exp Biol Med (Maywood) Feb;231(2)204-14, 2006 |
| **Prion Diseases** | DP7 aptamer | Proske D et al., Chembiochem. 2002 Aug 2;3(8):717-25. |
| **Prion Diseases** | Thioaptamer 97 | King DJ et al., J Mol Biol. 2007 Jun 15;369(4):1001-14. Epub 2007 Feb 9 |
| **Prion Diseases** | SAF-93 aptamer | Rhie A et al., J Biol Chem. 2003 Oct 10;278(41):39697-705. Epub 2003 Aug 5 |
| **Prion Diseases** | 15B3 (anti-PrPSc antibody) | Korth C et al., Nature 390:74-77, 1997 |
| **Prion Diseases** | monoclonal anti PrPSc antibody P1:1 | Jones M et al., Brain Pathol. 2008 May 26. |
| **Prion Diseases** | 1.5D7, 1.6F4 antibodies | Cordes H, J Immunol Methods Sep 15;337(2)106-20, 2008 |

FIG. 2f

| Cancer Lineage, Group Comparison, Other Significant Disease State | Binding Agents | Select Reference(s) |
|---|---|---|
| **Prion Diseases** | monoclonal antibody 14D3 | Krasemann S et al., Mol Med. 1996 Nov;2(6):725-34 |
| **Prion Diseases** | monoclonal antibody 4F2 | Krasemann S et al., Mol Med. 1996 Nov;2(6):725-34 |
| **Prion Diseases** | monoclonal antibody 8G8 | Krasemann S et al., Mol Med. 1996 Nov;2(6):725-34 |
| **Prion Diseases** | monoclonal antibody 12F10 | Krasemann S et al., Mol Med. 1996 Nov;2(6):725-34 |
| **Sepsis** | HA-1A monoclonal antibody | Cross AS and Opal S Journal of Endotoxin Research, Vol. 1, No. 1, 57-69 (1994) |
| **Sepsis** | E-5 monoclonal antibody | Cross AS and Opal S Journal of Endotoxin Research, Vol. 1, No. 1, 57-69 (1994) |
| **Sepsis** | TNF-alpha monoclonal antibody | Abraham E et al., JAMA Vol. 273 No. 12, March 22, 1995 |
| **Sepsis** | Afelimomab | Vincent JL Int J Clin Pract. 2000 Apr;54(3):190- 3 |
| **Sepsis** | E-selectin binding agent | Tsokos M et al., Int Journal of Legal Medicine, Volume 113, Number 6:338-342, 2000 |
| **Schizophrenia** | L-selectin binding agent | Iwata Y et al., Schizophr Res. 2007 Jan;89(1- 3):154-60. Epub 2006 Oct 17 |
| **Schizophrenia** | N-CAM binding agent | Vawter MP et al., Exp Neurol. 1998 Feb;149(2):424-32 |
| **Depression** | GPIb binding agent | Walsh MT et al., Life Sci. 2002 May 17;70(26):3155-65 |
| **GIST** | anti-DOG1 antibody | Espinosa F et al., Am J Surg Pathol Feb;32(2)210-8, 2008 |
| **Esophageal cancer** | CaSR binding agent | Justinich CJ et al., Am J Physiol Gastrointest Liver Physiol. 2008 Jan;294(1):G120-9. |
| **Gastric cancer** | Calpain nCL-2 binding agent | Hata et al., J. Biol. Chem., Vol. 281, Issue 16, 11214-11224, April 21, 2006 |
| **Gastric cancer** | drebrin binding agent | Keon BH et al., Journal of Cell Science, Vol 113, Issue 2 325-336 |
| **Osteoarthritis** | DDR-2 binding agent | Xu et al., Arthritis Rheum. 2007 Aug;56(8):2663-73. |
| **COPD** | CXCR3 binding agent | Freeman CM et al., Am J Pathol. 2007 Sep;171(3):767-76. |
| **COPD** | CCR5 binding agent | Freeman CM et al., Am J Pathol. 2007 Sep;171(3):767-76. |
| **COPD** | CXCR6 binding agent | Freeman CM et al., Am J Pathol. 2007 Sep;171(3):767-76. |
| **Asthma** | VIP binding agent | Nelson KB et alAnnals of Neurology 2001, 49:597-606. |
| **Asthma** | PACAP binding agent | Nelson KB et alAnnals of Neurology 2001, 49:597-606.. |
| **Asthma** | CGRP binding agent | Nelson KB et alAnnals of Neurology 2001, 49:597-606.. |
| **Asthma** | NT3 binding agent | Nelson KB et alAnnals of Neurology 2001, 49:597-606.. |
| **Asthma** | YKL-40 binding agent | Scot, I., Thorax 2008;63:365, A New Biomarker in Asthma |
| **Asthma** | S-nitrosothiols | Holgate, ST., Lancet. 1998 May 2;351(9112):1317-9. |
| **Asthma** | SCCA2 binding agent | Izuhara, K., Allergol Int. 2006 Dec ;55 (4):3617. |
| **Asthma** | PAI binding agent | Izuhara, K., Allergol Int. 2006 Dec ;55 (4):3617. |
| **Asthma** | amphiregulin binding agent | Izuhara, K., Allergol Int. 2006 Dec ;55 (4):3617. |
| **Asthma** | Periostin binding agent | Izuhara, K., Allergol Int. 2006 Dec ;55 (4):3617. |
| **Vulnerable plaque** | Gd-DTPA-g-mimRGD (Alpha v Beta 3 integrin binding peptide) | Burtea C et al., Cardiovasc Res. 2008 Apr 1;78(1):148-57. |
| **Vulnerable plaque** | MMP-9 binding agent | Blankenberg S et al., 2003 Circulation 107:1579-1585. |

FIG. 3a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Breast** | miR-21 | let-7 | | | | | Iorio et al., Cancer Research 65, 7065-7070, August 15, 2005. |
| **Breast** | miR-155 | miR-10b | | | | | Iorio et al., *supra.* |
| **Breast** | miR-206 | miR-125a | | | | | Iorio et al., *supra.* |
| **Breast** | miR-122a | miR-125b | | | | | Iorio et al., *supra.* |
| **Breast** | miR-210 | miR-145 | | | | | Iorio et al., *supra.* |
| **Breast** | | miR-143 | | | | | Michael et al.Mol Cancer Res 1: 882-891, 2003. |
| **Breast** | | miR-145 | | | | | Michael et al.*supra* |
| **Breast** | | miR-16 | | | | | Michael et al.*supra* |
| **Breast** | | let-7 | | | | | Michael et al.*supra.* |
| **Breast** | miR-21 | let-7 | | | | | Lu et al. Nature 435: 834-838, 2005. |
| **Breast** | miR-21 | let-7 | | | | | Volinia et al. Proc Natl Acad Sci USA 103: 2257-2261, 2006. |
| **Breast** | miR-155 | miR-10b | | | | | Volinia et al. *supra.* |
| **Breast** | miR-206 | miR-125a | | | | | Volinia et al. *supra.* |
| **Breast** | miR-122a | miR-125b | | | | | Volinia et al. *supra.* |
| **Breast** | miR-210 | miR-145 | | | | | Volinia et al. *supra.* |
| **Breast** | miR-21 | | | | | | Si et al. Oncogene 26: 2799-2803, 2006. |
| **Breast** | | | | | hsp70 | | Wolfers et al. 2001 Nat Med 793): 297-302. |
| **Breast** | | | | | MART-1 | | Wolfers et al. 2001 Nat Med 793): 297-302. |
| **Breast** | | | | | TRP | | Wolfers et al. 2001 Nat Med 793): 297-302. |
| **Breast** | | | | | HER2 | | Wolfers et al. 2001 Nat Med 793): 297-302. |
| **Breast** | | | | | hsp70 | | Koga et al., 2005, Antican, Res 25(6A):3703-5 |
| **Breast** | | | | | MART-1 | | Koga et al., *supra.* |
| **Breast** | | | | | TRP | | Koga et al., *supra.* |
| **Breast** | | | | | HER2 | | Koga et al., *supra.* |
| **Breast** | . | | | | GASS | | Mourtada-Maarabouni et at 2008 |
| **Breast** | | | ER | | ER | | Oldenhuls CN et al., Eur J Cancer. 2008 May;44(7):946- 53. Epub 2008 Apr 7; Payne SJ et al., Histopathology. 2008 Jan;52(1):82-90 |
| **Breast** | | | PR | | PR | | Oldenhuis et al., *supra.*; Payne et al., *supra.* |
| **Breast** | | | HER2 | | | | Oldenhuis et al., *supra.*; Payne et al., *supra* |

FIG. 3b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Breast** | | | MUC1 | | | | Singh R, Bandyopadhyay D, Cancer Biol Ther. 2007 Apr;6(4):481-6 |
| **Breast** | | | | | Class III b-tubulin | | Galmarini CM et al., Clin Cancer Res. 2008 Jul 15;14(14):4511-6 |
| **Breast** | | | EGFR | | | | Rajkumar T, Gullick WJ, Breast Cancer Res Treat. 1994 Jan;29(1):3-9 |
| **Breast** | | | | KRAS | | | Hollestelle A et al., Mol Cancer Res. 2007 Feb;5(2):195-201 |
| **Breast** | | | | | VEGFA | | Linderholm BK et al., Cancer Res. 2001 Mar 1:61(5):2256-60 |
| **Breast** | | | | B-Raf | | | Hollestelle A et al., Mol Cancer Res. 2007 Feb;5(2):195-201 |
| **Breast** | | | | CYP2D6 | | | Punglia RS et al., J Natl Cancer Inst. 2008 May 7;100(9):642-8 |

FIG. 4a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| Ovarian | | | ERCC1 | | | | Rosell R "et al., Drugs Today (Barc). 2003 Oct;39(10):775-86 |
| Ovarian | | | ER | | | | Geisler JP et al., Eur J Gynaecol Oncol. 2008;29(2):126-8; Fujimoto J et al., J Steroid Biochem Mol Biol. 2007 May;104(3-5):301-4 |
| Ovarian | | | TOP01 | | | | Naniwa, J et al., . Int J Gynecol Cancer, 2007. 17(1): p. 76-82 |
| Ovarian | | | TOP2A | | | | Chekerov R et al., Neoplasia. 2006 Jan;8(1):38-45. |
| Ovarian | | | AR | | | | Ito K et al., Int J Cancer. 2002 Jun 10;99(5):652-7; Akahira JI et al., Jpn J Cancer Res. 2001 Sep;92(9):926-32 |
| Ovarian | | | PTEN | | | | Chen Y et al., Chin Med Sci J. 2004 Mar;19(1):25-30 |
| Ovarian | | | HER2/ neu | | | | Mileo AM et al., Int J Biol Markers. 1992 Jan-Mar;7(1):47-51 |
| Ovarian | | | EGFR | | | | Vermeij J et al., BMC Cancer. 2008 Jan 8;8:3; Lassus H et al., J Mol Med. 2006 Aug;84(8):671-81 |
| Ovarian | | | | KRAS | | | Mayr D et al., Gynecol Oncol. 2006 Dec;103(3):883-7 |
| Ovarian | | | | | VEGFA | | Osada R et al., Hum Pathol. 2006 Nov;37(11):1414-25. |
| Ovarian | | | | | VEGFR2 | | Chen BY et al., Zhonghua Zhong Liu Za Zhi. 2005 Jan;27(1):33-7 |
| Ovarian | | | | B-Raf | | | Sieben NL et al., J Pathol. 2004 Mar;202(3):336-40 |
| Ovarian | miR-200a | miR-199a | | | | | Iorio el al. Cancer Res. 2007; 67: (18). September 15, 2007 |
| Ovarian | miR-141 | miR-140 | | | | | Iorio el al. *Supra.* |
| Ovarian | miR-200c | miR-145 | | | | | Iorio el al. *Supra.* |
| Ovarian | miR-200b | miR-125b-1 | | | | | Iorio el al. *Supra.* |
| Ovarian | | | | | HER2 | | Steffensen KD et al., Int J Oncol. 2008 Jul;33(1):195-204 |

FIG. 4b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Ovarian** | miR-21 | | | | | | Taylor et al., Gynecologic Oncology 110 (2008) 13-21. |
| **Ovarian** | miR-141 | | | | | | Taylor et al., *supra.* |
| **Ovarian** | miR-200a | | | | | | Taylor et al., *supra.* |
| **Ovarian** | miR-200b | | | | | | Taylor et al., *supra.* |
| **Ovarian** | mIR-200c | | | | | | Taylor et al., *supra.* |
| **Ovarian** | miR-203 | | | | | | Taylor et al., *supra.*. |
| **Ovarian** | miR-205 | | | | | | Taylor et al., *supra.*. |
| **Ovarian** | miR-214 | | | | | | Taylor et al., *supra.* |
| **Ovarian** | miR-215 | | | | | | Taylor et al., *supra.*. |

FIG. 5

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| Lung | miR-21 | | | | | | Markou A et al., Clin Chem. 2008 Oct;54(10):1696-704 |
| Lung | miR-205 | | | | | | Markou A et al., *supra.* |
| Lung | miR-221 | | | | | | Garofalo M et al., Oncogene. 2008 Jun 19;27(27):3845-55 |
| Lung | miR-221 (protective) | | | | | | Yu SL et al., Cancer Cell. 2008 Jan;13(1):48-57 |
| Lung | Let-7a(protective) | | | | | | Yu SL et al., *supra.* |
| Lung | miR-137 (risky) | | | | | | Yu SL et al., *supra.* |
| Lung | miR-372(risky) | | | | | | Yu SL et al., *supra.* |
| Lung | miR-122a(risky) | | | | | | Yu SL et al., *supra.* |
| Lung | | | EGFR | | | | Rosell R et al., Clin Cancer Res. 2006 12(24):7222-31 |
| Lung | | | | | KRAS | | Zhang Z et al., Cancer Biol Ther. 2006 Nov;5(11):1481-6 |
| Lung | | | PTEN | | | | Sos ML et al., J Thorac Oncol. 2008 Feb;3(2):170-3 |
| Lung | | | RRM1 | | | | Souglakos et al., 2008; Rosell et al., 2004 |
| Lung | | | RRM2 | | | | Souglakos et al., 2008 |
| Lung | | | | | hENT1 | | Oguri T et al., Cancer Lett. 2007 Oct 18;256(1):112-9. |
| Lung | | | ABCB1 | | | | Sekine I et al., J Thorac Oncol. 2006 Jan;1(1):31-7; Ushijima R et al., Anticancer Res. 2007 Nov-Dec;27(6C):4351-8 |
| Lung | | | ABCG2 | | | | Nakano H et al., Cancer. 2008 Mar 1;112(5):1122-30 |
| Lung | | | LRP | | | | Paredes Lario A et al., Arch Bronconeumol. 2007 Sep;43(9):479-84 |
| Lung | | | class III b- tubulin | | | | Sève P et al., Clin Cancer Res. 2005 Aug 1;11(15):5481-6; Sève P, Clin Cancer Res. 2007 Feb 1;13(3):994-9 |
| Lung | | | | EGFR | | | Rosell R et al., Clin Cancer Res. 2006 Dec 15;12(24):7222-31 |
| Lung | | | | KRAS | | | Massarelli E et al., Clin Cancer Res, 2007. 13(10): p. 2890-6 |
| Lung | | | | B-Raf | | | Yousem SA et al., Am J Surg Pathol. 2008 Sep;32(9):1317-21. |
| Lung | | | | UGT1A1 | | | Han JY et al., J Clin Oncol. 2006 May 20;24(15):2237-44 |
| Lung | | | VEGFR 2/3 | | | | PCT Publication No. WO/2009/105223 |

FIG. 6a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Colon** | | miR-143 | | | | | Michael et al., 2003, Mol Cancer Res 1(12): 882-91 |
| **Colon** | | miR-145 | | | | | Michael et al., 2003, *supra.* |
| **Colon** | | miR-143 | | | | | Akao et al., 2006, Oncol Rep 16(4): 845-50 |
| **Colon** | | miR-126 | | | | | Guo et al., 2008, Plant Physiol 165(16): 1745-55 |
| **Colon** | | miR-34b | | | | | Toyota et al., 2008, Cancer Res 68(11): 4123-31 |
| **Colon** | | miR-34c | | | | | Toyota et al., 2008, *supra.* |
| **Colon** | | let-7 | | | | | Akao et al., 2006, Oncol Rep, 16(4): 845-50 |
| **Colon** | miR-24-1 | | | | | | Volinia et al. Proc Natl Acad Sci USA 103: 2257-2261, 2006. |
| **Colon** | miR-29b-2 | | | | | | Volinia et al. *supra.* |
| **Colon** | miR-20a | | | | | | Volinia et al. *supra.* |
| **Colon** | miR-10a | | . | | | | Volinia et al. *supra.*" |
| **Colon** | miR-32 | | | | | | Volinia et al. *supra.* |
| **Colon** | miR-203 | | | | | | Volinia et al. *supra.* |
| **Colon** | miR-106a | | | | | | Volinia et al. *supra.* |
| **Colon** | miR-17-5p | | | | | | Volinia et al. *supra.* |
| **Colon** | miR-30c | | | | | | Volinia et al. *supra.* |
| **Colon** | miR-223 | | | | | | Volinia et al. *supra.* |
| **Colon** | miR-126 | | | | | | Volinia et al. *supra.*" |
| **Colon** | miR-128b | | | | | | Volinia et al. *supra.* |
| **Colon** | miR-21 | | | | | | Volinia et al. *supra.* |
| **Colon** | miR-24-2 | | | | | | Volinia et al. *supra.* |
| **Colon** | miR-99b | | | | | | Volinia et al. *supra.* |
| **Colon** | miR-155 | | | | | | Volinia et al. *supra.* |
| **Colon** | miR-213 | | | | | | Volinia et al. *supra.* |
| **Colon** | miR-150 | | | | | | Volinia et al. *supra.* |
| **Colon** | miR-107 | | | | | | Volinia et al. *supra.* |
| **Colon** | miR-191 | | | | | | Volinia et al. *supra.*" |
| **Colon** | mIR-221 | | | | | | Volinia et al. *supra.* |
| **Colon** | | miR-9-3 | | | | | Volinia et al. *supra.* |
| **Colon** | | miR-34a | | | | | Tazawa et al., 2007, J Urol, 156(3): 967-71 |
| **Colon** | | miR-145 | | | | | Schepeler et al., 2008, Cancer Res, 68(15): 6416-23 |
| **Colon** | | miR-455 | | | | | Schepeler et al., *supra.* |
| **Colon** | | miR-484 | | | | | Schepeler et al., *supra.* |
| **Colon** | | miR-101 | | | | | Schepeler et al., *supra.* |
| **Colon** | miR-20a | | | | | | Schepeler et al., *supra.* |
| **Colon** | MiR-510 | | | | | | Schepeler et al., *supra.* |
| **Colon** | miR-92 | | | | | | Schepeler et al., *supra.* |
| **Colon** | miR-513 | | | | | | Schepeler et al., *supra.* |

FIG. 6b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Colon** | miR-19a | | | | | | Bandres et al., 2006, Mol Cancer, 5:29 |
| **Colon** | miR-21 | | | | | | Bandres et al., *supra.* |
| **Colon** | miR-20 | | | | | | Bandres et al., *supra.* |
| **Colon** | miR-183 | | | | | | Bandres et al., *supra.* |
| **Colon** | miR-96 | | | | | | Bandres et al., *supra.* |
| **Colon** | miR-135b | | | | | | Bandres et al., *supra.* |
| **Colon** | miR-31 | | | | | | Bandres et al., *supra.* |
| **Colon** | | miR-145 | | | | | Bandres et al., *supra*.36 |
| **Colon** | | miR-133b | | | | | Bandres et al., *supra.* |
| **Colon** | | miR-129 | | | | | Bandres et al., *supra.* |
| **Colon** | | miR-124a | | | | | Bandres et al., *supra.* |
| **Colon** | | miR-30-3p | | | | | Bandres et al., *supra.* |
| **Colon** | | miR-328 | | | | | Bandres et al., *supra.* |
| **Colon** | | miR-106a | | | | | Diaz et al., 2008, Br J Anaesth, 101(2): 161-4 |
| **Colon** | | miR-17-5p | | | | | Diaz et al., *supra.* |
| **Colon** | mIR-21 | | | | | | Schetter et al. 2008, JAMA, 299(4): 425 |
| **Colon** | miR-92 | | | | | | Schetter et al. *supra.* |
| **Colon** | miR-222 | | | | | | Schetter et al. *supra.* |
| **Colon** | miR-181b | | | | | | Schetter et al. *supra.* |
| **Colon** | miR-210 | | | | | | Schetter et al. *supra.* |
| **Colon** | miR-20a | | | | | | Schetter et al. *supra.* |
| **Colon** | miR-106a | | | | | | Schetter et al. *supra.* |
| **Colon** | miR-93 | | | | | | Schetter et al. *supra.* |
| **Colon** | miR-335 | | | | | | Schetter et al. *supra.* |
| **Colon** | miR-338 | | | | | | Schetter et al. *supra.* |
| **Colon** | miR-133b | | | | | | Schetter et al. *supra.* |
| **Colon** | miR-346 | | | | | | Schetter et al. *supra.* |
| **Colon** | miR-106b | | | | | | Schetter et al. *supra.* |
| **Colon** | miR-153a | | | | | | Schetter et al. *supra.* |
| **Colon** | miR-219 | | | | | | Schetter et al. *supra.* |
| **Colon** | miR-34a | | | | | | Schetter et al. *supra.* |
| **Colon** | miR-99b | | | | | | Schetter et al. *supra.* |
| **Colon** | miR-185 | | | | | | Schetter et al. *supra.* |
| **Colon** | miR-223 | | | | | | Schetter et al. *supra.* |
| **Colon** | miR-211 | | | | | | Schetter et al. *supra.* |
| **Colon** | miR-135a | | | | | | Schetter et al. *supra.* |
| **Colon** | miR-127 | | | | | | Schetter et al. *supra.* |
| **Colon** | miR-203 | | | | | | Schetter et al. *supra.* |
| **Colon** | miR-212 | | | | | | Schetter et al. *supra.* |
| **Colon** | miR-95 | | | | | | Schetter et al. *supra.* |
| **Colon** | miR-17-5p | | | | | | Schetter et al. *supra.* |
| **Colon** | | miR-342 | | | | | Schetter et al. *supra.* |
| **Colon** | | miR-192 | | | | | Schetter et al. *supra.* |
| **Colon** | | miR-1 | | | | | Schetter et al. *supra.* |
| **Colon** | | miR-34b | | | | | Schetter et al. *supra.* |

FIG. 6c

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| Colon | | miR-215 | | | | | Schetter et al. *supra.* |
| Colon | | miR-192 | | | | | Schetter et al. *supra.* |
| Colon | | miR-301 | | | | | Schetter et al. *supra.* |
| Colon | | miR-324-5p | | | | | Schetter et al. *supra.* |
| Colon | | miR-30a-3p | | | | | Schetter et al. *supra.* |
| Colon | | miR-34c | | | | | Schetter et al. *supra.* |
| Colon | | miR-331 | | | | | Schetter et al. *supra.* |
| Colon | | miR-148b | | | | | Schetter et al. *supra.* |
| Colon | | | | | AFRs | | Choi et al., 2007, J Ethnopharmacol 110(1): 49-55. |
| Colon | | | | | Rabs | | Choi et al., *supra.* |
| Colon | | | | | ADAM10 | | Choi et al., *supra.* |
| Colon | | | | | CD44 | | Choi et al., *supra.* |
| Colon | | | | | NG2 | | Choi et al., *supra.*. |
| Colon | | | | | ephrin-B1 | | Choi et al., *supra.* |
| Colon | | | | | MIF | | Choi et al., *supra.* |
| Colon | | | | | b-catenin | | Choi et al., *supra.* |
| Colon | | | | | Junction | | Choi et al., *supra.* |
| Colon | | | | | plakoglobin | | Choi et al., *supra.* |
| Colon | | | | | glalectin-4 | | Choi et al., *supra.* |
| Colon | | | | | RACK1 | | Choi et al., *supra.* |
| Colon | | | | | tetrspanin-8 | | Choi et al., *supra.* |
| Colon | | | | | FastL | | Choi et al., *supra.* |
| Colon | | | | | TRAIL | | Choi et al., *supra.* |
| Colon | | | | | A33 | | Choi et al., *supra.* |
| Colon | | | | | CEA | | Choi et al., *supra.* |
| Colon | | | | | EGFR | | Choi et al., *supra.* |
| Colon | | | | | dipeptidase 1 | | Choi et al., *supra.* |
| Colon | | | | | hsc-70 | | Choi et al., *supra.* |
| Colon | | | | | tetraspanins | | Choi et al., *supra.* |
| Colon | | | | | ESCRT | | Choi et al., *supra.* |
| Colon | | | EFNB1 | | | | Huber et al., 2005, Gastroenterol Nurs 28(6): 510-1. |
| Colon | | | ERCC1 | | | | Shirota Y et al., J Clin Oncol, 2001. 19(23): p. 4298-304 |
| Colon | | | | | TS | | Cascinu S et al., Ann Oncol, 2001. 12(2): p. 239-44; Ciaparrone M et al., Oncology, 2006. 70(5): p. 366-77 |
| Colon | | | | | PTEN | | Frattini et al., 2007 |

FIG. 6d

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| Colon | | | | | TOPO1 | | Braun MS et al., J Clin Oncol, 2008. 26(16): p. 2690-8 |
| Colon | | | HER2 | | | | Ochs AM et al., Clin Colorectal Cancer. 2004 Nov;4(4):262-7 |
| Colon | | | VEGF | | | | Ochs AM et al., *supra.* |
| Colon | | | EGFR | | | | Cappuzo et al 2008, Sartore-Bianche et al 2007 |
| Colon | | | | EGFR | | | Zhang X et al., Oncol Rep. 2008 Jun;19(6):1541-4; Riese DJ 2nd et al., Bioessays. 2007 Jun;29(6):558-65 |
| Colon | | | | KRAS | | | Amado RG et al., J Clin Oncol, 2008. 26(10): p. 1626-34; De Roock W et al., Ann Oncol, 2008. 19(3): p. 508-15. |
| Colon | | | | VEGFA | | | Uthoff SM et al., Int J Cancer. 2002 Sep 1;101(1):32-6. |
| Colon | | | | B-Raf | | | Ogino S et al., Gut. 2008 Oct 2; Matos P et al., Gastroenterology. 2008 Sep;135(3):899-906 |
| Colon | | | | APC | | | Conlin A et al., Gut, 2005. 54(9): p. 1283-6 |
| Colon | | | | p53 | | | Conlin A et al., *supra.* |

FIG. 7

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| Adenoma versus Hyperplastic Polyp | | | ABCA8 | | | did not find any | Galamb et al., 2008,Cancer Epidemiol Biomarkers Prev 17(10): 2835-45 |
| Adenoma versus Hyperplastic Polyp | | | KIAA1199 | | | | Galamb et al., *supra.* |
| Adenoma versus Hyperplastic Polyp | | | GCG | | | | Galamb et al., *supra.* |
| Adenoma versus Hyperplastic Polyp | | | MAMDC2 | | | | Galamb et al., *supra.* |
| Adenoma versus Hyperplastic Polyp | | | C2orf32 | | | | Galamb et al., *supra.* |
| Adenoma versus Hyperplastic Polyp | | | 229670_at | | | | Galamb et al., *supra.* |
| Adenoma versus Hyperplastic Polyp | | | IGF1 | | | | Galamb et al., *supra.* |
| Adenoma versus Hyperplastic Polyp | | | PCDH7 | | | | Galamb et al., *supra.* |
| Adenoma versus Hyperplastic Polyp | | | PRDX6 | | | | Galamb et al., *supra.* |
| Adenoma versus Hyperplastic Polyp | | | | BRAF | | | Kim YH et al., Int J Cancer. 2008 Dec 1;123(11):2587-93 |
| Adenoma versus Hyperplastic Polyp | | | | KRAS | | | Rashid A et al., Gastroenterology. 2000 Aug;119(2)•323-32 |
| Adenoma versus Hyperplastic Polyp | | | PCNA | | | | Barletta A et al., Anticancer Res. 1998 May-Jun;18(3A):1677-82 |
| Adenoma versus Hyperplastic Polyp | | | COX2 | | . | | McLean MH et al., Histopathology. 2008 Jun;52(7):806-15. Epub 2008 May 6. |
| Adenoma versus Hyperplastic Polyp | | | MUC6 | | | | Owens SR et al., Mod Pathol. 2008 Jun;21(6):660-9. |
| Adenoma versus Hyperplastic Polyp | | | | | hTERT | | Oka S et al., Scand J Gastroenterol. 2002 Oct;37(10):1194-200 |

FIG. 8

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| IBD versus normal | | | REG1A | | | | Galamb et al., 2008, "Inflammation, Adenoma and Cancer Objective Classification of Colon Biopsy Specimens with Gene Expression Signature", Dis Markers, 25(1): 1-16 |
| IBD versus normal | | | MMP3 | | | | Galamb et al., *supra*. |

FIG. 9a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Adenoma versus CRC** | | | GREM1 | | | | Galamb et al., 2008, Dis Markers, 25(1): 1-16. |
| **Adenoma versus CRC** | | | DDR2 | | | | Galamb et al., *supra.* |
| **Adenoma versus CRC** | | | GUCY1A3 | | | | Galamb et al., *supra.* |
| **Adenoma versus CRC** | | | TNS1 | | | | Galamb et al., *supra.* |
| **Adenoma versus CRC** | | | ADAMTS1 | | | | Galamb et al., *supra.* |
| **Adenoma versus CRC** | | | FBLN1 | | | | Galamb et al., *supra.* |
| **Adenoma versus CRC** | | | FLJ38028 | | | | Galamb et al., *supra.* |
| **Adenoma versus CRC** | | | RDX | | | | Galamb et al., *supra.* |
| **Adenoma versus CRC** | | | FAM129A | | | | Galamb et al., *supra.* |
| **Adenoma versus CRC** | | | ASPN | | | | Galamb et al., *supra.* |
| **Adenoma versus CRC** | | | FRMD6 | | | | Galamb et al., *supra.* |
| **Adenoma versus CRC** | | | MCC | | | | Galamb et al., *supra.* |
| **Adenoma versus CRC** | | | RBMS1 | | | | Galamb et al., *supra.* |
| **Adenoma versus CRC** | | | SNAI2 | | | | Galamb et al., *supra.* |
| **Adenoma versus CRC** | | | MEIS1 | | | | Galamb et al., *supra.* |
| **Adenoma versus CRC** | | | DOCK10 | | | | Galamb et al., *supra.* |
| **Adenoma versus CRC** | | | PLEKHC1 | | | | Galamb et al., *supra.* |
| **Adenoma versus CRC** | | | FAM126A | | | | Galamb et al., *supra.* |
| **Adenoma versus CRC** | | | TBC1D9 | | | | Galamb et al., *supra.* |
| **Adenoma versus CRC** | | | VWF | | | | Galamb et al., *supra.* |
| **Adenoma versus CRC** | | | DCN | | | | Galamb et al., *supra.* |
| **Adenoma versus CRC** | | | ROBO1 | | | | Galamb et al., *supra.* |
| **Adenoma versus CRC** | | | MSRB3 | | | | Galamb et al., *supra.* |
| **Adenoma versus CRC** | | | LATS2 | | | | Galamb et al., *supra.* |

FIG. 9b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Adenoma versus CRC** | | | MEF2C | | | | Galamb et al., *supra.* |
| **Adenoma versus CRC** | | | IGFBP3 | | | | Galamb et al., *supra.* |
| **Adenoma versus CRC** | | | GNB4 | | | | Galamb et al., *supra.* |
| **Adenoma versus CRC** | | | RCN3 | | | | Galamb et al., *supra.* |
| **Adenoma versus CRC** | | | AKAP12 | | | | Galamb et al., *supra.* |
| **Adenoma versus CRC** | | | RFTN1 | | | | Galamb et al., *supra.* |
| **Adenoma versus CRC** | | | 226834_at | | | | Galamb et al., *supra.* |
| **Adenoma versus CRC** | | | COL5A1 | | | | Galamb et al., *supra.* |
| **Adenoma versus CRC** | | | GNG2 | | | | Galamb et al., *supra.* |
| **Adenoma versus CRC** | | | NR3C1 | | | | Galamb et al., *supra.* |
| **Adenoma versus CRC** | | | SPARCL1 | | | | Galamb et al., *supra.* |
| **Adenoma versus CRC** | | | MAB21L2 | | | | Galamb et al., *supra.* |
| **Adenoma versus CRC** | | | AXIN2 | | | | Galamb et al., *supra.* |
| **Adenoma versus CRC** | | | 236894_at | | | | Galamb et al., *supra.* |
| **Adenoma versus CRC** | | ' | AEBP1 | | | | Galamb et al., *supra.* |
| **Adenoma versus CRC** | | | AP1S2 | | | | Galamb et al., *supra.* |
| **Adenoma versus CRC** | | | C10orf56 | | | | Galamb et al., *supra.* |
| **Adenoma versus CRC** | | | LPHN2 | | | | Galamb et al., *supra.* |
| **Adenoma versus CRC** | | | AKT3 | | | | Galamb et al., *supra.* |
| **Adenoma versus CRC** | | | FRMD6 | | | | Galamb et al., *supra.* |
| **Adenoma versus CRC** | | | COL15A1 | | | | Galamb et al., *supra.* |
| **Adenoma versus CRC** | | | CRYAB | | | | Galamb et al., *supra.* |
| **Adenoma versus CRC** | | | COL14A1 | | | | Galamb et al., *supra.* |
| **Adenoma versus CRC** | | | LOC286167 | | | | Galamb et al., *supra.* |

FIG. 9c

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Adenoma versus CRC** | | | QKI | | | | Galamb et al., *supra.* |
| **Adenoma versus CRC** | | | WWTR1 | | | | Galamb et al., *supra.* |
| **Adenoma versus CRC** | | | GNG11 | | | | Galamb et al., *supra.* |
| **Adenoma versus CRC** | | | PAPPA | | | | Galamb et al., *supra.* |
| **Adenoma versus CRC** | | | ELDT1 | | | | Galamb et al., *supra.* |

FIG. 10

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **IBD versus CRC** | | | 227458_at | | | | Galamb et al., 2008, Helicobacter, 13(2); 112-26. |
| **IBD versus CRC** | | | INDO | | | | Galamb et al., *supra.* |
| **IBD versus CRC** | | | CXCL9 | | | | Galamb et al., *supra.* |
| **IBD versus CRC** | | • | CCR2 | | | | Galamb et al., *supra.* |
| **IBD versus CRC** | | | CD38 | | | | Galamb et al., *supra.* |
| **IBD versus CRC** | | | RARRES3 | | | | Galamb et al., *supra.* |
| **IBD versus CRC** | | | CXCL10 | | | | Galamb et al., *supra.* |
| **IBD versus CRC** | | | FAM26F | | | | Galamb et al., *supra.* |
| **IBD versus CRC** | | | TNIP3 | | | | Galamb et al., *supra.* |
| **IBD versus CRC** | | | NOS2A | | | | Galamb et al., *supra.* |
| **IBD versus CRC** | | | CCRL1 | | | | Galamb et al., *supra.* |
| **IBD versus CRC** | | | TLR8 | | | | Galamb et al., *supra.* |
| **IBD versus CRC** | | | IL18BP | | | | Galamb et al., *supra.* |
| **IBD versus CRC** | | | FCRL5 | | | | Galamb et al., *supra.* |
| **IBD versus CRC** | | | SAMD9L | | | | Galamb et al., *supra.* |
| **IBD versus CRC** | | | ECGF1 | | | | Galamb et al., *supra.* |
| **IBD versus CRC** | | | TNFSF13B | | | | Galamb et al., *supra.* |
| **IBD versus CRC** | | | GBP5 | | | | Galamb et al., *supra.* |
| **IBD versus CRC** | | | GBP1 | | | | Galamb et al., *supra.* |

FIG. 11a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| CRC Dukes B versus Dukes C-D | | | TMEM37* | | | | Galamb et al., 2008, Helicobacter, 13(2); 112-26. |
| CRC Dukes B versus Dukes C-D | | | IL33 | | | | Galamb et al., *supra.* |
| CRC Dukes B versus Dukes C-D | | | CA4 | | | | Galamb et al., *supra.* |
| CRC Dukes B versus Dukes C-D | | | CCDC58 | | | | Galamb et al., *supra.* |
| CRC Dukes B versus Dukes C-D | | | CLIC6 | | | | Galamb et al., *supra.* |
| CRC Dukes B versus Dukes C-D | | | VSNL1 | | | | Galamb et al., *supra.* |
| CRC Dukes B versus Dukes C-D | | | ESPN | | | | Galamb et al., *supra.* |
| CRC Dukes B versus Dukes C-D | | | APCDDI | | | | Galamb et al., *supra.* |
| CRC Dukes B versus Dukes C-D | | | C13orf18 | | | | Galamb et al., *supra.* |
| CRC Dukes B versus Dukes C-D | | | CYP4X1 | | | | Galamb et al., *supra.* |
| CRC Dukes B versus Dukes C-D | | | ATP2A3 | | | | Galamb et al., *supra.* |
| CRC Dukes B versus Dukes C-D | | | LOC646627 | | | | Galamb et al., *supra.* |
| CRC Dukes B versus Dukes C-D | | | MUPCDH | | | | Galamb et al., *supra.* |
| CRC Dukes B versus Dukes C-D | | | ANPEP | | | | Galamb et al., *supra.* |
| CRC Dukes B versus Dukes C-D | | | C1orf115 | | | | Galamb et al., *supra.* |
| CRC Dukes B versus Dukes C-D | | | HSD3B2 | | | | Galamb et al., *supra.* |
| CRC Dukes B versus Dukes C-I) | | | GBA3 | | | | Galamb et al., *supra.* |
| CRC Dukes B versus Dukes C-D | | | GABRB2 | | | | Galamb et al., *supra.* |
| CRC Dukes B versus Dukes C-13 | | | GYLTL1 B | | | | Galamb et al., *supra.* |
| CRC Dukes B versus Dukes C-D | | | LYZ | | | | Galamb et al., *supra.* |
| CRC Dukes B versus Dukes C-D | | | SPC25 | | | | Galamb et al., *supra.* |
| CRC Dukes B versus Dukes C-D | | | CDKN2B | | | | Galamb et al., *supra.* |
| CRC Dukes B versus Dukes C-D | | | FAM89A | | | | Galamb et al., *supra.* |

FIG. 11b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| CRC Dukes B versus Dukes C-D | | | MOGAT2 | | | | Galamb et al., *supra.* |
| CRC Dukes B versus Dukes C-D | | | SEMA6D | | | | Galamb et al., *supra.* |
| CRC Dukes B versus Dukes C-D | | | 229376_at | | | | Galamb et al., *supra.* |
| CRC Dukes B versus Dukes C-D | | | TSPAN5 | | | | Galamb et al., *supra.* |
| CRC Dukes B versus Dukes C-D | | | IL6R | | | | Galamb et al., *supra.* |
| CRC Dukes B versus Dukes C-D | | | SLC26A2 | | | | Galamb et al., *supra.* |
| CRC Dukes B versus Dukes C-D | | | | | PAR4 | | Madoz-Gúrpide et al., Mol. Cell. Prot. 6:2150-64, 2007 |
| CRC Dukes B versus Dukes C-D | | | | | DIABLO | | Madoz-Gúrpide J et al., *supra.* |
| CRC Dukes B versus Dukes C-D | | | | | caspase-3 | | Madoz-Gúrpide J et al., *supra* |
| CRC Dukes B versus Dukes C-D | | | | | p53 | | Madoz-Gúrpide J et al., *supra* |
| CRC Dukes B versus Dukes C-D | | | | | TRF1 | | Madoz-Gúrpide J et al., *supra* |
| CRC Dukes B versus Dukes C-D | | | | | c-myc | | Madoz-Gúrpide J et al., *supra* |

FIG. 12a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Adenoma with low grade versus high grade dysplasia** | | | SI | | | | Galamb et al., 2008, Dis Markers, 25(1): 1-16 |
| **Adenoma with low grade versus high grade dysplasia** | | | DMBT1 | | | | Galamb et al. *supra.* |
| **Adenoma with low grade versus high grade dysplasia** | | | CFI* | | | | Galamb et al. *supra.* |
| **Adenoma with low grade versus high grade dysplasia** | | | AQP1 | | | | Galamb et al. *supra.* |
| **Adenoma with low grade versus high grade dysplasia** | | | APOD | | | | Galamb et al. *supra..* |
| **Adenoma with low grade versus high grade dysplasia** | | | TNFRSF17 | | | | Galamb et al. *supra.* |
| **Adenoma with low grade versus high grade dysplasia** | | | CXCL10 | | | | Galamb et al. *supra.* |
| **Adenoma with low grade versus high grade dysplasia** | | | CTSE | | | | Galamb et al. *supra..* |
| **Adenoma with low grade versus high grade dysplasia** | | | IGHA1 | | | | Galamb et al. *supra.* |
| **Adenoma with low grade versus high grade dysplasia** | | | SLC9A3 | | | | Galamb et al. *supra..* |
| **Adenoma with low grade versus high grade dysplasia** | | | SLC7A1 | | | | Galamb et al. *supra..* |
| **Adenoma with low grade versus high grade dysplasia** | | | BATF2 | | | | Galamb et al. *supra.* |
| **Adenoma with low grade versus high grade dysplasia** | | | SOCS1 | | | | Galamb et al. *supra.* |
| **Adenoma with low grade versus high grade dysplasia** | | | DOCK2 | | | | Galamb et al. *supra.* |
| **Adenoma with low grade versus high grade dysplasia** | | | NOS2A | | | | Galamb et al. *supra.* |
| **Adenoma with low grade versus high grade dysplasia** | | | HK2 | | | | Galamb et al. *supra.* |

FIG. 12b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Adenoma with low grade versus high grade dysplasia | | | CXCL2 | | | | Galamb et al. *supra.* |
| Adenoma with low grade versus high grade dysplasia | | | IL15RA | | | | Galamb et al. *supra..* |
| Adenoma with low grade versus high grade dysplasia | | | POU2AF1 | | | | Galamb et al. *supra.* |
| Adenoma with low grade versus high grade dysplasia | | | CLEC3B | | | | Galamb et al. *supra.* |
| Adenoma with low grade versus high grade dysplasia | | | ANI3BP | | | | Galamb et al. *supra.* |
| Adenoma with low grade versus high grade dysplasia | | | MGC13057 | | | | Galamb et al. *supra.* |
| Adenoma with low grade versus high grade dysplasia | | | LCK* | | | | Galamb et al. *supra.* |
| Adenoma with low grade versus high grade dysplasia | | | C4BPA | | | | Galamb et al. *supra.* |
| Adenoma with low grade versus high grade dysplasia | | | HOXC6 | | | | Galamb et al. *supra.* |
| Adenoma with low grade versus high grade dysplasia | | | GOLT1A | | | | Galamb et al. *supra.* |
| Adenoma with low grade versus high grade dysplasia | | | C2orf32 | | | | Galamb et al. *supra.* |
| Adenoma with low grade versus high grade dysplasia | | | IL10RA | | | | Galamb et al. *supra.* |
| Adenoma with low grade versus high grade dysplasia | | | 240856_at | | | | Galamb et al. *supra.* |
| Adenoma with low grade versus high grade dysplasia | | | SOCS3 | | | | Galamb et al. *supra.* |
| Adenoma with low grade versus high grade dysplasia | | | MEIS3P1 | | | | Galamb et al. *supra.* |
| Adenoma with low grade versus high grade dysplasia | | | HIPK1 | | | | Galamb et al. *supra.* |

FIG. 12c

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Adenoma with low grade versus high grade dysplasia** | | | GLS | | | | Galamb et al. *supra.* |
| **Adenoma with low grade versus high grade dysplasia** | | | CPLX1 | | | | Galamb et al. *supra.* |
| **Adenoma with low grade versus high grade dysplasia** | | | 236045_x_at | | | | Galamb et al. *supra.* |
| **Adenoma with low grade versus high grade dysplasia** | | | GALC | | | | Galamb et al. *supra.* |
| **Adenoma with low grade versus high grade dysplasia** | | | AMN | | | | Galamb et al. *supra.* |
| **Adenoma with low grade versus high grade dysplasia** | | | CCDC69 | | | | Galamb et al. *supra.* |
| **Adenoma with low grade versus high grade dysplasia** | | | CCL28 | | | | Galamb et al. *supra.* |
| **Adenoma with low grade versus high grade dysplasia** | | | CPA3 | | | | Galamb et al. *supra.* |
| **Adenoma with low grade versus high grade dysplasia** | | | TRIB2 | | | | Galamb et al. *supra.* |
| **Adenoma with low grade versus high grade dysplasia** | | | HMGA2 | | | | Galamb et al. *supra.* |
| **Adenoma with low grade versus high grade dysplasia** | | | PLCL2 | | | | Galamb et al. *supra.* |
| **Adenoma with low grade versus high grade dysplasia** | | | NR3C1 | | | | Galamb et al. *supra.* |
| **Adenoma with low grade versus high grade dysplasia** | | | EIF5A | | | | Galamb et al. *supra.* |
| **Adenoma with low grade versus high grade dysplasia** | | | LARP4 | | | | Galamb et al. *supra.* |
| **Adenoma with low grade versus high grade dysplasia** | | | RP5-1022P6.2 | | | | Galamb et al. *supra.* |
| **Adenoma with low grade versus high grade dysplasia** | | | PHLDB2 | | | | Galamb et al. *supra.* |

FIG. 12d

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Adenoma with low grade versus high grade dysplasia | | | FKBP1B | | | | Galamb et al. *supra.* |
| Adenoma with low grade versus high grade dysplasia | | | INDO | | | | Galamb et al. *supra.* |
| Adenoma with low grade versus high grade dysplasia | | | CLDN8 | | | | Galamb et al. *supra.* |
| Adenoma with low grade versus high grade dysplasia | | | CNTN3 | | | | Galamb et al. *supra.* |
| Adenoma with low grade versus high grade dysplasia | | | PBEF1 | | | | Galamb et al. *supra.* |
| Adenoma with low grade versus high grade dysplasia | | | SLC16A9 | | | | Galamb et al. *supra.* |
| Adenoma with low grade versus high grade dysplasia | | | CDC25B | | | | Galamb et al. *supra.* |
| Adenoma with low grade versus high grade dysplasia | | | TPSB2 | | | | Galamb et al. *supra.* |
| Adenoma with low grade versus high grade dysplasia | | | PBEF1 | | | | Galamb et al. *supra.* |
| Adenoma with low grade versus high grade dysplasia | | | ID4 | | | | Galamb et al. *supra.* |
| Adenoma with low grade versus high grade dysplasia | | | GJB5 | | | | Galamb et al. *supra.* |
| Adenoma with low grade versus high grade dysplasia | | | CHN2 | | | | Galamb et al. *supra.* |
| Adenoma with low grade versus high grade dysplasia | | | LIMCH1 | | | | Galamb et al. *supra.* |
| Adenoma with low grade versus high grade dysplasia | | | CXCL9 | | | | Galamb et al. *supra.* |

FIG. 13a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| UC vs CD | | | IFITM1 | | | | Wu F., et al., 2007, Inflamm Bowel Dis, 13(7): 807-21. |
| UC vs CD | | | IFITM3 | | | | Wu F., et al., 2007 *supra*. |
| UC vs CD | | | STAT1 | | | | Wu F., et al., 2007 *supra* |
| UC vs CD | | | STAT3 | | | | Wu F., et al., 2007 *supra* |
| UC vs CD | | | TAP1 | | • | | Wu F., et al., 2007 *supra* |
| UC vs CD | | | PSME2 | | | | Wu F., et al., 2007 *supra* |
| UC vs CD | | | PSMB8 | | | | Wu F., et al., 2007 *supra* |
| UC vs CD | | | HNF4G | | | | Wu F., et al., 2007 *supra* |
| UC vs CD | | | KLF5 | | | | Wu F., et al., 2007 *supra* |
| UC vs CD | | | AQP8 | | | | Wu F., et al., 2007 *supra* |
| UC vs CD | | | APT2B1 | | | | Wu F., et al., 2007 *supra* |
| UC vs CD | | | SLC16A | | | | Wu F., et al., 2007 *supra* |
| UC vs CD | | | MFAP4 | | | | Galamb et al., 2008, Helicobacter, 13(2); 112-26. |
| UC vs CD | | | CCNG2 | | | | Galamb et al., *supra*. |
| UC vs CD | | | SLC44A4 | | | | Galamb et al., *supra*. |
| UC vs CD | | | DDAH1 | | | | Galamb et al., *supra*. |
| UC vs CD | | | TOB1 | | | | Galamb et al., *supra*. |
| UC vs CD | | | 231152_at | | | | Galamb et al., *supra*. |
| UC vs CD | | | MKNK1 | | | | Galamb et al., *supra*. |
| UC vs CD | | | CEACAM7* | | | | Galamb et al., *supra*. |
| UC vs CD | | | 1562836_at | | | | Galamb et al., *supra*. |
| UC vs CD | | | CDC42SE2 | | | | Galamb et al., *supra*. |
| UC vs CD | | | PSD3 | | | | Galamb et al., *supra*. |
| UC vs CD | | | 231169_at | | | | Galamb et al., *supra*. |
| UC vs CD | | | IGL@* | | | | Galamb et al., *supra*. |
| UC vs CD | | | GSN | | | | Galamb et al., *supra*. |
| UC vs CD | | | GPM6B | | | | Galamb et al., *supra*. |
| UC vs CD | | | CDV3* | | | | Galamb et al., *supra*. |
| UC vs CD | | | PDPK1 | | | | Galamb et al., *supra*. |
| UC vs CD | | | ANP32E | | | | Galamb et al., *supra*. |
| UC vs CD | | | ADAM9 | | | | Galamb et al., *supra*. |
| UC vs CD | | | CDH1 | | | | Galamb et al., *supra*. |
| UC vs CD | | | NLRP2 | | | | Galamb et al., *supra*. |
| UC vs CD | | | 215777_at | | | | Galamb et al., *supra*. |
| UC vs CD | | | OSBPL1 | | | | Galamb et al., *supra*. |
| UC vs CD | | | VNN1 | | | | Galamb et al., *supra*. |
| UC vs CD | | | RABGAP1L | | | | Galamb et al., *supra*. |
| UC vs CD | | | PHACTR2 | | | | Galamb et al., *supra*. |
| UC vs CD | | | ASH1L | | | | Galamb et al., *supra*. |
| UC vs CD | | | 213710_s_at | | | | Galamb et al., *supra*. |
| UC vs CD | | | CDH1 | | | | Galamb et al., *supra*. |
| UC vs CD | | | NLRP2 | | | | Galamb et al., *supra*. |
| UC vs CD | | | 215777_at | | | | Galamb et al., *supra*. |
| UC vs CD | | | OSBPLI | | | | Galamb et al., *supra*. |

FIG. 13b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **UC vs CD** | | | VNN1 | | | | Galamb et al., *supra.* |
| **UC vs CD** | | | RABGAP1L | | | | Galamb et al., *supra.* |
| **UC vs CD** | | | PHACTR2 | | | | Galamb et al., *supra.* |
| **UC vs CD** | | | ASH1 | | | | Galamb et al., *supra.* |
| **UC vs CD** | | | 213710_s_at | | | | Galamb et al., *supra.* |
| **UC vs CD** | | | ZNF3 | | | | Galamb et al., *supra.* |
| **UC vs CD** | | | FUT2 | | | | Galamb et al., *supra.* |
| **UC vs CD** | | | IGHA1 | | | | Galamb et al., *supra.* |
| **UC vs CD** | | | EDEM1 | | | | Galamb et al., *supra.* |
| **UC vs CD** | | | GPR171 | | | | Galamb et al., *supra.* |
| **UC vs CD** | | | 229713_at | | | | Galamb et al., *supra.* |
| **UC vs CD** | | | LOC643187 | | | | Galamb et al., *supra.* |
| **UC vs CD** | | | FLVCRI | | | | Galamb et al., *supra.* |
| **UC vs CD** | | | SNAP23* | | | | Galamb et al., *supra.* |
| **UC vs CD** | | | ETNK1 | | | | Galamb et al., *supra.* |
| **UC vs CD** | | | LOC728411 | | | | Galamb et al., *supra.* |
| **UC vs CD** | | | POSTN | | | | Galamb et al., *supra.* |
| **UC vs CD** | | | MUC12 | | | | Galamb et al., *supra.* |
| **UC vs CD** | | | HOXA5 | | | | Galamb et al., *supra.* |
| **UC vs CD** | | | SIGLEC1 | | | | Galamb et al., *supra.* |
| **UC vs CD** | | | LARP5 | | | | Galamb et al., *supra.* |
| **UC vs CD** | | | PIGR | | | | Galamb et al., *supra.* |
| **UC vs CD** | | | SPTBN1 | | | | Galamb et al., *supra.* |
| **UC vs CD** | | | UFM1 | | | | Galamb et al., *supra.* |
| **UC vs CD** | | | C6orf62 | | | | Galamb et al., *supra.* |
| **UC vs CD** | | | WDR90 | | | | Galamb et al., *supra.* |
| **UC vs CD** | | | ALDH1A3 | | | | Galamb et al., *supra.* |
| **UC vs CD** | | | F2RL1 | | | | Galamb et al., *supra.* |
| **UC vs CD** | | | IGHV1-69 | | | | Galamb et al., *supra.* |
| **UC vs CD** | | | DUOX2 | | | | Galamb et al., *supra.* |
| **UC vs CD** | | | RAB5A | | | | Galamb et al., *supra.* |
| **UC vs CD** | | | CP | | | | Galamb et al., *supra.* |
| **UC vs CD** | | | | CARD15 | | | Radford-Smith et al 2007, Gastroenterology 132(7): 2313-9. |
| **UC vs CD** | | | | | (P)ASCA | | Li X et al., World J Gastroenterol. 2008 Sep 7;14(33):5115-24. |

FIG. 14

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Hyperplastic polyp versus normal** | | | SLC6A14 | | | | Galamb et al., 2008, Cancer Epidemiol Biomarkers Prev, 17(10): 2835-45 |
| **Hyperplastic polyp versus normal** | | | ARHGEF10 | | | | Galamb et al., *supra.* |
| **Hyperplastic polyp versus normal** | | | ALS2 | | | | Galamb et al., *supra.* |
| **Hyperplastic polyp versus normal** | | | IL1RN | | | | Galamb et al., *supra.* |
| **Hyperplastic polyp versus normal** | | | SPRY4 | | | | Galamb et al., *supra.* |
| **Hyperplastic polyp versus normal** | | | PTGER3 | | | | Galamb et al., *supra.* |
| **Hyperplastic polyp versus normal** | | | TRIM29 | | | | Galamb et al., *supra.* |
| **Hyperplastic polyp versus normal** | | | SERPINB5 | | | | Galamb et al., *supra.* |
| **Hyperplastic polyp versus normal** | | | 1560327_at | | | | Galamb et al., *supra.* |
| **Hyperplastic polyp versus normal** | | | ZAK | | | | Galamb et al., *supra.* |
| **Hyperplastic polyp versus normal** | | | BAG4 | | | | Galamb et al., *supra.* |
| **Hyperplastic polyp versus normal** | | | TRIB3 | | | | Galamb et al., *supra.* |
| **Hyperplastic polyp versus normal** | | | TTL | | | | Galamb et al., *supra.* |
| **Hyperplastic polyp versus normal** | | | FOXQ1 | | | | Galamb et al., *supra.* |

FIG. 15

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Adenoma with low grade dysplasia versus normal** | | | UGT2A3 | | | | Galamb et al., 2008, Dis Markers, 25(1): 1-16. |
| **Adenoma with low grade dysplasia versus normal** | | | KLK11 | | | | Galamb et al., *supra.* |
| **Adenoma with low grade dysplasia versus normal** | | | KIAA1199 | | | | Galamb et al., *supra.* |
| **Adenoma with low grade dysplasia versus normal** | | | FOXQ1 | | | | Galamb et al., *supra.* |
| **Adenoma with high grade dysplasia versus normal** | | | CLDN8 | | | | Galamb et al., *supra.* |
| **Adenoma with high grade dysplasia versus normal** | | | ABCA8 | | | | Galamb et al., *supra.* |
| **Adenoma with high grade dysplasia versus normal** | | | PYY | | | | Galamb et al., *supra.* |

FIG. 16

| **Cancer Lineage, Group Comparison, Other Significant Disease State** | **Up-regulated miRs** | **Down-regulated miRs** | **mRNAs** | **Mutational Analysis** | **Proteins, Ligands, Peptides** | **snoRNA** | **Select Reference(s)** |
|---|---|---|---|---|---|---|---|
| **Adenoma versus normal** | | | KIAA1199 | | | | Galamb et al., 2008, Dis Markers, 25(1): 1-16. |
| **Adenoma versus normal** | | | FOXQ1 | | | | Galamb et al., *supra.* |
| **Adenoma versus normal** | | | CA7 | | | | Galamb et al., *supra.* |
| **Adenoma versus normal** | | | | | Clusterin | | Chen X et al., Proc Natl Acad Sci U S A. 2003 Aug 5;100(16):9530-5. |

FIG. 17

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| CRC versus normal | | | VWF | | | | Galamb et al., 2008, Dis Markers, 25(1): 1-16 |
| CRC versus normal | | | IL8 | | | | Galamb et al., *supra.* |
| CRC versus normal | | | CHI3L1 | | | | Galamb et al., *supra.* |
| CRC versus normal | | | S100A8 | | | | Galamb et al., *supra.* |
| CRC versus normal | | | GREM1 | | | | Galamb et al., *supra.* |
| CRC versus normal | | | ODC | | | | Hu HY et al., World J Gastroenterol. 2005 Apr 21;11(15):2244-8. |
| CRC versus normal | | | | KRAS | | | Amado RG et al., J Clin Oncol, 2008.26(10): p. 1626-34; De Roock W et al., Ann Oncol, 2008. 19(3): p. 508-15. |
| CRC versus normal | | | | BRAF | | | Ogino S et al., Gut. 2008 Oct 2; Matos P et al., Gastroenterology. 2008 Sep;135(3):899-906. |
| CRC versus normal | | | | APC | | | Conlin A et al., Gut, 2005. 54(9): p. 1283-6. |
| CRC versus normal | | | | MSH2 | | | Davidson NO, Keio J Med. 2007 Mar;56(1):14-20. |
| CRC versus normal | | | | MLH1 | | | Davidson NO, Keio *supra.* |
| CRC versus normal | | | | | cytokeratin 13 | | Madoz-Gúrpide J et al., Molecular & Cellular Proteomics 6:2150-2164, 2007. |
| CRC versus normal | | | | | calcineurin | | Madoz-Gúrpide J et al., *supra.* |
| CRC versus normal | | | | | CHK1 | | Madoz-Gúrpide J et al., *supra.* |
| CRC versus normal | | | | | clathrin light chain | | Madoz-Gúrpide J et al., *supra.* |
| CRC versus normal | | | | | phospho-ERK | | Madoz-Gúrpide J et al., *supra.* |
| CRC versus normal | | | | | phospho-PTK2 | | Madoz-Gúrpide J et al., *supra.* |
| CRC versus normal | | | | | MDM2 | | Madoz-Gúrpide J et al., *supra.* |

FIG. 18

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Benign Prostatic Hyperplasia** | | | | | Intact Fibronectin | | Janković MM, Kosanović MM, Dis Markers, 2008;25(1):49-58. |

FIG. 19a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Prostate** | | | | | FASLG | | Huber et al., 2005, Gastroenterol Nurs 28(6): 510-1. |
| **Prostate** | | | | | TNFSF10 | | Huber et al., 2005, *supra.* |
| **Prostate** | | | | | FASLG | | Adreola et al., JEM 195:10 1303-1316 (2002) |
| **Prostate** | | | | | TNFSF10 | | Adreola et al., *supra.* |
| **Prostate** | | | | | FASLG | | Abusamra et al., 2005, Blood Cells Mol Dis, 35(2): 169-73 |
| **Prostate** | | | | | TNFSF10 | | Abusamra et al., 2005, *supra.* |
| **Prostate** | | | | | FASLG | | Kim et al., Int J Cancer. 2008 Dec 1;123(11):2587-93. |
| **Prostate** | | | | | TNFSF10 | | Kim et al., *supra.* |
| **Prostate** | | | | | FASLG | | Taylor et al., 2003, Int J Oncol 22(6): 1311-7 |
| **Prostate** | | | | | TNFSF10 | | Taylor et al., *supra.* |
| **Prostate** | | let-7a | | | | | Porkka et al., 2007, Cancer Res, 67(13): 6130-5 |
| **Prostate** | | let-7b | | | | | Porkka et al., *supra.* |
| **Prostate** | | let-7c | | | | | Porkka et al., *supra.* |
| **Prostate** | | let-7d | | | | | Porkka et al., *supra.* |
| **Prostate** | | let-7g | | | | | Porkka et al., *supra.* |
| **Prostate** | | miR-16 | | | | | Porkka et al., *supra.* |
| **Prostate** | | miR-23a | | | | | Porkka et al., *supra.* |
| **Prostate** | | miR-23b | | | | | Porkka et al., *supra.* |
| **Prostate** | | miR-26a | | | | | Porkka et al., *supra.* |
| **Prostate** | | miR-92 | | | | | Porkka et al., *supra.* |
| **Prostate** | | miR-99a | | | | | Porkka et al., *supra.* |
| **Prostate** | | miR-103 | | | | | Porkka et al., *supra.* |
| **Prostate** | | miR-125a | | | | | Porkka et al., *supra.* |
| **Prostate** | | miR-125b | | | | | Porkka et al., *supra.* |
| **Prostate** | | miR-143 | | | | | Porkka et al., *supra.* |
| **Prostate** | | miR-145 | | | | | Porkka et al., *supra.* |
| **Prostate** | | miR-195 | | | | | Porkka et al., *supra.* |
| **Prostate** | | miR-199 | | | | | Porkka et al., *supra.* |
| **Prostate** | | miR-221 | | | | | Porkka et al., *supra.* |
| **Prostate** | | miR-222 | | | | | Porkka et al., *supra.* |
| **Prostate** | | miR-497 | | | | | Porkka et al., *supra.* |
| **Prostate** | | let-7f | | | | | Porkka et al., *supra.* |
| **Prostate** | | miR-19b | | | | | Porkka et al., *supra.* |
| **Prostate** | | miR-22 | | | | | Porkka et al., *supra.* |
| **Prostate** | | miR-26b | | | | | Porkka et al., *supra.* |
| **Prostate** | | miR-27a | | | | | Porkka et al., *supra.* |

FIG. 19b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Prostate** | | miR-27b | | | | | Porkka et al., *supra.* |
| **Prostate** | | miR-29a | | | | | Porkka et al., *supra.* |
| **Prostate** | | miR-29b | | | | | Porkka et al., *supra.* |
| **Prostate** | | miR-30_5p | | | | | Porkka et al., *supra.* |
| **Prostate** | | miR-30c | | | | | Porkka et al., *supra.* |
| **Prostate** | | miR-100 | | | | | Porkka et al., *supra.* |
| **Prostate** | | miR-141 | | | | | Porkka et al., *supra.* |
| **Prostate** | | miR-148a | | | | | Porkka et al., *supra.* |
| **Prostate** | | miR-205 | | | | | Porkka et al., *supra.* |
| **Prostate** | miR-202 | | | | | | Porkka et al., *supra.* |
| **Prostate** | miR-210 | | | | | | Porkka et al., *supra.* |
| **Prostate** | miR-296 | | | | | | Porkka et al., *supra.* |
| **Prostate** | miR-320 | | | | | | Porkka et al., *supra.* |
| **Prostate** | miR-370 | | | | | | Porkka et al., *supra.* |
| **Prostate** | miR-373 | | | | | | Porkka et al., *supra.* |
| **Prostate** | miR-498 | | | | | | Porkka et al., *supra.* |
| **Prostate** | miR-503 | | | | | | Porkka et al., *supra.* |
| **Prostate** | miR-184 | | | | | | Porkka et al., *supra.* |
| **Prostate** | miR-198 | | | | | | Porkka et al., *supra.* |
| **Prostate** | miR-302c | | | | | | Porkka et al., *supra.* |
| **Prostate** | miR-345 | | | | | | Porkka et al., *supra.*5 |
| **Prostate** | miR-491 | | | | | | Porkka et al., *supra.* |
| **Prostate** | miR-513 | | | | | | Porkka et al., *supra.* |
| **Prostate** | miR-32 | | | | | | Ambs et al., 2008, Cancer Res, 68(15): 6162-70 |
| **Prostate** | miR-182 | | | | | | Ambs et al., *supra.* |
| **Prostate** | miR-31 | | | | | | Ambs et al., *supra.* |
| **Prostate** | miR-26a-1/2 | | | | | | Ambs et al., *supra.*-70 |
| **Prostate** | miR-200c | | | | | | Ambs et al., *supra.* |
| **Prostate** | miR-375 | | | | | | Ambs et al., *supra.* |
| **Prostate** | miR-196a-1/2 | | | | | | Ambs et al., *supra.* |
| **Prostate** | miR-370 | | | | | | Ambs et al., *supra.* |
| **Prostate** | miR-425 | | | | | | Ambs et al., *supra.* |
| **Prostate** | miR-425 | | | | | | Ambs et al., *supra.* |
| **Prostate** | miR-194-1/2 | | | | | | Ambs et al., *supra.* |
| **Prostate** | miR-181a-1/2 | | | | | | Ambs et al., *supra.* |
| **Prostate** | miR-34b | | | | | | Ambs et al., *supra.* |

FIG. 19c

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Prostate** | let-7i | | | | | | Ambs et al., *supra.* |
| **Prostate** | miR-188 | | | | | | Ambs et al., *supra.* |
| **Prostate** | miR-25 | | | | | | Ambs et al., *supra.* |
| **Prostate** | miR-106b | | | | | | Ambs et al., *supra.* |
| **Prostate** | miR-449 | | | | | | Ambs et al., *supra.* |
| **Prostate** | miR-99b | | | | | | Ambs et al., *supra.* |
| **Prostate** | miR-93 | | | | | | Ambs et al., *supra.* |
| **Prostate** | miR-92-1/2 | | | | | | Ambs et al., *supra.* |
| **Prostate** | miR-125a | | | | | | Ambs et al., *supra.* |
| **Prostate** | | miR-520h | | | | | Ambs et al., *supra.* |
| **Prostate** | | miR-494 | | | | | Ambs et al., *supra.* |
| **Prostate** | | miR-490 | | | | | Ambs et al., *supra.* |
| **Prostate** | | miR-133a-1 | | | | | Ambs et al., *supra.* |
| **Prostate** | | miR-1-2 | | | | | Ambs et al., *supra.* |
| **Prostate** | | miR-218-2 | | | | | Ambs et al., *supra.* |
| **Prostate** | | miR-220 | | | | | Ambs et al., *supra.* |
| **Prostate** | | miR-128a | | | | | Ambs et al., *supra.* |
| **Prostate** | | miR-221 | | | | | Ambs et al., *supra.* |
| **Prostate** | | miR-499 | | | | | Ambs et al., *supra.* |
| **Prostate** | | miR-329 | | | | | Ambs et al., *supra.* |
| **Prostate** | | miR-340 | | | | | Ambs et al., *supra.* |
| **Prostate** | | miR-345 | | | | | Ambs et al., *supra.* |
| **Prostate** | | miR-410 | | | | | Ambs et al., *supra.* |
| **Prostate** | | miR-126 | | | | | Ambs et al., *supra.* |
| **Prostate** | | miR-205. | | | | | Ambs et al., *supra.* |
| **Prostate** | | miR-7-1/2 | | | | | Ambs et al., *supra.* |
| **Prostate** | | miR-145 | | | | | Ambs et al., *supra.* |
| **Prostate** | | miR-34a | | | | | Ambs et al., *supra.* |
| **Prostate** | | miR-487 | | | | | Ambs et al., *supra.* |
| **Prostate** | | let-7b | | | | | Ambs et al., *supra.* |
| **Prostate** | | | | | | U50 | Dong et al., 2008, Prostate 68(4): 381-99. |
| **Prostate** | | | AR | | | | |
| **Prostate** | miR-141 | | | | | | Mitchell et al. PNAS 2008 |
| **Prostate** | | | PCA3 | | | | Marks et. Al, Urology 69: 532-535, 2007. |

FIG. 20a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Melanoma** | | | | | Alix | | Mears et al., 2004, Proteomics 4(12): 4019-31. |
| **Melanoma** | | | | | hsp70 | | Mears et al., *supra.* |
| **Melanoma** | | | | | Gib2 | | Mears et al., *supra.* |
| **Melanoma** | | | | | Gia | | Mears et al., *supra.* |
| **Melanoma** | | | | | moesin | | Mears et al., *supra.* |
| **Melanoma** | | | | | GAPDH | | Mears et al., *supra.* |
| **Melanoma** | | | | | malate dehydro-genase | | Mears et al., *supra.* |
| **Melanoma** | | | | | p120 catenin | | Mears et al., *supra.* |
| **Melanoma** | | | | | PGRL | | Mears et al., *supra.* |
| **Melanoma** | | | | | syntaxin-binding protein 1 & 2 | | Mears et al., *supra.* |
| **Melanoma** | | | | | septin-2 | | Mears et al., *supra.* |
| **Melanoma** | | | | | WD-repeat containing protein 1 | | Mears et al., *supra.* |
| **Melanoma** | | miR-9 | | | | | Schultz et al., 2008, Cell Res 18(5): 549-57. |
| **Melanoma** | | miR-15a | | | | | Schultz et al., *supra.* |
| **Melanoma** | | miR-17-3p | | | | | Schultz et al., *supra.* |
| **Melanoma** | miR-19a | | | | | | Schultz et al., *supra.* |
| **Melanoma** | | miR-23b | | | | | Schultz et al., *supra.* |
| **Melanoma** | | miR-27a | | | | | Schultz et al., *supra.* |
| **Melanoma** | | miR-28 | | | | | Schultz et al., *supra.* |
| **Melanoma** | | miR-29b | | | | | Schultz et al., *supra.* |
| **Melanoma** | | miR-30b | | | | | Schultz et al., *supra.* |
| **Melanoma** | | miR-31 | | | | | Schultz et al., *supra.* |
| **Melanoma** | | miR-34b | | | | | Schultz et al., *supra.* |
| **Melanoma** | | m1R-34c | | | | | Schultz et al., *supra.* |
| **Melanoma** | | miR-95 | | | | | Schultz et al., *supra.* |
| **Melanoma** | | miR-96 | | | | | Schultz et al., *supra.* |
| **Melanoma** | | miR-100 | | • | | | Schultz et al., *supra.* |
| **Melanoma** | | miR-104 | | | | | Schultz et al., *supra.* |
| **Melanoma** | | miR-105 | | | | | Schultz et al., *supra.* |
| **Melanoma** | | miR-106a | | | | | Schultz et al., *supra.* |
| **Melanoma** | | miR-107 | | | | | Schultz et al., *supra.* |
| **Melanoma** | | miR-122a | | | | | Schultz et al., *supra.* |
| **Melanoma** | | miR-124a | | | | | Schultz et al., *supra.* |

FIG. 20b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Melanoma** | | miR-125b | | | | | Schultz et al., *supra.* |
| **Melanoma** | | miR-127 | | | | | Schultz et al., *supra.* |
| **Melanoma** | | miR-128a | | | | | Schultz et al., *supra.* |
| **Melanoma** | | miR-128b | | | | | Schultz et al., *supra.* |
| **Melanoma** | | miR-129 . | | | | | Schultz et al., *supra.* |
| **Melanoma** | | miR-135a | | | | | Schultz et al., *supra.* |
| **Melanoma** | | miR-135b | | | | | Schultz et al., *supra.* |
| **Melanoma** | | miR-137 | | | | | Schultz et al., *supra.* |
| **Melanoma** | | miR-138 | | | | | Schultz et al., *supra.* |
| **Melanoma** | | miR-139 | | | | | Schultz et al., *supra.* |
| **Melanoma** | | miR-140 | | | | | Schultz et al., *supra.* |
| **Melanoma** | | miR-141 | | | | | Schultz et al., *supra.* |
| **Melanoma** | miR-144 | | | | | | Schultz et al., *supra.* |
| **Melanoma** | | miR-149 | | | | | Schultz et al., *supra.* |
| **Melanoma** | | miR-154 | | | | | Schultz et al., *supra.* |
| **Melanoma** | | miR-154#3 | | | | | Schultz et al., *supra.* |
| **Melanoma** | | miR-181a | | | | | Schultz et al., *supra.* |
| **Melanoma** | | miR-182 | | | | | Schultz et al., *supra.* |
| **Melanoma** | | miR-183 | | | | | Schultz et al., *supra.* |
| **Melanoma** | | miR-184 | | | | | Schultz et al., *supra.* |
| **Melanoma** | | miR-185 | | | | | Schultz et al., *supra.* |
| **Melanoma** | | miR-189 | | | | | Schultz et al., *supra.* |
| **Melanoma** | | miR-190 | | | | | Schultz et al., *supra.* |
| **Melanoma** | | miR-199 | | | | | Schultz et al., *supra.* |
| **Melanoma** | | miR-199b | | | | | Schultz et al., *supra.* |
| **Melanoma** | | miR-200a | | | | | Schultz et al., *supra.* |
| **Melanoma** | | miR-200b | | | | | Schultz et al., *supra.* |
| **Melanoma** | miR-200c | | | | | | Schultz et al., *supra.* |
| **Melanoma** | | miR-204 | | | | | Schultz et al., *supra.* |
| **Melanoma** | miR-211 | | | | | | Schultz et al., *supra.* |
| **Melanoma** | | miR-213 | | | | | Schultz et al., *supra.* |
| **Melanoma** | | miR-215 | | | | | Schultz et al., *supra.* |
| **Melanoma** | | miR-216 | | | | | Schultz et al., *supra.* |
| **Melanoma** | | miR-219 | | | | | Schultz et al., *supra.* |
| **Melanoma** | | miR-222 | | | | | Schultz et al., *supra.* |
| **Melanoma** | | miR-224 | | | | | Schultz et al., *supra.* |
| **Melanoma** | | miR-299 | | | | | Schultz et al., *supra.* |
| **Melanoma** | | miR-302a | | | | | Schultz et al., *supra.* |
| **Melanoma** | | miR-302b | | | | | Schultz et al., *supra.* |
| **Melanoma** | | miR-302c | | | | | Schultz et al., *supra.* |
| **Melanoma** | | miR-302d | | | | | Schultz et al., *supra.* |
| **Melanoma** | | miR-323 | | | | | Schultz et al., *supra.* |

FIG. 20c

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Melanoma** | miR-324-5p | | | | | | Schultz et al., *supra.* |
| **Melanoma** | | miR-325 | | | | | Schultz et al., *supra.* |
| **Melanoma** | miR-331 | | | • | | | Schultz et al., *supra.* |
| **Melanoma** | miR-374 | | | | | | Schultz et al., *supra.* |
| **Melanoma** | | let-7a | | | | | Schultz et al., *supra.* |
| **Melanoma** | | let-7b | | | | | Schultz et al., *supra.* |
| **Melanoma** | | let-7d | | | | | Schultz et al., *supra.* |
| **Melanoma** | | let-7e | | | | | Schultz et al., *supra.* |
| **Melanoma** | | let-7g | | | | | Schultz et al., *supra.* |
| **Melanoma** | | | | CDK4 | | | Castelli et al., J Cell Physiology 182(3)323-31, 2000. |
| **Melanoma** | | | MUM-1 | | | | Castelli et al., *supra.* |
| **Melanoma** | | | beta-catenin | | | | Castelli et al., *supra.* |
| **Melanoma** | | | Nop/5/Sik | | | | Nakamoto et al., American Journal of Pathology 159(4), 2001. |
| **Melanoma** | | | | | | H/ACA (U107f) | Luo and Li, 2007, J Ind Microbiol Biotechnol 34(2): 117-22. |
| **Melanoma** | | | | | | SNO RA11D | Yang et al., nar 34:5112-5123, 2006 |
| **Melanoma** | | | | | DUSP-1 | | |

FIG. 21a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Pancreatic** | miR-221 | | | | | | Bloomston et al., 2008, J Gastrointest Surg. Dec;11(12):1680-5. |
| **Pancreatic** | miR-181a | | | | | | Bloomston et al., *supra.* |
| **Pancreatic** | miR-155 | | | | | | Bloomston et al., *supra* |
| **Pancreatic** | miR-210 | | | | | | Bloomston et al., *supra* |
| **Pancreatic** | miR-213 | | | | | | Bloomston et al., *supra.* |
| **Pancreatic** | miR-181b | | | | | | Bloomston et al., *supra* |
| **Pancreatic** | miR-222 | | | | | | Bloomston et al., *supra.* |
| **Pancreatic** | miR-181b-2 | | | | | | Bloomstom et al., *supra.* |
| **Pancreatic** | miR-21 | | | | | | Bloomstom et al., *supra.* |
| **Pancreatic** | miR-181b-1 | | | | | | Bloomstom et al., *supra.* |
| **Pancreatic** | miR-181c | | | | | | Bloomstom et al., *supra.* |
| **Pancreatic** | miR-220 | | | | | | Bloomstom et al., *supra.* |
| **Pancreatic** | miR-181d | | | | | | Bloomstom et al., *supra.* |
| **Pancreatic** | miR-223 | | | | | | Bloomstom et al., *supra.* |
| **Pancreatic** | miR-100-1/2 | | | | | | Bloomstom et al., *supra.* |
| **Pancreatic** | miR-125a | | | | | | Bloomstom et al., *supra.* |
| **Pancreatic** | miR-143 | | | | | | Bloomstom et al., *supra.* |
| **Pancreatic** | miR-10a | | | | | | Bloomstom et al., *supra.* |
| **Pancreatic** | mi R-146 | | | | | | Bloomstom et al., *supra.* |
| **Pancreatic** | miR-99 | | | | | | Bloomstom et al., *supra.* |
| **Pancreatic** | miR-100 | | | | | | Bloomstom et al., *supra.* |
| **Pancreatic** | miR-199a-1 | | | | | | Bloomstom et al., *supra.* |
| **Pancreatic** | miR-10b | | | | | | Bloomstom et al., *supra.* |
| **Pancreatic** | miR-199a-2 | | | | | | Bloomstom et al., *supra.* |
| **Pancreatic** | miR-107 | | | | | | Bloomstom et al., *supra.* |
| **Pancreatic** | miR-103-2 | | | | | | Bloomstom et al., *supra.* |
| **Pancreatic** | miR-125b-1 | | | | | | Bloomstom et al., *supra.* |
| **Pancreatic** | miR-205 | | | | | | Bloomstom et al., *supra.* |
| **Pancreatic** | miR-23a | | | | | | Bloomstom et al., *supra.* |
| **Pancreatic** | | miR-148a | | | | | Bloomstom et al., *supra.* |
| **Pancreatic** | | mIR-148b | | | | | Bloomstom et al., *supra.* |
| **Pancreatic** | | miR-375 | | | | | Bloomstom et al., *supra.* |
| **Pancreatic** | miR-221 | | | | | | Lee et al., 2006, J Biol Chem 281(5): 2649-53. |
| **Pancreatic** | miR-424 | | | | | | Lee at al., *supra.* |

FIG. 21b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Pancreatic | miR-301 | | | | | | Lee at al., *supra.* |
| Pancreatic | miR-100 | | | | | | Lee at al., *supra.* |
| Pancreatic | miR-376a | | | | | | Lee at al., *supra.* |
| Pancreatic | miR-125b-1 | | | | | | Lee at al., *supra.* |
| Pancreatic | miR-21 | | | | | | Lee at al., *supra.* |
| Pancreatic | | miR-345 | | | | | Lee at al., *supra.* |
| Pancreatic | miR-16-1 | | | | | | Lee at al., *supra.* |
| Pancreatic | miR-181a | | | | | | Lee at al., *supra.* |
| Pancreatic | miR-181c | | | | | | Lee at al., *supra.* |
| Pancreatic | miR-92 | | | | | | Lee at al., *supra.* |
| Pancreatic | miR-15 | | | | | | Lee at al., *supra.* |
| Pancreatic | | miR-142 | | | | | Lee at al., *supra.* |
| Pancreatic | miR-155 | | | | | | Lee at al., *supra.* |
| Pancreatic | let-7f-1 | | | | | | Lee at al., *supra.* |
| Pancreatic | miR-212 | | | | | | Lee at al., *supra.* |
| Pancreatic | miR-107 | | | | | | Lee at al., *supra.* |
| Pancreatic | miR-024-1/2 | | | | | | Lee at al., *supra.* |
| Pancreatic | let-7d | | | | | | Lee at al., *supra.* |
| Pancreatic | | miR-139 | | | | | Lee at al., *supra.* |
| Pancreatic | | | | KRAS | | | Shibata D et al., Baillieres Clin Gastroenterol. 1990 Mar;4(1):151-69. |
| Pancreatic | | | | CTNNLB1 | | | Shi C et al., Adv Anat Pathol. 2008 Jul;15(4):185-95. |
| Pancreatic | | | . | AKT | | | Kang SP and Siaf MW, JOP. J Pancreas (Online) 2008; 9(3):251-266. |
| Pancreatic | | | | NCOA3 | | | Kang SP and Siaf MW, *supra.* |
| Pancreatic | | | | B-RAF | | | Kang SP and Siaf MW, *supra* |
| Pancreatic | | | PSCA | | | | Koorstra JB et al., Pancreatology. 2008;8(2)110-25. Epub 2008 Apr 1. |
| Pancreatic | | | Meso-thelin | | | | Koorstra JB et al., *supra.* |
| Pancreatic | | | Osteo-pontin | | | | Koorstra JB et al., *supra.* |

FIG. 22

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Brain** | miR-21 | | | | | | Mathupala et al., 2007, DNA Cell Biol, 26(5): 301-10 |
| **Brain** | miR-10b | | | | | | Ciafre et al., 2005, Biochem Biophys Res 2005 Sep 9;334(4):1351. |
| **Brain** | miR-130a | | | | | | Ciafre et al., *supra.* |
| **Brain** | miR-221 | | | | | | Ciafre et al., *supra.* |
| **Brain** | miR-125b-1 | | | | | | Ciafre et al., *supra.* |
| **Brain** | miR-125b-2 | | | | | | Ciafre et al., *supra.* |
| **Brain** | miR-9-2 | | | | | | Ciafre et al., *supra.* |
| **Brain** | miR-21 | | | | | | Ciafre et al., *supra.* |
| **Brain** | miR-25 | | | | | | Ciafre et al., *supra.* |
| **Brain** | miR-23 | | | | | | Ciafre et al., *supra.* |
| **Brain** | | miR-128a | | | | | Ciafre et al., *supra.* |
| **Brain** | | miR-181c | | | | | Ciafre et al., *supra.* |
| **Brain** | | miR-181a | | | | | Ciafre et al., *supra.* |
| **Brain** | | miR-181b | | | | | Ciafre et al., *supra.* |
| **Brain** | | | MGMT | | | | Blank M et al., JBC May 11; 276(19)16464-8, 2001 |
| **Brain** | | | | | EGFR | | Hicke et al., J. Biol. Chem. 276, 48644-48654, 2001; Daniels et al., PNAS 100, 15416-15421, 2003 |

FIG. 23a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Psoriasis** | miR-146b | | | | | | Sonkoly et al., 2007, PLoS ONE, 2(7): e610 |
| **Psoriasis** | miR-20a | | | | | | Sonkoly et al., *supra.* |
| **Psoriasis** | miR-146a | | | | | | Sonkoly et al., *supra.* |
| **Psoriasis** | miR-31 | | | | | | Sonkoly et al., *supra.* |
| **Psoriasis** | miR-200a | | | | | | Sonkoly et al., *supra.* |
| **Psoriasis** | miR-17-5p | | | | | | Sonkoly et al., *supra.* |
| **Psoriasis** | miR-30e-5p | | | | | | Sonkoly et al., *supra.* |
| **Psoriasis** | miR-141 | | | | | | Sonkoly et al., *supra.* |
| **Psoriasis** | miR-203 | | | | | | Sonkoly et al., *supra.* |
| **Psoriasis** | miR-142-3p | | | | | | Sonkoly et al., *supra.* |
| **Psoriasis** | miR-21 | | | | | | Sonkoly et al., *supra.* |
| **Psoriasis** | miR-106a | | | | | | Sonkoly et al., *supra.* |
| **Psoriasis** | | miR-125b | | | | | Sonkoly et al., *supra.* |
| **Psoriasis** | | miR-99b | | | | | Sonkoly et al., *supra.* |
| **Psoriasis** | | miR-122a | | | | | Sonkoly et al., *supra.* |
| **Psoriasis** | | miR-197 | | | | | Sonkoly et al., *supra.* |
| **Psoriasis** | | miR-100 | | | | | Sonkoly et al., *supra.* |
| **Psoriasis** | | miR-381 | | | | | Sonkoly et al., *supra.* |
| **Psoriasis** | | miR-518b | | | | | Sonkoly et al., *supra.* |
| **Psoriasis** | | miR-524 | | | | | Sonkoly et al., *supra.* |
| **Psoriasis** | | let-7e | | | | | Sonkoly et al., *supra.* |
| **Psoriasis** | | miR-30c | | | | | Sonkoly et al., *supra.* |
| **Psoriasis** | | miR-365 | | | | | Sonkoly et al., *supra.* |
| **Psoriasis** | | miR-133b | | | | | Sonkoly et al., *supra.* |
| **Psoriasis** | | miR-10a | | | | | Sonkoly et al., *supra.* |
| **Psoriasis** | | miR-133a | • | | | | Sonkoly et al., *supra.* |
| **Psoriasis** | | miR-22 | | | | | Sonkoly et al., *supra.* |
| **Psoriasis** | | miR-326 | | | | | Sonkoly et al., *supra.* |
| **Psoriasis** | | miR-215 | | | | | Sonkoly et al., *supra.* |
| **Psoriasis** | | | IL-20 | | | | Stenderup K et al., Ann N Y Acad Sci. 2007 Sep;1110:368-81. |
| **Psoriasis** | | | VEGFR-1 | | | | Man XY et al., J Cell Mol Med. 2008 Apr;12(2):649-60 |
| **Psoriasis** | | | VEGFR-2 | | | | Man XY et al., *supra.* |
| **Psoriasis** | | | VEGFR-3 | | | | Man XY et al., *supra.* |

FIG. 23b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Psoriasis** | | | EGR1 | | | | Fang M et al., Genomic Med. 2007;1(1-2):75-85. Epub 2007 Jul 25 |
| **Psoriasis** | | | | MGST2 | | | Yan KL et al., J Invest Dermatol. 2006 May;126(5):1003-5. |

FIG. 24a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Cardiovascular Disease | | | | | CK-MB | | Wu AH et al., 1996, Clin Chem, 42(4): 651-2 |
| Cardiovascular Disease | | | | | cTnI (cardiac troponin) | | Wu AH et al., *supra.* |
| Cardiovascular Disease | | | | | C-reactive protein | | Rifai N and Ridker PM, Clin Chem. 2001 Mar;47(3):403-11. |
| Cardiovascular Disease | | | | | cardiac Troponin (cTn) | | O'Brien PJ, Toxicology. 2008 Mar 20;245(3):206-18. |
| Cardiovascular Disease | | | | | IL-6 | | Ikonomidis I et al., Atherosclerosis. 2008 Jul;199(1):3-11. |
| Cardiovascular Disease | | | | | MCSF | | Ikonomidis I et al., *supra.* |
| Cardiovascular Disease | | | | | BNP | | Wang TJ et al., N Engl J Med. 350 (7): 655-63 |
| Cardiovascular Disease | | miR-1 | | | | | van Rooij et al., 2008, Circ. Res, 103(9): 919-28 |
| Cardiovascular Disease | miR-195 | | | | | | van Rooij et al., *supra.* |
| Cardiovascular Disease | miR-208 | | | | | | van Rooij et al., *supra.* |
| Cardiovascular Disease | | miR-1 | | | | | Ikeda et al., 2007, Physiol Genomics 31(3): 367-73. |
| Cardiovascular Disease | miR-214 | | | | | | Ikeda et al., 2007, *supra.* |
| Cardiovascular Disease | let-7b | | | | | | Ikeda et al., *supra.* |
| Cardiovascular Disease | let-7c | | | | | | Ikeda et al., *supra.* |
| Cardiovascular Disease | let-7e | | | | | | Ikeda et al., *supra.* |
| Cardiovascular Disease | | miR-10a | | | | | Ikeda et al., *supra.* |
| Cardiovascular Disease | miR-15b | | | | | | Ikeda et al., *supra.* |
| Cardiovascular Disease | | miR-17-5p | | | | | Ikeda et al., *supra.* |
| Cardiovascular Disease | | miR-19a | | | | | Ikeda et al., *supra.* |
| Cardiovascular Disease | | miR-19b | | | | | Ikeda et al., *supra.* |
| Cardiovascular Disease | | miR-20a | | | | | Ikeda et al., *supra.* |
| Cardiovascular Disease | | miR-20b | | | | | Ikeda et al., *supra.* |

FIG. 24b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Cardiovascular Disease | miR-23a | | | | | | Ikeda et al., *supra.* |
| Cardiovascular Disease | miR-24 | | | | | | Ikeda et al., *supra.* |
| Cardiovascular Disease | | miR-26b | | | | | Ikeda et al., *supra.* |
| Cardiovascular Disease | miR-27a | | | | | | Ikeda et al., *supra.* |
| Cardiovascular Disease | miR-27b | | | | | | Ikeda et al., *supra.* |
| Cardiovascular Disease | | miR-28 | | | | | Ikeda et al., *supra.* |
| Cardiovascular Disease | | miR-30e-5p | | | | | Ikeda et al., *supra.* |
| Cardiovascular Disease | miR-93 | | | | | | Ikeda et al., *supra.* |
| Cardiovascular Disease | miR-99b | | | | | | Ikeda et al., *supra.* |
| Cardiovascular Disease | miR-100 | | | | | | Ikeda et al., *supra.* |
| Cardiovascular Disease | | miR-101 | | | | | Ikeda et al., *supra.* |
| Cardiovascular Disease | miR-103 | | | | | | Ikeda et al., *supra.* |
| Cardiovascular Disease | | miR-106a | | | | | Ikeda et al., *supra.* |
| Cardiovascular Disease | miR-125b | | | | | | Ikeda et al., *supra.* |
| Cardiovascular Disease | | miR-126 | | | | | Ikeda et al., *supra.* |
| Cardiovascular Disease | miR-140 | | | | | | Ikeda et al., *supra.* |
| Cardiovascular Disease | miR-145 | | | | | | Ikeda et al., *supra.* |
| Cardiovascular Disease | miR-181a | | | | | | Ikeda et al., *supra.* |
| Cardiovascular Disease | miR-191 | | | | | | Ikeda et al., *supra.* |
| Cardiovascular Disease | miR-195 | | | | | | Ikeda et al., *supra.* |
| Cardiovascular Disease | miR-199a | | | | | | Ikeda et al., *supra.* |
| Cardiovascular Disease | | miR-222 | | | | | Ikeda et al., *supra.* |
| Cardiovascular Disease | miR-320 | | | | | | Ikeda et al., *supra.* |
| Cardiovascular Disease | miR-342 | | | | | | Ikeda et al., *supra.* |

FIG. 24c

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Cardiovascular Disease** | | miR-374 | | | | | Ikeda et al., *supra.* |
| **Cardiovascular Disease** | | miR-422b | | | | | Ikeda et al., *supra.* |
| **Cardiovascular Disease** | | miR-423 | | | | | Ikeda et al., *supra.* |
| **Cardiovascular Disease** | miR-451 | | | | | | Ikeda et al., *supra.* |
| **Cardiovascular Disease** | miR-499 | | | | | | Ikeda et al., *supra.* |
| **Cardiovascular Disease** | | | | MYH7 | | | Buvoli M et al., Trends Cardiovasc Med. 2008 May;18(4):141-9. |
| **Cardiovascular Disease** | | | | SCN5A | | | Makita N et al., J Clin Invest. 2008 Jun;118(6):2219-29,. |
| **Cardiovascular Disease** | | | | CHRM2 | | | Zhang L et al., Circ Res. 2008 Jun 6;102(11):1426-32. Epub 2008 May 1. |
| **Cardiovascular Disease** | | | MRP14 | | | | Healy AM et al., Circulation 113:2278-2284, 2006. |
| **Cardiovascular Disease** | | | CD69 | | | | Healy AM et al., *supra.* |
| **Cardiovascular Disease** | | | | | CRP | | Moura LM et al., Expert Rev Cardiovasc Ther. 2008 Aug;6(7):945-54. |
| **Cardiovascular Disease** | | | | | BPN | | Moura LM et al., *supra.* |
| **Cardiovascular Disease** | | | | | CD40 & CD4OL | | Ferroni P and Guadagni F, Cardiovasc Hematol Disord Drug Targets. 2008 Sep;8(3):194-202. |

FIG. 25

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Hematological malignancies – TALL** | | | HOX11 | | | | Fernando et al., Cancer Cell, 1: 75-87, 2002. |
| **Hematological malignancies – TALL** | | | TAL1 | | | | Fernando et al., Cancer Cell, 1: 75-87, 2002. |
| **Hematological malignancies – TALL** | | | LY1 | | | | Fernando et al., Cancer Cell, 1: 75-87, 2002. |
| **Hematological malignancies – TALL** | | | LMO1 | | | | Fernando et al., Cancer Cell, 1: 75-87, 2002. |
| **Hematological malignancies – TALL** | | | LMO2 | | | | Fernando et al., Cancer Cell, 1: 75-87, 2002. |
| **Hematological malignancies** | | | | c-kit | | | Ravandi F et al., Clin Cancer Res. 2003 Feb;9(2):535-52 |
| **Hematological malignancies** | | | | PDGFR | | | Ravandi F et al., Clin Cancer Res. 2003 Feb;9(2):535-53 |
| **Hematological malignancies** | | | | ABL | | | Ravandi F et al., Clin Cancer Res. 2003 Feb;9(2):535-54 |

FIG. 26a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **B-Cell Chronic Lymphocytic Leukemias** | | miR-213 | | | | | Calin et al., 2004, Proc Natl Acad Sci U S A 101(32): 11755-60. |
| **B-Cell Chronic Lymphocytic Leukemias** | miR-183-prec | | | | | | Calin et al., *supra.* |
| **B-Cell Chronic Lymphocytic Leukemias** | miR-190 | | | | | | Calin et al., *supra.* |
| **B-Cell Chronic Lymphocytic Leukemias** | miR-24-1-prec | | | | | | Calin et al., *supra.* |
| **B-Cell Chronic Lymphocytic Leukemias** | miR-33 | | | | | | Calin et al., *supra.* |
| **B-Cell Chronic Lymphocytic Leukemias** | miR-19a | | | | | | Calin et al., *supra.* |
| **B-Cell Chronic Lymphocytic Leukemias** | miR-140 | | | | | | Calin et al., *supra.* |
| **B-Cell Chronic Lymphocytic Leukemias** | miR-123 | | | | | | Calin et al., *supra.* |
| **B-Cell Chronic Lymphocytic Leukemias** | miR-10b | | | | | | Calin et al., *supra.* |
| **B-Cell Chronic Lymphocytic Leukemias** | miR-15b-prec | | | | | | Calin et al., *supra.* |
| **B-Cell Chronic Lymphocytic Leukemias** | miR-92-1 | | | | | | Calin et al., *supra.* |
| **B-Cell Chronic Lymphocytic Leukemias** | miR-188 | | | | | | Calin et al., *supra.* |
| **B-Cell Chronic Lymphocytic Leukemias** | miR-154 | | | | | | Calin et al., *supra.* |
| **B-Cell Chronic Lymphocytic Leukemias** | | miR-220 | | | | | Calin et al., *supra.* |
| **B-Cell Chronic Lymphocytic Leukemias** | miR-217 | | | | | | Calin et al., *supra.* |
| **B-Cell Chronic Lymphocytic Leukemias** | miR-101 | | | | | | Calin et al., *supra.* |
| **B-Cell Chronic Lymphocytic Leukemias** | miR-141-prec | | | | | | Calin et al., *supra.* |
| **B-Cell Chronic Lymphocytic Leukemias** | miR-153-prec | | | | | | Calin et al., *supra.* |
| **B-Cell Chronic Lymphocytic Leukemias** | miR-196-2 | | | | | | Calin et al., *supra.* |
| **B-Cell Chronic Lymphocytic Leukemias** | miR-134 | | | | | | Calin et al., *supra.* |
| **B-Cell Chronic Lymphocytic Leukemias** | miR-141 | | | | | | Calin et al., *supra.* |
| **B-Cell Chronic Lymphocytic Leukemias** | miR-132 | | | | | | Calin et al., *supra.* |
| **B-Cell Chronic Lymphocytic Leukemias** | miR-192 | | | | | | Calin et al., *supra.* |

FIG. 26b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **B-Cell Chronic Lymphocytic Leukemias** | miR-181b-prec | | | | | | Calin et al., *supra.* |
| **B-Cell Chronic Lymphocytic Leukemias** | | | ZAP70 | IGHV | | | Plass C et al., 2007 British Journal of Haematology, 139, 744-752, " |
| **B-Cell Chronic Lymphocytic Leukemias** | | | | P53 | | | Plass C et al., *supra.* |
| **B-Cell Chronic Lymphocytic Leukemias** | | | | ATM | | | Plass C et al., *supra.* |
| **B-Cell Chronic Lymphocytic Leukemias** | | | AdipoR1 | | | | Molica S et al., 2008 Sep 27, Leuk Lymphoma 49(1): 62-7. |

FIG. 27

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **B-cell lymphoma** | | | | | | U50 | Tanaka et al., Genes Cells 5(4)277-87, 2000. |
| **B-cell lymphoma** | miR-17-92 polycistron | | | | | | Inomata M et al., Blood. 2008 Oct 21. |
| **B-cell lymphoma-DLBCL** | miR-155 | | | | | | Lawrie CH et al., Br J Haematol. 2008 May;141(5):672-5. |
| **B-cell lymphoma-DLBCL** | miR-210 | | | | | | Lawrie CH et al., Br J Haematol. 2008 May;141(5):672-5. |
| **B-cell lymphoma-DLBCL** | miR-21 | | | | | | Lawrie CH et al., Br J Haematol. 2008 May;141(5):672-5. |

FIG. 28

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **B-cell lymphoma-DLBCL-germinal center-like** | | | A-myb | | | | Rosenwald et al., 2002, Semin Oncol 29(3): 258-63. |
| **B-cell lymphoma-DLBCL-germinal center-like** | | | LMO2 | | | | Rosenwald et al., *supra.* |
| **B-cell lymphoma-DLBCL-germinal center-like** | | | JNK3 | | | | Rosenwald et al., *supra* |
| **B-cell lymphoma-DLBCL-germinal center-like** | | | CD10 | | | | Rosenwald et al., *supra* |
| **B-cell lymphoma-DLBCL-germinal center-like** | | | bcl-6 | | | | Rosenwald et al., *supra* |
| **B-cell lymphoma-DLBCL-activated B-cell-like** | | | Cyclin D2 | | | | Rosenwald et al., *supra* |
| **B-cell lymphoma-DLBCL-activated B-cell-like** | | | IRF4 | | | | Rosenwald et al., *supra.* |
| **B-cell lymphoma-DLBCL-activated B-cell-like** | | | Flip | | | | Rosenwald et al., *supra* |
| **B-cell lymphoma-DLBCL-activated B-cell-like** | | | CD44 | | | | Rosenwald et al., *supra* |
| **B-cell lymphoma-DLBCL** | miR-155 | | | | | | Lawrie CH et al., Br J Haematol. 2008 May;141(5):672-5. |
| **B-cell lymphoma-DLBCL** | miR-210 | | | | | | Lawrie CH et al., *supra.* |
| **B-cell lymphoma-DLBCL** | miR-21 | | | | | | Lawrie CH et al., *supra.* |

FIG. 29

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Burkitt's lymphoma** | | pri-miR-155 | | | | | Kluiver J et al., Oncogene. 2007 May 31;26(26):3769-76. |
| **Burkitt's lymphoma** | | | | | BCL6 | | Rosenwald, A & G. Ott, Ann Oncol. 2008 Jun;19 Suppl 4:iv67-9. |
| **Burkitt's lymphoma** | | | | | KI-67 | | Rosenwald, A & G. Ott, *supra.* |
| **Burkitt's lymphoma** | | | MYC | | | | Dave SS et al., N Engl J Med. 2006 Jun 8;354(23):2431-42. |
| **Burkitt's lymphoma** | | | TERT | | | | Dave et al., *supra.* |
| **Burkitt's lymphoma** | | | NS | | | | Dave et al., *supra.* |
| **Burkitt's lymphoma** | | | NP | | | | Dave et al., *supra.* |
| **Burkitt's lymphoma** | | | MAZ | | | | Dave et al., *supra.* |
| **Burkitt's lymphoma** | | | RCF3 | | | | Dave et al., *supra.* |
| **Burkitt's lymphoma** | | | BYSL | | | | Dave et al., *supra.* |
| **Burkitt's lymphoma** | | | IDES | | | | Dave et al., *supra.* |
| **Burkitt's lymphoma** | | | CDC7 | | | | Dave et al., *supra.* |
| **Burkitt's lymphoma** | | | TCL1A | | | | Dave et al., *supra.* |
| **Burkitt's lymphoma** | | | AUTS2 | | | | Dave et al., *supra.* |
| **Burkitt's lymphoma** | | | MYBL1 | | | | Dave et al., *supra.* |
| **Burkitt's lymphoma** | | | BMP7 | | | | Dave et al., *supra.* |
| **Burkitt's lymphoma** | | | ITPR3 | | | | Dave et al., *supra.* |
| **Burkitt's lymphoma** | | | CDC2 | | | | Dave et al., *supra.* |
| **Burkitt's lymphoma** | | | BACK2 | | | | Dave et al., *supra.* |
| **Burkitt's lymphoma** | | | TTK | | | | Dave et al., *supra.* |
| **Burkitt's lymphoma** | | | MME | | | | Dave et al., *supra.* |
| **Burkitt's lymphoma** | | | ALOX5 | | | | Dave et al., *supra.* |
| **Burkitt's lymphoma** | | | TOP1 | | | | Dave et al., *supra.* |

FIG. 30a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Hepatocellular Carcinoma** | | let-7a-1 | | | | | Gramantieri et al., 2007, Cancer Res 67(13): 6092-9 |
| **Hepatocellular Carcinoma** | | let-7a-2 | | | | | Gramantieri et al., *supra.* |
| **Hepatocellular Carcinoma** | | let-7a-3 | | | | . | Gramantieri et al., *supra.* |
| **Hepatocellular Carcinoma** | | let-7b | | | | | Gramantieri et al., *supra.* |
| **Hepatocellular Carcinoma** | | let-7c | | | - | | Gramantieri et al., *supra.* |
| **Hepatocellular Carcinoma** | | let-7d | | | | | Gramantieri et al., *supra.* |
| **Hepatocellular Carcinoma** | | let-7e | | | | | Gramantieri et al., *supra.* |
| **Hepatocellular Carcinoma** | | let-7f-2 | | | | | Gramantieri et al., *supra.* |
| **Hepatocellular Carcinoma** | | let-fg | | | | | Gramantieri et al., *supra.* |
| **Hepatocellular Carcinoma** | | miR-122a | | | | | Gramantieri et al., *supra.* |
| **Hepatocellular Carcinoma** | | miR-124a-2 | | | | | Gramantieri et al., *supra.* |
| **Hepatocellular Carcinoma** | | miR-130a | | | | | Gramantieri et al., *supra.* |
| **Hepatocellular Carcinoma** | | miR-132 | | | | | Gramantieri et al., *supra.* |
| **Hepatocellular Carcinoma** | | miR-136 | | | | | Gramantieri et al., *supra.* |
| **Hepatocellular Carcinoma** | | miR-141 | | | | | Gramantieri et al., *supra.* |
| **Hepatocellular Carcinoma** | | miR-142 | | | | | Gramantieri et al., *supra.* |
| **Hepatocellular Carcinoma** | | miR-143 | | | | | Gramantieri et al., *supra.* |
| **Hepatocellular Carcinoma** | | miR-145 | | | | | Gramantieri et al., *supra.* |
| **Hepatocellular Carcinoma** | | miR-146 | | | | | Gramantieri et al., *supra.* |
| **Hepatocellular Carcinoma** | | miR-150 | | | | | Gramantieri et al., *supra.* |
| **Hepatocellular Carcinoma** | | miR-155(BIC) | | | | | Gramantieri et al., *supra.* |
| **Hepatocellular Carcinoma** | | miR-181a-1 | | | | | Gramantieri et al., *supra.* |
| **Hepatocellular Carcinoma** | | miR-181a-2 | | | | | Gramantieri et al., *supra.* |

FIG. 30b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Hepatocellular Carcinoma** | | miR-181c | | | | | Gramantieri et al., *supra.* |
| **Hepatocellular Carcinoma** | | miR-195 | | | | | Gramantieri et al., *supra.* |
| **Hepatocellular Carcinoma** | | miR-199a-1-5p | | | | | Gramantieri et al., *supra.* |
| **Hepatocellular Carcinoma** | | miR-199a-2-5p | | | | | Gramantieri et al., *supra.* |
| **Hepatocellular Carcinoma** | | miR-199b | | | | | Gramantieri et al., *supra.* |
| **Hepatocellular Carcinoma** | | miR-200b | | | | | Gramantieri et al., *supra.* |
| **Hepatocellular Carcinoma** | | miR-214 | | | | | Gramantieri et al., *supra.* |
| **Hepatocellular Carcinoma** | miR-221 | | | | | | Gramantieri et al., *supra.* |
| **Hepatocellular Carcinoma** | | miR-223 | | | | | Gramantieri et al., *supra.* |
| **Hepatocellular Carcinoma** | | pre-mIR-594 | | | | | Gramantieri et al., *supra.* |
| **Hepatocellular Carcinoma** | | | FAT10 | | | | Lukasiak S et al., Methods Mol Biol. 2008;429:59-72. |

FIG. 31

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Cervical Cancer | | | HPV E6 | | | | Liang et al., Clin Oncol 134(8)899-907, 2008, "Galectin-9 |
| Cervical Cancer | | | HPV E7 | | | | |
| Cervical Cancer | | | p53 | | | | |

FIG. 32

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Endometrial Cancer** | miR-185 | miR-71 | | | | N/A | Boren T et al., Gynecologic Oncology 110 (2008) 206-215. |
| **Endometrial Cancer** | miR-106a | miR-221 | | | | | Boren et al., *supra.* |
| **Endometrial Cancer** | miR-181a | miR-193 | | | | | Boren et al., *supra.* |
| **Endometrial Cancer** | miR-210 | miR-152 | | | | | Boren et al., *supra.* |
| **Endometrial Cancer** | miR-423 | miR-30c | | | | | Boren et al., *supra.* |
| **Endometrial Cancer** | miR-103 | | | | - | | Boren et al., *supra.* |
| **Endometrial Cancer** | miR-107 | | | | | | Boren et al., *supra.* |
| **Endometrial Cancer** | let-7c | | | | | | Boren et al., *supra.* |
| **Endometrial Cancer** | | | | PTEN | | | Doll A et al., J Steroid Biochem Mol Biol. 2008 Feb;108(3-5):221-9. |
| **Endometrial Cancer** | | | | K-RAS | | | Doll et al., *supra.* |
| **Endometrial Cancer** | | | | B-catenin | | | Doll et al., *supra.* |
| **Endometrial Cancer** | | | | p53 | | | Doll et al., *supra.* |
| **Endometrial Cancer** | | | | Her2/neu | | | Doll et al., *supra.* |
| **Endometrial Cancer** | | | | | NLRP7 | | Ohno S et al., Anticancer Res. 2008 Jul-Aug;28(4C):2493-7. |
| **Endometrial Cancer** | | | | | AlphaV Beta6 integrin | | Hecht JL et al., Appl Immunohistochem Mol Morphol. 2008 Aug 11. |

FIG. 33a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Head and Neck Cancer** | | | HPV E6 | | | N/A | Ragin CC et al., J Dent Res. 2007 Feb;86(2):104-14 |
| **Head and Neck Cancer** | | | HPV E7 | | | | Ragin CC et al., *supra.* |
| **Head and Neck Cancer** | | | p53 | | | | van Houten VM et al., J Pathol. 2002 Dec;198(4):476-86. |
| **Head and Neck Cancer** | miR-21 | miR-494 | | | | | Chang SS et al., Int J Cancer. 2008 Sep 16;123(12):2791¬2797. |
| **Head and Neck Cancer** | let-7 | | | | | | Chang SS et al., *supra.* |
| **Head and Neck Cancer** | miR-18 | | | | | | Chang SS et al., *supra.* |
| **Head and Neck Cancer** | miR-29c | | | | | | Chang SS et al., *supra.* |
| **Head and Neck Cancer** | miR-142-3p | | | | | | Chang SS et al., *supra.* |
| **Head and Neck Cancer** | miR-155 | | | | | | Chang SS et al., *supra.* |
| **Head and Neck Cancer** | miR-146b | | | | | | Chang SS et al., *supra.* |
| **Head and Neck Cancer** | miR-205 | | | | | | Tran N et al., Biochem Biophys Res Commun. 2007 Jun 22;358(1):12-7. |
| **Head and Neck Cancer** | miR-21 | | | | | | Tran N et at, *supra.* |
| **Head and Neck Cancer** | | | | GSTM1 | | | Rusin P et al., Postepy Hg Med Dosw (Online). 2008 Sep 23;62:490-501. |
| **Head and Neck Cancer** | | | | GSTT1 | | | Rusin P et al., Postepy Hig Med Dosw (Online). 2008 Sep 23;62:490-501. |
| **Head and Neck Cancer** | | | | GSTP1 | | | Rusin P et al., *supra.* |
| **Head and Neck Cancer** | | | | OGG1 | | | Rusin P et al., *supra.* |
| **Head and Neck Cancer** | | | | XRCC1 | | | Rusin P et al., *supra.* |
| **Head and Neck Cancer** | | | | XPD | | | Rusin P et al., *supra.* |
| **Head and Neck Cancer** | | | | RAD51 | | | Rusin P et al., *supra.* |

FIG. 33b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Head and Neck Cancer** | | | IL-8 | | | | Palka KT et al., 2008, Semin Oncol 35(3): 198-210. |
| **Head and Neck Cancer** | | | SAT | | | | Palka KT et al., *supra.* |
| **Head and Neck Cancer** | | | H3FA3 | | | | Palka KT et al., *supra.* |
| **Head and Neck Cancer** | | | EGFR | EGFR | EGFR | | Sheikh Ali MA et al., Cancer Sci. 2008 Aug;99(8):1589-94 |
| **Head and Neck Cancer** | | | | p53 | | | Kanatas A and Harris A , Tumori 94(3): 444; author reply 444. |
| **Head and Neck Cancer** | | | | | | | Ferris RL and Grandis JR, Clinical Cancer Research 13, 5663-5664, October 1, 2007." |
| **Head and Neck Cancer** | | | | | EphB4 | | Yavrouian EJ et al., Arch Otolaryngol Head Neck Surg. 2008 Sep;134(9):985-91. |
| **Head and Neck Cancer** | | | | | EphrinB2 | | Yavrouian EJ et al., *supra.* |

FIG. 34

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Irritable Bowel Disease** | | | | | Il-16 | | Seegert D, et al., 2001, Gut, 48(3): 326-32 |
| **Irritable Bowel Disease** | | | | | Il-1 beta | | Seegert D, et al., *supra.* |
| **Irritable Bowel Disease** | | | | | Il-12 | | Seegert D, et al., *supra* |
| **Irritable Bowel Disease** | | | | | TNF-alpha | | Seegert D, et al., *supra* |
| **Irritable Bowel Disease** | | | | | interferon gamma | | Seegert D, et al., *supra* |
| **Irritable Bowel Disease** | | | | | Il-6 | | Seegert D, et al., *supra* |
| **Irritable Bowel Disease** | | | | | Rantes | | Seegert D, et al., *supra* |
| **Irritable Bowel Disease** | | | | | MCP-1 | | Seegert D, et al., *supra* |
| **Irritable Bowel Disease** | | | | CARD 15 | | | Li X et al., World J Gastroenterol. 2008 Sep 7;14(33):5115-24. |
| **Irritable Bowel Disease** | | | | | Resistin | | Li X et al., *supra.* |
| **Irritable Bowel Disease** | | | Trypsinogen IV | | | | Kerckhoffs AP et al., Neurogastroenterol Motil. 2008 Aug;20(8):900-7.." |
| **Irritable Bowel Disease** | | | | | 5-HT | | Kerckhoffs AP et al., *supra.* |

FIG. 35

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Diabetes** | | | IL-8 | | | | Nair S et al., Diabetologia. 2005 September; 48(9): 1784-1788. |
| **Diabetes** | | | CTSS | | | | Nair S et al., *supra.* |
| **Diabetes** | | | ITGB2 | | | | Nair S et al., *supra.* |
| **Diabetes** | | | HLA-DRA | | | | Nair S et al., *supra.* |
| **Diabetes** | | | CD53 | | | | Nair S et al., *supra.* |
| **Diabetes** | | | PLAG27 | | | | Nair S et al., *supra.* |
| **Diabetes** | | | MMP9 | | | | Nair S et al., *supra.* |
| **Diabetes** | | | | | RBP4 | . | Nair S et al., *supra.* |

FIG. 36

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Barrett's Esophagus | | | | p53 | p53 | | Hamelin R, et al., 1994, Gastroenterology, 107(4): 1012-8 |
| Barrett's Esophagus | miR-21 | | | | | | Watson DI, et al., 2007, World J Surg 31(3): 447-9. |
| Barrett's Esophagus | miR-143 | | | | | | Watson DI, et al., *supra*.. |
| Barrett's Esophagus | miR-145 | | | | | | Watson DI, et al., *supra*.. |
| Barrett's Esophagus | miR-194 | | | | | | Watson DI, et al., *supra*.. |
| Barrett's Esophagus | miR-215 | | | | | | Watson DI, et al., *supra*.. |
| Barrett's Esophagus | | | | | MUC1 | | Burjonrappa SC et al., Indian J Cancer. 2007 Jan-Mar;44(1):1-5. |
| Barrett's Esophagus | | | | | MUC2 | | Burjonrappa SC et al., *supra*. |
| Barrett's Esophagus | | | | | MUC6 | | Glickman JN et al., Am J Surg Pathol. 2003 Oct;27(10):1357- 65 |
| Barrett's Esophagus | | | S100A2 | | | | Lee OJ et al., Neoplasia. 2006 Oct;8(10):843-50 |
| Barrett's Esophagus | | | S100A4 | | | | Lee OJ et al., *supra*. |

FIG. 37

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Fibromyalgia** | | | NR2D | | | | Kim SH et al., J Rheumatol. 2006 Apr;33(4):785-8. |

FIG. 38

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Stroke** | | | MMP9 | | | | Sharp FR et al., Stroke. 2007 Feb;38(2 Suppl):691-3. |
| **Stroke** | | | S100-P | | | | Sharp FR et al., *supra.* |
| **Stroke** | | | S100A12 | | | | Sharp FR et al., *supra.* |
| **Stroke** | | | S100A9 | | | | Sharp FR et al., *supra.* |
| **Stroke** | | | coag factor V | | | | Sharp FR et al., *supra.* |
| **Stroke** | | | Arginasel | | | | Sharp FR et al., *supra.* |
| **Stroke** | | | CA-IV | | | | Sharp FR et al., *supra.* |
| **Stroke** | | | monocarboxylic acid transporter | | | | Sharp FR et al., *supra.* |
| **Stroke** | | | ets-2 | | | | Sharp FR et al., *supra.* |
| **Stroke** | | | EIF2alpha | | | | Sharp FR et al., *supra.* |
| **Stroke** | | | cytoskeleton associated protein 4 | | | | Sharp FR et al., *supra.* |
| **Stroke** | | | N-formylpeptide receptor | | | | Sharp FR et al., *supra.* |
| **Stroke** | | | Ribonuclease2 | | | | Sharp FR et al., *supra.* |
| **Stroke** | | | N-acetylneuraminate pyruvate lyase | | | | Sharp FR et al., *supra.* |
| **Stroke** | | | BCL-6 | | | | Sharp FR et al., *supra.* |
| **Stroke** | | | Glycogen phosphorylase | | | | Sharp FR et al., *supra.* |
| **Stroke** | | | | | Lp-PLA2 | | http://www.doctorslounge.com/neurology/news/stroke_lp-pla2_crp.shtml; Gorelick PB, Am J Cardiol. 2008 Jun 16;101(12A):34F-40F |
| **Stroke** | | | | | hs-CRP | | http://www.doctorslounge.com/neurology/news/stroke_lp-pla2_crp.shtml |

FIG. 39

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Multiple Sclerosis** | | | IL-6 | | | | Kinter J et al., Int MS J. 2008 Jun;15(2):51-8. |
| **Multiple Sclerosis** | | | IL-17 | | | | Tajouri L et al., Curr Genomics. 2007 May:8(3):181-9.. |
| **Multiple Sclerosis** | | | PAR-3 | | | | Tajouri L et al., *supra.* |
| **Multiple Sclerosis** | | | IL-17 | | | | Tajouri L et al., *supra* |
| **Multiple Sclerosis** | | | T1/ST2 | | | | Tajouri L et al., *supra* |
| **Multiple Sclerosis** | | | JunD | | | | Tajouri L et al., *supra* |
| **Multiple Sclerosis** | | | 5-LO | | | | Tajouri L et al., *supra* |
| **Multiple Sclerosis** | | | LTA4H | | | | Tajouri L et al., *supra* |
| **Multiple Sclerosis** | | | MBP | | | | Tajouri L et al., *supra* |
| **Multiple Sclerosis** | | | PLP | | | | Tajouri L et al., *supra* |
| **Multiple Sclerosis** | | | alpha-beta crystallin | | | | Tajouri L et al., *supra* |

FIG. 40a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Parkinsons Disease | | miR-133b | | | | | Kim J. et al., Science. 2007 Aug 31;317(5842):1220-4. |
| Parkinsons Disease | | | | FGF20 | | | Wang G. et al., 2008, FEBS Lett 582 (25-26): 3663-8 |
| Parkinsons Disease | | | | alpha-synuclein | | | Mizuta I. et al., 2008, Hum Genet, 124(1): 89-94 |
| Parkinsons Disease | | | | FGF20 | | | Mizuta I. et al., *supra.* |
| Parkinsons Disease | | | | NDUFV2 | | | Mizuta I. et al., *supra.* |
| Parkinsons Disease | | | | FGF2 | | | Mizuta I. et al., *supra.* |
| Parkinsons Disease | | | | CALB1 | | | Mizuta I. et al., *supra.v* |
| Parkinsons Disease | | | | B2M | | | Mizuta I. et al., *supra.* |
| Parkinsons Disease | | | Nurr1 | | | | Altar CA, Neuropsychopharm. 2008 Oct 15. |
| Parkinsons Disease | | | BDNF | | | | Altar CA, *supra.* |
| Parkinsons Disease | | | TrkB | | | | Altar CA, *supra.* |
| Parkinsons Disease | | | gstml | | | | Altar CA, *supra.* |
| Parkinsons Disease | | | S100 beta | | | | Altar CA, *supra.* |
| Parkinsons Disease | | | | | apo-H | | Shi M et al., Neurobiol Dis. 2008 Sep 26. |
| Parkinsons Disease | | | | | Ceruloplasmin | | Shi M et al., *supra.* |
| Parkinsons Disease | | | | | BDNF | | Zhang et al., 2008 Am. J. Clin. Pathol. 129, 526-9. |
| Parkinsons Disease | | | | | IL-8 | | Zhang et al., *supra.* |
| Parkinsons Disease | | | | | Beta2-microglobulin | | Zhang et al., *supra* |
| Parkinsons Disease | | | | | apoAII | | Zhang et al., *supra* |
| Parkinsons Disease | | | | | tau | | Zhang et al., *supra* |
| Parkinsons Disease | | | | | ABeta1-42 | | Zhang et al., *supra* |

FIG. 40b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Parkinsons Disease | | | | | DJ-1 | | Waragai et al., 2007 Neurosci. Lett. 425, 18¬22 & Waragai et al 2006 Biochem. Biophys. Res. Commun. 345, 967-72. |

FIG. 41

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Rheumatic Disease** | miR-146a | | | | | | Pauley KM et al., Arthritis Res Ther. 2008 Aug 29;10(4):R101. [Epub ahead of print]; Stanczyk J et al., Arthritis Rheum. 2008 Apr;58(4):1001-9. |
| **Rheumatic Disease** | miR-155 | | | | | | Pauley KM et al., *supra.*; Stanczyk J et al., *supra.* |
| **Rheumatic Disease** | mIR-132 | | | | | | Pauley KM et al., *supra.*; Stanczyk J et al., *supra.* |
| **Rheumatic Disease** | mIR-16 | | | | | | Pauley KM et al., *supra.*;Stanczyk J et al., *supra.* |
| **Rheumatic Disease** | miR-181 | | | | | | TiNat Clin Pract Rheumatol. 2008 Oct;4(10):534- 41. Epub 2008 Aug 26.ii E et al., |
| **Rheumatic Disease** | | | HOXD10 | | | | Galligan CL et al., Genes Immun. 2007 Sep;6(6):480-91. Epub 2007 Jun 14 . |
| **Rheumatic Disease** | | | HOXD11 | | | | Galligan CL et al., *supra.* |
| **Rheumatic Disease** | | | HOXD13 | | | | Galligan CL et al., *supra* |
| **Rheumatic Disease** | | | CCL8 | | | | Galligan CL et al., *supra* |
| **Rheumatic Disease** | | | LIM homeobox2 | | | | Galligan CL et al., *supra* |
| **Rheumatic Disease** | | | CENP-E | | | | Kullmann F et al., Arthritis Res. 1999;1(1):71-80. Epub 1999 Oct 26. |
| **Rheumatic Disease** | | | | | | | Anderson AK et al., Arthritis Res Ther. 2008;10(2):204. Epub 2008 Mar 14. |
| **Rheumatic Disease** | | | | | TNFalpha | | Anderson AK et al., *supra.* |

FIG. 42a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Alzheimers Disease | | | | APP | | | Vassar et al., 2005 Subcell. Biochem. 38, pp. 79–103. |
| Alzheimers Disease | | | | presenilin1 | | | Vassar et al., *supra.* |
| Alzheimers Disease | | | | presenilin2 | | | Vassar et al., *supra.* |
| Alzheimers Disease | | miR-107 | | | | | Wang WX et al., 2008, FEBS Lett. 582(25-26): 3663-8 |
| Alzheimers Disease | | miR-29a | | | | | Hebert SS et al., 2008, Proc Natl Aced Sci U.S.A., 105(17): 6415-20 |
| Alzheimers Disease | | miR-29b-1 | | | | | Hebert SS et al., *supra.* |
| Alzheimers Disease | | miR-9 | | | | | Hebert SS et al., *supra.* |
| Alzheimers Disease | | | | | BACE1 | | Hebert SS et al., *supra.* |
| Alzheimers Disease | | | HIF-1alpha | | | | Zhang et al., 2008 Am. J. Clin. Pathol. 129, 526-9. |
| Alzheimers Disease | | | BACE1 | | | | Zhang et al., *supra.* |
| Alzheimers Disease | | | | APOE4 | | | Thomas P and Fenech M, Mutagenesis. 2007 Jan;22(1):15-33. Epub 2006 Dec 8 |
| Alzheimers Disease | . | | Reelin | | Reelin | | Botella-Lopez A et al., Proc Nail Acad Sci U S A. 2006 Apr 4;103(14):5573-8. Epub 2006 Mar 27 |
| Alzheimers Disease | | | CHRNA 7 | | | | Altar CA, Neuropsychopharmacology. 2008 Oct 15. |
| Alzheimers Disease | | | 3Rtau/4 Rtau | | | | Altar CA, *supra.* |
| Alzheimers Disease | | | | | Cystatin C | | Simonsen et al., 2008 Neurobiol. Aging. 29, 961-8 |
| Alzheimers Disease | | | | | Truncated Cystatin C | | Simonsen et al., *supra.* |
| Alzheimers Disease | | | | | Amyloid Beta | | Simonsen et al., *supra.* |
| Alzheimers Disease | | | | | C3a | | Simonsen et al., *supra.* |

FIG. 42b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Alzheimers Disease** | | | | | t-Tau | | Simonsen et al., *supra.* |
| **Alzheimers Disease** | | | | | Complement factor H | | Hye et al., 2006 Brain. 129, 3042-50 |
| **Alzheimers Disease** | | | | | Alpha-2-macroglobulin | | Hye et al., *supra.* |

FIG. 43

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Prion Diseases** | | | | | PrP© | | Takemura K et al., Exp Biol Med (Maywood) Feb;231(2)204-14, 2006 |
| **Prion Diseases** | | | | | 14-3-3 | | Kubler E et al , British Medical Bulletin 66:267-279, 2003 |
| **Prion Diseases** | | | | | NSE | | Kubler E et al , British Medical Bulletin 66:267-279, 2003 |
| **Prion Diseases** | | | | | S-100 | | Kubler E et al , British Medical Bulletin 66:267-279, 2003 |
| **Prion Diseases** | | | | | Tau | | Kubler E et al , British Medical Bulletin 66:267-279, 2003 |
| **Prion Diseases** | | | | | AQP-4 | | Kubler E et al , British Medical Bulletin 66:267-279, 2003 |
| **Prion Diseases** | | | Amyloid B4 | | | | Tamguney G et al., J Gen Virol. 2008 Jul;89(Pt 7):1777-88 |
| **Prion Diseases** | | | App | | | | Tamguney G et al., J Gen Virol. 2008 Jul;89(Pt 7):1777-88 |
| **Prion Diseases** | | | IL-1R1 | | | | Tamguney G et al., J Gen Virol. 2008 Jul;89(Pt 7):1777-88 |
| **Prion Diseases** | | | SOD1 | | | | Tamguney G et al., J Gen Virol. 2008 Jul;89(Pt 7):1777-88 |

FIG. 44

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Sepsis** | | | 15-Hydroxy-PG dehydrogenase (up) | | | | Tang MP et al., Am J Respir Crit Care Med 176:676-684, 2007 |
| **Sepsis** | | | LAIR1 (up) | | | | Tang MP et al., *supra.* |
| **Sepsis** | | | NFKB1A (up) | | | | Tang MP et al., *supra.* |
| **Sepsis** | | | TLR2 | | | | Johnson SB et al., Annals of Surgery 245,Number 4, April 2007, 245(4): 611-21. |
| **Sepsis** | | | PGLYPRI | | | • | Johnson SB et al., *supra.* |
| **Sepsis** | | | TLR4 | | | | Johnson SB et al., *supra.* |
| **Sepsis** | | | MD2 | | | | Johnson SB et al., *supra.* |
| **Sepsis** | | | TLR5 | | | | Johnson SB et al., *supra.* |
| **Sepsis** | | | IFNAR2 | | | | Johnson SB et al., *supra.* |
| **Sepsis** | | | IRAK2 | | | | Johnson SB et al., *supra.* |
| **Sepsis** | | | IRAK3 | | | | Johnson SB et al., *supra.* |
| **Sepsis** | | | IRAK4 | | | | Johnson SB et al., *supra.* |
| **Sepsis** | | | PI3K | | | | Johnson SB et al., *supra.* |
| **Sepsis** | | | PI3KCB | • | | | Johnson SB et al., *supra.* |
| **Sepsis** | | | MAP2K6 | | | | Johnson SB et al., *supra.* |
| **Sepsis** | | | MAPK14 | | | | Johnson SB et al., *supra.* |
| **Sepsis** | | | NFKBIA | | | | Johnson SB et al., *supra.* |
| **Sepsis** | | | NFKB1 | | | | Johnson SB et al., *supra.* |
| **Sepsis** | | | IL1R1 | | | | Johnson SB et al., *supra.* |
| **Sepsis** | | | MAP2K1IP1 | | | | Johnson SB et al., *supra.* |
| **Sepsis** | | | MKNK1 | | | | Johnson SB et al., *supra.* |
| **Sepsis** | | | FAS | | | | Johnson SB et al., *supra.* |
| **Sepsis** | | | CASP4 | | | | Johnson SB et al., *supra.* |
| **Sepsis** | | | GADD45B | | | | Johnson SB et al., *supra.* |
| **Sepsis** | | | SOCS3 | | | | Johnson SB et al., *supra.* |
| **Sepsis** | | | TNFSF10 | | | | Johnson SB et al., *supra.* |
| **Sepsis** | | | TNFSF13B | | | | Johnson SB et al., *supra.* |
| **Sepsis** | | | OSM | | | | Johnson SB et al., *supra.* |
| **Sepsis** | | | HGF | | | | Johnson SB et al., *supra.* |
| **Sepsis** | | | IL18R1 | | | | Johnson SB et al., *supra.* |

FIG. 45

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Chronic Neuropathic Pain | | | ICAM-1 (rodent) | | | | Rodriguez Parkitna J et al., J Physiol Pharmacol. 2006 Sep;57(3):401-14. |
| Chronic Neuropathic Pain | | | CGRP (rodent) | | | | Rodriguez Parkitna J et al., J Physiol Pharmacol. 2006 Sep;57(3):401-14. |
| Chronic Neuropathic Pain | | | TIMP-1 (rodent) | | | | Rodriguez Parkitna J et al., J Physiol Pharmacol. 2006 Sep;57(3):401-14. |
| Chronic Neuropathic Pain | | | CLR-1 (rodent) | | | | Rodriguez Parkitna J et al., J Physiol Pharmacol. 2006 Sep;57(3):401-14. |
| Chronic Neuropathic Pain | | | HSP-27 (rodent) | | | | Kim DS et al., Neuroreport. 2001 Oct 29;12(15):3401-5 |
| Chronic Neuropathic Pain | | | FABP (rodent) | | | | Kim DS et al., Neuroreport. 2001 Oct 29;12(15):3401-5 |
| Chronic Neuropathic Pain | | | Apolipo-protein D (rodent) | | | | Kim DS et al., Neuroreport. 2001 Oct 29;12(15):3401-5 |
| Chronic Neuropathic Pain | | | | | Chemokines | | White FA et al., Proc Natl Acad Sci U S A. 2007 Dec 18;104(51):20151-8 |
| Chronic Neuropathic Pain | | | | | Chemokine receptor (CCR2/4) | | White FA et al., Proc Natl Acad Sci U S A. 2007 Dec 18;104(51):20151-8 |

FIG. 46

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Periperhal Neuropathic Pain** | | | | | OX42 (rodent) | | Blackbeard J et al., J Neurosci Methods. 2007 Aug 30;164(2):207-17 |
| **Periperhal Neuropathic Pain** | | | | | ED9 (rodent) | | Blackbeard J et al., J Neurosci Methods. 2007 Aug 30;164(2):207-17 |

FIG. 47

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Schizophrenia** | | | IFITM3 | | ATP5B | | Altar CA, Neuropsychopharm. 2008 Oct 15. |
| **Schizophrenia** | | | SERPINA3 | | ATP5H | | Altar CA, *supra.* |
| **Schizophrenia** | | | GLS | | ATP6V1B | | Altar CA, *supra.* |
| **Schizophrenia** | | | ALDH7A1B ASP1 | | DNM1 | | Altar CA, *supra.* |
| **Schizophrenia** | | | | | NDUFV2 | | Altar CA, *supra.* |
| **Schizophrenia** | | | | | NSF | | Altar CA, *supra.* |
| **Schizophrenia** | | | | | PDHB | | Altar CA, *supra.* |
| **Schizophrenia** | miR-181b | | | | | | Beveridge NJ et al., Hum Moi Genet. 2008 Apr 15;17(8):1156-68. Epub 2008 Jan 9 |
| **Schizophrenia** | | miR-7 | | | | | Perkins DO et al., Genome Biol. 2007;8(2):R27. |
| **Schizophrenia** | | miR-24 | | | | | Perkins DO et al., *supra.* |
| **Schizophrenia** | | miR-26b | | | | | Perkins DO et al., *supra* |
| **Schizophrenia** | | miR-29b | | | | | Perkins DO et al., *supra* |
| **Schizophrenia** | | miR-30b | | | | | Perkins DO et al., *supra* |
| **Schizophrenia** | | miR-30e | | | | | Perkins DO et al., *supra* |
| **Schizophrenia** | | miR-92 | | | | | Perkins DO et al., *supra* |
| **Schizophrenia** | | miR-195 | | | | | Perkins DO et al., *supra* |
| **Schizophrenia** | | | | DISCI | | | Millar JK et al., J Physiol. 2007 Oct 15;584(Pt 2):401-5. |
| **Schizophrenia** | | | | dysbindin | | | Chen XW et al., J Cell Biol. 2008 Jun 2;181(5):791-801 |
| **Schizophrenia** | | | | neuregulin-1 | | | Harrison PJ, Novartis Found Symp. 2007;288:246-55; discussion 255-9, 276-81 |
| **Schizophrenia** | | | | seratonin 2a receptor | | | Erdmann J et al., Volume 97, Number 5 / March, 1996 614-619 |
| **Schizophrenia** | | | | NURR1 | | | Buervenich Set al., Volume 96 Issue 6, Pages 808- 813 |

FIG. 48

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Bipolar Disorder** | | | FGF2 | | | | Altar CA, Neuropsychopharm. 2008 Oct 15. |
| **Bipolar Disorder** | | | ALDH7A1 | | | | Altar CA, *supra.* |
| **Bipolar Disorder** | | | AGXT2L1 | | | | Altar CA, *supra.* |
| **Bipolar Disorder** | | | AQP4 | | | | Altar CA, *supra.* |
| **Bipolar Disorder** | | | PCNT2 | | | | Anitha A et al., Biol Psychiatry. 2008 Apr 1;63(7):678-85. Epub 2007 Sep 20 |
| **Bipolar Disorder** | | | | Dysbindin | | | Goes FS et al., Curr Psychiatry Rep. 2008 Apr;10(2):178-89 "The genetics of psychotic bipolar disorder." |
| **Bipolar Disorder** | | | | DAOA/G30 | | | Goes FS et al., Curr Psychiatry Rep. 2008 Apr;10(2):178-89. |
| **Bipolar Disorder** | | | | DISCI | | | Goes FS et al., Curr Psychiatry Rep. 2008 Apr;10(2):178-89. |
| **Bipolar Disorder** | | | | neuregulin-1 | | | Goes FS et al., Curr Psychiatry Rep, 2008 Apr;10(2):178-89. |

FIG. 49

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Depression** | | | FGFR1 | | | | Altar CA, Neuropsychopharinacology. 2008 Oct 15. |
| **Depression** | | | FGFR2 | | | | Altar CA, Neuropsychopharmacology. 2008 Oct 15. |
| **Depression** | | | FGFR3 | | | | Altar CA, Neuropsychopharmacology. 2008 Oct 15. |
| **Depression** | | | AQP4 | | | | Altar CA, Neuropsychopharmacology. 2008 Oct 15. |

FIG. 50

| **Cancer Lineage, Group Comparison, Other Significant Disease State** | **Up-regulated miRs** | **Down-regulated miRs** | **mRNAs** | **Mutational Analysis** | **Proteins, Ligands, Peptides** | **snoRNA** | **Select Reference(s)** |
|---|---|---|---|---|---|---|---|
| **GIST** | | | | | PDGFRA | | Yang J et al., Cancer. 2008 Oct 1;113(7):1532-43 |
| **GIST** | | | | | c-kit | | Yang J et al., *supra.* |
| **GIST** | | | DOG-1 | | | | Espinosa F et al., Am J Surg Pathol Feb;32(2)210-8, 2008 |
| **GIST** | | | PKC-theta | PKC-theta | | | Blay P et al., CM Cancer Res. 2004 Jun 15;10(12 Pt 1):4089-95 |
| **GIST** | | | KIT | | | | Allander SV et al., Cancer Res. 2001 Dec 15;61(24):8624-8. |
| **GIST** | | | GPR20 | | | | Allander SV et al., *supra.* |
| **GIST** | | | PRKCQ | | | | Allander SV et al., *supra* |
| **GIST** | | | KCNK3 | | | | Allander SV et al., *supra* |
| **GIST** | | | KCNH2 | | | | Allander SV et al., *supra* |
| **GIST** | | | SCG2 | | | | Allander SV et al., *supra* |
| **GIST** | | | TNFRSF 6B | | | | Allander SV et al., *supra* |
| **GIST** | | | CD34 | | | | Allander SV et al., *supra* |

FIG. 51a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **RCC** | | Mir-141 | | | | | Nakada C et al., J Pathol. 2008 Aug 28 |
| **RCC** | | Mir200c | | | | | Nakada C et al., *supra.* |
| **RCC** | | | laminin receptor 1 | | | | Ohno Y et al., Oncol Rep. 2008 Sep;20(3):501-9. |
| **RCC** | | | betaig-h3 | | | | Ohno Y et al., *supra.* |
| **RCC** | | | | VHL | | | Nickerson ML et al., Clin Cancer Res. 2008 Aug 1;14(15):4726-34 |
| **RCC** | | | | | HIF1alpha | | Rathmell WK, Chen S, Expert Rev Anticancer Ther. 2008 Jan;8(1):63-73. |
| **RCC** | | | | | VEGF | | Rathmell WK, Chen S, *supra.* |
| **RCC** | | | | | PDGFRA | | Rathmell WK, Chen S, *supra.* |
| **RCC** | | | Galectin-1 | | | | Young AN, Am J Pathol. 2001 May;158(5):1639-51. |
| **RCC** | | | a-2 Macroglobulin | | | | Young AN, *supra.* |
| **RCC** | | | Adipophilin | | | | Young AN, *supra.* |
| **RCC** | | | Angiopoietin 2 | | | | Young AN, *supra.* |
| **RCC** | | . | Caldesmon 1 | | | | Young AN, *supra.* |
| **RCC** | | | Class II MHC-associated invariant chain (CD74) | | | | Young AN, *supra.* |
| **RCC** | | | Collagen IV-a1 | | | | Young AN, *supra.* |
| **RCC** | | | Complement component | | | | Young AN, *supra.* |
| **RCC** | | | Complement component 3 | | | | Young AN, *supra.* |

FIG. 51b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **RCC** | | | Cytochrome P450, subfamily IIJ polypeptide 2 | | | | Young AN, *supra.* |
| **RCC** | | | Delta sleep-Inducing peptide | | | | Young AN, *supra.* |
| **RCC** | | | Fc g receptor illa (CD16) | | | | Young AN, *supra.* |
| **RCC** | | | HLA-B | | | | Young AN, *supra.* |
| **RCC** | | | HLA-DR a | | | | Young AN, *supra.* |
| **RCC** | | | HLA-DR b | | | | Young AN, *supra.* |
| **RCC** | | | HLA-SB | | | | Young AN, *supra.* |
| **RCC** | | | IFN-induced transmembrane protein 3 | | | | Young AN, *supra.* |
| **RCC** | | | IFN-induced transmembrane protein 1 | | | | Young AN, *supra.* |
| **RCC** | | | Lysyl Oxidase | | | | Young AN, *supra.* |

FIG. 52

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Cirrhosis** | | | NLT | | | | Simonson GD et al., Journal of Cell Science 107, 1065-1072 (1994) |
| **Cirrhosis** | | | | | NLT | | Simonson GD et al., *supra.* |
| **Cirrhosis** | | | | | HBsAg | | Wang, W. et al., Hepatology. 1991 Jul;14(1):29-37. |
| **Cirrhosis** | | | | | AST | | Wai CT, et al. Hepatology. 2003;38:518-526. |
| **Cirrhosis** | | | | | YKL-40 | | Patel K, et al., Gastroenterology. 2004;126 (suppl 2):A-708. [S1645] |
| **Cirrhosis** | | | | | Hyaluronic acid | | Patel K, et al., *supra.* |
| **Cirrhosis** | | | | | TIMP-1 | | Patel K, et al., *supra.* |
| **Cirrhosis** | | | | | alpha 2 macroglobulin | | Patel K, et al., *supra.* |
| **Cirrhosis** | | | | | a-1-antitrypsin PI Z allele | | *Hum Hered* 1992;42:235-241 |
| **Cirrhosis** | | | | | haptoglobin | | *Hum Hered* 1992;42:235-241 |
| **Cirrhosis** | | | | | acid phosphatase ACP AC | | *Hum Hered* 1992;42:235-241 |

FIG. 53

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Esphageal cancer (adeno)** | miR-192 | miR-27b | | | | | Feber A et al., J Thorac Cardiovasc Surg. 2008 Feb;135(2):255-60 |
| **Esphageal cancer (adeno)** | miR-194 | miR-205 | | | | | Feber A et al., *supra.* |
| **Esphageal cancer (adeno)** | miR-21 | miR-203 | | | | | Feber A et al., *supra.* |
| **Esphageal cancer (adeno)** | miR-200c | miR-342 | | | | | Feber A et al., *supra.* |
| **Esphageal cancer (adeno)** | miR-93 | let-7c | | | | | Feber A et al., *supra.* |
| **Esphageal cancer (adeno)** | | miR-125b | | | | | Feber A et al., *supra.* |
| **Esphageal cancer (adeno)** | | miR-100 | | | | | Feber A et al., *supra.* |
| **Esphageal cancer (adeno)** | | miR-152 | | | | | Feber A et al., *supra.* |
| **Esphageal cancer (squamous)** | miR-342 | miR-192 | | | | | Feber A et al., *supra.* |
| **Esphageal cancer (squamous)** | miR-152 | miR-194 | | | | | Feber A et al., *supra.* |
| **Esphageal cancer (squamous)** | miR-93 | miR-27b | | | | | Feber A et al., *supra.* |
| **Esphageal cancer (squamous)** | | miR-205 | | | | | Feber A et al., *supra.* |
| **Esphageal cancer (squamous)** | | miR-203 | | | | | Feber A et al., *supra.* |
| **Esphageal cancer (squamous)** | | miR-200c | | | | | Feber A et al., *supra.* |
| **Esphageal cancer (squamous)** | | let-7c | | | | | Feber A et al., *supra.* |
| **Esphageal cancer (squamous)** | | miR-100 | | | | | Feber A et al., *supra.* |
| **Esphageal cancer** | miR-25 | miR-100 | | | | | Guo Y et al., Cancer Res. 2008 Jan 1;68(1):26-33. |
| **Esphageal cancer** | miR-424 | miR-99a | | | | | Guo Y et al., *supra.* |
| **Esphageal cancer** | miR-151 | miR-29c | | | | | Guo Y et al., *supra.* |
| **Esphageal cancer** | | miR-140 | | | | | Guo Y et al., *supra.* |
| **Esphageal cancer** | | miR-103 | | | | | Guo Y et al., *supra.* |
| **Esphageal cancer** | | miR-107 | | | | | Guo Y et al., *supra.* |
| **Esphageal cancer** | | | MTHFR | | | | Höfler H et al., Adv Exp Med Biol. 2006;587:115-20. |

FIG. 54

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Gastric cancer** | miR-106a | | | | | | Xiao B et al., Clin Chim Acta. 2008 Oct 30. |
| **Gastric cancer** | miR-21 | | | | | | Zhang Z et al., Lab Invest. 2008 Sep 15. |
| **Gastric cancer** | | let-7a | | | | | Zhang HH et al., World J Gastroenterol. 2007 May 28;13(20):2883-8. |
| **Gastric cancer** | miR-21 | | | | | | Volinia S et al., Proc Natl Acad Sci U S A. 2006 Feb 14;103(7):2257-61. |
| **Gastric cancer** | miR-191 | | | | | | Volinia S et al., Proc Natl Acad Sci U S A. 2006 Feb 14;103(7):2257-61. |
| **Gastric cancer** | miR-223 | | | | | | Volinia S et al., Proc Natl Acad Sci U S A. 2006 Feb 14;103(7):2257-61. |
| **Gastric cancer** | miR-24-1 | | | | | | Volinia S et al., Proc Natl Acad Sci U S A. 2006 Feb 14;103(7):2257-61. |
| **Gastric cancer** | miR-24-2 | | | | | | Volinia S et al., Proc Natl Acad Sci U S A. 2006 Feb 14;103(7):2257-61. |
| **Gastric cancer** | miR-107 | | | | | | Volinia S et al., Proc Natl Acad Sci U S A. 2006 Feb 14;103(7):2257-61. |
| **Gastric cancer** | miR-92-2 | | | | | | Volinia S et al., Proc Natl Acad Sci U S A. 2006 Feb 14;103(7):2257-61. |
| **Gastric cancer** | miR-214 | | | | | | Volinia S et al., Proc Natl Acad Sci U S A. 2006 Feb 14;103(7):2257-61. |
| **Gastric cancer** | miR-25 | | | | | | Volinia S et al., Proc Natl Acad Sci U S A. 2006 Feb 14;103(7):2257-61. |
| **Gastric cancer** | miR-221 | | | | | | Volinia S et al., Proc Natl Acad Sci U S A. 2006 Feb 14;103(7):2257-61. |
| **Gastric cancer** | | | RRM2 | | | | Kolesar J et al., Cancer Chemother Pharmacol. 2008 Oct 22. |
| **Gastric cancer** | | | EphA4 | | EphA4 | | Oki M et al., World J Gastroenterol. 2008 Oct 7;14(37):5650-6 |
| **Gastric cancer** | | | survivin | | | | Yie SM et al., Ann Surg Oncol. 2008 Nov;15(11):3073-82. |
| **Gastric cancer** | | | | APC | | | Lea IA et al., Carcinogenesis. 2007 September;28(9): 1851–1858. |

FIG. 55

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Autism** | | | | | GM1 | | Lekman et al., Acta Paediatrica 1995, vol. 84, no7, pp. 787-790. |
| **Autism** | | | | | GDIa | | Lekman et al., *supra.* |
| **Autism** | | | | | GDIb | | Lekman et al., *supra* |
| **Autism** | | | | | GTIb | | Lekman et al., *supra* |
| **Autism** | miR-484 | | | | | | Ablu-Elneel, Liu et al., Neurogenetics (2008) 9:153-161 |
| **Autism** | miR-21 | | | | | | Ablu-Elneel, Liu et al., *supra.* |
| **Autism** | miR-212 | | | | | | Ablu-Elneel, Liu et al., *supra.* |
| **Autism** | miR-23a | | | | | | Ablu-Elneel, Liu et al., *supra.* |
| **Autism** | miR-598 | | | | | | Ablu-Elneel, Liu et al., *supra.* |
| **Autism** | miR-95 | | | | | | Ablu-Elneel, Liu et al., *supra.* |
| **Autism** | miR-129 | | | | | | Ablu-Elneel, Liu et al., *supra.* |
| **Autism** | miR-431 | | | | | | Ablu-Elneel, Liu et al., *supra.* |
| **Autism** | miR-7 | | | | | | Ablu-Elneel, Liu et al., *supra.* |
| **Autism** | miR-15a | | | | | | Ablu-Elneel, Liu et al., *supra.* |
| **Autism** | miR-27a | | | | | | Ablu-Elneel, Liu et al., *supra.* |
| **Autism** | miR-15b | | | | | | Ablu-Elneel, Liu et al., *supra.* |
| **Autism** | miR-148b | | | | | | Ablu-Elneel, Liu et al., *supra.* |
| **Autism** | miR-132 | | | | | | Ablu-Elneel, Liu et al., *supra.* |
| **Autism** | miR-128 | | | | | | Ablu-Elneel, Liu et al., *supra.* |
| **Autism** | | miR-93 | | | | | Ablu-Elneel, Liu et al., *supra.* |
| **Autism** | | miR-106a | | | | | Ablu-Elneel, Liu et al., *supra.* |
| **Autism** | | miR-539 | | | | | Ablu-Elneel, Liu et al., *supra.* |
| **Autism** | | miR-652 | | | | | Ablu-Elneel, Liu et al., *supra.* |
| **Autism** | | miR-550 | | | | | Ablu-Elneel, Liu et al., *supra.* |
| **Autism** | | miR-432 | | | | | Ablu-Elneel, Liu et al., *supra.* |
| **Autism** | | miR-193b | | | | | Ablu-Elneel, Liu et al., *supra.* |
| **Autism** | | miR-181d | | | | | Ablu-Elneel, Liu et al., *supra.* |
| **Autism** | | miR-146b | | | | | Ablu-Elneel, Liu et al., *supra.* |
| **Autism** | | miR-140 | | | | | Ablu-Elneel, Liu et al., *supra.* |
| **Autism** | | miR-381 | | | | | Ablu-Elneel, Liu et al., *supra.* |
| **Autism** | | miR-320a | | | | | Ablu-Elneel, Liu et al., *supra.* |
| **Autism** | | miR-106b | | | | | Ablu-Elneel, Liu et al., *supra.* |

FIG. 56

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Organ Rejection** | | | | | matrix metallo-protein-9 | | American Physiological Society (2006, November 4). Proteins May Predict Lung Transplant Rejection. ScienceDaily. Retrieved |
| **Organ Rejection** | | | | | proteinase 3 | | American Physiological Society, *supra.* |
| **Organ Rejection** | | | | | HNP | | American Physiological Society, *supra.* |
| **Organ Rejection** | miR-658 | | | | | | W. Sui et al., Transplant Immunology 19 (2008) 81-85 |
| **Organ Rejection** | miR-125a | | | | | | W. Sui et al.., *supra.* |
| **Organ Rejection** | miR-320 | | | | | | W. Sui et al.., *supra.* |
| **Organ Rejection** | miR-381 | | | | | | W. Sui et al.., *supra.* |
| **Organ Rejection** | miR-628 | | | | | | W. Sui et al.., *supra.* |
| **Organ Rejection** | miR-602 | | | | | | W. Sui et al.., *supra.* |
| **Organ Rejection** | miR-629 | | | | | | W. Sui et al.., *supra.* |
| **Organ Rejection** | miR-125a | | | | | | W. Sui et al.., *supra.* |
| **Organ Rejection** | | miR-324-3p | | | | | W. Sui et al.., *supra.* |
| **Organ Rejection** | | miR-611 | | | | | W. Sui et al.., *supra.* |
| **Organ Rejection** | | miR-654 | | | | | W. Sui et al.., *supra.* |
| **Organ Rejection** | | miR-330_MM1 | | | | | W. Sui et al.., *supra.* |
| **Organ Rejection** | | miR-524 | | | | | W. Sui et al.., *supra.* |
| **Organ Rejection** | | miR-17-3p_MM1 | | | | | W. Sui et al.., *supra.* |
| **Organ Rejection** | | miR-483 | | | | | W. Sui et al.., *supra.* |
| **Organ Rejection** | | miR-663 | | | | | W. Sui et al.., *supra.* |
| **Organ Rejection** | | miR-516-5p | | | | | W. Sui et al.., *supra.* |
| **Organ Rejection** | | miR-326 | | | | | W. Sui et al.., *supra.* |
| **Organ Rejection** | | miR-197_MM2 | | | | | W. Sui et al.., *supra.* |
| **Organ Rejection** | | miR-346 | | | | | W. Sui et al.., *supra.* |

FIG. 57

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **methicillin-resistant Staphylococcus aureus** | | | | | ETA | | M. Ben Nejma et al.., Diagnostic Microbiology and Infectious Disease 55 (2006) 21– 25 |
| **methicillin-resistant Staphylococcus aureus** | | | | | ETB | | M. Ben Nejma et al. / Diagnostic Microbiology and Infectious Disease 55 (2006) 21– 26 |
| **methicillin-resistant Staphylococcus aureus** | | | | | TSST-1 | | M. Ben Nejma et al. / Diagnostic Microbiology and Infectious Disease 55 (2006) 21– 27 |
| **methicillin-resistant Staphylococcus aureus** | | | | | leukocidins | | M. Ben Nejma et al. / Diagnostic Microbiology and Infectious Disease 55 (2006) 21– 28 |
| **methicillin-resistant Staphylococcus aureus** | | | | mecA | | | M. Ben Nejma et al. / Diagnostic Microbiology and Infectious Disease 55 (2006) 21– 29 |
| **methicillin-resistant Staphylococcus aureus** | | | | Protein A SNPs | | | Frénay HM et al., J Clin Microbiol. 1994 Mar;32(3):846-7. |
| **methicillin-resistant Staphylococcus aureus** | | | TSST-1 | | | | Chini V et al., Lett Appl Microbiol. 2007 Nov;45(5):479-84. |

FIG. 58

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Vulnerable plaque** | | | | | IL-6 | | Maier W et al., 2005 Circulation 111:1355-1361. |
| **Vulnerable plaque** | | | | | MMP-9 | | Blankenberg S et al., 2003 Circulation 107:1579-1585. |
| **Vulnerable plaque** | | | | | PAPP-A | | Elesber AA et al., 2006 Eur Heart J 27:1678-1684. |
| **Vulnerable plaque** | | | | | D-dimer | | Danesh j et al., JAMA 2005, 294:1799-1809, Danesh J, Circulation 2001, 103:2323-2327 |
| **Vulnerable plaque** | | | | | fibrinogen | | Danesh et al. 2005, Danesh et al. 2001 |
| **Vulnerable plaque** | | | | | Lp-PLA2 | | Zalewski A et al., Arterioscler Thromb Vasc Biol. 2005;25:923-931 |
| **Vulnerable plaque** | | | | | SCD40L | | Koenig W and Khuseyinova N, Arterioscler Thromb Vasc Biol. 2007;27:15-26. |
| **Vulnerable plaque** | | | | | IL-18 | | Koenig W and Khuseyinova N, Arterioscler Thromb Vasc Biol. 2007;27:15-26. |
| **Vulnerable plaque** | | | | | oxLDL | | Koenig W and Khuseyinova N, Arterioscler Thromb Vasc Biol. 2007;27:15-26. |
| **Vulnerable plaque** | | | | | GPx-1 | | Koenig W and Khuseyinova N, Arterioscler Thromb Vasc Biol. 2007;27:15-26. |
| **Vulnerable plaque** | | | | | MCP-1 | | Koenig W and Khuseyinova N, Arterioscler Thromb Vasc Biol. 2007;27:15-26. |
| **Vulnerable plaque** | | | | | PIGF | | Koenig W and Khuseyinova N, Arterioscler Thromb Vasc Biol. 2007;27:15-26. |
| **Vulnerable plaque** | | | | | CRP | | Koenig W and Khuseyinova N, Arterioscler Thromb Vasc Biol. 2007;27:15-26. |

FIG. 59a

| 5' Upstream Fusion Gene Partner | 3' downstream Fusion Gene Partner | Cancer Lineage |
|---|---|---|
| ACSL3 | ETV1 | Prostate cancer |
| AKAP9 | BRAF | Papillary thyroid carcinoma |
| Alpha | TFEB | Renal cell carcinoma |
| ARHGAP20 | BRWD3 | B-cell chronic lymphocytic leukemia (B-CLL) |
| ASPSCR1 | TFE3 | Renal-cell carcinoma |
| ATIC | ALK | Anaplastic large cell lymphoma (ALCL) |
| BCL11B | TLX3 | T-cell acute lymphoblastic / lymphocytic leukemia (T-ALL) |
| BCL3 | MYC | B-cell chronic lymphocytic leukemia (B-CLL) |
| BCL7A | MYC | B-cell chronic lymphocytic leukemia (B-CLL) |
| BCR | ABL1 | Chronic myelogenous leukemia (CML) |
| BCR | FGFR1 | CML-like Myeoproliferative disorder (MPD) |
| BCR | JAK2 | Chronic myelogenous leukemia (CML) |
| BCR | PDGFRA | Atypical CML |
| BIRC3 | MALT1 | B-cell non Hodgkin lymphoma, MALT-lymphomas |
| BRD4 | NUT | Poorly differenitated epithelial carcinoma (Aggressive midline carcinoma) |
| BRWD3 | ARHGAP20 | B-cell chronic lymphocytic leukemia (B-CLL) |
| BTG1 | MYC | B-cell chronic lymphocytic leukemia (B-CLL) |
| CARS | ALK | Inflammatory myofibroblastic tumor |
| CANT1 | ETV4 | Prostate cancer |
| CBFB | MYH11 | Acute myelogenous leukemia (AML) |
| CCDC6 | PDGFRB | Philadelphia chr negative Myeoproliferative disorder (MPD) |
| CCDC6 | RET | Pappilary thyroid carcinoma |
| CCND1 | FSTL3 | Chronic myelogenous leukemia (CML) |
| CD74 | ROS1 | Non small cell lung carcinoma (NSCLC) |
| CDH11 | USP6 | Aneurysmal bone cyst |
| CDK6 | EVI1 | Myeolid leukemia |
| CDK6 | MLL | Acute lymphoblastic / lymphocytic leukemia (ALL) |
| CDK6 | TLX3 | Acute lymphoblastic / lymphocytic leukemia (ALL) |
| CEP110 | FGFR1 | Myeloproliferative disorder (Myeoproliferative disorder (MPD)) |
| CHCHD7 | PLAG1 | Pleomorphic salivary gland adenomas (PA) (Head and Neck) |
| CHIC2 | ETV6 | Acute myelogenous leukemia (AML) |
| CIITA | BCL6 | Diffuse large B-cell lymphoma (DLBCL) |
| CLTC | ALK | Diffuse large B-cell lymphoma (DLBCL) |
| CLTC | TFE3 | Pediatric renal adenocarcinoma |
| C15ORF21 | ETV1 | Prostate cancer |
| COL1A1 | PDGFB | Dermatofibrosarcoma protuberans |
| COL1A1 | USP6 | Aneurysmal bone cyst |
| COL1A2 | PLAG1 | Lipoblastoma |

FIG. 59b

| 5' Upstream Fusion Gene Partner | 3' downstream Fusion Gene Partner | Cancer Lineage |
|---|---|---|
| CRC1 | MAML2 | Mucoepidermoid carcinoma |
| CRTC1 | MAML2 | Mucoepidermoid carcinomas , Warthin's tumor |
| CRTC3 | MAML2 | Mucoepidermoid carcinoma |
| CTNNB1 | PLAG1 | Pleomorphic salivary gland adenomas (PA) (Head and Neck) |
| DDX5 | ETV4 | Prostate cancer |
| EIF4A2 | BCL6 | Non-Hodgkin lymphoma (NHL) |
| EML1 | ABL1 | T-cell acute lymphoblastic / lymphocytic leukemia (T-ALL) |
| EML4 | ALK | Non small cell lung carcinoma (NSCLC) |
| EPC1 | PHF1 | Endometiral stromal sarcoma |
| ERC1 | RET | Papillary thyroid carcinoma |
| ETV6 | ABL1 | Chronic myelogenous leukemia (CML), Acute myelogenous leukemia (AML), Acute lymphoblastic / lymphocytic leukemia (ALL) |
| ETV6 | ABL2 | T-cell acute lymphoblastic / lymphocytic leukemia (T-ALL), Acute myelogenous leukemia (AML) |
| ETV6 | ACSL6 | Polycythemia vera |
| ETV6 | ARNT | Acute myelogenous leukemia (AML) |
| ETV6 | CDX2 | Acute myelogenous leukemia (AML) |
| ETV6 | EVI1 | Chronic myelogenous leukemia (CML) |
| ETV6 | FGFR3 | Peripheral T-cell lymphoma |
| ETV6 | FLT3 | ALL, Myeoproliferative disorder (MPD) |
| ETV6 | HLXB9 | Acute myelogenous leukemia (AML) |
| ETV6 | JAK2 | Philadelphia chr negative Myeoproliferative disorder (MPD), B cell malignancies |
| ETV6 | MDS2 | Myelodisplastic syndrome |
| ETV6 | MN1 | Chronic myelogenous leukemia (CML) |
| ETV6 | NTRK3 | Secretory breast cancer |
| ETV6 | PDGFRB | Chronic myelomonocytic leukemia (CMML) |
| ETV6 | PER1 | Acute myelogenous leukemia (AML) |
| ETV6 | RUNX1 | Acute lymphoblastic / lymphocytic leukemia (ALL) |
| ETV6 | SYK | Myelodisplastic syndrome |
| ETV6 | TCBA1 | Chronic myelogenous leukemia (CML) |
| ETV6 | TTL | Acute lymphoblastic / lymphocytic leukemia (ALL) |
| EWSR1 | ATF1 | Soft tissue sarcoma |
| EWSR1 | DDIT3 | Myxoid liposarcoma |
| EWSR1 | ERG | Ewing sarcomas |
| EWSR1 | ETV1 | Ewing sarcomas |
| EWSR1 | ETV4 | Ewing sarcomas |
| EWSR1 | FEV | Ewing sarcomas |
| EWSR1 | FLI1 | Ewing sarcomas |

FIG. 59c

| 5' Upstream Fusion Gene Partner | 3' downstream Fusion Gene Partner | Cancer Lineage |
|---|---|---|
| EWSR1 | NR4A3 | Malignant tumor of soft tissue origin |
| EWSR1 | POU5F1 | Undifferentiated bone tumor |
| EWSR1 | TEC | Ewing sarcomas |
| EWSR1 | WT1 | Soft tissue sarcoma |
| EWSR1 | ZNF278 | Small round cell sarcoma |
| EWSR1 | ZNF384 | Acute lymphoblastic leukemia |
| FGFR1OP | FGFR1 | Stem-cell myeloproliferative disorder characterized by myeloid hyperplasia, T -cell lymphoblastic leukemia/lymphoma and peripheral blood eosinophilia, and it generally progresses to acute myeloid leukemia; |
| FGFR1OP2 | FGFR1 | Myeoproliferative disorder (MPD) is characterized by myeloid hyperplasia, eosinophilia and T-cell or B-cell lymphoblastic lymphoma |
| FHIT | HMGA2 | Pleomorphic salivary gland adenomas (PA) (Head and Neck) |
| FIP1L1 | PDGFRA | Hypereosinophilia |
| FLT3 | ETV6 | Hypereosinophilia |
| FLJ35294 | ETV1 | Prostate cancer |
| FUS | ATF1 | Angiomatoid fibrous histiocytoma (AFH) |
| FUS | CREB3L1 | Fibromyxoid sarcoma |
| FUS | CREB3L2 | Low-grade fibromyxoid sarcoma (LGFMS) |
| FUS | DDIT3 | Myxoid liposarcoma |
| FUS | DDIT3 | The Myxoid/Round Cell Liposarcoma |
| FUS | ERG | Ewing sarcomas |
| GAPDH | BCL6 | B-cell non hodgkin lymphoma (B-NHL), Diffuse large B-cell lymphoma (DLBCL) |
| GOLGA5 | RET | Papillary thyroid carcinoma |
| GOPC | ROS1 | Glioblastoma |
| HAS2 | PLAG1 | Lipoblastoma |
| HERV | ETV1 | Prostate cancer |
| HIP1 | PDGFRB | Chronic myelomonocytic leukemia (CMML) |
| HIST1H4I | BCL6 | B-cell Non-Hodgkin lymphoma (NHL) (NHL) |
| HMGA1 | LAMA4 | Pulmonary chondroid hamartoma |
| HMGA2 | CCNB1IP1 | Benign mesenchymal tumors |
| HMGA2 | COX6C | Uterine leiomyoma |
| HMGA2 | CXCR7 | Lipoma |
| HMGA2 | FHIT | Pleomorphic salivary gland adenomas (PA) (Head andNeck) |
| HMGA2 | LHFP | Solitary lipomas |
| HMGA2 | LPP | Lipoma, parosteal lipoma, and pulmonary chondroid hamartoma |
| HMGA2 | NFIB | Pleomorphic salivary gland adenomas (PA) (Head and Neck) |
| HMGA2 | RAD51L1 | Uterine leiomyomata |

FIG. 59d

| 5' Upstream Fusion Gene Partner | 3' downstream Fusion Gene Partner | Cancer Lineage |
|---|---|---|
| HNRPA2B1 | ETV1 | Prostate cancer |
| HOOK3 | RET | Pappilary thyroid carcinoma |
| HRH4 | RET | Pappilary thyroid carcinoma |
| HSP90AA1 | BCL6 | B cell Non-Hodgkin lymphoma (NHL) (B-NHL) |
| HSP90AB1 | BCL6 | B-cell tumors |
| IGH | MYC | Burkitt's lymphoma |
| IKZF1 | BCL6 | Diffuse large B-cell lymphoma (DLBCL) |
| IL2 | TNFRSF17 | T-cell acute lymphoblastic leukemia (T-ALL) |
| IL21R | BCL6 | Diffuse large B-cell lymphoma (DLBCL) |
| ITK | SYK | Unspecified peripheral T-cell lymphoma |
| JAZF1 | PHF1 | Endometrial stromal sarcomas |
| JAZF1 | SUZ12 | endometrial stromal tumors and endometrial stromal sarcoma |
| KIAA1509 | PDGFRA | Chronic eosinophilic leukemia (CEL) |
| KIAA1618 | ALK | Anaplastic large-cell lymphoma (ALCL) |
| KLK2 | ETV4 | Prostate cancer |
| KTN1 | RET | Papillary thyroid carcinoma |
| LCP1 | BCL6 | Non Hodgkin follicular, Burkitt lymphomas |
| LIFR | PLAG1 | Pleomorphic salivary gland adenomas (PA) (Head and Neck) |
| MALAT1 | TFEB | Pediatric renal neoplasm |
| MEF2D | DAZAP1 | Acute myelogenous leukemia (AML) |
| MLL | ABI1 | acute non lymphoblastic leukemia |
| MLL | AFF1 | Acute lymphoblastic / lymphocytic leukemia (ALL), Acutemyelogenous leukemia (AML) |
| MLL | AFF3 | Acute lymphoblastic / lymphocytic leukemia (ALL) |
| MLL | AFF4 | Acute lymphoblastic / lymphocytic leukemia (ALL) |
| MLL | ARHGAP26 | Acute monocytic leukemia (Acute myelogenous leukemia (AML) (M5b) |
| MLL | ARHGEF12 | Acute myelogenous leukemia (AML) |
| MLL | CASC5 | Acute myelogenous leukemia (AML) |
| MLL | CBL | Acute myelogenous leukemia (AML) |
| MLL | CLP1 | Monoblastic leukemia |
| MLL | CREBBP | Acute myelogenous leukemia (AML) |
| MLL | CXXC6 | Acute lymphoblastic / lymphocytic leukemia (ALL) |
| MLL | DAB2IP | Acute myelogenous leukemia (AML) |
| MLL | ELL | Acute myelogenous leukemia (AML) |
| MLL | EP300 | Acute myelogenous leukemia (AML) |
| MLL | EPS15 | Acute myelogenous leukemia (AML) |
| MLL | FNBP1 | Acute myelogenous leukemia (AML) |
| MLL | FOXO3A | Acute myelogenous leukemia (AML) |

FIG. 59e

| 5' Upstream Fusion Gene Partner | 3' downstream Fusion Gene Partner | Cancer Lineage |
|---|---|---|
| MLL | GAS7 | Acute lymphoblastic / lymphocytic leukemia (ALL) |
| MLL | GMPS | Acute myelogenous leukemia (AML) |
| MLL | GPHN | Acute myelogenous leukemia (AML) |
| MLL | LASP1 | Infant acute myeloid leukemia Acute myelogenous leukemia (AML)-M4 |
| MLL | LPP | Secondary acute leukemia |
| MLL | MAPRE1 | Pro-B acute lymphoblastic leukemia |
| MLL | MLL | Acute myeloid and lymphoid leukemia |
| MLL | MLLT1 | Acute myelogenous leukemia (AML) |
| MLL | MLLT10 | Pediatric acute megakaryoblastic leukemia AND acute monoblastic leukemia |
| MLL | MLLT11 | Acute myelogenous leukemia (AML) |
| MLL | MLLT3 | Acute myelogenous leukemia (AML) |
| MLL | MLLT4 | M4/M5 ANLL |
| MLL | MLLT6 | Acute myelogenous leukemia (AML) |
| MLL | MLLT7 | Acute leukemias |
| MLL | MYO1F | Acute myelogenous leukemia (AML) |
| MLL | PICALM | Acute myelogenous leukemia (AML) |
| MLL | RARA | M5 acute non lymphocytic leukemia (ANLL) |
| MLL | SEPT11 | Chronic neutrophilic leukemia |
| MLL | SEPT2 | Acute myelogenous leukemia (AML), therapy-related myelodysplastic syndrome |
| MLL | SEPT5 | De novo acute non lymphocytic leukemia |
| MLL | SEPT6 | Acute myelogenous leukemia (AML) |
| MLL | SEPT9 | Myeloid neoplasia |
| MLL | SH3GL1 | Acute leukemia |
| MLL | SORBS2 | Acute myelogenous leukemia (AML) |
| MLL | ZFYVE19 | Acute myelogenous leukemia (AML) |
| MSI2 | HOXA9 | Chronic myelogenous leukemia (CML) |
| MSN | ALK | Anaplastic large cell lymphoma (ALCL) |
| MYC | BCL7A | High-grade B cell Non-Hodgkin lymphoma (NHL) |
| MYC | BTG1 | B-cell chronic lymphocytic leukemia (B-CLL) |
| MYH9 | ALK | Anaplastic large cell lymphoma (ALCL) |
| MYST3 | ASXL2 | Therapy-related myelodysplastic syndrome |
| MYST3 | CREBBP | Acute myelogenous leukemia (AML) |
| MYST3 | EP300 | Acute myelomonocytic or monocytic leukaemia (M4 or M5 Acute myelogenous leukemia (AML)) |
| MYST3 | NCOA2 | Acute leukemia |
| MYST4 | CREBBP | Acute myelogenous leukemia (AML) |
| NACA | BCL6 | Non-Hodgkin lymphoma (NHL) |

FIG. 59f

| 5' Upstream Fusion Gene Partner | 3' downstream Fusion Gene Partner | Cancer Lineage |
|---|---|---|
| NCOA4 | RET | Papillary thyroid carcinoma |
| NIN | PDGFRB | Chronic myeloprolifetrative disorder with eosinophilia |
| NONO | TFE3 | Renal cell carcinoma |
| NPM1 | ALK | Anaplastic large-cell lymphomas (ALCL) |
| NPM1 | MLF1 | Acute myelogenous leukemia (AML) |
| NPM1 | RARA | Acute promyelocytic leukemia (APML) |
| NUMA1 | RARA | Atypical M3 acute non lyphoblastic leukemia (ANLL) |
| NUP214 | ABL1 | T-cell acute lymphoblastic / lymphocytic leukemia (T-ALL) |
| NUP214 | DEK | Acute myelogenous leukemia (AML) and myelodysplastic syndrome |
| NUP214 | SET | Acute undifferentiated leukemia (AUL) |
| NUP98 | ADD3 | T-cell acute lymphoblastic leukemia with biphenotipic characteristics (T/myeloid) |
| NUP98 | CCDC28A | Acute megakaryoblastic leukemia, AND T cell acute lymphoblastic leukaemia (T-ALL) |
| NUP98 | DDX10 | De novo or secondary myeloid malignancies |
| NUP98 | HOXA11 | Juvenile myelomonocytic leukemia (JMML) |
| NUP98 | HOXA13 | Acute myelogenous leukemia (AML) |
| NUP98 | HOXA9 | Acute myelogenous leukemia (AML) |
| NUP98 | HOXC11 | Acute myelogenous leukemia (AML) |
| NUP98 | HOXC13 | Acute myelogenous leukemia (AML) |
| NUP98 | HOXD11 | Acute myelomonocytic leukaemia |
| NUP98 | HOXD13 | Acute myelogenous leukemia (AML) |
| NUP98 | JARID1A | Acute leukemia |
| NUP98 | NSD1 | Childhood acute myelogenous leukemia (AML) |
| NUP98 | PRRX1 | M2-ANLL, Non hodgkin lymphoma (NHL) |
| NUP98 | PRRX2 | Acute myelogenous leukemia (AML) |
| NUP98 | PSIP1 | Acute non lymphoblastic leukemia |
| NUP98 | RAP1GDS1 | T acute lymphoblastic leukaemia |
| NUP98 | TOP1 | Acute myelogenous leukemia (AML) |
| NUP98 | WHSC1L1 | Acute myelogenous leukemia (AML) |
| NUT | BRD4 | Midline carcinoma |
| OMD | USP6 | Aneurysmal bone cyst |
| PAX3 | FOXO1 | Rhabdomyosarcoma |
| PAX5 | ETV6 | Acute lymphoblastic / lymphocytic leukemia (ALL) |
| PAX7 | FOXO1 | Alveolar rhabdomyosarcomas |
| PAX8 | PPARy | Follicular thyroid carcinoma |
| PCM1 | JAK2 | Myeloproliferative disorder (MPD) and acute erythroid leukemia |
| PCM1 | RET | Papillary thyroid carcinoma |
| PDE4DIP | PDGFRB | Chronic eosinophilic leukemia (CEL) |

FIG. 59g

| 5' Upstream Fusion Gene Partner | 3' downstream Fusion Gene Partner | Cancer Lineage |
|---|---|---|
| PICALM | MLLT10 | CML, Acute myelogenous leukemia (AML) |
| PIM1 | BCL6 | Diffuse large B-cell lymphoma (DLBCL) |
| PML | RARA | Acute promyelocytic leukemia (APML) |
| POU2AF1 | BCL6 | Non-Hodgkin lymphoma (NHL) |
| PRCC | TFE3 | Renal cell carcinoma |
| PRDM16 | EVI1 | MDS and Acute myelogenous leukemia (AML) |
| PRKAR1A | RET | Papillary thyroid carcinoma |
| RABEP1 | PDGFRB | Myeloproliferative disorder (MPD) and Acute myelogenousleukemia (AML), |
| RANBP2 | ALK | Infammatory myofibroblastic tumors (IMT) |
| RBM15 | MKL1 | Acute myelogenous leukemia (AML) |
| RFG | RET | Papillary thyroid carcinoma |
| RFG9 | RET | Papillary thyroid carcinoma |
| RHOH | BCL6 | Follicular centrocytic-centroblastic lymphoma. |
| Ria | RET | Papillary thyroid carcinoma |
| RLF | MYCL1 | Small-cell lung cancer (SCLC) |
| RPN1 | EVI1 | Acute non lymphocytic leukemia (ANLL), Myelodysplastic syndrome |
| RUNX1 | CBFA2T3 | Myeloid malignancies. |
| RUNX1 | EVI1 | Acute myelogenous leukemia (AML), therapy-related MDS and chronic myeloid leukemia in blastic phase |
| RUNX1 | MDS1 | Acute myelogenous leukemia (AML), therapy-related MDS and chronic myeloid leukemia in blastic phase |
| RUNX1 | RPL22 | Acute myelogenous leukemia (AML) |
| RUNX1 | RUNX1T1 | Acute myelogenous leukemia (AML) |
| RUNX1 | SH3D19 | Acute myelogenous leukemia (AML) |
| RUNX1 | USP42 | Acute myelogenous leukemia (AML) |
| RUNX1 | YTHDF2 | Acute myelogenous leukemia (AML) |
| RUNX1 | ZNF687 | Acute myelogenous leukemia (AML) |
| SEC31A | ALK | Diffuse large B-cell lymphoma (DLBCL) |
| SENP6 | TCBA1 | T-cell lymphoma |
| SFPQ | TFE3 | Renal cell carcinoma |
| SFRS3 | BCL6 | Follicular lymphoma |
| SLC5A3 | ERG | Prostate cancer |
| SLC45A3 | ETV1 | Prostate cancer |
| SLC45A3 | ETV5 | Prostate cancer |
| SPECC1 | PDGFRB | Juvenile myelomonocytic leukemia |
| SS18 | SSX1 | Synovial sarcoma |
| SS18 | SSX2 | Synovial sarcoma |
| SS18 | SSX4 | Synovial sarcoma |

FIG. 59h

| 5' Upstream Fusion Gene Partner | 3' downstream Fusion Gene Partner | Cancer Lineage |
|---|---|---|
| SS18L1 | SSX1 | Synovial sarcoma |
| STAT5B | RARA | Acute promyelocytic leukemia (APML) |
| TAF15 | NR4A3 | Ewing's sarcoma/primitive neuroectodermal tumor |
| TAF15 | TEC | Ewing sarcomas |
| TAF15 | ZNF384 | Acute myelogenous leukemia (AML) |
| TAL1 | STIL | T-cell malignancies (T-ALL) |
| TCBA1 | ETV6 | Acute lymphoblastic / lymphocytic leukemia (ALL) |
| TCEA1 | PLAG1 | Pleomorphic salivary gland adenomas (PA) (Head and Neck) |
| TCF12 | NR4A3 | Extraskeletal myxoid chondrosarcoma |
| TCF12 | TEC | Extraskeletal myxoid chondrosarcoma |
| TCF3 | HLF | pre-B-cell acute lymphoblastic leukemia |
| TCF3 | PBX1 | Acute lymphoblastic / lymphocytic leukemia (ALL) |
| TCF3 | TFPT | Acute lymphoblastic / lymphocytic leukemia (ALL) |
| TFG | ALK | Anaplastic large cell lymphoma (ALCL), Non small cell lung carcinoma (NSCLC) |
| TFG | NR4A3 | Extraskeletal myxoid chondrosarcoma |
| TFG | NTRK1 | Papillary thyroid carcinoma |
| TFRC | BCL6 | B-cell non hodgkin lymphoma (B-NHL), Diffuse large B-cell lymphoma (DLBCL) |
| THRAP3 | USP6 | Aneurysmal bone cysts |
| TIAF1 | FGFR1 | Myeoproliferative disorder (MPD) |
| TMPRSS2 | ERG | Prostate cancer |
| TMPRSS2 | ETV1 | Prostate cancer |
| TMPRSS2 | ETV4 | Prostate cancer |
| TMPRSS2 | ETV5 | Prostate cancer |
| TP53BP1 | PDGFRB | CML-like disorder associated with eosinophilia |
| TPM3 | ALK | Anaplastic large cell lymphoma (ALCL) |
| TPM3 | NTRK1 | Papillary thyroid carcinoma |
| TPM3 | PDGFRB | Chronic eosinophilic leukemia (CEL) |
| TPM3 | TPR | Papillary thyroid carcinoma |
| TPM4 | ALK | Inflammatory Myofibroblastic Tumors |
| TPR | MET | Papillary thyroid carcinoma |
| TPR | NTRK1 | Papillary thyroid carcinoma |
| TRIM24 | FGFR1 | Myeoproliferative disorder (MPD) |
| TRIM24 | RARA | Myeoproliferative disorder (MPD) |
| TRIM24 | RET | Papillary thyroid carcinoma |
| TRIM27 | RET | Papillary thyroid carcinoma |
| TRIM33 | RET | Papillary thyroid carcinoma |
| TRIP11 | PDGFRB | Acute myelogenous leukemia (AML) |

FIG. 59i

| 5' Upstream Fusion Gene Partner | 3' downstream Fusion Gene Partner | Cancer Lineage |
|---|---|---|
| TTL | ETV6 | Acute lymphoblastic / lymphocytic leukemia (ALL) |
| ZBTB16 | RARA | Acute promyelocytic leukemia (APML) |
| ZMYM2 | FGFR1 | Stem cell leukemia lymphoma syndrome (SCLL). |

FIG. 60a

| Gene | miRNA Associated with Gene |
|---|---|
| Androgen receptor | miR-124a, miR-130a, miR-130b,miR-143, miR-149, miR-194, miR-29b, miR-29c, miR-301, miR-30a-5p, miR-30d, miR-30e-5p, miR-337, miR-342, miR-368, miR-488, miR-493-5p, miR-506, miR-512-5p, miR-644, miR-768-5p, miR-801 |
| DNMT3B | miR-618, miR-1253, miR-765, miR-561, miR-330-5p, miR-326, miR-188, miR-203, miR-221, miR-222, miR-26a, miR-26b, miR-29a, miR-29b, miR-29c, miR-370, miR-379, miR-429, miR-519e*, miR-598, miR-618, miR-635 |
| GART | miR-101, miR-141, miR-144, miR-182, miR-189, miR-199a , miR-199b, miR-200a, miR-200b, miR-202, miR-203, miR-223, miR-329, miR-383, miR-429, miR-433, miR-485-5p, miR-493-5p, miR-499, miR-519a, miR-519b, miR-519c, miR-569, miR-591, miR-607, miR-627, miR-635, miR-659 |
| MGMT | miR-122a, miR-142-3p, miR-17-3p, miR-181a, miR-181b, miR-181c, miR-181d, miR-199b, miR-200a*, miR-217, miR-302b*, miR-32, miR-324-3p, miR-34a, miR-371, miR-425-5p, miR-496, miR-514, miR-515-3p, miR-516-3p, miR-574, miR-597, miR-603, miR-653, miR-655, miR-92, miR-92b, miR-99a |
| Top2B | miR-548f, miR-548a-3p, miR-548g, miR-513a-3p, miR-548c-3p, miR-101, miR-653, miR-548d-3p, miR-575, miR-297, miR-576-3p, miR-548b-3p, miR-624, miR-548n, miR-758, miR-1253, miR-1324, miR-23b, miR-320a, miR-320b, miR-1183, miR-1244, miR-23a, miR-451, miR-568, miR-1276 , miR-548e, miR-590-3p, miR-1, miR-101, miR-126, miR-126*, miR-129, miR-136, miR-140, miR-141, miR-144, miR-147, miR-149, miR-18, miR-181b, miR-181c, miR-182, miR-184 , miR-186, miR-189, miR-191, miR-19a, miR-19b, miR-200a, miR-206, miR-210, miR-218, miR-223, miR-23a, miR-23b , miR-24, miR-27a, miR-302, miR-30a, miR-31, miR-320, miR, 23, miR-362, miR-374, miR-383, miR-409-3p, miR-451, miR-489, miR-493-3p, miR-514, miR-542-3p, miR-544, miR-548a, miR-548b, miR-548c, miR-548d, miR-559, miR-568, miR-575, miR-579, miR-585, miR-591, miR-598, miR-613, miR-649, miR-651, miR-758, miR-768-3p, miR-9* |
| HSP90 | miR-1, miR-513a-3p, miR-548d-3, miR-642, miR-206, miR-450b-3p, miR-152, miR-148, miR-148b, miR-188-3p, miR-23a, miR-23b, miR-578, miR-653, miR-1206, miR-192, miR-215, miR-181b, miR-181d, miR-223, miR-613, miR-769-3p, miR-99a, miR-100, miR-454, miR-548n, miR-640, miR-99b, miR-150, miR-181a, miR-181c, miR-522, miR-624, miR-1, miR-130a, miR-130b, miR-146, miR-148a, miR-148b, miR-152, miR-181a, miR-181b, miR-181c, miR-204, miR-206, miR-211, miR-212, miR-215, miR-223, miR-23a, miR-23b, miR-301, miR-31, miR-325, miR-363*, miR-566, miR-9, miR-99b |
| ASPM | miR-1, miR-122a, miR-135a, miR-135b, miR-137, miR-153, miR-190, miR-206, miR-320, miR-380-3p, miR-382, miR-433, miR-453, miR-493-5p, miR-496, miR-499, miR-507, miR-517b, miR-548a, miR-548c, miR-567, miR-568, miR-580, miR-602, miR-651, miR-653, miR-758, miR-9* |
| SPARC | miR-768-5p, miR-203, miR-196, miR-569, miR-187, miR-641, miR-1275, miR-432, miR-622, miR-296-3p, miR-646, miR-96b, miR-499-5p, miR-590-5p, miR-495, miR-625, miR-1244, miR-512-5p, miR-1206, miR-1303, miR-186, miR-302d, miR-494, miR-562, miR-573, miR-10a, miR-203, miR-204, miR-211, miR-29a, miR-29b, miR-29c, miR-29c, miR-339, miR-433, miR-452, miR-515-5p, miR-517a, miR-517b, miR-517c, miR-592, miR-96 |

FIG. 60b

| Gene | miRNA Associated with Gene |
|---|---|
| PFKB3 | miR-513a-3p, miR-1286, miR-488, miR-539, miR-658, miR-524-5p, miR-1258, miR-150, miR-216b, miR-377, miR-135a, miR-26a, miR-548a-5p, miR-26b, miR-520d-5p , miR-224, miR-1297, miR-1197, miR-182, miR-452, miR-509-3-5p, miR-548m, miR-625, miR-509-5p, miR-1266, miR-135b , miR-190b, miR-496, miR-616, miR-621, miR-650, miR-105, miR-19a, miR-346, miR-620, miR-637, miR-651, miR-1283, miR-590-3p, miR-942, miR-1185, miR-577, miR-602, miR-1305, miR-220c, miR-1270, miR-1282, miR-432, miR-491-5p, miR-548n, miR-765, miR-768-3p, miR-924 |
| HMMR | miR-936, miR-656, miR-105, miR-361-5p, miR-194, miR-374a, miR-590-3p, miR-186, miR-769-5p, miR-892a, miR-380, miR-875-3p, miR-208a, miR-208b, miR-586, miR-125a-3p, miR-630, miR-374b, miR-411, miR-629, miR-1286, miR-1185, miR-16, miR-200b, miR-671-5p, miR-95, miR-421, miR-496, miR-633, miR-1243, miR-127-5p, miR-143, miR-15b, miR-200c, miR-24, miR-34c-3p |
| CENPF | miR-30c, miR-30b, miR-190, miR-508-3p, miR-384, miR-512-5p, miR-548p, miR-297, miR-520f, miR-376a, miR-1184, miR-577, miR-708, miR-205, miR-376b, miR-520g, miR-520h, miR-519d, miR-596, miR-768-3p, miR-340, miR-620, miR-539, miR-567, miR-671-5, miR-1183, miR-129-3p, miR-636, miR-106a, miR-1301, miR-17, miR-20a, miR-570, miR-656, miR-1263, miR-1324, miR-142-5p, miR-28-5p, miR-302b, miR-452, miR-520d-3p, miR-548o, miR-892b, miR-302d, miR-875-3p, miR-106b, miR-1266, miR-1323, miR-20b, miR-221, miR-520e, miR-664, miR-920, miR-922, miR-93, miR-1228, miR-1271, miR-30e, miR-483-3p, miR-509-3-5p, miR-515-3p, miR-519e, miR-520b, miR-520c-3p, miR-582-3p |
| NCAPG2 | miR-876-5p, miR-1260, miR-1246, miR-548c-3p, miR-1224-3p, miR-619, miR-605, miR-490-5p, miR-186, miR-448, miR-129-5p, miR-188-3p, miR-516b, miR-342-3p, miR-127, miR-548k, miR-654-3p, miR-1290, miR-656, miR-34b, miR-520g, miR-1231, miR-1289, miR-1229, miR-23a, miR-23b, miR-616, miR-620 |
| EGFR | miR-105, miR-128a, miR-128b, miR-140, miR-141, miR-146a, miR-146b, miR-27a, miR-27b, miR-302a, miR-302d, miR-370, miR-548c,miR-574, miR-587, miR-7 |
| SSTR3 | miR-125a, miR-125b, miR-133a, miR-133b, miR-136, miR-150, miR-21, miR-380-5p, miR-504,miR-550, miR-671, miR-766, miR-767-3p |

| Protein Name | vcap average | lncap average | normalaverage |
|---|---|---|---|
| Biotin | 33236 | 40207 | 52224 |
| bcl-XL | 19205 | 24857 | 9458 |
| Estriol | 16066 | 23435 | 16560 |
| Heat Shock Protein 27/hsp27 | 10172 | 22822 | 43471 |
| CD45RO | 15037 | 20251 | 10114 |
| CNPase | 11269 | 19646 | 11675 |
| ERCC1 | 15292 | 19036 | 1597 |
| Keratin 15 | 13459 | 17580 | 9325 |
| CD81/TAPA-1 | 4967 | 17031 | 194 |
| Laminin B1/b1 | 4609 | 14848 | 10241 |
| MyoD1 | 7144 | 12472 | 15022 |
| HPV 16 | 12742 | 11185 | 15094 |
| Gai1 | 4163 | 10716 | 1361 |
| CD9 | 7009 | 10146 | 191 |
| Epithelial Specific Antigen | 10850 | 9754 | 1275 |
| Cyclin E | 5111 | 9068 | 6280 |
| MHC II (HLA-DP and DR) | 6936 | 8943 | 4757 |
| E2F-2 | 2890 | 8801 | 3094 |
| CD63 | 4591 | 8501 | 2783 |
| Amyloid Beta (APP) | 4663 | 7896 | 5893 |
| Streptavidin | 6348 | 7658 | 7909 |
| Mast Cell Chymase | 1818 | 7582 | 433 |
| AIF (Apoptosis Inducing Factor) | 4263 | 7322 | 7686 |
| CD42b | 1717 | 6787 | 10836 |
| MHC II (HLA-DP and DR) | 6936 | 8943 | 4757 |
| Calmodulin | 3353 | 4722 | 1861 |

FIG. 63

Screening Scheme

| 5 Detection Antibodies | x | 20 Capture Antibodies | | = | 100 Combinations Screened |
|---|---|---|---|---|---|
| CD63 | | CD9 | Rab | | |
| CD9 | | PSCA | IgG | | |
| CD81 | | TNFR | CD81 | | |
| B7H3 | | CD63 2X | STEAP | | |
| EpCam | | B7H3 | PCSA | | |
| | | Rab IgG | PSMA | | |
| | | MFG-E8 | 5T4 | | |
| | | EpCam 2X | CD24 | | |
| | | CD63 | TMEM211 | | |

General vesicle biomarker antibodies: CD9, CD63, CD81
Cell of Origin biomarker antibodies: PSCA, MFG-E8, Rab, STEAP, PCSA, PSMA, 5T4, TMEM211
Cancer biomarker antibodies: EpCam, B7H3, CD24
Control antibodies: Rab IgG, IgG

FIG. 64C

| | Sensitivity | Specificity | Confidence |
|---|---|---|---|
| EpCam vs CD63 | 87.5% | 80% | 99% |
| CD63 vs CD81 | 90% | 100% | 99% |
| CD63 vs CD63 | 60% | 80% | 99% |
| CD9 vs CD63 | 60% | 80% | 99% |

FIG. 73A

B. EpCam vs. CD63

| | | | |
|---|---|---|---|
| True Positive | 7 | 8 | True Negative |
| False Negative | 1 | 2 | False Positive |

C. CD81 vs. CD63

| | | | |
|---|---|---|---|
| True Positive | 4 | 10 | True Negative |
| False Negative | 1 | 0 | False Positive |

D. CD63 vs. CD63

| | | | |
|---|---|---|---|
| True Positive | 3 | 8 | True Negative |
| False Negative | 2 | 2 | False Positive |

E. CD9 vs. CD63

| | | | |
|---|---|---|---|
| True Positive | 3 | 8 | True Negative |
| False Negative | 2 | 2 | False Positive |

FIG. 73B-E

| Detector vs Capture | Sensitivity | Specificity | Confidence |
|---|---|---|---|
| Epcam vs CD63 | 95% | ND | 99% |
| Epcam vs CD9 | 90% | ND | 99% |
| CD63 vs CD63 | 100% | ND | 99% |
| CD9 vs CD63 | 100% | ND | 99% |
| CD66 vs CD9 | 85% | ND | 99% |

FIG. 74A

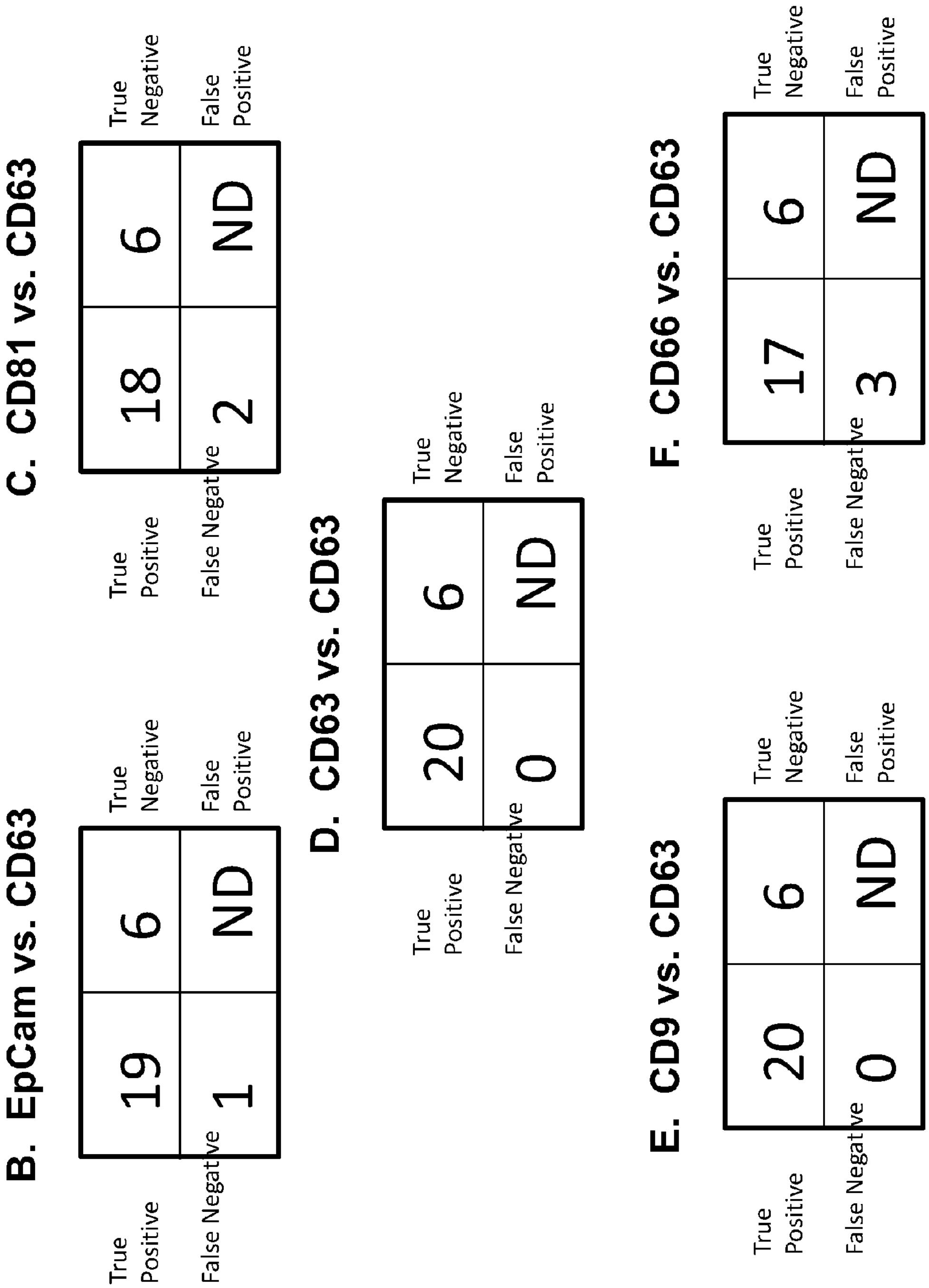

FIG. 74 B-F

B. EpCam vs. CD63

|  | True Negative | False Positive |
|---|---|---|
| True Positive | 19 | 6 |
| False Negative | 1 | ND |

C. CD81 vs. CD63

|  | True Negative | False Positive |
|---|---|---|
| True Positive | 18 | 6 |
| False Negative | 2 | ND |

D. CD63 vs. CD63

|  | True Negative | False Positive |
|---|---|---|
| True Positive | 20 | 6 |
| False Negative | 0 | ND |

E. CD9 vs. CD63

|  | True Negative | False Positive |
|---|---|---|
| True Positive | 20 | 6 |
| False Negative | 0 | ND |

F. CD66 vs. CD63

|  | True Negative | False Positive |
|---|---|---|
| True Positive | 17 | 6 |
| False Negative | 3 | ND |

FIG. 74 B-F

| | VCAP Exosomes avg CT | Normal Plasma Exosomes avg ct |
|---|---|---|
| miR-629 | 30.63 | |
| miR-141 | 25.69 | 38.78 |
| miR-671-3p | 31.31 | 36.93 |
| miR-9 | 28.72 | 38.69 |
| miR-491 | 27.89 | 37.47 |
| miR-182 | 26.83 | 36.3 |
| miR-125a-3p | 31.26 | 38.51 |
| miR-324-5p | 27.74 | 35.98 |
| miR-148b | 29.11 | 36.51 |
| miR-222 | 24.06 | 31.33 |

FIG. 76B

| Vesicle | Prostate | Cancer-1 | Cancer-2 | Cancer-3 | QC-1 | QC-2 | Sensitivity | Specificity | Sensitivity | Specificity |
|---|---|---|---|---|---|---|---|---|---|---|
| | | | | | | | With BPH | With BPH | Without BPH | Without BPH |
| 3000 | 100 | na | 200 | na | 4000 | na | 85.70% | 58.00% | 85.70% | 71.40% |
| 3000 | 100 | 350 | 100 | na | 4000 | na | 85.70% | 74.10% | 85.70% | 85.70% |
| 3000 | 100 | 125 | 125 | 50 | 4000 | na | 71.40% | 83.00% | 71.40% | 90.40% |
| 3000 | 100 | 100 | 100 | 50 | 4000 | 8000 | 71.40% | 87.00% | 71.40% | 90.40% |
| 3000 | 100 | 100 | 150 | 50 | 4000 | na | 64.30% | 90.30% | 64.20% | 90.40% |
| 3000 | 100 | 100 | 150 | 150 | 4000 | na | 35.70% | 93.40% | 35.70% | 95.20% |

FIG. 79

Area Under the Curve (AUC)

| With BPH | Without BPH | PSA | PCA3 |
|---|---|---|---|
| 0.899 | 0.951 | 0.673 | 0.713 |

| | | |
|---|---|---|
| Mann Whitney test | | |
| P value | | 0.0396 |

| | Normal | Cancer |
|---|---|---|
| Number of values | 16 | 45 |
| | | |
| Minimum | 35.00 | 42.00 |
| 25% Percentile | 53.75 | 83.00 |
| Median | 99.50 | 140.0 |
| 75% Percentile | 164.0 | 329.5 |
| Maximum | 477.0 | 707.0 |
| | | |
| Mean | 132.7 | 226.2 |
| Std. Deviation | 116.8 | 190.1 |
| Std. Error | 29.19 | 28.34 |
| | | |
| Lower 95% CI of mean | 70.44 | 169.1 |
| Upper 95% CI of mean | 194.9 | 283.3 |

Mann Whitney test

| | | |
|---|---|---|
| P value | | 0.0178 |

| | Normal | Cancer |
|---|---|---|
| Number of values | 16 | 45 |
| Minimum | 13.00 | 19.00 |
| 25% Percentile | 24.13 | 46.50 |
| Median | 50.75 | 70.00 |
| 75% Percentile | 59.38 | 128.5 |
| Maximum | 151.0 | 545.0 |
| Mean | 52.69 | 105.1 |
| Std. Deviation | 33.59 | 98.36 |
| Std. Error | 8.397 | 14.66 |
| Lower 95% CI of mean | 34.79 | 75.50 |
| Upper 95% CI of mean | 70.59 | 134.6 |

| | | |
|---|---|---|
| Mann Whitney test | | |
| P value | | < 0.0001 |

| | Normal | Cancer |
|---|---|---|
| Number of values | 16 | 45 |
| | | |
| Minimum | 14.00 | 39.00 |
| 25% Percentile | 42.75 | 181.5 |
| Median | 59.25 | 366.0 |
| 75% Percentile | 160.5 | 818.8 |
| Maximum | 300.5 | 3671 |
| | | |
| Mean | 97.22 | 624.6 |
| Std. Deviation | 84.63 | 718.6 |
| Std. Error | 21.16 | 107.1 |
| | | |
| Lower 95% CI of mean | 52.12 | 408.7 |
| Upper 95% CI of mean | 142.3 | 840.5 |

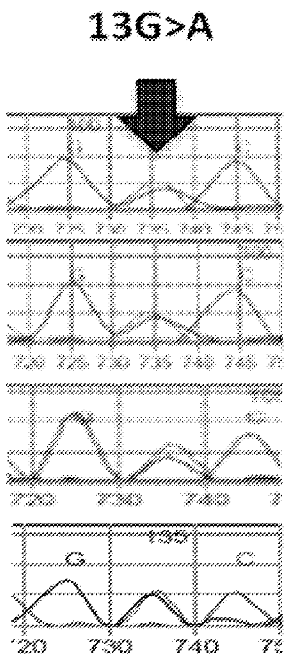
A. CRC cell line cDNA from vesicles
B. CRC cell line cDNA from cells
C. Plasma-derived vesicle cDNA from CRC patient
D. FFPE DNA from CRC patient
FIG. 101A-D

BIOMARKERS FOR THERANOSTICS

CROSS-REFERENCE

This application is a U.S. national stage entry of International Application No. PCT/US2011/026750 filed on Mar. 1, 2011, which application claims the benefit of U.S. Provisional Patent Application Nos. 61/274,124 filed on Mar. 1, 2010; 61/357,517 filed on Jun. 22, 2010; and 61/364,785 filed on Jul. 15, 2010; each of which applications is incorporated by reference herein in its entirety.

BACKGROUND

Biomarkers for conditions and diseases such as cancer include biological molecules such as proteins, peptides, lipids, RNAs, DNA and variations and modifications thereof.

The identification of specific biomarkers, such as DNA, RNA and proteins, can provide biosignatures that are used for the diagnosis, prognosis, or theranosis of conditions or diseases. Biomarkers can be detected in bodily fluids, including circulating DNA, RNA, proteins, and vesicles. Circulating biomarkers include proteins such as PSA and CA125, and nucleic acids such as SEPT9 DNA and PCA3 messenger RNA (mRNA). Circulating biomarkers also include circulating vesicles. Vesicles are membrane encapsulated structures that are shed from cells and have been found in a number of bodily fluids, including blood, plasma, serum, breast milk, ascites, bronchoalveolar lavage fluid and urine. Vesicles can take part in the communication between cells as transport vehicles for proteins, RNAs, DNAs, viruses, and prions. MicroRNAs are short RNAs that regulate the transcription and degradation of messenger RNAs. MicroRNAs have been found in bodily fluids and have been observed as a component within vesicles shed from tumor cells. The analysis of circulating biomarkers associated with diseases, including vesicles and/or microRNA, can aid in detection of disease or severity thereof, determining predisposition to a disease, as well as making treatment decisions.

Vesicles present in a biological sample provide a source of biomarkers, e.g., the markers are present within a vesicle (vesicle payload), or are present on the surface of a vesicle. Characteristics of vesicles (e.g., size, surface antigens, determination of cell-of-origin, payload) can also provide a diagnostic, prognostic or theranostic readout. There remains a need to identify biomarkers that can be used to detect and treat disease. microRNA and other biomarkers associated with vesicles as well as the characteristics of a vesicle can provide a diagnosis, prognosis, or theranosis.

The present invention provides methods and systems for characterizing a phenotype by detecting biomarkers that are indicative of disease or disease progress. The biomarkers can be circulating biomarkers including vesicles and microRNA.

SUMMARY

Disclosed herein are methods and compositions for characterizing a phenotype by analyzing a vesicle, such as a vesicle present in a biological sample derived from a subject's cell. Characterizing a phenotype for a subject or individual may include, but is not limited to, the diagnosis of a disease or condition, the prognosis of a disease or condition, the determination of a disease stage or a condition stage, a drug efficacy, a physiological condition, organ distress or organ rejection, disease or condition progression, therapy-related association to a disease or condition, or a specific physiological or biological state.

In an aspect, the invention provides a method of theranosing a disease or disorder in a subject in need thereof, comprising: identifying a biosignature of a vesicle population in a sample from the subject, wherein the biosignature comprises a presence or level of one or more cell-specific biomarker and/or a presence or level of one or more one or more disease-specific biomarker, and a presence or level of one or more general vesicle biomarker; and comparing the biosignature to a reference, wherein the comparison is indicative of whether the subject is a responder or non-responder to a therapeutic agent, thereby theranosing the disease or disorder. In some embodiments, the subject has not been exposed to the therapeutic agent previously. In other embodiments, the theranosis comprises determining a treatment efficacy. The methods provided herein can be performed in vitro, wherein the biomarkers are assessed in an in vitro setting.

In some embodiments, the subject is not currently being treated for the disease or disorder. In other embodiments, the subject is on an existing treatment for the disease or disorder. The method can further comprise administering the therapeutic agent to the subject.

The methods of identifying a biosignature can be performed in a single assay. For example, a number of biomarkers can be assessed using a multiplexed approach. In some embodiments, all markers in the biosignature are assessed in a multiplexed assay. In other embodiments, some of the biomarkers are assessed in a single assay and one or more other biomarker is assessed in a different assay, which can also be a multiplexed assay. As an example, multiple vesicle surface biomarkers can be assessed in a first multiplex assay, and multiple microRNAs can be assessed in a second multiplex assay. The results of the first and second multiplex assays can be combined to identify a biosignature comprising the vesicle surface biomarkers and the microRNAs.

In some embodiments, the sample that is assessed comprises a bodily fluid. The bodily fluid can comprise any appropriate bodily fluid, including without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood. In some embodiments, the bodily fluid comprises serum or plasma.

The vesicle population comprises any useful population of vesicles. In some embodiments, the vesicle population has a diameter between 20 nm and 1500 nm. In other embodiments, the vesicle population comprises vesicles with a diameter between 20 nm and 800 nm. In other embodiments, the vesicle population comprises vesicles with a diameter between 20 nm and 200 nm.

The vesicle population can be subjected to size exclusion chromatography, density gradient centrifugation, differential centrifugation, nanomembrane ultrafiltration, immunoabsorbent capture, affinity purification, affinity capture, immunoassay, microfluidic separation, or combinations thereof. These methods can be performed on the sample to isolate or capture the desired vesicles. The vesicle population can also be assessed without first performing a technique to isolate or capture the vesicle population.

The one or more cell-specific biomarker, one or more disease-specific biomarker, and one or more general vesicle biomarker can comprise proteins. The proteins can be vesicle surface antigens and/or vesicle payload. In some embodiments, the one or more disease-specific biomarker comprises EpCAM, B7H3, CD24, Tissue Factor, or a combination thereof. In some embodiments, the one or more general vesicle biomarker comprises CD63, CD9, CD81, CD82, CD37, CD53, Rab-5b, MFG-E8, Annexin V, or a combination thereof.

The biosignature of the invention can be identified using a binding agent. In some embodiments, identifying the biosignature comprises contacting the sample with at least two binding agents specific for two different analytes. For example, identifying the biosignature can comprise contacting the sample with at least three binding agents specific for three different analytes. The binding agent can be any useful entity that can bind to a biomarker of interest. Bindings agents for use with the invention include without limitation an antigen, DNA molecule, RNA molecule, antibody, antibody fragment, aptamer, peptoid, zDNA, peptide nucleic acid (PNA), locked nucleic acids (LNA), lectin, peptide, dendrimer, membrane protein labeling agent, or chemical compound.

Identifying the biosignature of the invention can comprise assessment of one or more nucleic acid. Identifying the biosignature of the invention can also comprise assessment of one or more nucleic acid, peptide, protein, lipid, antigen, carbohydrate, and/or proteoglycan. The one or more nucleic acid can be, without limitation, DNA, mRNA, microRNA, snoRNA, snRNA, rRNAs, tRNAs, siRNA, hnRNA, or shRNA. In some embodiments, the nucleic acid comprises one or more microRNA. The microRNA can be a circulating biomarker or can be associated with a vesicle, e.g., as vesicle payload. The one or more nucleic acid can be one or more of miR-21, miR-205, miR-92, miR-147 miR-141 or miR-574. The one or more nucleic acid can be one or more microRNA listed in FIGS. 3-6, 19-24, 26-30, 32, 33, 36, 40-42, 47, 51, 53-57, and/or 60. The one or more nucleic acid can be one or more microRNA selected from miR-21, miR-205, miR-92, miR-147 or miR-574.

Statistical discriminate analysis and classification methods can be used to identify whether the subject is a responder or non-responder. As used herein, a responder includes a subject that is predicted to respond to a candidate treatment, whether or not the treatment is efficacious thereafter. A responder also includes a subject with a partial response to a current treatment. In some embodiments, identifying the subject as a non-responder or responder to the therapeutic agent comprises correlating the biosignature of the subject against a set of biosignatures from previously identified responders and non-responders to a therapeutic agent. The subject can be identified as a responder if the subject's biosignature correlates more closely with the set of biosignatures from previously identified responders than with the set of biosignatures from previously identified non-responders. The subject can be identified as a non-responder if the subject's biosignature correlates more closely with the set of biosignatures from previously identified non-responders than with the set of biosignatures from previously identified responders. In some embodiments, identifying the subject as a non-responder or responder to the therapeutic agent comprises classifying the biosignature of the subject using a classifier trained using previously identified responders and non-responders.

The methods of the invention can be used for the theranosis of a cancer. For example, the cancer can be prostate cancer, colorectal cancer, lung cancer, breast cancer, ovarian cancer or melanoma.

The methods of the invention can be used to theranose a prostate cancer. In one embodiment, the disease or disorder comprises prostate cancer and the biosignature comprises: one or more of PCSA and PSMA; and one or more of B7H3 and EpCam. In another embodiment, the disease or disorder comprises prostate cancer and the biosignature comprises PCSA.

The methods of the invention can be used to theranose a colorectal cancer. In one embodiment, the disease or disorder comprises colorectal cancer and the biosignature comprises: one or more of DR3, STEAP, Epha2, TMEM211, unc93A, A33, CD24, NGAL, EpCam, MUC17, TROP2 and TETS. In another embodiment, the disease or disorder comprises colorectal cancer and the biosignature comprises: one or more of CD9, EGFR, CD63, MUC1, TGM2, CD81, TIMP, EPHA2, TMEM211, UNC93A, CD66e, CD24, Ferritin, EpCAM, NGAL, GPR30, p53, MUC17, NCAM and B7H3. In still another embodiment, the disease or disorder comprises colorectal cancer and the biosignature comprises: one or more of CD9, EPHA2, EGFR, CD63, MUC1, TGM2, CD81, TIMP1, GPR110, MMP9, TMEM211, UNC93, CD66e, CD24, Nga1, EpCAM, GPR30, OPN, MUC17, p53, MUC2, Ncam and TSG101. In embodiments, the disease or disorder comprises colorectal cancer and the biosignature comprises: TMEM211 and CD24. In other embodiments, the disease or disorder comprises colorectal cancer and the biosignature comprises: EpCam and CD66. In one embodiment, the disease or disorder comprises colorectal cancer and the biosignature comprises: one or more of EGFR, EPHA2, p53, and KRAS.

The methods of the invention can be used to theranose a breast cancer. In one embodiment, the disease or disorder comprises breast cancer and the biosignature comprises: one or more of CD9, HSP70, Ga13, MIS, EGFR, ER, ICB3, CD63, B7H4, MUC1, DLL4, CD81, ERB3, VEGF, BCA225, BRCA, CA125, CD174, CD24, ERB2, NGAL, GPR30, CYFRA21, CD31, cMET, MUC2 and ERB4. In another embodiment, the disease or disorder comprises breast cancer and the biosignature comprises: one or more of CD9, EphA2, EGFR, B7H3, PSMA, PCSA, CD63, STEAP, CD81, B7H3, STEAP1, ICAM1 (CD54), A33, DR3, CD66e, MFG-e8, Hepsin, TMEM211, TROP-2, EGFR, Mammoglobin, Hepsin, NPGP/NPFF2, PSCA, 5T4, NGAL, NK-2, EpCam, NK-1R, 5T4, PA1-1, and CD45. In still other embodiments, the disease or disorder comprises breast cancer and the biosignature comprises: one or more of BRCA, cMET, DLL4, EphA2, EGFR, ER, ERB2, ERB3, ERB4, and VEGF.

The methods of the invention can also be used to theranose a lung cancer. In embodiments of the invention, the disease or disorder comprises lung cancer and the biosignature comprises: one or more of SPB, SPC, TFF3, PGP9.5, CD9, MS4A1, NDUFB7, Cal3, iC3b, CD63, MUC1, TGM2, CD81, B7H3, DR3, MACC1, TrkB, Tissue Factor (TF), TIMP1, GPCR (GPR110), MMP9, MMP1, TMEM211, TWEAK, CDADC1, UNC93, APC, A33, CD66e, CD24, ErbB2, CD10, BDNF, Ferritin, Seprase, NGAL, EpCam, ErbB2, Osteopontin (OPN), LDH, HSP70, MUC2, NCAM, CXCL12, Haptoglobin (HAP), CRP, and Gro-alpha. In other embodiments, the disease or disorder comprises lung cancer and the biosignature comprises: one or more of EPHA2, CD24, EGFR, and CEA. In still other embodiments, the disease or disorder comprises lung cancer and the biosignature comprises: one or more of SPB, SPC, NSE, PGP9.5, CD9, P2RX7, NDUFB7, NSE, Ga13, Osteopontin, CHI3L1, EGFR, B7H3, iC3b, MUC1, Mesothelin, SPA, TPA, PCSA, CD63, AQP5, DLL4, CD81, DR3, PSMA, GPCR 110 (GPR110), EPHA2, CEACAM, PTP, CABYR, TMEM211, ADAM28, UNC93a, A33, CD24, CD10, NGAL, EpCam, MUC17, TROP2 and MUC2. In one embodiment, the disease or disorder comprises lung cancer and the biosignature comprises: one or more of SPB, SPC, PSP9.5, NDUFB7, Ga13, iC3b, MUC1, GPCR 110, CABYR and MUC17. In another embodiment, the disease or disorder comprises lung cancer and the biosignature comprises: one or more of CD9, CD63, CD81, B7H3, PRO GRP, CYTO 18, FTH1, TGM2, CENPH, ANNEXIN V, ANNEXIN V, ERB2, EGFR, CRP, VEGF, CYTO 19, CCL2, Osteopontin (OST19), Osteopontin (OST22), BTUB, CD45, TIMP, NACC1, MMP9, BRCA1, P27, NSE, M2PK, HCG, MUC1, CEA, CEACAM, CYTO 7, EPCAM, MS4A1, MUC1, MUC2, PGP9, SPA, SPA, SPD, P53, GPCR (GPR110), SFTPC, UNCR2, NSE, INGA3, INTG b4, MMP1, PNT, RACK1, NAP2, HLA, BMP2, PTHIR, PAN ADH, NCAM, CD151, CKS1, FSHR, HIF, KRAS, LAMP2, SNAIL, TRIM29, TSPAN1, TWIST1, ASPH and AURKB. The disease can be a lung cancer and the biosignature can include: one or more of ASPH, BRCA1, EGFR, EPHA2, ErbB2, HIF, KRAS, MS4A1, P27, P53, ADH, PGP9, PGP9.5, VEGF.

The invention can be used to theranose a cancer by identifying a biosignature comprising a drug associated biomarker. In an embodiment, the disease or disorder comprises cancer and the biosignature comprises: one or more of ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, hENT-1, Her2/Neu, HGF, HIF1A, HIG1, HSP90, HSP90AA1, HSPCA, IGF-IR, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKB1A, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SRC, SSTR1, SSTR2, SSTR3, SSTR4, SSTR5, Survivin, TK1, TLE3, TNF, TOP1, TOP2A, TOP2B, TS, TXN, TXNRD1, TYMS, VDR, VEGF, VEGFA, VEGFC, VHL, YES1, and ZAP70; and one or more general vesicle biomarker. The overexpression, underexpression or mutation of the one or more marker as compared to a reference is used to select the therapeutic agent. The one or more marker can include KRAS. A mutation in KRAS as compared to a wild type reference can be used to select the therapeutic agent. In an embodiment, the mutation is KRAS is determined by sequencing KRAS mRNA. The KRAS mRNA that is assessed can be payload within the vesicle population.

The one or more general vesicle biomarker used to assess the vesicle population includes vesicle markers that are commonly found in the vesicles of interest. For example, the one or more general vesicle biomarker can be one or more tetraspanin, such as CD9, CD63 and/or CD81. The one or more general vesicle biomarker can be one or more of CD63, CD9, CD81, CD82, CD37, CD53, Rab-5b, MFG-E8, and Annexin V. The one or more general vesicle biomarker can also be one or more marker listed in Table 3.

The methods of the invention can be used for the theranosis of any disease or disorder that can be assessed through biomarker analysis, e.g., that of circulating biomarkers and/or vesicles. The disease or disorder includes without limitation a cancer, a premalignant condition, an inflammatory disease, an immune disease, an autoimmune disease or disorder, a cardiovascular disease or disorder, neurological disease or disorder, infectious disease or pain.

In some embodiments, the cancer comprises breast cancer, ovarian cancer, lung cancer, non-small cell lung cancer, small cell lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer, a glioblastoma, hepatocellular carcinoma, cervical cancer, endometrial cancer, head and neck cancer, esophageal cancer, gastrointestinal stromal tumor (GIST), renal cell carcinoma (RCC), gastric cancer, colorectal cancer (CRC), CRC Dukes B, CRC Dukes C-D, a hematological malignancy, B-cell chronic lymphocytic leukemia, B-cell lymphoma-DLBCL, B-cell lymphoma-DLBCL-germinal center-like, B-cell lymphoma-DLBCL-activated B-cell-like, or Burkitt's lymphoma.

The cancer can also comprise an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor.

The premalignant condition can be without limitation actinic keratosis, atrophic gastritis, leukoplakia, erythroplasia, Lymphomatoid Granulomatosis, preleukemia, fibrosis, cervical dysplasia, uterine cervical dysplasia, xeroderma pigmentosum, Barrett's Esophagus, colorectal polyp, a transformative viral infection, HIV, HPV, or other growth or lesion at risk of becoming malignant.

In some embodiments, the autoimmune disease comprises inflammatory bowel disease (IBD), Crohn's disease (CD), ulcerative colitis (UC), pelvic inflammation, vasculitis, psoriasis, diabetes, autoimmune hepatitis, multiple sclerosis, myasthenia gravis, Type I diabetes, rheumatoid arthritis, psoriasis, systemic lupus erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis.

In some embodiments, the cardiovascular disease comprises atherosclerosis, congestive heart failure, vulnerable plaque, stroke, ischemia, high blood pressure, stenosis, vessel occlusion or a thrombotic event.

The neurological disease theranosed by the subject methods includes without limitation Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome.

In some embodiments, the pain comprises fibromyalgia, chronic neuropathic pain, or peripheral neuropathic pain. In other embodiments, the infectious disease comprises a bacterial infection, viral infection, yeast infection, Whipple's Disease, Prion Disease, cirrhosis, methicillin-resistant *staphylococcus aureus*, HIV, HCV, hepatitis, syphilis, meningitis, malaria, tuberculosis, influenza.

In another aspect, the invention provides a method of theranosing a disease or disorder in a subject in need thereof, comprising: identifying a biosignature of a vesicle population in a sample from the subject, wherein the biosignature comprises a mutation of KRAS, BRAF, PIK3CA, and/or c-kit; and comparing the biosignature to a reference to identify the presence of a mutation in the KRAS, BRAF, PIK3CA, and/or c-kit, thereby theranosing the disease or disorder. The mutation can be detected in mRNA isolated from the vesicle population. In some embodiments, the biosignature comprises a mutation in KRAS. A mutation in KRAS can be useful in determining whether to treat the subject with an EGFR inhibitor, including without limitation panitumumab and cetuximab. A mutation in KRAS can indicate resistance to EGFR inhibitor treatment.

In another aspect, the invention provides the use of a reagent to carry out any of the methods of the invention. The reagent can be used for the theranosis of a disease or disorder. In a related aspect, the invention also provides a kit comprising a reagent to carry out any of the methods of the invention.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

FIG. 1(*a*)-(*g*) represents a table which lists exemplary cancers by lineage, group comparisons of cells/tissue, and specific disease states and antigens specific to those cancers, group cell/tissue comparisons and specific disease states. Furthermore, the antigen can be a biomarker. The one or more biomarkers can be present or absent, underexpressed or overexpressed, mutated, or modified, such as epigentically modified or post-translationally modified.

FIG. 2(*a*)-(*f*) represents a table which lists exemplary cancers by lineage, group comparisons of cells/tissue, and specific disease states and binding agents specific to those cancers, group cell/tissue comparisons and specific disease states.

FIG. 3(*a*)-(*b*) represents a table which lists exemplary breast cancer biomarkers that can be derived and analyzed from a vesicle specific to breast cancer to create a breast cancer specific vesicle biosignature. Furthermore, the one or more biomarkers can be present or absent, underexpressed or overexpressed, mutated, or modified, such as epigentically modified or post-translationally modified.

FIG. 4(*a*)-(*b*) represents a table which lists exemplary ovarian cancer biomarkers that can be derived from and analyzed from a vesicle specific to ovarian cancer to create an ovarian cancer specific biosignature. Furthermore, the one or more biomarkers can be present or absent, underexpressed or overexpressed, mutated, or modified, such as epigentically modified or post-translationally modified.

FIG. 5 represents a table which lists exemplary lung cancer biomarkers that can be derived from and analyzed from a vesicle specific to lung cancer to create a lung cancer specific biosignature. Furthermore, the one or more biomarkers can be present or absent, underexpressed or overexpressed, mutated, or modified, such as epigentically modified or post-translationally modified.

FIG. 6(*a*)-(*d*) represents a table which lists exemplary colon cancer biomarkers that can be derived from and analyzed from a vesicle specific to colon cancer to create a colon cancer specific biosignature. Furthermore, the one or more biomarkers can be present or absent, underexpressed or overexpressed, mutated, or modified, such as epigentically modified or post-translationally modified.

FIG. 7 represents a table which lists exemplary biomarkers specific to an adenoma versus a hyperplastic polyp that can be derived and analyzed from a vesicle specific to adenomas versus hyperplastic polyps. Furthermore, the one or more biomarkers can be present or absent, underexpressed or overexpressed, mutated, or modified, such as epigentically modified or post-translationally modified.

FIG. 8 is a table which lists exemplary biomarkers specific to inflammatory bowel disease (IBD) versus normal tissue that can be derived and analyzed from a vesicle specific inflammatory bowel disease versus normal tissue. Furthermore, the one or more biomarkers can be present or absent, underexpressed or overexpressed, mutated, or modified, such as epigentically modified or post-translationally modified.

FIG. 9(*a*)-(*c*) represents a table which lists exemplary biomarkers specific to an adenoma versus colorectal cancer (CRC) that can be derived and analyzed from a vesicle specific to adenomas versus colorectal cancer. Furthermore, the one or more biomarkers can be present or absent, underexpressed or overexpressed, mutated, or modified, such as epigentically modified or post-translationally modified.

FIG. 10 represents a table which lists exemplary biomarkers specific to IBD versus CRC that can be derived and analyzed from a vesicle specific to IBD versus CRC. Furthermore, the one or more biomarkers can be present or absent, underexpressed or overexpressed, mutated, or modified, such as epigentically modified or post-translationally modified.

FIG. 11(*a*)-(*b*) represents a table which lists exemplary biomarkers specific to CRC Dukes B versus Dukes C-D that can be derived and analyzed from a vesicle specific to CRC Dukes B versus Dukes C-D. Furthermore, the one or more biomarkers can be present or absent, underexpressed or overexpressed, mutated, or modified, such as epigentically modified or post-translationally modified.

FIG. 12(*a*)-(*d*) represents a table which lists exemplary biomarkers specific to an adenoma with low grade dysplasia versus an adenoma with high grade dysplasia that can be derived and analyzed from a vesicle specific to an adenoma with low grade dysplasia versus an adenoma with high grade dysplasia. Furthermore, the one or more biomarkers can be present or absent, underexpressed or overexpressed, mutated, or modified, such as epigentically modified or post-translationally modified.

FIG. 13(*a*)-(*b*) represents a table which lists exemplary biomarkers specific to ulcerative colitis (UC) versus Crohn's Disease (CD) that can be derived and analyzed from a vesicle specific to UC versus CD. Furthermore, the one or more biomarkers can be present or absent, underexpressed or overexpressed, mutated, or modified, such as epigentically modified or post-translationally modified.

FIG. 14 represents a table which lists exemplary biomarkers specific to a hyperplastic polyp versus normal tissue that can be derived and analyzed from a vesicle specific to a hyperplastic polyp versus normal tissue. Furthermore, the one or more biomarkers can be present or absent, underexpressed or overexpressed, mutated, or modified, such as epigentically modified or post-translationally modified.

FIG. 15 is a table which lists exemplary biomarkers specific to an adenoma with low grade dysplasia versus normal tissue that can be derived and analyzed from a vesicle specific to an adenoma with low grade dysplasia versus normal tissue. Furthermore, the one or more biomarkers can be present or absent, underexpressed or overexpressed, mutated, or modified, such as epigentically modified or post-translationally modified.

FIG. 16 is a table which lists exemplary biomarkers specific to an adenoma versus normal tissue that can be derived and analyzed from a vesicle specific to an adenoma versus normal tissue. Furthermore, the one or more biomarkers can be present or absent, underexpressed or overexpressed, mutated, or modified, such as epigentically modified or post-translationally modified.

FIG. 17 represents a table which lists exemplary biomarkers specific to CRC versus normal tissue that can be derived and analyzed from a vesicle specific to CRC versus normal tissue. Furthermore, the one or more biomarkers can be present or absent, underexpressed or overexpressed, mutated, or modified, such as epigentically modified or post-translationally modified.

FIG. 18 is a table which lists exemplary biomarkers specific to benign prostatic hyperplasia that can be derived from and analyzed from a vesicle specific to benign prostatic hyperplasia. Furthermore, the one or more biomarkers can be present or absent, underexpressed or overexpressed, mutated, or modified, such as epigentically modified or post-translationally modified.

FIG. 19(*a*)-(*c*) represents a table which lists exemplary prostate cancer biomarkers that can be derived from and analyzed from a vesicle specific to prostate cancer to create a prostate cancer specific, biosignature. Furthermore, the one or more biomarkers can be present or absent, underexpressed or overexpressed, mutated, or modified, such as epigentically modified or post-translationally modified.

FIG. 20(*a*)-(*c*) represents a table which lists exemplary melanoma biomarkers that can be derived from and analyzed from a vesicle specific to melanoma to create a melanoma specific biosignature. Furthermore, the one or more biomarkers can be present or absent, underexpressed or overexpressed, mutated, or modified, such as epigentically modified or post-translationally modified.

FIG. 21(*a*)-(*b*) represents a table which lists exemplary pancreatic cancer biomarkers that can be derived from and analyzed from a vesicle specific to pancreatic cancer to create a pancreatic cancer specific biosignature. Furthermore, the one or more biomarkers can be present or absent, underexpressed or overexpressed, mutated, or modified, such as epigentically modified or post-translationally modified.

FIG. 22 is a table which lists exemplary biomarkers specific to brain cancer that can be derived from and analyzed from a vesicle specific to brain cancer to create a brain cancer specific biosignature. Furthermore, the one or more biomarkers can be present or absent, underexpressed or overexpressed, mutated, or modified, such as epigentically modified or post-translationally modified.

FIG. 23(*a*)-(*b*) represents a table which lists exemplary psoriasis biomarkers that can be derived from and analyzed from a vesicle specific to psoriasis to create a psoriasis specific biosignature. Furthermore, the one or more biomarkers can be present or absent, underexpressed or overexpressed, mutated, or modified, such as epigentically modified or post-translationally modified.

FIG. 24(*a*)-(*c*) represents a table which lists exemplary cardiovascular disease biomarkers that can be derived from and analyzed from a vesicle specific to cardiovascular disease to create a cardiovascular disease specific biosignature. Furthermore, the one or more biomarkers can be present or absent, underexpressed or overexpressed, mutated, or modified, such as epigentically modified or post-translationally modified.

FIG. 25 is a table which lists exemplary biomarkers specific to hematological malignancies that can be derived from and analyzed from a vesicle specific to hematological malignancies to create a specific biosignature for hematological malignancies. Furthermore, the one or more biomarkers can be present or absent, underexpressed or overexpressed, mutated, or modified, such as epigentically modified or post-translationally modified.

FIG. 26(*a*)-(*b*) represents a table which lists exemplary biomarkers specific to B-Cell Chronic Lymphocytic Leukemias that can be derived from and analyzed from a vesicle specific to B-Cell Chronic Lymphocytic Leukemias to create a specific biosignature for B-Cell Chronic Lymphocytic Leukemias. Furthermore, the one or more biomarkers can be present or absent, underexpressed or overexpressed, mutated, or modified, such as epigentically modified or post-translationally modified.

FIG. 27 is a table which lists exemplary biomarkers specific to B-Cell Lymphoma and B-Cell Lymphoma-DLBCL that can be derived from and analyzed from a vesicle specific to B-Cell Lymphoma and B-Cell Lymphoma-DLBCL. Furthermore, the one or more biomarkers can be present or absent, underexpressed or overexpressed, mutated, or modified, such as epigentically modified or post-translationally modified.

FIG. 28 represents a table which lists exemplary biomarkers specific to B-Cell Lymphoma-DLBCL-germinal center-like and B-Cell Lymphoma-DLBCL-activated B-cell-like and B-cell lymphoma-DLBCL that can be derived from and analyzed from a vesicle specific to B-Cell Lymphoma-DLBCL-germinal center-like and B-Cell Lymphoma-DLBCL-activated B-cell-like and B-cell lymphoma-DLBCL. Furthermore, the one or more biomarkers can be present or absent, underexpressed or overexpressed, mutated, or modified, such as epigentically modified or post-translationally modified.

FIG. 29 represents a table which lists exemplary Burkitt's lymphoma biomarkers that can be derived from and analyzed from a vesicle specific to Burkitt's lymphoma to create a Burkitt's lymphoma specific biosignature. Furthermore, the one or more biomarkers can be present or absent, underexpressed or overexpressed, mutated, or modified, such as epigentically modified or post-translationally modified.

FIG. 30(*a*)-(*b*) represents a table which lists exemplary hepatocellular carcinoma biomarkers that can be derived from and analyzed from a vesicle specific to hepatocellular carcinoma to create a specific biosignature for hepatocellular carcinoma. Furthermore, the one or more biomarkers can be present or absent, underexpressed or overexpressed, mutated, or modified, such as epigentically modified or post-translationally modified.

FIG. 31 is a table which lists exemplary biomarkers for cervical cancer that can be derived from and analyzed from a vesicle specific to cervical cancer. Furthermore, the one or more biomarkers can be present or absent, underexpressed or overexpressed, mutated, or modified, such as epigentically modified or post-translationally modified.

FIG. 32 represents a table which lists exemplary biomarkers for endometrial cancer that can be derived from and analyzed from a vesicle specific to endometrial cancer to create a specific biosignature for endometrial cancer. Furthermore, the one or more biomarkers can be present or absent, underexpressed or overexpressed, mutated, or modified, such as epigentically modified or post-translationally modified.

FIG. 33(*a*)-(*b*) represents a table which lists exemplary biomarkers for head and neck cancer that can be derived from and analyzed from a vesicle specific to head and neck cancer to create a specific biosignature for head and neck cancer. Furthermore, the one or more biomarkers can be present or absent, underexpressed or overexpressed, mutated, or modified, such as epigentically modified or post-translationally modified.

FIG. 34 represents a table which lists exemplary biomarkers for inflammatory bowel disease (IBD) that can be derived from and analyzed from a vesicle specific to IBD to create a specific biosignature for IBD. Furthermore, the one or more biomarkers can be present or absent, underexpressed or overexpressed, mutated, or modified, such as epigentically modified or post-translationally modified.

FIG. 35 is a table which lists exemplary biomarkers for diabetes that can be derived from and analyzed from a vesicle specific to diabetes to create a specific biosignature for diabetes. Furthermore, the one or more biomarkers can be present or absent, underexpressed or overexpressed, mutated, or modified, such as epigentically modified or post-translationally modified.

FIG. 36 is a table which lists exemplary biomarkers for Barrett's Esophagus that can be derived from and analyzed from a vesicle specific to Barrett's Esophagus to create a specific biosignature for Barrett's Esophagus. Furthermore, the one or more biomarkers can be present or absent, underexpressed or overexpressed, mutated, or modified, such as epigentically modified or post-translationally modified.

FIG. 37 is a table which lists exemplary biomarkers for fibromyalgia that can be derived from and analyzed from a vesicle specific to fibromyalgia. Furthermore, the one or more biomarkers can be present or absent, underexpressed or overexpressed, mutated, or modified, such as epigentically modified or post-translationally modified.

FIG. 38 represents a table which lists exemplary biomarkers for stroke that can be derived from and analyzed from a vesicle specific to stroke to create a specific biosignature for stroke. Furthermore, the one or more biomarkers can be present or absent, underexpressed or overexpressed, mutated, or modified, such as epigentically modified or post-translationally modified.

FIG. 39 is a table which lists exemplary biomarkers for Multiple Sclerosis (MS) that can be derived from and analyzed from a vesicle specific to MS to create a specific biosignature for MS. Furthermore, the one or more biomarkers can be present or absent, underexpressed or overexpressed, mutated, or modified, such as epigentically modified or post-translationally modified.

FIG. 40(*a*)-(*b*) represents a table which lists exemplary biomarkers for Parkinson's Disease that can be derived from and analyzed from a vesicle specific to Parkinson's Disease to create a specific biosignature for Parkinson's Disease. Furthermore, the one or more biomarkers can be present or absent, underexpressed or overexpressed, mutated, or modified, such as epigentically modified or post-translationally modified.

FIG. 41 represents a table which lists exemplary biomarkers for Rheumatic Disease that can be derived from and analyzed from a vesicle specific to Rheumatic Disease to create a specific biosignature for Rheumatic Disease. Furthermore, the one or more biomarkers can be present or absent, underexpressed or overexpressed, mutated, or modified, such as epigentically modified or post-translationally modified.

FIG. 42(*a*)-(*b*) represents a table which lists exemplary biomarkers for Alzheimer's Disease that can be derived from and analyzed from a vesicle specific to Alzheimer's Disease to create a specific biosignature for Alzheimer's Disease. Furthermore, the one or more biomarkers can be present or absent, underexpressed or overexpressed, mutated, or modified, such as epigentically modified or post-translationally modified.

FIG. 43 is a table which lists exemplary biomarkers for Prion Diseases that can be derived from and analyzed from a vesicle specific to Prion Diseases to create a specific biosignature for Prion Diseases. Furthermore, the one or more biomarkers can be present or absent, underexpressed or overexpressed, mutated, or modified, such as epigentically modified or post-translationally modified.

FIG. 44 represents a table which lists exemplary biomarkers for sepsis that can be derived from and analyzed from a vesicle specific to sepsis to create a specific biosignature for sepsis. Furthermore, the one or more biomarkers can be present or absent, underexpressed or overexpressed, mutated, or modified, such as epigentically modified or post-translationally modified.

FIG. 45 is a table which lists exemplary biomarkers for chronic neuropathic pain that can be derived from and analyzed from a vesicle specific to chronic neuropathic pain. Furthermore, the one or more biomarkers can be present or absent, underexpressed or overexpressed, mutated, or modified, such as epigentically modified or post-translationally modified.

FIG. 46 is a table which lists exemplary biomarkers for peripheral neuropathic pain that can be derived from and analyzed from a vesicle specific to peripheral neuropathic pain. Furthermore, the one or more biomarkers can be present or absent, underexpressed or overexpressed, mutated, or modified, such as epigentically modified or post-translationally modified.

FIG. 47 represents a table which lists exemplary biomarkers for Schizophrenia that can be derived from and analyzed from a vesicle specific to Schizophrenia to create a specific biosignature for Schizophrenia. Furthermore, the one or more biomarkers can be present or absent, underexpressed or overexpressed, mutated, or modified, such as epigentically modified or post-translationally modified.

FIG. 48 is a table which lists exemplary biomarkers for bipolar disorder or disease that can be derived from and analyzed from a vesicle specific to bipolar disorder to create a specific biosignature for bipolar disorder. Furthermore, the one or more biomarkers can be present or absent, underexpressed or overexpressed, mutated, or modified, such as epigentically modified or post-translationally modified.

FIG. 49 is a table which lists exemplary biomarkers for depression that can be derived from and analyzed from a vesicle specific to depression to create a specific biosignature for depression. Furthermore, the one or more biomarkers can be present or absent, underexpressed or overexpressed, mutated, or modified, such as epigentically modified or post-translationally modified.

FIG. 50 is a table which lists exemplary biomarkers for gastrointestinal stromal tumor (GIST) that can be derived from and analyzed from a vesicle specific to GIST to create a specific biosignature for GIST. Furthermore, the one or more biomarkers can be present or absent, underexpressed or overexpressed, mutated, or modified, such as epigentically modified or post-translationally modified.

FIG. 51(*a*)-(*b*) represents a table which lists exemplary biomarkers for renal cell carcinoma (RCC) that can be derived from and analyzed from a vesicle specific to RCC to create a specific biosignature for RCC. Furthermore, the one or more biomarkers can be present or absent, underexpressed or overexpressed, mutated, or modified, such as epigentically modified or post-translationally modified.

FIG. 52 is a table which lists exemplary biomarkers for cirrhosis that can be derived from and analyzed from a vesicle specific to cirrhosis to create a specific biosignature for cirrhosis. Furthermore, the one or more biomarkers can be present or absent, underexpressed or overexpressed, mutated, or modified, such as epigentically modified or post-translationally modified.

FIG. 53 is a table which lists exemplary biomarkers for esophageal cancer that can be derived from and analyzed from a vesicle specific to esophageal cancer to create a specific biosignature for esophageal cancer. Furthermore, the one or more biomarkers can be present or absent, underexpressed or overexpressed, mutated, or modified, such as epigentically modified or post-translationally modified.

FIG. 54 is a table which lists exemplary biomarkers for gastric cancer that can be derived from and analyzed from a vesicle specific to gastric cancer to create a specific biosignature for gastric cancer. Furthermore, the one or more biomarkers can be present or absent, underexpressed or overexpressed, mutated, or modified, such as epigentically modified or post-translationally modified.

FIG. 55 is a table which lists exemplary biomarkers for autism that can be derived from and analyzed from a vesicle specific to autism to create a specific biosignature for autism. Furthermore, the one or more biomarkers can be present or absent, underexpressed or overexpressed, mutated, or modified, such as epigentically modified or post-translationally modified.

FIG. 56 is a table which lists exemplary biomarkers for organ rejection that can be derived from and analyzed from a vesicle specific to organ rejection to create a specific biosignature for organ rejection. Furthermore, the one or more biomarkers can be present or absent, underexpressed or overexpressed, mutated, or modified, such as epigentically modified or post-translationally modified.

FIG. 57 is a table which lists exemplary biomarkers for methicillin-resistant *staphylococcus aureus* that can be derived from and analyzed from a vesicle specific to methicillin-resistant *staphylococcus aureus* to create a specific biosignature for methicillin-resistant *staphylococcus aureus*. Furthermore, the one or more biomarkers can be present or absent, underexpressed or overexpressed, mutated, or modified, such as epigentically modified or post-translationally modified.

FIG. 58 is a table which lists exemplary biomarkers for vulnerable plaque that can be derived from and analyzed from a vesicle specific to vulnerable plaque to create a specific biosignature for vulnerable plaque. Furthermore, the one or more biomarkers can be present or absent, underexpressed or overexpressed, mutated, or modified, such as epigentically modified or post-translationally modified.

FIG. 59(*a*)-(*i*) is a table which lists exemplary gene fusions that can be derived from, or analyzed from a vesicle. The gene fusion can be biomarker, and can be present or absent, underexpressed or overexpressed, or modified, such as epigentically modified or post-translationally modified.

FIG. 60(*a*)-(*b*) is a table of genes and their associated miRNAs, of which the gene, such as the mRNA of the gene, their associated miRNAs, or any combination thereof, can be used as one or more biomarkers that can be analyzed from a vesicle. Furthermore, the one or more biomarkers can be present or absent, underexpressed or overexpressed, mutated, or modified.

FIG. 63 illustrates results obtained from screening for proteins on vesicles, which can be used as a biomarker for the vesicles. Antibodies to the proteins can be used as binding agents. Examples of proteins identified as a biomarker for a vesicle include Bcl-XL, ERCC1, Keratin 15, CD81/TAPA-1, CD9, Epithelial Specific Antigen (ESA), and Mast Cell Chymase. The biomarker can be present or absent, underexpressed or overexpressed, mutated, or modified in or on a vesicle and used in characterizing a condition.

FIGS. 64A-E illustrate methods of characterizing a phenotype by assessing vesicle biosignatures. FIG. 64A is a schematic of a planar substrate coated with a capture antibody, which captures vesicles expressing that protein. The capture antibody is for a vesicle protein that is specific or not specific for vesicles derived from diseased cells ("disease vesicle"). The detection antibody binds to the captured vesicle and provides a fluorescent signal. The detection antibody can detect an antigen that is generally associated with vesicles, or is associated with a cell-of-origin or a disease, e.g., a cancer. FIG. 64B is a schematic of a bead coated with a capture antibody, which captures vesicles expressing that protein. The capture antibody is for a vesicle protein that is specific or not specific for vesicles derived from diseased cells ("disease vesicle"). The detection antibody binds to the captured vesicle and provides a fluorescent signal. The detection antibody can detect an antigen that is generally associated with vesicles, or is associated with a cell-of-origin or a disease, e.g., a cancer. FIG. 64C is an example of a screening scheme that can be performed by multiplexing using the beads as shown in FIG. 64B. FIG. 64D presents illustrative schemes for capturing and detecting vesicles to characterize a phenotype. FIG. 64E presents illustrative schemes for assessing vesicle payload to characterize a phenotype.

FIG. 73 illustrates (A) the sensitivity and specificity, and the confidence level, for detecting prostate cancer using antibodies to the listed proteins listed as the detector and capture antibodies. CD63, CD9, and CD81 are general markers and EpCam is a cancer marker. The individual results are depicted in (B) for EpCam versus CD63, with 99% confidence, 100% (n=8) cancer patient samples were different from the Generalized Normal Distribution and with 99% confidence, 77% (n=10) normal patient samples were not different from the Generalized Normal Distribution; (C) for CD81 versus CD63, with 99% confidence, 90% (n=5) cancer patient samples were different from the Generalized Normal Distribution; with 99% confidence, 77% (n=10) normal patient samples were not different from the Generalized Normal Distribution; (D) for CD63 versus CD63, with 99% confidence, 60% (n=5) cancer patient samples were different from the Generalized Normal Distribution; with 99% confidence, 80% (n=10) normal patient samples were not different from the Generalized Normal Distribution; (E) for CD9 versus CD63, with 99% confidence, 90% (n=5) cancer patient samples were different from the Generalized Normal Distribution; with 99% confidence, 77% (n=10) normal patient samples were not different from the Generalized Normal Distribution.

FIG. 74 illustrates (A) the sensitivity and the confidence level for detecting colon cancer using antibodies to the listed proteins listed as the detector and capture antibodies. CD63, CD9 are general markers, EpCam is a cancer marker, and CD66 is a colon marker. The individual results are depicted in (B) for EpCam versus CD63, with 99% confidence, 95% (n=20) cancer patient samples were different from the Generalized Normal Distribution; with 99% confidence, 100% (n=6) normal patient samples were not different from the Generalized Normal Distribution; (C) for EpCam versus CD9, with 99% confidence, 90% (n=20) cancer patient samples were different from the Generalized Normal Distribution; with 99% confidence, 77% (n=6) normal patient samples were not different from the Generalized Normal Distribution; (D) for CD63 versus CD63, with 99% confidence, 60% (n=20) cancer patient samples were different from the Generalized Normal Distribution; with 99% confidence, 80% (n=6) normal patient samples were not different from the Generalized Normal Distribution; (E) for CD9 versus CD63, with 99% confidence, 90% (n=20) cancer patient samples were different from the Generalized Normal Distribution; with 99% confidence, 77% (n=6) normal patient samples were not different from the Generalized Normal Distribution; (F) for CD66 versus CD9, with 99% confidence, 90% (n=20) cancer patient samples were different from the Generalized Normal Distribution; with 99% confidence, 77% (n=6) normal patient samples were not different from the Generalized Normal Distribution.

FIG. 79 depicts a table of the sensitivity and specificity for different prostate signatures. "Exosome" lists the threshold value or reference value of vesicle levels, "Prostate" lists the threshold value or reference value used for prostate vesicles, "Cancer-1," "Cancer-2," and "Cancer-3" lists the threshold values or reference values for the three different biosignatures for prostate cancer, the "QC-1" and "QC-2" columns list the threshold values or reference values for quality control, or reliability, and the last four columns list the specificities and sensitivities for benign prostate hyperplasia (BPH).

FIG. 100A illustrates a fold-change (Y-axis) in capture antibody antigens (X-axis) in CRC vesicle samples versus normals as measured by antibody array. FIG. 100B is similar except that the Y-axis represents the median fluorescence intensity (MFI) in CRC and normal samples as indicated by the legend. FIG. 100C is similar to FIG. 100B performed on an additional sample set.

FIG. 101A-D illustrates KRAS sequencing in a colorectal cancer (CRC) cell line and patient sample. Samples comprise genomic DNA obtained from the cell line (B) or from a tissue sample from the patient (D), or cDNA obtained from RNA payload within vesicles shed from the cell line (A) or from a plasma sample from the patient (C).

DETAILED DESCRIPTION OF THE INVENTION

Disclosed herein are methods and systems for characterizing a phenotype of a biological sample, e.g., a sample from a cell culture, an organism, or a subject. The phenotype can be characterized by assessing one or more biomarkers. The biomarkers can be associated with a vesicle or vesicle population, either presented vesicle surface antigens or vesicle payload. As used herein, vesicle payload comprises entities encapsulated within a vesicle. Vesicle associated biomarkers can comprise both membrane bound and soluble biomarkers. The biomarkers can also be circulating biomarkers, such as microRNA or protein assessed in a bodily fluid. Unless otherwise specified, the terms "purified" or "isolated" as used herein in reference to vesicles or biomarker components mean partial or complete purification or isolation of such components from a cell or organism. Furthermore, unless otherwise specified, reference to vesicle isolation using a binding agent includes binding a vesicle with the binding agent whether or not such binding results in complete isolation of the vesicle apart from other biological entities in the starting material.

Figure 61A:
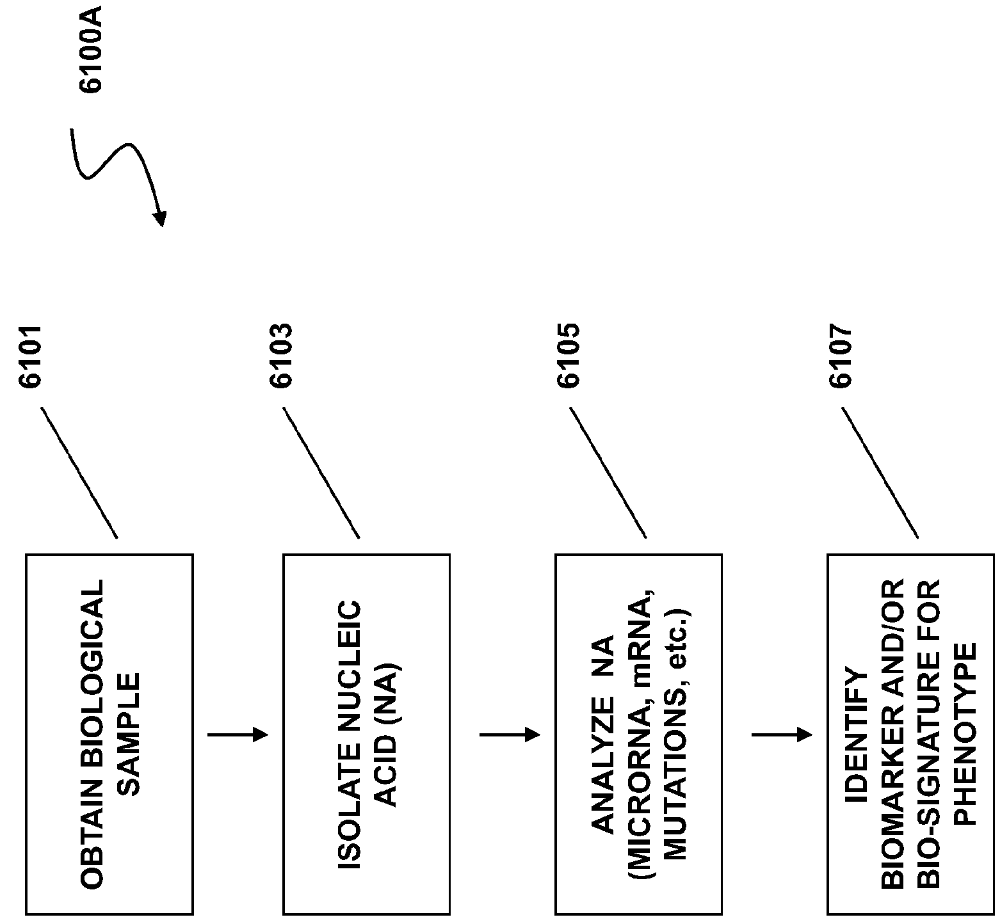
FIG. 61A depicts a method of identifying a biosignature comprising nucleic acid to characterize a phenotype.
Figure 61B:
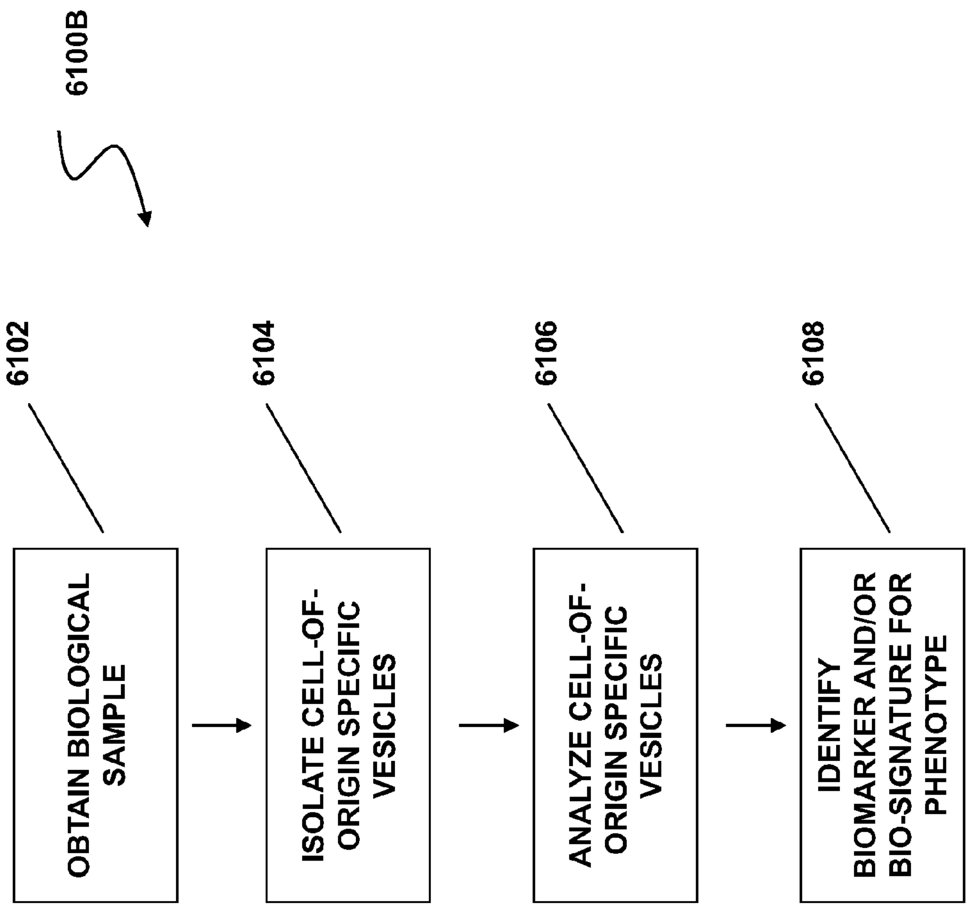
FIG. 61B depicts a method of identifying a biosignature of a vesicle or vesicle population to characterize a phenotype.

A method of characterizing a phenotype by analyzing a circulating biomarker, e.g., a nucleic acid biomarker, is depicted in scheme 6100A of FIG. 61A, as a non-limiting illustrative example. In a first step 6101, a biological sample is obtained, e.g., a bodily fluid, tissue sample or cell culture. Nucleic acids are isolated from the sample 6103. The nucleic acid can be DNA or RNA, e.g., microRNA. Assessment of such nucleic acids can provide a biosignature for a phenotype. By sampling the nucleic acids associated with target phenotype (e.g., disease versus healthy, pre- and post-treatment), one or more nucleic acid markers that are indicative of the phenotype can be determined. Various aspects of the present invention are directed to biosignatures determined by assessing one or more nucleic acid molecules (e.g., microRNA) present in the sample 6105, where the biosignature corresponds to a predetermined phenotype 6107. FIG. 61B illustrates a scheme 6100B of using vesicles to isolate the nucleic acid molecules. In one example, a biological sample is obtained 6102, and one or more vesicles, e.g., vesicles from a particular cell-of-origin and/or vesicles associated with a particular disease state, are isolated from the sample 6104. The vesicles are analyzed 6106 by characterizing surface antigens associated with the vesicles and/or determining the presence or levels of components present within the vesicles ("payload"). Unless specified otherwise, the term "antigen" as used herein refers generally to a biomarker that can be bound by a binding agent, whether the binding agent is an antibody, aptamer, lectin, or other binding agent for the biomarker and regardless of whether such biomarker illicits an immune response in a host. Vesicle payload may be protein, including peptides and polypeptides, and/or nucleic acids such as DNA and RNAs. RNA payload includes messenger RNA (mRNA) and microRNA (also referred to herein as miRNA or miR). A phenotype is characterized based on the biosignature of the vesicles 6108. In another illustrative method of the invention, schemes 6100A and 6100B are performed together to characterize a phenotype. In such a scheme, vesicles and nucleic acids, e.g., microRNA, are assessed, thereby characterizing the phenotype.

In a related aspect, methods are provided herein for the discovery of biomarkers comprising assessing vesicle surface markers or payload markers in one sample and comparing the markers to another sample. Markers that distinguish between the samples can be used as biomarkers according to the invention. Such samples can be from a subject or group of subjects. For example, the groups can be, e.g., known responders and non-responders to a given treatment for a given disease or disorder. Biomarkers discovered to distinguish the known responders and non-responders provide a biosignature of whether a subject is likely to respond to a treatment such as a therapeutic agent, e.g., a drug or biologic.

Phenotypes

Disclosed herein are products and processes for characterizing a phenotype of an individual by analyzing a vesicle such as a membrane vesicle. A phenotype can be any observable characteristic or trait of a subject, such as a disease or condition, a disease stage or condition stage, susceptibility to a disease or condition, prognosis of a disease stage or condition, a physiological state, or response to therapeutics. A phenotype can result from a subject's gene expression as well as the influence of environmental factors and the interactions between the two, as well as from epigenetic modifications to nucleic acid sequences.

A phenotype in a subject can be characterized by obtaining a biological sample from a subject and analyzing one or more vesicles from the sample. For example, characterizing a phenotype for a subject or individual may include detecting a disease or condition (including pre-symptomatic early stage detecting), determining the prognosis, diagnosis, or theranosis of a disease or condition, or determining the stage or progression of a disease or condition. Characterizing a phenotype can also include identifying appropriate treatments or treatment efficacy for specific diseases, conditions, disease stages and condition stages, predictions and likelihood analysis of disease progression, particularly disease recurrence, metastatic spread or disease relapse. A phenotype can also be a clinically distinct type or subtype of a condition or disease, such as a cancer or tumor. Phenotype determination can also be a determination of a physiological condition, or an assessment of organ distress or organ rejection, such as post-transplantation. The products and processes described herein allow assessment of a subject on an individual basis, which can provide benefits of more efficient and economical decisions in treatment.

In an aspect, the invention relates to the analysis of vesicles to provide a biosignature to predict whether a subject is likely to respond to a treatment for a disease or disorder. Characterizating a phenotype includes predicting the responder/non-responder status of the subject, wherein a responder responds to a treatment for a disease and a non-responder does not respond to the treatment. Vesicles can be analyzed in the subject and compared to vesicle analysis of previous subjects that were known to respond or not to a treatment. If the vesicle biosignature in a subject more closely aligns with that of previous subjects that were known to respond to the treatment, the subject can be characterized, or predicted, as a responder to the treatment. Similarly, if the vesicle biosignature in the subject more closely aligns with that of previous subjects that did not respond to the treatment, the subject can be characterized, or predicted as a non-responder to the treatment. The treatment can be for any appropriate disease, disorder or other condition. The method can be used in any disease setting where a vesicle biosignature that correlates with responder/non-responder status is known.

The term "phenotype" as used herein can mean any trait or characteristic that is attributed to a vesicle biosignature that is identified utilizing methods of the invention. For example, a phenotype can be the identification of a subject as likely to respond to a treatment, or more broadly, it can be a diagnostic, prognostic or theranostic determination based on a characterized biosignature for a sample obtained from a subject.

In some embodiments, the phenotype comprises a disease or condition such as those listed in Table 1. For example, the phenotype can comprise the presence of or likelihood of developing a tumor, neoplasm, or cancer. A cancer detected or assessed by products or processes described herein includes, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma.

The phenotype can be a premalignant condition, such as actinic keratosis, atrophic gastritis, leukoplakia, erythroplasia, Lymphomatoid Granulomatosis, preleukemia, fibrosis, cervical dysplasia, uterine cervical dysplasia, xeroderma pigmentosum, Barrett's Esophagus, colorectal polyp, or other abnormal tissue growth or lesion that is likely to develop into a malignant tumor. Transformative viral infections such as HIV and HPV also present phenotypes that can be assessed according to the invention.

The cancer characterized by the methods of the invention can comprise, without limitation, a carcinoma, a sarcoma, a lymphoma or leukemia, a germ cell tumor, a blastoma, or other cancers. Carcinomas include without limitation epithelial neoplasms, squamous cell neoplasms squamous cell carcinoma, basal cell neoplasms basal cell carcinoma, transitional cell papillomas and carcinomas, adenomas and adenocarcinomas (glands), adenoma, adenocarcinoma, linitis plastica insulinoma, glucagonoma, gastrinoma, vipoma, cholangiocarcinoma, hepatocellular carcinoma, adenoid cystic carcinoma, carcinoid tumor of appendix, prolactinoma, oncocytoma, hurthle cell adenoma, renal cell carcinoma, grawitz tumor, multiple endocrine adenomas, endometrioid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, warthin's tumor, thymoma, specialized gonadal neoplasms, sex cord stromal tumor, thecoma, granulosa cell tumor, arrhenoblastoma, sertoli leydig cell tumor, glomus tumors, paraganglioma, pheochromocytoma, glomus tumor, nevi and melanomas, melanocytic nevus, malignant melanoma, melanoma, nodular melanoma, dysplastic nevus, lentigo maligna melanoma, superficial spreading melanoma, and malignant acral lentiginous melanoma. Sarcoma includes without limitation Askin's tumor, botryodies, chondrosarcoma, Ewing's sarcoma, malignant hemangio endothelioma, malignant schwannoma, osteosarcoma, soft tissue sarcomas including: alveolar soft part sarcoma, angiosarcoma, cystosarcoma phyllodes, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, lymphosarcoma, malignant fibrous histiocytoma, neurofibrosarcoma, rhabdomyosarcoma, and synovialsarcoma. Lymphoma and leukemia include without limitation chronic lymphocytic leukemia/small lymphocytic lymphoma, B-cell prolymphocytic leukemia, lymphoplasmacytic lymphoma (such as waldenstrom macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical hodgkin lymphomas (nodular sclerosis, mixed cellularity, lymphocyte-rich, lymphocyte depleted or not depleted), and nodular lymphocyte-predominant hodgkin lymphoma. Germ cell tumors include without limitation germinoma, dysgerminoma, seminoma, nongerminomatous germ cell tumor, embryonal carcinoma, endodermal sinus turmor, choriocarcinoma, teratoma, polyembryoma, and gonadoblastoma. Blastoma includes without limitation nephroblastoma, medulloblastoma, and retinoblastoma. Other cancers include without limitation labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In a further embodiment, the cancer under analysis may be a lung cancer including non-small cell lung cancer and small cell lung cancer (including small cell carcinoma (oat cell cancer), mixed small cell/large cell carcinoma, and combined small cell carcinoma), colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

In embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor. The methods of the invention can be used to characterize these and other cancers. Thus, characterizing a phenotype can be providing a diagnosis, prognosis or theranosis of one of the cancers disclosed herein.

The phenotype can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis.

The phenotype can also comprise a cardiovascular disease, such as atherosclerosis, congestive heart failure, vulnerable plaque, stroke, or ischemia. The cardiovascular disease or condition can be high blood pressure, stenosis, vessel occlusion or a thrombotic event.

The phenotype can also comprise a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain.

The phenotype may also comprise an infectious disease, such as a bacterial, viral or yeast infection. For example, the disease or condition may be Whipple's Disease, Prion Disease, cirrhosis, methicillin-resistant *staphylococcus aureus*, HIV, hepatitis, syphilis, meningitis, malaria, tuberculosis, or influenza. Viral proteins, such as HIV or HCV-like particles can be assessed in a vesicle, to characterize a viral condition.

The phenotype can also comprise a perinatal or pregnancy related condition (e.g. preeclampsia or preterm birth), metabolic disease or condition, such as a metabolic disease or condition associated with iron metabolism. For example, hepcidin can be assayed in a vesicle to characterize an iron deficiency. The metabolic disease or condition can also be diabetes, inflammation, or a perinatal condition.

The methods of the invention can be used to characterize these and other diseases and disorders that can be assessed via biomarkers. Thus, characterizing a phenotype can be providing a diagnosis, prognosis or theranosis of one of the diseases and disorders disclosed herein.

Subject

One or more phenotypes of a subject can be determined by analyzing one or more vesicles, such as vesicles, in a biological sample obtained from the subject. A subject or patient can include, but is not limited to, mammals such as bovine, avian, canine, equine, feline, ovine, porcine, or primate animals (including humans and non-human primates). A subject can also include a mammal of importance due to being endangered, such as a Siberian tiger; or economic importance, such as an animal raised on a farm for consumption by humans, or an animal of social importance to humans, such as an animal kept as a pet or in a zoo. Examples of such animals include, but are not limited to, carnivores such as cats and dogs; swine including pigs, hogs and wild boars; ruminants or ungulates such as cattle, oxen, sheep, giraffes, deer, goats, bison, camels or horses. Also included are birds that are endangered or kept in zoos, as well as fowl and more particularly domesticated fowl, i.e. poultry, such as turkeys and chickens, ducks, geese, guinea fowl. Also included are domesticated swine and horses (including race horses). In addition, any animal species connected to commercial activities are also included such as those animals connected to agriculture and aquaculture and other activities in which disease monitoring, diagnosis, and therapy selection are routine practice in husbandry for economic productivity and/or safety of the food chain.

The subject can have a pre-existing disease or condition, such as cancer. Alternatively, the subject may not have any known pre-existing condition. The subject may also be non-responsive to an existing or past treatment, such as a treatment for cancer.

Samples

The biological sample obtained from the subject can be any bodily fluid. For example, the biological sample can be peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. A biological sample may also include the blastocyl cavity, umbilical cord blood, or maternal circulation which may be of fetal or maternal origin. The biological sample may also be a tissue sample or biopsy from which vesicles and other circulating biomarkers may be obtained. For example, cells from the sample can be cultured and vesicles isolated from the culture (see for example, Example 1). In various embodiments, biomarkers or more particularly biosignatures disclosed herein can be assessed directly from such biological samples (e.g., identification of presence or levels of nucleic acid or polypeptide biomarkers or functional fragments thereof) utilizing various methods, such as extraction of nucleic acid molecules from blood, plasma, serum or any of the foregoing biological samples, use of protein or antibody arrays to identify polypeptide (or functional fragment) biomarker(s), as well as other array, sequencing, PCR and proteomic techniques known in the art for identification and assessment of nucleic acid and polypeptide molecules.

Table 1 lists illustrative examples of diseases, conditions, or biological states and a corresponding list of biological samples from which vesicles may be analyzed.

TABLE 1

Examples of Biological Samples for Vesicle Analysis for Various Diseases, Conditions, or Biological States

| Illustrative Disease, Condition or Biological State | Illustrative Biological Samples |
|---|---|
| Cancers/neoplasms affecting the following tissue types/bodily systems: breast, lung, ovarian, colon, rectal, prostate, pancreatic, brain, bone, connective tissue, glands, skin, lymph, nervous system, endocrine, germ cell, genitourinary, hematologic/blood, bone marrow, muscle, eye, esophageal, fat tissue, thyroid, pituitary, spinal cord, bile duct, heart, gall bladder, bladder, testes, cervical, endometrial, renal, ovarian, digestive/gastrointestinal, stomach, head and neck, liver, leukemia, respiratory/thorasic, cancers of unknown primary (CUP) | Blood, serum, cerebrospinal fluid (CSF), urine, sputum, ascites, synovial fluid, semen, nipple aspirates, saliva, bronchoalveolar lavage fluid, tears, oropharyngeal washes, feces, peritoneal fluids, pleural effusion, sweat, tears, aqueous humor, pericardial fluid, lymph, chyme, chyle, bile, stool water, amniotic fluid, breast milk, pancreatic juice, cerumen, Cowper's fluid or pre-ejaculatory fluid, female ejaculate, interstitial fluid, menses, mucus, pus, sebum, vaginal lubrication, vomit |
| Neurodegenerative/neurological disorders: Parkinson's disease, Alzheimer's Disease and multiple sclerosis, Schizophrenia, and bipolar disorder, spasticity disorders, epilepsy | Blood, serum, CSF, urine |
| Cardiovascular Disease: atherosclerosis, cardiomyopathy, endocarditis, vunerable plaques, infection | Blood, serum, CSF, urine |
| Stroke: ischemic, intracerebral hemorrhage, subarachnoid hemorrhage, transient ischemic attacks (TIA) | Blood, serum, CSF, urine |
| Pain disorders: peripheral neuropathic pain and chronic neuropathic pain, and fibromyalgia, | Blood, serum, CSF, urine |
| Autoimmune disease: systemic and localized diseases, rheumatic disease, Lupus, Sjogren's syndrome | Blood, serum, CSF, urine, synovial fluid |
| Digestive system abnormalities: Barrett's esophagus, irritable bowel syndrome, ulcerative colitis, Crohn's disease, Diverticulosis and Diverticulitis, Celiac Disease | Blood, serum, CSF, urine |

TABLE 1-continued

| Examples of Biological Samples for Vesicle Analysis for Various Diseases, Conditions, or Biological States | |
|---|---|
| Illustrative Disease, Condition or Biological State | Illustrative Biological Samples |
| Endocrine disorders: diabetes mellitus, various forms of Thyroiditis,, adrenal disorders, pituitary disorders | Blood, serum, CSF, urine |
| Diseases and disorders of the skin: psoriasis | Blood, serum, CSF, urine, synovial fluid, tears |
| Urological disorders: benign prostatic hypertrophy (BPH), polycystic kidney disease, interstitial cystitis | Blood, serum, urine |
| Hepatic disease/injury: Cirrhosis, induced hepatotoxicity (due to exposure to natural or synthetic chemical sources) | Blood, serum, urine |
| Kidney disease/injury: acute, sub-acute, chronic conditions, Podocyte injury, focal segmental glomerulosclerosis | Blood, serum, urine |
| Endometriosis | Blood, serum, urine, vaginal fluids |
| Osteoporosis | Blood, serum, urine, synovial fluid |
| Pancreatitis | Blood, serum, urine, pancreatic juice |
| Asthma | Blood, serum, urine, sputum, bronchiolar lavage fluid |
| Allergies | Blood, serum, urine, sputum, bronchiolar lavage fluid |
| Prion-related diseases | Blood, serum, CSF, urine |
| Viral Infections: HIV/AIDS | Blood, serum, urine |
| Sepsis | Blood, serum, urine, tears, nasal lavage |
| Organ rejection/transplantation | Blood, serum, urine, various lavage fluids |
| Differentiating conditions: adenoma versus hyperplastic polyp, irritable bowel syndrome (IBS) versus normal, classifying Dukes stages A, B, C, and/or D of colon cancer, adenoma with low-grade hyperplasia versus high-grade hyperplasia, adenoma versus normal, colorectal cancer versus normal, IBS versus, ulcerative colitis (UC) versus Crohn's disease (CD), | Blood, serum, urine, sputum, feces, colonic lavage fluid |
| Pregnancy related physiological states, conditions, or affiliated diseases: genetic risk, adverse pregnancy outcomes | Maternal serum, amniotic fluid, cord blood |

The biological sample may be obtained through a third party, such as a party not performing the analysis of the biomarkers, whether direct assessment of a biological sample or by profiling one or more vesicles obtained from the biological sample. For example, the sample may be obtained through a clinician, physician, or other health care manager of a subject from which the sample is derived. Alternatively, the biological sample may obtained by the same party analyzing the vesicle. In addition, biological samples be assayed, are archived (e.g., frozen) or ortherwise stored in under preservative conditions.

The volume of the biological sample used for biomarker analysis can be in the range of between 0.1-20 mL, such as less than about 20, 15, 10, 9, 8, 7, 6, 5, 4, 3, 2, 1 or 0.1 mL.

A sample of bodily fluid can be used as a sample for characterizing a phenotype. For example, biomarkers in the sample can be assessed to provide a diagnosis, prognosis and/or theranosis of a disease. The biomarkers can be circulating biomarkers, such as circulating proteins or nucleic acids. The biomarkers can also be associated with a vesicle or vesicle population. Methods of the invention can be applied to assess one or more vesicles, as well as one or more different vesicle populations that may be present in a biological sample or in a subject. Analysis of one or more biomarkers in a biological sample can be used to determine whether an additional biological sample should be obtained for analysis. For example, analysis of one or more vesicles in a sample of bodily fluid can aid in determining whether a tissue biopsy should be obtained.

Vesicles

Methods of the invention can include assessing one or more vesicles, including assessing vesicle populations. A vesicle, as used herein, is a membrane vesicle that is shed from cells. Vesicles or membrane vesicles include without limitation: circulating microvesicles (cMVs), microvesicle, exosome, nanovesicle, dexosome, bleb, blebby, prostasome, microparticle, intralumenal vesicle, membrane fragment, intralumenal endosomal vesicle, endosomal-like vesicle, exocytosis vehicle, endosome vesicle, endosomal vesicle, apoptotic body, multivesicular body, secretory vesicle, phospholipid vesicle, liposomal vesicle, argosome, texasome, secresome, tolerosome, melanosome, oncosome, or exocytosed vehicle. Furthermore, although vesicles may be produced by different cellular processes, the methods of the invention are not limited to or reliant on any one mechanism, insofar as such vesicles are present in a biological sample and are capable of being characterized by the methods disclosed herein. Indeed, unless otherwise specified, methods that make use of a species of vesicle can be applied to other types of vesicles. Vesicles comprise spherical structures with a lipid bilayer similar to cell membranes which surrounds an inner compartment which can contain soluble components, sometimes referred to as the payload. In some embodiments, the methods of the invention make use of exosomes, which are small secreted vesicles of about 40-100 nm in diameter. For a review of membrane vesicles, including types and characterizations, see *Thery et al., Nat Rev Immunol.* 2009 Aug. 9(8): 581-93. Some properties of different types of vesicles include those in Table 2:

TABLE 2

| Vesicle Properties | | | | | | |
|---|---|---|---|---|---|---|
| Feature | Exosomes | Microvesicles | Ectosomes | Membrane particles | Exosome-like vesicles | Apoptotic vesicles |
| Size | 50-100 nm | 100-1,000 nm | 50-200 nm | 50-80 nm | 20-50 nm | 50-500 nm |
| Density in sucrose | 1.13-1.19 g/ml | | | 1.04-1.07 g/ml | 1.1 g/ml | 1.16-1.28 g/ml |
| EM appearance | Cup shape | Irregular shape, electron dense | Bilamellar round structures | Round | Irregular shape | Heterogeneous |
| Sedimentation | 100,000 g | 10,000 g | 160,000-200,000 g | 100,000-200,000 g | 175,000 g | 1,200 g, 10,000 g, 100,000 g |
| Lipid composition | Enriched in cholesterol, sphingomyelin and ceramide; contains lipid rafts; expose PPS | Expose PPS | Enriched in cholesterol and diacylglycerol; expose PPS | | No lipid rafts | |
| Major protein markers | Tetraspanins (e.g., CD63, CD9), Alix, TSG101 | Integrins, selectins and CD40 ligand | CR1 and proteolytic enzymes; no CD63 | CD133; no CD63 | TNFRI | Histones |
| Intracellular origin | Internal compartments (endosomes) | Plasma membrane | Plasma membrane | Plasma membrane | | |

Abbreviations: phosphatidylserine (PPS); electron microscopy (EM)

Vesicles include shed membrane bound particles, or "microparticles," that are derived from either the plasma membrane or an internal membrane. Vesicles can be released into the extracellular environment from cells. Cells releasing vesicles include without limitation cells that originate from, or are derived from, the ectoderm, endoderm, or mesoderm. The cells may have undergone genetic, environmental, and/or any other variations or alterations. For example, the cell can be tumor cells. A vesicle can reflect any changes in the source cell, and thereby reflect changes in the originating cells, e.g., cells having various genetic mutations. In one mechanism, a vesicle is generated intracellularly when a segment of the cell membrane spontaneously invaginates and is ultimately exocytosed (see for example, Keller et al., *Immunol. Lett.* 107 (2): 102-8 (2006)). Vesicles also include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the vesicle lumen, including but not limited to tumor-derived microRNAs or intracellular proteins. Blebs and blebbing are further described in Charras et al., *Nature Reviews Molecular and Cell Biology,* Vol. 9, No. 11, p. 730-736 (2008). A vesicle shed into circulation or bodily fluids from tumor cells may be referred to as a "circulating tumor-derived vesicle." When such vesicle is an exosome, it may be referred to as a circulating-tumor derived exosome (CTE). In some instances, a vesicle can be derived from a specific cell of origin. CTE, as with a cell-of-origin specific vesicle, typically have one or more unique biomarkers that permit isolation of the CTE or cell-of-origin specific vesicle, e.g., from a bodily fluid and sometimes in a specific manner. For example, a cell or tissue specific markers are utilized to identify the cell of origin. Examples of such cell or tissue specific markers are disclosed herein and can further be accessed in the Tissue-specific Gene Expression and Regulation (TiGER) Database, available at bioinfo.wilmer.jhu.edu/tiger/; Liu et al. (2008) TiGER: a database for tissue-specific gene expression and regulation. BMC Bioinformatics. 9:271; TissueDistributionDBs, available at genome.dkfz-heidelberg.de/menu/tissue_db/index.html.

A vesicle can have a diameter of greater than about 10 nm, 20 nm, or 30 nm. A vesicle can have a diameter of greater than 40 nm, 50 nm, 100 nm, 200 nm, 500 nm, 1000 nm or greater than 10,000 nm. A vesicle can have a diameter of about 30-1000 nm, about 30-800 nm, about 30-200 nm, or about 30-100 nm. In some embodiments, the vesicle has a diameter of less than 10,000 nm, 1000 nm, 800 nm, 500 nm, 200 nm, 100 nm, 50 nm, 40 nm, 30 nm, 20 nm or less than 10 nm. As used herein the term "about" in reference to a numerical value means that variations of 10% above or below the numerical value are within the range ascribed to the specified value. Typical sizes for various types of vesicles are shown in Table 2. Vesicles can be assessed to measure the diameter of a single vesicle or any number of vesicles. For example, the range of diameters of a vesicle population or an average diameter of a vesicle population can be determined. Vesicle diameter can be assessed using methods known in the art, e.g., imaging technologies such as electron microscopy. In an embodiment, a diameter of one or more vesicles is determined using optical particle detection. See, e.g., U.S. Pat. No. 7,751,053, entitled "Optical Detection and Analysis of Particles" and issued Jul. 6, 2010; and U.S. Pat. No. 7,399,600, entitled "Optical Detection and Analysis of Particles" and issued Jul. 15, 2010.

In some embodiments, vesicles are directly assayed from a biological sample without prior isolation, purification, or concentration from the biological sample. For example, the amount of vesicles in the sample can by itself provide a biosignature that provides a diagnostic, prognostic or theranostic determination. Alternatively, the vesicle in the sample may be isolated, captured, purified, or concentrated from a sample prior to analysis. As noted, isolation, capture or purification as used herein comprises partial isolation, partial capture or partial purification apart from other components in the sample. Vesicle isolation can be performed using various techniques as described herein, e.g., chromatography, filtration, centrifugation, flow cytometry, affinity capture (e.g., to a planar surface or bead), and/or using microfluidics.

Vesicles such as exosomes can be assessed to provide a phenotypic characterization by comparing vesicle characteristics to a reference. In some embodiments, surface antigens on a vesicle are assessed. The surface antigens can provide an indication of the anatomical origin and/or cellular of the vesicles and other phenotypic information, e.g., tumor status. For example, wherein vesicles found in a patient sample, e.g., a bodily fluid such as blood, serum or plasma, are assessed for surface antigens indicative of colorectal origin and the presence of cancer. The surface antigens may comprise any informative biological entity that can be detected on the vesicle membrane surface, including without limitation surface proteins, lipids, carbohydrates, and other membrane components. For example, positive detection of colon derived vesicles expressing tumor antigens can indicate that the patient has colorectal cancer. As such, methods of the invention can be used to characterize any disease or condition associated with an anatomical or cellular origin, by assessing, for example, disease-specific and cell-specific biomarkers of one or more vesicles obtained from a subject.

In another embodiment, one or more vesicle payloads are assessed to provide a phenotypic characterization. The payload with a vesicle comprises any informative biological entity that can be detected as encapsulated within the vesicle, including without limitation proteins and nucleic acids, e.g., genomic or cDNA, mRNA, or functional fragments thereof, as well as microRNAs (miRs). In addition, methods of the invention are directed to detecting vesicle surface antigens (in addition or exclusive to vesicle payload) to provide a phenotypic characterization. For example, vesicles can be characterized by using binding agents (e.g., antibodies or aptamers) that are specific to vesicle surface antigens, and the bound vesicles can be further assessed to identify one or more payload components disclosed therein. As described herein, the levels of vesicles with surface antigens of interest or with payload of interest can be compared to a reference to characterize a phenotype. For example, overexpression in a sample of cancer-related surface antigens or vesicle payload, e.g., a tumor associated mRNA or microRNA, as compared to a reference, can indicate the presence of cancer in the sample. The biomarkers assessed can be present or absent, increased or reduced based on the selection of the desired target sample and comparison of the target sample to the desired reference sample. Non-limiting examples of target samples include: disease; treated/not-treated; different time points, such as a in a longitudinal study; and non-limiting examples of reference sample: non-disease; normal; different time points; and sensitive or resistant to candidate treatment(s).

MicroRNA

Various biomarker molecules can be assessed in biological samples or vesicles obtained from such biological samples. MicroRNAs comprise one class biomarkers assessed via methods of the invention. MicroRNAs, also referred to herein as miRNAs or miRs, are short RNA strands approximately 21-23 nucleotides in length. MiRNAs are encoded by genes that are transcribed from DNA but are not translated into protein and thus comprise non-coding RNA. The miRs are processed from primary transcripts known as pri-miRNA to short stem-loop structures called pre-miRNA and finally to the resulting single strand miRNA. The pre-miRNA typically forms a structure that folds back on itself in self-complementary regions. These structures are then processed by the nuclease Dicer in animals or DCL1 in plants. Mature miRNA molecules are partially complementary to one or more messenger RNA (mRNA) molecules and can function to regulate translation of proteins. Identified sequences of miRNA can be accessed at publicly available databases, such as www.microRNA.org, www.mirbase.org, or www.mirz.unibas.ch/cgi/miRNA.cgi.

miRNAs are generally assigned a number according to the naming convention "mir-[number]." The number of a miRNA is assigned according to its order of discovery relative to previously identified miRNA species. For example, if the last published miRNA was mir-121, the next discovered miRNA will be named mir-122, etc. When a miRNA is discovered that is homologous to a known miRNA from a different organism, the name can be given an optional organism identifier, of the form [organism identifier]-mir-[number]. Identifiers include hsa for *Homo sapiens* and mmu for *Mus Musculus*. For example, a human homolog to mir-121 might be referred to as hsa-mir-121 whereas the mouse homolog can be referred to as mmu-mir-121.

Mature microRNA is commonly designated with the prefix "miR" whereas the gene or precursor miRNA is designated with the prefix "mir." For example, mir-121 is a precursor for miR-121. When differing miRNA genes or precursors are processed into identical mature miRNAs, the genes/precursors can be delineated by a numbered suffix. For example, mir-121-1 and mir-121-2 can refer to distinct genes or precursors that are processed into miR-121. Lettered suffixes are used to indicate closely related mature sequences. For example, mir-121a and mir-121b can be processed to closely related miRNAs miR-121a and miR-121b, respectively. In the context of the invention, any microRNA (miRNA or miR) designated herein with the prefix mir-*or miR-*is understood to encompass both the precursor and/or mature species, unless otherwise explicitly stated otherwise.

Sometimes it is observed that two mature miRNA sequences originate from the same precursor. When one of the sequences is more abundant that the other, a "*" suffix can be used to designate the less common variant. For example, miR-121 would be the predominant product whereas miR-121*is the less common variant found on the opposite arm of the precursor. If the predominant variant is not identified, the miRs can be distinguished by the suffix "5p" for the variant from the 5' arm of the precursor and the suffix "3p" for the variant from the 3' arm. For example, miR-121-5p originates from the 5' arm of the precursor whereas miR-121-3p originates from the 3' arm. Less commonly, the 5p and 3p variants are referred to as the sense ("s") and anti-sense ("as") forms, respectively. For example, miR-121-5p may be referred to as miR-121-s whereas miR-121-3p may be referred to as miR-121-as.

The above naming conventions have evolved over time and are general guidelines rather than absolute rules. For example, the let- and lin-families of miRNAs continue to be referred to by these monikers. The mir/miR convention for precursor/mature forms is also a guideline and context should be taken into account to determine which form is referred to. Further details of miR naming can be found at www.mirbase.org or Ambros et al., A uniform system for microRNA annotation, RNA 9:277-279 (2003).

Plant miRNAs follow a different naming convention as described in Meyers et al., Plant Cell. 2008 20(12):3186-3190.

A number of miRNAs are involved in gene regulation, and miRNAs are part of a growing class of non-coding RNAs that is now recognized as a major tier of gene control. In some cases, miRNAs can interrupt translation by binding to regulatory sites embedded in the 3'-UTRs of their target mRNAs, leading to the repression of translation. Target recognition involves complementary base pairing of the target site with the miRNA's seed region (positions 2-8 at the miRNA's 5' end), although the exact extent of seed complementarity is not precisely determined and can be modified by 3' pairing. In other cases, miRNAs function like small interfering RNAs (siRNA) and bind to perfectly complementary mRNA sequences to destroy the target transcript.

Characterization of a number of miRNAs indicates that they influence a variety of processes, including early development, cell proliferation and cell death, apoptosis and fat metabolism. For example, some miRNAs, such as lin-4, let-7, mir-14, mir-23, and bantam, have been shown to play critical roles in cell differentiation and tissue development. Others are believed to have similarly important roles because of their differential spatial and temporal expression patterns.

The miRNA database available at miRBase (www.mirbase.org) comprises a searchable database of published miRNA sequences and annotation. Further information about miRBase can be found in the following articles, each of which is incorporated by reference in its entirety herein: Griffiths-Jones et al., miRBase: tools for microRNA genomics. NAR 2008 36(Database Issue):D154-D158; Griffiths-Jones et al., miRBase: microRNA sequences, targets and gene nomenclature. NAR 2006 34(Database Issue):D140-D144; and Griffiths-Jones, S. The microRNA Registry. NAR 2004 32(Database Issue):D109-D111. Representative miRNAs contained in Release 16 of miRBase, made available September 2010.

Techniques to isolate and characterize vesicles and miRs are known to those of skill in the art. In addition to the methodology presented herein, additional methods can be found in U.S. Pat. No. 7,888,035, entitled "METHODS FOR ASSESSING RNA PATTERNS" and issued Feb. 15, 2011; and International Patent Application Nos. PCT/US2010/058461, entitled "METHODS AND SYSTEMS FOR ISOLATING, STORING, AND ANALYZING VESICLES" and filed Nov. 30, 2010; and PCT/US2011/021160, entitled "DETECTION OF GASTROINTESTINAL DISORDERS" and filed Jan. 13, 2011; each of which applications are incorporated by reference herein in their entirety.

Circulating Biomarkers

Circulating biomarkers include biomarkers that are detectable in body fluids, such as blood, plasma, serum. Examples of circulating cancer biomarkers include cardiac troponin T (cTnT), prostate specific antigen (PSA) for prostate cancer and CA 125 for ovarian cancer. Circulating biomarkers according to the invention include any appropriate biomarker that can be detected in bodily fluid, including without limitation protein, nucleic acids, e.g., DNA, mRNA and microRNA, lipids, carbohydrates and metabolites. Circulating biomarkers can include biomarkers that are not associated with cells, such as biomarkers that are membrane associated, embedded in membrane fragments, part of a biological complex, or free in solution. In one embodiment, circulating biomarkers are biomarkers that are associated with one or more vesicles present in the biological fluid of a subject.

Circulating biomarkers have been identified for use in characterization of various phenotypes. See, e.g., Ahmed N, et al., Proteomic-based identification of haptoglobin-1 precursor as a novel circulating biomarker of ovarian cancer. Br. J. Cancer 2004; Mathelin et al., Circulating proteinic biomarkers and breast cancer, Gynecol Obstet Fertil. 2006 July-August; 34(7-8):638-46. Epub 2006 July 28; Ye et al., Recent technical strategies to identify diagnostic biomarkers for ovarian cancer. Expert Rev Proteomics. 2007 February; 4(1): 121-31; Carney, Circulating oncoproteins HER2/neu, EGFR and CAIX (MN) as novel cancer biomarkers. Expert Rev Mol Diagn. 2007 May; 7(3):309-19; Gagnon, Discovery and application of protein biomarkers for ovarian cancer, Curr Opin Obstet Gynecol. 2008 February; 20(1):9-13; Pasterkamp et al., Immune regulatory cells: circulating biomarker factories in cardiovascular disease. Clin Sci (Lond). 2008 August; 115(4):129-31; PCT Patent Publication WO/2007/088537; U.S. Pat. Nos. 7,745,150 and 7,655,479; U.S. Patent Publications 20110008808, 20100330683, 20100248290, 20100222230, 20100203566, 20100173788, 20090291932, 20090239246, 20090226937, 20090111121, 20090004687, 20080261258, 20080213907, 20060003465, 20050124071, and 20040096915, each of which applications is incorporated herein by reference in its entirety.

Vesicle Isolation

A vesicle may be purified or concentrated prior to analysis. Analysis of a vesicle can include quantitiating the amount one or more vesicle populations of a biological sample. For example, a heterogeneous population of vesicles can be quantitated, or a homogeneous population of vesicles, such as a population of vesicles with a particular biomarker profile, a particular biosignature, or derived from a particular cell type can be isolated from a heterogeneous population of vesicles and quantitated. Analysis of a vesicle can also include detecting, quantitatively or qualitatively, one or more particular biomarker profile or biosignature of a vesicle, as described herein.

A vesicle can be stored and archived, such as in a bio-fluid bank and retrieved for analysis as necessary. A vesicle may also be isolated from a biological sample that has been previously harvested and stored from a living or deceased subject. In addition, a vesicle may be isolated from a biological sample which has been collected as described in King et al., *Breast Cancer Res* 7(5): 198-204 (2005). A vesicle can be isolated from an archived or stored sample. Alternatively, a vesicle may be isolated from a biological sample and analyzed without storing or archiving of the sample. Furthermore, a third party may obtain or store the biological sample, or obtain or store the vesicle for analysis.

An enriched population of vesicles can be obtained from a biological sample. For example, vesicles may be concentrated or isolated from a biological sample using size exclusion chromatography, density gradient centrifugation, differential centrifugation, nanomembrane ultrafiltration, immunoabsorbent capture, affinity purification, microfluidic separation, or combinations thereof.

Size exclusion chromatography, such as gel permeation columns, centrifugation or density gradient centrifugation, and filtration methods can be used. For example, a vesicle can be isolated by differential centrifugation, anion exchange and/or gel permeation chromatography (for example, as described in U.S. Pat. No. 6,899,863 and U.S. Pat. No. 6,812,023), sucrose density gradients, organelle electrophoresis (for example, as described in U.S. Pat. No. 7,198,923), magnetic activated cell sorting (MACS), or with a nanomembrane ultrafiltration concentrator. Various combinations of isolation or concentration methods can be used.

Highly abundant proteins, such as albumin and immunoglobulin, may hinder isolation of vesicles from a biological sample. For example, a vesicle can be isolated from a biological sample using a system that utilizes multiple antibodies that are specific to the most abundant proteins found in a biological sample, such as blood. Such a system can remove up to several proteins at once, thus unveiling the lower abundance species such as cell-of-origin specific vesicles.

This type of system can be used for isolation of vesicles from biological samples such as blood, cerebrospinal fluid or urine. The isolation of vesicles from a biological sample may also be enhanced by high abundant protein removal methods as described in Chromy et al. *J Proteome Res* 2004; 3:1120-1127. In another embodiment, the isolation of vesicles from a biological sample may also be enhanced by removing serum proteins using glycopeptide capture as described in Zhang et al, *Mol Cell Proteomics* 2005; 4:144-155. In addition, vesicles from a biological sample such as urine may be isolated by differential centrifugation followed by contact with antibodies directed to cytoplasmic or anti-cytoplasmic epitopes as described in Pisitkun et al., *Proc Natl Acad Sci USA*, 2004; 101:13368-13373.

Isolation or enrichment of a vesicle from a biological sample can also be enhanced by use of sonication (for example, by applying ultrasound), detergents, other membrane-activating agents, or any combination thereof. For example, ultrasonic energy can be applied to a potential tumor site, and without being bound by theory, release of vesicles from a tissue can be increased, allowing an enriched population of vesicles that can be analyzed or assessed from a biological sample using one or more methods disclosed herein.

Filters

A vesicle can be isolated from a biological sample by filtering a biological sample from a subject through a filtration module and collecting from the filtration module a retentate comprising the vesicle, thereby isolating the vesicle from the biological sample. The method can comprise filtering a biological sample from a subject through a filtration module comprising a filter; and collecting from the filtration module a retentate comprising the vesicle, thereby isolating the vesicle from the biological sample. In one embodiment, the filter retains molecules greater than about 100 kiloDaltons.

The method can further comprise determining a biosignature of the vesicle. The method can also further comprise applying the retentate to a plurality of substrates, wherein each substrate is coupled to one or more capture agents, and each subset of the plurality of substrates comprises a different capture agent or combination of capture agents than another subset of the plurality of substrates.

Also provided herein is a method of determining a biosignature of a vesicle in a sample comprising: filtering a biological sample from a subject with a disorder through a filtration module, collecting from the filtration module a retentate comprising one or more vesicles, and determining a biosignature of the one or more vesicles. In one embodiment, the filtration module comprises a filter that retains molecules greater than about 100 or 150 kiloDaltons.

The method disclosed herein can further comprise characterizing a phenotype in a subject by filtering a biological sample from a subject through a filtration module, collecting from the filtration module a retentate comprising one or more vesicles; detecting a biosignature of the one or more vesicles; and characterizing a phenotype in the subject based on the biosignature, wherein characterizing is with at least 70% sensitivity. In some embodiments, characterizing comprises determining an amount of one or more vesicle having the biosignature. Furthermore, the characterizing can be from about 80% to 100% sensitivity.

Also provided herein is a method for multiplex analysis of a plurality of vesicles. In some embodiments, the method comprises filtering a biological sample from a subject through a filtration module; collecting from the filtration module a retentate comprising the plurality of vesicles, applying the plurality of vesicles to a plurality of capture agents, wherein the plurality of capture agents is coupled to a plurality of substrates, and each subset of the plurality of substrates is differentially labeled from another subset of the plurality of substrates; capturing at least a subset of the plurality of vesicles; and determining a biosignature for at least a subset of the captured vesicles. In one embodiment, each substrate is coupled to one or more capture agents, and each subset of the plurality of substrates comprises a different capture agent or combination of capture agents as compared to another subset of the plurality of substrates. In some embodiments, at least a subset of the plurality of substrates is intrinsically labeled, such as comprising one or more labels. The substrate can be a particle or bead, or any combination thereof. In one embodiment, the filtration module comprises a filter that retains molecules greater than about 100 or 150 kiloDaltons.

In some embodiments, the method for multiplex analysis of a plurality of vesicles comprises filtering a biological sample from a subject through a filtration module, wherein the filtration module comprises a filter that retains molecules greater than about 100 kiloDaltons; collecting from the filtration module a retentate comprising the plurality of vesicles; applying the plurality of vesicles to a plurality of capture agents, wherein the plurality of capture agents is coupled to a microarray; capturing at least a subset of the plurality of vesicles on the microarray; and determining a biosignature for at least a subset of the captured vesicles. In one embodiment, the filtration module comprises a filter that retains molecules greater than about 100 or 150 kiloDaltons.

The biological sample can be clarified prior to isolation by filtration. For example, non-vesicle components such as cellular debris can be removed. The clarification can be by low-speed centrifugation, such as at about 5,000×g, 4,000×g, 3,000×g, 2,000×g, 1,000×g, or less. The supernatant, or clarified biological sample, containing the vesicle can then be collected and filtered to isolate the vesicle from the clarified biological sample. In some embodiments, the biological sample is not clarified prior to isolation of a vesicle by filtration.

In some embodiments, isolation of a vesicle from a sample does not use high-speed centrifugation, such as ultracentrifugation. For example, isolation may not require the use of centrifugal speeds, such as about 100,000×g or more. In some embodiments, isolation of a vesicle from a sample uses speeds of less than 50,000×g, 40,000×g, 30,000×g, 20,000×g, 15,000×g, 12,000×g, or 10,000×g.

The filtration module utilized to isolate the vesicle from the biological sample can be a fiber-based filtration cartridge. For example, the fiber can be a hollow polymeric fiber, such as a polypropylene hollow fiber. A biological sample can be introduced into the filtration module by pumping the sample fluid, such as a biological fluid as disclosed herein, into the module with a pump device, such as a peristaltic pump. The pump flow rate can vary, such as at about 0.25, 0.5, 1, 1.5, 2, 2.5, 3, 3.5, 4, 4.5, 5, 6, 7, 8, 9, or 10 mL/minute.

The filtration module can be a membrane filtration module. For example, the membrane filtration module can comprise a filter disc membrane, such as a hydrophilic polyvinylidene difluoride (PVDF) filter disc membrane housed in a stirred cell apparatus (e.g., comprising a magnetic stirrer). In some embodiments, the sample moves through the filter as a result of a pressure gradient established on either side of the filter membrane.

The filter can comprise a material having low hydrophobic absorptivity and/or high hydrophilic properties. For example, the filter can have an average pore size for vesicle retention and permeation of most proteins as well as a surface that is hydrophilic, thereby limiting protein adsorption. For example, the filter can comprise a material selected from the group consisting of polypropylene, PVDF, polyethylene, polyfluoroethylene, cellulose, secondary cellulose acetate, polyvinylalcohol, and ethylenevinyl alcohol (EVAL®, Kuraray Co., Okayama, Japan). Additional materials that can be utilized in a filter include, but are not limited to, polysulfone and polyethersulfone.

The filtration module can have a filter that retains molecules greater than about 50, 60, 70, 80, 90, 100, 110, 120, 130, 140, 150, 160, 170, 180, 190, 200, 250, 300, 400, or 500 kiloDaltons (kDa), such as a filter that has a MWCO (molecular weight cut off) of about 50, 60, 70, 80, 90, 100, 110, 120, 130, 140, 150, 160, 170, 180, 190, 200, 250, 300, 400, or 500. In some embodiments, the filter within the filtration module has an average pore diameter of about 0.01 μm to about 0.15 μm, and in some embodiments from about 0.05 μm to about 0.12 gm. In some embodiments, the filter has an average pore diameter of about 0.06 μm, 0.07. μm, 0.08 μm, 0.09 μm, 0.1 μm, or 0.11 μm.

The filtration module can be a commerically available column, such as a column typically used for concentrating proteins or for isoatling proteins. Examples include, but are not limited to, columns from Millpore (Billerica, Mass.), such as Amicon® centrifugal filters, or from Pierce® (Rockford, Ill.), such as Pierce Concentrator filter devices. The filters can be as described in U.S. Pat. No. 6,269,957 or U.S. Pat. No. 6,357,601, both of which applications are incorporated by reference in their entirety herein.

The retentate comprising the isolated vesicle can be collected from the filtration module. The retentate can be collected by flushing the retentate from the filter. Selection of a filter composition having hydrophilic surface properties, thereby limiting protein adsorption, can be used, without being bound by theory, for easier collection of the retentate and minimize use of harsh or time-consuming collection techniques.

The collected retentate can then be used subsequent analysis, such as assessing a biosignature of one or more vesicles in the retentate, as further described herein. The analysis can be directly performed on the collected retentate. Alternatively, the collected retentate can be further concentrated or purified, prior to analysis of one or more vesicles. For example, the retentate can be further concentrated or vesicles further isolated from the retentate using size exclusion chromatography, density gradient centrifugation, differential centrifugation, immunoabsorbent capture, affinity purification, microfluidic separation, or combinations thereof, such as described herein. In some embodiments, the retentate can undergo another step of filtration. Alternatively, prior to isolation of a vesicle using a filter, the vesicle is concentrated or isolated using size exclusion chromatography, density gradient centrifugation, differential centrifugation, immunoabsorbent capture, affinity purification, microfluidic separation, or combinations thereof For example, prior to filtering a biological sample through a filtration module with a filter that retains molecules greater than about 50, 60, 70, 80, 90, 100, 110, 120, 130, 140, 150, 160, 170, 180, 190, 200, 250, 300, 400, or 500 kiloDaltons (kDa), such as a filter that has a MWCO (molecular weight cut off) of about 50, 60, 70, 80, 90, 100, 110, 120, 130, 140, 150, 160, 170, 180, 190, 200, 250, 300, 400, or 500, the biological sample may first be filtered through a filter having a porosity or pore size of between about 0.01 μm to about 2 μm, about 0.05 μm to about 1.5 μm. In some embodiments, the filter has a pore size of about 0.5, 0.6, 0.7, 0.8, 0.9, 1.0, 1.1, 1.2, 1.3, 1.4, 1.5, 1.6, 1.7, 1.8, 1.9 or 2.0 μm. The filter may be a syringe filter. Thus, in one embodiment, the method comprises filtering the biological sample through a filter, such as a syringe filter, wherein the syringe filter has a porosity of greater than about 1 μm, prior to filtering the sample through a filtration module comprising a filter that retains molecules greater than about 100 or 150 kiloDaltons.

The filtration module can be a component of a microfluidic device. Microfluidic devices, which may also be referred to as "lab-on-a-chip" systems, biomedical micro-electro-mechanical systems (bioMEMs), or multicomponent integrated systems, can be used for isolating, and analyzing, vesicles. Such systems miniaturize and compartmentalize processes that allow for binding of vesicles, detection of biomarkers, and other processes, such as further described herein A microfluidic device can also be used for isolation of a vesicle by comprising a filtration module. For example, a microfluidic device can use one more channels for isolating a vesicle from a biological sample based on size from a biological sample. A biological sample can be introduced into one or more microfluidic channels, which selectively allows the passage of vesicles. The microfluidic device can further comprise binding agents, or more than one filtration module to select vesicles based on a property of the vesicles, for example, size, shape, deformability, biomarker profile, or biosignature.

Binding Agents

A binding agent is an agent that binds to a circulating biomarker, such as a vesicle or a component of a vesicle. The binding agent can be used as a capture agent and/or a detection agent. A capture agent can bind and capture a circulating biomarker, such as by binding a component or biomarker of a vesicle. For example, the capture agent can be a capture antibody or capture antigen that binds to an antigen on a vesicle. A detection agent can bind to a circulating biomarker thereby facilitating detection of the biomarker. For example, a capture agent comprising an antigen or aptamer that is sequestered to a substrate can be used to capture a vesicle in a sample, and a detection agent comprising an antigen or aptamer that carries a label can be used to detect the captured vesicle via detection of the detection agent's label. In some embodiments, a vesicle is assessed using capture and detection agents that recognize the same vesicle biomarkers. For example, a vesicle population can be captured using a tetraspanin such as by using an anti-CD9 antibody bound to a substrate, and the captured vesicles can be detected using a fluorescently labeled anti-CD9 antibody to label the captured vesicles. In other embodiments, a vesicle is assessed using capture and detection agents that recognize different vesicle biomarkers. For example, a vesicle population can be captured using a cell-specific marker such as by using an anti-PCSA antibody bound to a substrate, and the captured vesicles can be detected using a fluorescently labeled anti-CD9 antibody to label the captured vesicles. Similarly, the vesicle population can be captured using a general vesicle marker such as by using an anti-CD9 antibody bound to a substate, and the captured vesicles can be detected using a fluorescently labeled antibody to a cell-specific or disease specific marker to label the captured vesicles.

In one embodiment, a vesicle is captured using a capture agent that binds to a biomarker on a vesicle. The capture agent can be coupled to a substrate and used to isolate a vesicle, as further described herein. In one embodiment, a capture agent is used for affinity capture or isolation of a vesicle present in a substance or sample.

A binding agent can be used after a vesicle is concentrated or isolated from a biological sample. For example, a vesicle can first be isolated from a biological sample before a vesicle with a specific biosignature is isolated or detected. The vesicle with a specific biosignature can be isolated or detected using a binding agent for the biomarker. A vesicle with the specific biomarker can be isolated or detected from a heterogeneous population of vesicles. Alternatively, a binding agent may be used on a biological sample comprising vesicles without a prior isolation or concentration step. For example, a binding agent is used to isolate or detect a vesicle with a specific biosignature directly from a biological sample.

A binding agent can be a nucleic acid, protein, or other molecule that can bind to a component of a vesicle. The binding agent can comprise DNA, RNA, monoclonal antibodies, polyclonal antibodies, Fabs, Fab', single chain antibodies, synthetic antibodies, aptamers (DNA/RNA), peptoids, zDNA, peptide nucleic acids (PNAs), locked nucleic acids (LNAs), lectins, synthetic or naturally occurring chemical compounds (including but not limited to drugs, labeling reagents), dendrimers, or a combination thereof. For example, the binding agent can be a capture antibody. In embodiments of the invention, the binding agent is membrane protein labeling agent. See, e.g., the membrane protein labeling agents disclosed in Alroy et al., US. Patent Publication US 2005/0158708. In an embodiment, vesicles are isolated or captured as described herein, and one or more membrane protein labeling agent is used to detect the vesicles.

In some instances, a single binding agent can be employed to isolate or detect a vesicle. In other instances, a combination of different binding agents may be employed to isolate or detect a vesicle. For example, at least 2, 3, 4, 5, 6, 7, 8, 9, 10, 11, 12, 13, 14, 15, 16, 17, 18, 19, 20, 25, 50, 75 or 100 different binding agents may be used to isolate or detect a vesicle from a biological sample. Furthermore, the one or more different binding agents for a vesicle can form a biosignature of a vesicle, as further described below.

Different binding agents can also be used for multiplexing. For example, isolation or detection of more than one population of vesicles can be performed by isolating or detecting each vesicle population with a different binding agent. Different binding agents can be bound to different particles, wherein the different particles are labeled. In another embodiment, an array comprising different binding agents can be used for multiplex analysis, wherein the different binding agents are differentially labeled or can be ascertained based on the location of the binding agent on the array. Multiplexing can be accomplished up to the resolution capability of the labels or detection method, such as described below. The binding agents can be used to detect the vesicles, such as for detecting cell-of-origin specific vesicles. A binding agent or multiple binding agents can themselves form a binding agent profile that provides a biosignature for a vesicle. One or more binding agents can be selected from FIG. 2. For example, if a vesicle population is detected or isolated using two, three, four or more binding agents in a differential detection or isolation of a vesicle from a heterogeneous population of vesicles, the particular binding agent profile for the vesicle population provides a biosignature for the particular vesicle population. The vesicle can be detected using any number of binding agents in a multiplex fashion. Thus, the binding agent can also be used to form a biosignature for a vesicle. The biosignature can be used to characterize a phenotype.

The binding agent can be a lectin. Lectins are proteins that bind selectively to polysaccharides and glycoproteins and are widely distributed in plants and animals. For example, lectins such as those derived from *Galanthus nivalis* in the form of *Galanthus nivalis* agglutinin ("GNA"), *Narcissus pseudonarcissus* in the form of *Narcissus pseudonarcissus* agglutinin ("NPA") and the blue green algae *Nostoc ellipsosporum* called "cyanovirin" (Boyd et al. *Antimicrob Agents Chemother* 41(7): 1521 1530, 1997; Hammar et al. *Ann N Y Acad Sci* 724: 166 169, 1994; Kaku et al. *Arch Biochem Biophys* 279(2): 298 304, 1990) can be used to isolate a vesicle. These lectins can bind to glycoproteins having a high mannose content (Chervenak et al. *Biochemistry* 34(16): 5685 5695, 1995). High mannose glycoprotein refers to glycoproteins having mannose-mannose linkages in the form of α-1→3 or α-1→+6 mannose-mannose linkages.

The binding agent can be an agent that binds one or more lectins. Lectin capture can be applied to the isolation of the biomarker cathepsin D since it is a glycosylated protein capable of binding the lectins *Galanthus nivalis* agglutinin (GNA) and concanavalin A (ConA).

Methods and devices for using lectins to capture vesicles are described in International Patent Applications PCT/US2010/058461, entitled "METHODS AND SYSTEMS FOR ISOLATING, STORING, AND ANALYZING VESICLES" and filed Nov. 30, 2010; PCT/US2009/066626, entitled "AFFINITY CAPTURE OF CIRCULATING BIOMARKERS" and filed Dec. 3, 2009; PCT/US2010/037467, entitled "METHODS AND MATERIALS FOR ISOLATING EXOSOMES" and filed Jun. 4, 2010; and PCT/US2007/006101, entitled "EXTRACORPOREAL REMOVAL OF MICROVESICULAR PARTICLES" and filed Mar. 9, 2007, each of which applications is incorporated by reference herein in its entirety.

The binding agent can be an antibody. For example, a vesicle may be isolated using one or more antibodies specific for one or more antigens present on the vesicle. For example, a vesicle can have CD63 on its surface, and an antibody, or capture antibody, for CD63 can be used to isolate the vesicle. Alternatively, a vesicle derived from a tumor cell can express EpCam, the vesicle can be isolated using an antibody for EpCam and CD63. Other antibodies for isolating vesicles can include an antibody, or capture antibody, to CD9, PSCA, TNFR, CD63, B7H3, MFG-E8, EpCam, Rab, CD81, STEAP, PCSA, PSMA, or 5T4. Other antibodies for isolating vesicles can include an antibody, or capture antibody, to DR3, STEAP, epha2, TMEM211, MFG-E8, Tissue Factor (TF), unc93A, A33, CD24, NGAL, EpCam, MUC17, TROP2, or TETS.

In some embodiments, the capture agent is an antibody to CD9, CD63, CD81, PSMA, PCSA, B7H3, EpCam, PSCA, ICAM, STEAP, or EGFR. The capture agent can also be used to identify a biomarker of a vesicle. For example, a capture agent such as an antibody to CD9 would identify CD9 as a biomarker of the vesicle. In some embodiments, a plurality of capture agents can be used, such as in multiplex analysis. The plurality of captures agents can comprise binding agents to one or more of: CD9, CD63, CD81, PSMA, PCSA, B7H3, EpCam, PSCA, ICAM, STEAP, and EGFR. In some embodiments, the plurality of capture agents comprise binding agents to CD9, CD63, CD81, PSMA, PCSA, B7H3, MFG-E8, and/or EpCam. In yet other embodiments, the plurality of capture agents comprises binding agents to CD9, CD63, CD81, PSMA, PCSA, B7H3, EpCam, PSCA, ICAM, STEAP, and/or EGFR. The plurality of capture agents comprises binding agents to TMEM211, MFG-E8, Tissue Factor (TF), and/or CD24.

The antibodies referenced herein can be immunoglobulin molecules or immunologically active portions of immunoglobulin molecules, i.e., molecules that contain an antigen binding site that specifically binds an antigen and synthetic antibodies. The immunoglobulin molecules can be of any class (e.g., IgG, IgE, IgM, IgD or IgA) or subclass of immunoglobulin molecule. Antibodies include, but are not limited to, polyclonal, monoclonal, bispecific, synthetic, humanized and chimeric antibodies, single chain antibodies, Fab fragments and $F(ab')_2$ fragments, Fv or Fv' portions, fragments produced by a Fab expression library, anti-idiotypic (anti-Id) antibodies, or epitope-binding fragments of any of the above. An antibody, or generally any molecule, "binds specifically" to an antigen (or other molecule) if the antibody binds preferentially to the antigen, and, e.g., has less than about 30%, 20%, 10%, 5% or 1% cross-reactivity with another molecule.

The binding agent can also be a polypeptide or peptide. Polypeptide is used in its broadest sense and may include a sequence of subunit amino acids, amino acid analogs, or peptidomimetics. The subunits may be linked by peptide bonds. The polypeptides may be naturally occurring, processed forms of naturally occurring polypeptides (such as by enzymatic digestion), chemically synthesized or recombinantly expressed. The polypeptides for use in the methods of the present invention may be chemically synthesized using standard techniques. The polypeptides may comprise D-amino acids (which are resistant to L-amino acid-specific proteases), a combination of D- and L-amino acids, β amino acids, or various other designer or non-naturally occurring amino acids (e.g., β-methyl amino acids, Ca-methyl amino acids, and Na-methyl amino acids, etc.) to convey special properties. Synthetic amino acids may include ornithine for lysine, and norleucine for leucine or isoleucine. In addition, the polypeptides can have peptidomimetic bonds, such as ester bonds, to prepare polypeptides with novel properties. For example, a polypeptide may be generated that incorporates a reduced peptide bond, i.e., $R_1—CH_2—NH—R_2$, where $R_1$ and $R_2$ are amino acid residues or sequences. A reduced peptide bond may be introduced as a dipeptide subunit. Such a polypeptide would be resistant to protease activity, and would possess an extended half-live in vivo. Polypeptides can also include peptoids (N-substituted glycines), in which the side chains are appended to nitrogen atoms along the molecule's backbone, rather than to the a-carbons, as in amino acids. Polypeptides and peptides are intended to be used interchangeably throughout this application, i.e. where the term peptide is used, it may also include polypeptides and where the term polypeptides is used, it may also include peptides.

A vesicle may be isolated, captured or detected using a binding agent. The binding agent can be an agent that binds a vesicle "housekeeping protein," or general vesicle biomarker. The biomarker can be CD63, CD9, CD81, CD82, CD37, CD53, or Rab-5b. Tetraspanins, a family of membrane proteins with four transmembrane domains, can be used as general vesicle markers. The tetraspanins include CD151, CD53, CD37, CD82, CD81, CD9 and CD63. There have been over 30 tetraspanins identified in mammals, including the TSPAN1 (TSP-1), TSPAN2 (TSP-2), TSPAN3 (TSP-3), TSPAN4 (TSP-4, NAG-2), TSPAN5 (TSP-5), TSPAN6 (TSP-6), TSPAN7 (CD231, TALLA-1, A15), TSPAN8 (CO-029), TSPAN9 (NET-5), TSPAN10 (Oculospanin), TSPAN11 (CD151-like), TSPAN12 (NET-2), TSPAN13 (NET-6), TSPAN14, TSPAN15 (NET-7), TSPAN16 (TM4-B), TSPAN17, TSPAN18, TSPAN19, TSPAN20 (UP1b, UPK1B), TSPAN21 (UP1a, UPK1A), TSPAN22 (RDS, PRPH2), TSPAN23 (ROM1), TSPAN24 (CD151), TSPAN25 (CD53), TSPAN26 (CD37), TSPAN27 (CD82), TSPAN28 (CD81), TSPAN29 (CD9), TSPAN30 (CD63), TSPAN31 (SAS), TSPAN32 (TSSC6), TSPAN33, and TSPAN34. Other commonly observed vesicle marker include those listed in Table 3. Any of these proteins can be used as vesicle markers.

TABLE 3

Proteins Observed in Vesicles from Multiple Cell Types

| Class | Protein |
|---|---|
| Antigen Presentation | MHC class I, MHC class II, Integrins, Alpha 4 beta 1, Alpha M beta 2, Beta 2 |
| Immunoglobulin family | ICAM1/CD54, P-selection |
| Cell-surface peptidases | Dipeptidylpeptidase IV/CD26, Aminopeptidase n/CD13 |
| Tetraspanins | CD9, CD37, CD63, CD81 |
| Heat-shock proteins | Hsp70, Hsp84/90 |
| Cytoskeletal proteins | Actin, Actin-binding proteins, Tubulin |
| Membrane transport and fusion | Annexin I, Annexin II, Annexin IV, Annexin V, Annexin VI, RAB7/RAP1B/RADGDI |
| Signal transduction | Gi2alpha/14-3-3, CBL/LCK |

The binding agent can also be an agent that binds to a vesicle derived from a specific cell type, such as a tumor cell (e.g. binding agent for Tissue factor, EpCam, B7H3 or CD24) or a specific cell-of-origin. The binding agent used to isolate or detect a vesicle can be a binding agent for an antigen selected from FIG. 1. The binding agent for a vesicle can also be selected from those listed in FIG. 2. The binding agent can be for an antigen such as a tetraspanin, MFG-E8, Annexin V, 5T4, B7H3, caveolin, CD63, CD9, E-Cadherin, Tissue factor, MFG-E8, TMEM211, CD24, PSCA, PCSA, PSMA, Rab-5B, STEAP, TNFR1, CD81, EpCam, CD59, CD81, ICAM, EGFR, or CD66. One or more binding agents, such as one or more binding agents for two or more of the antigens, can be used for isolating or detecting a vesicle. The binding agent used can be selected based on the desire of isolating or detecting a vesicle derived from a particular cell type or cell-of-origin specific vesicle.

A binding agent can also be linked directly or indirectly to a solid surface or substrate. A solid surface or substrate can be any physically separable solid to which a binding agent can be directly or indirectly attached including, but not limited to, surfaces provided by microarrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, TEFLON™, etc.), polysaccharides, nylon or nitrocellulose, resins, silica or silica-based materials including silicon and modified silicon, carbon, metals, inorganic glasses, plastics, ceramics, conducting polymers (including polymers such as polypyrole and polyindole); micro or nano-structured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In addition, as is known the art, the substrate may be coated using passive or chemically-derivatized coatings with any number of materials, including polymers, such as dextrans, acrylamides, gelatins or agarose. Such coatings can facilitate the use of the array with a biological sample.

For example, an antibody used to isolate a vesicle can be bound to a solid substrate such as a well, such as commercially available plates (e.g. from Nunc, Milan Italy). Each well can be coated with the antibody. In some embodiments, the antibody used to isolate a vesicle is bound to a solid substrate such as an array. The array can have a predetermined spatial arrangement of molecule interactions, binding islands, biomolecules, zones, domains or spatial arrangements of binding islands or binding agents deposited within discrete boundaries. Further, the term array may be used herein to refer to multiple arrays arranged on a surface, such as would be the case where a surface bore multiple copies of an array. Such surfaces bearing multiple arrays may also be referred to as multiple arrays or repeating arrays.

A binding agent can also be bound to particles such as beads or microspheres. For example, an antibody specific for a component of a vesicle can be bound to a particle, and the antibody-bound particle is used to isolate a vesicle from a biological sample. In some embodiments, the microspheres may be magnetic or fluorescently labeled. In addition, a binding agent for isolating vesicles can be a solid substrate itself. For example, latex beads, such as aldehyde/sulfate beads (Interfacial Dynamics, Portland, Oreg.) can be used.

A binding agent bound to a magnetic bead can also be used to isolate a vesicle. For example, a biological sample such as serum from a patient can be collected for colon cancer screening. The sample can be incubated with anti-CCSA-3 (Colon Cancer—Specific Antigen) coupled to magnetic microbeads. A low-density microcolumn can be placed in the magnetic field of a MACS Separator and the column is then washed with a buffer solution such as Tris-buffered saline. The magnetic immune complexes can then be applied to the column and unbound, non-specific material can be discarded. The CCSA-3 selected vesicle can be recovered by removing the column from the separator and placing it on a collection tube. A buffer can be added to the column and the magnetically labeled vesicle can be released by applying the plunger supplied with the column. The isolated vesicle can be diluted in IgG elution buffer and the complex can then be centrifuged to separate the microbeads from the vesicle. The pelleted isolated cell-of-origin specific vesicle can be resuspended in buffer such as phosphate-buffered saline and quantitated. Alternatively, due to the strong adhesion force between the antibody captured cell-of-origin specific vesicle and the magnetic microbeads, a proteolytic enzyme such as trypsin can be used for the release of captured vesicles without the need for centrifugation. The proteolytic enzyme can be incubated with the antibody captured cell-of-origin specific vesicles for at least a time sufficient to release the vesicles.

A binding agent, such as an antibody, for isolating vesicles is preferably contacted with the biological sample comprising the vesicles of interest for at least a time sufficient for the binding agent to bind to a component of the vesicle. For example, an antibody may be contacted with a biological sample for various intervals ranging from seconds days, including but not limited to, about 10 minutes, 30 minutes, 1 hour, 3 hours, 5 hours, 7 hours, 10 hours, 15 hours, 1 day, 3 days, 7 days or 10 days.

A binding agent, such as an antibody specific to an antigen listed in FIG. 1, or a binding agent listed in FIG. 2, can be labeled with, including but not limited to, a magnetic label, a fluorescent moiety, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles. The label can be, but not be limited to, fluorophores, quantum dots, or radioactive labels. For example, the label can be a radioisotope (radionuclides), such as $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$, or $^{213}Bi$. The label can be a fluorescent label, such as a rare earth chelate (europium chelate), fluorescein type, such as, but not limited to, FITC, 5-carboxyfluorescein, 6-carboxy fluorescein; a rhodamine type, such as, but not limited to, TAMRA; dansyl; Lissamine; cyanines; phycoerythrins; Texas Red; and analogs thereof. The fluorescent label can be one or more of FAM, dRHO, 5-FAM, 6FAM, dR6G, JOE, HEX, VIC, TET, dTAMRA, TAMRA, NED, dROX, PET, BHQ, Gold540 and LIZ.

A binding agent can be directly or indirectly labeled, e.g., the label is attached to the antibody through biotin-streptavidin. Alternatively, an antibody is not labeled, but is later contacted with a second antibody that is labeled after the first antibody is bound to an antigen of interest.

For example, various enzyme-substrate labels are available or disclosed (see for example, U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, but are not limited to, horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); alkaline phosphatase (AP) with para-nitrophenyl phosphate as chromogenic substrate; and β-D-galactosidase ((β-D-Gal) with a chromogenic substrate (e.g., p-nitrophenyl-β-D-galactosidase) or fluorogenic substrate 4-methylumbelliferyl-β-D-galactosidase.

Depending on the method of isolation or detection used, the binding agent may be linked to a solid surface or substrate, such as arrays, particles, wells and other substrates described above. Methods for direct chemical coupling of antibodies, to the cell surface are known in the art, and may include, for example, coupling using glutaraldehyde or maleimide activated antibodies. Methods for chemical coupling using multiple step procedures include biotinylation, coupling of trinitrophenol (TNP) or digoxigenin using for example succinimide esters of these compounds. Biotinylation can be accomplished by, for example, the use of D-biotinyl-N-hydroxysuccinimide. Succinimide groups react effectively with amino groups at pH values above 7, and preferentially between about pH 8.0 and about pH 8.5. Biotinylation can be accomplished by, for example, treating the cells with dithiothreitol followed by the addition of biotin maleimide.

Flow Cytometry

Isolation or detection of a vesicle using a particle such as a bead or microsphere can also be performed using flow cytometry. Flow cytometry can be used for sorting microscopic particles suspended in a stream of fluid. As particles pass through they can be selectively charged and on their exit can be deflected into separate paths of flow. It is therefore possible to separate populations from an original mix, such as a biological sample, with a high degree of accuracy and speed. Flow cytometry allows simultaneous multiparametric analysis of the physical and/or chemical characteristics of single cells flowing through an optical/electronic detection apparatus. A beam of light, usually laser light, of a single frequency (color) is directed onto a hydrodynamically focused stream of fluid. A number of detectors are aimed at the point where the stream passes through the light beam; one in line with the light beam (Forward Scatter or FSC) and several perpendicular to it (Side Scatter or SSC) and one or more fluorescent detectors.

Each suspended particle passing through the beam scatters the light in some way, and fluorescent chemicals in the particle may be excited into emitting light at a lower frequency than the light source. This combination of scattered and fluorescent light is picked up by the detectors, and by analyzing fluctuations in brightness at each detector (one for each fluorescent emission peak), it is possible to deduce various facts about the physical and chemical structure of each individual particle. FSC correlates with the cell size and SSC depends on the inner complexity of the particle, such as shape of the nucleus, the amount and type of cytoplasmic granules or the membrane roughness. Some flow cytometers have eliminated the need for fluorescence and use only light scatter for measurement.

Flow cytometers can analyze several thousand particles every second in "real time" and can actively separate out and isolate particles having specified properties. They offer high-throughput automated quantification, and separation, of the set parameters for a high number of single cells during each analysis session. Flow cytomers can have multiple lasers and fluorescence detectors, allowing multiple labels to be used to more precisely specify a target population by their phenotype. Thus, a flow cytometer, such as a multicolor flow cytometer, can be used to detect one or more vesicles with multiple fluorescent labels or colors. In some embodiments, the flow cytometer can also sort or isolate different vesicle populations, such as by size or by different markers.

The flow cytometer may have one or more lasers, such as 1, 2, 3, 4, 5, 6, 7, 8, 9, 10 or more lasers. In some embodiments, the flow cytometer can detect more than one color or fluorescent label, such as at least 2, 3, 4, 5, 6, 7, 8, 9, 10, 11, 12, 13, 14, 15, 16, 17, 18, 19, or 20 different colors or fluorescent labels. For example, the flow cytometer can have at least 2, 3, 4, 5, 6, 7, 8, 9, 10, 11, 12, 13, 14, 15, 16, 17, 18, 19, or 20 fluorescence detectors.

Examples of commerically available flow cytometers that can be used to detect or analyze one or more vesicles, to sort or separate different populations of vesicles, include, but are not limited to the MoFlo™ XDP Cell Sorter (Beckman Coulter, Brea, Calif.), MoFlo™ Legacy Cell Sorter (Beckman Coulter, Brea, Calif.), BD FACSAria™ Cell Sorter (BD Biosciences, San Jose, Calif.), BD™ LSRII (BD Biosciences, San Jose, Calif.), and BD FACSCalibur™ (BD Biosciences, San Jose, Calif.). Use of multicolor or multi-fluor cytometers can be used in multiplex analysis of vesicles, as further described below. In some embodiments, the flow cytometer can sort, and thereby collect or sort more than one population of vesicles based one or more characteristics. For example, two populations of vesicles differ in size, such that the vesicles within each population have a similar size range and can be differentially detected or sorted. In another embodiment, two different populations of vesicles are differentially labeled.

The data resulting from flow-cytometers can be plotted in 1 dimension to produce histograms or seen in 2 dimensions as dot plots or in 3 dimensions with newer software. The regions on these plots can be sequentially separated by a series of subset extractions which are termed gates. Specific gating protocols exist for diagnostic and clinical purposes especially in relation to hematology. The plots are often made on logarithmic scales. Because different fluorescent dye's emission spectra overlap, signals at the detectors have to be compensated electronically as well as computationally. Fluorophores for labeling biomarkers may include those described in Ormerod, *Flow Cytometry* 2nd ed, Springer-Verlag, New York (1999), and in Nida et al., *Gynecologic Oncology* 2005; 4 889-894 which is incorporated herein by reference.

Multiplexing

Multiplex experiments comprise experiments that can simultaneously measure multiple analytes in a single assay. Vesicles and associated biomarkers can be assessed in a multiplex fashion. Different binding agents can be used for multiplexing different vesicle populations. Different vesicle populations can be isolated or detected using different binding agents. Each population in a biological sample can be labeled with a different signaling label, such as a fluorophore, quantum dot, or radioactive label, such as described above. The label can be directly conjugated to a binding agent or indirectly used to detect a binding agent that binds a vesicle. The number of populations detected in a multiplexing assay is dependent on the resolution capability of the labels and the summation of signals, as more than two differentially labeled vesicle populations that bind two or more affinity elements can produce summed signals.

Multiplexing of at least 2, 3, 4, 5, 6, 7, 8, 9, 10, 11, 12, 13, 14, 15, 16, 17, 18, 19, 20, 25, 50, 75 or 100 different vesicle populations may be performed. For example, one population of vesicles specific to a cell-of-origin can be assayed along with a second population of vesicles specific to a different cell-of-origin, where each population is labeled with a different label. Alternatively, a population of vesicles with a particular biomarker or biosignature can be assayed along with a second population of vesicles with a different biomarker or biosignature. In some cases, hundreds or thousands of vesicles are assessed in a single assay.

In one embodiment, multiplex analysis is performed by applying a plurality of vesicles comprising more than one population of vesicles to a plurality of substrates, such as beads. Each bead is coupled to one or more capture agents. The plurality of beads is divided into subsets, where beads with the same capture agent or combination of capture agents form a subset of beads, such that each subset of beads has a different capture agent or combination of capture agents than another subset of beads. The beads can then be used to capture vesicles that comprise a component that binds to the capture agent. The different subsets can be used to capture different populations of vesicles. The captured vesicles can then be analyzed by detecting one or more biomarkers.

Flow cytometry can be used in combination with a particle-based or bead based assay. Multiparametric immunoassays or other high throughput detection assays using bead coatings with cognate ligands and reporter molecules with specific activities consistent with high sensitivity automation can be used. For example, beads in each subset can be differentially labeled from another subset. In a particle based assay system, a binding agent or capture agent for a vesicle, such as a capture antibody, can be immobilized on addressable beads or microspheres. Each binding agent for each individual binding assay (such as an immunoassay when the binding agent is an antibody) can be coupled to a distinct type of microsphere (i.e., microbead) and the binding assay reaction takes place on the surface of the microspheres. Microspheres can be distinguished by different labels, for example, a microsphere with a specific capture agent would have a different signaling label as compared to another microsphere with a different capture agent. For example, microspheres can be dyed with discrete fluorescence intensities such that the fluorescence intensity of a microsphere with a specific binding agent is different than that of another microsphere with a different binding agent.

The microsphere can be labeled or dyed with at least 2 different labels or dyes. In some embodiments, the microsphere is labeled with at least 3, 4, 5, 6, 7, 8, 9, or 10 different labels. Different microspheres in a plurality of microspheres can have more than one label or dye, wherein various subsets of the microspheres have various ratios and combinations of the labels or dyes permitting detection of different microspheres with different binding agents. For example, the various ratios and combinations of labels and dyes can permit different fluorescent intensities. Alternatively, the various ratios and combinations maybe used to generate different detection patters to identify the binding agent. The microspheres can be labeled or dyed externally or may have intrinsic fluorescence or signaling labels. Beads can be loaded separately with their appropriate binding agents and thus, different vesicle populations can be isolated based on the different binding agents on the differentially labeled microspheres to which the different binding agents are coupled.

In another embodiment, multiplex analysis can be performed using a planar substrate, wherein the the substrate comprises a plurality of capture agents. The plurality of capture agents can capture one or more populations of vesicles, and one or more biomarkers of the captured vesicles detected. The planar substrate can be a microarray or other substrate as further described herein.

Novel Binding Agents

A vesicle may be isolated or detected using a binding agent for a novel component of a vesicle, such as an antibody for a novel antigen specific to a vesicle of interest. Novel antigens that are specific to a vesicle of interest may be isolated or identified using different test compounds of known composition bound to a substrate, such as an array or a plurality of particles, which can allow a large amount of chemical/structural space to be adequately sampled using only a small fraction of the space. The novel antigen identified can also serve as a biomarker for the vesicle. For example, a novel antigen identified for a cell-of-origin specific vesicle can be a useful biomarker.

A binding agent can be identified by screening either a homogeneous or heterogeneous vesicle population against test compounds. Since the composition of each test compound on the substrate surface is known, this constitutes a screen for affinity elements. For example, a test compound array comprises test compounds at specific locations on the substrate addressable locations, and can be used to identify one or more binding agents for a vesicle. The test compounds can all be unrelated or related based on minor variations of a core sequence or structure. The different test compounds may include variants of a given test compound (such as polypeptide isoforms), test compounds that are structurally or compositionally unrelated, or a combination thereof.

A test compound can be a peptoid, polysaccharide, organic compound, inorganic compound, polymer, lipids, nucleic acid, polypeptide, antibody, protein, polysaccharide, or other compound. The test compound can be natural or synthetic. The test compound can comprise or consist of linear or branched heteropolymeric compounds based on any of a number of linkages or combinations of linkages (e.g., amide, ester, ether, thiol, radical additions, metal coordination, etc.), dendritic structures, circular structures, cavity structures or other structures with multiple nearby sites of attachment that serve as scaffolds upon which specific additions are made. The test compound can be spotted on a substrate or synthesized in situ, using standard methods in the art. In addition, the test compound can be spotted or synthesized in situ in combinations in order to detect useful interactions, such as cooperative binding.

The test compound can be a polypeptide with known amino acid sequence, thus, detection of a test compound binding with a vesicle can lead to identification of a polypeptide of known amino sequence that can be used as a binding agent. For example, a homogenous population of vesicles can be applied to a spotted array on a slide containing between a few and 1,000,000 test polypeptides having a length of variable amino acids. The polypeptides can be attached to the surface through the C-terminus. The sequence of the polypeptides can be generated randomly from 19 amino acids, excluding cysteine. The binding reaction can include a non-specific competitor, such as excess bacterial proteins labeled with another dye such that the specificity ratio for each polypeptide binding target can be determined. The polypeptides with the highest specificity and binding can be selected. The identity of the polypeptide on each spot is known, and thus can be readily identified. Once the novel antigens specific to the homogeneous vesicle population, such as a cell-of-origin specific vesicle is identified, such cell-of-origin specific vesicles may subsequently be isolated using such antigens in methods described hereafter.

An array can also be used for identifying an antibody as a binding agent for a vesicle. Test antibodies can be attached to an array and screened against a heterogeneous population of vesicles to identify antibodies that can be used to isolate or identify a vesicle. A homogeneous population of vesicles such as cell-of-origin specific vesicles can also be screened with an antibody array. Other than identifying antibodies to isolate or detect a homogeneous population of vesicles, one or more protein biomarkers specific to the homogenous population can be identified. Commercially available platforms with test antibodies pre-selected or custom selection of test antibodies attached to the array can be used. For example, an antibody array from Full Moon Biosystems can be screened using prostate cancer cell derived vesicles identifying antibodies to Bcl-XL, ERCC1, Keratin 15, CD81/TAPA-1, CD9, Epithelial Specific Antigen (ESA), and Mast Cell Chymase as binding agents (see for example, FIG. 63), and the proteins identified can be used as biomarkers for the vesicles.

An antibody or synthetic antibody to be used as a binding agent can also be identified through a peptide array. Another method is the use of synthetic antibody generation through antibody phage display. M13 bacteriophage libraries of antibodies (e.g. Fabs) are displayed on the surfaces of phage particles as fusions to a coat protein. Each phage particle displays a unique antibody and also encapsulates a vector that contains the encoding DNA. Highly diverse libraries can be constructed and represented as phage pools, which can be used in antibody selection for binding to immobilized antigens. Antigen-binding phages are retained by the immobilized antigen, and the nonbinding phages are removed by washing. The retained phage pool can be amplified by infection of an *Escherichia coli* host and the amplified pool can be used for additional rounds of selection to eventually obtain a population that is dominated by antigen-binding clones. At this stage, individual phase clones can be isolated and subjected to DNA sequencing to decode the sequences of the displayed antibodies. Through the use of phase display and other methods known in the art, high affinity designer antibodies for vesicles can be generated.

Bead-based assays can also be used to identify novel binding agents to isolate or detect a vesicle. A test antibody or peptide can be conjugated to a particle. For example, a bead can be conjugated to an antibody or peptide and used to detect and quantify the proteins expressed on the surface of a population of vesicles in order to discover and specifically select for novel antibodies that can target vesicles from specific tissue or tumor types. Any molecule of organic origin can be successfully conjugated to a polystyrene bead through use of a commercially available kit according to manufacturer's instructions. Each bead set can be colored a certain detectable wavelength and each can be linked to a known antibody or peptide which can be used to specifically measure which beads are linked to exosomal proteins matching the epitope of previously conjugated antibodies or peptides. The beads can be dyed with discrete fluorescence intensities such that each bead with a different intensity has a different binding agent as described above.

For example, a purified vesicle preparation can be diluted in assay buffer to an appropriate concentration according to empirically determined dynamic range of assay. A sufficient volume of coupled beads can be prepared and approximately 1 μl of the antibody-coupled beads can be aliqouted into a well and adjusted to a final volume of approximately 50 μl. Once the antibody-conjugated beads have been added to a vacuum compatible plate, the beads can be washed to ensure proper binding conditions. An appropriate volume of vesicle preparation can then be added to each well being tested and the mixture incubated, such as for 15-18 hours. A sufficient volume of detection antibodies using detection antibody diluent solution can be prepared and incubated with the mixture for 1 hour or for as long as necessary. The beads can then be washed before the addition of detection antibody (biotin expressing) mixture composed of streptavidin phycoereythin. The beads can then be washed and vacuum aspirated several times before analysis on a suspension array system using software provided with an instrument. The identity of antigens that can be used to selectively extract the vesicles can then be elucidated from the analysis.

Assays using imaging systems can be utilized to detect and quantify proteins expressed on the surface of a vesicle in order to discover and specifically select for and enrich vesicles from specific tissue, cell or tumor types. Antibodies, peptides or cells conjugated to multiple well multiplex carbon coated plates can be used. Simultaneous measurement of many analytes in a well can be achieved through the use of capture antibodies arrayed on the patterned carbon working surface. Analytes can then be detected with antibodies labeled with reagents in electrode wells with an enhanced electrochemiluminescent plate. Any molecule of organic origin can be successfully conjugated to the carbon coated plate. Proteins expressed on the surface of vesicles can be identified from this assay and can be used as targets to specifically select for and enrich vesicles from specific tissue or tumor types.

The binding agent can also be an aptamer, which refers to nucleic acids that can bond molecules other than their complementary sequence. An aptamer typically contains 30-80 nucleic acids and can have a high affinity towards a certain target molecule (IQ's reported are between $10^{-11}$-$10^{-6}$ mole/1). An aptamer for a target can be identified using systematic evolution of ligands by exponential enrichment (SELEX) (Tuerk & Gold, *Science* 249:505-510, 1990; Ellington & Szostak, Nature 346:818-822, 1990), such as described in U.S. Pat. Nos. 5,270,163, 6,482, 594, 6,291, 184, 6,376, 190 and U.S. Pat. No. 6,458,539. A library of nucleic acids can be contacted with a target vesicle, and those nucleic acids specifically bound to the target are partitioned from the remainder of nucleic acids in the library which do not specifically bind the target. The partitioned nucleic acids are amplified to yield a ligand-enriched pool. Multiple cycles of binding, partitioning, and amplifying (i.e., selection) result in identification of one or more aptamers with the desired activity. Another method for identifying an aptamer to isolate vesicles is described in U.S. Pat. No. 6,376,190, which describes increasing or decreasing frequency of nucleic acids in a library by their binding to a chemically synthesized peptide. Modified methods, such as Laser SELEX or deSELEX as described in U.S. Patent Publication No. 20090264508 can also be used.

Microfluidics

The methods for isolating or identifying vesicles can be used in combination with microfluidic devices. The methods of isolating or detecting a vesicle, such as described herien, can be performed using a microfluidic device. Microfluidic devices, which may also be referred to as "lab-on-a-chip" systems, biomedical micro-electro-mechanical systems (bioMEMs), or multicomponent integrated systems, can be used for isolating and analyzing a vesicle. Such systems miniaturize and compartmentalize processes that allow for binding of vesicles, detection of biosignatures, and other processes.

A microfluidic device can also be used for isolation of a vesicle through size differential or affinity selection. For example, a microfluidic device can use one more channels for isolating a vesicle from a biological sample based on size or by using one or more binding agents for isolating a vesicle from a biological sample. A biological sample can be introduced into one or more microfluidic channels, which selectively allows the passage of a vesicle. The selection can be based on a property of the vesicle, such as the size, shape, deformability, or biosignature of the vesicle.

In one embodiment, a heterogeneous population of vesicles can be introduced into a microfluidic device, and one or more different homogeneous populations of vesicles can be obtained. For example, different channels can have different size selections or binding agents to select for different vesicle populations. Thus, a microfluidic device can isolate a plurality of vesicles wherein at least a subset of the plurality of vesicles comprises a different biosignature from another subset of the plurality of vesicles. For example, the microfluidic device can isolate at least 2, 3, 4, 5, 6, 7, 8, 9, 10, 15, 20, 25, 30, 40, 50, 60, 70, 80, 90, or 100 different subsets of vesicles, wherein each subset of vesicles comprises a different biosignature.

In some embodiments, the microfluidic device can comprise one or more channels that permit further enrichment or selection of a vesicle. A population of vesicles that has been enriched after passage through a first channel can be introduced into a second channel, which allows the passage of the desired vesicle or vesicle population to be further enriched, such as through one or more binding agents present in the second channel.

Array-based assays and bead-based assays can be used with microfluidic device. For example, the binding agent can be coupled to beads and the binding reaction between the beads and vesicle can be performed in a microfluidic device. Multiplexing can also be performed using a microfluidic device. Different compartments can comprise different binding agents for different populations of vesicles, where each population is of a different cell-of-origin specific vesicle population. In one embodiment, each population has a different biosignature. The hybridization reaction between the microsphere and vesicle can be performed in a microfluidic device and the reaction mixture can be delivered to a detection device. The detection device, such as a dual or multiple laser detection system can be part of the microfluidic system and can use a laser to identify each bead or microsphere by its color-coding, and another laser can detect the hybridization signal associated with each bead.

Examples of microfluidic devices that may be used, or adapted for use with vesicles, include but are not limited to those described in U.S. Pat. Nos. 7,591,936, 7,581,429, 7,579,136, 7,575,722, 7,568,399, 7,552,741, 7,544,506, 7,541,578, 7,518,726, 7,488,596, 7,485,214, 7,467,928, 7,452,713, 7,452,509, 7,449,096, 7,431,887, 7,422,725, 7,422,669, 7,419,822, 7,419,639, 7,413,709, 7,411,184, 7,402,229, 7,390,463, 7,381,471, 7,357,864, 7,351,592, 7,351,380, 7,338,637, 7,329,391, 7,323,140, 7,261,824, 7,258,837, 7,253,003, 7,238,324, 7,238,255, 7,233,865, 7,229,538, 7,201,881, 7,195,986, 7,189,581, 7,189,580, 7,189,368, 7,141,978, 7,138,062, 7,135,147, 7,125,711, 7,118,910, 7,118,661, 7,640,947, 7,666,361, 7,704,735; and International Patent Publication WO 2010/072410; each of which patents or applications are incorporated herein by reference in their entirety. Another example for use with methods disclosed herein is described in Chen et al., *"Microfluidic isolation and transcriptome analysis of serum vesicles," Lab on a Chip, Dec. 8, 2009 DOI: 10.1039/6916199f*

In one embodiment, a microfluidic device for isolating or detecting a vesicle comprises a channel of less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, of 60 mm in width, or between about 2-60, 3-50, 3-40, 3-30, 3-20, or 4-20 mm in width. The microchannel can have a depth of less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65 or 70 µm, or between about 10-70, 10-40, 15-35, or 20-30 µm. Furthermore, the microchannel can have a length of less than about 1, 2, 3, 3.5, 4, 4.5, 5, 5.5, 6, 6.5, 7, 7.5, 8, 8.5, 9, 9.5 or 10 cm. The microfluidic device can have grooves on its ceiling that are less than about 40, 41, 42, 43, 44, 45, 46, 47, 48, 49, 50, 51, 52, 53, 54, 55, 56, 57, 58, 59, 6, 65, 70, 75, or 80 µm wide, or between about 40-80, 40-70, 40-60 or 45-55 µm wide. The grooves can be less than about 1, 2, 3, 4, 5, 6, 7, 8, 9, 10, 11, 12, 13, 14, 15, 16, 17, 18, 19, 20, 25, 30, 35, 40, 45, or 50 µm deep, such as between about 1-50, 5-40, 5-30, 3-20 or 5-15 µm.

The microfluidic device can have one or more binding agents attached to a surface in a channel, or present in a channel. For example, the microchannel can have one or more capture agents, such as a capture agent for EpCam, CD9, PCSA, CD63, CD81, PSMA, B7H3, PSCA, ICAM, STEAP, and EGFR. In one embodiment, a microchannel surface is treated with avidin and a capture agent, such as an antibody, that is biotinylated can be injected into the channel to bind the avidin.

A biological sample can be flowed into the microfluidic device, or a microchannel, at rates such as at least about 1, 2, 3, 4, 5, 6, 7, 8, 9, 10, 11, 12, 13, 14, 15, 16, 17, 18, 19, 20, 25, 30, 35, 40, 45, or 50 µl per minute, such as between about 1-50, 5-40, 5-30, 3-20 or 5-15 µl per minute. One or more vesicles can be captured and directly detected in the microfludic device. Alternatively, the captured vesicle may be released and exit the microfluidic device prior to analysis. In another embodiment, one or more captured vesicles are lysed in the microchannel and the lysate can be analyzed. Lysis buffer can be flowed through the channel and lyse the captured vesicles. For example, the lysis buffer can be flowed into the device or microchannel at rates such as at least about a, 2, 3, 4, 5, 6, 7, 8, 9, 10, 11, 12, 13, 14, 15, 16, 17, 18, 19, 20, 25, 26, 27, 28, 29, 30, 35, 40, 45, or 50 µl per minute, such as between about 1-50, 5-40, 10-30, 5-30 or 10-35 µl per minute. The lysate can be collected and analyzed, such as performing RT-PCR, PCR, mass spectrometry, Western blotting, or other assays, to detect one or more biomarkers of the vesicle.

With methods of detecting isolated vesicles as described here, e.g., antibody affinity isolation, the consistency of the results can be optimized as necessary using various concentration or isolation procedures. Such steps can include agitation such as shaking or vortexing, different isolation techniques such as polymer based isolation, e.g., with PEG, and concentration to different levels during filtration or other steps. It will be understood by those in the art that such treatments can be applied at various stages of testing the vesicle containing sample. In one embodiment, the sample itself, e.g., a bodily fluid such as plasma or serum, is vortexed. In some embodiments, the sample is vortexed after one or more sample treatment step, e.g., vesicle isolation, has occurred. Agitation can occur at some or all appropriate sample treatment steps as desired.

The results can also be optimized as desirable by treating the vesicle-containing sample with various agents. Such agents include additives to control aggregation and/or additives to adjust pH or ionic strength. Additives that control aggregation include blocking agents such as bovine serum albumen (BSA) and milk, chaotropic agents such as guanidium hydro chloride, and detergents or surfactants. Useful ionic detergents include sodium dodecyl sulfate (SDS, sodium lauryl sulfate (SLS)), sodium laureth sulfate (SLS, sodium lauryl ether sulfate (SLES)), ammonium lauryl sulfate (ALS), cetrimonium bromide, cetrimonium chloride, cetrimonium stearate, and the like. Useful non-ionic (zwitterionic) detergents include polyoxyethylene glycols, polysorbate 20 (also known as Tween 20), other polysorbates (e.g., 40, 60, 65, 80, etc), Triton-X (e.g., X100, X114), 3[(3-cholamidopropyl)dimethylammonio]-1-propanesulfonate (CHAPS), CHAPSO, deoxycholic acid, sodium deoxycholate, NP-40, glycosides, octyl-thio-glucosides, maltosides, and the like. In some embodiments, Pluronic F-68, a surfactant shown to reduce platelet aggregation, is used to treat samples containing vesicles during isolation and/or detection. F68 can be used from a 0.1% to 10% concentration, e.g., a 1%, 2.5% or 5% concentration. The pH and/or ionic strength of the solution can be adjusted with various acids, bases, buffers or salts, including without limitation sodium chloride (NaCl), phosphate-buffered saline (PBS), tris-buffered saline (TBS), sodium phosphate, potassium chloride, potassium phosphate, sodium citrate and saline-sodium citrate (SSC) buffer. In some embodiments, NaCl is added at a concentration of 0.1% to 10%, e.g., 1%, 2.5% or 5% final concentration. In some embodiments, Tween 20 is added to 0.005 to 2% concentration, e.g., 0.05%, 0.25% or 0.5% final concentration. In some embodiments, BSA is added to 0.1% to 10% concentration, e.g., 3%, 3.5% or 7% concentration. In some embodiments, SSC/detergent (e.g., 20×SSC with 0.5% Tween 20 or 0.1% Triton-X 100) is added to 0.1% to 10% concentration, e.g., at 1.0% or 5.0% concentration.

It will be understood that the methods of detecting vesicles can be optimized as desired with various combinations of protocols and treatments as described herein. A detection protocol can be optimized by various combinations of agitation, isolation methods, and additives. In some embodiments, the patient sample is vortexed before and after isolation steps, and the sample is treated with blocking agents including BSA and F68. Such treatments may reduce the formation of large aggregates or protein or other biological debris and thus provide a more consistent detection reading.

Cell-of-Origin and Disease-Specific Vesicles

The bindings agent disclosed herein can be used to isolate or detect a vesicle, such as a cell-of-origin vesicle or vesicle with a specific biosignature. The beinding agent can be used to isolate or detect a heterogeneous population of vesicles from a sample or can be used to isolate or detect a homogeneous population of vesicles, such as cell-of-origin specific vesicles with specific biosignatures, from a heterogeneous population of vesicles.

A homogeneous population of vesicles, such as cell-of-origin specific vesicles, can be analyzed and used to characterize a phenotype for a subject. Cell-of-origin specific vesicles are esicles derived from specific cell types, which can include, but are not limited to, cells of a specific tissue, cells from a specific tumor of interest or a diseased tissue of interest, circulating tumor cells, or cells of maternal or fetal origin. The vesicles may be derived from tumor cells or lung, pancreas, stomach, intestine, bladder, kidney, ovary, testis, skin, colorectal, breast, prostate, brain, esophagus, liver, placenta, or fetal cells. The isolated vesicle can also be from a particular sample type, such as urinary vesicle.

A cell-of-origin specific vesicle from a biological sample can be isolated using one or more binding agents that are specific to a cell-of-origin. Vesicles for analysis of a disease or condition can be isolated using one or more binding agent specific for biomarkers for that disease or condition.

A vesicle can be concentrated prior to isolation or detection of a cell-of-origin specific vesicle, such as through centrifugation, chromatography, or filtration, as described above, to produce a heterogeneous population of vesicles prior to isolation of cell-of-origin specific vesicles. Alternatively, the vesicle is not concentrated, or the biological sample is not enriched for a vesicle, prior to isolation of a cell-of-origin vesicle.

FIG. 61 illustrates a flowchart which depicts one method 100 for isolating or identifying a cell-of-origin specific vesicle. First, a biological sample is obtained from a subject in step 102. The sample can be obtained from a third party or from the same party performing the analysis. Next, cell-of-origin specific vesicles are isolated from the biological sample in step 104. The isolated cell-of-origin specific vesicles are then analyzed in step 106 and a biomarker or biosignature for a particular phenotype is identified in step 108. The method may be used for a number of phenotypes. In some embodiments, prior to step 104, vesicles are concentrated or isolated from a biological sample to produce a homogeneous population of vesicles. For example, a heterogeneous population of vesicles may be isolated using centrifugation, chromatography, filtration, or other methods as described above, prior to use of one or more binding agents specific for isolating or identifying vesicles derived from specific cell types.

A cell-of-origin specific vesicle can be isolated from a biological sample of a subject by employing one or more binding agents that bind with high specificity to the cell-of-origin specific vesicle. In some instances, a single binding agent can be employed to isolate a cell-of-origin specific vesicle. In other instances, a combination of binding agents may be employed to isolate a cell-of-origin specific vesicle. For example, at least 2, 3, 4, 5, 6, 7, 8, 9, 10, 11, 12, 13, 14, 15, 16, 17, 18, 19, 20, 25, 50, 75, or 100 different binding agents may be used to isolate a cell-of-origin vesicle. Therefore, a vesicle population (e.g., vesicles having the same binding agent profile) can be identified by utilizing a single or a plurality of binding agents.

One or more binding agents can be selected based on their specificity for a target antigen(s) that is specific to a cell-of-origin, e.g., a cell-of-origin that is related to a tumor, autoimmune disease, cardiovascular disease, neurological disease, infection or other disease or disorder. The cell-of-origin can be from a cell that is informative for a diagnosis, prognosis, disease stratification, theranosis, prediction of responder/non-responder status, disease monitoring, treatment monitoring and the like as related to such diseases and disorders. The cell-of-origin can also be from a cell useful to discover biomarkers for use thereto. Non-limiting examples of antigens which may be used singularly, or in combination, to isolate a cell-of-origin specific vesicle, disease specific vesicle, or tumor specific vesicle, are shown in FIG. 1 and are also described herein. The antigen can comprise membrane bound antigens which are accessible to binding agents. The antigen can be a biomarker related to characterizing a phenotype.

One of skill will appreciate that any applicable antigen that can be used to isolate an informative vesicle is contemplated by the invention. Binding agents, e.g., antibodies, aptamers and lectins, can be chosen that recognize surface antigens and/or fragments thereof, as outlined herein. The binding agents can recognize antigens specific to the desired cell type or location and/or recognize biomarkers associated with the desired cells. The cells can be, e.g., tumor cells, other diseased cells, cells that serve as markers of disease such as activated immune cells, etc. One of skill will appreciate that binding agents for any cells of interest can be useful for isolating vesicles associated with those cells. One of skill will further appreciate that the binding agents disclosed herein can be used for detecting vesicles of interest. As a non-limiting example, a binding agent to a vesicle biomarker can be labeled directly or indirectly in order to detect vesicles bound by one of more of the same or different binding agents.

A number of targets for binding agents useful for binding to vesicles associated with cancer, autoimmune diseases, cardiovascular diseases, neurological diseases, infection or other disease or disorders are presented in Table 4. A vesicle derived from a cell associated with one of the listed disorders can be characterized using one of the antigens in the table. The binding agent, e.g., an antibody or aptamer, can recognize an epitope of the listed antigens, a fragment thereof, or binding agents can be used against any appropriate combination. Other antigens associated with the disease or disorder can be recognized as well in order to characterize the vesicle. One of skill will appreciate that any applicable antigen that can be used to assess an informative vesicle is contemplated by the invention for isolation, capture or detection in order to characterize a vesicle.

TABLE 4

Illustrative Antigens for Use in Characterizing Various Diseases and Disorders

| Disease or disorder | Target |
|---|---|
| Breast cancer, e.g., glandular or stromal cells | BCA-225, hsp70, MART1, ER, VEGFA, Class III b-tubulin, HER2/neu (for Her2+ breast cancer), GPR30, ErbB4 (JM) isoform, MPR8, MISIIR |
| Ovarian Cancer | CA125, VEGFR2, HER2, MISIIR, VEGFA, CD24 |
| Lung Cancer | CYFRA21-1, TPA-M, TPS, CEA, SCC-Ag, XAGE-1b, HLA Class 1, TA-MUC1, KRAS, hENT1, kinin B1 receptor, kinin B2 receptor, TSC403, HTI56, DC-LAMP |
| Colon Cancer | CEA, MUC2, GPA33, CEACAM5, ENFB1, CCSA-3, CCSA-4, ADAM10, CD44, NG2, ephrin B1, plakoglobin, galectin 4, RACK1, tetraspanin-8, FASL, A33, CEA, EGFR, dipeptidase 1, PTEN, Na(+)-dependent glucose transporter, UDP-glucuronosyltransferase 1A |
| Prostate Cancer | PSA, TMPRSS2, FASLG, TNFSF10, PSMA, NGEP, Il-7RI, CSCR4, CysLT1R, TRPM8, Kv1.3, TRPV6, TRPM8, PSGR, MISIIR, galectin-3, PCA3, TMPRSS2: ERG |

TABLE 4-continued

Illustrative Antigens for Use in Characterizing Various Diseases and Disorders

| Disease or disorder | Target |
|---|---|
| Brain Cancer | PRMT8, BDNF, EGFR, DPPX, Elk, Densin-180, BAI2, BAI3 |
| Blood Cancer (hematological malignancy) | CD44, CD58, CD31, CD11a, CD49d, GARP, BTS, Raftlin |
| Melanoma | DUSP1, TYRP1, SILV, MLANA, MCAM, CD63, Alix, hsp70, meosin, p120 catenin, PGRL, syntaxin binding protein 1 & 2, caveolin |
| Liver Cancer (hepatocellular carcinoma) | HBxAg, HBsAg, NLT |
| Cervical Cancer | MCT-1, MCT-2, MCT-4 |
| Endometrial Cancer | Alpha V Beta 6 integrin |
| Psoriasis | flt-1, VPF receptors, kdr |
| Autoimmune Disease | Tim-2 |
| Irritable Bowel Disease (IBD or Syndrome (IBS) | IL-16, IL-1beta, IL-12, TNF-alpha, interferon-gamma, IL-6, Rantes, II-12, MCP-1, 5HT |
| Diabetes, e.g., pancreatic cells | IL-6, CRP, RBP4 |
| Barrett's Esophagus | p53, MUC1, MUC6 |
| Fibromyalgia | neopterin, gp130 |
| Benign Prostatic Hyperplasia (BPH) | KIA1, intact fibronectin |
| Multiple Sclerosis | B7, B7-2, CD-95 (fas), Apo-1/Fas |
| Parkinson's Disease | PARK2, ceruloplasmin, VDBP, tau, DJ-1 |
| Rheumatic Disease | Citrulinated fibrin a-chain, CD5 antigen-like fibrinogen fragment D, CD5 antigen-like fibrinogen fragment B, TNF alpha |
| Alzheimer's Disease | APP695, APP751 or APP770, BACE1, cystatin C, amyloid β T-tau, complement factor H, alpha-2-macroglobulin |
| Head and Neck Cancer | EGFR, EphB4, Ephrin B2 |
| Gastrointestinal Stromal Tumor (GIST) | c-kit PDGFRA, NHE-3 |
| Renal Cell Carcinoma | c PDGFRA, VEGF, HIF 1 alpha |
| Schizophrenia | ATP5B, ATP5H, ATP6V1B, DNM1 |
| Peripheral Neuropathic Pain | OX42, ED9 |
| Chronic Neuropathic Pain | chemokine receptor (CCR2/4) |
| Prion Disease | PrPSc, 14-3-3 zeta, S-100, AQP4 |
| Stroke | S-100, neuron specific enolase, PARK7, NDKA, ApoC-I, ApoC-III, SAA or AT-III fragment, Lp-PLA2, hs-CRP |
| Cardiovascular Disease | FATP6 |
| Esophageal Cancer | CaSR |
| Tuberculosis | antigen 60, HSP, Lipoarabinomannan, Sulfolipid, antigen of acylated trehalose family, DAT, TAT, Trehalose 6,6-dimycolate (cord-factor) antigen |
| HIV | gp41, gp120 |
| Autism | VIP, PACAP, CGRP, NT3 |
| Asthma | YKL-40, S-nitrosothiols, SSCA2, PAI, amphiregulin, periostin |
| Lupus | TNFR |
| Cirrhosis | NLT, HBsAg |
| Influenza | hemagglutinin, neurominidase |
| Vulnerable Plaque | Alpha v. Beta 3 integrin, MMP9 |

A cell-of-origin specific vesicle may be isolated using novel binding agents, using methods as described herein. Furthermore, a cell-of-origin specific vesicle can also be isolated from a biological sample using isolation methods based on cellular binding partners or binding agents of such vesicles. Such cellular binding partners can include but are not limited to peptides, proteins, RNA, DNA, apatmers, cells or serum-associated proteins that only bind to such vesicles when one or more specific biomarkers are present. Isolation or deteciton of a cell-of-origin specific vesicle can be carried out with a single binding partner or binding agent, or a combination of binding partners or binding agents whose singular application or combined application results in cell-of-origin specific isolation or detection. Non-limiting examples of such binding agents are provided in FIG. 2. For example, a vesicle for characterizing breast cancer can be isolated with one or more binding agents including, but not limited to, estrogen, progesterone, Herceptin (Trastuzumab), CCND1, MYC PNA, IGF-1 PNA, MYC PNA, SC4 aptamer (Ku), AII-7 aptamer (ERB2), Galectin-3, mucin-type 0-glycans, L-PHA, Galectin-9, or any combination thereof.

A binding agent may also be used for isolating or detecting a cell-of-origin specific vesicle based on: i) the presence of antigens specific for cell-of-origin specific vesicles; ii) the absence of markers specific for cell-of-origin specific vesicles; or iii) expression levels of biomarkers specific for cell-of-origin specific vesicles. A heterogeneous population of vesicles can be applied to a surface coated with specific binding agents designed to rule out or identify the cell-of-origin characteristics of the vesicles. Various binding agents, such as antibodies, can be arrayed on a solid surface or substrate and the heterogeneous population of vesicles is allowed to contact the solid surface or substrate for a sufficient time to allow interactions to take place. Specific binding or non-binding to given antibody locations on the array surface or substrate can then serve to identify antigen specific characteristics of the vesicle population that are specific to a given cell-of-origin.

A cell-of-origin specific vesicle can be enriched or isolated using one or more binding agents using a magnetic capture method, fluorescence activated cell sorting (FACS) or laser cytometry as described above. Magnetic capture methods can include, but are not limited to, the use of magnetically activated cell sorter (MACS) microbeads or magnetic columns. Examples of immunoaffinity and magnetic particle methods that can be used are described in U.S. Pat. Nos. 4,551,435, 4,795,698, 4,925,788, 5,108,933, 5,186,827, 5,200,084 or 5,158,871. A cell-of-origin specific vesicle can also be isolated following the general methods described in U.S. Pat. No. 7,399,632, by using combination of antigens specific to a vesicle.

Any other appropriate method for isolating or otherwise enriching the cell-of-origin specific vesicles with respect to a biological sample may also be used in combination with the present invention. For example, size exclusion chromatography such as gel permeation columns, centrifugation or density gradient centrifugation, and filtration methods can be used in combination with the antigen selection methods described herein. The cell-of-origin specific vesicles may also be isolated following the methods described in Koga et al., *Anticancer Research,* 25:3703-3708 (2005), Taylor et al., *Gynecologic Oncology,* 110:13-21 (2008), Nanjee et al., *Clin Chem,* 2000; 46:207-223 or U.S. Pat. No. 7,232,653.

Accordingly, vesicles can be isolated that are isolated from cells derived from a tumor, or site of autoimmune disease, cardiovascular disease, neurological disease, infection or other disease or disorder. In some embodiments, the isolated vesicles are derived from cells related to such diseases and disorders, e.g., immune cells that play a role in the etiology of the disease and whose analysis is informative for a diagnosis, prognosis, disease stratification, theranosis, prediction of responder/non-responder status, disease monitoring, treatment monitoring and the like as relates to such diseases and disorders. The vesicles are further useful to discover biomarkers. The isolated vesicles can then be assessed for characterizing a phenotype as described herein.

Vesicle Assessment

A phenotype can be characterized for a subject by analyzing a biological sample from the subject and determining the level, amount, or concentration of one or more populations of vesicles in the sample. A vesicle can be purified or concentrated prior to determining the amount of vesicles. Alternatively, the amount of vesicles can be directly assayed from a sample, without prior purification or concentration. The vesicles can be cell-of-origin specific vesicles or vesicles with a specific biosignature. The amount of vesicles can be used when characterizing a phenotype, such as a diagnosis, prognosis, theranosis, or prediction of responder/non-responder status. In some embodiments, the amount is used to determine a physiological or biological state, such as pregnancy or the stage of pregnancy. The amount of vesicles can also be used to determine treatment efficacy, stage of a disease or condition, or progression of a disease or condition. For example, the amount of vesicles can be proportional or inversely proportional to an increase in disease stage or progression. The amount of vesicles can also be used to monitor progression of a disease or condition or to monitor a subject's response to a treatment.

The vesicles can be evaluated by comparing the level of vesicles with a reference level or value of vesicles. The reference value can be particular to physical or temporal endpoint. For example, the reference value can be from the same subject from whom a sample is assessed, or the reference value can be from a representative population of samples (e.g., samples from normal subjects not exhibiting a symptom of disease). Therefore, a reference value can provide a threshold measurement which is compared to a subject sample's readout for a vesicle population assayed in a given sample. Such reference values may be set according to data pooled from groups of sample corresponding to a particular cohort, including but not limited to age (e.g., newborns, infants, adolescents, young, middle-aged adults, seniors and adults of varied ages), racial/ethnic groups, normal versus diseased subjects, smoker v. non-smoker, subject receiving therapy versus untreated subject, different time points of treatment for a particular individual or group of subjects similarly diagnosed or treated or combinations thereof. Furthermore, by determining vesicle levels at different timepoints of treatment for a particular individual, the individual's response to the treatment or progression of a disease or condition for which the individual is being treated for, can be monitored.

A reference value may be based on samples assessed from the same subject so to provide individualized tracking. Frequent testing of a patient may provide better comparisons to the reference values previously established for a particular patient and would allow a physician to more accurately assess the patient's disease stage or progression, and to inform a better decision for treatment. The reduced intraindividual variance of vesicle levels can allow a more specific and individualized threshold to be defined for the patient. Temporal intrasubject variation allows each individual to serve as a longitudinal control for optimum analysis of disease or physiological state.

Reference values can be established for unaffected individuals (of varying ages, ethnic backgrounds and sexes) without a particular phenotype by determining the amount of vesicles in an unaffected individual. For example, a reference value for a reference population can be used as a baseline for detection of one or more vesicle populations in a test subject. If a sample from a subject has a level or value that is similar to the reference, the subject can be identified to not have the disease, or of having a low likelihood of developing a disease.

Alternatively, reference values or levels can be established for individuals with a particular phenotype by determining the amount of one or more populations of vesicles in an individual with the phenotype. In addition, an index of values can be generated for a particular phenotype. For example, different disease stages can have different values, such as obtained from individuals with the different disease stages. A subject's value can be compared to the index and a diagnosis or prognosis of the disease can be determined, such as the disease stage or progression. In other embodiments, an index of values is generated for therapeutic efficacies. For example, the level of vesicles of individuals with a particular disease can be generated and noted what treatments were effective for the individual. The levels can be used to generate values of which is a subject's value is compared, and a treatment or therapy can be selected for the individual, e.g., by predicting from the levels whether the subject is likely to be a responder or non-responder for a treatment.

In some embodiments, a reference value is determined for individuals unaffected with a particular cancer, by isolating or detecting vesicles with an antigen that specifically targets biomarkers for the particular cancer. As a non-limiting example, individuals with varying stages of colorectal cancer and noncancerous polyps can be surveyed using the same techniques described for unaffected individuals and the levels of circulating vesicles for each group can be determined. In some embodiments, the levels are defined as means±standard deviations from at least two separate experiments performed in at least triplicate. Comparisons between these groups can be made using statistical tests to determine statistical significance of distinguishing biomarkers observed. In some embodiments, statistical significance is determined using a parametric statistical test. The parametric statistical test can comprise, without limitation, a fractional factorial design, analysis of variance (ANOVA), a t-test, least squares, a Pearson correlation, simple linear regression, nonlinear regression, multiple linear regression, or multiple nonlinear regression. Alternatively, the parametric statistical test can comprise a one-way analysis of variance, two-way analysis of variance, or repeated measures analysis of variance. In other embodiments, statistical significance is determined using a nonparametric statistical test. Examples include, but are not limited to, a Wilcoxon signed-rank test, a Mann-Whitney test, a Kruskal-Wallis test, a Friedman test, a Spearman ranked order correlation coefficient, a Kendall Tau analysis, and a nonparametric regression test. In some embodiments, statistical significance is determined at a p-value of less than 0.05, 0.01, 0.005, 0.001, 0.0005, or 0.0001. The p-values can also be corrected for multiple comparisons, e.g., using a Bonferroni correction, a modification thereof, or other technique known to those in the art, e.g., the Hochberg correction, Holm-Bonferroni correction, Šidák correction, Dunnett's correction or Tukey's multiple comparisons. In some embodiments, an ANOVA is followed by Tukey's correction for post-test comparing of the biomarkers from each population.

Reference values can also be established for disease recurrence monitoring (or exacerbation phase in MS), for therapeutic response monitoring, or for predicting responder/non-responder status.

In some embodiments, a reference value for microRNA obtained from vesicles is determined using an artificial vesicle, also referred to herein as a synthetic vesicle. Methods for manufacturing artificial vesicles are known to those of skill in the art, e.g., using liposomes. Artificial vesicles can be manufactured using methods disclosed in US20060222654 and U.S. Pat. No. 4,448,765, which are incorporated herein by reference in its entirety. Artificial vesicles can be constructed with known markers to facilitate capture and/or detection. In some embodiments, artificial vesicles are spiked into a bodily sample prior to processing. The level of intact synthetic vesicle can be tracked during processing, e.g., using filtration or other isolation methods disclosed herein, to provide a control for the amount of vesicles in the initial versus processed sample. Similarly, artificial vesicles can be spiked into a sample before or after any processing steps. In some embodiments, artificial vesicles are used to calibrate equipment used for isolation and detection of vesicles.

Artificial vesicles can be produced and used a control to test the viability of an assay, such as a bead-based assay. The artificial vesicle can bind to both the beads and to the detection antibodies. Thus, the artificial vesicle contains the amino acid sequence/conformation that each of the antibodies binds. The artificial vesicle can comprise a purified protein or a synthetic peptide sequence to which the antibody binds. The artificial vesicle could be a bead, e.g., a polystyrene bead, that is capable of having biological molecules attached thereto. If the bead has an available carboxyl group, then the protein or peptide could be attached to the bead via an available amine group, such as using carbodiimide coupling.

In another embodiment, the artificial vesicle can be a polystyrene bead coated with avidin and a biotin is placed on the protein or peptide of choice either at the time of synthesis or via a biotin-maleimide chemistry. The proteins/peptides to be on the bead can be mixed together in ratio specific to the application the artificial vesicle is being used for, and then conjugated to the bead. These artificial vesicles can then serve as a link between the capture beads and the detection antibodies, thereby providing a control to show that the components of the assay are working properly.

The value can be a quantitative or qualitative value. The value can be a direct measurement of the level of vesicles (example, mass per volume), or an indirect measure, such as the amount of a specific biomarker. The value can be a quantitative, such as a numerical value. In other embodiments, the value is qualitiative, such as no vesicles, low level of vesicles, medium level, high level of vesicles, or variations thereof.

The reference value can be stored in a database and used as a reference for the diagnosis, prognosis, theranosis, disease stratification, disease monitoring, treatment monitoring or prediction of non-responder/responder status of a disease or condition based on the level or amount of microRNA, such as total amount of microRNA, or the amount of a specific population of microRNA, such as cell-of-origin specific microRNA or microRNA from vesicles with a specific biosignature. In an illustrative example, consider a method of determining a diagnosis for a cancer. MicroRNA from reference subjects with and without the cancer are assessed and stored in the database. The reference subjects provide biosignature indicative of the cancer or of another state, e.g., a healthy state. A sample from a test subject is then assayed and the microRNA biosignature is compared against those in the database. If the subject's biosignature correlates more closely with reference values indicative of cancer, a diagnosis of cancer may be made. Conversely, if the subject's biosignature correlates more closely with reference values indicative of a healthy state, the subject may be determined to not have the disease. One of skill will appreciate that this example is non-limiting and can be expanded for assessing other phenotypes, e.g., other diseases, prognosis, theranosis, disease stratification, disease monitoring, treatment monitoring or prediction of non-responder/responder status, and the like.

A biosignature for characterizing a phenotype can be determined by detecting microRNA and/or vesicles. The microRNA can be assessed within a vesicle. Alternately, the microRNA and vesicles in a sample are analyzed to characterize the phenotype without isolating the microRNA from the vesicles. Many analytical techniques are available to assess vesicles. In some embodiments, vesicle levels are characterized using mass spectrometry, flow cytometry, immunocytochemical staining, Western blotting, electrophoresis, chromatography or x-ray crystallography in accordance with procedures known in the art. For example, vesicles can be characterized and quantitatively measured using flow cytometry as described in Clayton et al., *Journal of Immunological Methods* 2001; 163-174, which is herein incorporated by reference in its entirety. Vesicle levels may be determined using binding agents as described above. For example, a binding agent to vesicles can be labeled and the label detected and used to determine the amount of vesicles in a sample. The binding agent can be bound to a substrate, such as arrays or particles, such as described above. Alternatively, the vesicles may be labeled directly.

Electrophoretic tags or eTags can be used to determine the amount of vesicles. eTags are small fluorescent molecules linked to nucleic acids or antibodies and are designed to bind one specific nucleic acid sequence or protein, respectively. After the eTag binds its target, an enzyme is used to cleave the bound eTag from the target. The signal generated from the released eTag, called a "reporter," is proportional to the amount of target nucleic acid or protein in the sample. The eTag reporters can be identified by capillary electrophoresis. The unique charge-to-mass ratio of each eTag reporter—that is, its electrical charge divided by its molecular weight—makes it show up as a specific peak on the capillary electrophoresis readout Thus by targeting a specific biomarker of a vesicle with an eTag, the amount or level of vesicles can be determined.

The vesicle level can determined from a heterogeneous population of vesicles, such as the total population of vesicles in a sample. Alternatively, the vesicles level is determined from a homogenous population, or substantially homogenous population of vesicles, such as the level of specific cell-of-origin vesicles, such as vesicles from prostate cancer cells. In yet other embodiments, the level is determined for vesicles with a particular biomarker or combination of biomarkers, such as a biomarker specific for prostate cancer. Determining the level vesicles can be performed in conjunction with determining the biomarker or combination of biomarkers of a vesicle. Alternatively, determining the amount of vesicle may be performed prior to or subsequent to determining the biomarker or combination of biomarkers of the vesicles.

Determining the amount of vesicles can be assayed in a multiplexed manner. For example, determining the amount of more than one population of vesicles, such as different cell-of-origin specific vesicles with different biomarkers or combination of biomarkers, can be performed, such as those disclosed herein.

Performance of a diagnostic or related test is typically assessed using statistical measures. The performance of the characterization can be assessed by measuring sensitivity, specificity and related measures. For example, a level of microRNAs of interest can be assayed to characterize a phenotype, such as detecting a disease. The sensitivity and specificity of the assay to detect the disease is determined.

A true positive is a subject with a characteristic, e.g., a disease or disorder, correctly identified as having the characteristic. A false positive is a subject without the characteristic that the test improperly identifies as having the characteristic.

A true negative is a subject without the characteristic that the test correctly identifies as not having the characteristic. A false negative is a person with the characteristic that the test improperly identifies as not having the characteristic. The ability of the test to distinguish between these classes provides a measure of test performance.

The specificity of a test is defined as the number of true negatives divided by the number of actual negatives (i.e., sum of true negatives and false positives). Specificity is a measure of how many subjects are correctly identified as negatives. A specificity of 100% means that the test recognizes all actual negatives—for example, all healthy people will be recognized as healthy. A lower specificity indicates that more negatives will be determined as positive.

The sensitivity of a test is defined as the number of true positives divided by the number of actual positives (i.e., sum of true positives and false negatives). Specificity is a measure of how many subjects are correctly identified as positives. A sensitivity of 100% means that the test recognizes all actual positives—for example, all sick people will be recognized as sick. A lower sensitivity indicates that more positives will be missed by being determined as negative.

The accuracy of a test is defined as the number of true positives and true negatives divided by the sum of all true and false positives and all true and false negatives. It provides one number that combines sensitivity and specificity measurements.

Sensitivity, specificity and accuracy are determined at a particular discrimination threshold value. For example, a common threshold for prostate cancer (PCa) detection is 4 ng/mL of prostate specific antigen (PSA) in serum. A level of PSA equal to or above the threshold is considered positive for PCa and any level below is considered negative. As the threshold is varied, the sensitivity and specificity will also vary. For example, as the threshold for detecting cancer is increased, the specificity will increase because it is harder to call a subject positive, resulting in fewer false positives. At the same time, the sensitivity will decrease. A receiver operating characteristic curve (ROC curve) is a graphical plot of the true positive rate (i.e., sensitivity) versus the false positive rate (i.e., 1—specificity) for a binary classifier system as its discrimination threshold is varied. The ROC curve shows how sensitivity and specificity change as the threshold is varied. The Area Under the Curve (AUC) of an ROC curve provides a summary value indicative of a test's performance over the entire range of thresholds. The AUC is equal to the probability that a classifier will rank a randomly chosen positive sample higher than a randomly chosen negative sample. An AUC of 0.5 indicates that the test has a 50% chance of proper ranking, which is equivalent to no discriminatory power (a coin flip also has a 50% chance of proper ranking). An AUC of 1.0 means that the test properly ranks (classifies) all subjects. The AUC is equivalent to the Wilcoxon test of ranks.

A biosignature according to the invention can be used to characterize a phenotype with at least 50, 51, 52, 53, 54, 55, 56, 57, 58, 59, 60, 61, 62, 63, 64, 65, 66, 67, 68, 69, or 70% sensitivity, such as with at least 71, 72, 73, 74, 75, 76, 77, 78, 79, 80, 81, 82, 83, 84, 85, 86, or 87% sensitivity. In some embodiments, the phenotype is characterized with at least 87.1, 87.2, 87.3, 87.4, 87.5, 87.6, 87.7, 87.8, 87.9, 88.0, or 89% sensitivity, such as at least 90% sensitivity. The phenotype can be characterized with at least 91, 92, 93, 94, 95, 96, 97, 98, 99 or 100% sensitivity.

A biosignature according to the invention can be used to characterize a phenotype of a subject with at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, or 97% specificity, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% specificity.

A biosignature according to the invention can be used to characterize a phenotype of a subject, e.g., based on microRNA level or other characteristic, with at least 50% sensitivity and at least 60, 65, 70, 75, 80, 85, 90, 95, 99, or 100% specificity; at least 55% sensitivity and at least 60, 65, 70, 75, 80, 85, 90, 95, 99, or 100% specificity; at least 60% sensitivity and at least 60, 65, 70, 75, 80, 85, 90, 95, 99, or 100% specificity; at least 65% sensitivity and at least 60, 65, 70, 75, 80, 85, 90, 95, 99, or 100% specificity; at least 70% sensitivity and at least 60, 65, 70, 75, 80, 85, 90, 95, 99, or 100% specificity; at least 75% sensitivity and at least 60, 65, 70, 75, 80, 85, 90, 95, 99, or 100% specificity; at least 80% sensitivity and at least 60, 65, 70, 75, 80, 85, 90, 95, 99, or 100% specificity; at least 85% sensitivity and at least 60, 65, 70, 75, 80, 85, 90, 95, 99, or 100% specificity; at least 86% sensitivity and at least 60, 65, 70, 75, 80, 85, 90, 95, 99, or 100% specificity; at least 87% sensitivity and at least 60, 65, 70, 75, 80, 85, 90, 95, 99, or 100% specificity; at least 88% sensitivity and at least 60, 65, 70, 75, 80, 85, 90, 95, 99, or 100% specificity; at least 89% sensitivity and at least 60, 65, 70, 75, 80, 85, 90, 95, 99, or 100% specificity; at least 90% sensitivity and at least 60, 65, 70, 75, 80, 85, 90, 95, 99, or 100% specificity; at least 91% sensitivity and at least 60, 65, 70, 75, 80, 85, 90, 95, 99, or 100% specificity; at least 92% sensitivity and at least 60, 65, 70, 75, 80, 85, 90, 95, 99, or 100% specificity; at least 93% sensitivity and at least 60, 65, 70, 75, 80, 85, 90, 95, 99, or 100% specificity; at least 94% sensitivity and at least 60, 65, 70, 75, 80, 85, 90, 95, 99, or 100% specificity; at least 95% sensitivity and at least 60, 65, 70, 75, 80, 85, 90, 95, 99, or 100% specificity; at least 96% sensitivity and at least 60, 65, 70, 75, 80, 85, 90, 95, 99, or 100% specificity; at least 97% sensitivity and at least 60, 65, 70, 75, 80, 85, 90, 95, 99, or 100% specificity; at least 98% sensitivity and at least 60, 65, 70, 75, 80, 85, 90, 95, 99, or 100% specificity; at least 99% sensitivity and at least 60, 65, 70, 75, 80, 85, 90, 95, 99, or 100% specificity; or substantially 100% sensitivity and at least 60, 65, 70, 75, 80, 85, 90, 95, 99, or 100% specificity.

A biosignature according to the invention can be used to characterize a phenotype of a subject with at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, or 97% accuracy, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% accuracy.

In some embodiments, a biosignature according to the invention is used to characterize a phenotype of a subject with an AUC of at least 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, or 0.97, such as with at least 0.971, 0.972, 0.973, 0.974, 0.975, 0.976, 0.977, 0.978, 0.978, 0.979, 0.980, 0.981, 0.982, 0.983, 0.984, 0.985, 0.986, 0.987, 0.988, 0.989, 0.99, 0.991, 0.992, 0.993, 0.994, 0.995, 0.996, 0.997, 0.998, 0.999 or 1.00.

Furthermore, the confidence level for determining the specificity, sensitivity, accuracy or AUC, may be determined with at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% confidence.

Other related performance measures include positive and negative likelihood ratios [positive LR=sensitivity/(1-specificity); negative LR=(1-sensitivity)/specificity]. Such measures can also be used to gauge test performance according to the methods of the invention.

Classification

Biosignature according to the invention can be used to classify a sample. Techniques for discriminate analysis are known to those of skill in the art. For example, a sample can be classified as, or predicted to be, a responder or non-responder to a given treatment for a given disease or disorder. Many statistical classification techniques are known to those of skill in the art. In supervised learning approaches, a group of samples from two or more groups are analyzed with a statistical classification method. Biomarkers can be discovered that can be used to build a classifier that differentiates between the two or more groups. A new sample can then be analyzed so that the classifier can associate the new with one of the two or more groups. Commonly used supervised classifiers include without limitation the neural network (multi-layer perceptron), support vector machines, k-nearest neighbors, Gaussian mixture model, Gaussian, naive Bayes, decision tree and radial basis function (RBF) classifiers. Linear classification methods include Fisher's linear discriminant, logistic regression, naive Bayes classifier, perceptron, and support vector machines (SVMs). Other classifiers for use with the invention include quadratic classifiers, k-nearest neighbor, boosting, decision trees, random forests, neural networks, pattern recognition, Bayesian networks and Hidden Markov models. One of skill will appreciate that these or other classifiers, including improvements of any of these, are contemplated within the scope of the invention.

Classification using supervised methods is generally performed by the following methodology:

In order to solve a given problem of supervised learning (e.g. learning to recognize handwriting) one has to consider various steps:

1. Gather a training set. These can include, for example, samples that are from a subject with or without a disease or disorder, subjects that are known to respond or not respond to a treatment, subjects whose disease progresses or does not progress, etc. The training samples are used to "train" the classifier.

2. Determine the input "feature" representation of the learned function. The accuracy of the learned function depends on how the input object is represented. Typically, the input object is transformed into a feature vector, which contains a number of features that are descriptive of the object. The number of features should not be too large, because of the curse of dimensionality; but should be large enough to accurately predict the output. The features might include a set of biomarkers such as those derived from vesicles as described herein.

3. Determine the structure of the learned function and corresponding learning algorithm. A learning algorithm is chosen, e.g., artificial neural networks, decision trees, Bayes classifiers or support vector machines. The learning algorithm is used to build the classifier.

4. Build the classifier. The learning algorithm is run the gathered training set. Parameters of the learning algorithm may be adjusted by optimizing performance on a subset (called a validation set) of the training set, or via cross-validation. After parameter adjustment and learning, the performance of the algorithm may be measured on a test set of naive samples that is separate from the training set.

Once the classifier is determined as described above, it can be used to classify a sample, e.g., that of a subject who is being analyzed by the methods of the invention. As an example, a classifier can be built using data for levels of microRNA of interest in reference subjects with and without a disease as the training and test sets. MicroRNA levels found in a sample from a test subject are assessed and the classifier is used to classify the subject as with or without the disease. As another example, a classifier can be built using data for levels of vesicle biomarkers of interest in reference subjects that have been found to respond or not respond to certain diseases as the training and test sets. The vesicle biomarker levels found in a sample from a test subject are assessed and the classifier is used to classify the subject as with or without the disease.

Unsupervised learning approaches can also be used with the invention. Clustering is an unsupervised learning approach wherein a clustering algorithm correlates a series of samples without the use the labels. The most similar samples are sorted into "clusters." A new sample could be sorted into a cluster and thereby classified with other members that it most closely associates. Many clustering algorithms well known to those of skill in the art can be used with the invention, such as hierarchical clustering.

Biosignatures

A biosignature can be obtained according to the invention by assessing a vesicle population, including surface and payload vesicle associated biomarkers, and/or circulating biomarkers including microRNA and protein. A biosignature derived from a subject can be used to characterize a phenotype of the subject. A biosignature can further include the level of one or more additional biomarkers, e.g., circulating biomarkers or biomarkers associated with a vesicle of interest. A biosignature of a vesicle of interest can include particular antigens or biomarkers that are present on the vesicle. The biosignature can also include one or more antigens or biomarkers that are carried as payload within the vesicle, including the microRNA under examination. The biosignature can comprise a combination of one or more antigens or biomarkers that are present on the vesicle with one or more biomarkers that are detected in the vesicle. The biosignature can further comprise other information about a vesicle aside from its biomarkers. Such information can include vesicle size, circulating half-life, metabolic half-life, and specific activity in vivo or in vitro. The biosignature can comprise the biomarkers or other characteristics used to build a classifier.

In some embodiments, the microRNA is detected directly in a biological sample. For example, RNA in a bodily fluid can be isolated using commercially available kits such as mirVana kits (Applied Biosystems/Ambion, Austin, Tex.), MagMAX™ RNA Isolation Kit (Applied Biosystems/Ambion, Austin, Tex.), and QIAzol Lysis Reagent and RNeasy Midi Kit (Qiagen Inc., Valencia Calif.). Particular species of microRNAs can be determined using array or PCR techniques as described below.

In some embodiments, the microRNA payload with vesicles is assessed in order to characterize a phenotype. The vesicles can be purified or concentrated prior to determining the biosignature. For example, a cell-of-origin specific vesicle can be isolated and its biosignature determined. Alternatively, the biosignature of the vesicle can be directly assayed from a sample, without prior purification or concentration. The biosignature of the invention can be used to determine a diagnosis, prognosis, or theranosis of a disease or condition or similar measures described herein. A biosignature can also be used to determine treatment efficacy, stage of a disease or condition, or progression of a disease or condition, or responder/non-responder status. Furthermore, a biosignature may be used to determine a physiological state, such as pregnancy.

A characteristic of a vesicle in and of itself can be assessed to determine a biosignature. The characteristic can be used to diagnose, detect or determine a disease stage or progression, the therapeutic implications of a disease or condition, or characterize a physiological state. Such characteristics include without limitation the level or amount of vesicles, vesicle size, temporal evaluation of the variation in vesicle half-life, circulating vesicle half-life, metabolic half-life of a vesicle, or activity of a vesicle.

Biomarkers that can be included in a biosignature include one or more proteins or peptides (e.g., providing a protein signature), nucleic acids (e.g. RNA signature as described, or a DNA signature), lipids (e.g. lipid signature), or combinations thereof. In some embodiments, the biosignature can also comprise the type or amount of drug or drug metabolite present in a vesicle, (e.g., providing a drug signature), as such drug may be taken by a subject from which the biological sample is obtained, resulting in a vesicle carrying the drug or metabolites of the drug.

A biosignature can also include an expression level, presence, absence, mutation, variant, copy number variation, truncation, duplication, modification, or molecular association of one or more biomarkers. A genetic variant, or nucleotide variant, refers to changes or alterations to a gene or cDNA sequence at a particular locus, including, but not limited to, nucleotide base deletions, insertions, inversions, and substitutions in the coding and non-coding regions. Deletions may be of a single nucleotide base, a portion or a region of the nucleotide sequence of the gene, or of the entire gene sequence. Insertions may be of one or more nucleotide bases. The genetic variant may occur in transcriptional regulatory regions, untranslated regions of mRNA, exons, introns, or exon/intron junctions. The genetic variant may or may not result in stop codons, frame shifts, deletions of amino acids, altered gene transcript splice forms or altered amino acid sequence.

In an embodiment, nucleic acid biomarkers, including nucleic acid payload within a vesicle, is assessed for nucleotide variants. The nucleic acid biomarker may comprise one or more RNA species, e.g., mRNA, miRNA, snoRNA, snRNA, rRNAs, tRNAs, siRNA, hnRNA, shRNA, or a combination thereof. Similarly, DNA payload can be assessed to form a DNA signature.

An RNA signature or DNA signature can also include a mutational, epigenetic modification, or genetic variant analysis of the RNA or DNA present in the vesicle. Epigenetic modifications include patterns of DNA methylation. See, e.g., Lesche R. and Eckhardt F., DNA methylation markers: a versatile diagnostic tool for routine clinical use. Curr Opin Mol Ther. 2007 June; 9(3):222-30, which is incorporated herein by reference in its entirety. Thus, a biomarker can be the methylation status of a segment of DNA.

A biosignature can comprise one or more miRNA signatures combined with one or more additional signatures including, but not limited to, an mRNA signature, DNA signature, protein signature, peptide signature, antigen signature, or any combination thereof. For example, the biosignature can comprise one or more miRNA biomarkers with one or more DNA biomarkers, one or more mRNA biomarkers, one or more snoRNA biomarkers, one or more protein biomarkers, one or more peptide biomarkers, one or more antigen biomarkers, one or more antigen biomarkers, one or more lipid biomarkers, or any combination thereof.

A biosignature can comprise a combination of one or more antigens or binding agents (such as ability to bind one or more binding agents), such as listed in FIGS. 1 and 2, respectively, or those described elsewhere herein. The biosignature can further comprise one or more other biomarkers, such as, but not limited to, miRNA, DNA (e.g. single stranded DNA, complementary DNA, or noncoding DNA), or mRNA.

The biosignature of a vesicle can comprise a combination of one or more antigens, such as shown in FIG. 1, one or more binding agents, such as shown in FIG. 2, and one or more biomarkers for a condition or disease, such as listed in FIGS. 3-60. The biosignature can comprise one or more biomarkers, for example miRNA, with one or more antigens specific for a cancer cell (for example, as shown in FIG. 1).

In some embodiments, a vesicle used in the subject methods has a biosignature that is specific to the cell-of-origin and is used to derive disease-specific or biological state specific diagnostic, prognostic or therapy-related biosignatures representative of the cell-of-origin. In other embodiments, a vesicle has a biosignature that is specific to a given disease or physiological condition that is different from the biosignature of the cell-of-origin for use in the diagnosis, prognosis, staging, therapy-related determinations or physiological state characterization. Biosignatures can also comprise a combination of cell-of-origin specific and non-specific vesicles.

Biosignatures can be used to evaluate diagnostic criteria such as presence of disease, disease staging, disease monitoring, disease stratification, or surveillance for detection, metastasis or recurrence or progression of disease. A biosignature can also be used clinically in making decisions concerning treatment modalities including therapeutic intervention. A biosignature can further be used clinically to make treatment decisions, including whether to perform surgery or what treatment standards should be utilized along with surgery (e.g., either pre-surgery or post-surgery). As an illustrative example, a microRNA (miRNA) biosignature that indicates an aggressive form of cancer may call for a more aggressive surgical procedure and/or more aggressive therapeutic regimen to treat the patient.

A biosignature can be used in therapy related diagnostics to provide tests useful to diagnose a disease or choose the correct treatment regimen, such as provide a theranosis. Theranostics includes diagnostic testing that provides the ability to affect therapy or treatment of a diseased state. Theranostics testing provides a theranosis in a similar manner that diagnostics or prognostic testing provides a diagnosis or prognosis, respectively. As used herein, theranostics encompasses any desired form of therapy related testing, including predictive medicine, personalized medicine, integrated medicine, pharmacodiagnostics and Dx/Rx partnering. Therapy related tests can be used to predict and assess drug response in individual subjects, i.e., to provide personalized medicine. Predicting a drug response can be determining whether a subject is a likely responder or a likely non-responder to a candidate therapeutic agent, e.g., before the subject has been exposed or otherwise treated with the treatment. Assessing a drug response can be monitoring a response to a drug, e.g., monitoring the subject's improvement or lack thereof over a time course after initiating the treatment. Therapy related tests are useful to select a subject for treatment who is particularly likely to benefit from the treatment or to provide an early and objective indication of treatment efficacy in an individual subject. Thus, a biosignature as disclosed herein may indicate that treatment should be altered to select a more promising treatment, thereby avoiding the great expense of delaying beneficial treatment and avoiding the financial and morbidity costs of administering an ineffective drug(s).

Therapy related diagnostics are also useful in clinical diagnosis and management of a variety of diseases and disorders, which include, but are not limited to cardiovascular disease, cancer, infectious diseases, sepsis, neurological diseases, central nervous system related diseases, endovascular related diseases, and autoimmune related diseases. Therapy related diagnostics also aid in the prediction of drug toxicity, drug resistance or drug response. Therapy related tests may be developed in any suitable diagnostic testing format, which include, but are not limited to, e.g., immunohistochemical tests, clinical chemistry, immunoassay, cell-based technologies, nucleic acid tests or body imaging methods. Therapy related tests can further include but are not limited to, testing that aids in the determination of therapy, testing that monitors for therapeutic toxicity, or response to therapy testing. Thus, a biosignature can be used to predict or monitor a subject's response to a treatment. A biosignature can be determined at different time points for a subject after initiating, removing, or altering a particular treatment.

In some embodiments, a determination or prediction as to whether a subject is responding to a treatment is made based on a change in the amount of one or more components of a biosignature (i.e., the microRNA, vesicles and/or biomarkers of interest), an amount of one or more components of a particular biosignature, or the biosignature detected for the components. In another embodiment, a subject's condition is monitored by determining a biosignature at different time points. The progression, regression, or recurrence of a condition is determined. Response to therapy can also be measured over a time course. Thus, the invention provides a method of monitoring a status of a disease or other medical condition in a subject, comprising isolating or detecting a biosignature from a biological sample from the subject, detecting the overall amount of the components of a particular biosignature, or detecting the biosignature of one or more components (such as the presence, absence, or expression level of a biomarker). The biosignatures are used to monitor the status of the disease or condition.

In some embodiments, a biosignature is used to determine whether a particular disease or condition is resistant to a drug. If a subject is drug resistant, a physician need not waste valuable time with such drug treatment. To obtain early validation of a drug choice or treatment regimen, a biosignature is determined for a sample obtained from a subject. The biosignature is used to assess whether the particular subject's disease has the biomarker associated with drug resistance. Such a determination enables doctors to devote critical time as well as the patient's financial resources to effective treatments.

Moreover, biosignature may be used to assess whether a subject is afflicted with disease, is at risk for developing disease or to assess the stage or progression of the disease. For example, a biosignature can be used to assess whether a subject has prostate cancer (for example, FIG. 68, 73) or colon cancer (for example, FIG. 69, 74). Furthermore, a biosignature can be used to determine a stage of a disease or condition, such as colon cancer (for example, FIGS. 71, 72).

Furthermore, determining the amount of vesicles, such a heterogeneous population of vesicles, and the amount of one or more homogeneous population of vesicles, such as a population of vesicles with the same biosignature, can be used to characterize a phenotype. For example, determination of the total amount of vesicles in a sample (i.e. not cell-type specific) and determining the presence of one or more different cell-of-origin specific vesicles can be used to characterize a phenotype. Threshold values, or reference values or amounts can be determined based on comparisons of normal subjects and subjects with the phenotype of interest, as further described below, and criteria based on the threshold or reference values determined. The different criteria can be used to characterize a phenotype.

One criterion can be based on the amount of a heterogeneous population of vesicles in a sample. In one embodiment, general vesicle markers, such as CD9, CD81, and CD63 can be used to determine the amount of vesicles in a sample. The expression level of CD9, CD81, CD63, or a combination thereof can be detected and if the level is greater than a threshold level, the criterion is met. In another embodiment, the criterion is met if level of CD9, CD81, CD63, or a combination thereof is lower than a threshold value or reference value. In another embodiment, the criterion can be based on whether the amount of vesicles is higher than a threshold or reference value. Another criterion can be based on the amount of vesicles with a specific biosignature. If the amount of vesicles with the specific biosignature is lower than a threshold or reference value, the criterion is met. In another embodiment, if the amount of vesicles with the specific biosignature is higher than a threshold or reference value, the criterion is met. A criterion can also be based on the amount of vesicles derived from a particular cell type. If the amount is lower than a threshold or reference value, the criterion is met. In another embodiment, if the amount is higher than a threshold value, the criterion is met.

In a non-limiting example, consider that vesicles from prostate cells are determined by detecting the biomarker PCSA or PSCA, and that a criterion is met if the level of detected PCSA or PSCA is greater than a threshold level. The threshold can be the level of the same markers in a sample from a control cell line or control subject. Another criterion can be based on whether the amount of vesicles derived from a cancer cell or comprising one or more cancer specific biomarkers. For example, the biomarkers B7H3, EpCam, or both, can be determined and a criterion met if the level of detected B7H3 and/or EpCam is greater than a threshold level or within a pre-determined range. If the amount is lower, or higher, than a threshold or reference value, the criterion is met. A criterion can also be the reliability of the result, such as meeting a quality control measure or value. A detected amount of B7H3 and/or EpCam in a test sample that is above the amount of these markers in a control sample may indicate the presence of a cancer in the test sample.

As described, analysis of multiple markers can be combined to assess whether a criterion is met. In an illustrative example, a biosignature is used to assess whether a subject has prostate cancer by detecting one or more of the general vesicle markers CD9, CD63 and CD81; one or more prostate epithelial markers including PCSA or PSMA; and one or more cancer markers such as B7H3 and/or EpCam. Higher levels of the markers in a sample from a subject than in a control individual without prostate cancer indicates the presence of the prostate cancer in the subject. In some embodiments, the multiple markers are assessed in a multiplex fashion.

One of skill will understand that such rules based on meeting criterion as described can be applied to any appropriate biomarker. For example, the criterion can be applied to vesicle characteristics such as amount of vesicles present, amount of vesicles with a particular biosignature present, amount of vesicle payload biomarkers present, amount of microRNA or other circulating biomarkers present, and the like. The ratios of appropriate biomarkers can be determined. As illustrative examples, the criterion could be a ratio of an vesicle surface protein to another vesicle surface protein, a ratio of an vesicle surface protein to a microRNA, a ratio of one vesicle population to another vesicle population, a ratio of one circulating biomarker to another circulating biomarker, etc.

A phenotype for a subject can be characterized based on meeting any number of useful criteria. In some embodiments, at least one criterion is used for each biomarker. In some embodiments, at least 1, 2, 3, 4, 5, 6, 7, 8, 9, 10, 15, 20, 30, 40, 50, 60, 70, 80, 90 or at least 100 criteria are used. For example, for the characterizing of a cancer, a number of different criteria can be used when the subject is diagnosed with a cancer: 1) if the amount of microRNA in a sample from a subject is higher than a reference value; 2) if the amount of a microRNA within cell type specific vesicles (i.e. vesicles derived from a specific tissue or organ) is higher than a reference value; or 3) if the amount of microRNA within vesicles with one or more cancer specific biomarkers is higher than a reference value. Similar rules can apply if the amount of microRNA is less than or the same as the reference. The method can further include a quality control measure, such that the results are provided for the subject if the samples meet the quality control measure. In some embodiments, if the criteria are met but the quality control is questionable, the subject is reassessed.

In other embodiments, a single measure is determined for assessment of multiple biomarkers, and the measure is compared to a reference. For illustration, a test for prostate cancer might comprise multiplying the level of PSA against the level of miR-141 in a blood sample. The criterion is met if the product of the levels is above a threshold, indicating the presense of the cancer. As another illustration, a number of binding agents to general vesicle markers can carry the same label, e.g., the same fluorophore. The level of the detected label can be compared to a threshold.

Criterion can be applied to multiple types of biomarkers in addition to multiple biomarkers of the same type. For example, the levels of one or more circulating biomarkers (e.g., RNA, DNA, peptides), vesicles, mutations, etc, can be compared to a reference. Different components of a biosignature can have different criteria. As a non-limiting example, a biosignature used to diagnose a cancer can include overexpression of one miR species as compared to a reference and underexpression of a vesicle surface antigen as compared to another reference.

A biosignature can be determined by comparing the amount of vesicles, the structure of a vesicle, or any other informative characteristic of a vesicle. Vesicle structure can be assessed using transmission electron microscopy, see for example, Hansen et al., *Journal of Biomechanics* 31, *Supplement* 1: 134-134(1) (1998), or scanning electron microscopy. Various combinations of methods and techniques or analyzing one or more vesicles can be used to determine a phenotype for a subject.

A biosignature can include without limitation the presence or absence, copy number, expression level, or activity level of a biomarker. Other useful components of a biosignature include the presence of a mutation (e.g., mutations which affect activity of a transcription or translation product, such as substitution, deletion, or insertion mutations), variant, or post-translation modification of a biomarker. Post-translational modification of a protein biomarker include without limitation acylation, acetylation, phosphorylation, ubiquitination, deacetylation, alkylation, methylation, amidation, biotinylation, gamma-carboxylation, glutamylation, glycosylation, glycyation, hydroxylation, covalent attachment of heme moiety, iodination, isoprenylation, lipoylation, prenylation, GPI anchor formation, myristoylation, farnesylation, geranylgeranylation, covalent attachment of nucleotides or derivatives thereof, ADP-ribosylation, flavin attachment, oxidation, palmitoylation, pegylation, covalent attachment of phosphatidylinositol, phosphopantetheinylation, polysialylation, pyroglutamate formation, racemization of proline by prolyl isomerase, tRNA-mediation addition of amino acids such as arginylation, sulfation, the addition of a sulfate group to a tyrosine, or selenoylation of the biomarker.

The methods described herein can be used to identify a biosignature that is associated with a disease, condition or physiological state. The biosignature can also be utilized to determine if a subject is afflicted with cancer or is at risk for developing cancer. A subject at risk of developing cancer can include those who may be predisposed or who have pre-symptomatic early stage disease.

A biosignature can also be utilized to provide a diagnostic or theranostic determination for other diseases including but not limited to autoimmune diseases, inflammatory bowel diseases, Alzheimer's disease, Parkinson's disease, Multiple Sclerosis, sepsis or pancreatitis or any disease, conditions or symptoms listed in FIGS. 3-58.

The biosignature can also be used to identify a given pregnancy state from the peripheral blood, umbilical cord blood, or amniotic fluid (e.g. miRNA signature specific to Downs Syndrome) or adverse pregnancy outcome such as pre-eclampsia, pre-term birth, premature rupture of membranes, intrauterine growth restriction or recurrent pregnancy loss. The biosignature can also be used to indicate the health of the mother, the fetus at all developmental stages, the pre-implantation embryo or a newborn.

A biosignature can be utilized for pre-symptomatic diagnosis. Furthermore, the biosignature can be utilized to detect disease, determine disease stage or progression, determine the recurrence of disease, identify treatment protocols, determine efficacy of treatment protocols or evaluate the physiological status of individuals related to age and environmental exposure.

Monitoring a biosignature of a vesicle can also be used to identify toxic exposures in a subject including, but not limited to, situations of early exposure or exposure to an unknown or unidentified toxic agent. Without being bound by any one specific theory for mechanism of action, vesicles can shed from damaged cells and in the process compartmentalize specific contents of the cell including both membrane components and engulfed cytoplasmic contents. Cells exposed to toxic agents/chemicals may increase vesicle shedding to expel toxic agents or metabolites thereof, thus resulting in increased vesicle levels. Thus, monitoring vesicle levels, vesicle biosignature, or both, allows assessment of an individual's response to potential toxic agent(s).

A vesicle and/or other biomarkers of the invention can be used to identify states of drug-induced toxicity or the organ injured, by detecting one or more specific antigen, binding agent, biomarker, or any combination thereof. The level of vesicles, changes in the biosignature of a vesicle, or both, can be used to monitor an individual for acute, chronic, or occupational exposures to any number of toxic agents including, but not limited to, drugs, antibiotics, industrial chemicals, toxic antibiotic metabolites, herbs, household chemicals, and chemicals produced by other organisms, either naturally occurring or synthetic in nature. In addition, a biosignature can be used to identify conditions or diseases, including cancers of unknown origin, also known as cancers of unknown primary (CUP).

A vesicle may be isolated from a biological sample as previously described to arrive at a heterogeneous population of vesicles. The heterogeneous population of vesicles can then be contacted with substrates coated with specific binding agents designed to rule out or identify antigen specific characteristics of the vesicle population that are specific to a given cell-of-origin. Further, as described above, the biosignature of a vesicle can correlate with the cancerous state of cells.

Compounds that inhibit cancer in a subject may cause a change, e.g., a change in biosignature of a vesicle, which can be monitored by serial isolation of vesicles over time and treatment course. The level of vesicles or changes in the level of vesicles with a specific biosignature can be monitored.

In one aspect, the present invention relates to biomarker discovery and biosignature discovery. In an embodiment, one or more subjects that respond to a therapy (responders) and one or more subjects that do not respond to the same therapy (non-responders) can have their vesicles interrogated. Interrogation can be performed to identify the presence of one or more biomarkers, including any of the biomarkers described herein. In one aspect, the presence, quantity, and payload of a miR are assayed. The payload of a miR can be, for example, and surface or internal protein, nucleic acid, lipid or carbohydrate.

The presence or absence of a biosignature in responders but not in the non-responders can be used for theranosis. A sample from responders may be analyzed for one or more of the following: amount of vesicles, amount of a unique subset or species of vesicles, biomarkers in such vesicles, biosignature of such vesicles, etc. In one instance, vesicles such as microvesicles or exosomes from responders and non-responders are analyzed for the presence and/or quantity of one or more miRNAs, such as miRNA 122, miR-548c-5p, miR-362-3p, miR-422a, miR-597, miR-429, miR-200a, and/or miR-200b. A difference in biosignatures between responders and non-responders can be used for theranosis. In another embodiment, vesicles are obtained from subjects having a disease or condition. Vesicles are also obtained from subjects free of such disease or condition. The vesicles from both groups of subjects are assayed for unique biosignatures that are associated with all subjects in that group but not in subjects from the other group. Such biosignatures or biomarkers can then used as a diagnostic for the presence or absence of the condition or disease, or to classify the subject as belonging on one of the groups (those with/without disease, aggressive/non-aggressive disease, responder/non-responder, etc).

In a further example, vesicles are assayed from patients having a stage I cancer and patients having stage II or III of the same cancer. A difference in biosignatures or biomarkers between vesicles from each group of patient is identified (e.g., vesicles from stage III cancer may have an increased expression of one or more genes or miR's), thereby identifying a biosignature or biomarker that distinguishes different stages of a disease. Such biosignature can then be used to prognose patients having the disease.

In some instances, a biosignature is determined by assaying vesicles from a subject over a period of time (e.g., every day, week, month, or year). Thus, responders and non-responders or patients in phase I and phase II/III can have their vesicles interrogated over time (e.g., every month). The payload or physical attributes of the vesicles in each point in time can be compared. A temporal pattern can thus form a biosignature that can then be used for theranosis, diagnosis, prognosis, disease stratification, treatment monitoring, disease monitoring or making a prediction of responder/non-responder status. As a non-limiting example, an increasing amount of a biomarker (e.g., miR 122) in vesiscles over a time course can be associated with metastatic cancer, as opposed to a stagnant amounts of the biomarker in vesiscles over the time course can be associated with non-metastatic cancer. A time course may last over at least 1 week, 2 weeks, 3 weeks, 4 weeks, 1 month, 6 weeks, 8 weeks, 2 months, 10 weeks, 12 weeks, 3 months, 4 months, 5 months, 6 months, 7 months, 8 months, 9 months, 10 months, 11 months, or at least 12 months.

The level of vesicles, level of vesicles with a specific biosignature, or a biosignature of a vesicle can also be used to assess the efficacy of a therapy for a condition. For example, the level of vesicles, level of vesicles with a specific biosignature, or a biosignature of a vesicle can be used to assess the efficacy of a cancer treatment, e.g., chemotherapy, radiation therapy, surgery, or any other therapeutic approach useful for inhibiting cancer in a subject. In addition, a biosignature can be used in a screening assay to identify candidate or test compounds or agents (e.g., proteins, peptides, peptidomimetics, peptoids, small molecules or other drugs) that have a modulatory effect on the biosignature of a vesicle. Compounds identified via such screening assays may be useful, for example, for modulating, e.g., inhibiting, ameliorating, treating, or preventing conditions or diseases.

For example, a biosignature for a vesicle can be obtained from a patient who is undergoing successful treatment for a particular cancer. Cells from a cancer patient not being treated with the same drug can be cultured and vesicles from the cultures obtained for determining biosignatures. The cells can be treated with test compounds and the biosignature of the vesicles from the cultures can be compared to the biosignature of the vesicles obtained from the patient undergoing successful treatment. The test compounds that results in biosignatures that are similar to those of the patient undergoing successful treatment can be selected for further studies.

The biosignature of a vesicle can also be used to monitor the influence of an agent (e.g., drug compounds) on the biosignature in clinical trials. Monitoring the level of vesicles, changes in the biosignature of a vesicle, or both, can also be used in a method of assessing the efficacy of a test compound, such as a test compound for inhibiting cancer cells.

The level of vesicles, the biosignature of a vesicle, or both, can also be used to determine the effectiveness of a particular therapeutic intervention (pharmaceutical or non-pharmaceutical) and to alter the intervention to 1) reduce the risk of developing adverse outcomes, 2) enhance the effectiveness of the intervention or 3) identify resistant states. Thus, in addition to diagnosing or confirming the presence of or risk for developing a disease, condition or a syndrome, the methods and compositions disclosed herein also provide a system for optimizing the treatment of a subject having such a disease, condition or syndrome. For example, a therapy-related approach to treating a disease, condition or syndrome by integrating diagnostics and therapeutics to improve the real-time treatment of a subject can be determined by identifying the biosignature of a vesicle.

Tests that identify the level of vesicles, the biosignature of a vesicle, or both, can be used to identify which patients are most suited to a particular therapy, and provide feedback on how well a drug is working, so as to optimize treatment regimens. For example, in pregnancy-induced hypertension and associated conditions, therapy-related diagnostics can flexibly monitor changes in important parameters (e.g., cytokine and/or growth factor levels) over time, to optimize treatment.

Within the clinical trial setting of investigational agents as defined by the FDA, MDA, EMA, USDA, and EMEA, therapy-related diagnostics as determined by a biosignature disclosed herein, can provide key information to optimize trial design, monitor efficacy, and enhance drug safety. For instance, for trial design, therapy-related diagnostics can be used for patient stratification, determination of patient eligibility (inclusion/exclusion), creation of homogeneous treatment groups, and selection of patient samples that are optimized to a matched case control cohort. Such therapy-related diagnostic can therefore provide the means for patient efficacy enrichment, thereby minimizing the number of individuals needed for trial recruitment. For example, for efficacy, therapy-related diagnostics are useful for monitoring therapy and assessing efficacy criteria. Alternatively, for safety, therapy-related diagnostics can be used to prevent adverse drug reactions or avoid medication error and monitor compliance with the therapeutic regimen.

In some embodiments, the invention provides a method of identifying responder and non-responders to a treatment undergoing clinical trials, comprising detecting biosignatures comprising microRNA in subjects enrolled in the clinical trial, and identifying biosignatures that distinguish between responders and non-responders. In a further embodiment, the biosignatures are measured in a drug naive subject and used to predict whether the subject will be a responder or non-responder. The prediction can be based upon whether the biosignatures of the drug naive subject correlate more closely with the clinical trial subjects identified as responders, thereby predicting that the drug naive subject will be a responder. Conversely, if the biosignatures of the drug naive subject correlate more closely with the clinical trial subjects identified as non-responders, the methods of the invention can predict that the drug naive subject will be a non-responder. The prediction can therefore be used to stratify potential responders and non-responders to the treatment. In some embodiments, the prediction is used to guide a course of treatment, e.g., by helping treating physicians decide whether to administer the drug. In some embodiments, the prediction is used to guide selection of patients for enrollment in further clinical trials. In a non-limiting example, biosignatures that predict responder/non-responder status in Phase II trials can be used to select patients for a Phase III trial, thereby increasing the likelihood of response in the Phase III patient population. One of skill will appreciate that the method can be adapted to identify biosignatures to stratify subjects on criteria other than responder/non-responder status. In one embodiment, the criterion is treatment safety. Therefore the method is followed as above to identify subjects who are likely or not to have adverse events to the treatment. In a non-limiting example, biosignatures that predict safety profile in Phase II trials can be used to select patients for a Phase III trial, thereby increasing the treatment safety profile in the Phase III patient population.

Therefore, the level of vesicles, the biosignature of a vesicle, or both, can be used to monitor drug efficacy, determine response or resistance to a given drug, or both, thereby enhancing drug safety. For example, in colon cancer, vesicles are typically shed from colon cancer cells and can be isolated from the peripheral blood and used to isolate one or more biomarkers e.g., KRAS mRNA which can then be sequenced to detect KRAS mutations. In the case of mRNA biomarkers, the mRNA can be reverse transcribed into cDNA and sequenced (e.g., by Sanger sequencing, pyrosequencing, NextGen sequencing, RT-PCR assays) to determine if there are mutations present that confer resistance to a drug (e.g., cetuximab or panitumimab). In another example, vesicles that are specifically shed from lung cancer cells are isolated from a biological sample and used to isolate a lung cancer biomarker, e.g., EGFR mRNA. The EGFR mRNA is processed to cDNA and sequenced to determine if there are EGFR mutations present that show resistance or response to specific drugs or treatments for lung cancer.

One or more biosignatures can be grouped so that information obtained about the set of biosignatures in a particular group provides a reasonable basis for making a clinically relevant decision, such as but not limited to a diagnosis, prognosis, or management of treatment, such as treatment selection.

As with most diagnostic markers, it is often desirable to use the fewest number of markers sufficient to make a correct medical judgment. This prevents a delay in treatment pending further analysis as well inappropriate use of time and resources.

Also disclosed herein are methods of conducting retrospective analysis on samples (e.g., serum and tissue biobanks) for the purpose of correlating qualitative and quantitative properties, such as biosignatures of vesicles, with clinical outcomes in terms of disease state, disease stage, progression, prognosis; therapeutic efficacy or selection; or physiological conditions. Furthermore, methods and compositions disclosed herein are utilized for conducting prospective analysis on a sample (e.g., serum and/or tissue collected from individuals in a clinical trial) for the purpose of correlating qualitative and quantitative biosignatures of vesicleswith clinical outcomes in terms of disease state, disease stage, progression, prognosis; therapeutic efficacy or selection; or physiological conditions can also be performed. As used herein, a biosignature for a vesicle can be used to identify a cell-of-origin specific vesicle. Furthermore, a biosignature can be determined based on a surface marker profile of a vesicle or contents of a vesicle.

The biosignatures used to characterize a phenotype according to the invention can comprise multiple components (e.g., microRNA, vesicles or other biomarkers) or characteristics (e.g., vesicle size or morphology). The biosignatures can comprise at least 2, 3, 4, 5, 6, 7, 8, 9, 10, 11, 12, 13, 14, 15, 16, 17, 18, 19, 20, 25, 30, 40, 50, 75, or 100 components or characteristics. A biosignature with more than one component or characteristic, such as at least 2, 3, 4, 5, 6, 7, 8, 9, 10, 11, 12, 13, 14, 15, 16, 17, 18, 19, 20, 25, 30, 40, 50, 75, or 100 components, may provide higher sensitivity and/or specificity in characterizing a phenotype. In some embodiments, assessing a plurality of components or characteristics provides increased sensitivity and/or specificity as compared to assessing fewer components or characteristics. On the other hand, it is often desirable to use the fewest number of components or characteristics sufficient to make a correct medical judgment. Fewer markers can avoid statistical overfitting of a classifier and can prevent a delay in treatment pending further analysis as well inappropriate use of time and resources. Thus, the methods of the invention comprise determining an optimal number of components or characteristics.

A biosignature according to the invention can be used to characterize a phenotype with a sensitivity, specificity, accuracy, or similar performance metric as described above. The biosignatures can also be used to build a classifier to classify a sample as belonging to a group, such as belonging to a group having a disease or not, a group having an aggressive disease or not, or a group of responders or non-responders. In one embodiment, a classifier is used to determine whether a subject has an aggressive or non-aggressive cancer. In the illustrative case of prostate cancer, this can help a physician to determine whether to watch the cancer, i.e., prescribe "watchful waiting," or perform a prostatectomy. In another embodiment, a classifier is used to determine whether a breast cancer patient is likely to respond or not to tamoxifen, thereby helping the physician to determine whether or not to treat the patient with tamoxifen or another drug.

Biomarkers

A biosignature used to characterize a phenotype can comprise one or more biomarkers. The biomarker can be a circulating marker, a membrane associated marker, or a component present within a vesicle or on a vesicle's surface. These biomarkers include without limitation a nucleic acid (e.g. RNA (mRNA, miRNA, etc.) or DNA), protein, peptide, polypeptide, antigen, lipid, carbohydrate, or proteoglycan.

The biosignature can include the presence or absence, expression level, mutational state, genetic variant state, or any modification (such as epigentic modification, post-translation modification) of a biomarker (e.g. any one or more biomarker listed in FIGS. 1, 3-60). The expression level of a biomarker can be compared to a control or reference, to determine the overexpression or underexpression (or upregulation or down-regulation) of a biomarker in a sample. In some embodiments, the control or reference level comprises the amount of a same biomarker, such as a miRNA, in a control sample from a subject that does not have or exhibit the condition or disease. In another embodiment, the control of reference levels comprises that of a housekeeping marker whose level is minimally affected, if at all, in different biological settings such as diseased versus non-diseased states. In yet another embodiment, the control or reference level comprises that of the level of the same marker in the same subject but in a sample taken at a different time point. Other types of controls are described herein.

Nucleic acid biomarkers include various RNA or DNA species. For example, the biomarker can be mRNA, microRNA (miRNA), small nucleolar RNAs (snoRNA), small nuclear RNAs (snRNA), ribosomal RNAs (rRNA), heterogeneous nuclear RNA (hnRNA), ribosomal RNAS (rRNA), siRNA, transfer RNAs (tRNA), or shRNA. The DNA can be double-stranded DNA, single stranded DNA, complementary DNA, or noncoding DNA. miRNAs are short ribonucleic acid (RNA) molecules which average about 22 nucleotides long. miRNAs act as post-transcriptional regulators that bind to complementary sequences in the three prime untranslated regions (3' UTRs) of target messenger RNA transcripts (mRNAs), which can result in gene silencing. One miRNA may act upon 1000s of mRNAs. miRNAs play multiple roles in negative regulation, e.g., transcript degradation and sequestering, translational suppression, and may also have a role in positive regulation, e.g., transcriptional and translational activation. By affecting gene regulation, miRNAs can influence many biologic processes. Different sets of expressed miRNAs are found in different cell types and tissues.

Biomarkers for use with the invention further include peptides, polypeptides, or proteins, which terms are used interchangeably throughout unless otherwise noted. In some embodiments, the protein biomarker comprises its modification state, truncations, mutations, expression level (such as overexpression or underexpression as compared to a reference level), and/or post-translational modifications, such as described above. In a non-limiting example, a biosignature for a disease can include a protein having a certain post-translational modification that is more prevalent in a sample associated with the disease than without.

A biosignature may include a number of the same type of biomarkers (e.g., two different microRNA species) or one or more of different types of biomarkers (e.g. mRNAs, miRNAs, proteins, peptides, ligands, and antigens).

One or more biosignatures can comprise at least one biomarker selected from those listed in FIGS. 1, 3-60. A specific cell-of-origin biosignature may include one or more biomarkers. FIGS. 3-58 depict tables which lists a number of disease or condition specific biomarkers that can be derived and analyzed from a vesicle. The biomarker can also be CD24, midkine, hepcidin, TMPRSS2-ERG, PCA-3, PSA, EGFR, EGFRvIII, BRAF variant, MET, cKit, PDGFR, Wnt, beta-catenin, K-ras, H-ras, N-ras, Raf, N-myc, c-myc, IGFR, PI3K, Akt, BRCA1, BRCA2, PTEN, VEGFR-2, VEGFR-1, Tie-2, TEM-1, CD276, HER-2, HER-3, or HER-4. The biomarker can also be annexin V, CD63, Rab-5b, or caveolin, or a miRNA, such as let-7a; miR-15b; miR-16; miR-19b; miR-21; miR-26a; miR-27a; miR-92; miR-93; miR-320 or miR-20. The biomarker can also be of any gene or fragment thereof as disclosed in PCT Publication No. WO2009/100029, such as those listed in Tables 3-15 therein.

Other biomarkers useful for assessment in methods and compositions disclosed herein include those associated with conditions or physiological states as disclosed in U.S. Pat. Nos. 6,329,179 and 7,625,573; U.S. Patent Publication Nos. 2002/106684, 2004/005596, 2005/0159378, 2005/0064470, 2006/116321, 2007/0161004, 2007/0077553, 2007/104738, 2007/0298118, 2007/0172900, 2008/0268429, 2010/0062450, 2007/0298118, 2009/0220944 and 2010/0196426; U.S. patent application Ser. Nos. 12/524,432, 12/524,398, 12/524,462; Canadian Patent CA 2453198; and International PCT Patent Publication Nos. WO1994022018, WO2001036601, WO2003063690, WO2003044166, WO2003076603, WO2005121369, WO2005118806, WO/2005/078124, WO2007126386, WO2007088537, WO2007103572, WO2009019215, WO2009021322, WO2009036236, WO2009100029, WO2009015357, WO2009155505, WO 2010/065968 and WO 2010/070276; each of which patent or application is incorporated herein by reference in their entirety. The biomarkers disclosed in these patents and applications, including vesicle biomarkers and microRNAs, can be assessed as part of a signature for characterizing a phenotype, such as providing a diagnosis, prognosis or theranosis of a cancer or other disease. Furthermore, the methods and techniques disclosed therein can be used to assess biomarkers, including vesicle biomarkers and microRNAs.

Another group of useful biomarkers for assessment in methods and compositions disclosed herein include those associated with cancer diagnostics, prognostics and theranostics as disclosed in U.S. Pat. Nos. 6,692,916, 6,960,439, 6,964,850, 7,074,586; U.S. patent application Ser. Nos. 11/159,376, 11/804,175, 12/594,128, 12/514,686, 12/514,775, 12/594,675, 12/594,911, 12/594,679, 12/741,787, 12/312,390; and International PCT Patent Application Nos. PCT/US2009/049935, PCT/US2009/063138, PCT/US2010/000037; each of which patent or application is incorporated herein by reference in their entirety. Usefule biomarkers further include those described in U.S. patent application Ser. No. 10/703,143 and U.S. Ser. No. 10/701,391 for inflammatory disease; Ser. No. 11/529,010 for rheumatoid arthritis; Ser. No. 11/454,553 and Ser. No. 11/827,892 for multiple sclerosis; Ser. No. 11/897,160 for transplant rejection; Ser. No. 12/524,677 for lupus; PCT/US2009/048684 for osteoarthritis; Ser. No. 10/742,458 for infectious disease and sepsis; Ser. No. 12/520,675 for sepsis; each of which patent or application is incorporated herein by reference in their entirety. The biomarkers disclosed in these patents and applications, including mRNAs, can be assessed as part of a signature for characterizing a phenotype, such as providing a diagnosis, prognosis or theranosis of a cancer or other disease. Furthermore, the methods and techniques disclosed therein can be used to assess biomarkers, including vesicle biomarkers and microRNAs.

Still other biomarkers useful for assessment in methods and compositions disclosed herein include those associated with conditions or physiological states as disclosed in Wieczorek et al., Isolation and characterization of an RNA-proteolipid complex associated with the malignant state in humans, Proc Natl Acad Sci USA. 1985 May; 82(10):3455-9; Wieczorek et al., Diagnostic and prognostic value of RNA-proteolipid in sera of patients with malignant disorders following therapy: first clinical evaluation of a novel tumor marker, Cancer Res. 1987 December 1; 47(23):6407-12; Escola et al. *Selective enrichment of tetraspan proteins on the internal vesicles of multivesicular endosomes and on exosomes secreted by human B-lymphocytes*. J. Biol. Chem. (1998) 273:20121-27; Pileri et al. *Binding of hepatitis C virus to CD*81 J Science, (1998) 282:938-41); Kopreski et al. *Detection of Tumor Messenger RNA in the Serum of Patients with Malignant Melanoma*, Clin. Cancer Res. (1999) 5:1961-1965; Carr et al. *Circulating Membrane Vesicles in Leukemic Blood*, Cancer Research, (1985) 45:5944-51; Weichert et al. Cytoplasmic CD24 expression in colorectal cancer independently correlates with shortened patient survival. Clinical Cancer Research, 2005, 11:6574-81); Iorio et al. *MicroRNA gene expression deregulation in human breast cancer*. Cancer Res (2005) 65:7065-70; Taylor et al. *Tumour-derived exosomes and their role in cancer-associated T-cell signaling defects* British J Cancer (2005) 92:305-11; Valadi et al. *Exosome-mediated transfer of mRNAs and microRNAs is a novel mechanism of genetic exchange between cells* Nature Cell Biol (2007) 9:654-59; Taylor et al. *Pregnancy-associated exosomes and their modulation of T cell signaling* J Immunol (2006) 176:1534-42; Koga et al. *Purification, characterization and biological significance of tumor-derived exosomes* Anticancer Res (2005) 25:3703-08; Seligson et al. *Epithelial cell adhesion molecule* (*KSA*) *expression: pathobiology and its role as an independent predictor of survival in renal cell carcinoma* Clin Cancer Res (2004) 10:2659-69; Clayton et al. (*Antigen-presenting cell exosomes are protected from complement-mediated lysis by expression of CD*55 *and CD*59. Eur J Immunol (2003) 33:522-31); Simak et al. *Cell Membrane Microparticles in Blood and Blood Products: Potentially Pathogenic Agents and Diagnostic Markers* Trans Med Reviews (2006) 20:1-26; Choi et al. *Proteomic analysis of microvesicles derived from human colorectal cancer cells* J Proteome Res (2007) 6:4646-4655; lero et al. *Tumour-released exosomes and their implications in cancer immunity* Cell Death Diff (2008) 15:80-88; Baj-Krzyworzeka et al. *Tumour-derived microvesicles carry several surface determinants and mRNA of tumour cells and transfer some of these determinants to monocytes* Cencer Immunol Immunother (2006) 55:808-18; Admyre et al. *B cell-derived exosomes can present allergen peptides and activate allergen-specific T cells to proliferate and produce TH2-like cytokines* J Allergy Clin Immunol (2007) 120:1418-1424; Aoki et al. *Identification and characterization of microvesicles secreted by* 3*T*3-*Ll adipocytes: redox-and hormone dependent induction of milk fat globule-epidermal growth factor* 8-*associated microvesicles* Endocrinol (2007) 148:3850-3862; Baj-Krzyworzeka et al. *Tumour-derived microvesicles carry several surface determinants and mRNA of tumour cells and transfer some of these determinants to monocytes* Cencer Immunol Immunother (2006) 55:808-18; Skog et al. *Glioblastoma microvesicles transport RNA and proteins that promote tumour growth and provide diagnostic biomarkers* Nature Cell Biol (2008) 10:1470-76; El-Hefnawy et al. *Characterization of amplifiable, circulating RNA in plasma and its potential as a tool for cancer diagnostics* Clin Chem (2004) 50:564-573; Pisitkun et al., *Proc Natl Acad Sci USA,* 2004; 101:13368-13373; Mitchell et al., Can urinary exosomes act as treatment response markers in Prostate Cancer?, Journal of Translational Medicine 2009, 7:4; Clayton et al., Human Tumor-Derived Exosomes Selectively Impair Lymphocyte Responses to Interleukin-2, Cancer Res 2007; 67: (15). Aug. 1, 2007; Rabesandratana et al. *Decay-accelerating factor* (*CD*55) *and membrane inhibitor of reactive lysis* (*CD*59) *are released within exosomes during In vitro maturation of reticulocytes*. Blood 91:2573-2580 (1998); Lamparski et al. *Production and characterization of clinical grade exosomes derived from dendritic cells*. J Immunol Methods 270:211-226 (2002); Keller et al. *CD*24 *is a marker of exosomes secreted into urine and amniotic fluid*. Kidney Int'l 72:1095-1102 (2007); Runz et al. *Malignant ascites-derived exosomes of ovarian carcinoma patients contain CD*24 *and EpCAM*. Gyn Oncol 107:563-571 (2007); Redman et al. *Circulating microparticles in normal pregnancy and preeclampsia placenta*. 29:73-77 (2008); Gutwein et al. *Cleavage of L* 1 *in exosomes and apoptotic membrane vesicles released from ovarian carcinoma cells*. Clin Cancer Res 11:2492-2501 (2005); Kristiansen et al., CD24 is an independent prognostic marker of survival in nonsmall cell lung cancer patients, Brit J Cancer 88:231-236 (2003); Lim and Oh, The Role of CD24 in Various Human Epithelial Neoplasias, Pathol Res Pract 201:479-86 (2005); Matutes et al., The Immunophenotype of Splenic Lymphoma with Villous Lymphocytes and its Relevance to the Differential Diagnosis With Other B-Cell Disorders, Blood 83:1558-1562 (1994); Pirruccello and Lang, Differential Expression of CD24-Related Epitopes in Mycosis Fungoides/Sezary Syndrome: A Potential Marker for Circulating Sezary Cells, Blood 76:2343-2347 (1990). The biomarkers disclosed in these publications, including vesicle biomarkers and microRNAs, can be assessed as part of a signature for characterizing a phenotype, such as providing a diagnosis, prognosis or theranosis of a cancer or other disease. Furthermore, the methods and techniques disclosed therein can be used to assess biomarkers, including vesicle biomarkers and microRNAs.

Still other biomarkers useful for assessment in methods and compositions disclosed herein include those associated with conditions or physiological states as disclosed in Rajendran et al., *Proc Natl Acad Sci USA* 2006; 103:11172-11177, Taylor et al., *Gynecol Oncol* 2008; 110:13-21, Zhou et al., *Kidney Int* 2008; 74:613-621, Buning et al., *Immunology* 2008, Prado et al. *J Immunol* 2008; 181:1519-1525, Vella et al. (2008) *Vet Immunol Immunopathol* 124(3-4): 385-93, Gould et al. (2003). *Proc Natl Acad Sci USA* 100(19): 10592-7, Fang et al. (2007). *PLoS Biol* 5(6): e158, Chen, B. J. and R. A. Lamb (2008). *Virology* 372(2): 221-32, Bhatnagar, S. and J. S. Schorey (2007). *J Biol Chem* 282(35): 25779-89, Bhatnagar et al. (2007) *Blood* 110(9): 3234-44, Yuyama, et al. (2008). *J Neurochem* 105(1): 217-24, Gomes et al. (2007). Neurosci Lett 428(1): 43-6, Nagahama et al. (2003). *Autoimmunity* 36(3): 125-31, Taylor, D. D., S. Akyol, et al. (2006). *J Immunol* 176(3): 1534-42, Peche, et al. (2006). *Am J Transplant* 6(7): 1541-50, lero, M, M Valenti, et al. (2008). *Cell Death and Differentiation* 15: 80-88, Gesierich, S., I. Berezoversuskiy, et al. (2006), *Cancer Res* 66(14): 7083-94, Clayton, A., A. Turkes, et al. (2004). Faseb J 18(9): 977-9, Skriner., K. Adolph, et al. (2006). *Arthritis Rheum* 54(12): 3809-14, Brouwer, R., G. J. Pruijn, et al. (2001). *Arthritis Res* 3(2): 102-6, Kim, S. H., N. Bianco, et al. (2006). *Mol Ther* 13(2): 289-300, Evans, C. H., S. C. Ghivizzani, et al. (2000). *Clin Orthop Relat Res* (*379 Suppl*): S300-7, Zhang, H. G., C. Liu, et al. (2006). J Immunol 176(12): 7385-93, Van Niel, G., *J. Mallegol*, et al. (2004). Gut 52: 1690-1697, Fiasse, R. and O. Dewit (2007). *Expert Opinion on Therapeutic Patents* 17(12): 1423-1441(19). The biomarkers disclosed in these publications, including vesicle biomarkers and microRNAs, can be assessed as part of a signature for characterizing a phenotype, such as providing a diagnosis, prognosis or theranosis of a cancer or other disease. Furthermore, the methods and techniques disclosed therein can be used to assess biomarkers, including vesicle biomarkers and microRNAs.

A biomarker that can be derived and analyzed from a vesicle is miRNA (miR), miRNA*nonsense (miR*), and other RNAs (including, but not limited to, mRNA, preRNA, priRNA, hnRNA, snRNA, siRNA, shRNA). A miRNA biomarker includes not only its miRNA and microRNA*nonsense, but its precursor molecules: pri-microRNAs (pri-miRs) and pre-microRNAs (pre-miRs). The sequence of a miRNA can be obtained from publicly available databases such as http://www.mirbase.org/, http://www.microrna.org/, or any others available. The biomarker can also be a nucleic acid molecule (e.g. DNA), protein, or peptide. The presence or absence, expression level, mutations (for example genetic mutations, such as deletions, translocations, duplications, nucleotide or amino acid substitutions, and the like) can be determined for the biomarker. Any epigenetic modulation or copy number variation of a biomarker can also be analyzed.

The one or more biomarkers analyzed can be indicative of a particular tissue or cell of origin, disease, or physiological state. Furthermore, the presence, absence or expression level of one or more of the biomarkers described herein can be correlated to a phenotype of a subject, including a disease, condition, prognosis or drug efficacy. The specific biomarker and biosignature set forth below constitute non-inclusive examples for each of the diseases, condition comparisons, conditions, and/or physiological states. Furthermore, the one or more biomarker assessed for a phenotype can be a cell-of-origin specific vesicle.

The one or more miRNAs used to characterize a phenotype may be selected from those disclosed in PCT Publication No. WO2009/036236. For example, one or more miRNAs listed in Tables 1-VI (FIGS. 6-11) therein can be used to characterize colon adenocarcinoma, colorectal cancer, prostate cancer, lung cancer, breast cancer, b-cell lymphoma, pancreatic cancer, diffuse large BCL cancer, CLL, bladder cancer, renal cancer, hypoxia-tumor, uterine leiomyomas, ovarian cancer, hepatitis C virus-associated hepatocellular carcinoma, ALL, Alzheimer's disease, myelofibrosis, myelofibrosis, polycythemia vera, thrombocythemia, HIV, or HIV-I latency, as further described herein.

The one or more miRNAs can be detected in a vesicle. The one or more miRNAs can be miR-223, miR-484, miR-191, miR-146a, miR-016, miR-026a, miR-222, miR-024, miR-126, and miR-32. One or more miRNAs can also be detected in PBMC. The one or more miRNAs can be miR-223, miR-150, miR-146b, miR-016, miR-484, miR-146a, miR-191, miR-026a, miR-019b, or miR-020a. The one or more miRNAs can be used to characterize a particular disease or condition. For example, for the disease bladder cancer, one or more miRNAs can be detected, such as miR-223, miR-26b, miR-221, miR-103-1, miR-185, miR-23b, miR-203, miR-17-5p, miR-23a, miR-205 or any combination thereof. The one or more miRNAs may be upregulated or overexpressed.

In some embodiments, the one or more miRNAs is used to characterize hypoxia-tumor. The one or more miRNA may be miR-23, miR-24, miR-26, miR-27, miR-103, miR-107, miR-181, miR-210, or miR-213, and may be upregulated. One or more miRNAs can also be used to characterize uterine leiomyomas. For example, the one or more miRNAs used to characterize a uterine leiomyoma may be a let-7 family member, miR-21, miR-23b, miR-29b, or miR-197. The miRNA can be upregulated.

Myelofibrosis can also be characterized by one or more miRNAs, such as miR-190, which can be upregulated; miR-31, miR-150 and miR-95, which can be downregulated, or any combination thereof. Furthermore, myelofibrosis, polycythemia vera or thrombocythemia can also be characterized by detecting one or more miRNAs, such as, but not limited to, miR-34a, miR-342, miR-326, miR-105, miR-149, miR-147, or any combination thereof. The one or more miRNAs may be downregulated.

Other examples of phenotypes that can be characterized by assessing a vesicle for one or more biomarkers are further described herein.

The one or more biomarkers can be detected using a probe. A probe can comprise an oligonucleotide, such as DNA or RNA, an aptamer, monoclonal antibody, polyclonal antibody, Fabs, Fab', single chain antibody, synthetic antibody, peptoid, zDNA, peptide nucleic acid (PNA), locked nucleic acid (LNA), lectin, synthetic or naturally occurring chemical compound (including but not limited to a drug or labeling reagent), dendrimer, or a combination thereof. The probe can be directly detected, for example by being directly labeled, or be indirectly detected, such as through a labeling reagent. The probe can selectively recognize a biomarker. For example, a probe that is an oligonucleotide can selectively hybridize to a miRNA biomarker.

In aspects, the invention provides for the diagnosis, theranosis, prognosis, disease stratification, disease staging, treatment monitoring or predicting responder/non-responder status of a disease or disorder in a subject. The invention comprises assessing vesicles from a subject, including assessing biomarkers present on the vesicles and/or assessing payload within the vesicles, such as protein, nucleic acid or other biological molecules. Any appropriate biomarker that can be assessed using a vesicle and that relates to a disease or disorder can be used the carry out the methods of the invention. Furthermore, any appropriate technique to assess a vesicle as described herein can be used. Exemplary biomarkers for specific diseases that can be assessed according to the methods of the invention include the following:

Breast Cancer

Breast cancer specific biomarkers can include one or more (for example, 2, 3, 4, 5, 6, 7, 8, or more) overexpressed miRs, underexpressed miRs, mRNA, genetic mutations, proteins, ligands, peptides, snoRNA, or any combination thereof, such as listed in FIG. 3.

One or more breast cancer specific biomarker can be assessed to provide a breast cancer specific biosignature. For example, the biosignature can comprise one or more overexpressed miRs, including but not limited to, miR-21, miR-155, miR-206, miR-122a, miR-210, miR-21, miR-21, miR-155, miR-206, miR-122a, miR-210, or miR-21, or any combination thereof.

The biosignature can also comprise one or more underexpressed miRs such as, but not limited to, let-7, miR-10b, miR-125a, miR-125b, miR-145, miR-143, miR-145, miR-16, let-7, let-7, let-7, miR-10b, miR-125a, miR-125b, or miR-145, or any combination thereof.

The mRNAs that may be analyzed can include, but are not limited to, ER, PR, HER2, MUC1, or EGFR, or any combination thereof. Mutations including, but not limited to, those related to KRAS, B-Raf, or CYP2D6, or any combination thereof can also be used as specific biomarkers from a vesicle for breast cancer. In addition, a protein, ligand, or peptide that can be used as biomarkers from a vesicle that is specific to breast cancer includes, but are not limited to, hsp70, MART-1, TRP, HER2, hsp70, MART-1, TRP, HER2, ER, PR, Class III b-tubulin, or VEGFA, or any combination thereof. Furthermore the snoRNA that can be used as an exosomal biomarker for breast cancer include, but are not limited to, GASS. The gene fusion ETV6-NTRK3 can also be used a biomarker for breast cancer.

The invention also provides an isolated vesicle comprising one or more breast cancer specific biomarkers, such as ETV6-NTRK3, or biomarkers listed in FIG. 3 and in FIG. 1 for breast cancer. A composition comprising the isolated vesicle is also provided. Accordingly, in some embodiments, the composition comprises a population of vesicles comprising one or more breast cancer specific biomarkers, such as ETV6-NTRK3, or biomarkers listed in FIG. 3 and in FIG. 1 for breast cancer. The composition can comprise a substantially enriched population of vesicles, wherein the population of vesicles is substantially homogeneous for breast cancer specific vesicles or vesicles comprising one or more breast cancer specific biomarkers, such as ETV6-NTRK3, or biomarkers listed in FIG. 3 and in FIG. 1 for breast cancer.

One or more breast cancer specific biomarkers, such as ETV6-NTRK3, or biomarkers listed in FIG. 3 and in FIG. 1 for breast cancer can also be detected by one or more systems disclosed herein, for characterizing a breast cancer. For example, a detection system can comprise one or more probes to detect one or more breast cancer specific biomarkers, such as ETV6-NTRK3, or biomarkers listed in FIG. 3 and in FIG. 1 for breast cancer, of one or more vesicles of a biological sample.

Ovarian Cancer

Ovarian cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 4, and can be used to create a ovarian cancer specific biosignature. For example, the biosignature can comprise one or more overexpressed miRs, such as, but not limited to, miR-200a, miR-141, miR-200c, miR-200b, miR-21, miR-141, miR-200a, miR-200b, miR-200c, miR-203, miR-205, miR-214, miR-199*, or miR-215, or any combination thereof. The biosignature can also comprise one or more underexpressed miRs such as, but not limited to, miR-199a, miR-140, miR-145, miR-100, miR-let-7 cluster, or miR-125b-1, or any combination thereof. The one or more mRNAs that may be analyzed can include without limitation ERCC1, ER, TOPO1, TOP2A, AR, PTEN, HER2/neu, CD24 or EGFR, or any combination thereof.

A biomarker mutation for ovarian cancer that can be assessed in a vesicle includes, but is not limited to, a mutation of KRAS, mutation of B-Raf, or any combination of mutations specific for ovarian cancer. The protein, ligand, or peptide that can be assessed in a vesicle can include, but is not limited to, VEGFA, VEGFR2, or HER2, or any combination thereof. Furthermore, a vesicle isolated or assayed can be ovarian cancer cell specific, or derived from ovarian cancer cells.

The invention also provides an isolated vesicle comprising one or more ovarian cancer specific biomarkers, such as CD24, those listed in FIG. 4 and in FIG. 1 for ovarian cancer. A composition comprising the isolated vesicle is also provided. Accordingly, in some embodiments, the composition comprises a population of vesicles comprising one or more ovarian cancer specific biomarkers, such as CD24, those listed in FIG. 4 and in FIG. 1 for ovarian cancer. The composition can comprise a substantially enriched population of vesicles, wherein the population of vesicles is substantially homogeneous for ovarian cancer specific vesicles or vesicles comprising one or more ovarian cancer specific biomarkers, such as CD24, those listed in FIG. 4 and in FIG. 1 for ovarian cancer.

One or more ovarian cancer specific biomarkers, such as CD24, those listed in FIG. 4 and in FIG. 1 for ovarian cancer can also be detected by one or more systems disclosed herein, for characterizing an ovarian cancer. For example, a detection system can comprise one or more probes to detect one or more ovarian cancer specific biomarkers, such as CD24, those listed in FIG. 4 and in FIG. 1 for ovarian cancer, of one or more vesicles of a biological sample.

Lung Cancer

Lung cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 5, and can be used to create a lung cancer specific biosignature.

The biosignature can comprise one or more overexpressed miRs, such as, but not limited to, miR-21, miR-205, miR-221 (protective), let-7a (protective), miR-137 (risky), miR-372 (risky), or miR-122a (risky), or any combination thereof. The biosignature can comprise one or more upregulated or overexpressed miRNAs, such as miR-17-92, miR-19a, miR-21, miR-92, miR-155, miR-191, miR-205 or miR-210; one or more downregulated or underexpressed miRNAs, such as miR-let-7, or any combination thereof. The one or more biomarker may be miR-92a-2*, miR-147, miR-574-5p, such as for small cell lung cancer.

The one or more mRNAs that may be analyzed can include, but are not limited to, EGFR, PTEN, RRM1, RRM2, ABCB1, ABCG2, LRP, VEGFR2, VEGFR3, class III b-tubulin, or any combination thereof.

A biomarker mutation for lung cancer that can be assessed in a vesicle includes, but is not limited to, a mutation of EGFR, KRAS, B-Raf, UGT1A1, or any combination of mutations specific for lung cancer. The protein, ligand, or peptide that can be assessed in a vesicle can include, but is not limited to, KRAS, hENTI, or any combination thereof.

The biomarker can also be midkine (MK or MDK). Furthermore, a vesicle isolated or assayed can be lung cancer cell specific, or derived from lung cancer cells.

The invention also provides an isolated vesicle comprising one or more lung cancer specific biomarkers, such as RLF-MYCL1, TGF-ALK, or CD74-ROS1, or those listed in FIG. 5 and in FIG. 1 for lung cancer. A composition comprising the isolated vesicle is also provided. Accordingly, in some embodiments, the composition comprises a population of vesicles comprising one or more lung cancer specific biomarkers, such as RLF-MYCL1, TGF-ALK, or CD74-ROS1, or those listed in FIG. 5 and in FIG. 1 for lung cancer. The composition can comprise a substantially enriched population of vesicles, wherein the population of vesicles is substantially homogeneous for lung cancer specific vesicles or vesicles comprising one or more lung cancer specific biomarkers, such as RLF-MYCL1, TGF-ALK, or CD74-ROS1, or those listed in FIG. 5 and in FIG. 1 for lung cancer.

One or more lung cancer specific biomarkers, such as RLF-MYCL1, TGF-ALK, or CD74-ROS1, or those listed in FIG. 5 and in FIG. 1 for lung cancer can also be detected by one or more systems disclosed herein, for characterizing a lung cancer. For example, a detection system can comprise one or more probes to detect one or more lung cancer specific biomarkers, such as RLF-MYCL1, TGF-ALK, or CD74-ROS1, or those listed in FIG. 5 and in FIG. 1 for lung cancer, of one or more vesicles of a biological sample.

Colon Cancer

Colon cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 6, and can be used to create a colon cancer specific biosignature. For example, the biosignature can comprise one or more overexpressed miRs, such as, but not limited to, miR-24-1, miR-29b-2, miR-20a, miR-10a, miR-32, miR-203, miR-106a, miR-17-5p, miR-30c, miR-223, miR-126, miR-128b, miR-21, miR-24-2, miR-99b, miR-155, miR-213, miR-150, miR-107, miR-191, miR-221, miR-20a, miR-510, miR-92, miR-513, miR-19a, miR-21, miR-20, miR-183, miR-96, miR-135b, miR-31, miR-21, miR-92, miR-222, miR-181b, miR-210, miR-20a, miR-106a, miR-93, miR-335, miR-338, miR-133b, miR-346, miR-106b, miR-153a, miR-219, miR-34a, miR-99b, miR-185, miR-223, miR-211, miR-135a, miR-127, miR-203, miR-212, miR-95, or miR-17-5p, or any combination thereof. The biosignature can also comprise one or more underexpressed miRs such as miR-143, miR-145, miR-143, miR-126, miR-34b, miR-34c, let-7, miR-9-3, miR-34a, miR-145, miR-455, miR-484, miR-101, miR-145, miR-133b, miR-129, miR-124a, miR-30-3p, miR-328, miR-106a, miR-17-5p, miR-342, miR-192, miR-1, miR-34b, miR-215, miR-192, miR-301, miR-324-5p, miR-30a-3p, miR-34c, miR-331, miR-548c-5p, miR-362-3p, miR-422a, or miR-148b, or any combination thereof.

The one or more biomarker can be an upregulated or overexpressed miRNA, such as miR-20a, miR-21, miR-106a, miR-181b or miR-203, for characterizing a colon adenocarcinoma. The one or more biomarker can be used to characterize a colorectal cancer, such as an upregulated or overexpressed miRNA selected from the group consisting of: miR-19a, miR-21, miR-127, miR-31, miR-96, miR-135b and miR-183, a downregulated or underexpressed miRNA, such as miR-30c, miR-133a, mir143, miR-133b or miR-145, or any combination thereof. The one or more biomarker can be used to characterize a colorectal cancer, such as an upregulated or overexpressed miRNA selected from the group consisting of: miR-548c-5p, miR-362-3p, miR-422a, miR-597, miR-429, miR-200a, and miR-200b, or any combination thereof.

The one or more mRNAs that may be analyzed can include, but are not limited to, EFNB1, ERCC1, HER2, VEGF, or EGFR, or any combination thereof. A biomarker mutation for colon cancer that can be assessed in a vesicle includes, but is not limited to, a mutation of EGFR, KRAS, VEGFA, B-Raf, APC, or p53, or any combination of mutations specific for colon cancer. The protein, ligand, or peptide that can be assessed in a vesicle can include, but is not limited to, AFRs, Rabs, ADAM10, CD44, NG2, ephrin-B1, MIF, b-catenin, Junction, plakoglobin, glalectin-4, RACK1, tetrspanin-8, FasL, TRAIL, A33, CEA, EGFR, dipeptidase 1, hsc-70, tetraspanins, ESCRT, TS, PTEN, or TOPO1, or any combination thereof. Furthermore, a vesicle isolated or assayed can be colon cancer cell specific, or derived from colon cancer cells.

The invention also provides an isolated vesicle comprising one or more colon cancer specific biomarkers, such as listed in FIG. 6 and in FIG. 1 for colon cancer. A composition comprising the isolated vesicle is also provided. Accordingly, in some embodiments, the composition comprises a population of vesicles comprising one or more colon cancer specific biomarkers, such as listed in FIG. 6 and in FIG. 1 for colon cancer. The composition can comprise a substantially enriched population of vesicles, wherein the population of vesicles is substantially homogeneous for colon cancer specific vesicles or vesicles comprising one or more colon cancer specific biomarkers, such as listed in FIG. 6 and in FIG. 1 for colon cancer.

One or more colon cancer specific biomarkers, such as listed in FIG. 6 and in FIG. 1 for colon cancer can also be detected by one or more systems disclosed herein, for characterizing a colon cancer. For example, a detection system can comprise one or more probes to detect one or more colon cancer specific biomarkers, such as listed in FIG. 6 and in FIG. 1 for colon cancer, of one or more vesicles of a biological sample.

Adenoma Versus Hyperplastic Polyp

Adenoma versus hyperplastic polyp specific biomarkers from a vesicle can include one or more (for example, 2, 3, 4, 5, 6, 7, 8, or more) overexpressed miRs, underexpressed miRs, mRNAs, genetic mutations, proteins, ligands, peptides, or any combination thereof, such as listed in FIG. 7, and can be used to create an adenoma versus hyperplastic polyp specific biosignature. For example, the one or more mRNAs that may be analyzed can include, but are not limited to, ABCA8, KIAA1199, GCG, MAMDC2, C2orf32, 229670_at, IGF1, PCDH7, PRDX6, PCNA, COX2, or MUC6, or any combination thereof.

A biomarker mutation to distinguish for adenoma versus hyperplastic polyp that can be assessed in a vesicle includes, but is not limited to, a mutation of KRAS, mutation of B-Raf, or any combination of mutations specific for distinguishing between adenoma versus hyperplastic polyp. The protein, ligand, or peptide that can be assessed in a vesicle can include, but is not limited to, hTERT.

The invention also provides an isolated vesicle comprising one or more specific biomarkers for distinguishing between an adenoma and a hyperplastic polyp, such as listed in FIG. 7. A composition comprising the isolated vesicle is also provided. Accordingly, in some embodiments, the composition comprises a population of vesicles comprising one or more specific biomarkers for distinguishing between an adenoma and a hyperplastic polyp, such as listed in FIG. 7. The composition can comprise a substantially enriched population of vesicles, wherein the population of vesicles is substantially homogeneous for having one or more specific biomarkers for distinguishing between an adenoma and a hyperplastic polyp, such as listed in FIG. 7.

One or more specific biomarkers for distinguishing between an adenoma and a hyperplastic polyp, such as listed in FIG. 7 can also be detected by one or more systems disclosed herein, for distinguishing between an adenoma and a hyperplastic polyp. For example, a detection system can comprise one or more probes to detect one or more specific biomarkers for distinguishing between an adenoma and a hyperplastic polyp, such as listed in FIG. 7, of one or more vesicles of a biological sample.

Irritable Bowel Disease (IBD)

IBD versus normal biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 8, and can be used to create a IBD versus normal specific biosignature. For example, the one or more mRNAs that may be analyzed can include, but are not limited to, REGIA, MMP3, or any combination thereof.

The invention also provides an isolated vesicle comprising one or more specific biomarkers for distinguishing between IBD and a normal sample, such as listed in FIG. 8. A composition comprising the isolated vesicle is also provided. Accordingly, in some embodiments, the composition comprises a population of vesicles comprising one or more specific biomarkers for distinguishing between IBD and a normal sample, such as listed in FIG. 8. The composition can comprise a substantially enriched population of vesicles, wherein the population of vesicles is substantially homogeneous for having one or more specific biomarkers for distinguishing between IBD and a normal sample, such as listed in FIG. 8.

One or more specific biomarkers for distinguishing between IBD and a normal sample, such as listed in FIG. 8 can also be detected by one or more systems disclosed herein, for distinguishing between IBD and a normal sample. For example, a detection system can comprise one or more probes to detect one or more specific biomarkers for distinguishing between IBD and a normal sample, such as listed in FIG. 8, of one or more vesicles of a biological sample.

Adenoma versus Colorectal Cancer (CRC)

Adenoma versus CRC specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 9, and can be used to create a Adenoma versus CRC specific biosignature. For example, the one or more mRNAs that may be analyzed can include, but are not limited to, GREM1, DDR2, GUCY1A3, TNS1, ADAMTS1, FBLN1, FLJ38028, RDX, FAM129A, ASPN, FRMD6, MCC, RBMS1, SNAI2, MEIS1, DOCK10, PLEKHC1, FAM126A, TBC1D9, VWF, DCN, ROBO1, MSRB3, LATS2, MEF2C, IGFBP3, GNB4, RCN3, AKAP12, RFTN1, 226834_at, COL5A1, GNG2, NR3C1*, SPARCL1, MAB21L2, AXIN2, 236894_at, AEBP1, AP1S2, C10orf56, LPHN2, AKT3, FRMD6, COL15A1, CRYAB, COL14A1, LOC286167, QKI, WWTR1, GNG11, PAPPA, or ELDT1, or any combination thereof.

The invention also provides an isolated vesicle comprising one or more specific biomarkers for distinguishing between an adenoma and a CRC, such as listed in FIG. 9. A composition comprising the isolated vesicle is also provided. Accordingly, in some embodiments, the composition comprises a population of vesicles comprising one or more specific biomarkers for distinguishing between an adenoma and a CRC, such as listed in FIG. 9. The composition can comprise a substantially enriched population of vesicles, wherein the population of vesicles is substantially homogeneous for having one or more specific biomarkers for distinguishing between an adenoma and a CRC, such as listed in FIG. 9.

One or more specific biomarkers for distinguishing between an adenoma and a CRC, such as listed in FIG. 9 can also be detected by one or more systems disclosed herein, for distinguishing between an adenoma and a CRC. For example, a detection system can comprise one or more probes to detect one or more specific biomarkers for distinguishing between an adenoma and a CRC, such as listed in FIG. 9, of one or more vesicles of a biological sample.

IBD versus CRC

IBD versus CRC specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 10, and can be used to create a IBD versus CRC specific biosignature. For example, the one or more mRNAs that may be analyzed can include, but are not limited to, 227458_at, INDO, CXCL9, CCR2, CD38, RARRES3, CXCL10, FAM26F, TNIP3, NOS2A, CCRL1, TLR8, IL18BP, FCRL5, SAMD9L, ECGF1, TNFSF13B, GBP5, or GBP1, or any combination thereof.

The invention also provides an isolated vesicle comprising one or more specific biomarkers for distinguishing between IBD and a CRC, such as listed in FIG. 10. A composition comprising the isolated vesicle is also provided. Accordingly, in some embodiments, the composition comprises a population of vesicles comprising one or more specific biomarkers for distinguishing between IBD and a CRC, such as listed in FIG. 10. The composition can comprise a substantially enriched population of vesicles, wherein the population of vesicles is substantially homogeneous for having one or more specific biomarkers for distinguishing between IBD and a CRC, such as listed in FIG. 10.

One or more specific biomarkers for distinguishing between IBD and a CRC, such as listed in FIG. 10 can also be detected by one or more systems disclosed herein, for distinguishing between IBD and a CRC. For example, a detection system can comprise one or more probes to detect one or more specific biomarkers for distinguishing between IBD and a CRC, such as listed in FIG. 10, of one or more vesicles of a biological sample.

CRC Dukes B Versus Dukes C-D

CRC Dukes B versus Dukes C-D specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 11, and can be used to create a CRC D-B versus C-D specific biosignature. For example, the one or more mRNAs that may be analyzed can include, but are not limited to, TMEM37*, IL33, CA4, CCDC58, CLIC6, VERSUSNL1, ESPN, APCDDI, C13orf18, CYP4X1, ATP2A3, LOC646627, MUPCDH, ANPEP, C1orf115, HSD3B2, GBA3, GABRB2, GYLTL1B, LYZ, SPC25, CDKN2B, FAM89A, MOGAT2, SEMA6D, 229376_at, TSPAN5, IL6R, or SLC26A2, or any combination thereof.

The invention also provides an isolated vesicle comprising one or more specific biomarkers for distinguishing between CRC Dukes B and a CRC Dukes C-D, such as listed in FIG. 11. A composition comprising the isolated vesicle is also provided. Accordingly, in some embodiments, the composition comprises a population of vesicles comprising one or more specific biomarkers for distinguishing between CRC Dukes B and a CRC Dukes C-D, such as listed in FIG. 11. The composition can comprise a substantially enriched population of vesicles, wherein the population of vesicles is substantially homogeneous for having one or more specific biomarkers for distinguishing between CRC Dukes B and a CRC Dukes C-D, such as listed in FIG. 11.

One or more specific biomarkers for distinguishing between CRC Dukes B and a CRC Dukes C-D, such as listed in FIG. 11 can also be detected by one or more systems disclosed herein, for distinguishing between CRC Dukes B and a CRC Dukes C-D. For example, a detection system can comprise one or more probes to detect one or more specific biomarkers for distinguishing between CRC Dukes B and a CRC Dukes C-D, such as listed in FIG. 11, of one or more vesicles of a biological sample.

Adenoma with Low Grade Dysplasia Versus Adenoma with High Grade Dysplasia

Adenoma with low grade dysplasia versus adenoma with high grade dysplasia specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 12, and can be used to create an adenoma low grade dysplasia versus adenoma high grade dysplasia specific biosignature. For example, the one or mRNAs that may be analyzed can include, but are not limited to, SI, DMBT1, CFI*, AQP1, APOD, TNFRSF17, CXCL10, CTSE, IGHA1, SLC9A3, SLC7A1, BATF2, SOCS1, DOCK2, NOS2A, HK2, CXCL2, IL15RA, POU2AF1, CLEC3B, ANI3BP, MGC13057, LCK*, C4BPA, HOXC6, GOLT1A, C2orf32, IL1ORA, 240856_at, SOCS3, MEIS3P1, HIPK1, GLS, CPLX1, 236045_x_at, GALC, AMN, CCDC69, CCL28, CPA3, TRIB2, HMGA2, PLCL2, NR3C1, EIF5A, LARP4, RP5-1022P6.2, PHLDB2, FKBP1B, INDO, CLDN8, CNTN3, PBEFI, SLC16A9, CDC25B, TPSB2, PBEFI, ID4, GJB5, CHN2, LIMCH1, or CXCL9, or any combination thereof.

The invention also provides an isolated vesicle comprising one or more specific biomarkers for distinguishing between adenoma with low grade dysplasia and adenoma with high grade dysplasia, such as listed in FIG. 12. A composition comprising the isolated vesicle is also provided. Accordingly, in some embodiments, the composition comprises a population of vesicles comprising one or more specific biomarkers for distinguishing between adenoma with low grade dysplasia and adenoma with high grade dysplasia, such as listed in FIG. 12. The composition can comprise a substantially enriched population of vesicles, wherein the population of vesicles is substantially homogeneous for having one or more specific biomarkers for distinguishing between adenoma with low grade dysplasia and adenoma with high grade dysplasia, such as listed in FIG. 12.

One or more specific biomarkers for distinguishing between adenoma with low grade dysplasia and adenoma with high grade dysplasia, such as listed in FIG. 12 can also be detected by one or more systems disclosed herein, for distinguishing between adenoma with low grade dysplasia and adenoma with high grade dysplasia. For example, a detection system can comprise one or more probes to detect one or more specific biomarkers for distinguishing between adenoma with low grade dysplasia and adenoma with high grade dysplasia, such as listed in FIG. 12, of one or more vesicles of a biological sample.

Ulcerative Colitis (UC) Versus Crohn's Disease (CD)

Ulcerative colitis (UC) versus Crohn's disease (CD) specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 13, and can be used to create a UC versus CD specific biosignature. For example, the one or more mRNAs that may be analyzed can include, but are not limited to, IFIM1, IFITM3, STAT1, STAT3, TAP1, PSME2, PSMB8, HNF4G, KLF5, AQP8, APT2B1, SLC16A, MFAP4, CCNG2, SLC44A4, DDAH1, TOB1, 231152_at, MKNK1, CEACAM7*, 1562836_at, CDC42SE2, PSD3, 231169_at, IGL@*, GSN, GPM6B, CDV3*, PDPK1, ANP32E, ADAM9, CDH1, NLRP2, 215777_at, OSBPL1, VNN1, RABGAP1L, PHACTR2, ASH1L, 213710_s_at, CDH1, NLRP2, 215777_at, OSBPL1, VNN1, RABGAP1L, PHACTR2, ASH1, 213710_s_at, ZNF3, FUT2, IGHA1, EDEM1, GPR171, 229713_at, LOC643187, FLVCR1, SNAP23*, ETNK1, LOC728411, POSTN, MUC12, HOXA5, SIGLEC1, LARP5, PIGR, SPTBN1, UFMI, C6orf62, WDR90, ALDH1A3, F2RL1, IGHV1-69, DUOX2, RAB5A, or CP, or any combination thereof can also be used as specific biomarkers from a vesicle for UC versus CD.

A biomarker mutation for distinguishing UC versus CD that can be assessed in a vesicle includes, but is not limited to, a mutation of CARD15, or any combination of mutations specific for distinguishing UC versus CD. The protein, ligand, or peptide that can be assessed in a vesicle can include, but is not limited to, (P)ASCA.

The invention also provides an isolated vesicle comprising one or more specific biomarkers for distinguishing between UC and CD, such as listed in FIG. 13. A composition comprising the isolated vesicle is also provided. Accordingly, in some embodiments, the composition comprises a population of vesicles comprising one or more specific biomarkers for distinguishing between UC and CD, such as listed in FIG. 13. The composition can comprise a substantially enriched population of vesicles, wherein the population of vesicles is substantially homogeneous for having one or more specific biomarkers for distinguishing between UC and CD, such as listed in FIG. 13.

One or more specific biomarkers for distinguishing between UC and CD, such as listed in FIG. 13 can also be detected by one or more systems disclosed herein, for distinguishing between UC and CD. For example, a detection system can comprise one or more probes to detect one or more specific biomarkers for distinguishing between UC and CD, such as listed in FIG. 13, of one or more vesicles of a biological sample.

Hyperplastic Polyp

Hyperplastic polyp versus normal specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 14, and can be used to create a hyperplastic polyp versus normal specific biosignature. For example, the one or more mRNAs that may be analyzed can include, but are not limited to, SLC6A14, ARHGEF10, ALS2, IL1RN, SPRY4, PTGER3, TRIM29, SERPINB5, 1560327_at, ZAK, BAG4, TRIB3, TTL, FOXQ1, or any combination.

The invention also provides an isolated vesicle comprising one or more hyperplastic polyp specific biomarkers, such as listed in FIG. 14. A composition comprising the isolated vesicle is also provided. Accordingly, in some embodiments, the composition comprises a population of vesicles comprising one or more hyperplastic polyp specific biomarkers, such as listed in FIG. 14. The composition can comprise a substantially enriched population of vesicles, wherein the population of vesicles is substantially homogeneous for hyperplastic polyp specific vesicles or vesicles comprising one or more hyperplastic polyp specific biomarkers, such as listed in FIG. 14.

One or more hyperplastic polyp specific biomarkers, such as listed in FIG. 14 can also be detected by one or more systems disclosed herein, for characterizing a hyperplastic polyp. For example, a detection system can comprise one or more probes to detect one or more listed in FIG. 14. One or more hyperplastic specific biomarkers, such as listed in FIG. 14, of one or more vesicles of a biological sample.

Adenoma with Low Grade Dysplasia Versus Normal

Adenoma with low grade dysplasia versus normal specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 15, and can be used to create an adenoma low grade dysplasia versus normal specific biosignature. For example, the RNAs that may be analyzed can include, but are not limited to, UGT2A3, KLK11, KIAA1199, FOXQ1, CLDN8, ABCA8, or PYY, or any combination thereof and can be used as specific biomarkers from a vesicle for Adenoma low grade dysplasia versus normal. Furthermore, the snoRNA that can be used as an exosomal biomarker for adenoma low grade dysplasia versus normal can include, but is not limited to, GASS.

The invention also provides an isolated vesicle comprising one or more specific biomarkers for distinguishing between adenoma with low grade dysplasia and normal, such as listed in FIG. 15. A composition comprising the isolated vesicle is also provided. Accordingly, in some embodiments, the composition comprises a population of vesicles comprising one or more specific biomarkers for distinguishing between adenoma with low grade dysplasia and normal, such as listed in FIG. 15. The composition can comprise a substantially enriched population of vesicles, wherein the population of vesicles is substantially homogeneous for having one or more specific biomarkers for distinguishing between adenoma with low grade dysplasia and normal, such as listed in FIG. 15.

One or more specific biomarkers for distinguishing between adenoma with low grade dysplasia and normal, such as listed in FIG. 15 can also be detected by one or more systems disclosed herein, for distinguishing between adenoma with low grade dysplasia and normal. For example, a detection system can comprise one or more probes to detect one or more specific biomarkers for distinguishing between adenoma with low grade dysplasia and normal, such as listed in FIG. 15, of one or more vesicles of a biological sample.

Adenoma versus Normal

Adenoma versus normal specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 16, and can be used to create an Adenoma versus normal specific biosignature. For example, the one or more mRNAs that may be analyzed can include, but are not limited to, KIAA1199, FOXQ1, or CA7, or any combination thereof. The protein, ligand, or peptide that can be used as a biomarker from a vesicle that is specific to adenoma versus. normal can include, but is not limited to, Clusterin.

The invention also provides an isolated vesicle comprising one or more specific biomarkers for distinguishing between adenoma and normal, such as listed in FIG. 16. A composition comprising the isolated vesicle is also provided. Accordingly, in some embodiments, the composition comprises a population of vesicles comprising one or more specific biomarkers for distinguishing between adenoma and normal, such as listed in FIG. 16. The composition can comprise a substantially enriched population of vesicles, wherein the population of vesicles is substantially homogeneous for having one or more specific biomarkers for distinguishing between adenoma and normal, such as listed in FIG. 16.

One or more specific biomarkers for distinguishing between adenoma and normal, such as listed in FIG. 16 can also be detected by one or more systems disclosed herein, for distinguishing between adenoma and normal. For example, a detection system can comprise one or more probes to detect one or more specific biomarkers for distinguishing between adenoma and normal, such as listed in FIG. 16, of one or more vesicles of a biological sample.

CRC versus Normal

CRC versus normal specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 17, and can be used to create a CRC versus normal specific biosignature. For example, the one or mRNAs that may be analyzed can include, but are not limited to, VWF, IL8, CHI3L1, S100A8, GREM1, or ODC, or any combination thereof and can be used as specific biomarkers from a vesicle for CRC versus normal.

A biomarker mutation for CRC versus normal that can be assessed in a vesicle includes, but is not limited to, a mutation of KRAS, BRAF, APC, MSH2, or MLH1, or any combination of mutations specific for distinguishing between CRC versus normal. The protein, ligand, or peptide that can be assessed in a vesicle can include, but is not limited to, cytokeratin 13, calcineurin, CHK1, clathrin light chain, phospho-ERK, phospho-PTK2, or MDM2, or any combination thereof.

The invention also provides an isolated vesicle comprising one or more specific biomarkers for distinguishing between CRC and normal, such as listed in FIG. 17. A composition comprising the isolated vesicle is also provided. Accordingly, in some embodiments, the composition comprises a population of vesicles comprising one or more specific biomarkers for distinguishing between CRC and normal, such as listed in FIG. 17. The composition can comprise a substantially enriched population of vesicles, wherein the population of vesicles is substantially homogeneous for having one or more specific biomarkers for distinguishing between CRC and normal, such as listed in FIG. 17.

One or more specific biomarkers for distinguishing between CRC and normal, such as listed in FIG. 17 can also be detected by one or more systems disclosed herein, for distinguishing between CRC and normal. For example, a detection system can comprise one or more probes to detect one or more specific biomarkers for distinguishing between CRC and normal, such as listed in FIG. 17, of one or more vesicles of a biological sample.

Benign Prostatic Hyperplasia (BPH)

Benign prostatic hyperplasia (BPH) specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 18, and can be used to create a BPH specific biosignature. The protein, ligand, or peptide that can be assessed in a vesicle can include, but is not limited to, intact fibronectin.

The invention also provides an isolated vesicle comprising one or more BPH specific biomarkers, such as listed in FIG. 18 and in FIG. 1 for BPH. A composition comprising the isolated vesicle is also provided. Accordingly, in some embodiments, the composition comprises a population of vesicles comprising one or more BPH specific biomarkers, such as listed in FIG. 18 and in FIG. 1 for BPH. The composition can comprise a substantially enriched population of vesicles, wherein the population of vesicles is substantially homogeneous for BPH specific vesicles or vesicles comprising one or more BPH specific biomarkers, such as listed in FIG. 18 and in FIG. 1 for BPH.

One or more BPH specific biomarkers, such as listed in FIG. 18 and in FIG. 1 for BPH, can also be detected by one or more systems disclosed herein, for characterizing a BPH. For example, a detection system can comprise one or more probes to detect one or more BPH specific biomarkers, such as listed in FIG. 18 and in FIG. 1 for BPH, of one or more vesicles of a biological sample.

Prostate Cancer

Prostate cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 19, and can be used to create a prostate cancer specific biosignature. For example, a biosignature for prostate cancer can comprise miR-9, miR-21, miR-141, miR-370, miR-200b, miR-210, miR-155, or miR-196a. In some embodiments, the biosignature can comprise one or more overexpressed miRs, such as, but not limited to, miR-202, miR-210, miR-296, miR-320, miR-370, miR-373, miR-498, miR-503, miR-184, miR-198, miR-302c, miR-345, miR-491, miR-513, miR-32, miR-182, miR-31, miR-26a-1/2, miR-200c, miR-375, miR-196a-1/2, miR-370, miR-425, miR-425, miR-194-1/2, miR-181a-1/2, miR- 34b, let-7i, miR-188, miR-25, miR-106b, miR-449, miR-99b, miR-93, miR-92-1/2, miR-125a, or miR-141, or any combination thereof.

The biosignature can also comprise one or more underexpressed miRs such as, but not limited to, let-7a, let-7b, let-7c, let-7d, let-7g, miR-16, miR-23a, miR-23b, miR-26a, miR-92, miR-99a, miR-103, miR-125a, miR-125b, miR-143, miR-145, miR-195, miR-199, miR-221, miR-222, miR-497, let-7f, miR-19b, miR-22, miR-26b, miR-27a, miR-27b, miR-29a, miR-29b, miR-30_5p, miR-30c, miR-100, miR-141, miR-148a, miR-205, miR-520h, miR-494, miR-490, miR-133a-1, miR-1-2, miR-218-2, miR-220, miR-128a, miR-221, miR-499, miR-329, miR-340, miR-345, miR-410, miR-126, miR-205, miR-7-1/2, miR-145, miR-34a, miR-487, or let-7b, or any combination thereof. The biosignature can comprise upregulated or overexpressed miR-21, downregulated or underexpressed miR-15a, miR-16-1, miR-143 or miR-145, or any combination thereof.

The one or more mRNAs that may be analyzed can include, but are not limited to, AR, PCA3, or any combination thereof and can be used as specific biomarkers from a vesicle for prostate cancer.

The protein, ligand, or peptide that can be assessed in a vesicle can include, but is not limited to, FASLG or TNFSF10 or any combination thereof. Furthermore, a vesicle isolated or assayed can be prostate cancer cell specific, or derived from prostate cancer cells. Furthermore, the snoRNA that can be used as an exosomal biomarker for prostate cancer can include, but is not limited to, U50. Examples of prostate cancer biosignatures are further described below.

The invention also provides an isolated vesicle comprising one or more prostate cancer specific biomarkers, such as ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer. In some embodiments, the isolated vesicle is EpCam+, CK+, CD45−. A composition comprising the isolated vesicle is also provided. Accordingly, in some embodiments, the composition comprises a population of vesicles comprising one or more prostate cancer specific biomarkers such as ACSL3-ETV1, C150RF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer. In some embodiments, the composition comprises a population of vesicles that are EpCam+, CK+, CD45−. The composition can comprise a substantially enriched population of vesicles, wherein the population of vesicles is substantially homogeneous for prostate cancer specific vesicles or vesicles comprising one or more prostate cancer specific biomarkers, such as ACSL3-ETV1, C15ORF21-ETV1, FLJ35294-ETV1, HERV-ETV1,TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer. In one embodiment, the composition can comprise a substantially enriched population of vesicles that are EpCam+, CK+, CD45−.

One or more prostate cancer specific biomarkers, such as ACSL3-ETV1, C15ORF21-ETV1, FLJ35294-ETV1, HERV-ETV1,TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer can also be detected by one or more systems disclosed herein, for characterizing a prostate cancer. In some embodiments, the biomarkers EpCam, CK (cytokeratin), and CD45 are detected by one or more of systems disclosed herein, for characterizing prostate cancer, such as determining the prognosis for a subject's prostate cancer, or the therapy-resistance of a subject. For example, a detection system can comprise one or more probes to detect one or more prostate cancer specific biomarkers, such as ACSL3-ETV1, C150RF21-ETV1, FLJ35294-ETV1, HERV-ETV1,TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer, of one or more vesicles of a biological sample. In one embodiment, the detection system can comprise one or more probes to detect EpCam, CK, CD45, or a combination thereof.

Melanoma

Melanoma specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 20, and can be used to create a melanoma specific biosignature. For example, the biosignature can comprise one or more overexpressed miRs, such as, but not limited to, miR-19a, miR-144, miR-200c, miR-211, miR-324-5p, miR-331, or miR-374, or any combination thereof. The biosignature can also comprise one or more underexpressed miRs such as, but not limited to, miR-9, miR-15a, miR-17-3p, miR-23b, miR-27a, miR-28, miR-29b, miR-30b, miR-31, miR-34b, miR-34c, miR-95, miR-96, miR-100, miR-104, miR-105, miR-106a, miR-107, miR-122a, miR-124a, miR-125b, miR-127, miR-128a, miR-128b, miR-129, miR-135a, miR-135b, miR-137, miR-138, miR-139, miR-140, miR-141, miR-149, miR-154, miR-154#3, miR-181a, miR-182, miR-183, miR-184, miR-185, miR-189, miR-190, miR-199, miR-199b, miR-200a, miR-200b, miR-204, miR-213, miR-215, miR-216, miR-219, miR-222, miR-224, miR-299, miR-302a, miR-302b, miR-302c, miR-302d, miR-323, miR-325, let-7a, let-7b, let-7d, let-7e, or let-7g, or any combination thereof.

The one or more mRNAs that may be analyzed can include, but are not limited to, MUM-1, beta-catenin, or Nop/5/Sik, or any combination thereof and can be used as specific biomarkers from a vesicle for melanoma.

A biomarker mutation for melanoma that can be assessed in a vesicle includes, but is not limited to, a mutation of CDK4 or any combination of mutations specific for melanoma. The protein, ligand, or peptide that can be assessed in a vesicle can include, but is not limited to, DUSP-1, Alix, hsp70, Gib2, Gia, moesin, GAPDH, malate dehydrogenase, p120 catenin, PGRL, syntaxin-binding protein 1 & 2, septin-2, or WD-repeat containing protein 1, or any combination thereof. The snoRNA that can be used as an exosomal biomarker for melanoma include, but are not limited to, H/ACA (U1070, SNORA11D, or any combination thereof. Furthermore, a vesicle isolated or assayed can be melanoma cell specific, or derived from melanoma cells.

The invention also provides an isolated vesicle comprising one or more melanoma specific biomarkers, such as listed in FIG. 20 and in FIG. 1 for melanoma. A composition comprising the isolated vesicle is also provided. Accordingly, in some embodiments, the composition comprises a population of vesicles comprising one or more melanoma specific biomarkers, such as listed in FIG. 20 and in FIG. 1 for melanoma. The composition can comprise a substantially enriched population of vesicles, wherein the population of vesicles is substantially homogeneous for melanoma specific vesicles or vesicles comprising one or more melanoma specific biomarkers, such as listed in FIG. 20 and in FIG. 1 for melanoma.

One or more melanoma specific biomarkers, such as listed in FIG. 20 and in FIG. 1 for melanoma can also be detected by one or more systems disclosed herein, for characterizing a melanoma. For example, a detection system can comprise one or more probes to detect one or more cancer specific biomarkers, such as listed in FIG. 20 and in FIG. 1 for melanoma, of one or more vesicles of a biological sample.

Pancreatic Cancer

Pancreatic cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 21, and can be used to create a pancreatic cancer specific biosignature. For example, the biosignature can comprise one or more overexpressed miRs, such as, but not limited to, miR-221, miR-181a, miR-155, miR-210, miR-213, miR-181b, miR-222, miR-181b-2, miR-21, miR-181b-1, miR-220, miR-181d, miR-223, miR-100-1/2, miR-125a, miR-143, miR-10a, miR-146, miR-99, miR-100, miR-199a-1, miR-10b, miR-199a-2, miR-221, miR-181a, miR-155, miR-210, miR-213, miR-181b, miR-222, miR-181b-2, miR-21, miR-181b-1, miR-181c, miR-220, miR-181d, miR-223, miR-100-1/2, miR-125a, miR-143, miR-10a, miR-146, miR-99, miR-100, miR-199a-1, miR-10b, miR-199a-2, miR-107, miR-103, miR-103-2, miR-125b-1, miR-205, miR-23a, miR-221, miR-424, miR-301, miR-100, miR-376a, miR-125b-1, miR-21, miR-16-1, miR-181a, miR-181c, miR-92, miR-15, miR-155, let-7f-1, miR-212, miR-107, miR-024-1/2, miR-18a, miR-31, miR-93, miR-224, or let-7d, or any combination thereof.

The biosignature can also comprise one or more underexpressed miRs such as, but not limited to, miR-148a, miR-148b, miR-375, miR-345, miR-142, miR-133a, miR-216, miR-217 or miR-139, or any combination thereof. The one or more mRNAs that may be analyzed can include, but are not limited to, PSCA, Mesothelin, or Osteopontin, or any combination thereof and can be used as specific biomarkers from a vesicle for pancreatic cancer.

A biomarker mutation for pancreatic cancer that can be assessed in a vesicle includes, but is not limited to, a mutation of KRAS, CTNNLB1, AKT, NCOA3, or B-RAF, or any combination of mutations specific for pancreatic cancer. The biomarker can also be BRCA2, PALB2, or p16. Furthermore, a vesicle isolated or assayed can be pancreatic cancer cell specific, or derived from pancreatic cancer cells.

The invention also provides an isolated vesicle comprising one or more pancreatic cancer specific biomarkers, such as listed in FIG. 21. A composition comprising the isolated vesicle is also provided. Accordingly, in some embodiments, the composition comprises a population of vesicles comprising one or more pancreatic cancer specific biomarkers, such as listed in FIG. 21. The composition can comprise a substantially enriched population of vesicles, wherein the population of vesicles is substantially homogeneous for pancreatic cancer specific vesicles or vesicles comprising one or more pancreatic cancer specific biomarkers, such as listed in FIG. 21.

One or more pancreatic cancer specific biomarkers, such as listed in FIG. 21, can also be detected by one or more systems disclosed herein, for characterizing a pancreatic cancer. For example, a detection system can comprise one or more probes to detect one or more pancreatic cancer specific biomarkers, such as listed in FIG. 21, of one or more vesicles of a biological sample.

Brain Cancer

Brain cancer (including, but not limited to, gliomas, glioblastomas, meinigiomas, acoustic neuroma/schwannomas, medulloblastoma) specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 22, and can be used to create a brain cancer specific biosignature. For example, the biosignature can comprise one or more overexpressed miRs, such as, but not limited to miR-21, miR-10b, miR-130a, miR-221, miR-125b-1, miR-125b-2, miR-9-2, miR-21, miR-25, or miR-123, or any combination thereof.

The biosignature can also comprise one or more underexpressed miRs such as, but not limited to, miR-128a, miR-181c, miR-181a, or miR-181b, or any combination thereof. The one or more mRNAs that may be analyzed include, but are not limited to, MGMT, which can be used as specific biomarker from a vesicle for brain cancer. The protein, ligand, or peptide that can be assessed in a vesicle can include, but is not limited to, EGFR.

The invention also provides an isolated vesicle comprising one or more brain cancer specific biomarkers, such as GOPC-ROS1, or those listed in FIG. 22 and in FIG. 1 for brain cancer. A composition comprising the isolated vesicle is also provided. Accordingly, in some embodiments, the composition comprises a population of vesicles comprising one or more brain cancer specific biomarkers, such as GOPC-ROS1, or those listed in FIG. 22 and in FIG. 1 for brain cancer. The composition can comprise a substantially enriched population of vesicles, wherein the population of vesicles is substantially homogeneous for brain cancer specific vesicles or vesicles comprising one or more brain cancer specific biomarkers, such as GOPC-ROS1, or those listed in FIG. 22 and in FIG. 1 for brain cancer.

One or more brain cancer specific biomarkers, such as listed in FIG. 22 and in FIG. 1 for brain cancer, can also be detected by one or more systems disclosed herein, for characterizing a brain cancer. For example, a detection system can comprise one or more probes to detect one or more brain cancer specific biomarkers, such as GOPC-ROS1, or those listed in FIG. 22 and in FIG. 1 for brain cancer, of one or more vesicles of a biological sample.

Psoriasis

Psoriasis specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 23, and can be used to create a psoriasis specific biosignature. For example, the biosignature can comprise one or more overexpressed miRs, such as, but not limited to, miR-146b, miR-20a, miR-146a, miR-31, miR-200a, miR-17-5p, miR-30e-5p, miR-141, miR-203, miR-142-3p, miR-21, or miR-106a, or any combination thereof. The biosignature can also comprise one or more underexpressed miRs such a, but not limited to, miR-125b, miR-99b, miR-122a, miR-197, miR-100, miR-381, miR-518b, miR-524, let-7e, miR-30c, miR-365, miR-133b, miR-10a, miR-133a, miR-22, miR-326, or miR-215, or any combination thereof.

The one or more mRNAs that may be analyzed can include, but are not limited to, IL-20, VEGFR-1, VEGFR-2, VEGFR-3, or EGR1, or any combination thereof and can be used as specific biomarkers from a vesicle for psoriasis. A biomarker mutation for psoriasis that can be assessed in a vesicle includes, but is not limited to, a mutation of MGST2, or any combination of mutations specific for psoriasis.

The invention also provides an isolated vesicle comprising one or more psoriasis specific biomarkers, such as listed in FIG. 23 and in FIG. 1 for psoriasis. A composition comprising the isolated vesicle is also provided. Accordingly, in some embodiments, the composition comprises a population of vesicles comprising one or more psoriasis specific biomarkers, such as listed in FIG. 23 and in FIG. 1 for psoriasis. The composition can comprise a substantially enriched population of vesicles, wherein the population of vesicles is substantially homogeneous for psoriasis specific vesicles or vesicles comprising one or more psoriasis specific biomarkers, such as listed in FIG. 23 and in FIG. 1 for psoriasis.

One or more psoriasis specific biomarkers, such as listed in FIG. 23 and in FIG. 1 for psoriasis, can also be detected by one or more systems disclosed herein, for characterizing psoriasis. For example, a detection system can comprise one or more probes to detect one or more psoriasis specific biomarkers, such as listed in FIG. 23 and in FIG. 1 for psoriasis, of one or more vesicles of a biological sample.

Cardiovascular Disease (CVD)

CVD specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 24, and can be used to create a CVD specific biosignature. For example, the biosignature can comprise one or more overexpressed miRs, such as, but not limited to, miR-195, miR-208, miR-214, let-7b, let-7c, let-7e, miR-15b, miR-23a, miR-24, miR-27a, miR-27b, miR-93, miR-99b, miR-100, miR-103, miR-125b, miR-140, miR-145, miR-181a, miR-191, miR-195, miR-199a, miR-320, miR-342, miR-451, or miR-499, or any combination thereof.

The biosignature can also comprise one or more underexpressed miRs such as, but not limited to, miR-1, miR-10a, miR-17-5p, miR-19a, miR-19b, miR-20a, miR-20b, miR-26b, miR-28, miR-30e-5p, miR-101, miR-106a, miR-126, miR-222, miR-374, miR-422b, or miR-423, or any combination thereof. The mRNAs that may be analyzed can include, but are not limited to, MRP14, CD69, or any combination thereof and can be used as specific biomarkers from a vesicle for CVD.

A biomarker mutation for CVD that can be assessed in a vesicle includes, but is not limited to, a mutation of MYH7, SCN5A, or CHRM2, or any combination of mutations specific for CVD.

The protein, ligand, or peptide that can be assessed in a vesicle can include, but is not limited to, CK-MB, cTnI (cardiac troponin), CRP, BPN, IL-6, MCSF, CD40, CD40L,or any combination thereof. Furthermore, a vesicle isolated or assayed can be a CVD cell specific, or derived from cardiac cells.

The invention also provides an isolated vesicle comprising one or more CVD specific biomarkers, such as listed in FIG. 24 and in FIG. 1 for CVD. A composition comprising the isolated vesicle is also provided. Accordingly, in some embodiments, the composition comprises a population of vesicles comprising one or more CVD specific biomarkers, such as listed in FIG. 24 and in FIG. 1 for CVD. The composition can comprise a substantially enriched population of vesicles, wherein the population of vesicles is substantially homogeneous for CVD specific vesicles or vesicles comprising one or more CVD specific biomarkers, such as listed in FIG. 24 and in FIG. 1 for CVD.

One or more CVD specific biomarkers, such as listed in FIG. 24 and in FIG. 1 for CVD, can also be detected by one or more systems disclosed herein, for characterizing a CVD. For example, a detection system can comprise one or more probes to detect one or more CVD specific biomarkers, such as listed in FIG. 24 and in FIG. 1 for CVD, of one or more vesicles of a biological sample.

An increase in an miRNA or combination or miRNA, such as miR-21, miR-129, miR-212, miR-214, miR-134, or a combination thereof (as disclosed in US Publication No. 2010/0010073), can be used to diagnose an increased risk of development or already the existence of cardiac hypertrophy and/or heart failure. A downregulation of miR-182, miR-290, or a combination thereof can be used to diagnose an increased risk of development or already the existence of cardiac hypertrophy and/or heart failure. An increased expression of miR-21, miR-129, miR-212, miR-214, miR-134, or a combination thereof with a reduced expression of miR-182, miR-290, or a combination thereof, may be used to diagnose an increased risk of development or the existence of cardiac hypertrophy and/or heart failure.

Blood Cancers

Hematological malignancies specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 25, and can be used to create a hematological malignancies specific biosignature. For example, the one or more mRNAs that may be analyzed can include, but are not limited to, HOX11, TAL1, LY1, LMO1, or LMO2, or any combination thereof and can be used as specific biomarkers from a vesicle for hematological malignancies.

A biomarker mutation for a blood cancer that can be assessed in a vesicle includes, but is not limited to, a mutation of c-kit, PDGFR, or ABL, or any combination of mutations specific for hematological malignancies.

The invention also provides an isolated vesicle comprising one or more blood cancer specific biomarkers, such as listed in FIG. 25 and in FIG. 1 for blood cancer. A composition comprising the isolated vesicle is also provided. Accordingly, in some embodiments, the composition comprises a population of vesicles comprising one or more blood cancer specific biomarkers, such as listed in FIG. 25 and in FIG. 1 for blood cancer. The composition can comprise a substantially enriched population of vesicles, wherein the population of vesicles is substantially homogeneous for blood cancer specific vesicles or vesicles comprising one or more blood cancer specific biomarkers, such as listed in FIG. 25 and in FIG. 1 for blood cancer.

One or more blood cancer specific biomarkers, such as listed in FIG. 25 and in FIG. 1 for blood cancer, can also be detected by one or more systems disclosed herein, for characterizing a blood cancer. For example, a detection system can comprise one or more probes to detect one or more blood cancer specific biomarkers, such as listed in FIG. 25 and in FIG. 1 for blood cancer, of one or more vesicles of a biological sample.

The one or more blood cancer specific biomarkers can also be a gene fusion selected from the group consisting of: TTL-ETV6, CDK6-MLL, CDK6-TLX3, ETV6-FLT3, ETV6-RUNX1, ETV6-TTL, MLL-AFF1, MLL-AFF3, MLL-AFF4, MLL-GAS7, TCBA1-ETV6, TCF3-PBX1 or TCF3-TFPT, for acute lymphocytic leukemia (ALL); BCL11B-TLX3, IL2-TNFRFS17, NUP214-ABL1, NUP98-CCDC28A, TAL1-STIL, or ETV6-ABL2, for T-cell acute lymphocytic leukemia (T-ALL); ATIC-ALK, KIAA1618-ALK, MSN-ALK, MYH9-ALK, NPM1-ALK, TGF-ALK or TPM3-ALK, for anaplastic large cell lymphoma (ALCL); BCR-ABL1, BCR-JAK2, ETV6-EVI1, ETV6-MN1 or ETV6-TCBA1, for chronic myelogenous leukemia (CML); CBFB-MYH11, CHIC2-ETV6, ETV6-ABL1, ETV6-ABL2, ETV6-ARNT, ETV6-CDX2, ETV6-HLXB9, ETV6-PER1, MEF2D-DAZAPI, AML-AFF1, MLL-ARHGAP26, MLL- ARHGEF12, MLL-CASC5, MLL-CBL, MLL-CREBBP, MLL-DAB21P, MLL-ELL, MLL-EP300, MLL-EPS15, MLL-FNBP1, MLL-FOXO3A, MLL-GMPS, MLL-GPHN, MLL-MLLT1, MLL-MLLT11, MLL-MLLT3, MLL-MLLT6, MLL-MYO1F, MLL-PICALM, MLL-SEPT2, MLL-SEPT6, MLL-SORBS2, MYST3-SORBS2, MYST-CREBBP, NPM1-MLF1, NUP98-HOXA13, PRDM16-EVI1, RABEP1-PDGFRB, RUNX1-EVI1, RUNX1-MDS1, RUNX1-RPL22, RUNX1-RUNX1T1, RUNX1-SH3D19, RUNX1-USP42, RUNX1-YTHDF2, RUNX1-ZNF687, or TAF15-ZNF-384, for AML; CCND1-FSTL3, for chronic lymphocytic leukemia (CLL); and FLIP1-PDGFRA, FLT3-ETV6, KIAA1509-PDGFRA, PDE4DIP-PDGFRB, NIN-PDGFRB, TP53BP1-PDGFRB, or TPM3-PDGFRB, for hyper eosinophilia/chronic eosinophilia.

The one or more biomarkers for CLL can also include one or more of the following upregulated or overexpressed miRNAs, such as miR-23b, miR-24-1, miR-146, miR-155, miR-195, miR-221, miR-331, miR-29a, miR-195, miR-34a, or miR-29c; one or more of the following downregulated or underexpressed miRs, such as miR-15a, miR-16-1, miR-29 or miR-223, or any combination thereof.

The one or more biomarkers for ALL can also include one or more of the following upregulated or overexpressed miRNAs, such as miR-128b, miR-204, miR-218, miR-331, miR-181b-1, miR-17-92; or any combination thereof.

B-Cell Chronic Lymphocytic Leukemia (B-CLL)

B-CLL specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 26, and can be used to create a B-CLL specific biosignature. For example, the biosignature can comprise one or more overexpressed miRs, such as, but not limited to, miR-183-prec, miR-190, miR-24-1-prec, miR-33, miR-19a, miR-140, miR-123, miR-10b, miR-15b-prec, miR-92-1, miR-188, miR-154, miR-217, miR-101, miR-141-prec, miR-153-prec, miR-196-2, miR-134, miR-141, miR-132, miR-192, or miR-181b-prec, or any combination thereof.

The biosignature can also comprise one or more underexpressed miRs such as, but not limited to, miR-213, miR-220, or any combination thereof. The one or more mRNAs that may be analyzed can include, but are not limited to, ZAP70, AdipoR1, or any combination thereof and can be used as specific biomarkers from a vesicle for B-CLL. A biomarker mutation for B-CLL that can be assessed in a vesicle includes, but is not limited to, a mutation of IGHV, P53, ATM, or any combination of mutations specific for B-CLL.

The invention also provides an isolated vesicle comprising one or more B-CLL specific biomarkers, such as BCL3-MYC, MYC-BTG1, BCL7A-MYC, BRWD3-ARHGAP20 or BTG1-MYC, or those listed in FIG. 26. A composition comprising the isolated vesicle is also provided. Accordingly, in some embodiments, the composition comprises a population of vesicles comprising one or more B-CLL specific biomarkers, such as BCL3-MYC, MYC-BTG1, BCL7A-MYC, BRWD3-ARHGAP20 or BTG1-MYC, or those listed in FIG. 26. The composition can comprise a substantially enriched population of vesicles, wherein the population of vesicles is substantially homogeneous for B-CLL specific vesicles or vesicles comprising one or more B-CLL specific biomarkers, such as BCL3-MYC, MYC-BTG1, BCL7A-MYC, BRWD3-ARHGAP20 or BTG1-MYC, or those listed in FIG. 26.

One or more B-CLL specific biomarkers, such as BCL3-MYC, MYC-BTG1, BCL7A-MYC, BRWD3-ARHGAP20 or BTG1-MYC, or those listed in FIG. 26, can also be detected by one or more systems disclosed herein, for characterizing a B-CLL. For example, a detection system can comprise one or more probes to detect one or more B-CLL specific biomarkers, such as BCL3-MYC, MYC-BTG1, BCL7A-MYC, BRWD3-ARHGAP20 or BTG1-MYC, or those listed in FIG. 26, of one or more vesicles of a biological sample.

B-Cell Lymphoma

B-cell lymphome specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 27, and can be used to create a B-cell lymphoma specific biosignature. For example, the biosignature can comprise one or more overexpressed miRs, such as, but not limited to, miR-17-92 polycistron, miR-155, miR-210, or miR-21, miR-19a, miR-92, miR-142 miR-155, miR-221 miR-17-92, miR-21, miR-191, miR-205, or any combination thereof. Furthermore the snoRNA that can be used as an exosomal biomarker for B-cell lymphoma can include, but is not limited to, U50.

The invention also provides an isolated vesicle comprising one or more B-cell lymphoma specific biomarkers, such as listed in FIG. 27. A composition comprising the isolated vesicle is also provided. Accordingly, in some embodiments, the composition comprises a population of vesicles comprising one or more B-cell lymphoma specific biomarkers, such as listed in FIG. 27. The composition can comprise a substantially enriched population of vesicles, wherein the population of vesicles is substantially homogeneous for B-cell lymphoma specific vesicles or vesicles comprising one or more B-cell lymphoma specific biomarkers, such as listed in FIG. 27.

One or more B-cell lymphoma specific biomarkers, such as listed in FIG. 27, can also be detected by one or more systems disclosed herein, for characterizing a B-cell lymphoma. For example, a detection system can comprise one or more probes to detect one or more B-cell lymphoma specific biomarkers, such as listed in FIG. 27, of one or more vesicles of a biological sample.

Diffuse Large B-Cell Lymphoma (DLBCL)

DLBCL specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 28, and can be used to create a DLBCL specific biosignature. For example, the biosignature can comprise one or more overexpressed miRs, such as, but not limited to, miR-17-92, miR-155, miR-210, or miR-21, or any combination thereof. The one or more mRNAs that may be analyzed can include, but are not limited to, A-myb, LMO2, JNK3, CD10, bcl-6, Cyclin D2, IRF4, Flip, or CD44, or any combination thereof and can be used as specific biomarkers from a vesicle for DLBCL.

The invention also provides an isolated vesicle comprising one or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28. A composition comprising the isolated vesicle is also provided. Accordingly, in some embodiments, the composition comprises a population of vesicles comprising one or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28. The composition can comprise a substantially enriched population of vesicles, wherein the population of vesicles is substantially homogeneous for DLBCL specific vesicles or vesicles comprising one or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28.

One or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28, can also be detected by one or more systems disclosed herein, for characterizing a DLBCL. For example, a detection system can comprise one or more probes to detect one or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28, of one or more vesicles of a biological sample.

Burkitt's Lymphoma

Burkitt's lymphoma specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 29, and can be used to create a Burkitt's lymphoma specific biosignature. For example, the biosignature can also comprise one or more underexpressed miRs such as, but not limited to, pri-miR-155, or any combination thereof. The one or more mRNAs that may be analyzed can include, but are not limited to, MYC, TERT, NS, NP, MAZ, RCF3, BYSL, IDE3, CDC7, TCL1A, AUTS2, MYBL1, BMP7, ITPR3, CDC2, BACK2, TTK, MME, ALOX5, or TOP1, or any combination thereof and can be used as specific biomarkers from a vesicle for Burkitt's lymphoma. The protein, ligand, or peptide that can be assessed in a vesicle can include, but is not limited to, BCL6, K1-67, or any combination thereof.

The invention also provides an isolated vesicle comprising one or more Burkitt's lymphoma specific biomarkers, such as IGH-MYC, LCP1-BCL6, or those listed in FIG. 29. A composition comprising the isolated vesicle is also provided. Accordingly, in some embodiments, the composition comprises a population of vesicles comprising one or more Burkitt's lymphoma specific biomarkers, such as IGH-MYC, LCP1-BCL6, or those listed in FIG. 29. The composition can comprise a substantially enriched population of vesicles, wherein the population of vesicles is substantially homogeneous for Burkitt's lymphoma specific vesicles or vesicles comprising one or more Burkitt's lymphoma specific biomarkers, such as IGH-MYC, LCP1-BCL6, or those listed in FIG. 29.

One or more Burkitt's lymphoma specific biomarkers, such as IGH-MYC, LCP1-BCL6, or those listed in FIG. 29, can also be detected by one or more systems disclosed herein, for characterizing a Burkitt's lymphoma. For example, a detection system can comprise one or more probes to detect one or more Burkitt's lymphoma specific biomarkers, such as IGH-MYC, LCP1-BCL6, or those listed in FIG. 29, of one or more vesicles of a biological sample.

Hepatocellular Carcinoma

Hepatocellular carcinoma specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 30 and can be used to create a hepatocellular carcinoma specific biosignature. For example, the biosignature can comprise one or more overexpressed miRs, such as, but not limited to, miR-221. The biosignature can also comprise one or more underexpressed miRs such as, but not limited to, let-7a-1, let-7a-2, let-7a-3, let-7b, let-7c, let-7d, let-7e, let-7f-2, let-fg, miR-122a, miR-124a-2, miR-130a, miR-132, miR-136, miR-141, miR-142, miR-143, miR-145, miR-146, miR-150, miR-155(BIC), miR-181a-1, miR-181a-2, miR-181c, miR-195, miR-199a-1-5p, miR-199a-2-5p, miR-199b, miR-200b, miR-214, miR-223, or pre-miR-594, or any combination thereof. The one or more mRNAs that may be analyzed can include, but are not limited to, FAT10.

The one or more biomarkers of a biosignature can also be used to characterize hepatitis C virus-associated hepatocellular carcinoma. The one or more biomarkers can be a miRNA, such as an overexpressed or underexpressed miRNA. For example, the upregulated or overexpressed miRNA can be miR-122, miR-100, or miR-10a and the downregulated miRNA can be miR-198 or miR-145.

The invention also provides an isolated vesicle comprising one or more hepatocellular carcinoma specific biomarkers, such as listed in FIG. 30 and in FIG. 1 for hepatocellular carcinoma. A composition comprising the isolated vesicle is also provided. Accordingly, in some embodiments, the composition comprises a population of vesicles comprising one or more hepatocellular carcinoma specific biomarkers, such as listed in FIG. 30 and in FIG. 1 for hepatocellular carcinoma. The composition can comprise a substantially enriched population of vesicles, wherein the population of vesicles is substantially homogeneous for hepatocellular carcinoma specific vesicles or vesicles comprising one or more hepatocellular carcinoma specific biomarkers, such as listed in FIG. 30 and in FIG. 1 for hepatocellular carcinoma.

One or more hepatocellular carcinoma specific biomarkers, such as listed in FIG. 30 and in FIG. 1 for hepatocellular carcinoma, can also be detected by one or more systems disclosed herein, for characterizing a hepatocellular carcinoma. For example, a detection system can comprise one or more probes to detect one or more hepatocellular carcinoma specific biomarkers, such as listed in FIG. 30 and in FIG. 1 for hepatocellular carcinoma, of one or more vesicles of a biological sample.

Cervical Cancer

Cervical cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 31, and can be used to create a cervical cancer specific biosignature. For example, the one or more mRNAs that may be analyzed can include, but are not limited to, HPV E6, HPV E7, or p53, or any combination thereof and can be used as specific biomarkers from a vesicle for cervical cancer.

The invention also provides an isolated vesicle comprising one or more cervical cancer specific biomarkers, such as listed in FIG. 31 and in FIG. 1 for cervical cancer. A composition comprising the isolated vesicle is also provided. Accordingly, in some embodiments, the composition comprises a population of vesicles comprising one or more cervical cancer specific biomarkers, such as listed in FIG. 31 and in FIG. 1 for cervical cancer. The composition can comprise a substantially enriched population of vesicles, wherein the population of vesicles is substantially homogeneous for cervical cancer specific vesicles or vesicles comprising one or more cervical cancer specific biomarkers, such as listed in FIG. 31 and in FIG. 1 for cervical cancer.

One or more cervical cancer specific biomarkers, such as listed in FIG. 31 and in FIG. 1 for cervical cancer, can also be detected by one or more systems disclosed herein, for characterizing a cervical cancer. For example, a detection system can comprise one or more probes to detect one or more cervical cancer specific biomarkers, such as listed in FIG. 31 and in FIG. 1 for cervical cancer, of one or more vesicles of a biological sample.

Endometrial Cancer

Endometrial cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 32 and can be used to create a endometrial cancer specific biosignature. For example, the biosignature can comprise one or more overexpressed miRs, such as, but not limited to, miR-185, miR-106a, miR-181a, miR-210, miR-423, miR-103, miR-107, or let-7c, or any combination thereof. The biosignature can also comprise one or more underexpressed miRs such as, but not limited to, miR-7i, miR-221, miR-193, miR-152, or miR-30c, or any combination thereof.

A biomarker mutation for endometrial cancer that can be assessed in a vesicle includes, but is not limited to, a mutation of PTEN, K-RAS, B-catenin, p53, Her2/neu, or any combination of mutations specific for endometrial cancer. The protein, ligand, or peptide that can be assessed in a vesicle can include, but is not limited to, NLRP7, AlphaV Beta6 integrin, or any combination thereof.

The invention also provides an isolated vesicle comprising one or more endometrial cancer specific biomarkers, such as listed in FIG. 32 and in FIG. 1 for endometrial cancer. A composition comprising the isolated vesicle is also provided. Accordingly, in some embodiments, the composition comprises a population of vesicles comprising one or more endometrial cancer specific biomarkers, such as listed in FIG. 32 and in FIG. 1 for endometrial cancer. The composition can comprise a substantially enriched population of vesicles, wherein the population of vesicles is substantially homogeneous for endometrial cancer specific vesicles or vesicles comprising one or more endometrial cancer specific biomarkers, such as listed in FIG. 32 and in FIG. 1 for endometrial cancer.

One or more endometrial cancer specific biomarkers, such as listed in FIG. 32 and in FIG. 1 for endometrial cancer, can also be detected by one or more systems disclosed herein, for characterizing a endometrial cancer. For example, a detection system can comprise one or more probes to detect one or more endometrial cancer specific biomarkers, such as listed in FIG. 32 and in FIG. 1 for endometrial cancer, of one or more vesicles of a biological sample.

Head and Neck Cancer

Head and neck cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 33, and can be used to create a head and neck cancer specific biosignature. For example, the biosignature can comprise one or more overexpressed miRs, such as, but not limited to, miR-21, let-7, miR-18, miR-29c, miR-142-3p, miR-155, miR-146b, miR-205, or miR-21, or any combination thereof. The biosignature can also comprise one or more underexpressed miRs such as, but not limited to, miR-494. The one or more mRNAs that may be analyzed include, but are not limited to, HPV E6, HPV E7, p53, IL-8, SAT, H3FA3, or EGFR, or any combination thereof and can be used as specific biomarkers from a vesicle for head and neck cancer.

A biomarker mutation for head and neck cancer that can be assessed in a vesicle includes, but is not limited to, a mutation of GSTM1, GSTT1, GSTP1, OGG1, XRCC 1, XPD, RAD51, EGFR, p53, or any combination of mutations specific for head and neck cancer. The protein, ligand, or peptide that can be assessed in a vesicle can include, but is not limited to, EGFR, EphB4, or EphB2, or any combination thereof.

The invention also provides an isolated vesicle comprising one or more head and neck cancer specific biomarkers, such as CHCHD7-PLAG1, CTNNB1-PLAG1, FHIT-HMGA2, HMGA2-NFIB, LIFR-PLAG1, or TCEA1-PLAG1, or those listed in FIG. 33 and in FIG. 1 for head and neck cancer. A composition comprising the isolated vesicle is also provided. Accordingly, in some embodiments, the composition comprises a population of vesicles comprising one or more head and neck cancer specific biomarkers, such as CHCHD7-PLAG1, CTNNB1-PLAG1, FHIT-HMGA2, HMGA2-NFIB, LIFR-PLAG1, or TCEA1-PLAG1, or those listed in FIG. 33 and in FIG. 1 for head and neck cancer. The composition can comprise a substantially enriched population of vesicles, wherein the population of vesicles is substantially homogeneous for head and neck cancer specific vesicles or vesicles comprising one or more head and neck cancer specific biomarkers, such as CHCHD7-PLAG1, CTNNB1-PLAG1, FHIT-HMGA2, HMGA2-NFIB, LIFR-PLAG1, or TCEA1-PLAG1, or those listed in FIG. 33 and in FIG. 1 for head and neck cancer.

One or more head and neck cancer specific biomarkers, such as listed in FIG. 33 and in FIG. 1 for head and neck cancer, can also be detected by one or more systems disclosed herein, for characterizing a head and neck cancer. For example, a detection system can comprise one or more probes to detect one or more head and neck cancer specific biomarkers, such as CHCHD7-PLAG1, CTNNB1-PLAG1, FHIT-HMGA2, HMGA2-NFIB, LIFR-PLAG1, or TCEA1-PLAG1, or those listed in FIG. 33 and in FIG. 1 for head and neck cancer, of one or more vesicles of a biological sample.

Inflammatory Bowel Disease (IBD)

IBD specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 34, and can be used to create a IBD specific biosignature. The one or more mRNAs that may be analyzed can include, but are not limited to, Trypsinogen IV, SERT, or any combination thereof and can be used as specific biomarkers from a vesicle for IBD.

A biomarker mutation for IBD that can be assessed in a vesicle can include, but is not limited to, a mutation of CARD15 or any combination of mutations specific for IBD. The protein, ligand, or peptide that can be assessed in a vesicle can include, but is not limited to, 11-16, 11-1beta, 11-12, TNF-alpha, interferon gamma, 11-6, Rantes, MCP-1, Resistin, or 5-HT, or any combination thereof.

The invention also provides an isolated vesicle comprising one or more IBD specific biomarkers, such as listed in FIG. 34 and in FIG. 1 for IBD. A composition comprising the isolated vesicle is also provided. Accordingly, in some embodiments, the composition comprises a population of vesicles comprising one or more IBD specific biomarkers, such as listed in FIG. 34 and in FIG. 1 for IBD. The composition can comprise a substantially enriched population of vesicles, wherein the population of vesicles is substantially homogeneous for IBD specific vesicles or vesicles comprising one or more IBD specific biomarkers, such as listed in FIG. 34 and in FIG. 1 for IBD.

One or more IBD specific biomarkers, such as listed in FIG. 34 and in FIG. 1 for IBD, can also be detected by one or more systems disclosed herein, for characterizing a IBD. For example, a detection system can comprise one or more probes to detect one or more IBD specific biomarkers, such as listed in FIG. 34 and in FIG. 1 for IBD, of one or more vesicles of a biological sample.

Diabetes

Diabetes specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 35, and can be used to create a diabetes specific biosignature. For example, the one or more mRNAs that may be analyzed can include, but are not limited to, 11-8, CTSS, ITGB2, HLA-DRA, CD53, PLAG27, or MMP9, or any combination thereof and can be used as specific biomarkers from a vesicle for diabetes. The protein, ligand, or peptide that can be assessed in a vesicle can include, but is not limited to, RBP4.

The invention also provides an isolated vesicle comprising one or more diabetes specific biomarkers, such as listed in FIG. 35 and in FIG. 1 for diabetes. A composition comprising the isolated vesicle is also provided. Accordingly, in some embodiments, the composition comprises a population of vesicles comprising one or more diabetes specific biomarkers, such as listed in FIG. 35 and in FIG. 1 for diabetes. The composition can comprise a substantially enriched population of vesicles, wherein the population of vesicles is substantially homogeneous for diabetes specific vesicles or vesicles comprising one or more diabetes specific biomarkers, such as listed in FIG. 35 and in FIG. 1 for diabetes.

One or more diabetes specific biomarkers, such as listed in FIG. 35 and in FIG. 1 for diabetes, can also be detected by one or more systems disclosed herein, for characterizing diabetes. For example, a detection system can comprise one or more probes to detect one or more diabetes specific biomarkers, such as listed in FIG. 35 and in FIG. 1 for diabetes, of one or more vesicles of a biological sample.

Barrett's Esophagus

Barrett's Esophagus specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 36, and can be used to create a Barrett's Esophagus specific biosignature. For example, the biosignature can comprise one or more overexpressed miRs, such as, but not limited to, miR-21, miR-143, miR-145, miR-194, or miR-215, or any combination thereof. The one or more mRNAs that may be analyzed include, but are not limited to, S100A2, S100A4, or any combination thereof and can be used as specific biomarkers from a vesicle for Barrett's Esophagus.

A biomarker mutation for Barrett's Esophagus that can be assessed in a vesicle includes, but is not limited to, a mutation of p53 or any combination of mutations specific for Barrett's Esophagus. The protein, ligand, or peptide that can be assessed in a vesicle can include, but is not limited to, p53, MUC1, MUC2, or any combination thereof.

The invention also provides an isolated vesicle comprising one or more Barrett's Esophagus specific biomarkers, such as listed in FIG. 36 and in FIG. 1 for Barrett's Esophagus. A composition comprising the isolated vesicle is also provided. Accordingly, in some embodiments, the composition comprises a population of vesicles comprising one or more Barrett's Esophagus specific biomarkers, such as listed in FIG. 36 and in FIG. 1 for Barrett's Esophagus. The composition can comprise a substantially enriched population of vesicles, wherein the population of vesicles is substantially homogeneous for Barrett's Esophagus specific vesicles or vesicles comprising one or more Barrett's Esophagus specific biomarkers, such as listed in FIG. 36 and in FIG. 1 for Barrett's Esophagus.

One or more Barrett's Esophagus specific biomarkers, such as listed in FIG. 36 and in FIG. I for Barrett's Esophagus, can also be detected by one or more systems disclosed herein, for characterizing a Barrett's Esophagus. For example, a detection system can comprise one or more probes to detect one or more Barrett's Esophagus specific biomarkers, such as listed in FIG. 36 and in FIG. 1 for Barrett's Esophagus, of one or more vesicles of a biological sample.

Fibromyalgia

Fibromyalgia specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 37, and can be used to create a fibromyalgia specific biosignature. The one or more mRNAs that may be analyzed can include, but are not limited to, NR2D which can be used as a specific biomarker from a vesicle for fibromyalgia.

The invention also provides an isolated vesicle comprising one or more fibromyalgia specific biomarkers, such as listed in FIG. 37 and in FIG. 1 for fibromyalgia. A composition comprising the isolated vesicle is also provided. Accordingly, in some embodiments, the composition comprises a population of vesicles comprising one or more fibromyalgia specific biomarkers, such as listed in FIG. 37 and in FIG. 1 for fibromyalgia. The composition can comprise a substantially enriched population of vesicles, wherein the population of vesicles is substantially homogeneous for fibromyalgia specific vesicles or vesicles comprising one or more fibromyalgia specific biomarkers, such as listed in FIG. 37 and in FIG. 1 for fibromyalgia.

One or more fibromyalgia specific biomarkers, such as listed in FIG. 37 and in FIG. 1 for fibromyalgia, can also be detected by one or more systems disclosed herein, for characterizing a fibromyalgia. For example, a detection system can comprise one or more probes to detect one or more fibromyalgia specific biomarkers, such as listed in FIG. 37 and in FIG. 1 for fibromyalgia, of one or more vesicles of a biological sample.

Stroke

Stroke specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 38, and can be used to create a stroke specific biosignature. For example, the one or more mRNAs that may be analyzed can include, but are not limited to, MMP9, S100-P, S100A12, S100A9, coag factor V, Arginasel, CA-IV, monocarboxylic acid transporter, ets-2, EIF2alpha, cytoskeleton associated protein 4, N-formylpeptide receptor, Ribonuclease2, N-acetylneuraminate pyruvate lyase, BCL-6, or Glycogen phosphorylase, or any combination thereof and can be used as specific biomarkers from a vesicle for stroke.

The invention also provides an isolated vesicle comprising one or more stroke specific biomarkers, such as listed in FIG. 38 and in FIG. 1 for stroke. A composition comprising the isolated vesicle is also provided. Accordingly, in some embodiments, the composition comprises a population of vesicles comprising one or more stroke specific biomarkers, such as listed in FIG. 38 and in FIG. 1 for stroke. The composition can comprise a substantially enriched population of vesicles, wherein the population of vesicles is substantially homogeneous for stroke specific vesicles or vesicles comprising one or more stroke specific biomarkers, such as listed in FIG. 38 and in FIG. 1 for stroke.

One or more stroke specific biomarkers, such as listed in FIG. 38 and in FIG. 1 for stroke, can also be detected by one or more systems disclosed herein, for characterizing a stroke. For example, a detection system can comprise one or more probes to detect one or more stroke specific biomarkers, such as listed in FIG. 38 and in FIG. 1 for stroke, of one or more vesicles of a biological sample.

Multiple Sclerosis (MS)

MS specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 39, and can be used to create a MS specific biosignature. For example, the one or more mRNAs that may be analyzed can include, but are not limited to, IL-6, IL-17, PAR-3, IL-17, T1/ST2, JunD, 5-LO, LTA4H, MBP, PLP, or alpha-beta crystallin, or any combination thereof and can be used as specific biomarkers from a vesicle for MS.

The invention also provides an isolated vesicle comprising one or more MS specific biomarkers, such as listed in FIG. 39 and in FIG. 1 for MS. A composition comprising the isolated vesicle is also provided. Accordingly, in some embodiments, the composition comprises a population of vesicles comprising one or more MS specific biomarkers, such as listed in FIG. 39 and in FIG. 1 for MS. The composition can comprise a substantially enriched population of vesicles, wherein the population of vesicles is substantially homogeneous for MS specific vesicles or vesicles comprising one or more MS specific biomarkers, such as listed in FIG. 39 and in FIG. 1 for MS.

One or more MS specific biomarkers, such as listed in FIG. 39 and in FIG. 1 for MS, can also be detected by one or more systems disclosed herein, for characterizing a MS. For example, a detection system can comprise one or more probes to detect one or more MS specific biomarkers, such as listed in FIG. 39 and in FIG. 1 for MS, of one or more vesicles of a biological sample.

Parkinson's Disease

Parkinson's disease specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 40, and can be used to create a Parkinson's disease specific biosignature. For example, the biosignature can include, but is not limited to, one or more underexpressed miRs such as miR-133b. The one or more mRNAs that may be analyzed can include, but are not limited to Nurr1, BDNF, TrkB, gstm1, or S100 beta, or any combination thereof and can be used as specific biomarkers from a vesicle for Parkinson's disease.

A biomarker mutation for Parkinson's disease that can be assessed in a vesicle includes, but is not limited to, a mutation of FGF20, alpha-synuclein, FGF20, NDUFV2, FGF2, CALB1, B2M, or any combination of mutations specific for Parkinson's disease. The protein, ligand, or peptide that can be assessed in a vesicle can include, but is not limited to, apo-H, Ceruloplasmin, BDNF, IL-8, Beta2-microglobulin, apoA11, tau, ABeta1-42, DJ-1, or any combination thereof.

The invention also provides an isolated vesicle comprising one or more Parkinson's disease specific biomarkers, such as listed in FIG. 40 and in FIG. 1 for Parkinson's disease A composition comprising the isolated vesicle is also provided. Accordingly, in some embodiments, the composition comprises a population of vesicles comprising one or more Parkinson's disease specific biomarkers, such as listed in FIG. 40 and in FIG. 1 for Parkinson's disease. The composition can comprise a substantially enriched population of vesicles, wherein the population of vesicles is substantially homogeneous for Parkinson's disease specific vesicles or vesicles comprising one or more Parkinson's disease specific biomarkers, such as listed in FIG. 40 and in FIG. 1 for Parkinson's disease.

One or more Parkinson's disease specific biomarkers, such as listed in FIG. 40 and in FIG. 1 for Parkinson's disease, can also be detected by one or more systems disclosed herein, for characterizing a Parkinson's disease. For example, a detection system can comprise one or more probes to detect one or more Parkinson's disease specific biomarkers, such as listed in FIG. 40 and in FIG. 1 for Parkinson's disease, of one or more vesicles of a biological sample.

Rheumatic Disease

Rheumatic disease specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 41, and can be used to create a rheumatic disease specific biosignature. For example, the biosignature can also comprise one or more underexpressed miRs such as, but not limited to, miR-146a, miR-155, miR-132, miR-16, or miR-181, or any combination thereof. The one or more mRNAs that may be analyzed can include, but are not limited to, HOXD10, HOXD11, HOXD13, CCL8, LIM homeobox2, or CENP-E, or any combination thereof and can be used as specific biomarkers from a vesicle for rheumatic disease. The protein, ligand, or peptide that can be assessed in a vesicle can include, but is not limited to, TNFα.

The invention also provides an isolated vesicle comprising one or more rheumatic disease specific biomarkers, such as listed in FIG. 41 and in FIG. 1 for rheumatic disease. A composition comprising the isolated vesicle is also provided. Accordingly, in some embodiments, the composition comprises a population of vesicles comprising one or more rheumatic disease specific biomarkers, such as listed in FIG. 41 and in FIG. 1 for rheumatic disease. The composition can comprise a substantially enriched population of vesicles, wherein the population of vesicles is substantially homogeneous for rheumatic disease specific vesicles or vesicles comprising one or more rheumatic disease specific biomarkers, such as listed in FIG. 41 and in FIG. 1 for rheumatic disease.

One or more rheumatic disease specific biomarkers, such as listed in FIG. 41 and in FIG. 1 for rheumatic disease, can also be detected by one or more systems disclosed herein, for characterizing a rheumatic disease. For example, a detection system can comprise one or more probes to detect one or more rheumatic disease specific biomarkers, such as listed in FIG. 41 and in FIG. 1 for rheumatic disease, of one or more vesicles of a biological sample.

Alzheimer's Disease

Alzheimer's disease specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 42, and can be used to create a Alzheimers disease specific biosignature. For example, the biosignature can also comprise one or more underexpressed miRs such as miR-107, miR-29a, miR-29b-1, or miR-9, or any combination thereof. The biosignature can also comprise one or more overexpressed miRs such as miR-128 or any combination thereof.

The one or more mRNAs that may be analyzed can include, but are not limited to, HIF-la, BACE1, Reelin, CHRNA7, or 3Rtau/4Rtau, or any combination thereof and can be used as specific biomarkers from a vesicle for Alzheimer's disease.

A biomarker mutation for Alzheimer's disease that can be assessed in a vesicle includes, but is not limited to, a mutation of APP, presenilin1, presenilin2, APOE4, or any combination of mutations specific for Alzheimer's disease. The protein, ligand, or peptide that can be assessed in a vesicle can include, but is not limited to, BACE1, Reelin, Cystatin C, Truncated Cystatin C, Amyloid Beta, C3a, t-Tau, Complement factor H, or alpha-2-macroglobulin, or any combination thereof.

The invention also provides an isolated vesicle comprising one or more Alzheimer's disease specific biomarkers, such as listed in FIG. 42 and in FIG. 1 for Alzheimer's disease. A composition comprising the isolated vesicle is also provided. Accordingly, in some embodiments, the composition comprises a population of vesicles comprising one or more Alzheimer's disease specific biomarkers, such as listed in FIG. 42 and in FIG. 1 for Alzheimer's disease. The composition can comprise a substantially enriched population of vesicles, wherein the population of vesicles is substantially homogeneous for Alzheimer's disease specific vesicles or vesicles comprising one or more Alzheimer's disease specific biomarkers, such as listed in FIG. 42 and in FIG. 1 for Alzheimer's disease.

One or more Alzheimer's disease specific biomarkers, such as listed in FIG. 42 and in FIG. 1 for Alzheimer's disease, can also be detected by one or more systems disclosed herein, for characterizing a Alzheimer's disease. For example, a detection system can comprise one or more probes to detect one or more Alzheimer's disease specific biomarkers, such as listed in FIG. 42 and in FIG. 1 for Alzheimer's disease, of one or more vesicles of a biological sample.

Prion Disease

Prion specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 43, and can be used to create a prion specific biosignature. For example, the one or more mRNAs that may be analyzed can include, but are not limited to, Amyloid B4, App, IL-1R1, or SOD1, or any combination thereof and can be used as specific biomarkers from a vesicle for a prion. The protein, ligand, or peptide that can be assessed in a vesicle can include, but is not limited to, PrP(c), 14-3-3, NSE, S-100, Tau, AQP-4, or any combination thereof.

The invention also provides an isolated vesicle comprising one or more prion disease specific biomarkers, such as listed in FIG. 43 and in FIG. 1 for prion disease. A composition comprising the isolated vesicle is also provided. Accordingly, in some embodiments, the composition comprises a population of vesicles comprising one or more prion disease specific biomarkers, such as listed in FIG. 43 and in FIG. 1 for prion disease. The composition can comprise a substantially enriched population of vesicles, wherein the population of vesicles is substantially homogeneous for prion disease specific vesicles or vesicles comprising one or more prion disease specific biomarkers, such as listed in FIG. 43 and in FIG. 1 for prion disease.

One or more prion disease specific biomarkers, such as listed in FIG. 43 and in FIG. 1 for prion disease, can also be detected by one or more systems disclosed herein, for characterizing a prion disease. For example, a detection system can comprise one or more probes to detect one or more prion disease specific biomarkers, such as listed in FIG. 43 and in FIG. 1 for prion disease, of one or more vesicles of a biological sample.

Sepsis

Sepsis specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 44, and can be used to create a sepsis specific biosignature. For example, the one or more mRNAs that may be analyzed can include, but are not limited to, 15-Hydroxy-PG dehydrogenase (up), LAIR1 (up), NFKB1A (up), TLR2, PGLYPR1, TLR4, MD2, TLR5, IFNAR2, IRAK2, IRAK3, IRAK4, PI3K, PI3KCB, MAP2K6, MAPK14, NFKB1A, NFKB1, IL1R1, MAP2K1IP1, MKNK1, FAS, CASP4, GADD45B, SOCS3, TNFSF10, TNFSFI3B, OSM, HGF, or IL18R1, or any combination thereof and can be used as specific biomarkers from a vesicle for sepsis.

The invention also provides an isolated vesicle comprising one or more sepsis specific biomarkers, such as listed in FIG. 44. A composition comprising the isolated vesicle is also provided. Accordingly, in some embodiments, the composition comprises a population of vesicles comprising one or more sepsis specific biomarkers, such as listed in FIG. 44. The composition can comprise a substantially enriched population of vesicles, wherein the population of vesicles is substantially homogeneous for sepsis specific vesicles or vesicles comprising one or more sepsis specific biomarkers, such as listed in FIG. 44.

One or more sepsis specific biomarkers, such as listed in FIG. 44, can also be detected by one or more systems disclosed herein, for characterizing a sepsis. For example, a detection system can comprise one or more probes to detect one or more sepsis specific biomarkers, such as listed in FIG. 44, of one or more vesicles of a biological sample.

Chronic Neuropathic Pain

Chronic neuropathic pain (CNP) specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 45, and can be used to create a CNP specific biosignature. For example, the one or more mRNAs that may be analyzed can include, but are not limited to, ICAM-1 (rodent), CGRP (rodent), TIMP-1 (rodent), CLR-1 (rodent), HSP-27 (rodent), FABP (rodent), or apolipoprotein D (rodent), or any combination thereof and can be used as specific biomarkers from a vesicle for CNP. The protein, ligand, or peptide that can be assessed in a vesicle can include, but is not limited to, chemokines, chemokine receptors (CCR2/4), or any combination thereof.

The invention also provides an isolated vesicle comprising one or more chronic neuropathic pain specific biomarkers, such as listed in FIG. 45 and in FIG. 1 for chronic neuropathic pain. A composition comprising the isolated vesicle is also provided. Accordingly, in some embodiments, the composition comprises a population of vesicles comprising one or more chronic neuropathic pain specific biomarkers, such as listed in FIG. 45 and in FIG. 1 for chronic neuropathic pain. The composition can comprise a substantially enriched population of vesicles, wherein the population of vesicles is substantially homogeneous for chronic neuropathic pain specific vesicles or vesicles comprising one or more chronic neuropathic pain specific biomarkers, such as listed in FIG. 45 and in FIG. 1 for chronic neuropathic pain.

One or more chronic neuropathic pain specific biomarkers, such as listed in FIG. 45 and in FIG. 1 for chronic neuropathic pain, can also be detected by one or more systems disclosed herein, for characterizing a chronic neuropathic pain. For example, a detection system can comprise one or more probes to detect one or more chronic neuropathic pain specific biomarkers, such as listed in FIG. 45 and in FIG. 1 for chronic neuropathic pain, of one or more vesicles of a biological sample.

Peripheral Neuropathic Pain

Peripheral neuropathic pain (PNP) specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 46, and can be used to create a PNP specific biosignature. For example, the protein, ligand, or peptide that can be assessed in a vesicle can include, but is not limited to, OX42, ED9, or any combination thereof.

The invention also provides an isolated vesicle comprising one or more peripheral neuropathic pain specific biomarkers, such as listed in FIG. 46 and in FIG. 1 for peripheral neuropathic pain. A composition comprising the isolated vesicle is also provided. Accordingly, in some embodiments, the composition comprises a population of vesicles comprising one or more peripheral neuropathic pain specific biomarkers, such as listed in FIG. 46 and in FIG. 1 for peripheral neuropathic pain. The composition can comprise a substantially enriched population of vesicles, wherein the population of vesicles is substantially homogeneous for peripheral neuropathic pain specific vesicles or vesicles comprising one or more peripheral neuropathic pain specific biomarkers, such as listed in FIG. 46 and in FIG. 1 for peripheral neuropathic pain.

One or more peripheral neuropathic pain specific biomarkers, such as listed in FIG. 46 and in FIG. 1 for peripheral neuropathic pain, can also be detected by one or more systems disclosed herein, for characterizing a peripheral neuropathic pain. For example, a detection system can comprise one or more probes to detect one or more peripheral neuropathic pain specific biomarkers, such as listed in FIG. 46 and in FIG. 1 for peripheral neuropathic pain, of one or more vesicles of a biological sample.

Schizophrenia

Schizophrenia specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 47, and can be used to create a schizophrenia specific biosignature. For example, the biosignature can comprise one or more overexpressed miRs, such as, but not limited to, miR-181b. The biosignature can also comprise one or more underexpressed miRs such as, but not limited to, miR-7, miR-24, miR-26b, miR-29b, miR-30b, miR-30e, miR-92, or miR-195, or any combination thereof.

The one or more mRNAs that may be analyzed can include, but are not limited to, IFITM3, SERPINA3, GLS, or ALDH7A1BASP1, or any combination thereof and can be used as specific biomarkers from a vesicle for schizophrenia. A biomarker mutation for schizophrenia that can be assessed in a vesicle includes, but is not limited to, a mutation of to DISC1, dysbindin, neuregulin-1, seratonin 2a receptor, NURR1,or any combination of mutations specific for schizophrenia.

The protein, ligand, or peptide that can be assessed in a vesicle can include, but is not limited to, ATP5B, ATP5H, ATP6V1B, DNM1, NDUFV2, NSF, PDHB, or any combination thereof.

The invention also provides an isolated vesicle comprising one or more schizophrenia specific biomarkers, such as listed in FIG. 47 and in FIG. 1 for schizophrenia. A composition comprising the isolated vesicle is also provided. Accordingly, in some embodiments, the composition comprises a population of vesicles comprising one or more schizophrenia specific biomarkers, such as listed in FIG. 47 and in FIG. 1 for schizophrenia. The composition can comprise a substantially enriched population of vesicles, wherein the population of vesicles is substantially homogeneous for schizophrenia specific vesicles or vesicles comprising one or more schizophrenia specific biomarkers, such as listed in FIG. 47 and in FIG. 1 for schizophrenia.

One or more schizophrenia specific biomarkers, such as listed in FIG. 47 and in FIG. 1 for schizophrenia, can also be detected by one or more systems disclosed herein, for characterizing a schizophrenia. For example, a detection system can comprise one or more probes to detect one or more schizophrenia specific biomarkers, such as listed in FIG. 47 and in FIG. 1 for schizophrenia, of one or more vesicles of a biological sample.

Bipolar Disease

Bipolar disease specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 48, and can be used to create a bipolar disease specific biosignature. For example, the one or more mRNAs that may be analyzed can include, but are not limited to, FGF2, ALDH7A1, AGXT2L1, AQP4, or PCNT2, or any combination thereof and can be used as specific biomarkers from a vesicle for bipolar disease. A biomarker mutation for bipolar disease that can be assessed in a vesicle includes, but is not limited to, a mutation of Dysbindin, DAOA/G30, DISC1, neuregulin-1, or any combination of mutations specific for bipolar disease.

The invention also provides an isolated vesicle comprising one or more bipolar disease specific biomarkers, such as listed in FIG. 48. A composition comprising the isolated vesicle is also provided. Accordingly, in some embodiments, the composition comprises a population of vesicles comprising one or more bipolar disease specific biomarkers, such as listed in FIG. 48. The composition can comprise a substantially enriched population of vesicles, wherein the population of vesicles is substantially homogeneous for bipolar disease specific vesicles or vesicles comprising one or more bipolar disease specific biomarkers, such as listed in FIG. 48.

One or more bipolar disease specific biomarkers, such as listed in FIG. 48, can also be detected by one or more systems disclosed herein, for characterizing a bipolar disease. For example, a detection system can comprise one or more probes to detect one or more bipolar disease specific biomarkers, such as listed in FIG. 48, of one or more vesicles of a biological sample.

Depression

Depression specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 49, and can be used to create a depression specific biosignature. For example, the one or more mRNAs that may be analyzed can include, but are not limited to, FGFR1, FGFR2, FGFR3, or AQP4, or any combination thereof can also be used as specific biomarkers from a vesicle for depression.

The invention also provides an isolated vesicle comprising one or more depression specific biomarkers, such as listed in FIG. 49. A composition comprising the isolated vesicle is also provided. Accordingly, in some embodiments, the composition comprises a population of vesicles comprising one or more depression specific biomarkers, such as listed in FIG. 49. The composition can comprise a substantially enriched population of vesicles, wherein the population of vesicles is substantially homogeneous for depression specific vesicles or vesicles comprising one or more depression specific biomarkers, such as listed in FIG. 49.

One or more depression specific biomarkers, such as listed in FIG. 49, can also be detected by one or more systems disclosed herein, for characterizing a depression. For example, a detection system can comprise one or more probes to detect one or more depression specific biomarkers, such as listed in FIG. 49, of one or more vesicles of a biological sample.

Gastrointestinal Stromal Tumor (GIST)

GIST specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 50, and can be used to create a GIST specific biosignature. For example, the one or more mRNAs that may be analyzed can include, but are not limited to, DOG-1, PKC-theta, KIT, GPR20, PRKCQ, KCNK3, KCNH2, SCG2, TNFRSF6B, or CD34, or any combination thereof and can be used as specific biomarkers from a vesicle for GIST.

A biomarker mutation for GIST that can be assessed in a vesicle includes, but is not limited to, a mutation of PKC-theta or any combination of mutations specific for GIST. The protein, ligand, or peptide that can be assessed in a vesicle can include, but is not limited to, PDGFRA, c-kit, or any combination thereof.

The invention also provides an isolated vesicle comprising one or more GIST specific biomarkers, such as listed in FIG. 50 and in FIG. 1 for GIST. A composition comprising the isolated vesicle is also provided. Accordingly, in some embodiments, the composition comprises a population of vesicles comprising one or more GIST specific biomarkers, such as listed in FIG. 50 and in FIG. 1 for GIST. The composition can comprise a substantially enriched population of vesicles, wherein the population of vesicles is substantially homogeneous for GIST specific vesicles or vesicles comprising one or more GIST specific biomarkers, such as listed in FIG. 50 and in FIG. 1 for GIST.

One or more GIST specific biomarkers, such as listed in FIG. 50 and in FIG. 1 for GIST, can also be detected by one or more systems disclosed herein, for characterizing a GIST. For example, a detection system can comprise one or more probes to detect one or more GIST specific biomarkers, such as listed in FIG. 50 and in FIG. 1 for GIST, of one or more vesicles of a biological sample.

Renal Cell Carcinoma

Renal cell carcinoma specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 51, and can be used to create a renal cell carcinoma specific biosignature. For example, the biosignature can also comprise one or more underexpressed miRs such as, but not limited to, miR-141, miR-200c, or any combination thereof. The one or more upregulated or overexpressed miRNA can be miR-28, miR-185, miR-27, miR-let-7f-2, or any combination thereof.

The one or more mRNAs that may be analyzed can include, but are not limited to, laminin receptor 1, betaig-h3, Galectin-1, a-2 Macroglobulin, Adipophilin, Angiopoietin 2, Caldesmon 1, Class II MHC-associated invariant chain (CD74), Collagen IV-al, Complement component, Complement component 3, Cytochrome P450, subfamily IIJ polypeptide 2, Delta sleep-inducing peptide, Fc g receptor IIIa (CD16), HLA-B, HLA-DRa, HLA-DRb, HLA-SB, IFN-induced transmembrane protein 3, IFN-induced transmembrane protein 1, or Lysyl Oxidase, or any combination thereof and can be used as specific biomarkers from a vesicle for renal cell carcinoma.

A biomarker mutation for renal cell carcinoma that can be assessed in a vesicle includes, but is not limited to, a mutation of VHL or any combination of mutations specific renal cell carcinoma.

The protein, ligand, or peptide that can be assessed in a vesicle can include, but is not limited to, IF1alpha, VEGF, PDGFRA, or any combination thereof.

The invention also provides an isolated vesicle comprising one or more RCC specific biomarkers, such as ALPHA-TFEB, NONO-TFE3, PRCC-TFE3, SFPQ-TFE3, CLTC-TFE3, or MALAT1-TFEB, or those listed in FIG. 51 and in FIG. 1 for RCC. A composition comprising the isolated vesicle is also provided. Accordingly, in some embodiments, the composition comprises a population of vesicles comprising one or more RCC specific biomarkers, such as ALPHA-TFEB, NONO-TFE3, PRCC-TFE3, SFPQ-TFE3, CLTC-TFE3, or MALAT1-TFE, or those listed in FIG. 51 and in FIG. 1 for RCC. The composition can comprise a substantially enriched population of vesicles, wherein the population of vesicles is substantially homogeneous for RCC specific vesicles or vesicles comprising one or more RCC specific biomarkers, such as ALPHA-TFEB, NONO-TFE3, PRCC-TFE3, SFPQ-TFE3, CLTC-TFE3, or MALAT1-TFE, or those listed in FIG. 51 and in FIG. 1 for RCC.

One or more RCC specific biomarkers, such as ALPHA-TFEB, NONO-TFE3, PRCC-TFE3, SFPQ-TFE3, CLTC-TFE3, or MALAT1-TFE, or those listed in FIG. 51 and in FIG. 1 for RCC, can also be detected by one or more systems disclosed herein, for characterizing a RCC. For example, a detection system can comprise one or more probes to detect one or more RCC specific biomarkers, such as ALPHA-TFEB, NONO-TFE3, PRCC-TFE3, SFPQ-TFE3, CLTC-TFE3, or MALAT1-TFE, or those listed in FIG. 51 and in FIG. 1 for RCC, of one or more vesicles of a biological sample.

Cirrhosis

Cirrhosis specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 52, and can be used to create a cirrhosis specific biosignature. The one or more mRNAs that may be analyzed include, but are not limited to, NLT, which can be used as aspecific biomarker from a vesicle for cirrhosis.

The protein, ligand, or peptide that can be assessed in a vesicle can include, but is not limited to, NLT, HBsAG, AST, YKL-40, Hyaluronic acid, TIMP-1, alpha 2 macroglobulin, a-1-antitrypsin PIZ allele, haptoglobin, or acid phosphatase ACP AC, or any combination thereof.

The invention also provides an isolated vesicle comprising one or more cirrhosis specific biomarkers, such as those listed in FIG. 52 and in FIG. 1 for cirrhosis. A composition comprising the isolated vesicle is also provided. Accordingly, in some embodiments, the composition comprises a population of vesicles comprising one or more cirrhosis specific biomarkers, such as those listed in FIG. 52 and in FIG. 1 for cirrhosis. The composition can comprise a substantially enriched population of vesicles, wherein the population of vesicles is substantially homogeneous for cirrhosis specific vesicles or vesicles comprising one or more cirrhosis specific biomarkers, such as those listed in FIG. 52 and in FIG. 1 for cirrhosis.

One or more cirrhosis specific biomarkers, such as those listed in FIG. 52 and in FIG. 1 for cirrhosis, can also be detected by one or more systems disclosed herein, for characterizing cirrhosis. For example, a detection system can comprise one or more probes to detect one or more cirrhosis specific biomarkers, such as those listed in FIG. 52 and in FIG. 1 for cirrhosis, of one or more vesicles of a biological sample.

Esophageal Cancer

Esophageal cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 53, and can be used to create a esophageal cancer specific biosignature. For example, the biosignature can comprise one or more overexpressed miRs, such as, but not limited to, miR-192, miR-194, miR-21, miR-200c, miR-93, miR-342, miR-152, miR-93, miR-25, miR-424, or miR-151, or any combination thereof. The biosignature can also comprise one or more underexpressed miRs such as, but not limited to, miR-27b, miR-205, miR-203, miR-342, let-7c, miR-125b, miR-100, miR-152, miR-192, miR-194, miR-27b, miR-205, miR-203, miR-200c, miR-99a, miR-29c, miR-140, miR-103, or miR-107, or any combination thereof. The one or more mRNAs that may be analyzed include, but are not limited to, MTHFR and can be used as specific biomarkers from a vesicle for esophageal cancer.

The invention also provides an isolated vesicle comprising one or more esophageal cancer specific biomarkers, such as listed in FIG. 53 and in FIG. 1 for esophageal cancer. A composition comprising the isolated vesicle is also provided. Accordingly, in some embodiments, the composition comprises a population of vesicles comprising one or more esophageal cancer specific biomarkers, such as listed in FIG. 53 and in FIG. 1 for esophageal cancer. The composition can comprise a substantially enriched population of vesicles, wherein the population of vesicles is substantially homogeneous for esophageal cancer specific vesicles or vesicles comprising one or more esophageal cancer specific biomarkers, such as listed in FIG. 53 and in FIG. 1 for esophageal cancer.

One or more esophageal cancer specific biomarkers, such as listed in FIG. 53 and in FIG. 1 for esophageal cancer, can also be detected by one or more systems disclosed herein, for characterizing a esophageal cancer. For example, a detection system can comprise one or more probes to detect one or more esophageal cancer specific biomarkers, such as listed in FIG. 53 and in FIG. 1 for esophageal cancer, of one or more vesicles of a biological sample.

Gastric Cancer

Gastric cancer specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 54, and can be used to create a gastric cancer specific biosignature. For example, the biosignature can comprise one or more overexpressed miRs, such as, but not limited to, miR-106a, miR-21, miR-191, miR-223, miR-24-1, miR-24-2, miR-107, miR-92-2, miR-214, miR-25, or miR-221, or any combination thereof. The biosignature can also comprise one or more underexpressed miRs such as, but not limited to, let-7a.

The one or more mRNAs that may be analyzed include, but are not limited to, RRM2, EphA4, or survivin, or any combination thereof and can be used as specific biomarkers from a vesicle for gastric cancer. A biomarker mutation for gastric cancer that can be assessed in a vesicle includes, but is not limited to, a mutation of APC or any combination of mutations specific for gastric cancer. The protein, ligand, or peptide that can be assessed in a vesicle can include, but is not limited to EphA4.

The invention also provides an isolated vesicle comprising one or more gastric cancer specific biomarkers, such as listed in FIG. 54. A composition comprising the isolated vesicle is also provided. Accordingly, in some embodiments, the composition comprises a population of vesicles comprising one or more gastric cancer specific biomarkers, such as listed in FIG. 54. The composition can comprise a substantially enriched population of vesicles, wherein the population of vesicles is substantially homogeneous for gastric cancer specific vesicles or vesicles comprising one or more gastric cancer specific biomarkers, such as listed in FIG. 54.

One or more gastric cancer specific biomarkers, such as listed in FIG. 54, can also be detected by one or more systems disclosed herein, for characterizing a gastric cancer. For example, a detection system can comprise one or more probes to detect one or more gastric cancer specific biomarkers, such as listed in FIG. 54, of one or more vesicles of a biological sample.

Autism

Autism specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 55, and can be used to create an autism specific biosignature. For example, the biosignature can comprise one or more overexpressed miRs, such as, but not limited to, miR-484, miR-21, miR-212, miR-23a, miR-598, miR-95, miR-129, miR-431, miR-7, miR-15a, miR-27a, miR-15b, miR-148b, miR-132, or miR-128, or any combination thereof. The biosignature can also comprise one or more underexpressed miRs such as, but not limited to, miR-93, miR-106a, miR-539, miR-652, miR-550, miR-432, miR-193b, miR-181d, miR-146b, miR-140, miR-381, miR-320a, or miR-106b, or any combination thereof. The protein, ligand, or peptide that can be assessed in a vesicle can include, but is not limited to, GM1, GD1a, GD1b, or GT1b, or any combination thereof.

The invention also provides an isolated vesicle comprising one or more autism specific biomarkers, such as listed in FIG. 55 and in FIG. 1 for autism. A composition comprising the isolated vesicle is also provided. Accordingly, in some embodiments, the composition comprises a population of vesicles comprising one or more autism specific biomarkers, such as listed in FIG. 55 and in FIG. 1 for autism. The composition can comprise a substantially enriched population of vesicles, wherein the population of vesicles is substantially homogeneous for autism specific vesicles or vesicles comprising one or more autism specific biomarkers, such as listed in FIG. 55 and in FIG. 1 for autism.

One or more autism specific biomarkers, such as listed in FIG. 55 and in FIG. 1 for autism, can also be detected by one or more systems disclosed herein, for characterizing a autism. For example, a detection system can comprise one or more probes to detect one or more autism specific biomarkers, such as listed in FIG. 55 and in FIG. 1 for autism, of one or more vesicles of a biological sample.

Organ Rejection

Organ rejection specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 56, and can be used to create an organ rejection specific biosignature. For example, the biosignature can comprise one or more overexpressed miRs, such as, but not limited to, miR-658, miR-125a, miR-320, miR-381, miR-628, miR-602, miR-629, or miR-125a, or any combination thereof. The biosignature can also comprise one or more underexpressed miRs such as, but not limited to, miR-324-3p, miR-611, miR-654, miR-330_MM1, miR-524, miR-17-3p_MM1, miR-483, miR-663, miR-516-5p, miR-326, miR-197_MM2, or miR-346, or any combination thereof. The protein, ligand, or peptide that can be assessed in a vesicle can include, but is not limited to, matix metalloprotein-9, proteinase 3, or HNP, or any combinations thereof. The biomarker can be a member of the matrix metalloproteinases.

The invention also provides an isolated vesicle comprising one or more organ rejection specific biomarkers, such as listed in FIG. 56. A composition comprising the isolated vesicle is also provided. Accordingly, in some embodiments, the composition comprises a population of vesicles comprising one or more organ rejection specific biomarkers, such as listed in FIG. 56. The composition can comprise a substantially enriched population of vesicles, wherein the population of vesicles is substantially homogeneous for organ rejection specific vesicles or vesicles comprising one or more organ rejection specific biomarkers, such as listed in FIG. 56.

One or more organ rejection specific biomarkers, such as listed in FIG. 56, can also be detected by one or more systems disclosed herein, for characterizing a organ rejection. For example, a detection system can comprise one or more probes to detect one or more organ rejection specific biomarkers, such as listed in FIG. 56, of one or more vesicles of a biological sample.

Methicillin-Resistant *Staphylococcus aureus*

Methicillin-resistant *Staphylococcus aureus* specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 57, and can be used to create a methicillin-resistant *Staphylococcus aureus* specific biosignature.

The one or more mRNAs that may be analyzed include, but are not limited to, TSST-1 which can be used as a specific biomarker from a vesicle for methicillin-resistant *Staphylococcus aureus*. A biomarker mutation for methicillin-resistant *Staphylococcus aureus* that can be assessed in a vesicle includes, but is not limited to, a mutation of mecA, Protein A SNPs, or any combination of mutations specific for methicillin-resistant *Staphylococcus aureus*. The protein, ligand, or peptide that can be assessed in a vesicle can include, but is not limited to, ETA, ETB, TSST-1, or leukocidins, or any combination thereof.

The invention also provides an isolated vesicle comprising one or more methicillin-resistant *Staphylococcus aureus* specific biomarkers, such as listed in FIG. 57. A composition comprising the isolated vesicle is also provided. Accordingly, in some embodiments, the composition comprises a population of vesicles comprising one or more methicillin-resistant *Staphylococcus aureus* specific biomarkers, such as listed in FIG. 57. The composition can comprise a substantially enriched population of vesicles, wherein the population of vesicles is substantially homogeneous for methicillin-resistant *Staphylococcus aureus* specific vesicles or vesicles comprising one or more methicillin-resistant *Staphylococcus aureus* specific biomarkers, such as listed in FIG. 57.

One or more methicillin-resistant *Staphylococcus aureus* specific biomarkers, such as listed in FIG. 57, can also be detected by one or more systems disclosed herein, for characterizing a methicillin-resistant *Staphylococcus aureus*. For example, a detection system can comprise one or more probes to detect one or more methicillin-resistant *Staphylococcus aureus* specific biomarkers, such as listed in FIG. 57, of one or more vesicles of a biological sample.

Vulnerable Plaque

Vulnerable plaque specific biomarkers from a vesicle can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 58, and can be used to create a vulnerable plaque specific biosignature. The protein, ligand, or peptide that can be assessed in a vesicle can include, but is not limited to, IL-6, MMP-9, PAPP-A, D-dimer, fibrinogen, Lp-PLA2, SCD40L, Il-18, oxLDL, GPx-1, MCP-1, PIGF, or CRP, or any combination thereof.

The invention also provides an isolated vesicle comprising one or more vulnerable plaque specific biomarkers, such as listed in FIG. 58 and in FIG. 1 for vulnerable plaque. A composition comprising the isolated vesicle is also provided. Accordingly, in some embodiments, the composition comprises a population of vesicles comprising one or more vulnerable plaque specific biomarkers, such as listed in FIG. 58 and in FIG. 1 for vulnerable plaque. The composition can comprise a substantially enriched population of vesicles, wherein the population of vesicles is substantially homogeneous for vulnerable plaque specific vesicles or vesicles comprising one or more vulnerable plaque specific biomarkers, such as listed in FIG. 58 and in FIG. 1 for vulnerable plaque.

One or more vulnerable plaque specific biomarkers, such as listed in FIG. 58 and in FIG. 1 for vulnerable plaque, can also be detected by one or more systems disclosed herein, for characterizing a vulnerable plaque. For example, a detection system can comprise one or more probes to detect one or more vulnerable plaque specific biomarkers, such as listed in FIG. 58 and in FIG. 1 for vulnerable plaque, of one or more vesicles of a biological sample.

Autoimmune Disease

The invention also provides an isolated vesicle comprising one or more autoimmune disease specific biomarkers, such as listed in FIG. 1 for autoimmune disease. A composition comprising the isolated vesicle is also provided. Accordingly, in some embodiments, the composition comprises a population of vesicles comprising one or more autoimmune disease specific biomarkers, such as listed in FIG. 1 for autoimmune disease. The composition can comprise a substantially enriched population of vesicles, wherein the population of vesicles is substantially homogeneous for autoimmune disease specific vesicles or vesicles comprising one or more autoimmune disease specific biomarkers, such as listed in FIG. 1 for autoimmune disease.

One or more autoimmune disease specific biomarkers, such as listed in FIG. 1 for autoimmune disease, can also be detected by one or more systems disclosed herein, for characterizing a autoimmune disease. For example, a detection system can comprise one or more probes to detect one or more autoimmune disease specific biomarkers, such as listed in FIG. 1 for autoimmune disease, of one or more vesicles of a biological sample.

Tuberculosis (TB)

The invention also provides an isolated vesicle comprising one or more TB disease specific biomarkers, such as listed in FIG. 1 for TB disease. A composition comprising the isolated vesicle is also provided. Accordingly, in some embodiments, the composition comprises a population of vesicles comprising one or more TB disease specific biomarkers, such as listed in FIG. 1 for TB disease. The composition can comprise a substantially enriched population of vesicles, wherein the population of vesicles is substantially homogeneous for TB disease specific vesicles or vesicles comprising one or more TB disease specific biomarkers, such as listed in FIG. 1 for TB disease.

One or more TB disease specific biomarkers, such as listed in FIG. 1 for TB disease, can also be detected by one or more systems disclosed herein, for characterizing a TB disease. For example, a detection system can comprise one or more probes to detect one or more TB disease specific biomarkers, such as listed in FIG. 1 for TB disease, of one or more vesicles of a biological sample.

HIV

The invention also provides an isolated vesicle comprising one or more HIV disease specific biomarkers, such as listed in FIG. 1 for HIV disease. A composition comprising the isolated vesicle is also provided. Accordingly, in some embodiments, the composition comprises a population of vesicles comprising one or more HIV disease specific biomarkers, such as listed in FIG. 1 for HIV disease. The composition can comprise a substantially enriched population of vesicles, wherein the population of vesicles is substantially homogeneous for HIV disease specific vesicles or vesicles comprising one or more HIV disease specific biomarkers, such as listed in FIG. 1 for HIV disease.

One or more HIV disease specific biomarkers, such as listed in FIG. 1 for HIV disease, can also be detected by one or more systems disclosed herein, for characterizing a HIV disease. For example, a detection system can comprise one or more probes to detect one or more HIV disease specific biomarkers, such as listed in FIG. 1 for HIV disease, of one or more vesicles of a biological sample.

The one or more biomarker can also be a miRNA, such as an upregulated or overexpressed miRNA. The upregulated miRNA can be miR-29a, miR-29b, miR-149, miR-378 or miR-324-5p. One or more biomarkers can also be used to characterize HIV-1 latency, such as by assessing one or more miRNAs. The miRNA can be miR-28, miR-125b, miR-150, miR-223 and miR-382, and upregulated.

Asthma

The invention also provides an isolated vesicle comprising one or more asthma disease specific biomarkers, such as listed in FIG. 1 for asthma disease. A composition comprising the isolated vesicle is also provided. Accordingly, in some embodiments, the composition comprises a population of vesicles comprising one or more asthma disease specific biomarkers, such as listed in FIG. 1 for asthma disease. The composition can comprise a substantially enriched population of vesicles, wherein the population of vesicles is substantially homogeneous for asthma disease specific vesicles or vesicles comprising one or more asthma disease specific biomarkers, such as listed in FIG. 1 for asthma disease.

One or more asthma disease specific biomarkers, such as listed in FIG. 1 for asthma disease, can also be detected by one or more systems disclosed herein, for characterizing a asthma disease. For example, a detection system can comprise one or more probes to detect one or more asthma disease specific biomarkers, such as listed in FIG. 1 for asthma disease, of one or more vesicles of a biological sample.

Lupus

The invention also provides an isolated vesicle comprising one or more lupus disease specific biomarkers, such as listed in FIG. 1 for lupus disease. A composition comprising the isolated vesicle is also provided. Accordingly, in some embodiments, the composition comprises a population of vesicles comprising one or more lupus disease specific biomarkers, such as listed in FIG. 1 for lupus disease. The composition can comprise a substantially enriched population of vesicles, wherein the population of vesicles is substantially homogeneous for lupus disease specific vesicles or vesicles comprising one or more lupus disease specific biomarkers, such as listed in FIG. 1 for lupus disease.

One or more lupus disease specific biomarkers, such as listed in FIG. 1 for lupus disease, can also be detected by one or more systems disclosed herein, for characterizing a lupus disease. For example, a detection system can comprise one or more probes to detect one or more lupus disease specific biomarkers, such as listed in FIG. 1 for lupus disease, of one or more vesicles of a biological sample.

Influenza

The invention also provides an isolated vesicle comprising one or more influenza disease specific biomarkers, such as listed in FIG. 1 for influenza disease. A composition comprising the isolated vesicle is also provided. Accordingly, in some embodiments, the composition comprises a population of vesicles comprising one or more influenza disease specific biomarkers, such as listed in FIG. 1 for influenza disease. The composition can comprise a substantially enriched population of vesicles, wherein the population of vesicles is substantially homogeneous for influenza disease specific vesicles or vesicles comprising one or more influenza disease specific biomarkers, such as listed in FIG. 1 for influenza disease.

One or more influenza disease specific biomarkers, such as listed in FIG. 1 for influenza disease, can also be detected by one or more systems disclosed herein, for characterizing a influenza disease. For example, a detection system can comprise one or more probes to detect one or more influenza disease specific biomarkers, such as listed in FIG. 1 for influenza disease, of one or more vesicles of a biological sample.

Thyroid Cancer

The invention also provides an isolated vesicle comprising one or more thyroid cancer specific biomarkers, such as AKAP9-BRAF, CCDC6-RET, ERC1-RETM, GOLGA5-RET, HOOK3-RET, HRH4-RET, KTN1-RET, NCOA4-RET, PCM1-RET, PRKARA1A-RET, RFG-RET, RFG9-RET, Ria-RET, TGF-NTRK1, TPM3-NTRK1, TPM3-TPR, TPR-MET, TPR-NTRK1, TRIM24-RET, TRIM27-RET or TRIM33-RET, characteristic of papillary thyroid carcinoma; or PAX8-PPARy, characteristic of follicular thyroid cancer. A composition comprising the isolated vesicle is also provided. Accordingly, in some embodiments, the composition comprises a population of vesicles comprising one or more thyroid cancer specific biomarkers, such as listed in FIG. 1 for thyroid cancer. The composition can comprise a substantially enriched population of vesicles, wherein the population of vesicles is substantially homogeneous for thyroid cancer specific vesicles or vesicles comprising one or more thyroid cancer specific biomarkers, such as listed in FIG. 1 for thyroid cancer.

One or more thyroid cancer specific biomarkers, such as listed in FIG. 1 for thyroid cancer, can also be detected by one or more systems disclosed herein, for characterizing a thyroid cancer. For example, a detection system can comprise one or more probes to detect one or more thyroid cancer specific biomarkers, such as listed in FIG. 1 for thyroid cancer, of one or more vesicles of a biological sample.

Gene Fusions

The one or more biomarkers assessed of vesicle, can be a gene fusion, such as one or more listed in FIG. 59. A fusion gene is a hybrid gene created by the juxtaposition of two previously separate genes. This can occur by chromosomal translocation or inversion, deletion or via trans-splicing. The resulting fusion gene can cause abnormal temporal and spatial expression of genes, such as leading to abnormal expression of cell growth factors, angiogenesis factors, tumor promoters or other factors contributing to the neoplastic transformation of the cell and the creation of a tumor. Such fusion genes can be oncogenic due to the juxtaposition of: 1) a strong promoter region of one gene next to the coding region of a cell growth factor, tumor promoter or other gene promoting oncogenesis leading to elevated gene expression, or 2) due to the fusion of coding regions of two different genes, giving rise to a chimeric gene and thus a chimeric protein with abnormal activity.

An example of a fusion gene is BCR-ABL, a characteristic molecular aberration in ~90% of chronic myelogenous leukemia (CML) and in a subset of acute leukemias (Kurzrock et al., *Annals of Internal Medicine* 2003; 138(10):819-830). The BCR-ABL results from a translocation between chromosomes 9 and 22. The translocation brings together the 5' region of the BCR gene and the 3' region of ABL1, generating a chimeric BCR-ABL1 gene, which encodes a protein with constitutively active tyrosine kinase activity (Mittleman et al., Nature *Reviews Cancer* 2007; 7(4):233-245). The aberrant tyrosine kinase activity leads to de-regulated cell signaling, cell growth and cell survival, apoptosis resistance and growth factor independence, all of which contribute to the pathophysiology of leukemia (Kurzrock et al., *Annals of Internal Medicine* 2003; 138(10):819-830).

Another fusion gene is IGH-MYC, a defining feature of ~80% of Burkitt's lymphoma (Ferry et al. *Oncologist* 2006; 11(4):375-83). The causal event for this is a translocation between chromosomes 8 and 14, bringing the c-Myc oncogene adjacent to the strong promoter of the immunoglobin heavy chain gene, causing c-myc overexpression (Mittleman et al., *Nature Reviews Cancer* 2007; 7(4):233-245). The c-myc rearrangement is a pivotal event in lymphomagenesis as it results in a perpetually proliferative state. It has wide ranging effects on progression through the cell cycle, cellular differentiation, apoptosis, and cell adhesion (Ferry et al. *Oncologist* 2006; 11(4):375-83).

A number of recurrent fusion genes have been catalogued in the Mittleman database (cgap.nci.nih.gov/Chromosomes/Mitelman) and can be assessed in a vesicle, and used to characterize a phenotype. The gene fusion can be used to characterize a hematological malignancy or epithelial tumor. For example, TMPRSS2-ERG, TMPRSS2-ETV and SLC45A3-ELK4 fusions can be detected and used to characterize prostate cancer; and ETV6-NTRK3 and ODZ4-NRG1 for breast cancer.

Furthermore, assessing the presence or absence, or expression level of a fusion gene can be used to diagnosis a phenotype such as a cancer as well as a monitoring a therapeutic response to selecting a treatment. For example, the presence of the BCR-ABL fusion gene is a characteristic not only for the diagnosis of CML, but is also the target of the Novartis drug Imatinib mesylate (Gleevec), a receptor tyrosine kinase inhibitor, for the treatment of CML. Imatinib treatment has led to molecular responses (disappearance of BCR-ABL+ blood cells) and improved progression-free survival in BCR-ABL+CML patients (Kantarjian et al., *Clinical Cancer Research* 2007; 13(4): 1089-1097).

Assessing a vesicle for the presence, absence, or expression level of a gene fusion can be of by assessing a heterogeneous population of vesicles for the presence, absence, or expression level of a gene fusion. Alternatively, the vesicle that is assessed can be derived from a specific cell type, such as cell-of-origin specific vesicle, as described above. Illustrative examples of use of fusions that can be assessed to characterize a phenotype include the following:

Breast Cancer

To characterize a breast cancer, a vesicle can be assessed for one or more breast cancer specific fusions, including, but not limited to, ETV6-NTRK3. The vesicle can be derived from a breast cancer cell.

Lung Cancer

To characterize a lung cancer, a vesicle can be assessed for one or more lung cancer specific fusions, including, but not limited to, RLF-MYCL1, TGF-ALK, or CD74-ROS1. The vesicle can be derived from a lung cancer cell.

Prostate Cancer

To characterize a prostate cancer, a vesicle can be assessed for one or more prostate cancer specific fusions, including, but not limited to, ACSL3-ETV1, C15ORF21-ETV1, FLJ35294-ETV1, HERV-ETV1,TMPRSS2-ERG, TMPRSS2-ETV1/4/5, TMPRSS2-ETV4/5, SLC5A3-ERG, SLC5A3-ETV1, SLC5A3-ETV5 or KLK2-ETV4. The vesicle can be derived from a prostate cancer cell.

Brain Cancer

To characterize a brain cancer, a vesicle can be assessed for one or more brain cancer specific fusions, including, but not limited to, GOPC-ROS1. The vesicle can be derived from a brain cancer cell.

Head and Neck Cancer

To characterize a head and neck cancer, a vesicle can be assessed for one or more head and neck cancer specific fusions, including, but not limited to, CHCHD7-PLAG1, CTNNB1-PLAG1, FHIT-HMGA2, HMGA2-NFIB, LIFR-PLAG1, or TCEA1-PLAG1. The vesicle can be derived from a head and/or neck cancer cell.

Renal Cell Carcinoma (RCC)

To characterize a RCC, a vesicle can be assessed for one or more RCC specific fusions, including, but not limited to, ALPHA-TFEB, NONO-TFE3, PRCC-TFE3, SFPQ-TFE3, CLTC-TFE3, or MALAT1-TFEB. The vesicle can be derived from a RCC cell.

Thyroid Cancer

To characterize a thyroid cancer, a vesicle can be assessed for one or more thyroid cancer specific fusions, including, but not limited to, AKAP9-BRAF, CCDC6-RET, ERC1-RETM, GOLGA5-RET, HOOK3-RET, HRH4-RET, KTN1-RET, NCOA4-RET, PCM1-RET, PRKARA1A-RET, RFG-RET, RFG9-RET, Ria-RET, TGF-NTRK1, TPM3-NTRK1, TPM3-TPR, TPR-MET, TPR-NTRK1, TRIM24-RET, TRIM27-RET or TRIM33-RET, characteristic of papillary thyroid carcinoma; or PAX8-PPARy, characteristic of follicular thyroid cancer. The vesicle can be derived from a thyroid cancer cell.

Blood Cancers

To characterize a blood cancer, a vesicle can be assessed for one or more blood cancer specific fusions, including, but not limited to, TTL-ETV6, CDK6-MLL, CDK6-TLX3, ETV6-FLT3, ETV6-RUNX1, ETV6-TTL, MLL-AFF1, MLL-AFF3, MLL-AFF4, MLL-GAS7, TCBA1-ETV6, TCF3-PBX1 or TCF3-TFPT, characteristic of acute lymphocytic leukemia (ALL); BCLI1B-TLX3, IL2-TNFRFS17, NUP214-ABL1, NUP98-CCDC28A, TAL1-STIL, or ETV6-ABL2, characteristic of T-cell acute lymphocytic leukemia (T-ALL); ATIC-ALK, KIAA1618-ALK, MSN-ALK, MYH9-ALK, NPM1-ALK, TGF-ALK or TPM3-ALK, characteristic of anaplastic large cell lymphoma (ALCL); BCR-ABL1, BCR-JAK2, ETV6-EVI1, ETV6-MN1 or ETV6-TCBA1, characteristic of chronic myelogenous leukemia (CML); CBFB-MYH11, CHIC2-ETV6, ETV6-ABL1, ETV6-ABL2, ETV6-ARNT, ETV6-CDX2, ETV6-HLXB9, ETV6-PER1, MEF2D-DAZAPI, AML-AFF1, MLL-ARHGAP26, MLL-ARHGEF12, MLL-CASC5, MLL-CBL, MLL-CREBBP, MLL-DAB21P, MLL-ELL, MLL-EP300, MLL-EPS15, MLL-FNBP1, MLL-FOXO3A, MLL-GMPS, MLL-GPHN, MLL-MLLT1, MLL-MLLT11, MLL-MLLT3, MLL-MLLT6, MLL-MYOIF, MLL-PICALM, MLL-SEPT2, MLL-SEPT6, MLL-SORBS2, MYST3-SORBS2, MYST-CREBBP, NPM1-MLF1, NUP98-HOXA13, PRDM16-EVI1, RABEP1-PDGFRB, RUNX1-EVI1, RUNX1-MDS1, RUNX1-RPL22, RUNX1-RUNX1T1, RUNX1-SH3D19, RUNX1-USP42, RUNX1-YTHDF2, RUNX1-ZNF687, or TAF15-ZNF-384, characteristic of AML; CCND1-FSTL3, characteristic of chronic lymphocytic leukemia (CLL); BCL3-MYC, MYC-BTG1, BCL7A-MYC, BRWD3-ARHGAP20 or BTG1-MYC, characteristic of B-cell chronic lymphocytic leukemia (B-CLL); CITTA-BCL6, CLTC-ALK, IL21R-BCL6, PIM1-BCL6, TFCR-BCL6, IKZF1-BCL6 or SEC31A-ALK, characteristic of diffuse large B-cell lymphomas (DLBCL); FLIP1-PDGFRA, FLT3-ETV6, KIAA1509-PDGFRA, PDE4DIP-PDGFRB, NIN-PDGFRB, TP53BP1-PDGFRB, or TPM3-PDGFRB, characteristic of hyper eosinophilia/chronic eosinophilia; IGH-MYC or LCP1-BCL6, characteristic of Burkitt's lymphoma. The vesicle can be derived from a blood cancer cell.

The invention also provides an isolated vesicle comprising one or more gene fusions as disclosed herein, such as listed in FIG. 59. A composition comprising the isolated vesicle is also provided. Accordingly, in some embodiments, the composition comprises a population of vesicles comprising one or more gene fusions, such as listed in FIG. 59. The composition can comprise a substantially enriched population of vesicles, wherein the population of vesicles is substantially homogeneous for vesicles comprising one or more gene fusions, such as listed in FIG. 59.

Also provided herein is a detection system for detecting one or more gene fusions, such as gene fusions listed in FIG. 59. For example, a detection system can comprise one or more probes to detect one or more gene fusions listed in FIG. 59. Detection of the one or more gene fusions can be used to charcaterize a cancer.

Gene-Associated MiRNA Biomarkers

The one or more biomarkers assessed can also include one or more genes selected from the group consisting of PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, and TOP2B. The microRNA that interacts with the one or more genes can also be a biomarker (see for example, FIG. 60). Furthermore, the one or more biomarkers can be used to characterize prostate cancer.

The invention also provides an isolated vesicle comprising one or more one or more biomarkers consisting of PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, and TOP2B; or the microRNA that interacts with the one or more genes (see for example, FIG. 60). The invention further provides a composition comprising the isolated vesicle. Accordingly, in some embodiments, the composition comprises a population of vesicles comprising one or more biomarkers consisting of PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, and TOP2B; or the microRNA that interacts with the one or more genes, such as listed in FIG. 60. The composition can comprise a substantially enriched population of vesicles, wherein the population of vesicles is substantially homogeneous for vesicles comprising one or more biomarkers consisting of PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, and TOP2B; or the microRNA that interacts with the one or more genes, such as listed in FIG. 60.

One or more prostate cancer specific biomarkers, such as listed in FIG. 60 can also be detected by one or more systems disclosed herein. For example, a detection system can comprise one or more probes to detect one or more prostate cancer specific biomarkers, such as listed in FIG. 60, of one or more vesicles of a biological sample.

The miRNA that interacts with PFKFB3 can be miR-513a-3p, miR-128, miR-488, miR-539, miR-658, miR-524-5p, miR-1258, miR-150, miR-216b, miR-377, miR-135a, miR-26a, miR-548a-5p, miR-26b, miR-520d-5p, miR-224, miR-1297, miR-1197, miR-182, miR-452, miR-509-3-5p, miR-548m, miR-625, miR-509-5p, miR-1266, miR-135b, miR-190b, miR-496, miR-616, miR-621, miR-650, miR-105, miR-19a, miR-346, miR-620, miR-637, miR-651, miR-1283, miR-590-3p, miR-942, miR-1185, miR-577, miR-602, miR-1305, miR-220c, miR-1270, miR-1282, miR-432, miR-491-5p, miR-548n, miR-765, miR-768-3p or miR-924, and can be used as a biomarker.

The invention also provides an isolated vesicle comprising one or more one or more miRNA that interacts with PFKFB3. Also provided herein is a composition comprising the isolated vesicle. Accordingly, in some embodiments, the composition comprises a population of vesicles comprising one or more biomarkers consisting of miRNA that interacts with PFKFB3. The composition can comprise a substantially enriched population of vesicles, wherein the population of vesicles is substantially homogeneous for vesicles comprising one or more miRNA that interacts with PFKFB3. Furthermore, the one or more miRNA that interacts with PFKFB3can also be detected by one or more systems disclosed herein. For example, a detection system can comprise one or more probes to detect one or more one or more miRNA that interacts with PFKFB3 of one or more vesicles of a biological sample.

The miRNA that interacts with RHAMM can be miR-936, miR-656, miR-105, miR-361-5p, miR-194, miR-374a, miR-590-3p, miR-186, miR-769-5p, miR-892a, miR-380, miR-875-3p, miR-208a, miR-208b, miR-586, miR-125a-3p, miR-630, miR-374b, miR-411, miR-629, miR-1286, miR-1185, miR-16, miR-200b, miR-671-5p, miR-95, miR-421, miR-496, miR-633, miR-1243, miR-127-5p, miR-143, miR-15b, miR-200c, miR-24 or miR-34c-3p.

The invention also provides an isolated vesicle comprising one or more one or more miRNA that interacts with RHAMM. The invention further provides a composition comprising the isolated vesicle. Accordingly, in some embodiments, the composition comprises a population of vesicles comprising one or more biomarkers consisting of miRNA that interacts with RHAMM. The composition can comprise a substantially enriched population of vesicles, wherein the population of vesicles is substantially homogeneous for vesicles comprising one or more miRNA that interacts with RHAMM. Furthermore, the one or more miRNA that interacts with RHAMM can also be detected by one or more systems disclosed herein. For example, a detection system can comprise one or more probes to detect one or more one or more miRNA that interacts with RHAMM of one or more vesicles of a biological sample.

The miRNA that interacts with CENPF can be miR-30c, miR-30b, miR-190, miR-508-3p, miR-384, miR-512-5p, miR-548p, miR-297, miR-520f, miR-376a, miR-1184, miR-577, miR-708, miR-205, miR-376b, miR-520g, miR-520h, miR-519d, miR-596, miR-768-3p, miR-340, miR-620, miR-539, miR-567, miR-671-5p, miR-1183, miR-129-3p, miR-636, miR-106a, miR-1301, miR-17, miR-20a, miR-570, miR-656, miR-1263, miR-1324, miR-142-5p, miR-28-5p, miR-302b, miR-452, miR-520d-3p, miR-548o, miR-892b, miR-302d, miR-875-3p, miR-106b, miR-1266, miR-1323, miR-20b, miR-221, miR-520e, miR-664, miR-920, miR-922, miR-93, miR-1228, miR-1271, miR-30e, miR-483-3p, miR-509-3-5p, miR-515-3p, miR-519e, miR-520b, miR-520c-3p or miR-582-3p.

Also provided herein is a vesicle comprising one or more one or more miRNA that interacts with CENPF. The invention further provides a composition comprising the isolated vesicle. Accordingly, in some embodiments, the composition comprises a population of vesicles comprising one or more biomarkers consisting of miRNA that interacts with CENPF. The composition can comprise a substantially enriched population of vesicles, wherein the population of vesicles is substantially homogeneous for vesicles comprising one or more miRNA that interacts with CENPF. Furthermore, the one or more miRNA that interacts with CENPF can also be detected by one or more systems disclosed herein. For example, a detection system can comprise one or more probes to detect one or more one or more miRNA that interacts with CENPF of one or more vesicles of a biological sample.

The miRNA that interacts with NCAPG can be miR-876-5p, miR-1260, miR-1246, miR-548c-3p, miR-1224-3p, miR-619, miR-605, miR-490-5p, miR-186, miR-448, miR-129-5p, miR-188-3p, miR-516b, miR-342-3p, miR-1270, miR-548k, miR-654-3p, miR-1290, miR-656, miR-34b, miR-520 g, miR-1231, miR-1289, miR-1229, miR-23a, miR-23b, miR-616 or miR-620.

The invention also provides an isolated vesicle comprising one or more one or more miRNA that interacts with NCAPG. The invention further provides a composition comprising the isolated vesicle. Accordingly, in some embodiments, the composition comprises a population of vesicles comprising one or more biomarkers consisting of miRNA that interacts with NCAPG. The composition can comprise a substantially enriched population of vesicles, wherein the population of vesicles is substantially homogeneous for vesicles comprising one or more miRNA that interacts with NCAPG. Furthermore, the one or more miRNA that interacts with NCAPG can also be detected by one or more systems disclosed herein. For example, a detection system can comprise one or more probes to detect one or more one or more miRNA that interacts with NCAPG of one or more vesicles of a biological sample.

The miRNA that interacts with Androgen Receptor can be miR-124a, miR-130a, miR-130b, miR-143, miR-149, miR-194, miR-29b, miR-29c, miR-301, miR-30a-5p, miR-30d, miR-30e-5p, miR-337, miR-342, miR-368, miR-488, miR-493-5p, miR-506, miR-512-5p, miR-644, miR-768-5p or miR-801.

The miRNA that interacts with EGFR can be miR-105, miR-128a, miR-128b, miR-140, miR-141, miR-146a, miR-146b, miR-27a, miR-27b, miR-302a, miR-302d, miR-370, miR-548c, miR-574, miR-587 or miR-7.

The invention also provides an isolated vesicle, comprising one or more one or more miRNA that interacts with AR. The invention further provides a composition comprising the isolated vesicle. Accordingly, in some embodiments, the composition comprises a population of vesicles comprising one or more biomarkers consisting of miRNA that interacts with AR. The composition can comprise a substantially enriched population of vesicles, wherein the population of vesicles is substantially homogeneous for vesicles comprising one or more miRNA that interacts with AR. Furthermore, the one or more miRNA that interacts with AR can also be detected by one or more systems disclosed herein. For example, a detection system can comprise one or more probes to detect one or more one or more miRNA that interacts with AR of one or more vesicles of a biological sample.

The miRNA that interacts with HSP90 can be miR-1, miR-513a-3p, miR-548d-3p, miR-642, miR-206, miR-450b-3p, miR-152, miR-148a, miR-148b, miR-188-3p, miR-23a, miR-23b, miR-578, miR-653, miR-1206, miR-192, miR-215, miR-181b, miR-181d, miR-223, miR-613, miR-769-3p, miR-99a, miR-100, miR-454, miR-548n, miR-640, miR-99b, miR-150, miR-181a, miR-181c, miR-522, miR-624, miR-130a, miR-130b, miR-146, miR-148a, miR-148b, miR-152, miR-181a, miR-181b, miR-181c, miR-204, miR-206, miR-211, miR-212, miR-215, miR-223, miR-23a, miR-23b, miR-301, miR-31, miR-325, miR-363, miR-566, miR-9 or miR-99b.

The invention also provides an isolated vesicle, comprising one or more one or more miRNA that interacts with HSP90. The invention further provides a composition comprising the isolated vesicle. Accordingly, in some embodiments, the composition comprises a population of vesicles comprising one or more biomarkers consisting of miRNA that interacts with HSP90. The composition can comprise a substantially enriched population of vesicles, wherein the population of vesicles is substantially homogeneous for vesicles comprising one or more miRNA that interacts with HSP90. Furthermore, the one or more miRNA that interacts with HSP90 can also be detected by one or more systems disclosed herein. For example, a detection system can comprise one or more probes to detect one or more one or more miRNA that interacts with HSP90 of one or more vesicles of a biological sample.

The miRNA that interacts with SPARC can be miR-768-5p, miR-203, miR-196a, miR-569, miR-187, miR-641, miR-1275, miR-432, miR-622, miR-296-3p, miR-646, miR-196b, miR-499-5p, miR-590-5p, miR-495, miR-625, miR-1244, miR-512-5p, miR-1206, miR-1303, miR-186, miR-302d, miR-494, miR-562, miR-573, miR-10a, miR-203, miR-204, miR-211, miR-29, miR-29b, miR-29c, miR-339, miR-433, miR-452, miR-515-5p, miR-517a, miR-517b, miR-517c, miR-592 or miR-96.

The invention also provides an isolated vesicle comprising one or more one or more miRNA that interacts with SPARC. The invention further provides a composition comprising the isolated vesicle. Accordingly, in some embodiments, the composition comprises a population of vesicles comprising one or more biomarkers consisting of miRNA that interacts with SPARC. The composition can comprise a substantially enriched population of vesicles, wherein the population of vesicles is substantially homogeneous for vesicles comprising one or more miRNA that interacts with SPARC. Furthermore, the one or more miRNA that interacts with SPARC can also be detected by one or more systems disclosed herein. For example, a detection system can comprise one or more probes to detect one or more one or more miRNA that interacts with SPARC of one or more vesicles of a biological sample.

The miRNA that interacts with DNMT3B can be miR-618, miR-1253, miR-765, miR-561, miR-330-5p, miR-326, miR-188, miR-203, miR-221, miR-222, miR-26a, miR-26b, miR-29a, miR-29b, miR-29c, miR-370, miR-379, miR-429, miR-519e, miR-598, miR-618 or miR-635.

The invention also provides an isolated vesicle comprising one or more one or more miRNA that interacts with DNMT3B. The invention further provides a composition comprising the isolated vesicle. Accordingly, in some embodiments, the composition comprises a population of vesicles comprising one or more biomarkers consisting of miRNA that interacts with DNMT3B. The composition can comprise a substantially enriched population of vesicles, wherein the population of vesicles is substantially homogeneous for vesicles comprising one or more miRNA that interacts with DNMT3B. Furthermore, the one or more miRNA that interacts with DNMT3B can also be detected by one or more systems disclosed herein. For example, a detection system can comprise one or more probes to detect one or more one or more miRNA that interacts with DNMT3B of one or more vesicles of a biological sample.

The miRNA that interacts with GARTcan be miR-101, miR-141, miR-144, miR-182, miR-189, miR-199a, miR-199b, miR-200a, miR-200b, miR-202, miR-203, miR-223, miR-329, miR-383, miR-429, miR-433, miR-485-5p, miR-493-5p, miR-499, miR-519a, miR-519b, miR-519c, miR-569, miR-591, miR-607, miR-627, miR-635, miR-636 or miR-659.

The invention also provides an isolated vesicle comprising one or more one or more miRNA that interacts with GART. The invention further provides a composition comprising the isolated vesicle. Accordingly, in some embodiments, the composition comprises a population of vesicles comprising one or more biomarkers consisting of miRNA that interacts with GART. The composition can comprise a substantially enriched population of vesicles, wherein the population of vesicles is substantially homogeneous for vesicles comprising one or more miRNA that interacts with GART. Furthermore, the one or more miRNA that interacts with GART can also be detected by one or more systems disclosed herein. For example, a detection system can comprise one or more probes to detect one or more one or more miRNA that interacts with GART of one or more vesicles of a biological sample.

The miRNA that interacts with MGMT can be miR-122a, miR-142-3p, miR-17-3p, miR-181a, miR-181b, miR-181c, miR-181d, miR-199b, miR-200a, miR-217, miR-302b, miR-32, miR-324-3p, miR-34a, miR-371, miR-425-5p, miR-496, miR-514, miR-515-3p, miR-516-3p, miR-574, miR-597, miR-603, miR-653, miR-655, miR-92, miR-92b or miR-99a.

The invention also provides an isolated vesicle comprising one or more one or more miRNA that interacts with MGMT. The invention further provides a composition comprising the isolated vesicle. Accordingly, in some embodiments, the composition comprises a population of vesicles comprising one or more biomarkers consisting of miRNA that interacts with MGMT. The composition can comprise a substantially enriched population of vesicles, wherein the population of vesicles is substantially homogeneous for vesicles comprising one or more miRNA that interacts with MGMT. Furthermore, the one or more miRNA that interacts with MGMT can also be detected by one or more systems disclosed herein. For example, a detection system can comprise one or more probes to detect one or more one or more miRNA that interacts with MGMT of one or more vesicles of a biological sample.

The miRNA that interacts with SSTR3 can be miR-125a, miR-125b, miR-133a, miR-133b, miR-136, miR-150, miR-21, miR-380-5p, miR-504, miR-550, miR-671, miR-766 or miR-767-3p.

The invention also provides an isolated vesicle comprising one or more one or more miRNA that interacts with SSTR3. The invention further provides a composition comprising the isolated vesicle. Accordingly, in some embodiments, the composition comprises a population of vesicles comprising one or more biomarkers consisting of miRNA that interacts with SSTR3. The composition can comprise a substantially enriched population of vesicles, wherein the population of vesicles is substantially homogeneous for vesicles comprising one or more miRNA that interacts with SSTR3. Furthermore, the one or more miRNA that interacts with SSTR3 can also be detected by one or more systems disclosed herein. For example, a detection system can comprise one or more probes to detect one or more one or more miRNA that interacts with SSTR3 of one or more vesicles of a biological sample.

The miRNA that interacts with TOP2B can be miR-548f, miR-548a-3p, miR-548g, miR-513a-3p, miR-548c-3p, miR-101, miR-653, miR-548d-3p, miR-575, miR-297, miR-576-3p, miR-548b-3p, miR-624, miR-548n, miR-758, miR-1253, miR-1324, miR-23b, miR-320a, miR-320b, miR-1183, miR-1244, miR-23a, miR-451, miR-568, miR-1276, miR-548e, miR-590-3p, miR-1, miR-101, miR-126, miR-129, miR-136, miR-140, miR-141, miR-144, miR-147, miR-149, miR-18, miR-181b, miR-181c, miR-182, miR-184, miR-186, miR-189, miR-191, miR-19a, miR-19b, miR-200a, miR-206, miR-210, miR-218, miR-223, miR-23a, miR-23b, miR-24, miR-27a, miR-302, miR-30a, miR-31, miR-320, miR-323, miR-362, miR-374, miR-383, miR-409-3p, miR-451, miR-489, miR-493-3p, miR-514, miR-542-3p, miR-544, miR-548a, miR-548b, miR-548c, miR-548d, miR-559, miR-568, miR-575, miR-579, miR-585, miR-591, miR-598, miR-613, miR-649, miR-651, miR-758, miR-768-3p or miR-9.

Also provided herein is a vesicle comprising one or more one or more miRNA that interacts with TOP2B. The invention further provides a composition comprising the isolated vesicle. Accordingly, in some embodiments, the composition comprises a population of vesicles comprising one or more biomarkers consisting of miRNA that interacts with TOP2B. The composition can comprise a substantially enriched population of vesicles, wherein the population of vesicles is substantially homogeneous for vesicles comprising one or more miRNA that interacts with TOP2B. Furthermore, the one or more miRNA that interacts with TOP2B can also be detected by one or more systems disclosed herein. For example, a detection system can comprise one or more probes to detect one or more one or more miRNA that interacts with TOP2B of one or more vesicles of a biological sample.

Other MicroRNA Biomarkers

Other microRNAs that can be detected or assessed in a vesicle and used to characterize a phenotype include, but are not limited to, hsa-let-7a, hsa-let-7b, hsa-let-7c, hsa-let-7d, hsa-let-7e, hsa-let-7f, hsa-miR-15a, hsa-miR-16, hsa-miR-17-5p, hsa-miR-17-3p, hsa-miR-18a, hsa-miR-19a, hsa-miR-19b, hsa-miR-20a, hsa-miR-21, hsa-miR-22, hsa-miR-23a, hsa-miR-189, hsa-miR-24, hsa-miR-25, hsa-miR-26a, hsa-miR-26b, hsa-miR-27a, hsa-miR-28, hsa-miR-29a, hsa-miR-30a-5p, hsa-miR-30a-3p, hsa-miR-3I, hsa-miR-32, hsa-miR-33, hsa-miR-92, hsa-miR-93, hsa-miR-95, hsa-miR-96, hsa-miR-98, hsa-miR-99a, hsa-miR-100, hsa-miR-101, hsa-miR-29b, hsa-miR-103, hsa-miR-105, hsa-miR-106a, hsa-miR-107, hsa-miR-192, hsa-miR-196a, hsa-miR-197, hsa-miR-198, hsa-miR-199a, hsa-miR-199a*, hsa-miR-208, hsa-miR-129, hsa-miR-148a, hsa-miR-30c, hsa-miR-30d, hsa-miR-139, hsa-miR-147, hsa-miR-7, hsa-miR-10a, hsa-miR-10b, hsa-miR-34a, hsa-miR-181a, hsa-miR-181b, hsa-miR-181c, hsa-miR-182, hsa-miR-182*, hsa-miR-183, hsa-miR-187, hsa-miR-199b, hsa-miR-203, hsa-miR-204, hsa-miR-205, hsa-miR-210, hsa-miR-211, hsa-miR-212, hsa-miR-181a*, hsa-miR-214, hsa-miR-215, hsa-miR-216, hsa-miR-217, hsa-miR-218, hsa-miR-219, hsa-miR-220, hsa-miR-221, hsa-miR-222, hsa-miR-223, hsa-miR-224, hsa-miR- 200b, hsa-let-7g, hsa-let-7i, hsa-miR-1, hsa-miR-15b, hsa-miR-23b, hsa-miR-27b, hsa-miR-30b, hsa-miR-122a, hsa-miR-124a, hsa-miR-125b, hsa-miR-128 a, hsa-miR-130a, hsa-miR-132, hsa-miR-133a, hsa-miR-135a, hsa-miR-137, hsa-miR-138, hsa-miR-140, hsa-miR-141, hsa-miR-142-5p, hsa-miR-142-3p, hsa-miR-143, hsa-miR-144, hsa-miR-145, hsa-miR-152, hsa-miR-153, hsa-miR-191, hsa-miR-9, hsa-miR-9*, hsa-miR-125a, hsa-miR-126*, hsa-miR-126, hsa-miR-127, hsa-miR-134, hsa-miR-136, hsa-miR-146a, hsa-miR-149, hsa-miR-150, hsa-miR-154, hsa-miR-154*, hsa-miR-184, hsa-miR-185, hsa-miR-186, hsa-miR-188, hsa-miR-190, hsa-miR-193a, hsa-miR-194, hsa-miR-195, hsa-miR-206, hsa-miR-320, hsa-miR-200c, hsa-miR-155, hsa-miR-128b, hsa-miR-106b, hsa-miR-29 c, hsa-miR-200a, hsa-miR-302a*, hsa-miR-302a, hsa-miR-34b, hsa-miR-34c, hsa-miR-299-3p, hsa-miR-301, hsa-miR-99b, hsa-miR-296, hsa-miR-130b, hsa-miR-30e-5p, hsa-miR-30e-3p, hsa-miR-361, hsa-miR-362, hsa-miR-363, hsa-miR-365, hsa-mir-302b*, hsa-miR-302b, hsa-miR-302c*, hsa-miR-302c, hsa-miR-302 d, hsa-miR-367, hsa-miR-368, hsa-miR-369-3p, hsa-miR-370, hsa-miR-371, hsa-miR-372, hsa-miR-373*, hsa-miR-373, hsa-miR-374, hsa-miR-375, hsa-miR-376a, hsa-miR-377, hsa-miR-378, hsa-miR-422b, hsa-miR-379, hsa-miR-380-5p, hsa-miR-380-3p, hsa-miR-381, hsa-miR-382, hsa-miR-383, hsa-miR-340, hsa-miR-330, hsa-miR-328, hsa-miR-342, hsa-miR-337, hsa-miR-323, hsa-miR-326, hsa-miR-151, hsa-miR-135b, hsa-miR-148b, hsa-miR-331, hsa-miR-324-5p, hsa-miR-324-3p, hsa-miR-338, hsa-miR-339, hsa-miR-335, hsa-miR-133b, hsa-miR-325, hsa-miR-345, hsa-miR-346, ebv-miR-BHRF1-1, ebv-miR-BHRF1-2*, ebv-miR-BHRF1-2, ebv-miR-BHRF1-3, ebv-miR-BART1-5p, ebv-miR-BART2, hsa-miR-384, hsa-miR-196b, hsa-miR-422a, hsa-miR-423, hsa-miR-424, hsa-miR-425-3p, hsa-miR-18b, hsa-miR-20b, hsa-miR-448, hsa-miR-429, hsa-miR-449, hsa-miR-450, hcmv-miR-UL22A, hcmv-miR-UL22A*, hcmv-miR-UL36, hcmv-miR-UL112, hcmv-miR-ULI48D, hcmv-miR-US5-1, hcmv-miR-US5-2, hcmv-miR-US25-1, hcmv-miR-US25-2-5p, hcmv-miR-US25-2-3p, hcmv-miR-US33, hsa-miR-191*, hsa-miR-200a*, hsa-miR-369-5p, hsa-miR-431, hsa-miR-433, hsa-miR-329, hsa-miR-453, hsa-miR-451, hsa-miR-452, hsa-miR-452*, hsa-miR-409-5p, hsa-miR-409-3p, hsa-miR-412, hsa-miR-410, hsa-miR-376b, hsa-miR-483, hsa-miR-484, hsa-miR-485-5p, hsa-miR-485-3p, hsa-miR-486, hsa-miR-487a, kshv-miR-K12-10a, kshv-miR-K12-10b, kshv-miR-K12-11, kshv-miR-K12-1, kshv-miR-K12-2, kshv-miR-K12-9*, kshv-miR-K12-9, kshv-miR-K12-8, kshv-miR-K12-7, kshv-miR-K12-6-5p, kshv-miR-K12-6-3p, kshv-miR-K12-5, kshv-miR-K12-4-5p, kshv-miR-K12-4-3p, kshv-miR-K12-3, kshv-miR-K12-3*, hsa-miR-488, hsa-miR-489, hsa-miR-490, hsa-miR-491, hsa-miR-511, hsa-miR-146b, hsa-miR-202*, hsa-miR-202, hsa-miR-492, hsa-miR-493-5p, hsa-miR-432, hsa-miR-432*, hsa-miR-494, hsa-miR-495, hsa-miR-496, hsa-miR-193b, hsa-miR-497, hsa-miR-181d, hsa-miR-512-5p, hsa-miR-512-3p, hsa-miR-498, hsa-miR-520e, hsa-miR-515-5p, hsa-miR-515-3p, hsa-miR-519e*, hsa-miR-519e, hsa-miR-520f, hsa-miR-526c, hsa-miR-519c, hsa-miR-520a*, hsa-miR-520a, hsa-miR-526b, hsa-miR-526b*, hsa-miR-519b, hsa-miR-525, hsa-miR-525*, hsa-miR-523, hsa-miR-518f*, hsa-miR-518f, hsa-miR-520b, hsa-miR-518b, hsa-miR-526a, hsa-miR-520c, hsa-miR-518c*, hsa-miR-518c, hsa-miR-524*, hsa-miR-524, hsa-miR-517*, hsa-miR-517a, hsa-miR-519d, hsa-miR-521, hsa-miR-520d*, hsa-miR-520d, hsa-miR-517b, hsa-miR-520 g, hsa-miR-516-5p, hsa-miR-516-3p, hsa-miR-518e, hsa-miR-527, hsa-miR-518a, hsa-miR-518d, hsa-miR-517c, hsa-miR-520h, hsa-miR-522, hsa-miR-519a, hsa-miR-499, hsa-miR-500, hsa-miR-501, hsa-miR-502, hsa-miR-503, hsa-miR-504, hsa-miR-505, hsa-miR-513, hsa-miR-506, hsa-miR-507, hsa-miR-508, hsa-miR-509, hsa-miR-510, hsa-miR-514, hsa-miR-532, hsa-miR-299-5p, hsa-miR-18a*, hsa-miR-455, hsa-miR-493-3p, hsa-miR-539, hsa-miR-544, hsa-miR-545, hsa-miR-487b, hsa-miR-551a, hsa-miR-552, hsa-miR-553, hsa-miR-554, hsa-miR-92b, hsa-miR-555, hsa-miR-556, hsa-miR-557, hsa-miR-558, hsa-miR-559, hsa-miR-560, hsa-miR-561, hsa-miR-562, hsa-miR-563, hsa-miR-564, hsa-miR-565, hsa-miR-566, hsa-miR-567, hsa-miR-568, hsa-miR-551b, hsa-miR-569, hsa-miR-570, hsa-miR-571, hsa-miR-572, hsa-miR-573, hsa-miR-574, hsa-miR-575, hsa-miR-576, hsa-miR-577, hsa-miR-578, hsa-miR-579, hsa-miR-580, hsa-miR-581, hsa-miR-582, hsa-miR-583, hsa-miR-584, hsa-miR-585, hsa-miR-548a, hsa-miR-586, hsa-miR-587, hsa-miR-548b, hsa-miR-588, hsa-miR-589, hsa-miR-550, hsa-miR-590, hsa-miR-591, hsa-miR-592, hsa-miR-593, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615, hsa-miR-616, hsa-miR-548c, hsa-miR-617, hsa-miR-618, hsa-miR-619, hsa-miR-620, hsa-miR-621, hsa-miR-622, hsa-miR-623, hsa-miR-624, hsa-miR-625, hsa-miR-626, hsa-miR-627, hsa-miR-628, hsa-miR-629, hsa-miR-630, hsa-miR-631, hsa-miR-33b, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-548d, hsa-miR-661, hsa-miR-662, hsa-miR-663, hsa-miR-449b, hsa-miR-653, hsa-miR-411, hsa-miR-654, hsa-miR-655, hsa-miR-656, hsa-miR-549, hsa-miR-657, hsa-miR-658, hsa-miR-659, hsa-miR-660, hsa-miR-421, hsa-miR-542-5p, hcmv-miR-US4, hcmv-miR-UL70-5p, hcmv-miR-UL70-3p, hsa-miR-363*, hsa-miR-376a*, hsa-miR-542-3p, ebv-miR-BART1-3p, hsa-miR-425-5p, ebv-miR-BART3-5p, ebv-miR-BART3-3p, ebv-miR-BART4, ebv-miR-BART5, ebv-miR-BART6-5p, ebv-miR-BART6-3p, ebv-miR-BART7, ebv-miR-BART8-5p, ebv-miR-BART8-3p, ebv-miR-BART9, ebv-miR-BART10, ebv-miR-BART11-5p, ebv-miR-BART11-3p, ebv-miR-BART12, ebv-miR-BART13, ebv-miR-BART14-5p, ebv-miR-BART14-3p, kshv-miR-K12-12, ebv-miR-BART15, ebv-miR-BART16, ebv-miR-BART17-5p, ebv-miR-BART17-3p, ebv-miR-BART18, ebv-miR-BART19, ebv-miR-BART20-5p, ebv-miR-BART20-3p, hsv1-miR-H1, hsa-miR-758, hsa-miR-671, hsa-miR-668, hsa-miR-767-5p, hsa-miR-767-3p, hsa-miR-454-5p, hsa-miR-454-3 p, hsa-miR-769-5p, hsa-miR-769-3p, hsa-miR-766, hsa-miR-765, hsa-miR-768-5p, hsa-miR-768-3p, hsa-miR-770-5p, hsa-miR-802, hsa-miR-801, and hsa-miR-675.

For example, without being bound by theory, miR-128A5 miR-129 and miR-128B are highly enriched in brain; miR-194, miR-148 and miR-192 are highly enriched in liver; mIR-96, miR-150, miR-205, miR-182 and miR-183 are highly enriched in the thymus; miR-204, miR-10B5 miR-154 and miR134 are highly enriched in testes; and miR-122, miR-210, miR-221, miR-141, miR-23A, miR-200C and miR-136 are highly enriched in the placenta. The biosignature comprising one or more of the aforementioned miRs can be used to distinguish positive and negative lymph nodes from a subject with cervical, colon or breast cancer.

In another embodiment, a biosignature can comprise one or more of the following miRs: miR-125b-1, miR125b-2, miR- 145, miR-21, miR-155, miR-10b, miR-009-1 (miR131-1), miR-34 (miR-170), miR-102 (miR-29b), miR-123 (miR-126), miR-140-as, miR-125a, miR-125b-1, miR-125b-2, miR-194, miR-204, miR-213, let-7a-2, let-7a-3, let-7d (let-7d-v1), let-7f-2, let-71 (let-7d-v2), miR-101-1, miR-122a, miR-128b, miR-136, miR-143, miR-149, miR-191, miR-196-1, miR-196-2, miR-202, miR-203, miR-206, and miR-210, which can be used to characterize breast cancer.

In another embodiment, miR-375 expression is detected in a vesicle and used to characterize pancreatic insular or acinar tumors.

In yet another embodiment, one or more of the following miRs can be detected in a vesicle: miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126. miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, and miR-375, wherein high expression or overexpression of the one or more miRs can be used to characterize pancreatic cancer.

Expression of one or more of the following miRs: miR-101, miR-126, miR-99a, miR-99-prec, miR-106, miR-339, miR-99b, miR-149, miR-33, miR-135and miR-20 can be detected in a vesicle and used to characterize megakaryocytopoiesis.

It is believed cell proliferation has been correlated with the expression of miR-31, miR-92, miR-99a, miR-100, miR-125a, miR-129, miR-130a, miR-150, miR-187, miR-190, miR-191, miR-193, miR 204, miR-210, miR-21 1, miR-212, miR-213, miR-215, miR-216, miR-217, miR 218, miR-224, miR-292, miR-294, miR-320, miR-324, miR-325, miR-326, miR-330, miR-331, miR-338, miR-341, miR-369, miR-370, et-7a, Let-7b, Let-7c, Let-7d, Let-7g, miR-7, miR-9, miR-10a, miR-10b, miR-15a, miR-18, miR-19a, miR-17-3p, miR-20, miR-23b, miR-25, miR-26a, miR-26a, miR-30e-5p, miR-31, miR-32, miR-92, miR-93, miR-100, miR-125a, miR-125b, miR-126, miR-127, miR-128, miR-129, miR-130a, miR-135, miR-138, miR-139, miR-140, miR-141, miR-143, miR-145, miR-146, miR-150, miR-154, miR-155, miR-181a, miR-182, miR-186, miR-187, miR-188, miR-190, miR-191, miR-193, miR-194, miR-196, miR-197, miR-198, miR-199, miR-201, miR-204, miR-216, miR-218, miR-223, miR-293, miR-291-3p, miR-294, miR-295, miR-322, miR-333, miR-335, miR-338, miR-341, miR-350, miR-369, miR-373, miR-410, and miR-412. Detection one or more of the above miRs can be used to characterize a cancer.

Other examples of miRs that detected in a vesicle and used to characterize cancer is disclosed in U.S. Pat. No. 7,642,348, describing identification of 3,765 unique nucleic acid sequences correlated with prostate cancer), and U.S. Pat. No. 7,592,441, which describes microRNAs related to liver cancer.

Other microRNAs that are expressed commonly in solid cancer, such as colon cancer, lung cancer, breast cancer, stomach cancer, prostate cancer, and pancreatic cancer, can also be detected in a vesicle and used to characterize a cancer. For example, one or more of the following miRs: miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, and miR-106a, can be detected in a vesicle and used to characterize a solid cancer.

Other examples of microRNAs that can be detected in a vesicle are disclosed in PCT Publication Nos. WO2006126040, WO2006033020, WO2005116250, and WO2005111211, US Publications Nos. US20070042982 and US20080318210; and EP Publication Nos. EP1784501A2 and EP1751311A2, each of which is incorporated by reference.

Biomarker Detection

A biosignature can be detected qualitatively or quantitatively by detecting a presence, level or concentration of a microRNA, vesicle or other biomarkers, as disclosed herein. These biosignature components can be detected using a number of techniques known to those of skill in the art. For example, a biomarker can be detected by microarray analysis, polymerase chain reaction (PCR) (including PCR-based methods such as real time polymerase chain reaction (RT-PCR), quantitative real time polymerase chain reaction (Q-PCR/qPCR) and the like), hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, nucleic acid sequencing, single strand conformation polymorphism (SSCP), denaturing gradient gel electrophoresis (DGGE), temperature gradient gel electrophoresis (TGGE), restriction fragment polymorphisms, serial analysis of gene expression (SAGE), or combinations thereof. A biomarker, such as a nucleic acid, can be amplified prior to detection. A biomarker can also be detected by immunoassay, immunoblot, immunoprecipitation, enzyme-linked immunosorbent assay (ELISA; EIA), radio-immunoassay (RIA), flow cytometry, or electron microscopy (EM).

Biosignatures can be detected using capture agents and detection agents, as described herein. A capture agent can comprise an antibody, aptamer or other entity which recognizes a biomarker and can be used for capturing the biomarker. Biomarkers that can be captured include circulating biomarkers, e.g., a protein, nucleic acid, lipid or biological complex in solution in a bodily fluid. Similarly, the capture agent can be used for capturing a vesicle. A detection agent can comprise an antibody or other entity which recognizes a biomarker and can be used for detecting the biomarker vesicle, or which recognizes a vesicle and is useful for detecting a vesicle. In some embodiments, the detection agent is labeled and the label is detected, thereby detecting the biomarker or vesicle. The detection agent can be a binding agent, e.g., an antibody or aptamer. In other embodiments, the detection agent comprises a small molecule such as a membrane protein labeling agent. See, e.g., the membrane protein labeling agents disclosed in Alroy et al., US. Patent Publication US 2005/0158708. In an embodiment, vesicles are isolated or captured as described herein, and one or more membrane protein labeling agent is used to detect the vesicles. In many cases, the antigen or other vesicle-moiety that is recognized by the capture and detection agents are interchangeable. As a non-limiting example, consider a vesicle having a cell-of-origin specific antigen on its surface and a cancer-specific antigen on its surface. In one instance, the vesicle can be captured using an antibody to the cell-of-origin specific antigen, e.g., by tethering the capture antibody to a substrate, and then the vesicle is detected using an antibody to the cancer-specific antigen, e.g., by labeling the detection antibody with a fluorescent dye and detecting the fluorescent radiation emitted by the dye. In another instance, the vesicle can be captured using an antibody to the cancer specific antigen, e.g., by tethering the capture antibody to a substrate, and then the vesicle is detected using an antibody to the cell-of-origin specific antigen, e.g., by labeling the detection antibody with a fluorescent dye and detecting the fluorescent radiation emitted by the dye.

In some embodiments, a same biomarker is recognized by both a capture agent and a detection agent. This scheme can be used depending on the setting. In one embodiment, the biomarker is sufficient to detect a vesicle of interest, e.g., to capture cell-of-origin specific vesicles. In other embodiments, the biomarker is multifunctional, e.g., having both cell-of-origin specific and cancer specific properties. The biomarker can be used in concert with other biomarkers for capture and detection as well.

One method of detecting a biomarker comprises purifying or isolating a heterogeneous population of vesicles from a biological sample, as described above, and performing a sandwich assay. A vesicle in the population can be captured with a capture agent. The capture agent can be a capture antibody, such as a primary antibody. The capture antibody can be bound to a substrate, for example an array, well, or particle. The captured or bound vesicle can be detected with a detection agent, such as a detection antibody. For example, the detection antibody can be for an antigen of the vesicle. The detection antibody can be directly labeled and detected. Alternatively, the detection agent can be indirectly labeled and detected, such as through an enzyme linked secondary antibody that can react with the detection agent. A detection reagent or detection substrate can be added and the reaction detected, such as described in PCT Publication No. WO2009092386. In an illustrative example wherein the capture agent binds Rab-5b and the detection agent binds or detects CD63 or caveolin-1, the capture agent can be an anti-Rab 5b antibody and the detection agent can be an anti-CD63 or anti-caveolin-1 antibody. In some embodiments, the capture agent binds CD9, PSCA, TNFR, CD63, B7H3, MFG-E8, EpCam, Rab, CD81, STEAP, PCSA, PSMA, or 5T4. For example, the capture agent can be an antibody to CD9, PSCA, TNFR, CD63, B7H3, MFG-E8, EpCam, Rab, CD81, STEAP, PCSA, PSMA, or 5T4. The capture agent can also be an antibody to MFG-E8, Annexin V, Tissue Factor, DR3, STEAP, epha2, TMEM211, unc93A, A33, CD24, NGAL, EpCam, MUC17, TROP2, or TETS. The detection agent can be an agent that binds or detects CD63, CD9, CD81, B7H3, or EpCam, such as a detection antibody to CD63, CD9, CD81, B7H3, or EpCam. Various combinations of capture and/or detection agents can be used in concert. In an embodiment, the capture agents comprise PCSA, PSMA, B7H3 and optionally EpCam, and the detection agents comprise one or more tetraspanin such as CD9, CD63 and CD81. In another embodiment, the capture agents comprise TMEM211 and CD24, and the detection agents comprise one or more tetraspanin such as CD9, CD63 and CD81. In another embodiment, the capture agents comprise CD66 and EpCam, and the detection agents comprise one or more tetraspanin such as CD9, CD63 and CD81. Increasing numbers of such tetraspanins and/or other general vesicle markers can improve the detection signal in some cases. Proteins or other circulating biomarkers can also be detected using sandwich approaches. The captured vesicles can be collected and used to analyze the payload contained therein, e.g., mRNA, microRNAs, DNA and soluble protein.

In some embodiments, the capture agent binds or targets EpCam, B7H3 or CD24, and the one or more biomarkers detected on the vesicle are CD9 and/or CD63. In one embodiment, the capture agent binds or targets EpCam, and the one or more biomarkers detected on the vesicle are CD9, EpCam and/or CD81. The single capture agent can be selected from CD9, PSCA, TNFR, CD63, B7H3, MFG-E8, EpCam, Rab, CD81, STEAP, PCSA, PSMA, or 5T4. The single capture agent can also be an antibody to DR3, STEAP, epha2, TMEM211, unc93A, A33, CD24, NGAL, EpCam, MUC17, TROP2, MFG-E8, TF, Annexin V or TETS. In some embodiments, the single capture agent is selected from PCSA, PSMA, B7H3, CD81, CD9 and CD63.

In other embodiments, the capture agent targets PCSA, and the one or more biomarkers detected on the captured vesicle are B7H3 and/or PSMA. In other embodiments, the capture agent targets PSMA, and the one or more biomarkers detected on the captured vesicle are B7H3 and/or PCSA. In other embodiments, the capture agent targets B7H3, and the one or more biomarkers detected on the captured vesicle are PSMA and/or PCSA. In yet other embodiments, the capture agent targets CD63 and the one or more biomarkers detected on the vesicle are CD81, CD83, CD9 and/or CD63. The different capture agent and biomarker combinations disclosed herein can be used to characterize a phenotype, such as detecting, diagnosing or prognosing a disease, e.g., a cancer. In some embodiments, vesicles are analyzed to characterize prostate cancer using a capture agent targeting EpCam and detection of CD9 and CD63; a capture agent targeting PCSA and detection of B7H3 and PSMA; or a capture agent of CD63 and detection of CD81. In other embodiments, vesicles are used to characterize colon cancer using capture agent targeting CD63 and detection of CD63, or a capture agent targeting CD9 coupled with detection of CD63. One of skill will appreciate that targets of capture agents and detection agents can be used interchangeably. In an illustrative example, consider a capture agent targeting PCSA and detection agents targeting B7H3 and PSMA. Because all of these markers are useful for detecting PCa derived vesicles, B7H3 or PSMA could be targeted by the capture agent and PCSA could be recognized by a detection agent. For example, in some embodiments, the detection agent targets PCSA, and one or more biomarkers used to capture the vesicle comprise B7H3 and/or PSMA. In other embodiments, the detection agent targets PSMA, and the one or more biomarkers used to capture the vesicle comprise B7H3 and/or PCSA. In other embodiments, the detection agent targets B7H3, and the one or more biomarkers used to capture the vesicle comprise PSMA and/or PCSA. In some embodiments, the invention provides a method of detecting prostate cancer cells in bodily fluid using capture agents and/or detection agents to PSMA, B7H3 and/or PCSA. The bodily fluid can comprise blood, including serum or plasma. The bodily fluid can comprise ejaculate or sperm. In further embodiments, the methods of detecting prostate cancer further use capture agents and/or detection agents to CD81, CD83, CD9 and/or CD63. The method further provides a method of characterizing a GI disorder, comprising capturing vesicles with one or more of DR3, STEAP, epha2, TMEM211, unc93A, A33, CD24, NGAL, EpCam, MUC17, TROP2, and TETS, and detecting the captured vesicles with one or more general vesicle antigen, such as CD81, CD63 and/or CD9. Additional agents can improve the test performance, e.g., improving test accuracy or AUC, either by providing additional biological discriminatory power and/or by reducing experimental noise.

Techniques of detecting biomarkers for use with the invention include the use of a planar substrate such as an array (e.g., biochip or microarray), with molecules immobilized to the substrate as capture agents that facilitate the detection of a particular biosignature. The array can be provided as part of a kit for assaying one or more biomarkers or vesicles. A molecule that identifies the biomarkers described above and shown in FIG. 3-60, as well as antigens in FIG. 1, can be included in an array for detection and diagnosis of diseases including presymptomatic diseases. In some embodiments, an array comprises a custom array comprising biomolecules selected to specifically identify biomarkers of interest. Customized arrays can be modified to detect biomarkers that increase statistical performance, e.g., additional biomolecules that identifies a biosignature which lead to improved cross-validated error rates in multivariate prediction models (e.g., logistic regression, discriminant analysis, or regression tree models). In some embodiments, customized array(s) are constructed to study the biology of a disease, condition or syndrome and profile biosignatures in defined physiological states. Markers for inclusion on the customized array be chosen based upon statistical criteria, e.g., having a desired level of statistical significance in differentiating between phenotypes or physiological states. In some embodiments, standard significance of p-value=0.05 is chosen to exclude or include biomolecules on the microarray. The p-values can be corrected for multiple comparisons. As an illustrative example, nucleic acids extracted from samples from a subject with or without a disease can be hybridized to a high density microarray that binds to thousands of gene sequences. Nucleic acids whose levels are significantly different between the samples with or without the disease can be selected as biomarkers to distinguish samples as having the disease or not. A customized array can be constructed to detect the selected biomarkers. In some embodiments, customized arrays comprise low density microarrays, which refer to arrays with lower number of addressable binding agents, e.g., tens or hundreds instead of thousands. Low density arrays can be formed on a substrate. In some embodiments, customizable low density arrays use PCR amplification in plate wells, e.g., TaqMan® Gene Expression Assays (Applied Biosystems by Life Technologies Corporation, Carlsbad, Calif.).

A planar array generally contains addressable locations (e.g., pads, addresses, or micro-locations) of biomolecules in an array format. The size of the array will depend on the composition and end use of the array. Arrays can be made containing from 2 different molecules to many thousands. Generally, the array comprises from two to as many as 100,000 or more molecules, depending on the end use of the array and the method of manufacture. A microarray for use with the invention comprises at least one biomolecule that identifies or captures a biomarker present in a biosignature of interest, e.g., a microRNA or other biomolecule or vesicle that makes up the biosignature. In some arrays, multiple substrates are used, either of different or identical compositions. Accordingly, planar arrays may comprise a plurality of smaller substrates.

The present invention can make use of many types of arrays for detecting a biomarker, e.g., a biomarker associated with a biosignature of interest. Useful arrays or microarrays include without limitation DNA microarrays, such as cDNA microarrays, oligonucleotide microarrays and SNP microarrays, microRNA arrays, protein microarrays, antibody microarrays, tissue microarrays, cellular microarrays (also called transfection microarrays), chemical compound microarrays, and carbohydrate arrays (glycoarrays). These arrays are described in more detail above. In some embodiments, microarrays comprise biochips that provide high-density immobilized arrays of recognition molecules (e.g., antibodies), where biomarker binding is monitored indirectly (e.g., via fluorescence). FIG. 2A shows an illustrative configuration in which capture antibodies against a vesicle antigen of interest are tethered to a surface. The captured vesicles are then detected using detector antibodies against the same or different vesicle antigens of interest. The capture antibodies can be substituted with tethered aptamers as available and desirable. Fluorescent detectors are shown. Other detectors can be used similarly, e.g., enzymatic reaction, detectable nanoparticles, radiolabels, and the like. In other embodiments, an array comprises a format that involves the capture of proteins by biochemical or intermolecular interaction, coupled with detection by mass spectrometry (MS). The vesicles can be eluted from the surface and the payload therein, e.g., microRNA, can be analyzed.

An array or microarray that can be used to detect one or more biomarkers of a biosignature can be made according to the methods described in U.S. Pat. Nos. 6,329,209; 6,365,418; 6,406,921; 6,475,808; and 6,475,809, and U.S. patent application Ser. No. 10/884,269, each of which is herein incorporated by reference in its entirety. Custom arrays to detect specific selections of sets of biomarkers described herein can be made using the methods described in these patents. Commercially available microarrays can also be used to carry out the methods of the invention, including without limitation those from Affymetrix (Santa Clara, Calif.), Illumina (San Diego, Calif.), Agilent (Santa Clara, Calif.), Exiqon (Denmark), or Invitrogen (Carlsbad, Calif.). Custom and/or commercial arrays include arrays for detection proteins, nucleic acids, and other biological molecules and entities (e.g., cells, vesicles, virii) as described herein.

In some embodiments, molecules to be immobilized on an array comprise proteins or peptides. One or more types of proteins may be immobilized on a surface. In certain embodiments, the proteins are immobilized using methods and materials that minimize the denaturing of the proteins, that minimize alterations in the activity of the proteins, or that minimize interactions between the protein and the surface on which they are immobilized.

Array surfaces useful may be of any desired shape, form, or size. Non-limiting examples of surfaces include chips, continuous surfaces, curved surfaces, flexible surfaces, films, plates, sheets, or tubes. Surfaces can have areas ranging from approximately a square micron to approximately 500 $cm^2$. The area, length, and width of surfaces may be varied according to the requirements of the assay to be performed. Considerations may include, for example, ease of handling, limitations of the material(s) of which the surface is formed, requirements of detection systems, requirements of deposition systems (e.g., arrayers), or the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within microwell plates having any number of wells. In such embodiments, the bottoms of the wells may serve as surfaces for the formation of arrays, or arrays may be formed on other surfaces and then placed into wells. In certain embodiments, such as where a surface without wells is used, binding islands may be formed or molecules may be immobilized on a surface and a gasket having holes spatially arranged so that they correspond to the islands or biomolecules may be placed on the surface. Such a gasket is preferably liquid tight. A gasket may be placed on a surface at any time during the process of making the array and may be removed if separation of groups or arrays is no longer necessary.

In some embodiments, the immobilized molecules can bind to one or more biomarkers or vesicles present in a biological sample contacting the immobilized molecules. In some embodiments, the immobilized molecules modify or are modified by molecules present in the one or more vesicles contacting the immobilized molecules. Contacting the sample typically comprises overlaying the sample upon the array.

Modifications or binding of molecules in solution or immobilized on an array can be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces are measured; techniques using radioisotopes, including conventional radioisotope binding and scintillation proximity assays (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as atomic force microscopy (AFM), scanning force microscopy (SFM) or scanning electron microscopy (SEM); and techniques such as electrochemical, impedance, acoustic, microwave, and IR/Raman detection. See, e.g., Mere L, et al., "*Miniaturized FRET assays and microfluidics: key components for ultra-high-throughput screening,*" *Drug Discovery Today* 4(8):363-369 (1999), and references cited therein; Lakowicz J R, *Principles of Fluorescence Spectroscopy, 2nd Edition, Plenum Press* (1999), or Jain K K: *Integrative Omics, Pharmacoproteomics, and Human Body Fluids. In: Thongboonkerd V, ed, ed. Proteomics of Human Body Fluids: Principles, Methods and Applications. Volume 1: Totowa, N.J.: Humana Press,* 2007, each of which is herein incorporated by reference in its entirety.

Microarray technology can be combined with mass spectroscopy (MS) analysis and other tools. Electrospray interface to a mass spectrometer can be integrated with a capillary in a microfluidics device. For example, one commercially available system contains eTag reporters that are fluorescent labels with unique and well-defined electrophoretic mobilities; each label is coupled to biological or chemical probes via cleavable linkages. The distinct mobility address of each eTag reporter allows mixtures of these tags to be rapidly deconvoluted and quantitated by capillary electrophoresis. This system allows concurrent gene expression, protein expression, and protein function analyses from the same sample Jain K K: *Integrative Omics, Pharmacoproteomics, and Human Body Fluids. In: Thongboonkerd V, ed., ed. Proteomics of Human Body Fluids: Principles, Methods and Applications. Volume 1: Totowa, N.J.: Humana Press,* 2007, which is herein incorporated by reference in its entirety.

A biochip can include components for a microfluidic or nanofluidic assay. A microfluidic device can be used for isolating or analyzing biomarkers, such as determining a biosignature. Microfluidic systems allow for the miniaturization and compartmentalization of one or more processes for isolating, capturing or detecting a vesicle, detecting a microRNA, detecting a circulating biomarker, detecting a biosignature, and other processes. The microfluidic devices can use one or more detection reagents in at least one aspect of the system, and such a detection reagent can be used to detect one or more biomarkers. In one embodiment, the device detects a biomarker on an isolated or bound vesicle. Various probes, antibodies, proteins, or other binding agents can be used to detect a biomarker within the microfluidic system. The detection agents may be immobilized in different compartments of the microfluidic device or be entered into a hybridization or detection reaction through various channels of the device.

A vesicle in a microfluidic device can be lysed and its contents detected within the microfluidic device, such as proteins or nucleic acids, e.g., DNA or RNA such as miRNA or mRNA. The nucleic acid may be amplified prior to detection, or directly detected, within the microfluidic device. Thus microfluidic system can also be used for multiplexing detection of various biomarkers. In an embodiment, vesicles are captured within the microfluidic device, the captured vesicles are lysed, and a biosignature of microRNA from the vesicle payload is determined. The biosignature can further comprise the capture agent used to capture the vesicle.

Novel nanofabrication techniques are opening up the possibilities for biosensing applications that rely on fabrication of high-density, precision arrays, e.g., nucleotide-based chips and protein arrays otherwise know as heterogeneous nanoarrays. Nanofluidics allows a further reduction in the quantity of fluid analyte in a microchip to nanoliter levels, and the chips used here are referred to as nanochips. (See, e.g., Unger M et al., *Biotechniques* 1999; 27(5):1008-14, Kartalov E P et al., *Biotechniques* 2006; 40(1):85-90, each of which are herein incorporated by reference in their entireties.) Commercially available nanochips currently provide simple one step assays such as total cholesterol, total protein or glucose assays that can be run by combining sample and reagents, mixing and monitoring of the reaction. Gel-free analytical approaches based on liquid chromatography (LC) and nanoLC separations (*Cutillas et al. Proteomics,* 2005; 5:101-112 and *Cutillas et al., Mol Cell Proteomics* 2005; 4:1038-1051, each of which is herein incorporated by reference in its entirety) can be used in combination with the nanochips.

Further provided herein is a rapid detection device that facilitates the detection of a particular biosignature in a biological sample. The device can integrate biological sample preparation with polymerase chain reaction (PCR) on a chip. The device can facilitate the detection of a particular biosignature of a vesicle in a biological sample, and an example is provided as described in *Pipper et al., Angewandte Chemie,* 47(21), p. 3900-3904 (2008), which is herein incorporated by reference in its entirety. A biosignature can be incorporated using micro-/nano-electrochemical system (MEMS/NEMS) sensors and oral fluid for diagnostic applications as described in Li et al., *Adv Dent Res* 18(1): 3-5 (2005), which is herein incorporated by reference in its entirety.

As an alternative to planar arrays, assays using particles, such as bead based assays as described herein, can be used in combination with flow cytometry. Multiparametric assays or other high throughput detection assays using bead coatings with cognate ligands and reporter molecules with specific activities consistent with high sensitivity automation can be used. In a bead based assay system, a binding agent for a biomarker or vesicle, such as a capture agent (e.g. capture antibody), can be immobilized on an addressable microsphere. Each binding agent for each individual binding assay can be coupled to a distinct type of microsphere (i.e., microbead) and the assay reaction takes place on the surface of the microsphere, such as depicted in FIG. 64B. A binding agent for a vesicle can be a capture antibody coupled to a bead. Dyed microspheres with discrete fluorescence intensities are loaded separately with their appropriate binding agent or capture probes. The different bead sets carrying different binding agents can be pooled as necessary to generate custom bead arrays. Bead arrays are then incubated with the sample in a single reaction vessel to perform the assay. Examples of microfluidic devices that may be used, or adapted for use with the invention, include but are not limited to those described herein.

Figure 64A:
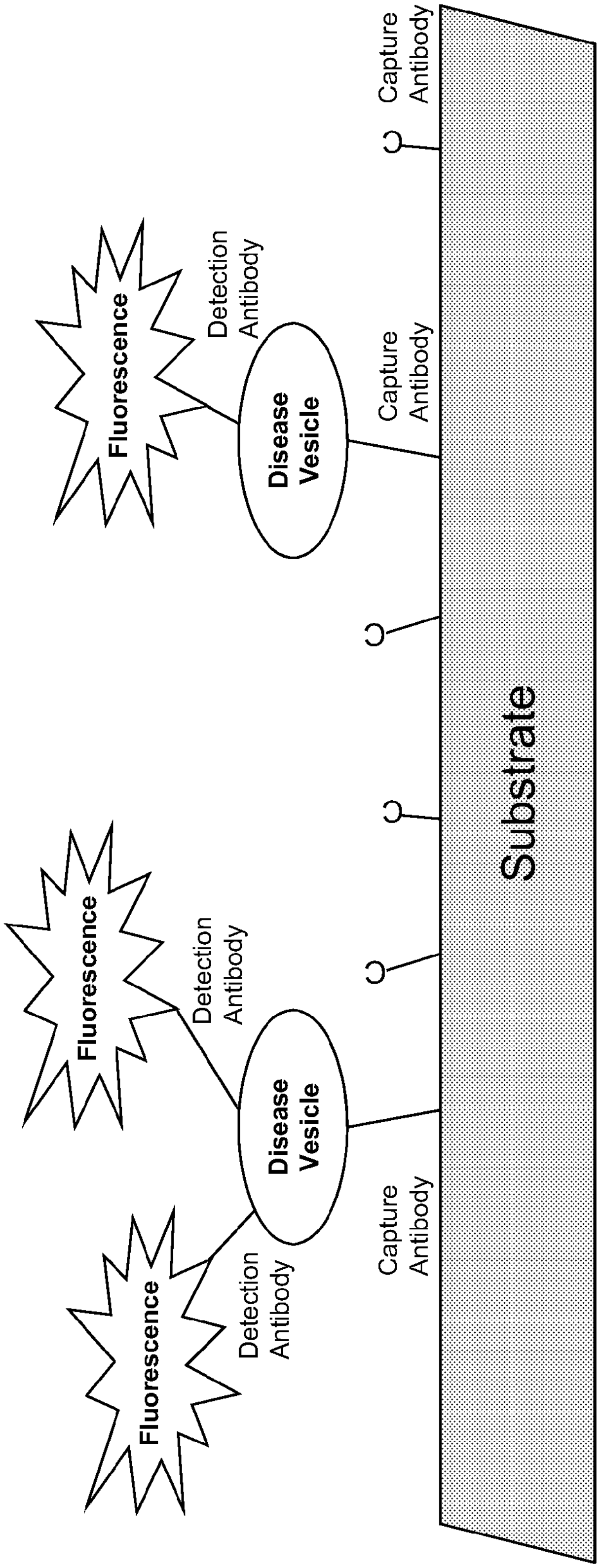
Figure 64B:
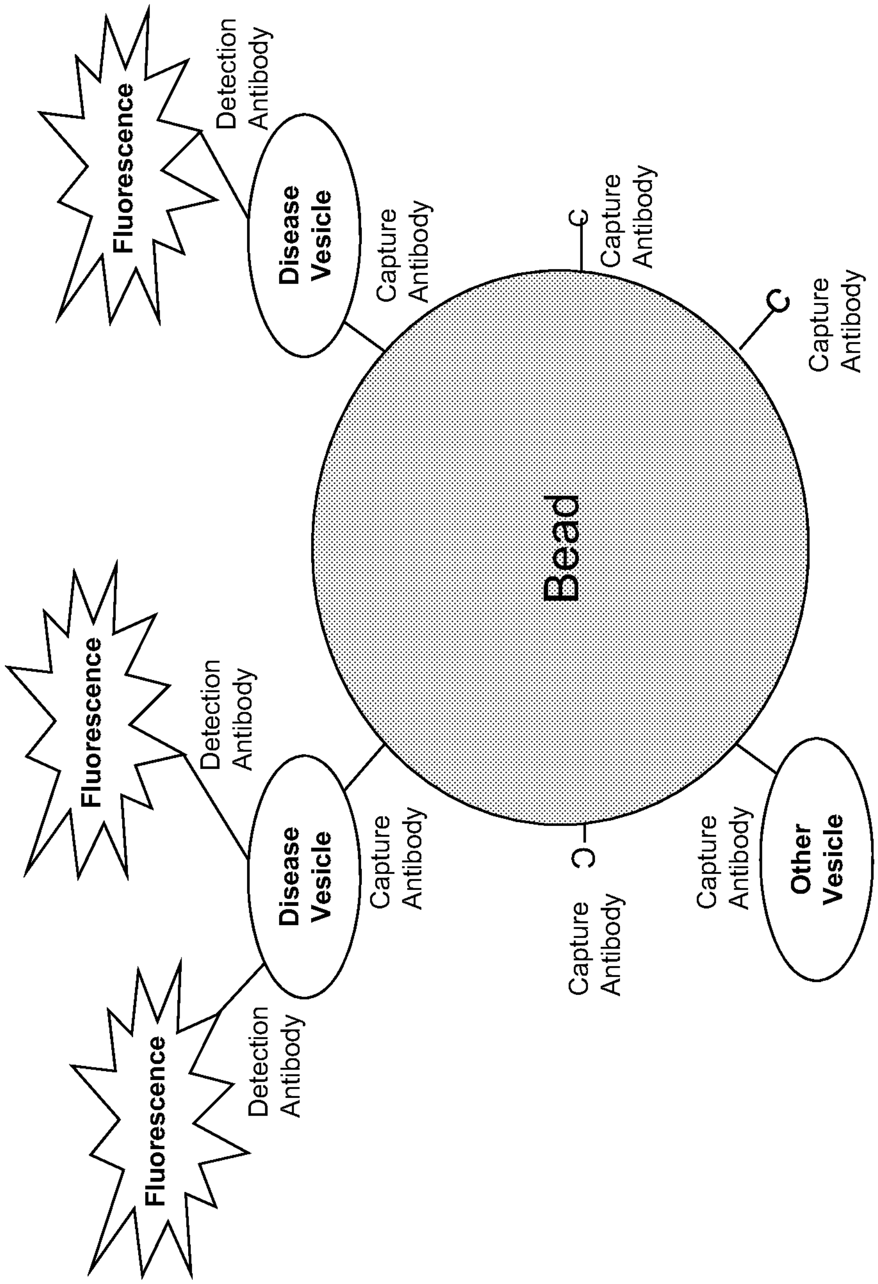

Product formation of the biomarker with an immobilized capture molecule or binding agent can be detected with a fluorescence based reporter system (see for example, FIG. 64A-B). The biomarker can either be labeled directly by a fluorophore or detected by a second fluorescently labeled capture biomolecule. The signal intensities derived from captured biomarkers can be measured in a flow cytometer. The flow cytometer can first identify each microsphere by its individual color code. For example, distinct beads can be dyed with discrete fluorescence intensities such that each bead with a different intensity has a different binding agent. The beads can be labeled or dyed with at least 2 different labels or dyes. In some embodiments, the beads are labeled with at least 3, 4, 5, 6, 7, 8, 9, or 10 different labels. The beads with more than one label or dye can also have various ratios and combinations of the labels or dyes. The beads can be labeled or dyed externally or may have intrinsic fluorescence or signaling labels.

The amount of captured biomarkers on each individual bead can be measured by the second color fluorescence specific for the bound target. This allows multiplexed quantitation of multiple targets from a single sample within the same experiment. Sensitivity, reliability and accuracy are compared or can be improved to standard microtiter ELISA procedures. An advantage of a bead-based system is the individual coupling of the capture biomolecule or binding agent for a vesicle to distinct microspheres provides multiplexing capabilities. For example, as depicted in FIG. 64C, a combination of 5 different biomarkers to be detected (detected by antibodies to antigens such as CD63, CD9, CD81, B7H3, and EpCam) and 20 biomarkers for which to capture a vesicle, (using capture antibodies, such as antibodies to CD9, PSCA, TNFR, CD63, B7H3, MFG-E8, EpCam, Rab, CD81, STEAP, PCSA, PSMA, 5T4, and/or CD24) can result in approximately 100 combinations to be detected. As shown in FIG. 64C as "EpCam 2x," "CD63 2X," multiple antibodies to a single target can be used to probe detection against various epitopes. In another example, multiplex analysis comprises capturing a vesicle using a binding agent to CD24 and detecting the captured vesicle using a binding agent for CD9, CD63, and/or CD81. The captured vesicles can be detected using a detection agent such as an antibody. The detection agents can be labeled directly or indirectly, as described herein.

Multiplexing of at least 2, 3, 4, 5, 6, 7, 8, 9, 10, 11, 12, 13, 14, 15, 16, 17, 18, 19, 20, 25, 50, 75 or 100 different biomarkers may be performed. For example, an assay of a heterogeneous population of vesicles can be performed with a plurality of particles that are differentially labeled. There can be at least 2, 3, 4, 5, 6, 7, 8, 9, 10, 11, 12, 13, 14, 15, 16, 17, 18, 19, 20, 25, 50, 75 or 100 differentially labeled particles. The particles may be externally labeled, such as with a tag, or they may be intrinsically labeled. Each differentially labeled particle can be coupled to a capture agent, such as a binding agent, for a vesicle, resulting in capture of a vesicle. The multiple capture agents can be selected to characterize a phenotype of interest, including capture agents against general vesicle biomarkers, cell-of-origin specific biomarkers, and disease biomarkers. One or more biomarkers of the captured vesicle can then be detected by a plurality of binding agents. The binding agent can be directly labeled to facilitate detection. Alternatively, the binding agent is labeled by a secondary agent. For example, the binding agent may be an antibody for a biomarker on the vesicle. The binding agent is linked to biotin. A secondary agent comprises streptavidin linked to a reporter and can be added to detect the biomarker. In some embodiments, the captured vesicle is assayed for at least 2, 3, 4, 5, 6, 7, 8, 9, 10, 11, 12, 13, 14, 15, 16, 17, 18, 19, 20, 25, 50, 75 or 100 different biomarkers. For example, multiple detectors, i.e., detection of multiple biomarkers of a captured vesicle or population of vesicles, can increase the signal obtained, permitted increased sensitivity, specificity, or both, and the use of smaller amounts of samples. For example, detection with more than one general vesicle marker can improve the signal as compared to using a lesser number of detection markers, such as a single marker. To illustrate, detection of vesicles with labeled binding agents to two or three of CD9, CD63 and CD81 can improve the signal compared to detection with any one of the tetraspanins individually.

An immunoassay based method or sandwich assay can also be used to detect a biomarker of a vesicle. An example includes ELISA. A binding agent or capture agent can be bound to a well. For example an antibody to an antigen of a vesicle can be attached to a well. A biomarker on the captured vesicle can be detected based on the methods described herein. FIG. 64A shows an illustrative schematic for a sandwich-type of immunoassay. The capture antibody can be against a vesicle antigen of interest, e.g., a general vesicle biomarker, a cell-of-origin marker, or a disease marker. In the figure, the captured vesicles are detected using fluorescently labeled antibodies against vesicle antigens of interest. Multiple capture antibodies can be used, e.g., in distinguishable addresses on an array or different wells of an immunoassay plate. The detection antibodies can be against the same antigen as the capture antibody, or can be directed against other markers. The capture antibodies can be substituted with alternate binding agents, such as tethered aptamers or lectins, and/or the detector antibodies can be similarly substituted, e.g., with detectable (e.g., labeled) aptamers, lectins or other binding proteins or entities. In an embodiment, one or more capture agents to a general vesicle biomarker, a cell-of-origin marker, and/or a disease marker are used along with detection agents against general vesicle biomarker, such as tetraspanin molecules including without limitation one or more of CD9, CD63 and CD81.

Figure 64D:
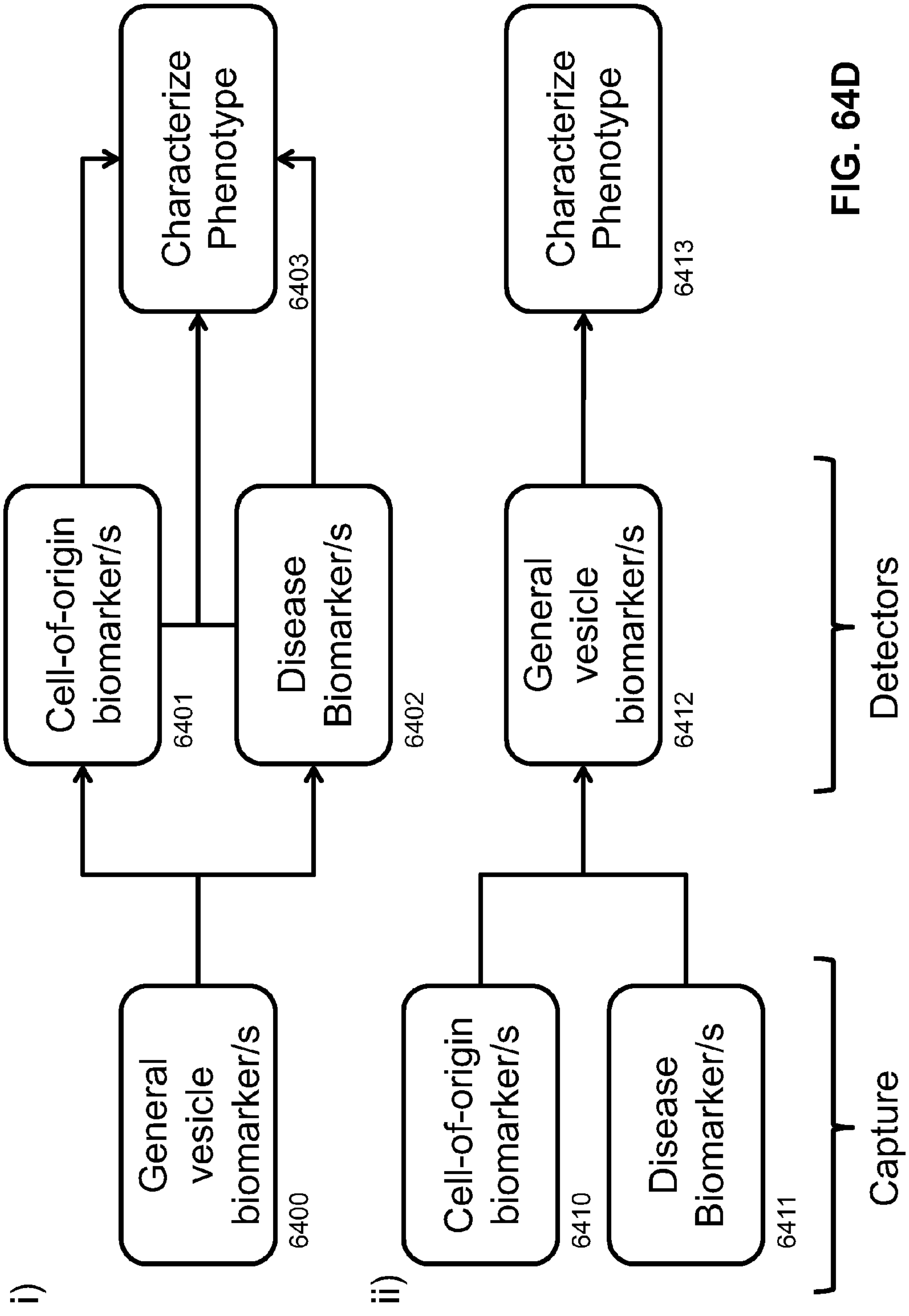

FIG. 64D presents an illustrative schematic for analyzing vesicles according to the methods of the invention. Capture agents are used to capture vesicles, detectors are used to detect the captured vesicles, and the level or presence of the captured and detected antibodies is used to characterize a phenotype. Capture agents, detectors and characterizing phenotypes can be any of those described herein. For example, capture agents include antibodies or aptamers tethered to a substrate that recognize a vesicle antigen of interest, detectors include labeled antibodies or aptamers to a vesicle antigen of interest, and characterizing a phenotype includes a diagnosis, prognosis, or theranosis of a disease. In the scheme shown in FIG. 64D i), a population of vesicles is captured with one or more capture agents against general vesicle biomarkers (6400). The captured vesicles are then labeled with detectors against cell-of-origin biomarkers (6401) and/or disease specific biomarkers (6402). If only cell-of-origin detectors are used (6401), the biosignature used to characterize the phenotype (6403) can include the general vesicle markers (6400)

and the cell-of-origin biomarkers (6401). If only disease detectors are used (6402), the biosignature used to characterize the phenotype (6403) can include the general vesicle markers (6400) and the disease biomarkers (6402). Alternately, detectors are used to detect both cell-of-origin biomarkers (6401) and disease specific biomarkers (6402). In this case, the biosignature used to characterize the phenotype (6403) can include the general vesicle markers (6400), the cell-of-origin biomarkers (6401) and the disease biomarkers (6402). The biomarkers combinations are selected to characterize the phenotype of interest and can be selected from the biomarkers and phenotypes described herein.

In the scheme shown in FIG. 64D ii), a population of vesicles is captured with one or more capture agents against cell-of-origin biomarkers (6410) and/or disease biomarkers (6411). The captured vesicles are then detected using detectors against general vesicle biomarkers (6412). If only cell-of-origin capture agents are used (6410), the biosignature used to characterize the phenotype (6413) can include the cell-of-origin biomarkers (6410) and the general vesicle markers (6412). If only disease biomarker capture agents are used (6411), the biosignature used to characterize the phenotype (6413) can include the disease biomarkers (6411) and the general vesicle biomarkers (6412). Alternately, capture agents to one or more cell-of-origin biomarkers (6410) and one or more disease specific biomarkers (6411) are used to capture vesicles. In this case, the biosignature used to characterize the phenotype (6413) can include the cell-of-origin biomarkers (6410), the disease biomarkers (6411), and the general vesicle markers (6413). The biomarkers combinations are selected to characterize the phenotype of interest and can be selected from the biomarkers and phenotypes described herein.

Biomarkers comprising vesicle payload can be analyzed to characterize a phenotype. Payload comprises the biological entities contained within a vesicle membrane. These entities include without limitation nucleic acids, e.g., mRNA, microRNA, or DNA fragments; protein, e.g., soluble and membrane associated proteins; carbohydrates; lipids; metabolites; and various small molecules, e.g., hormones. The payload can be part of the cellular milieu that is encapsulated as a vesicle is formed in the cellular environment. In some embodiments of the invention, the payload is analyzed in addition to detecting vesicle surface antigens. Specific populations of vesicles can be captured as described above then the payload in the captured vesicles can be used to characterize a phenotype. For example, vesicles captured on a substrate can be further isolated to assess the payload therein. Alternately, the vesicles in a sample are detected and sorted without capture. The vesicles so detected can be further isolated to assess the payload therein. In an embodiment, vesicle populations are sorted by flow cytometry and the payload in the sorted vesicles is analyzed. In the scheme shown in FIG. 64E iii), a population of vesicles is captured and/or detected (6420) using one or more of cell-of-origin biomarkers (6420), disease biomarkers (6421), and general vesicle markers (6422). The payload of the isolated vesicles is assessed (6423). A biosignature detected within the payload can be used to characterize a phenotype (6424). In a non-limiting example, a vesicle population can be analyzed in a plasma sample from a patient using antibodies against one or more vesicle antigens of interest. The antibodies can be capture antibodies which are tethered to a substrate to isolate a desired vesicle population. Alternately, the antibodies can be directly labeled and the labeled vesicles isolated by sorting with flow cytometry. The presence or level of microRNA or mRNA extracted from the isolated vesicle population can be used to detect a biosignature. The biosignature is then used to diagnose, prognose or theranose the patient.

In other embodiments, vesicle payload is analyzed in a vesicle population without first capturing or detected subpopulations of vesicles. For example, vesicles can be generally isolated from a sample using centrifugation, filtration, chromatography, or other techniques as described herein. The payload of the isolated vesicles can be analyzed thereafter to detect a biosignature and characterize a phenotype. In the scheme shown in FIG. 64E iv), a population of vesicles is isolated (6430) and the payload of the isolated vesicles is assessed (6431). A biosignature detected within the payload can be used to characterize a phenotype (6432). In a non-limiting example, a vesicle population is isolated from a plasma sample from a patient using size exclusion and membrane filtration. The presence or level of microRNA or mRNA extracted from the vesicle population is used to detect a biosignature. The biosignature is then used to diagnose, prognose or theranose the patient.

A peptide or protein biomarker can be analyzed by mass spectrometry or flow cytometry. Proteomic analysis of a vesicle may be carried out by immunocytochemical staining, Western blotting, electrophoresis, SDS-PAGE, chromatography, x-ray crystallography or other protein analysis techniques in accordance with procedures well known in the art. In other embodiments, the protein biosignature of a vesicle may be analyzed using 2 D differential gel electrophoresis as described in, Chromy et al. *J Proteome Res*, 2004; 3: 1120-1127, which is herein incorporated by reference in its entirety, or with liquid chromatography mass spectrometry as described in Zhang et al. *Mol Cell Proteomics,* 2005; 4:144-155, which is herein incorporated by reference in its entirety. A vesicle may be subjected to activity-based protein profiling described for example, in Berger et al., *Am J Pharmacogenomics,* 2004; 4:371-381, which is in incorporated by reference in its entirety. In other embodiments, a vesicle may be profiled using nanospray liquid chromatography-tandem mass spectrometry as described in Pisitkun et al., *Proc Natl Acad Sci USA,* 2004; 101: 13368-13373, which is herein incorporated by reference in its entirety. In another embodiment, the vesicle may be profiled using tandem mass spectrometry (MS) such as liquid chromatography/MS/MS (LC-MS/MS) using for example a LTQ and LTQ-FT ion trap mass spectrometer. Protein identification can be determined and relative quantitation can be assessed by comparing spectral counts as described in Smalley et al., *J Proteome Res,* 2008; 7:2088-2096, which is herein incorporated by reference in its entirety.

The expression of circulating protein biomarkers or protein payload within a vesicle can also be identified. The latter analysis can optionally follow the isolation of specific vesicles using capture agents to capture populations of interest. In an embodiment, immunocytochemical staining is used to analyze protein expression. The sample can be resuspended in buffer, centrifuged at 100×g for example, for 3 minutes using a cytocentrifuge on adhesive slides in preparation for immunocytochemical staining. The cytospins can be air-dried overnight and stored at −80° C. until staining. Slides can then be fixed and blocked with serum-free blocking reagent. The slides can then be incubated with a specific antibody to detect the expression of a protein of interest. In some embodiments, the vesicles are not purified, isolated or concentrated prior to protein expression analysis.

Biosignatures comprising vesicle payload can be characterized by analysis of a metabolite marker or metabolite within the vesicle. Various metabolite-oriented approaches have been described such as metabolite target analyses, metabolite profiling, or metabolic fingerprinting, see for example, Denkert et al., *Molecular Cancer* 2008; 7: 4598-4617, Ellis et al., *Analyst* 2006; 8: 875-885, Kuhn et al., *Clinical Cancer Research* 2007; 24: 7401-7406, Fiehn 0., *Comp Funct Genomics* 2001; 2:155-168, Fancy et al., *Rapid Commun Mass Spectrom* 20(15): 2271-80 (2006), Lindon et al., *Pharm Res,* 23(6): 1075-88 (2006), Holmes et al., *Anal Chem.* 2007 April 1; 79(7):2629-40. *Epub* 2007 February 27. *Erratum in: Anal Chem.* 2008 August 1; 80(15):6142-3, Stanley et al., *Anal Biochem.* 2005 August 15; 343(2): 195-202., Lehtimaki et al., *J Biol Chem.* 2003 November 14; 278(46): 45915-23, each of which is herein incorporated by reference in its entirety.

Peptides can be analyzed by systems described in Jain K K: *Integrative Omics, Pharmacoproteomics, and Human Body Fluids. In: Thongboonkerd V, ed, ed. Proteomics of Human Body Fluids: Principles, Methods and Applications. Volume* 1*: Totowa, N.J.: Humana Press,* 2007, which is herein incorporated by reference in its entirety. This system can generate sensitive molecular fingerprints of proteins present in a body fluid as well as in vesicles. Commercial applications which include the use of chromatography/mass spectroscopy and reference libraries of all stable metabolites in the human body, for example Paradigm Genetic's Human Metabolome Project, may be used to determine a metabolite biosignature. Other methods for analyzing a metabolic profile can include methods and devices described in U.S. Pat. No. 6,683,455 (Metabometrix), U.S. Patent Application Publication Nos. 20070003965 and 20070004044 (Biocrates Life Science), each of which is herein incorporated by reference in its entirety. Other proteomic profiling techniques are described in Kennedy, *Toxicol Lett* 120:379-384 (2001), Berven et al., *Curr Pharm Biotechnol* 7(3): 147-58 (2006), Conrads et al., *Expert Rev Proteomics* 2(5): 693-703, Decramer et al., *World J Urol* 25(5): 457-65 (2007), Decramer et al., *Mol Cell Proteomics* 7(10): 1850-62 (2008), Decramer et al., *Contrib Nephrol,* 160: 127-41 (2008), *Diamandis, J Proteome Res* 5(9): 2079-82 (2006), Immler et al., *Proteomics* 6(10): 2947-58 (2006), Khan et al., *J Proteome Res* 5(10): 2824-38 (2006), Kumar et al., *Biomarkers* 11(5): 385-405 (2006), Noble et al., *Breast Cancer Res Treat* 104(2): 191-6 (2007), Omenn, Dis Markers 20(3): 131-4 (2004), Powell et al., *Expert Rev Proteomics* 3(1): 63-74 (2006), Rai et al., *Arch Pathol Lab Med,* 126(12): 1518-26 (2002), Ramstrom et al., *Proteomics,* 3(2): 184-90 (2003), Tammen et al., *Breast Cancer Res Treat,* 79(1): 83-93 (2003), Theodorescu et al., *Lancet Oncol,* 7(3): 230-40 (2006), or Zurbig et al., *Electrophoresis,* 27(11): 2111-25 (2006).

For analysis of mRNAs, miRNAs or other small RNAs, the total RNA can be isolated using any known methods for isolating nucleic acids such as methods described in U.S. Patent Application Publication No. 2008132694, which is herein incorporated by reference in its entirety. These include, but are not limited to, kits for performing membrane based RNA purification, which are commercially available. Generally, kits are available for the small-scale (30 mg or less) preparation of RNA from cells and tissues, for the medium scale (250 mg tissue) preparation of RNA from cells and tissues, and for the large scale (1 g maximum) preparation of RNA from cells and tissues. Other commercially available kits for effective isolation of small RNA-containing total RNA are available. Such methods can be used to isolate nucleic acids from vesicles.

Alternatively, RNA can be isolated using the method described in U.S. Pat. No. 7,267,950, which is herein incorporated by reference in its entirety. U.S. Pat. No. 7,267,950 describes a method of extracting RNA from biological systems (cells, cell fragments, organelles, tissues, organs, or organisms) in which a solution containing RNA is contacted with a substrate to which RNA can bind and RNA is withdrawn from the substrate by applying negative pressure. Alternatively, RNA may be isolated using the method described in U.S. Patent Application No. 20050059024, which is herein incorporated by reference in its entirety, which describes the isolation of small RNA molecules. Other methods are described in U.S. Patent Application No. 20050208510, 20050277121, 20070238118, each of which is incorporated by reference in its entirety.

In one embodiment, mRNA expression analysis can be carried out on mRNAs from a vesicle isolated from a sample. In some embodiments, the vesicle is a cell-of-origin specific vesicle. An expression pattern generated from a vesicle can be indicative of a given disease state, disease stage, therapy related signature, or physiological condition.

In one embodiment, once the total RNA has been isolated, cDNA can be synthesized and either qRT-PCR assays (e.g. Applied Biosystem's Taqman® assays) for specific mRNA targets can be performed according to manufacturer's protocol, or an expression microarray can be performed to look at highly multiplexed sets of expression markers in one experiment. Methods for establishing gene expression profiles include determining the amount of RNA that is produced by a gene that can code for a protein or peptide. This can be accomplished by quantitative reverse transcriptase PCR (qRT-PCR), competitive RT-PCR, real time RT-PCR, differential display RT-PCR, Northern Blot analysis or other related tests. While it is possible to conduct these techniques using individual PCR reactions, it is also possible to amplify complementary DNA (cDNA) or complementary RNA (cRNA) produced from mRNA and analyze it via microarray.

The level of a miRNA product in a sample can be measured using any appropriate technique that is suitable for detecting mRNA expression levels in a biological sample, including but not limited to Northern blot analysis, RT-PCR, qRT-PCR, in situ hybridization or microarray analysis. For example, using gene specific primers and target cDNA, qRT-PCR enables sensitive and quantitative miRNA measurements of either a small number of target miRNAs (via singleplex and multiplex analysis) or the platform can be adopted to conduct high throughput measurements using 96-well or 384-well plate formats. See for example, Ross J S et al, Oncologist. 2008 May; 13(5):477-93, which is herein incorporated by reference in its entirety. A number of different array configurations and methods for microarray production are known to those of skill in the art and are described in U.S. patents such as: U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; or U.S. Pat. No. 5,700,637; each of which is herein incorporated by reference in its entirety. Other methods of profiling miRNAs are described in Taylor et al., *Gynecol Oncol.* 2008 July; 110(1): 13-21, Gilad et al, *PLoS ONE.* 2008 Sep. 5; 3(9):e3148, Lee et al., *Annu Rev Pathol.* 2008 September 25 and Mitchell et al, *Proc Natl Acad Sci USA.* 2008 July 29; 105(30):10513-8, Shen R et al, *BMC Genomics.* 2004 Dec. 14; 5(1):94, Mina L et al, *Breast Cancer Res Treat.* 2007 June; 103(2): 197-208, Zhang L et al, *Proc Natl Acad Sci USA.* 2008 May 13; 105(19):7004-9, Ross J S et al, *Oncologist.* 2008 May; 13(5):477-93, Schetter A J et al, JAMA. 2008 January 30; 299(4):425-36, Staudt L M, *N Engl J Med* 2003; 348:1777-85, Mulligan G et al, Blood. 2007 April 15; 109(8):3177-88. *Epub* 2006 December 21, McLendon R et al, *Nature.* 2008 October 23; 455(7216):1061-8, and U.S. Pat. Nos. 5,538,848, 5,723,591, 5,876,930, 6,030,787, 6,258,569, and U.S. Pat. No. 5,804,375, each of which is herein incorporated by reference. In some embodiments, arrays of microRNA panels are use to simultaneously query the expression of multiple miRs. The Exiqon mIRCURY LNA microRNA PCR system panel (Exiqon, Inc., Woburn, Mass.) or the TaqMan® MicroRNA Assays and Arrays systems from Applied Biosystems (Foster City, Calif.) can be used for such purposes.

Microarray technology allows for the measurement of the steady-state mRNA or miRNA levels of thousands of transcripts or miRNAs simultaneously thereby presenting a powerful tool for identifying effects such as the onset, arrest, or modulation of uncontrolled cell proliferation. Two microarray technologies, such as cDNA arrays and oligonucleotide arrays can be used. The product of these analyses are typically measurements of the intensity of the signal received from a labeled probe used to detect a cDNA sequence from the sample that hybridizes to a nucleic acid sequence at a known location on the microarray. Typically, the intensity of the signal is proportional to the quantity of cDNA, and thus mRNA or miRNA, expressed in the sample cells. A large number of such techniques are available and useful. Methods for determining gene expression can be found in U.S. Pat. No. 6,271,002 to Linsley, et al.; U.S. Pat. No. 6,218,122 to Friend, et al.; U.S. Pat. No. 6,218,114 to Peck et al.; or U.S. Pat. No. 6,004,755 to Wang, et al., each of which is herein incorporated by reference in its entirety.

Analysis of an expression level can be conducted by comparing such intensities. This can be performed by generating a ratio matrix of the expression intensities of genes in a test sample versus those in a control sample. The control sample may be used as a reference, and different references to account for age, ethnicity and sex may be used. Different references can be used for different conditions or diseases, as well as different stages of diseases or conditions, as well as for determining therapeutic efficacy.

For instance, the gene expression intensities of mRNA or miRNAs derived from a diseased tissue, including those isolated from vesicles, can be compared with the expression intensities of the same entities in normal tissue of the same type (e.g., diseased breast tissue sample versus normal breast tissue sample). A ratio of these expression intensities indicates the fold-change in gene expression between the test and control samples. Alternatively, if vesicles are not normally present in from normal tissues (e.g. breast) then absolute quantitation methods, as is known in the art, can be used to define the number of miRNA molecules present without the requirement of miRNA or mRNA isolated from vesicles derived from normal tissue.

Gene expression profiles can also be displayed in a number of ways. A common method is to arrange raw fluorescence intensities or ratio matrix into a graphical dendogram where columns indicate test samples and rows indicate genes. The data is arranged so genes that have similar expression profiles are proximal to each other. The expression ratio for each gene is visualized as a color. For example, a ratio less than one (indicating down-regulation) may appear in the blue portion of the spectrum while a ratio greater than one (indicating up-regulation) may appear as a color in the red portion of the spectrum. Commercially available computer software programs are available to display such data.

mRNAs or miRNAs that are considered differentially expressed can be either over expressed or under expressed in patients with a disease relative to disease free individuals. Over and under expression are relative terms meaning that a detectable difference (beyond the contribution of noise in the system used to measure it) is found in the amount of expression of the mRNAs or miRNAs relative to some baseline. In this case, the baseline is the measured mRNA/miRNA expression of a non-diseased individual. The mRNA/miRNA of interest in the diseased cells can then be either over or under expressed relative to the baseline level using the same measurement method. Diseased, in this context, refers to an alteration of the state of a body that interrupts or disturbs, or has the potential to disturb, proper performance of bodily functions as occurs with the uncontrolled proliferation of cells. Someone is diagnosed with a disease when some aspect of that person's genotype or phenotype is consistent with the presence of the disease. However, the act of conducting a diagnosis or prognosis includes the determination of disease/status issues such as determining the likelihood of relapse or metastasis and therapy monitoring. In therapy monitoring, clinical judgments are made regarding the effect of a given course of therapy by comparing the expression of genes over time to determine whether the mRNA/miRNA expression profiles have changed or are changing to patterns more consistent with normal tissue.

Levels of over and under expression are distinguished based on fold changes of the intensity measurements of hybridized microarray probes. A 2X difference is preferred for making such distinctions or a p-value less than 0.05. That is, before an mRNA/miRNA is the to be differentially expressed in diseased/relapsing versus normal/non-relapsing cells, the diseased cell is found to yield at least 2 times more, or 2 times less intensity than the normal cells. The greater the fold difference, the more preferred is use of the gene as a diagnostic or prognostic tool. mRNA/miRNAs selected for the expression profiles of the instant invention have expression levels that result in the generation of a signal that is distinguishable from those of the normal or non-modulated genes by an amount that exceeds background using clinical laboratory instrumentation.

Statistical values can be used to confidently distinguish modulated from non-modulated mRNA/miRNA and noise. Statistical tests find the mRNA/miRNA most significantly different between diverse groups of samples. The Student's t-test is an example of a robust statistical test that can be used to find significant differences between two groups. The lower the p-value, the more compelling the evidence that the gene shows a difference between the different groups. Nevertheless, since microarrays measure more than one mRNA/miRNA at a time, tens of thousands of statistical tests may be performed at one time. Because of this, one is unlikely to see small p-values just by chance and adjustments for this using a Sidak correction as well as a randomization/permutation experiment can be made. A p-value less than 0.05 by the t-test is evidence that the gene is significantly different. More compelling evidence is a p-value less then 0.05 after the Sidak correction is factored in. For a large number of samples in each group, a p-value less than 0.05 after the randomization/permutation test is the most compelling evidence of a significant difference.

In one embodiment, a method of generating a posterior probability score to enable diagnostic, prognostic, therapy-related, or physiological state specific biosignature scores can be arrived at by obtaining mRNA or miRNA (biomarker) expression data from a statistically significant number of patients; applying linear discrimination analysis to the data to obtain selected biomarkers; and applying weighted expression levels to the selected biomarkers with discriminate function factor to obtain a prediction model that can be applied as a posterior probability score. Other analytical tools can also be used to answer the same question such as, logistic regression and neural network approaches.

For instance, the following can be used for linear discriminant analysis:

where, $I(p_s i_d)$=The log base 2 intensity of the probe set enclosed in parenthesis. d(cp)=The discriminant function for the disease positive class $d(C_N)$=The discriminant function for the disease negative class $P(_{CP})$=The posterior p-value for the disease positive class $P(_{CN})$=The posterior p-value for the disease negative class Numerous other well-known methods of pattern recognition are available. The following references provide some examples: *Weighted Voting*: Golub et al. (1999); *Support Vector Machines*: Su et al. (2001); and Ramaswamy et al. (2001); *K-nearest Neighbors*: Ramaswamy (2001); and *Correlation Coefficients*: van't Veer et al. (2002), all of which are herein incorporated by reference in their entireties.

A biosignature portfolio, further described below, can be established such that the combination of biomarkers in the portfolio exhibit improved sensitivity and specificity relative to individual biomarkers or randomly selected combinations of biomarkers. In one embodiment, the sensitivity of the biosignature portfolio can be reflected in the fold differences, for example, exhibited by a transcript's expression in the diseased state relative to the normal state. Specificity can be reflected in statistical measurements of the correlation of the signaling of transcript expression with the condition of interest. For example, standard deviation can be a used as such a measurement. In considering a group of biomarkers for inclusion in a biosignature portfolio, a small standard deviation in expression measurements correlates with greater specificity. Other measurements of variation such as correlation coefficients can also be used in this capacity.

Another parameter that can be used to select mRNA/miRNA that generate a signal that is greater than that of the non-modulated mRNA/miRNA or noise is the use of a measurement of absolute signal difference. The signal generated by the modulated mRNA/miRNA expression is at least 20% different than those of the normal or non-modulated gene (on an absolute basis). It is even more preferred that such mRNA/miRNA produce expression patterns that are at least 30% different than those of normal or non-modulated mRNA/miRNA.

MiRNA can also be detected and measured by amplification from a biological sample and measured using methods described in U.S. Pat. No. 7,250,496, U.S. Application Publication Nos. 20070292878, 20070042380 or 20050222399 and references cited therein, each of which is herein incorporated by reference in its entirety. The microRNA can be assessed as in U.S. Pat. No. 7,888,035, entitled "METHODS FOR ASSESSING RNA PATTERNS," issued Feb. 15, 2011, which application is incorporated by reference herein in its entirety.

Peptide nucleic acids (PNAs) which are a new class of synthetic nucleic acid analogs in which the phosphate—sugar polynucleotide backbone is replaced by a flexible pseudo-peptide polymer may be utilized in analysis of a biosignature. PNAs are capable of hybridizing with high affinity and specificity to complementary RNA and DNA sequences and are highly resistant to degradation by nucleases and proteinases. Peptide nucleic acids (PNAs) are an attractive new class of probes with applications in cytogenetics for the rapid in situ identification of human chromosomes and the detection of copy number variation (CNV). Multicolor peptide nucleic acid-fluorescence in situ hybridization (PNA-FISH) protocols have been described for the identification of several human CNV-related disorders and infectious diseases. PNAs can also be utilized as molecular diagnostic tools to non-invasively measure oncogene mRNAs with tumor targeted radionuclide-PNA-peptide chimeras. Methods of using PNAs are described further in Pellestor F et al, *Curr Pharm Des.* 2008; 14(24):2439-44, Tian X et al, *Ann N Y Acad Sci.* 2005 November; 1059: 106-44, Paulasova P and Pellestor F, *Annales de Génétique*, 47 (2004) 349-358, Stender H. *Expert Rev Mol Diagn.* 2003 September; 3(5):649-55. *Review*, Vigneault et al., *Nature Methods*, 5(9), 777-779 (2008), each reference is herein incorporated by reference in its entirety. These methods can be used to screen the genetic materials isolated from a vesicle. When applying these techniques to a cell-of-origin specific vesicle, they can be used to identify a given molecular signal that directly pertains to the cell of origin.

Mutational analysis may be carried out for mRNAs and DNA, including those that are identified from a vesicle. For mutational analysis of a target or biomarker that is of RNA origin, the RNA (mRNA, miRNA or other) can be reverse transcribed into cDNA and subsequently sequenced or assayed, such as for known SNPs (by Taqman SNP assays, for example) or single nucleotide mutations, as well as using sequencing to look for insertions or deletions to determine mutations present in the cell-of-origin. Multiplexed ligation dependent probe amplification (MLPA) could alternatively be used for the purpose of identifying CNV in small and specific areas of interest. For example, once the total RNA has been obtained from isolated colon cancer-specific vesicles, cDNA can be synthesized and primers specific for exons 2 and 3 of the KRAS gene can be used to amplify these two exons containing codons 12, 13 and 61 of the KRAS gene. The same primers used for PCR amplification can be used for Big Dye Terminator sequence analysis on the ABI 3730 to identify mutations in exons 2 and 3 of KRAS. Mutations in these codons are known to confer resistance to drugs such as Cetuximab and Panitumimab. Methods of conducting mutational analysis are described in Maheswaran S et al, Jul. 2, 2008 (10.1056/NEJMoa0800668) and Orita, M et al, *PNAS* 1989, (86): 2766-70, each of which is herein incorporated by reference in its entirety.

Other methods of conducting mutational analysis include miRNA sequencing. Applications for identifying and profiling miRNAs can be done by cloning techniques and the use of capillary DNA sequencing or "next-generation" sequencing technologies. The new sequencing technologies currently available allow the identification of low-abundance miRNAs or those exhibiting modest expression differences between samples, which may not be detected by hybridization-based methods. Such new sequencing technologies include the massively parallel signature sequencing (MPSS) methodology described in Nakano et al. 2006*, Nucleic Acids Res.* 2006; 34:D731-D735. doi: 10.1093/nar/gkj077, the Roche/454 platform described in Margulies et al. 2005, Nature. 2005; 437:376-380 or the Illumina sequencing platform described in Berezikov et al. Nat. Genet. 20066; 38:1375-1377, each of which is incorporated by reference in its entirety.

Additional methods to determine a biosignature includes assaying a biomarker by allele-specific PCR, which includes specific primers to amplify and discriminate between two alleles of a gene simultaneously, single-strand conformation polymorphism (SSCP), which involves the electrophoretic separation of single-stranded nucleic acids based on subtle differences in sequence, and DNA and RNA aptamers. DNA and RNA aptamers are short oligonucleotide sequences that can be selected from random pools based on their ability to bind a particular molecule with high affinity. Methods of using aptamers are described in Ulrich H et al, *Comb Chem High Throughput Screen.* 2006 September; 9(8):619-32, Ferreira C S et al, *Anal Bioanal Chem.* 2008 February; 390(4): 1039-50, Ferreira C S et al, *Tumour Biol.* 2006; 27(6):289-301, each of which is herein incorporated by reference in its entirety.

Biomarkers can also be detected using fluorescence in situ hybridization (FISH). Methods of using FISH to detect and localize specific DNA sequences, localize specific mRNAs within tissue samples or identify chromosomal abnormalities are described in Shaffer D R et al, Clin Cancer Res. 2007 April 1; 13(7):2023-9, Cappuzo F et al, *Journal of Thoracic Oncology, Volume* 2, *Number* 5, May 2007, Moroni M et al, *Lancet Oncol.* 2005 May; 6(5):279-86, each of which is herein incorporated by reference in its entirety.

Figure 64E:
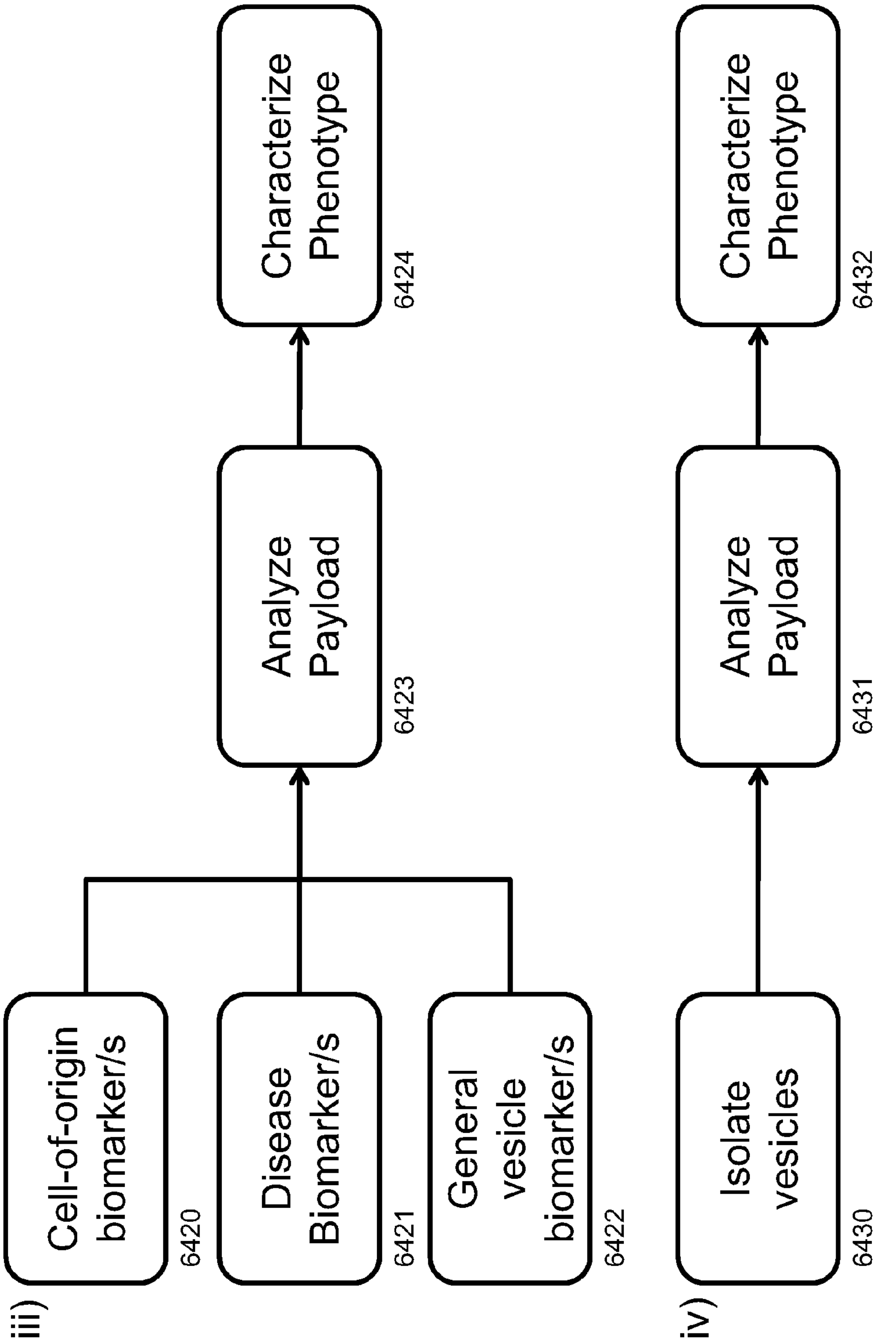
Figure 65A:
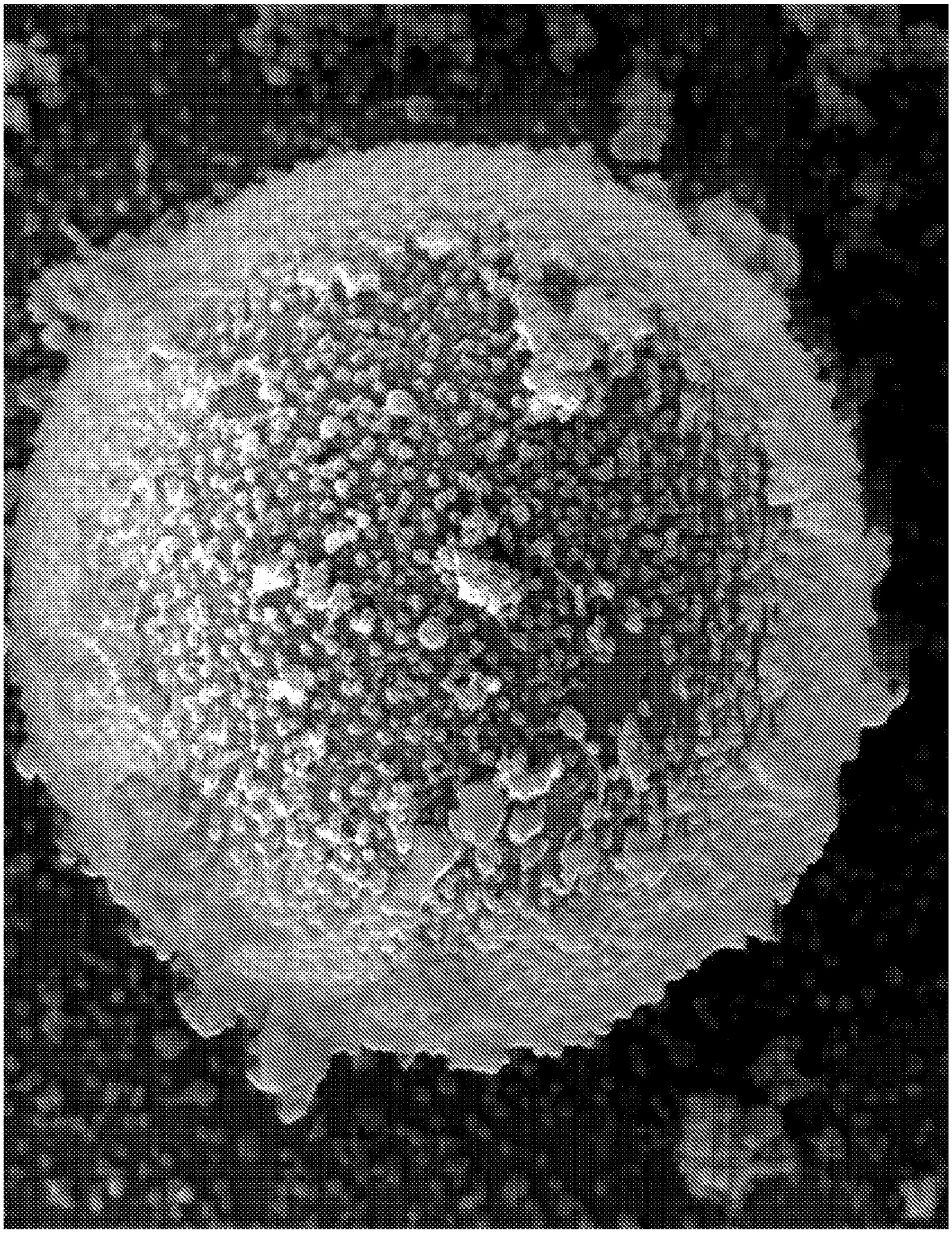
FIG. 65 depicts scanning electron micrographs (SEMs) of EpCam conjugated beads that have been incubated with VCaP vesicles. (A) A glass slide was coated with poly-L-lysine and incubated with the bead solution. After attachment, the beads were (i) fixed sequentially with glutaraldehyde and osmium tetroxide, 30 min per fix step with a few washes in between; (ii) gradually dehydrated in acetone, 20% increments, about 5-7 min per step; (iii) critical-point dried; and (iv) sputter-coated with gold. (B) Left: depicts a higher magnification of vesicles on an EpCam coated bead as in (A). Right: depicts vesicles isolated by ultracentrifugation and adhered to a poly-L-lysine coated glass slide and fixed and stained as in (A).
Figure 65B:
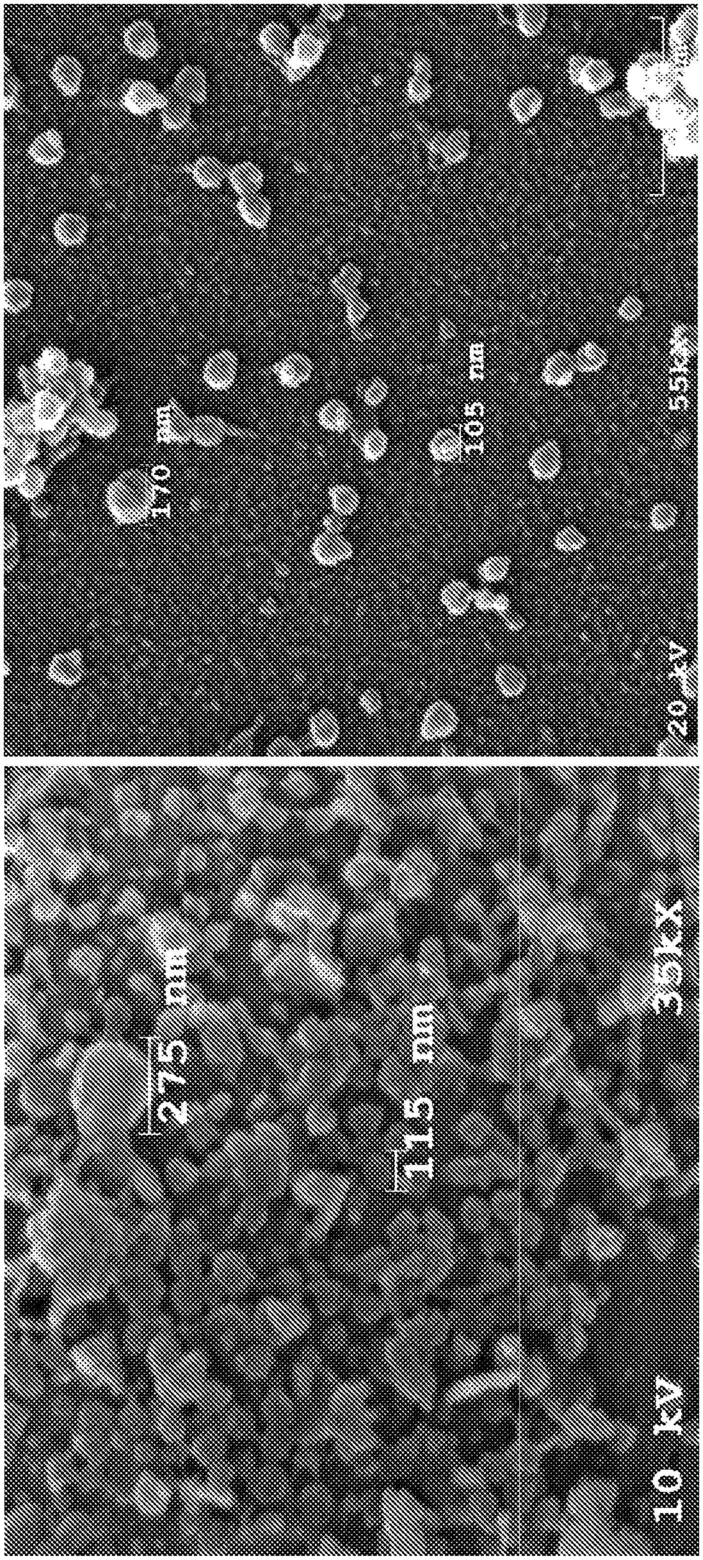

An illustrative schematic for analyzing a population of vesicles for their payload is presented in FIG. 64E. In an embodiment, the methods of the invention include characterizing a phenotype by capturing vesicles (230) and determining a level of microRNA species contained therein (231), thereby characterizing the phenotype (232).

A biosignature comprising a circulating biomarker or vesicle can comprise a binding agent thereto. The binding agent can be a DNA, RNA, aptamer, monoclonal antibody, polyclonal antibody, Fabs, Fab', single chain antibody, synthetic antibody, aptamer (DNA/RNA), peptoid, zDNA, peptide nucleic acid (PNA), locked nucleic acid (LNA), lectin, synthetic or naturally occurring chemical compounds (including but not limited to drugs and labeling reagents).

A binding agent can used to isolate or detect a vesicle by binding to a component of the vesicle, as described above. The binding agent can be used to detect a vesicle, such as for detecting a cell-of-origin specific vesicle. A binding agent or multiple binding agents can themselves form a binding agent profile that provides a biosignature for a vesicle. One or more binding agents can be selected from FIG. 2. For example, if a vesicle population is detected or isolated using two, three or four binding agents in a differential detection or isolation of a vesicle from a heterogeneous population of vesicles, the particular binding agent profile for the vesicle population provides a biosignature for the particular vesicle population.

As an illustrative example, a vesicle for characterizing a cancer can be detected with one or more binding agents including, but not limited to, PSA, PSMA, PCSA, PSCA, B7H3, EpCam, TMPRSS2, mAB 5D4, XPSM-A9, XPSM-A10, Galectin-3, E-selectin, Galectin-1, or E4 (IgG2a kappa), or any combination thereof.

The binding agent can also be for a general vesicle biomarker, such as a "housekeeping protein" or antigen. The biomarker can be CD9, CD63, or CD81. For example, the binding agent can be an antibody for CD9, CD63, or CD81. The binding agent can also be for other proteins, such as for tissue specific or cancer specific vesicles. The binding agent can be for PCSA, PSMA, EpCam, B7H3, or STEAP. The binding agent can be for DR3, STEAP, epha2, TMEM211, MFG-E8, Annexin V, TF, unc93A, A33, CD24, NGAL, EpCam, MUC17, TROP2, or TETS. For example, the binding agent can be an antibody or aptamer for PCSA, PSMA, EpCam, B7H3, DR3, STEAP, epha2, TMEM211, MFG-E8, Annexin V, TF, unc93A, A33, CD24, NGAL, EpCam, MUC17, TROP2, or TETS.

Figure 66:
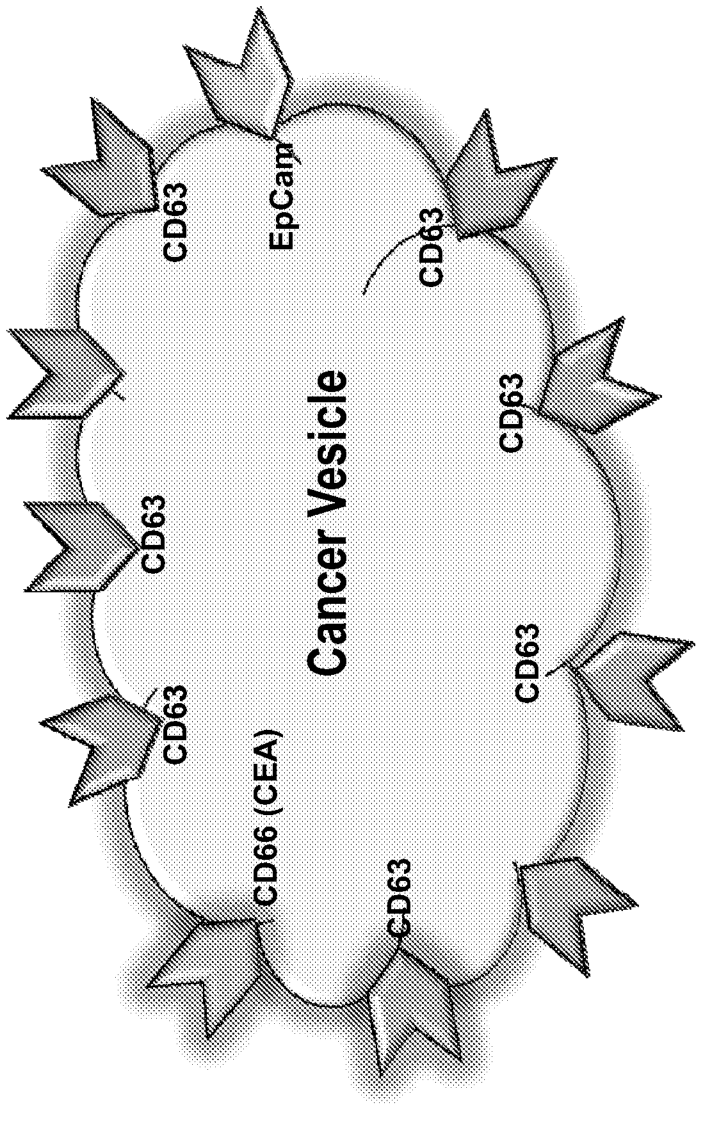
FIG. 66 is a schematic of protein expression patterns. Different proteins are typically not distributed evenly or uniformly on a vesicle shell. Vesicle-specific proteins are typically more common, while cancer-specific proteins are less common. Capture of a vesicle can be more easily accomplished using a more common, less cancer-specific protein, and cancer-specific proteins used in the detection phase.
Figure 67A:
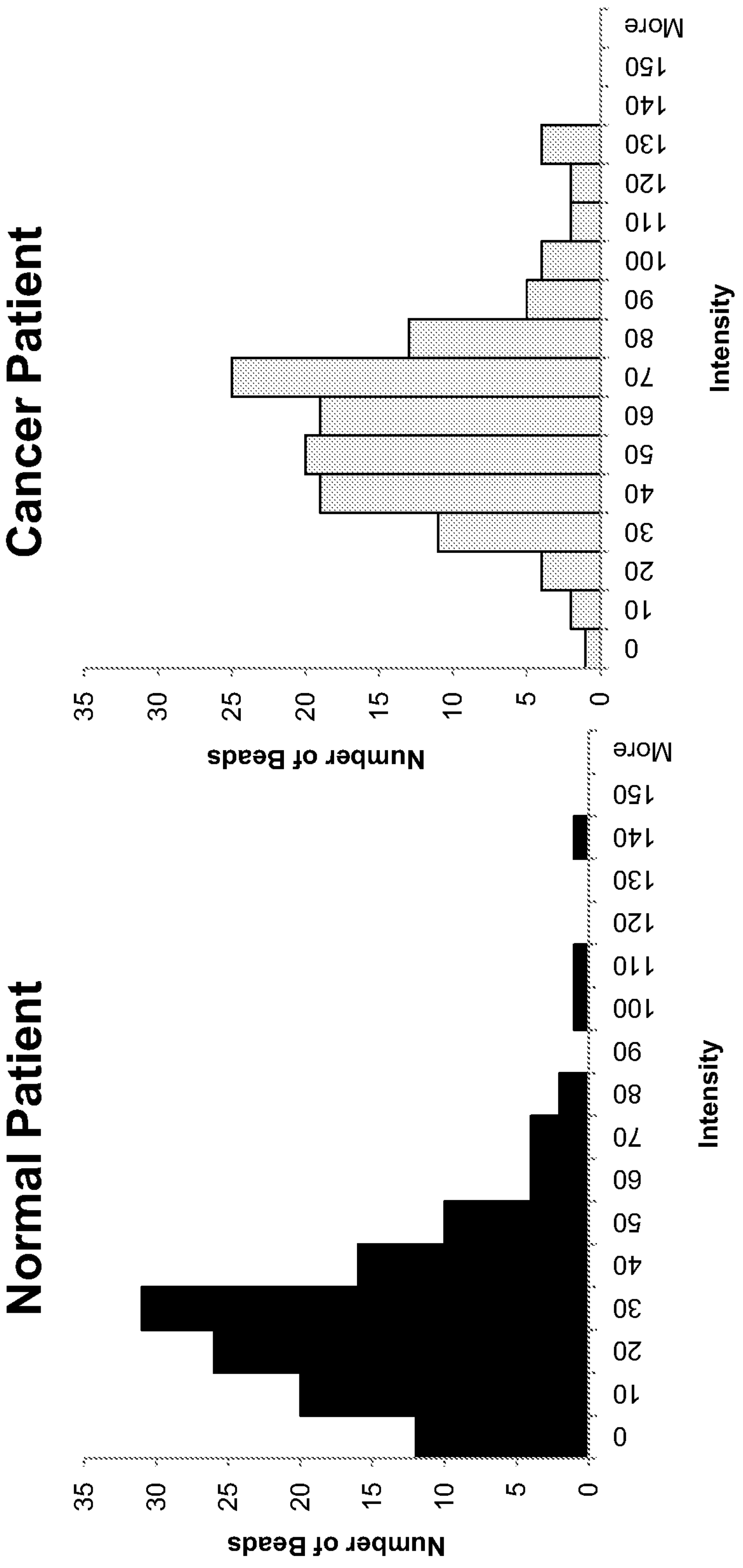
FIG. 67 illustrates a method of depicting results using a bead based method of detecting vesicles from a subject. (A) For an individual patient, a graph of the bead enumeration and signal intensity using a screening scheme as depicted in FIG. 64B, where ~100 capture beads are used for each capture/detection combination assay per patient. For a given patient, the output shows number of beads detected vs. intensity of signal. The number of beads captured at a given intensity is an indication of how frequently a vesicle expresses the detection protein at that intensity. The more intense the signal for a given bead, the greater the expression of the detection protein. (B) is a normalized graph obtained by combining normal patients into one curve and cancer patients into another, and using bio-statistical analysis to differentiate the curves. Data from each individual is normalized to account for variation in the number of beads read by the detection machine, added together, and then normalized again to account for the different number of samples in each population.
Figure 67B:
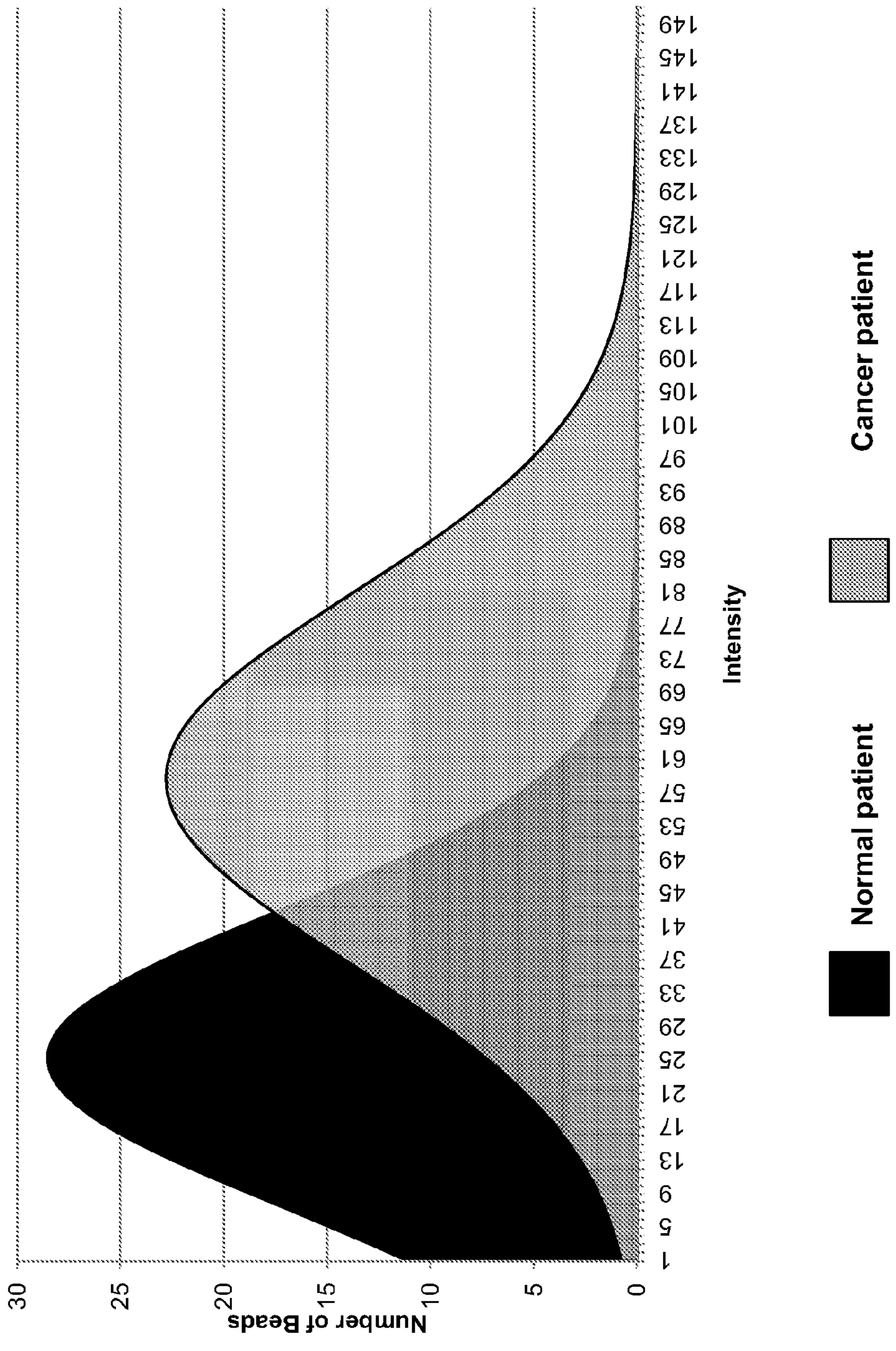
Figure 68A:
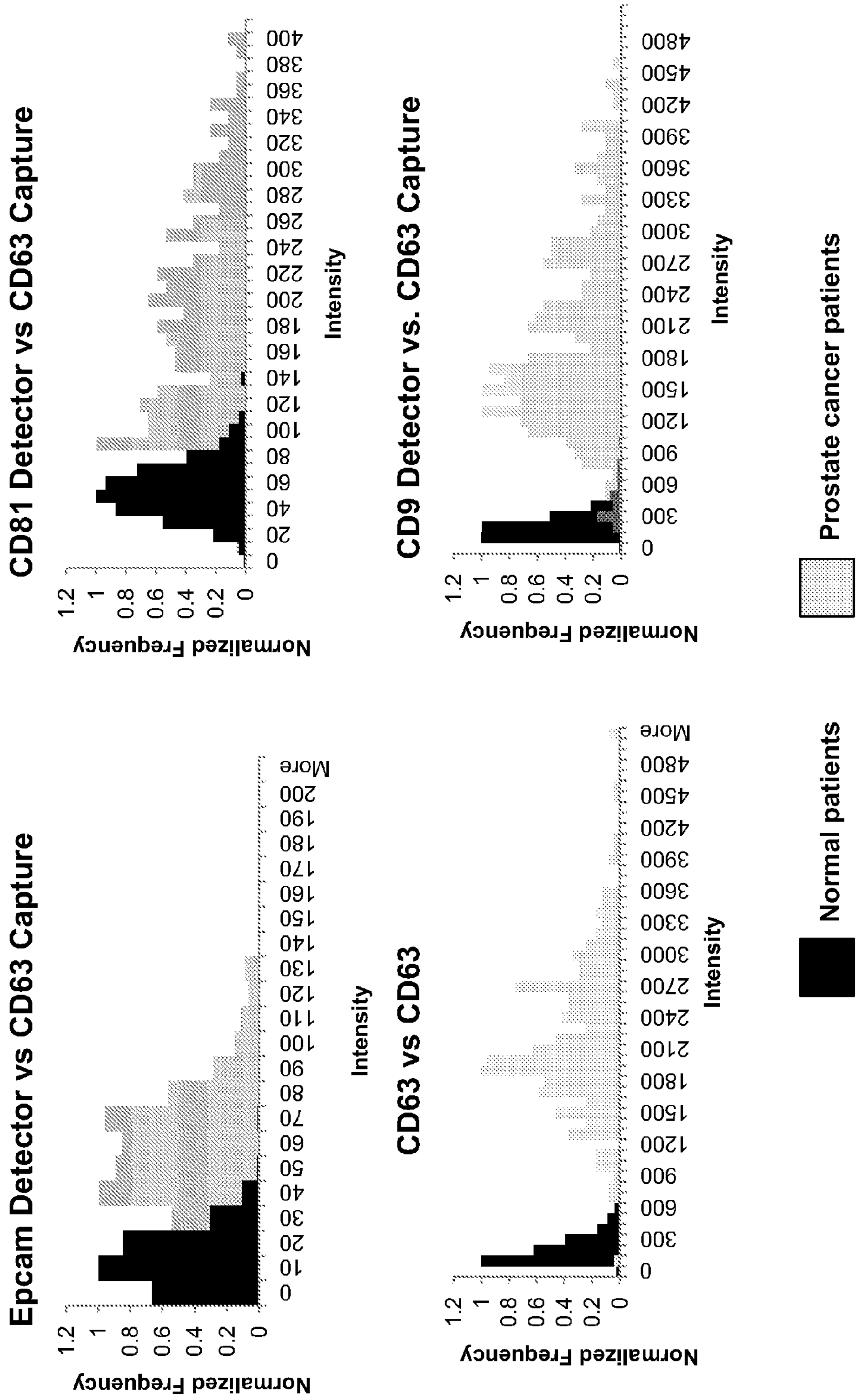
FIG. 68 illustrates prostate cancer biosignatures. (A) is a histogram of intensity values collected from a multiplexing experiment using a microsphere platform, where beads were functionalized with CD63 antibody, incubated with vesicles purified from patient plasma, and then labeled with a phycoerythrin (PE) conjugated EpCam antibody. The darker shaded bars (blue) represent the population from 12 normal subjects and the lighter shaded bars (green) are from 7 stage 3 prostate cancer patients. (B) is a normalized graph for each of the histograms shown in (A), as described in FIG. 67. The distributions are of a Gaussian fit to intensity values from the microsphere results of (A) for both prostate patient samples and normal samples. (C) is an example of one of the prostate biosignatures shown in (B), the CD63 versus CD63 biosignature (upper graph) where CD63 is used as the detector and capture antibody. The lower three panels show the results of flow cytometry on three prostate cancer cell lines (VCaP, LNcap, and 22RV1). Points above the horizontal line indicate beads that captured vesicles with CD63 that contain B7H3. Beads to the right of the vertical line indicate beads that have captured vesicles with CD63 that have PSMA. Those beads that are above and to the right of the lines have all three antigens. CD63 is a surface protein that is associated with vesicles, PSMA is surface protein that is associated with prostate cells, and B7H3 is a surface protein that is associated with aggressive cancers (specifically prostate, ovarian, and non-small-cell lung). The combination of all three antigens together identifies vesicles that are from cancer prostate cells. The majority of CD63 expressing prostate cancer vesicles also have prostate-specific membrane antigen, PSMA, and B7H3 (implicated in regulation of tumor cell migration and invasion and an indicator of aggressive cancer as well as clinical outcome). (D) is a prostate cancer vesicle topography. The upper panels show the results of capturing and labeling with CD63, CD9, and CD81 in various combinations. Almost all points are in the upper right quadrant indicating that these three markers are highly coupled. The lower row depicts the results of capturing cell line vesicles with B7H3 and labeling with CD63 and PSMA. Both VCaP and 22RV1 show that most vesicles captured with B7H3 also have CD63, and that there are two populations, those with PSMA and those without. The presence of B7H3 may be an indication of how aggressive the cancer is, as LNcap does not have a high amount of B7H3 containing vesicles (not many spots with CD63). LnCap is an earlier stage prostate cancer analogue cell line.
Figure 68B:
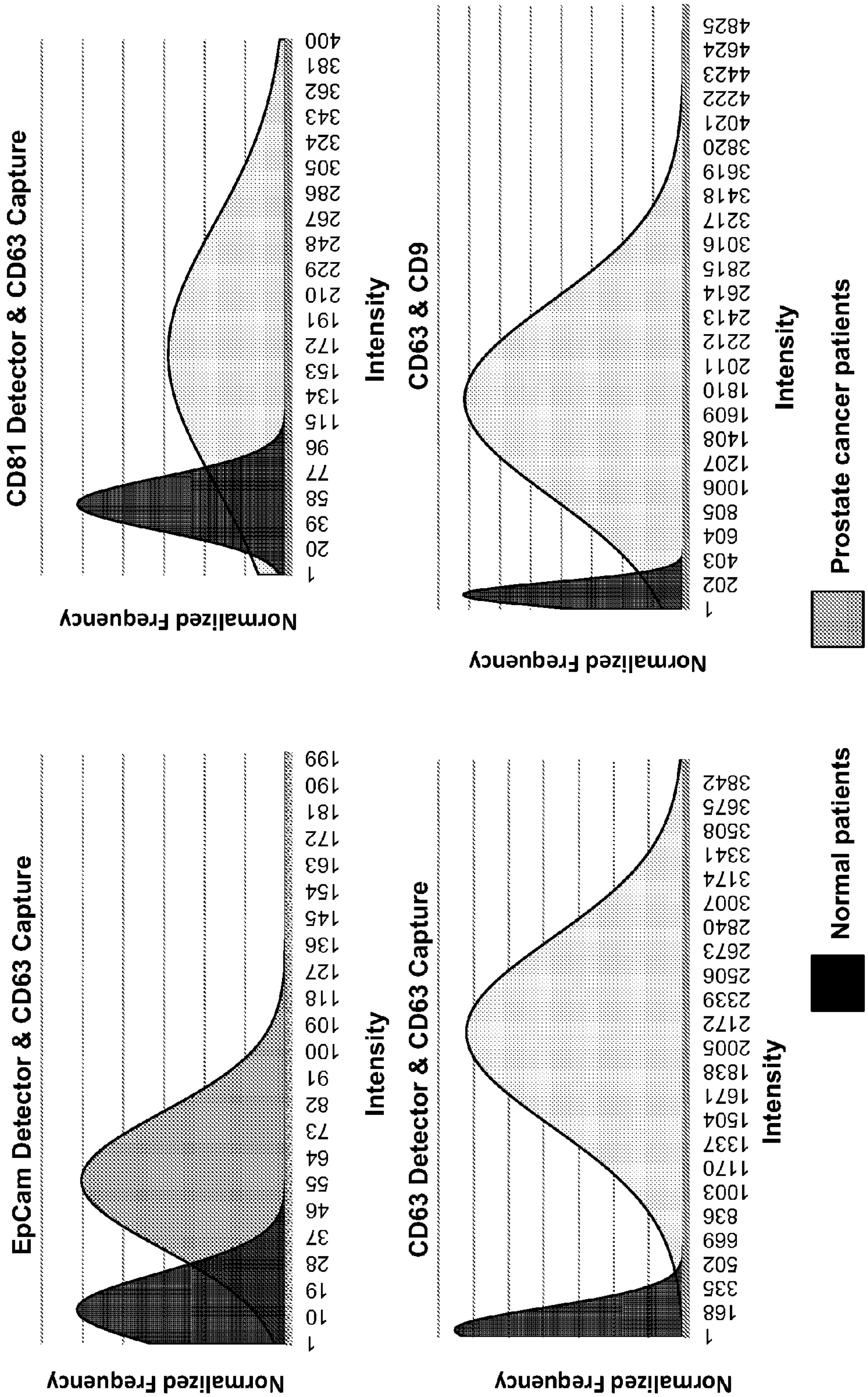
Figure 68C:
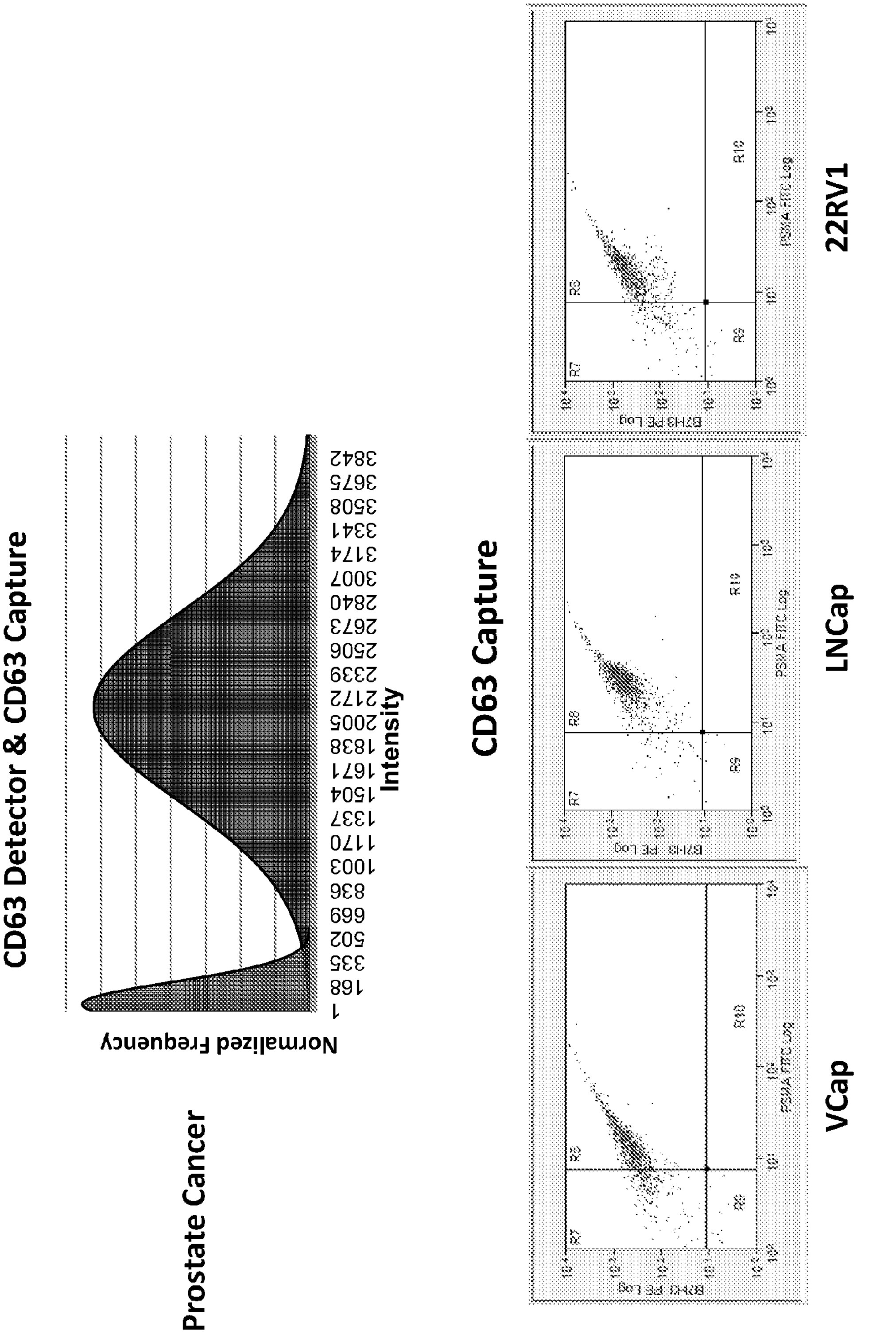
Figure 68D:
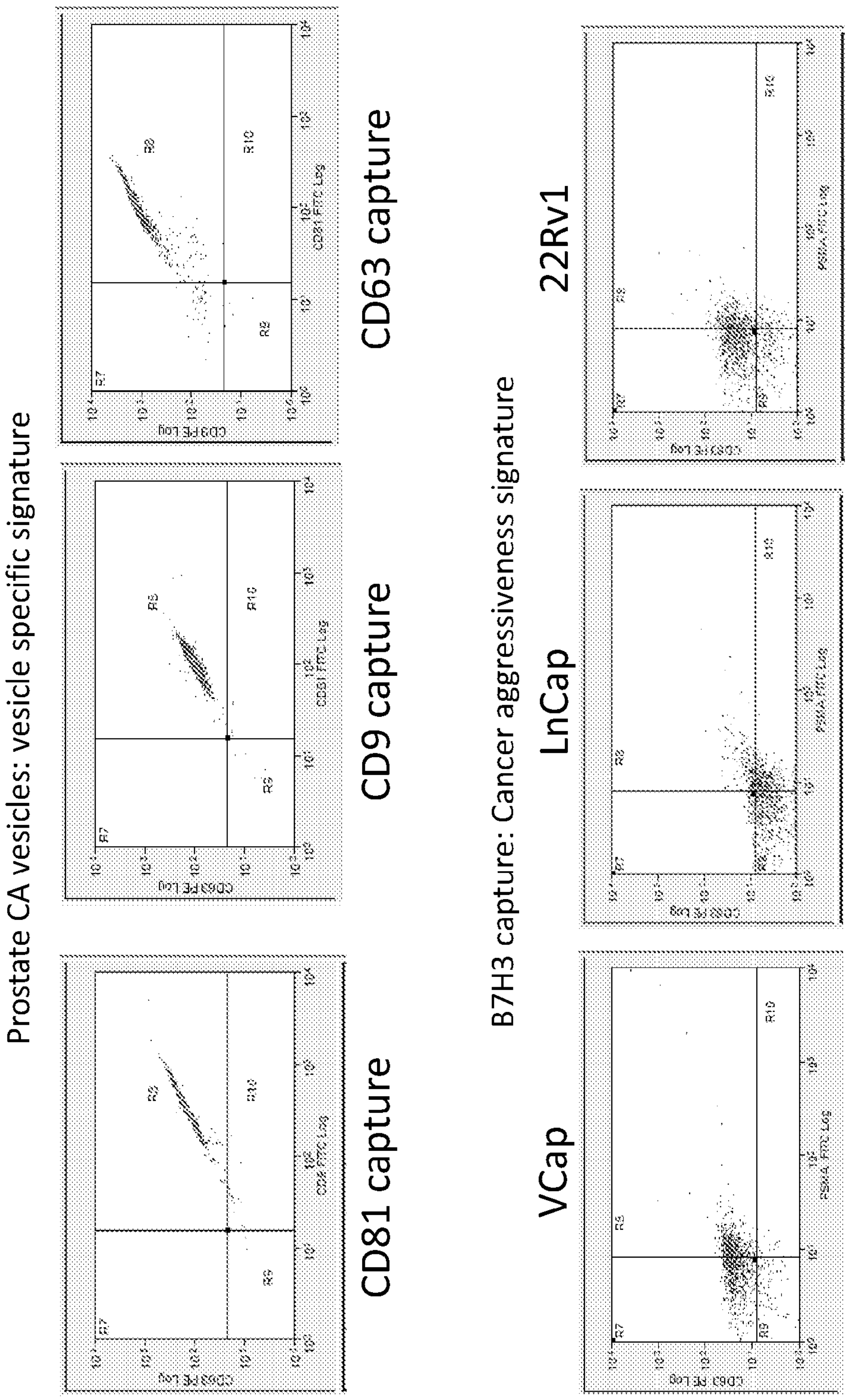

Various proteins are not typically distributed evenly or uniformly on a vesicle shell. See, e.g., FIG. 66, which illustrates a schematic of protein expression patterns. Vesicle-specific proteins are typically more common, while cancer-specific proteins are less common. In some embodiments, capture of a vesicle is accomplished using a more common, less cancer-specific protein, such as one or more housekeeping proteins or antigen or general vesicle antigen (e.g., a tetraspanin), and one or more cancer-specific biomarkers and/or one or more cell-of-origin specific biomarkers is used in the detection phase. In another embodiment, one or more cancer-specific biomarkers and/or one or more cell-of-origin specific biomarkers are used for capture, and one or more housekeeping proteins or antigen or general vesicle antigen (e.g., a tetraspanin) is used for detection. In embodiments, the same biomarker is used for both capture and detection. Different binding agents for the same biomarker can be used, such as antibodies or aptamers that bind different epitopes of an antigen.

Additional cellular binding partners or binding agents may be identified by any conventional methods known in the art, or as described herein, and may additionally be used as a diagnostic, prognostic or therapy-related marker.

As an illustrative example, a vesicle for analysis for lung cancer can be detected with one or more binding agents including, but not limited to, SCLC specific aptamer HCA 12, SCLC specific aptamer HCC03, SCLC specific aptamer HCH07, SCLC specific aptamer HCHO I, A-p50 aptamer (NF-KB), Cetuximab, Panitumumab, Bevacizumab, L19 Ab, F16 Ab, anti-CD45 (anti-ICAM-1, aka UV3), or L2G7 Ab (anti-HGF), or any combination thereof.

A vesicle for characterizing colon cancer can be detected with one or more binding agents including, but not limited to, angiopoietin 2 specific aptamer, beta-catenin aptamer, TCF1 aptamer, anti-Derlin1 ab, anti-RAGE, mAbgb3.1, Galectin-3, Cetuximab, Panitumumab, Matuzumab, Bevacizumab, or Mac-2, or any combination thereof.

A vesicle for characterizing adenoma versus colorectal cancer (CRC) can be detected with one or more binding agents including, but not limited to, Complement C3, histidine-rich glycoprotein, kininogen-1, or Galectin-3, or any combination thereof.

A vesicle for characterizing adenoma with low grade hyperplasia versus adenoma with high grade hyperplasia can be detected with a binding agent such as, but not limited to, Galectin-3 or any combination of binding agents specific for this comparison.

A vesicle for characterizing CRC versus normal state can be detected with one or more binding agents including, but not limited to, anti-ODC mAb, anti-CEA mAb, or Mac-2, or any combination thereof.

A vesicle for characterizing prostate cancer can be detected with one or more binding agents including, but not limited to, PSA, PSMA, TMPRSS2, mAB 5D4, XPSM-A9, XPSM-A10, Galectin-3, E-selectin, Galectin-1, or E4 (IgG2a kappa), or any combination thereof A vesicle for characterizing melanoma can be detected with one or more binding agents including, but not limited to, Tremelimumab (anti-CTLA4), Ipilimumumab (anti-CTLA4), CTLA-4 aptamers, STAT-3 peptide aptamers, Galectin-1, Galectin-3, or PNA, or any combination thereof.

A vesicle for characterizing pancreatic cancer can be detected with one or more binding agents including, but not limited to, H38-15 (anti-HGF) aptamer, H38-21(anti-HGF) aptamer, Matuzumab, Cetuximanb, or Bevacizumab, or any combination thereof.

A vesicle for characterizing brain cancer can be detected with one or more binding agents including, but not limited to, aptamer 111.1 (pigpen) and/or TTA1 (Tenascin-C) aptamer, or any combination thereof.

A vesicle for characterizing psoriasis can be detected with one or more binding agents including, but not limited to, E-selectin, ICAM-1, VLA-4, VCAM-1, alphaEbeta7, or any combination thereof.

A vesicle for characterizing cardiovascular disease (CVD) can be detected with one or more binding agents including, but not limited to, RB007 (factor IXA aptamer), ARC1779 (anti VWF) aptamer, or LOX1, or any combination thereof.

A vesicle for characterizing hematological malignancies can be detected with one or more binding agents including, but not limited to, anti-CD20 and/or anti-CD52, or any combination thereof.

A vesicle for characterizing B-cell chronic lymphocytic leukemias can be detected with one or more binding agents including, but not limited to, Rituximab, Alemtuzumab, Apt48 (BCL6), R0-60, or D-R15-8, or any combination thereof.

A vesicle for characterizing B-cell lymphoma can be detected with one or more binding agents including, but not limited to, Ibritumomab, Tositumomab, Anti-CD20 Antibodies, Alemtuzumab, Galiximab, Anti-CD40 Antibodies, Epratuzumab, Lumiliximab, HulD10, Galectin-3, or Apt48, or any combination thereof.

A vesicle for characterizing Burkitt's lymphoma can be detected with one or more binding agents including, but not limited to, TD05 aptamer, IgM mAB (38-13), or any combination thereof.

A vesicle for characterizing cervical cancer can be detected with one or more binding agents including, but not limited to, Galectin-9 and/or HPVE7 aptamer, or any combination thereof.

A vesicle for characterizing endometrial cancer can be detected with one or more binding agents including, but not limited to, Galectin-1 or any combinations of binding agents specific for endometrial cancer.

A vesicle for characterizing head and neck cancer can be detected with one or more binding agents including, but not limited to, (111)In-cMAb U36, anti-LOXL4, U36, BIWA-1, BIWA-2, BIWA-4, or BIWA-8, or any combination thereof.

A vesicle for characterizing IBD can be detected with one or more binding agents including, but not limited to, ACCA (anti-glycan Ab), ALCA(anti-glycan Ab), or AMCA (anti-glycan Ab), or any combination thereof.

A vesicle for characterizing diabetes can be detected with one or more binding agents including, but not limited to, RBP4 aptamer or any combination of binding agents specific for diabetes.

A vesicle for characterizing fibromyalgia can be detected with one or more binding agents including, but not limited to, L-selectin or any combination of binding agents specific for fibromyalgia.

A vesicle for characterizing multiple sclerosis (MS) can be detected with one or more binding agents including, but not limited to, Natalizumab (Tysabri) or any combination of binding agents specific for MS.

In addition, a vesicle for characterizing rheumatic disease can be detected with one or more binding agents including, but not limited to, Rituximab (anti-CD20 Ab) and/or Keliximab (anti-CD4 Ab), or any combination of binding agents specific for rheumatic disease.

A vesicle for characterizing Alzheimer disease can be detected with one or more binding agents including, but not limited to, TH14-BACE1 aptapers, S10-BACE1 aptapers, anti-Abeta, Bapineuzumab (AAB-001)—Elan, LY2062430 (anti-amyloid beta Ab)-Eli Lilly, or BACE1-Anti sense, or any combination thereof.

A vesicle for characterizing Prion specific diseases can be detected with one or more binding agents including, but not limited to, rhuPrP(c) aptamer, DP7 aptamer, Thioaptamer 97, SAF-93 aptamer, 15B3 (anti-PrPSc Ab), monoclonal anti PrPSc antibody P1:1, 1.5D7, 1.6F4 Abs, mab 14D3, mab 4F2, mab 8G8, or mab 12F10, or any combination thereof.

A vesicle for characterizing sepsis can be detected with one or more binding agents including, but not limited to, HA-1A mAb, E-5 mAb, TNF-alpha MAb, Afelimomab, or E-selectin, or any combination thereof.

A vesicle for characterizing schizophrenia can be detected with one or more binding agents including, but not limited to, L-selectin and/or N-CAM, or any combination of binding agents specific for schizophrenia.

A vesicle for characterizing depression can be detected with one or more binding agents including, but not limited to, GPIb or any combination of binding agents specific for depression.

A vesicle for characterizing GIST can be detected with one or more binding agents including, but not limited to, ANTI-DOG 1 Ab or any combination of binding agents specific for GIST.

A vesicle for characterizing esophageal cancer can be detected with one or more binding agents including, but not limited to, CaSR binding agent or any combination of binding agents specific for esophageal cancer.

A vesicle for characterizing gastric cancer can be detected with one or more binding agents including, but not limited to, Calpain nCL-2 binding agent and/or drebrin binding agent, or any combination of binding agents specific for gastric cancer.

A vesicle for characterizing COPD can be detected with one or more binding agents including, but not limited to, CXCR3 binding agent, CCR5 binding agent, or CXCR6 binding agent, or any combination of binding agents specific for COPD.

A vesicle for characterizing asthma can be detected with one or more binding agents including, but not limited to, VIP binding agent, PACAP binding agent, CGRP binding agent, NT3 binding agent, YKL-40 binding agent, S-nitrosothiols, SCCA2 binding agent, PA1 binding agent, amphiregulin binding agent, or Periostin binding agent, or any combination of binding agents specific for asthma.

A vesicle for characterizing vulnerable plaque can be detected with one or more binding agents including, but not limited to, Gd-DTPA-g-mimRGD (Alpha v Beta 3 integrin binding peptide), or MMP-9 binding agent, or any combination of binding agents specific for vulnerable plaque.

A vesicle for characterizing ovarian cancer can be detected with one or more binding agents including, but not limited to, (90) Y-muHMFG 1 binding agent and/or OC 125 (anti-CA 125 antibody), or any combination of binding agents specific for ovarian cancer.

The binding agent can also be for a general vesicle biomarker, such as a "housekeeping protein" or antigen. The biomarker can be CD9, CD63, or CD81. For example, the binding agent can be an antibody for CD9, CD63, or CD81. The binding agent can also be for other proteins, such as for prostate specific or cancer specific vesicles. The binding agent can be for PCSA, PSMA, EpCam, B7H3, or STEAP. For example, the binding agent can be an antibody for PCSA, PSMA, EpCam, B7H3, or STEAP.

Furthermore, additional cellular binding partners or binding agents may be identified by any conventional methods known in the art, or as described herein, and may additionally be used as a diagnostic, prognostic or therapy-related marker.

Biosignatures for Prostate Cancer, Colon Cancer and Ovarian Cancer

Prostate Cancer

A biosignature, such as the level of vesicles with a particular biosignature, can be used to characterize prostate cancer. As described above, a biosignature for prostate cancer can comprise a binding agent associated with prostate cancer (for example, as shown in FIG. 2), and one or more additional biomarkers, such as shown in FIG. 19. For example, a biosignature for prostate cancer can comprise a binding agent to PSA, PSMA, TMPRSS2, mAB 5D4, XPSM-A9, XPSM-A10, Galectin-3, E-selectin, Galectin-1, E4 (IgG2a kappa), or any combination thereof, with one or more additional biomarkers, such as one or more miRNA, one or more DNA, one or more additional peptide, protein, or antigen associated with prostate cancer, such as, but not limited to, those shown in FIG. 19.

A biosignature for prostate cancer can comprise an antigen associated with prostate cancer (for example, as shown in FIG. 1), and one or more additional biomarkers, such as shown in FIG. 19. A biosignature for prostate cancer can comprise one or more antigens associated with prostate cancer, such as, but not limited to, KIA1, intact fibronectin, PSA, TMPRSS2, FASLG, INFSF10, PSMA, NGEP, IL-7RI, CSCR4, CysLT1R, TRPM8, Kv1.3, TRPV6, TRPM8, PSGR, MISIIR, or any combination thereof. The biosignature for prostate cancer can comprise one or more of the aforementioned antigens and one or more additional biomarkers, such as, but not limited to miRNA, mRNA, DNA, or any combination thereof.

A biosignature for prostate cancer can also comprise one or more antigens associated with prostate cancer, such as, but not limited to, KIA1, intact fibronectin, PSA, TMPRSS2, FASLG, INFSF10, PSMA, NGEP, IL-7RI, CSCR4, CysLT1R, TRPM8, Kv1.3, TRPV6, TRPM8, PSGR, MISIIR, or any combination thereof, and one or more miRNA biomarkers, such as, but not limited to, miR-202, miR-210, miR-296, miR-320, miR-370, miR-373, miR-498, miR-503, miR-184, miR-198, miR-302c, miR-345, miR-491, miR-513, miR-32, miR-182, miR-31, miR-26a-1/2, miR-200c, miR-375, miR-196a-1/2, miR-370, miR-425, miR-425, miR-194-1/2, miR-181a-1/2, miR-34b, let-7i, miR-188, miR-25, miR-106b, miR-449, miR-99b, miR-93, miR-92-1/2, miR-125a, miR-141, let-7a, let-7b, let-7c, let-7d, let-7g, miR-16, miR-23a, miR-23b, miR-26a, miR-92, miR-99a, miR-103, miR-125a, miR-125b, miR-143, miR-145, miR-195, miR-199, miR-221, miR-222, miR-497, let-7f, miR-19b, miR-22, miR-26b, miR-27a, miR-27b, miR-29a, miR-29b, miR-30_5p, miR-30c, miR-100, miR-141, miR-148a, miR-205, miR-520h, miR-494, miR-490, miR-133a-1, miR-1-2, miR-218-2, miR-220, miR-128a, miR-221, miR-499, miR-329, miR-340, miR-345, miR-410, miR-126, miR-205, miR-7-1/2, miR-145, miR-34a, miR-487, or let-7b, or any combination thereof.

Furthermore, the miRNA for a prostate cancer biosignature can be a miRNA that interacts with PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, TOP2B, or any combination thereof, such as those described herein and depicted in FIG. 60. The miRNA can also be miR-9, miR-629, miR-141, miR-671-3p, miR-491, miR-182, miR-125a-3p, miR-324-5p, miR-148B, miR-222, or any combination thereof.

The biosignature for prostate cancer can comprise one or more antigens associated with prostate cancer, such as, but not limited to, KIA1, intact fibronectin, PSA, TMPRSS2, FASLG, TNFSF10, PSMA, NGEP, IL-7RI, CSCR4, CysLT1R, TRPM8, Kv1.3, TRPV6, TRPM8, PSGR, MISIIR, or any combination thereof, and one or more additional biomarkers such as, but not limited to, the aforementioned miRNAs, mRNAs (such as, but not limited to, AR or PCA3), snoRNA (such as, but not limited to, U50) or any combination thereof.

The biosignature can also comprise one or more gene fusions, such as ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4.

A vesicle can be isolated, assayed, or both, for one or more miRNA and one or more antigens associated with prostate cancer to provide a diagnostic, prognostic or theranostic profile, such as the stage of the cancer, the efficacy of the cancer, or other characteristics of the cancer. Alternatively, the vesicle can be directly assayed from a sample, such that the vesicle is not purified or concentrated prior to assaying for one or more miRNA or antigens associated with prostate cancer.

As depicted in FIG. 68, a prostate cancer biosignature can comprise assaying EpCam, CD63, CD81, CD9, or any combination thereof, of a vesicle. The prostate cancer biosignature can comprise detection of EpCam, CD9, CD63, CD81, PCSA or any combination thereof. For example, the prostate cancer biosignature can comprise EpCam, CD9, CD63 and CD81 or PCSA, CD9, CD63 and CD81 (see for example, FIG. 70A). The prostate cancer biosignature can also comprise PCSA, PSMA, B7H3, or any combination thereof (see for example, FIG. 70B).

Furthermore, assessing a plurality of biomarkers can provide increased sensitivity, specificity, or signal intensity, as compared to assessing less than a plurality of biomarkers. For example, assessing PSMA and B7H3 can provide increased sensitivity in detection as compared to assessing PSMA or B7H3 alone. Assessing CD9 and CD63 can provide increased sensitivity in detection as compared to assessing CD9 or CD63 alone. In one embodiment, one or more of the following biomarkers are detected: EpCam, CD9, PCSA, CD63, CD81, PSMA, B7H3, PSCA, ICAM, STEAP, and EGFR. In another embodiment, EpCam+, CK+, CD45− vesicles are detected.

Prostate cancer can also be characterized based on meeting at least 1, 2, 3, 4, 5, 6, 7, 8, 9, or 10 criteria. For example, a number of different criteria can be used: 1) if the amount of vesicles in a sample from a subject is higher than a reference value; 2) if the amount of prostate cell derived vesicles is higher than a reference value; and 3) if the amount of vesicles with one or more cancer specific biomarkers is higher than a reference value, the subject is diagnosed with prostate cancer. The method can further include a quality control measure.

In another embodiment, one or more biosignatures of a vesicle is used for the diagnosis between normal prostate and prostate cancer, or between normal prostate, BPH and PCa. Any appropriate biomarker disclosed herein can be used to distinguish PCa. In some embodiments, one or more general capture agents to a biomarker (or capture biomarker, a biomarker that is detected or bound by a capture agent) can be used to capture one or more vesicles from a sample from a subject.

Prostate specific biomarkers can be used to identify prostate specific vesicles. Cancer biomarkers can be used to identify cancer specific vesicles. In some embodiments, one or more of CD9, CD81 and CD63 are used as capture biomarkers. In some embodiments, PCSA is used as a prostate biomarker. In some embodiments, the one or more cancer biomarkers comprise one or more of EpCam and B7H3. Additional biomarkers that can distinguish PCa from normal include ICAM1, EGFR, STEAP1 and PSCA.

In some embodiments, the method of identifying prostate cancer in a subject comprises: (a) capturing a population of vesicles in a sample from the subject using a capture agent; (b) determining a level of one or more cancer biomarkers in the population of vesicles; (c) determining a level of one or more prostate biomarkers in the population of vesicles; and (d) identifying the subject as having prostate cancer if the level of the one or more cancer biomarkers and the level of one or more prostate biomarkers meet a predetermined threshold value. In some embodiments, the capture agent comprises one or more binding agents for CD9, CD81 and CD63. In some embodiments, the one or more prostate biomarkers comprises PCSA. In some embodiments, the one or more cancer biomarkers comprise one or more of EpCam and B7H3. In some embodiments, the predetermined threshold value comprises a measured value of a detectable label. For example, the detectable label can be a fluorescent moiety and the value can be a luminscence value of the moeity.

In another embodiment, the prognosis of prostate cancer is determined by detecting EpCam, CK (cytokeratin), and CD45 expression, such that a poor prognosis is provided when EpCam and CK are detected or detected at a high expression, and detection of CD45 is low or absent (ie. a vesicle that is EpCam+, CK+, CD45-).

The prostate cancer can be characterizing using one or more processes disclosed herein with at least 60, 61, 62, 63, 64, 65, 66, 67, 68, 69, or 70% sensitivity. The prostate cancer can be characterized with at least 80, 81, 82, 83, 84, 85, 86, or 87% sensitivity. For example, the prostate cancer can be characterized with at least 87.1, 87.2, 87.3, 87.4, 87.5, 87.6, 87.7, 87.8, 87.9, 88.0, or 89% sensitivity, such as with at least 90% sensitivity, such as at least 91, 92, 93, 94, 95, 96, 97, 98, 99 or 100% sensitivity.

The prostate cancer of a subject can also be characterized with at least 70, 71, 72, 73, 74, 75, 76, 77, 78, 79, 80, 81, 82, 83, 84, 85, 86, 87, 88, 89, 90, 91, 92, 93, 94, 95, 96, or 97% specificity, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% specificity.

The prostate cancer can also be characterized with at least 70% sensitivity and at least 80, 90, 95, 99, or 100% specificity; at least 80% sensitivity and at least 80, 85, 90, 95, 99, or 100% specificity; at least 85% sensitivity and at least 80, 85, 90, 95, 99, or 100% specificity; at least 86% sensitivity and at least 80, 85, 90, 95, 99, or 100% specificity; at least 87% sensitivity and at least 80, 85, 90, 95, 99, or 100% specificity; at least 88% sensitivity and at least 80, 85, 90, 95, 99, or 100% specificity; at least 89% sensitivity and at least 80, 85, 90, 95, 99, or 100% specificity; at least 90% sensitivity and at least 80, 85, 90, 95, 99, or 100% specificity; at least 95% sensitivity and at least 80, 85, 90, 95, 99, or 100% specificity; at least 99% sensitivity and at least 80, 85, 90, 95, 99, or 100% specificity; or at least 100% sensitivity and at least 80, 85, 90, 95, 99, or 100% specificity.

In some embodiments, the biosignature characterizes a phenotype of a subject with at least 70, 71, 72, 73, 74, 75, 76, 77, 78, 79, 80, 81, 82, 83, 84, 85, 86, 87, 88, 89, 90, 91, 92, 93, 94, 95, 96, or 97% accuracy, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% accuracy.

In some embodiments, the biosignature characterizes a phenotype of a subject with an AUC of at least 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, or 0.97, such as with at least 0.971, 0.972, 0.973, 0.974, 0.975, 0.976, 0.977, 0.978, 0.978, 0.979, 0.980, 0.981, 0.982, 0.983, 0.984, 0.985, 0.986, 0.987, 0.988, 0.989, 0.99, 0.991, 0.992, 0.993, 0.994, 0.995, 0.996, 0.997, 0.998, 0.999 or 1.00.

Furthermore, the confidence level for determining the specificity, sensitivity, accuracy and/or AUC can be determined with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% confidence.

Gastrointestinal Cancer

The gastrointestinal tract includes without limitation the oral cavity, gums, pharynx, tongue, salivary glands, esophagus, pancreas, liver, gallbladder, small intestine (duodenum, jejunum, ileum), bile duct, stomach, large intestine (cecum, colon, rectum), appendix and anus. The biosignature can be used to detect or characterize cancers of such components, e.g., colorectal cancer (CRC), stomach cancer, intestinal cancer, liver cancer or esophageal cancer.

Colon Cancer

A colon cancer biosignature can comprise any one or more antigens for colon cancer as listed in FIG. 1, any one or more binding agents associated with isolating or detecting a vesicle for characterizing colon cancer (for example, as shown in FIG. 2), any one or more additional biomarkers, such as shown in FIG. 6.

The biosignature can comprise one or more miRNA selected from the group consisting of miR-24-1, miR-29b-2, miR-20a, miR-10a, miR-32, miR-203, miR-106a, miR-17-5p, miR-30c, miR-223, miR-126, miR-128b, miR-21, miR-24-2, miR-99b, miR-155, miR-213, miR-150, miR-107, miR-191, miR-221, miR-20a, miR-510, miR-92, miR-513, miR-19a, miR-21, miR-20, miR-183, miR-96, miR-135b, miR-31, miR-21, miR-92, miR-222, miR-181b, miR-210, miR-20a, miR-106a, miR-93, miR-335, miR-338, miR-133b, miR-346, miR-106b, miR-153a, miR-219, miR-34a, miR-99b, miR-185, miR-223, miR-211, miR-135a, miR-127, miR-203, miR-212, miR-95, or miR-17-5p, or any combination thereof. The biosignature can also comprise one or more underexpressed miRs such as miR-143, miR-145, miR-143, miR-126, miR-34b, miR-34c, let-7, miR-9-3, miR-34a, miR-145, miR-455, miR-484, miR-101, miR-145, miR-133b, miR-129, miR-124a, miR-30-3p, miR-328, miR-106a, miR-17-5p, miR-342, miR-192, miR-1, miR-34b, miR-215, miR-192, miR-301, miR-324-5p, miR-30a-3p, miR-34c, miR-331, miR-148b, miR-548c-5p, miR-362-3p and miR422a The biosignature can comprise assessing one or more genes, such as EFNB1, ERCC1, HER2, VEGF, and EGFR. A biomarker mutation for colon cancer that can be assessed in a vesicle can also include one or more mutations of EGFR, KRAS, VEGFA, B-Raf, APC, or p53. The biosignature can also comprise one or more proteins, ligands, or peptides that can be assessed of avesicle, such as AFRs, Rabs, ADAM10, CD44, NG2, ephrin-B1, MIF, b-catenin, Junction, plakoglobin, glalectin-4, RACK1, tetrspanin-8, FasL, TRAIL, A33, CEA, EGFR, dipeptidase 1, hsc-70, tetraspanins, ESCRT, TS, PTEN, or TOPO1.

A vesicle can be isolated and assayed for to provide a diagnostic, prognostic or theranostic profile, such as the stage of the cancer, the efficacy of the cancer, or other characteristics of the cancer. Alternatively, the esicle can be directly assayed from a sample, such that the vesicles are not purified or concentrated prior to assaying for a biosignature associated with colon cancer.

Figure 69A:
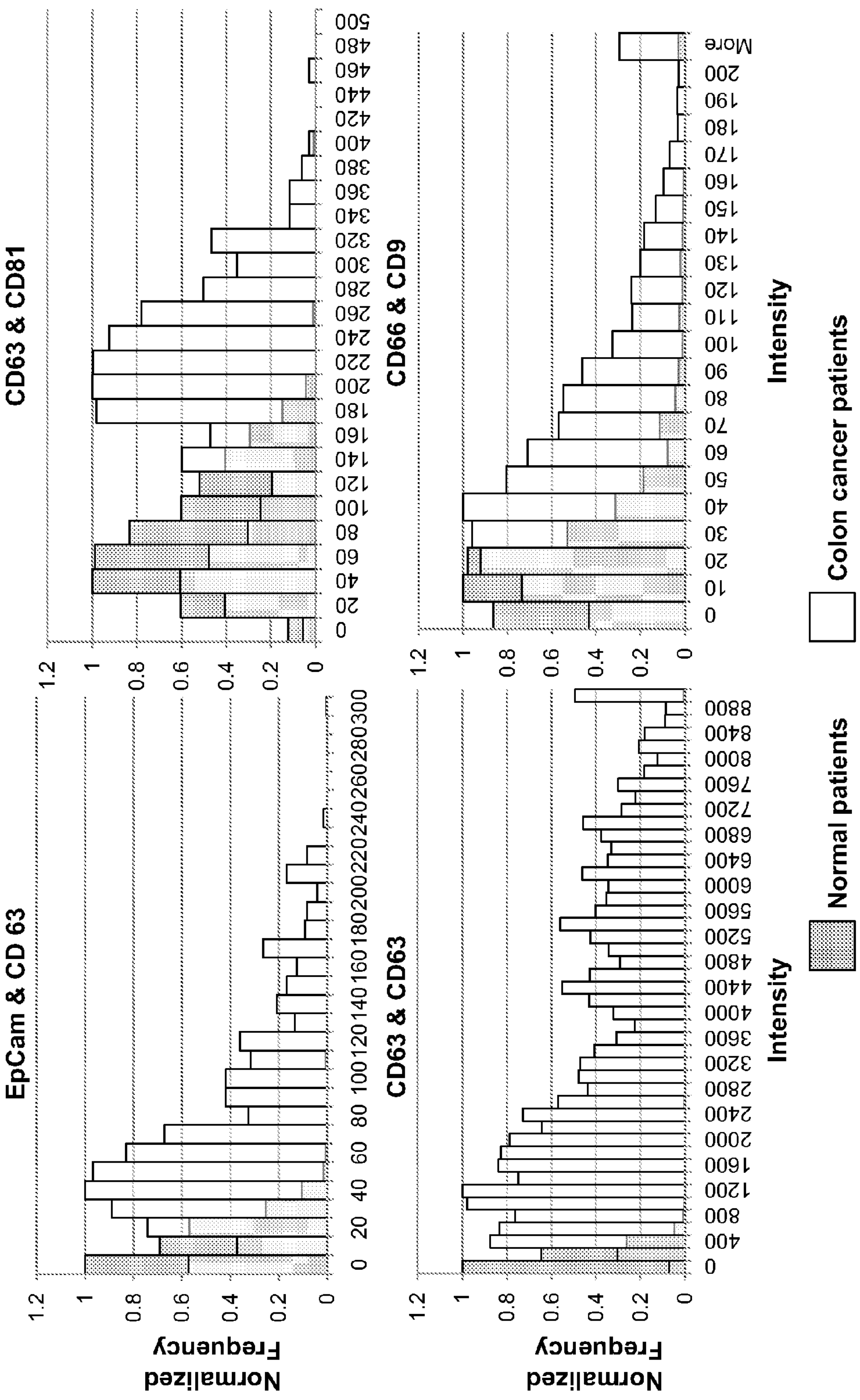
FIG. 69 illustrates colon cancer biosignatures. (A) depicts histograms of intensity values collected from various multiplexing experiments using a microsphere platform, where beads were functionalized with a capture antibody, incubated with vesicles purified form patient plasma, and then labeled with a detector antibody. The darker shaded bars (blue) represent the population from normals and the lighter shaded bars (green) are from colon cancer patients. (B) shows a normalized graph for each of the histograms shown in (A). (C) depicts a histogram of intensity values collected from a multiplexing experiment where beads where functionalized with CD66 antibody (the capture antibody), incubated with vesicles purified from patient plasma, and then labeled with a PE conjugated EpCam antibody (the detector antibody). The red population is from 6 normals and the green is from 21 colon cancer patients. Data from each individual was normalized to account for variation in the number of beads detected, added together, and then normalized again to account for the different number of samples in each population.
Figure 69B:
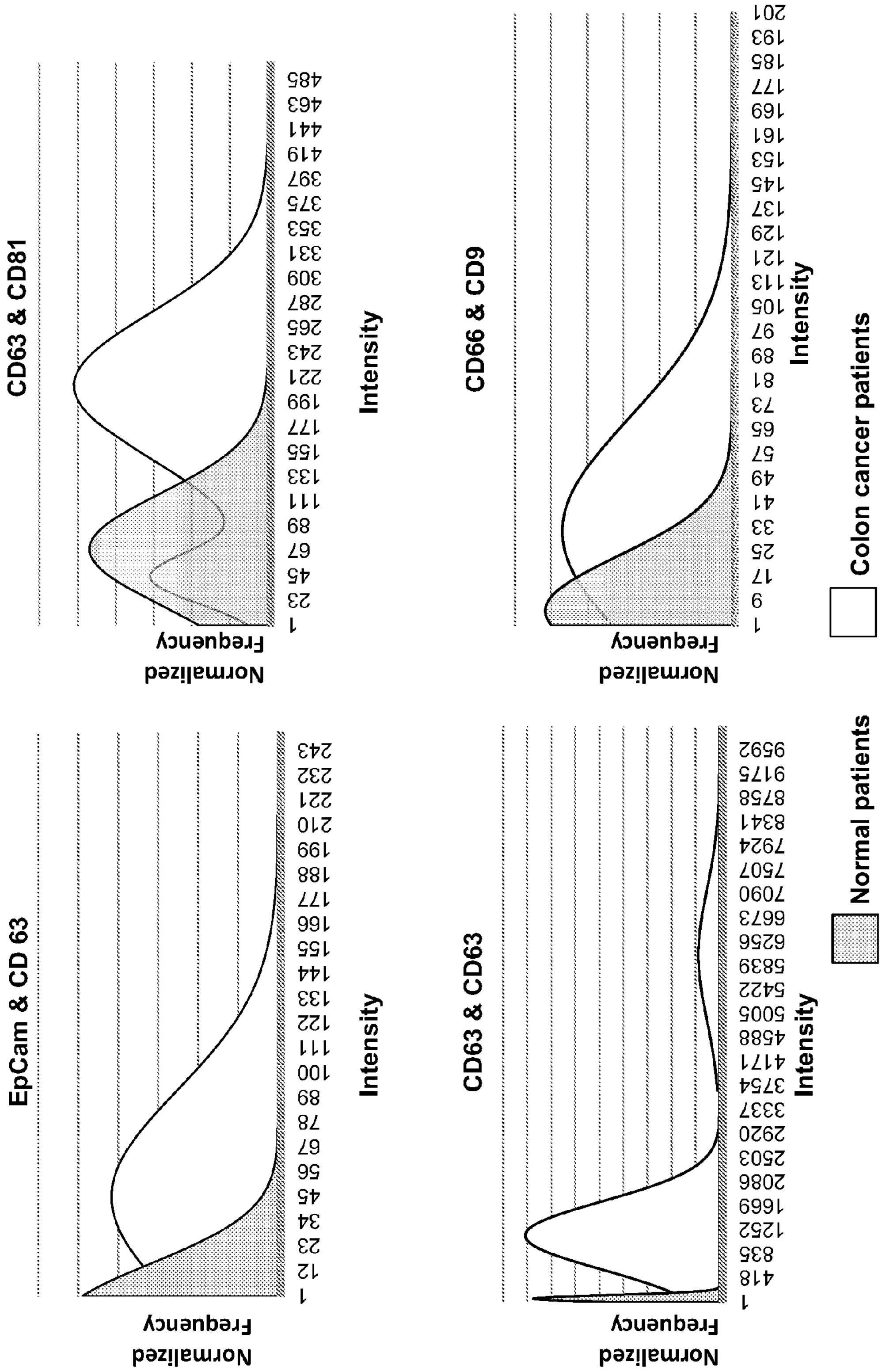
Figure 69C:
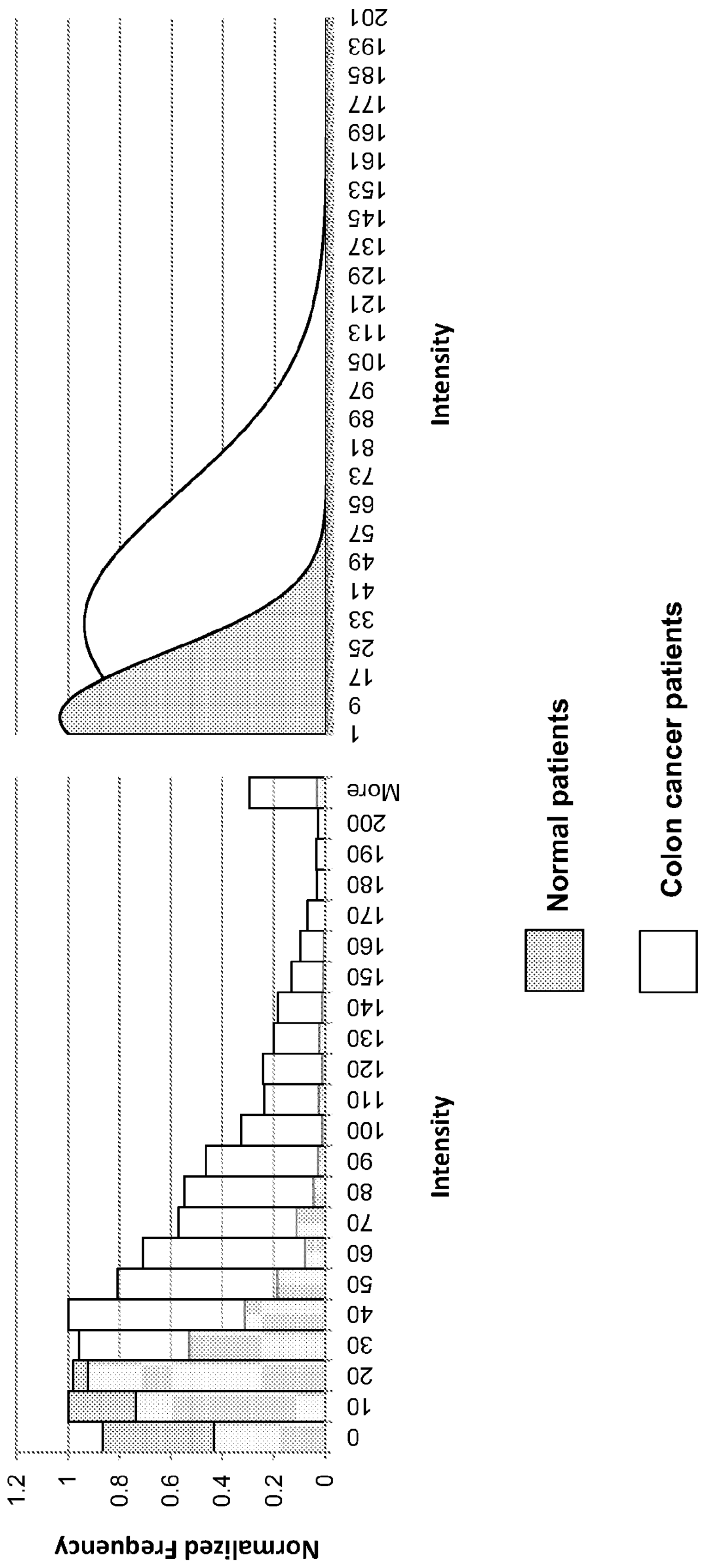
Figure 80:
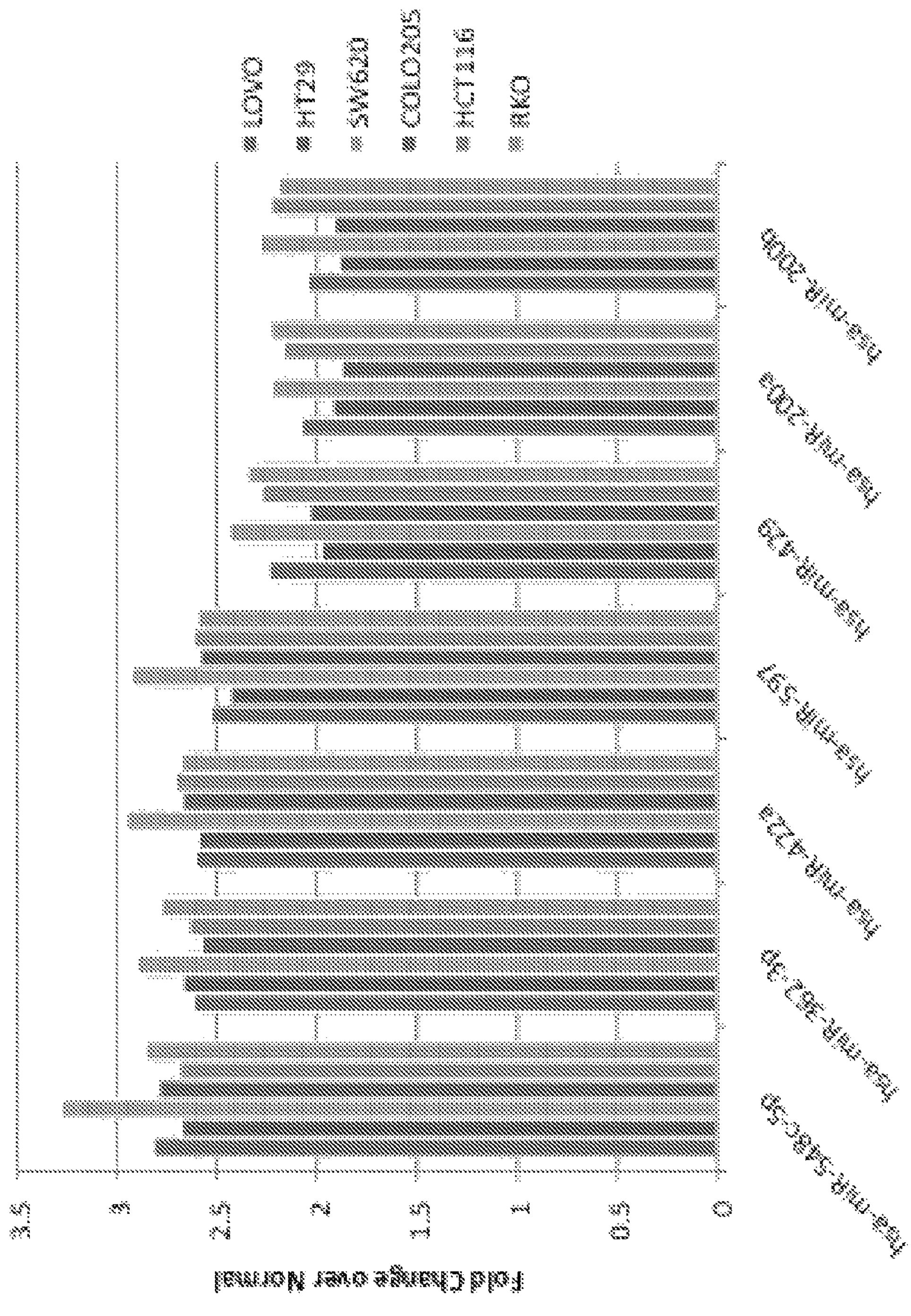
FIG. 80 illustrates TaqMan Low Density Array (TLDA) miRNA card comparison of colorectal cancer (CRC) cell lines versus normal vesicles. The CRC cell lines are indicated to the right of the plot. The Y-axis shows a fold-change in expression in the CRC cell lines compared to normal controls. The miRNAs surveyed are indicated on the X-axis, and from left to right are miR-548c-5p, miR-362-3p, miR-422a, miR-597, miR-429, miR-200a, and miR-200b. For each miR, the bars from left to right correspond to cell lines LOVO, HT29, SW260, COLO205, HCT116 and RKO. These miRNAs were not overexpressed in normal or melanoma cells.
Figure 81:
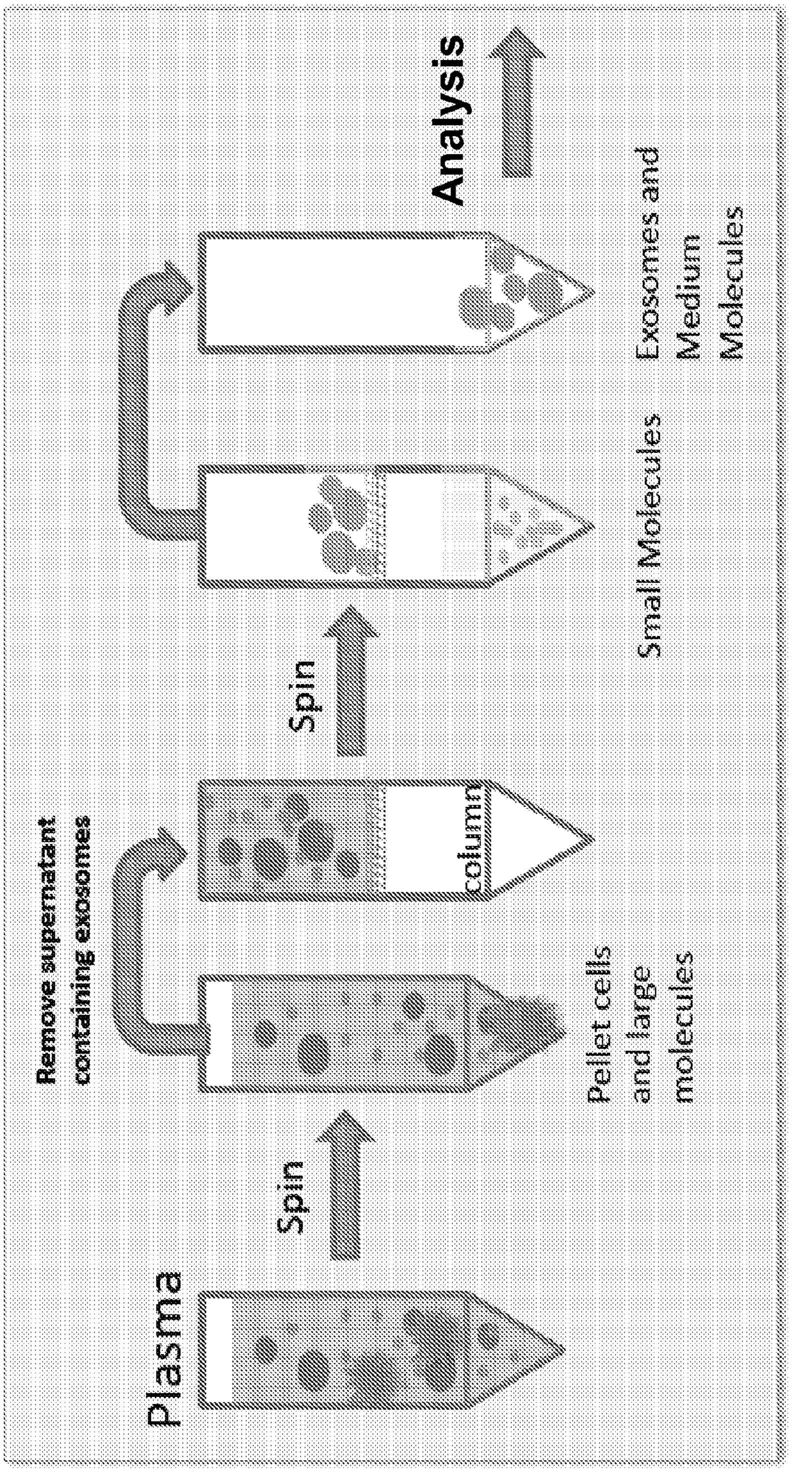
FIG. 81 represents a schematic of isolating vesicles from plasma using a column based filtering method, wherein the isolated vesicles are subsequently assessed using a microsphere platform.
Figure 82:
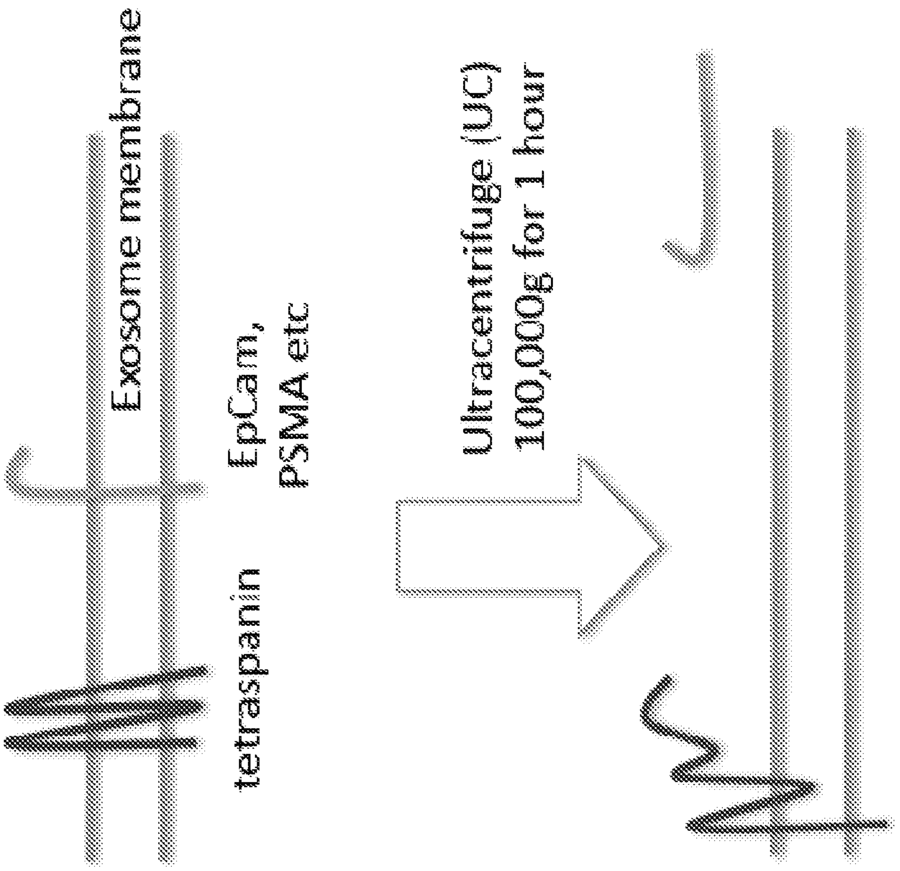
FIG. 82 represents a schematic of compression of a membrane of a vesicle due to high-speed centrifugation, such as ultracentrifugation. Such high-speed centrifugation may remove protein targets weakly anchored in the membrane as opposed to the tetraspanins which are more solidly anchored in the membrane. Without being bound by theory, as a result, ultracentifugation may reduce the cell specific targets in the vesicle, and thus not be detected in subsequent analysis of the biosignature of the vesicle.

As depicted in FIG. 69, a GI cancer, such as colon cancer, a biosignature can comprise detection of EpCam, CD63, CD81, CD9, CD66, or any combination thereof, of a vesicle. Furthermore, a colon cancer-biosignature for various stages of cancer can comprise CD63, CD9, EpCam, or any combination thereof (see for example, FIGS. 71 and 72). For example, the biosignature can comprise CD9 and EpCam. In some embodiments, the GI cancer biosignature comprises one or more miRNA selected from the group consisting of miR-548c-5p, miR-362-3p, miR-422a, miR-597, miR-429, miR-200a, and miR-200b. These miRNAs can be overexpressed in GI cancers, as shown in FIG. 80. The miRNA signature can be combined with the biomarkers listed above. The biosignatures can provide a diagnostic, prognostic or theranostic profile, such as the stage of the cancer, the efficacy of the cancer, or other characteristics of the cancer.

The colon cancer can be characterized-using one or more processes disclosed herein with at least 60, 61, 62, 63, 64, 65, 66, 67, 68, 69, or 70% sensitivity. The colon cancer can be characterized with at least 71, 72, 73, 74, 75, 76, 77, 78, 79, 80, 81, 82, 83, 84, 85, 86, or 87% sensitivity. For example, the colon cancer can be characterized with at least 87.1, 87.2, 87.3, 87.4, 87.5, 87.6, 87.7, 87.8, 87.9, 88.0, or 89% sensitivity, such as with at least 90% sensitivity, such as at least 91, 92, 93, 94, 95, 96, 97, 98, 99 or 100% sensitivity.

The colon cancer of a subject can also be characterized with at least 70, 71, 72, 73, 74, 75, 76, 77, 78, 79, 80, 81, 82, 83, 84, 85, 86, 87, 88, 89, 90, 91, 92, 93, 94, 95, 96, or 97% specificity, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% specificity.

The colon cancer can also be characterized with at least 70% sensitivity and at least 80, 90, 95, 99, or 100% specificity; at least 80% sensitivity and at least 80, 85, 90, 95, 99, or 100% specificity; at least 85% sensitivity and at least 80, 85, 90, 95, 99, or 100% specificity; at least 86% sensitivity and at least 80, 85, 90, 95, 99, or 100% specificity; at least 87% sensitivity and at least 80, 85, 90, 95, 99, or 100% specificity; at least 88% sensitivity and at least 80, 85, 90, 95, 99, or 100% specificity; at least 89% sensitivity and at least 80, 85, 90, 95, 99, or 100% specificity; at least 90% sensitivity and at least 80, 85, 90, 95, 99, or 100% specificity; at least 95% sensitivity and at least 80, 85, 90, 95, 99, or 100% specificity; at least 99% sensitivity and at least 80, 85, 90, 95, 99, or 100% specificity; or at least 100% sensitivity and at least 80, 85, 90, 95, 99, or 100% specificity.

Furthermore, the confidence level for determining the specificity, sensitivity, and/or other statistical performance measures may be with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% confidence.

Ovarian Cancer

A biosignature for characterizing ovarian cancer can comprise an antigen associated with ovarian cancer (for example, as shown in FIG. 1), and one or more additional biomarkers, such as shown in FIG. 4. In one embodiment, a biosignature for ovarian cancer can comprise one or more antigens associated with ovarian cancer, such as, but not limited to, CD24, CA125, VEGF1, VEGFR2, HER2, MISIIR, or any combination thereof. The biosignature for ovarian cancer can comprise one or more of the aforementioned antigens and one or more additional biomarker, such as, but not limited to miRNA, mRNA, DNA, or any combination thereof. The biosignature for ovarian cancer can comprise one or more antigens associated with ovarian cancer, such as, but not limited to, CD24, CA125, VEGF1, VEGFR2, HER2, MISIIR, or any combination thereof, with one or more miRNA biomarkers, such as, but not limited to, miR-200a, miR-141, miR-200c, miR-200b, miR-21, miR-141, miR-200a, miR-200b, miR-200c, miR-203, miR-205, miR-214, miR-215, miR-199a, miR-140, miR-145, miR-125b-1, or any combination thereof.

A biosignature for ovarian cancer can comprise one or more antigens associated with ovarian cancer, such as, but not limited to, CD24, CA125, VEGF1, VEGFR2, HER2, MISIIR, or any combination thereof, with one or more miRNA biomarkers (such as the aforementioned miRNA), mRNAs (such as, but not limited to, ERCC1, ER, TOPO1, TOP2A, AR, PTEN, HER2/neu, EGFR), mutations (including, but not limited to, those relating to KRAS and/or B-Raf) or any combination thereof.

A vesicle can be isolated, assayed or both, for one or more miRNA and one or more antigens associated with ovarian cancer to provide a diagnostic, prognostic or theranostic profile. Alternatively, the vesicle can be directly assayed from a sample, such that the vesicle is not purified or concentrated prior to assaying for one or more miRNA or antigens associated with ovarian cancer.

Organ Transplant Rejection and Autoimmune Conditions

A vesicle can also be used for determining phenotypes such as organ distress and/or organ transplant rejection. As used herein organ transplant includes partial organ or tissue transplant. The presence, absence or levels of one or more biomarkers present in a vesicle can be assessed to monitor organ rejection or success. The level or amount of vesicles in the sample can also be used to assess organ rejection or success. The assessment can be determined with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% specificity, sensitivity, or both. For example, the assessment can be determined with at least 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 998.2, 99.3, 99.4, 99.5, 99.6, 99.7, 99.8, 99.9% sensitivity, specificity, or both The vesicle can be purified or concentrated prior to analysis. Alternatively, the level, or amount, of vesicles can be directly assayed from a sample, without prior purification or concentration. The vesicle can be quantitated, su. For example, a cell or tissue-specific vesicle can be isolated using one or more binding agents specific for a particular organ. The cell-of-origin specific vesicle can be assessed for one or more molecular features, such as one or more biomarkers associated with organ distress or organ transplant rejection. The presence, absence or levels of one or more biomarkers present, can be assessed to monitor organ rejection or success.

One or more vesicles can be analyzed for the assessment, detection or diagnosis of the rejection of a tissue or organ transplant by a subject. The tissue or organ transplant rejection can be hyperacute, acute, or chronic rejection. The vesicle can also be analyzed for the assessment, detection or diagnosis of graft versus host disease in a subject. The subject can be the recipient of an autogenic, allogenic or xenogenic tissue or organ transplant.

The vesicle can also be analyzed to detect the rejection of a tissue or organ transplant. The vesicle may be produced by the tissue or organ transplant. Such tissues or organs include, but are not limited to, a heart, lung, pancreas, kidney, eye, cornea, muscle, bone marrow, skin, cartilage, bone, appendages, hair, face, tendon, stomach, intestine, vein, artery, differentiated cells, partially differentiated cells or stem cells.

The vesicle can comprise at least one biomarker which is used to assess, diagnose or determine the probability or occurrence of rejection of a tissue or organ transplant by a subject. A biomarker can also be used to assess, diagnose or detect graft versus host disease in a subject. The biomarker can be a protein, a polysaccharide, a fatty acid or a nucleic acid (such as DNA or RNA). The biomarker can be associated with the rejection of a specific tissue or organ or systemic organ failure. More than one biomarker can be analyzed, for example, one or more proteins marker can be analyzed in combination with one or more nucleic acid markers. The biomarker may be an intracellular or extracellular marker.

The vesicle can also be analyzed for at least one marker for the assessment, detection or diagnosis of cell apoptosis or necrosis associated with, or the causation of, rejection of a tissue or organ transplant by a subject.

The presence of a biomarker can be indicative of the rejection of a tissue or an organ by a subject, wherein the biomarker includes, but is not limited to, CD40, CD40 ligand, N-acetylmuramoyl-L-alanine amidase precursor, adiponectin, AMBP protein precursor, C4b-binding protein a-chain precursor, ceruloplasmin precursor, complement C3 precursor, complement component C9 precursor, complement factor D precursor, alpha1-B-glycoprotein, beta2-glycoprotein I precursor, heparin cofactor H precursor, Immunoglobulin mu chain C region protein, Leucine-rich alpha2-glycoprotein precursor, pigment epithelium-derived factor precursor, plasma retinol-binding protein precursor, translation initiation factor 3 subunit 10, ribosomal protein L7, beta-transducin, 1-TRAF, or lysyl-tRNA synthetase.

Rejection of a kidney by a subject can also be detected by analyzing vesicles for the presence of beta-transducin. Rejection of transplanted tissue can also be detected by isolating a cell-of-origin specific vesicles from CD40-expressing cells and detecting for the increase of Bcl-2 or TNFalpha.

Rejection of a liver transplant by a subject can be detected by analyzing the vesiclesfor the presence of an F1 antigen marker. The F1 antigen is, without being bound to theory, specific to liver to and can be used to detect an increase in liver cell-of-origin specific vesicles. This increase can be used as an early indication of organ distress/rejection.

Bronchiolitis obliterans due to bone marrow and/or lung transplantation or other causes, or graft atherosclerosis/graft phlebosclerosis can also be diagnosed by the analysis of a vesicle.

A vesicle can also be analyzed for the detection, diagnosis or assessment of an autoimmune or other immunological reaction-related phenotype in a subject. Examples of such a disorder include, but are not limited to, systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy and AIDs.

One or more biomarkers from the vesicles can be used to assess, diagnose or determine the probability of the occurrence of an autoimmune or other immunological reaction-related disorder in a subject. The biomarker can be a protein, a polysaccharide, a fatty acid or a nucleic acid (such as DNA or RNA). The biomarker can be associated with a specific autoimmune disorder, a systemic autoimmune disorder, or other immunological reaction-related disorder. More than one biomarker can be analyzed. For example one or more protein markers can be analyzed in combination with one or more nucleic acid markers. The biomarker can be an intracellular or extracellular marker. The biomarker can also be used to detect, diagnose or assess inflammation.

Analysis of vesicles from subjects can be used identify subjects with inflammation associated with asthma, sarcoidosis, emphysema, cystic fibrosis, idiopathic pulmonary fibrosis, chronic bronchitis, allergic rhinitis and allergic diseases of the lung such as hypersensitivity pneumonitis, eosinophilic pneumonia, as well as pulmonary fibrosis resulting from collagen, vascular, and autoimmune diseases such as rheumatoid arthritis.

Theranosis

As disclosed herein, methods are disclosed for characterizing a phenotype for a subject by assessing one or more biomarkers, including vesicle biomarkers and/or circulating biomarkers. The biomarkers can be assessed using methods for multiplexed analysis of vesicle biomarkers disclosed herein. Characterizing a phenotype can include providing a theranosis for a subject, such as determining if a subject is predicted to respond to a treatment or is predicted to be non-responsive to a treatment. A subject that responds to a treatment can be termed a responder whereas a subject that does not respond can be termed a non-responder. A subject suffering from a condition can be considered to be a responder for a treatment based on, but not limited to, an improvement of one or more symptoms of the condition; a decrease in one or more side effects of an existing treatment; an increased improvement, or rate of improvement, in one or more symptoms as compared to a previous or other treatment; or prolonged survival as compared to without treatment or a previous or other treatment. For example, a subject suffering from a condition can be considered to be a responder to a treatment based on the beneficial or desired clinical results including, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. Treatment also includes prolonging survival as compared to expected survival if not receiving treatment or if receiving a different treatment.

The systems and methods disclosed herein can be used to select a candidate treatment for a subject in need thereof. Selection of a therapy can be based on one or more characteristics of a vesicle, such as the biosignature of a vesicle, the amount of vesicles, or both. Vesicle typing or profiling, such as the identification of the biosignature of a vesicle, the amount of vesicles, or both, can be used to identify one or more candidate therapeutic agents for an individual suffering from a condition. For example, vesicle profiling can be used to determine if a subject is a non-responder or responder to a particular therapeutic, such as a cancer therapeutic if the subject is suffering from a cancer.

Vesicle profiling can be used to provide a diagnosis or prognosis for a subject, and a therapy can be selected based on the diagnosis or prognosis. Alternatively, therapy selection can be directly based on a subject's vesicle profile. Furthermore, a subject's vesicle profile can be used to follow the evolution of a disease, to evaluate the efficacy of a medication, adapt an existing treatment for a subject suffering from a disease or condition, or select a new treatment for a subject suffering from a disease or condition.

A subject's response to a treatment can be assessed using biomarkers, including vesicles, microRNA, and other circulating biomarkers. In one embodiment, a subject is determined, classified, or identified as a non-responder or responder based on the subject's vesicle profile assessed prior to any treatment. During pretreatment, a subject can be classifed as a non-responder or responder, thereby reducing unnecessary treatment options, and avoidance of possible side effects from ineffective therapeutics. Furthermore, the subject can be identified as a responder to a particular treatment, and thus vesicle profiling can be used to prolong survival of a subject, improve the subject's symptoms or condition, or both, by providing personalized treatment options. Thus, a subject suffering from a condition can have a biosignature generated from vesicles and other circulating biomarkers using one or more systems and methods disclosed herein, and the profile can then be used to determine whether a subject is a likely non-responder or responder to a particular treatment for the condition. Based on use of the biosignature to predict whether the subject is a non-responder or responder to the initially contemplated treatment, a particular treatment contemplated for treating the subject's condition can be selected for the subject, or another potentially more optimal treatment can be selected.

In one embodiment, a subject suffering from a condition is currently being treated with a therapeutic. A sample can be obtained from the subject before treatment and at one or more timepoints during treatment. A biosignature including vesicles or other biomarkers from the samples can be assessed and used to determine the subject's response to the drug, such as based on a change in the biosignature over time. If the subject is not responding to the treatment, e.g., the biosignature does not indicate that the patient is responding, the subject can be classified as being non-responsive to the treatment, or a non-responder. Similarly, one or more biomarkers associated with a worsening condition may be detected such that the biosignature is indicative of patient's failure to respond favorably to the treatment. In another example, one or more biomarkers associated with the condition remain the same despite treatment, indicating that the condition is not improving. Thus, based on the biosignature, a treatment regimen for the subject can be changed or adapted, including selection of a different therapeutic.

Alternatively, the subject can be determined to be responding to the treatment, and the subject can be classified as being responsive to the treatment, or a responder. For example, one or more biomarkers associated with an improvement in the condition or disorder may be detected. In another example, one or more biomarkers associated with the condition changes, thus indicating an improvement. Thus, the existing treatment can be continued. In another embodiment, even when there is an indication of improvement, the existing treatment may be adapted or changed if the biosignature indicates that another line of treatment may be more effective. The existing treatment may be combined with another therapeutic, the dosage of the current therapeutic may be increased, or a different candidate treatment or therapeutic may be selected. Criteria for selecting the different candidate treatment can depend on the setting. In one embodiment, the candidate treatment may have been known to be effective for subjects with success on the existing treatment. In another embodiment, the candidate treatment may have been known to be effective for other subjects with a similar biosignature.

In some embodiments, the subject is undergoing a second, third or more line of treatment, such as cancer treatment. A biosignature according to the invention can be determined for the subject prior to a second, third or more line of treatment, to determine whether a subject would be a responder or non-resonder to the second, third or more line of treatment. In another embodiment, a biosignature is determined for the subject during the second, third or more line of treatment, to determine if the subject is responding to the second, third or more line of treatment.

The methods and systems described herein for assessing one or more vesicles can be used to determine if a subject suffering from a condition is responsive to a treatment, and thus can be used to select a treatment that improves one or more symptoms of the condition; decreases one or more side effects of an existing treatment; increases the improvement, or rate of improvement, in one or more symptoms as compared to a previous or other treatment; or prolongs survival as compared to without treatment or a previous or other treatment. Thus, the methods described herein can be used to prolong survival of a subject by providing personalized treatment options, and/or may reduce unnecessary treatment options and unnecessary side effects for a subject.

The prolonged survival can be an increased progression-free survival (PFS), which denotes the chances of staying free of disease progression for an individual or a group of individuals suffering from a disease, e.g., a cancer, after initiating a course of treatment. It can refer to the percentage of individuals in the group whose disease is likely to remain stable (e.g., not show signs of progression) after a specified duration of time. Progression-free survival rates are an indication of the effectiveness of a particular treatment. In other embodiments, the prolonged survival is disease-free survival (DFS), which denotes the chances of staying free of disease after initiating a particular treatment for an individual or a group of individuals suffering from a cancer. It can refer to the percentage of individuals in the group who are likely to be free of disease after a specified duration of time. Disease-free survival rates are an indication of the effectiveness of a particular treatment. Two treatment strategies can be compared on the basis of the disease-free survival that is achieved in similar groups of patients. Disease-free survival is often used with the term overall survival when cancer survival is described.

The candidate treatment selected by vesicle profiling as described herein can be compared to a non-vesicle profiling selected treatment by comparing the progression free survival (PFS) using therapy selected by vesicle profiling (period B) with PFS for the most recent therapy on which the subject has just progressed (period A). In one setting, a PFSB/PFSA ratio >1.3 is used to indicate that the vesicle profiling selected therapy provides benefit for subject (see for example, Robert Temple, *Clinical measurement in drug evaluation*. Edited by Wu Ningano and G. T. Thicker John Wiley and Sons Ltd. 1995; Von Hoff D. D. *Clin Can Res.* 4: 1079, 1999: Dhani et al. *Clin Cancer Res.* 15: 118-123, 2009).

Other methods of comparing the treatment selected by vesicle profiling can be compared to a non-vesicle profiling selected treatment by determine response rate (RECIST) and percent of subjects without progression or death at 4 months. The term "about" as used in the context of a numerical value for PFS means a variation of +/− ten percent (10%) relative to the numerical value. The PFS from a treatment selected by vesicle profiling can be extended by at least 10%, 15%, 20%, 30%, 40%, 50%, 60%, 70%, 80%, or at least 90% as compared to a non-vesicle profiling selected treatment. In some embodiments, the PFS from a treatment selected by vesicle profiling can be extended by at least 100%, 150%, 200%, 300%, 400%, 500%, 600%, 700%, 800%, 900%, or at least about 1000% as compared to a non-vesicle profiling selected treatment. In yet other embodiments, the PFS ratio (PFS on vesicle profiling selected therapy or new treatment/PFS on prior therapy or treatment) is at least about 1.3. In yet other embodiments, the PFS ratio is at least about 1.1, 1.2, 1.3, 1.4, 1.5, 1.6, 1.7, 1.8, 1.9, or 2.0. In yet other embodiments, the PFS ratio is at least about 3, 4, 5, 6, 7, 8,9 or 10.

Similarly, the DFS can be compared in subjects whose treatment is selected with or without determining a biosignature according to the invention. The DFS from a treatment selected by vesicle profiling can be extended by at least 10%, 15%, 20%, 30%, 40%, 50%, 60%, 70%, 80%, or at least 90% as compared to a non-vesicle profiling selected treatment. In some embodiments, the DFS from a treatment selected by vesicle profiling can be extended by at least 100%, 150%, 200%, 300%, 400%, 500%, 600%, 700%, 800%, 900%, or at least about 1000% as compared to a non-vesicle profiling selected treatment. In yet other embodiments, the DFS ratio (DFS on vesicle profiling selected therapy or new treatment/DFS on prior therapy or treatment) is at least about 1.3. In yet other embodiments, the DFS ratio is at least about 1.1, 1.2, 1.3, 1.4, 1.5, 1.6, 1.7, 1.8, 1.9, or 2.0. In yet other embodiments, the DFS ratio is at least about 3, 4, 5, 6, 7, 8 9, or 10.

In some embodiments, the candidate treatment selected by microvescile profiling does not increase the PFS ratio or the DFS ratio in the subject; nevertheless vesicle profiling provides subject benefit. For example, in some embodiments no known treatment is available for the subject. In such cases, vesicle profiling provides a method to identify a candidate treatment where none is currently identified. The vesicle profiling may extend PFS, DFS or lifespan by at least 1 week, 2 weeks, 3 weeks, 4 weeks, 1 month, 5 weeks, 6 weeks, 7 weeks, 8 weeks, 2 months, 9 weeks, 10 weeks, 11 weeks, 12 weeks, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months or 2 years. The vesicle profiling may extend PFS, DFS or lifespan by at least 2½ years, 3 years, 4 years, 5 years, or more. In some embodiments, the methods of the invention improve outcome so that subject is in remission.

The effectiveness of a treatment can be monitored by other measures. A complete response (CR) comprises a complete disappearance of the disease: no disease is evident on examination, scans or other tests. A partial response (PR) refers to some disease remaining in the body, but there has been a decrease in size or number of the lesions by 30% or more. Stable disease (SD) refers to a disease that has remained relatively unchanged in size and number of lesions. Generally, less than a 50% decrease or a slight increase in size would be described as stable disease. Progressive disease (PD) means that the disease has increased in size or number on treatment. In some embodiments, vesicle profiling according to the invention results in a complete response or partial response. In some embodiments, the methods of the invention result in stable disease. In some embodiments, the invention is able to achieve stable disease where non-vesicle profiling results in progressive disease.

The theranosis based on a biosignature of the invention can be for a phenotype including without limitation those listed herein. Characterizing a phenotype includes determining a theranosis for a subject, such as predicting whether a subject is likely to respond to a treatment ("responder") or be non-responsive to a treatment ("non-responder"). As used herein, identifying a subject as a "responder" to a treatment or as a "non-responder" to the treatment comprises identifying the subject as either likely to respond to the treatment or likely to not respond to the treatment, respectively, and does not require determining a definitive prediction of the subject's response. One or more vesicles, or populations of vesicles, obtained from subject are used to determine if a subject is a non-responder or responder to a particular therapeutic, by assessing biomarkers disclosed herein, e.g., those listed in Table 5. Detection of a high or low expression level of a biomarker, or a mutation of a biomarker, can be used to select a candidate treatment, such as a pharmaceutical intervention, for a subject with a condition. Table 5 contains illustrative conditions and pharmaceutical interventions for those conditions. The table lists biomarkers that affect the efficacy of the intervention. The biomarkers can be assessed using the methods of the invention, e.g., as circulating biomarkers or in association with a vesicle.

TABLE 5

Examples of Biomarkers and Pharmaceutical Intervention for a Condition

| Condition | Pharmaceutial intervention | Biomarker |
|---|---|---|
| Peripheral Arterial Disease | Atorvastatin<br>Simvastatin<br>Rosuvastatin<br>Pravastatin<br>Fluvastatin<br>Lovastatin | C-reactive protein(CRP)<br>serum Amylyoid A (SAA)<br>interleukin-6<br>intracellular adhesion molecule (ICAM)<br>vascular adhesion molecule (VCAM)<br>CD40L<br>fibrinogen<br>fibrin D-dimer<br>fibrinopeptide A<br>von Willibrand factor<br>tissue plasminogen activator antigen (t-PA)<br>factor VII<br>prothrombin fragment 1<br>oxidized low density lipoprotein (oxLDL)<br>lipoprotein A |
| Non-Small Cell Lung Cancer | Erlotinib<br>Carboplatin<br>Paclitaxel<br>Gefitinib | EGFR<br>excision repair cross-complementation group 1 (ERCC1)<br>p53<br>Ras<br>p27<br>class III beta tubulin<br>breast cancer gene 1 (BRCA1)<br>breast cancer gene 1 (BRCA2)<br>ribonucleotide reductase messenger 1 (RRM1) |
| Colorectal Cancer | Panitumumab<br>Cetuximab | K-ras |
| Breast Cancer | Trastuzumab<br>Anthracyclines<br>Taxane<br>Methotrexate<br>fluorouracil | HER2<br>toposiomerase IIalpha<br>estrogen receptor<br>progesterone receptor |
| Alzheimer's Disease | Donepezil<br>Galantamine<br>Memantine<br>Rivastigmine<br>Tacrine | beta-amyloid protein<br>amyloid precursor protein (APP)<br>APP670/671<br>APP693<br>APP692<br>APP715<br>APP716<br>APP717<br>APP723<br>presenilin 1<br>presenilin 2<br>cerebrospinal fluid amyloid beta protein 42 (CSF-Abeta42)<br>cerebrospinal fluid amyloid beta protein 40 (CSF-Abeta40)<br>F2 isoprostane<br>4-hydroxynonenal<br>F4 neuroprostane<br>acrolein |

TABLE 5-continued

Examples of Biomarkers and Pharmaceutical Intervention for a Condition

| Condition | Pharmaceutial intervention | Biomarker |
|---|---|---|
| Arrhythmia | Disopyramide | SERCA |
| | Flecainide | AAP |
| | Lidocaine | Connexin 40 |
| | Mexiletine | Connexin 43 |
| | Moricizine | ATP-sensitive potassium channel |
| | Procainamide | Kv1.5 channel |
| | Propafenone | acetylcholine-activated posassium channel |
| | Quinidine | |
| | Tocainide | |
| | Acebutolol | |
| | Atenolol | |
| | Betaxolol | |
| | Bisoprolol | |
| | Carvedilol | |
| | Esmolol | |
| | Metoprolol | |
| | Nadolol | |
| | Propranolol | |
| | Sotalol | |
| | Timolol | |
| | Amiodarone | |
| | Azimilide | |
| | Bepridil | |
| | Dofetilide | |
| | Ibutilide | |
| | Tedisamil | |
| | Diltiazem | |
| | Verapamil | |
| | Azimilide | |
| | Dronedarone | |
| | Amiodarone | |
| | PM101 | |
| | ATI-2042 | |
| | Tedisamil | |
| | Nifekalant | |
| | Ambasilide | |
| | Ersentilide | |
| | Trecetilide | |
| | Almokalant | |
| | D-sotalol | |
| | BRL-32872 | |
| | HMR1556 | |
| | L768673 | |
| | Vernakalant | |
| | AZD70009 | |
| | AVE0118 | |
| | S9947 | |
| | NIP-141/142 | |
| | XEN-D0101/2 | |
| | Ranolazine | |
| | Pilsicainide | |
| | JTV519 | |
| | Rotigaptide | |
| | GAP-134 | |
| Rheumatoid arthritis | Methotrexate | 677CC/1298AA MTHFR |
| | infliximab | 677CT/1298AC MTHFR |
| | adalimumab | 677CT MTHFR |
| | etanercept | G80AA RFC-1 |
| | sulfasalazine | 3435TT MDR1 (ABCB1) |
| | | 3435TT ABCB1 |
| | | AMPD1/ATIC/ITPA |
| | | IL1-RN3 |
| | | HLA-DRB103 |
| | | CRP |
| | | HLA-D4 |
| | | HLA DRB-1 |
| | | anti-citrulline epitope containing peptides |
| | | anti-A1/RA33 |
| | | Erythrocyte sedimentation rate (ESR) |
| | | C-reactive protein (CRP) |
| | | SAA (serum amyloid-associated protein) |
| | | rheumatoid factor |
| | | IL-1 |
| | | TNF |
| | | IL-6 |
| | | IL-8 |
| | | IL-1Ra |
| | | Hyaluronic acid |
| | | Aggrecan |
| | | Glc-Gal-PYD |
| | | osteoprotegerin |
| | | RNAKL |
| | | carilage oligomeric matrix protein (COMP) |
| | | calprotectin |
| Arterial Fibrillation | warfarin | F1.2 |
| | aspirin | TAT |
| | anticoagulants | FPA |
| | heparin | beta-throboglobulin |
| | ximelagatran | platelet factor 4 |
| | | soluble P-selectin |
| | | IL-6 |
| | | CRP |
| HIV Infection | Zidovudine | HIV p24 antigen |
| | Didanosine | TNF-alpha |
| | Zalcitabine | TNFR-II |
| | Stavudine | CD3 |
| | Lamivudine | CD14 |
| | Saquinavir | CD25 |
| | Ritonavir | CD27 |
| | Indinavir | Fas |
| | Nevirane | FasL |
| | Nelfinavir | beta2 microglobulin |
| | Delavirdine | neopterin |
| | Stavudine | HIV RNA |
| | Efavirenz | HLA-B *5701 |
| | Etravirine | |
| | Enfuvirtide | |
| | Darunavir | |
| | Abacavir | |
| | Amprenavir | |
| | Lonavir/Ritonavirc | |
| | Tenofovir | |
| | Tipranavir | |
| Cardiovascular Disease | lisinopril | ACE inhibitor |
| | candesartan | angiotensin |
| | enalapril | |

Cancer

Vesicle biosignatures can be used in the theranosis of a cancer, such as identifying whether a subject suffering from cancer is a likely responder or non-responder to a particular cancer treatment. The subject methods can be used to theranose cancers including those listed herein, e.g., in the "Phenotype" section above. These include without limitation lung cancer, non-small cell lung cancerm small cell lung cancer (including small cell carcinoma (oat cell cancer), mixed small cell/large cell carcinoma, and combined small cell carcinoma), colon cancer, breast cancer, prostate cancer, liver cancer, pancreatic cancer, brain cancer, kidney cancer, ovarian cancer, stomach cancer, melanoma, bone cancer, gastric cancer, breast cancer, glioma, gliobastoma, hepatocellular carcinoma, papillary renal carcinoma, head and neck squamous cell carcinoma, leukemia, lymphoma, myeloma, or other solid tumors.

Cancer: Biosignatures

A biosignature can be determined to provide a theranosis for a subject. The biosignature of a vesicle can comprise one or more biomarkers such as, but not limited to, any one or more biomarkers as described herein, such as, but not limited to, those listed in FIGS. 1, 3, 6, 7, 9-12, 14-22, 25-33, 50-51, 53-54, 59, and 60.

The invention provides numerous methods of identifying a biosignature for characterizing a cancer. Further provided herein are biomarkers that are assessed to identify the biosignature. In one embodiment, a biosignature for prostate cancer comprises one or more of the following biomarkers: EpCam, CD9, PCSA, CD63, CD81, PSMA, B7H3, PSCA, ICAM, STEAP, and EGFR. In another embodiment, a biosignature for classifying a prostate cancer as being castration-resistant comprises EpCam+, CK+, CD45-vesicles. In another embodiment, a vesicle biosignature for small cell lung cancer comprises miR-92a-2*, miR-147, and/or miR-574-5p. In yet another embodiment, a biosignature for the theranosis of colorectal cancer comprises one or more miRs selected from the group consisting of: miR-548c-5p, miR-362-3p, miR-422a, miR-597, miR-429, miR-200a, and miR-200b.

Cancer: Standard of Care

Determining the biosignature of a vesicle, the amount of vesicles, or both, of a sample from a subject suffering from a cancer can be used select a standard of care for the subject. The biosignature can be used to determine if a subject is a non-responder or responder to a particular treatment or standard of care. The standard of care or treatment can be a cancer treatment such as radiation, surgery, chemotherapy or a combination thereof. The cancer treatment can be a therapeutic such as anti-cancer agents and chemotherapeutic regimens. Anti-cancer agents include, for example, anti-CD52 antibodies (e.g., Alemtuzumab), anti-CD20 antibodies (e.g., Rituximab), and anti-CD40 antibodies (e.g., SGN40); chemotherapeutic regimens include, for example, CHOP (cyclophosphamide, doxorubicin, vincristine, and prednisone); CVP (cyclophosphamide, vincristine, and prednisone); RCVP (Rituximab+CVP); RCHOP (Rituximab+CHOP); RICE (Rituximab+ifosamide, carboplatin, etoposide); RDHAP, (Rituximab+dexamethasone, cytarabine, cisplatin); RESHAP (Rituximab+etoposide, methylprednisolone, cytarabine, cisplatin); gemcitabine; combination treatment with vincristine, prednisone, and anthracycline, with or without asparaginase; combination treatment with daunorubicin, vincristine, prednisone, and asparaginase; combination treatment with teniposide and Ara-C(cytarabine); combination treatment with methotrexate and leucovorin; combination treatment with bleomycin, doxorubicin, etoposide, mechlorethamine, prednisone, vinblastine, and vincristine; small molecule inhibitors; and proteosome inhibitors including, for example, bortezomib.

Cancer therapies that can be identified as candidate treatments by the methods of the invention include without limitation: 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CC1-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate Dexamethasone Sodium Phosphate, Dexasone, Dexrazoxane, DHAD, DIC, Diodex Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexino, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin, Hex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Rubex®, Rubidomycin hydrochloride, Sandostatin®, Sandostatin LAR®, Sargramostim, Solu-Cortef®, Solu-Medrol®, Sorafenib, SPRYCEL™, ST1-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®, and any appropriate combinations thereof.

The candidate treatments identified according to the subject methods can be chosen from the class of therapeutic agents identified as Anthracyclines and related substances, Anti-androgens, Anti-estrogens, Antigrowth hormones (e.g., Somatostatin analogs), Combination therapy (e.g., vincristine, bcnu, melphalan, cyclophosphamide, prednisone (VBMCP)), DNA methyltransferase inhibitors, Endocrine therapy—Enzyme inhibitor, Endocrine therapy—other hormone antagonists and related agents, Folic acid analogs (e.g., methotrexate), Folic acid analogs (e.g., pemetrexed), Gonadotropin releasing hormone analogs, Gonadotropin-releasing hormones, Monoclonal antibodies (EGFR-Targeted—e.g., panitumumab, cetuximab), Monoclonal antibodies (Her2-Targeted—e.g., trastuzumab), Monoclonal antibodies (Multi-Targeted—e.g., alemtuzumab), Other alkylating agents, Other antineoplastic agents (e.g., asparaginase), Other antineoplastic agents (e.g., ATRA), Other antineoplastic agents (e.g., bexarotene), Other antineoplastic agents (e.g., celecoxib), Other antineoplastic agents (e.g., gemcitabine), Other antineoplastic agents (e.g., hydroxyurea), Other antineoplastic agents (e.g., irinotecan, topotecan), Other antineoplastic agents (e.g., pentostatin), Other cytotoxic antibiotics, Platinum compounds, Podophyllotoxin derivatives (e.g., etoposide), Progestogens, Protein kinase inhibitors (EGFR-Targeted), Protein kinase inhibitors (Her2 targeted therapy—e.g., lapatinib), Pyrimidine analogs (e.g., cytarabine), Pyrimidine analogs (e.g., fluoropyrimidines), Salicylic acid and derivatives (e.g., aspirin), Src-family protein tyrosine kinase inhibitors (e.g., dasatinib), Taxanes, Taxanes (e.g., nab-paclitaxel), Vinca Alkaloids and analogs, Vitamin D and analogs, Monoclonal antibodies (Multi-Targeted—e.g., bevacizumab), Protein kinase inhibitors (e.g., imatinib, sorafenib, sunitinib).

In some embodiments, the candidate treatments identified according to the subject methods are chosen from at least the groups of treatments consisting of 5-fluorouracil, abarelix, alemtuzumab, aminoglutethimide, anastrozole, asparaginase, aspirin, ATRA, azacitidine, bevacizumab, bexarotene, bicalutamide, calcitriol, capecitabine, carboplatin, celecoxib, cetuximab, chemotherapy, cholecalciferol, cisplatin, cytarabine, dasatinib, daunorubicin, decitabine, doxorubicin, epirubicin, erlotinib, etoposide, exemestane, flutamide, fulvestrant, gefitinib, gemcitabine, gonadorelin, goserelin, hydroxyurea, imatinib, irinotecan, lapatinib, letrozole, leuprolide, liposomal-doxorubicin, medroxyprogesterone, megestrol, megestrol acetate, methotrexate, mitomycin, nab-paclitaxel, octreotide, oxaliplatin, paclitaxel, panitumumab, pegaspargase, pemetrexed, pentostatin, sorafenib, sunitinib, tamoxifen, Taxanes, temozolomide, toremifene, trastuzumab, VBMCP, and vincristine.

Examples of biomarkers that can be detected, and treatment agents that can be selected or possibly avoided are listed in Table 6. For example, a biosignature is identified for a subject with a prostate cancer, wherein the biosignature comprises levels of androgen receptor (AR). Overexpression or overproduction of AR, such as high levels of mRNA levels or protein levels in a vesicle, provides an identification of candidate treatments for the subject. Such treatments include agents for treating the subject such as Bicalutamide, Flutamide, Leuprolide, or Goserelin. The subject is accordingly identified as a responder to Bicalutamide, Flutamide, Leuprolide, or Goserelin. In another illustrative example, BCRP mRNA, protein, or both is detected at high levels in a vesicle from a subject suffering from NSCLC. The subject may then be classified as a non-responder to the agents Cisplatin and Carboplatin, or the agents are considered to be less effective than other agents for treating NSCLC in the subject and not selected for use in treating the subject. Any of the following biomarkers can be assessed in a vesicle obtained from a subject, and the biomarker can be in the form including but not limited to one or more of a nucleic acid, polypeptide, peptide or peptide mimetic. In yet another illustrative example, a mutation in one or more of KRAS, BRAF, PIK3CA, and/or c-kit can be used to select a candidate treatment. For example, a mutation in KRAS or BRAF in a patient may indicate that cetuximab and/or panitumumab are likely to be less effective in treating the patient.

TABLE 6

Examples of Biomarkers, Lineage and Agents

| Biomarker | Lineage | Possibly Less Effective Agents | Possible Agents to Consider |
|---|---|---|---|
| AR (high expression) | Prostate | | Bicalutamide, Flutamide, Leuprolide, Goserelin |
| AR (high expression) | default | | Bicaluamide, Flutamide, Leuprolide, Goserelin |
| BCRP (high expression) | Non-small cell lung cancer (NSCLC) | Cisplatin, Carboplatin | |
| BCRP (low expression) | Non-small cell lung cancer (NSCLC) | | Cisplatin, Carboplatin |
| BCRP (high expression) | default | Cisplatin, Carboplatin | |
| BCRP (low expression) | default | | Cisplatin, Carboplatin |
| BRAF V600E (mutation positive) | Colorectal | Cetuximab, Panitumumab | |
| BRAF V600E (mutation negative) | Colorectal | | Cetuximab, Panitumumab |
| BRAF V600E (mutation positive) | All other | Cetuximab, Panitumumab | |
| BRAF V600E (mutation negative) | All other | | Cetuximab, Panitumumab |

TABLE 6-continued

Examples of Biomarkers, Lineage and Agents

| Biomarker | Lineage | Possibly Less Effective Agents | Possible Agents to Consider |
|---|---|---|---|
| BRAF V600E (mutation positive) | default | Cetuximab, Panitumumab | |
| BRAF V600E (mutation negative) | default | | Cetuximab, Panitumumab |
| CD52 (high expression) | Leukemia | | Alemtuzumab |
| CD52 (low expression) | Leukemia | Alemtuzumab | |
| CD52 (high expression) | default (Hematologic malignancies only) | | Alemtuzumab |
| CD52 (low expression) | default (Hematologic malignancies only) | Alemtuzumab | |
| c-kit | Uveal Melanoma | | |
| c-kit (high expression) | Gastrointestinal Stromal Tumors [GIST]; cKIT will not be performed on Uveal Melanoma as imatinib is not useful in the setting of WT cKIT positive uveal melanoma (see Hofmann et al. 2009) | | Imatinib |
| c-kit (high expression) | Extrahepatic Bile Duct Tumors; cKIT will not be performed on Uveal Melanoma as imatinib is not useful in the setting of WT cKIT positive uveal melanoma (see Hofmann et al. 2009) | | Imatinib |
| c-kit (high expression) | Acute myeloid leukemia (AML) | | Imatinib |
| c-kit (high expression) | default; cKIT will not be performed on Uveal Melanoma as imatinib is not useful in the setting of WT cKIT positive uveal melanoma (see Hofmann et al. 2009) | | Imatinib |
| EGFR (high copy number) | Head and neck squamous cell carcinoma (HNSCC) | | Erlotinib, Gefitinib |
| EGFR | Head and neck squamous cell carcinoma (HNSCC) | Erlotinib, Gefitinib | |
| EGFR (high copy number) | Non-small cell lung cancer (NSCLC) | | Erlotinib, Gefitinib |
| EGFR (low copy number) | Non-small cell lung cancer (NSCLC) | Erlotinib, Gefitinib | |
| EGFR (high copy number) | default | | Cetuxumab, Panitumumab, Erlotinib, Gefitinib |
| EGFR (low copy number) | default | Cetuxumab, Panitumumab, Erlotinib, Gefitinib | |
| ER (high expression) | Breast | Ixabepilone | Tamoxifen-based treatment, aromatase inhibitors (anastrazole, letrozole) |
| ER (low expression) | Breast | | Ixabepilone |
| ER (high expression) | Ovarian | | Tamoxifen-based treatment, aromatase inhibitors (anastrazole, letrozole) |
| ER (high expression) | default | | Tamoxifen-based treatment, aromatase inhibitors (anastrazole, letrozole) |
| ERCC1 (high expression) | Non-small cell lung cancer (NSCLC) | Carboplatin, Cisplatin | |
| ERCC1 (low expression) | Non-small cell lung cancer (NSCLC) | | Carboplatin, Cisplatin |
| ERCC1 (high expression) | Small Cell Lung Cancer (SCLC) | Carboplatin, Cisplatin | |
| ERCC1 (low expression) | Small Cell Lung Cancer (SCLC) | | Carboplatin, Cisplatin |
| ERCC1 (high expression) | Gastric | Oxaliplatin | |
| ERCC1 (low expression) | Gastric | | Oxaliplatin |
| ERCC1 (high expression) | default | Carboplatin, Cisplatin, Oxaliplatin | |
| ERCC1 (low expression) | default | | Carboplatin, Cisplatin, Oxaliplatin |

TABLE 6-continued

| Examples of Biomarkers, Lineage and Agents | | | |
|---|---|---|---|
| Biomarker | Lineage | Possibly Less Effective Agents | Possible Agents to Consider |
| HER-2 (high expression) | Breast | | Lapatinib, Trastuzumab |
| HER-2 (high expression) | default | | Lapatinib, Trastuzumab |
| KRAS (mutation positive) | Colorectal cancer | Cetuximab, Panitumumab | |
| KRAS (mutation negative) | Colorectal cancer | | Cetuximab, Panitumumab |
| KRAS (mutation positive) | Non-small cell lung cancer (NSCLC) | Erlotinib, Gefitinib | |
| KRAS (mutation negative) | Non-small cell lung cancer (NSCLC) | | Erlotinib, Gefitinib |
| KRAS (mutation positive) | Bronchioloalveolar carcinoma (BAC) or adenocarcinoma (BAC subtype) | Erlotinib | |
| KRAS (mutation negative) | Bronchioloalveolar carcinoma (BAC) or adenocarcinoma (BAC subtype) | | Erlotinib |
| KRAS (mutation positive) | Multiple myeloma | VBMCP/Cyclophosphamide | |
| KRAS (mutation negative) | Multiple myeloma | | VBMCP/Cyclophosphamide |
| KRAS (mutation positive) | default | Cetuximab, Panitumumab | |
| KRAS (mutation negative) | default | | Cetuximab, panitumumab |
| KRAS (mutation positive) | default | Cetuximab, Erlotinib, Panitumumab, Gefitinib | |
| KRAS (mutation negative) | default | | Cetuximab, Erlotinib, Panitumumab, Gefitinib |
| MGMT (high expression) | Pituitary tumors, oligodendroglioma | Temozolomide | |
| MGMT (low expression) | Pituitary tumors, oligodendroglioma | | Temozolomide |
| MGMT (high expression) | Neuroendocrine tumors | Temozolomide | |
| MGMT (low expression) | Neuroendocrine tumors | | Temozolomide |
| MGMT (high expression) | default | Temozolomide | |
| MGMT (low expression) | default | | Temozolomide |
| MRP1 (high expression) | Breast | Cyclophosphamide | |
| MRP1 (low expression) | Breast | | Cyclophosphamide |
| MRP1 (high expression) | Small Cell Lung Cancer (SCLC) | Etoposide | |
| MRP1 (low expression) | Small Cell Lung Cancer (SCLC) | | Etoposide |
| MRP1 (high expression) | Nodal Diffuse Large B-Cell Lymphoma | Cyclophosphamide/Vincristine | |
| MRP1 (low expression) | Nodal Diffuse Large B-Cell Lymphoma | | Cyclophosphamide/Vincristine |
| MRP1 (high expression) | default | Cyclophosphamide, Etoposide, Vincristine | |
| MRP1 (low expression) | default | | Cyclophosphamide, Etoposide, Vincristine |
| PDGFRA (high expression) | Malignant Solitary Fibrous Tumor of the Pleura (MSFT) | | Imatinib |
| PDGFRA (high expression) | Gastrointestinal stromal tumor (GIST) | | Imatinib |
| PDGFRA (high expression) | Default | | Imatinib |
| p-glycoprotein (high expression) | Acute myeloid leukemia (AML) | Etoposide | |
| p-glycoprotein (low expression) | Acute myeloid leukemia (AML) | | Etoposide |
| p-glycoprotein (high expression) | Diffuse Large B-cell Lymphoma (DLBCL) | Doxorubicin | |
| p-glycoprotein (low expression) | Diffuse Large B-cell Lymphoma (DLBCL) | | Doxorubicin |

TABLE 6-continued

| Examples of Biomarkers, Lineage and Agents | | | |
|---|---|---|---|
| Biomarker | Lineage | Possibly Less Effective Agents | Possible Agents to Consider |
| p-glycoprotein (high expression) | Lung | Etoposide | |
| p-glycoprotein (low expression) | Lung | | Etoposide |
| p-glycoprotein (high expression) | Breast | Doxorubicin | |
| p-glycoprotein (low expression) | Breast | | Doxorubicin |
| p-glycoprotein (high expression) | Ovarian | Paclitaxel | |
| p-glycoprotein (low expression) | Ovarian | | Paclitaxel |
| p-glycoprotein (high expression) | Head and neck squamous cell carcinoma (HNSCC) | Vincristine | |
| p-glycoprotein (low expression) | Head and neck squamous cell carcinoma (HNSCC) | | Vincristine |
| p-glycoprotein (high expression) | default | Vincristine, Etoposide, Doxorubicin, Paclitaxel | |
| p-glycoprotein (low expression) | default | | Vincristine, Etoposide, Doxorubicin, Paclitaxel |
| PR (high expression) | Breast | Chemoendocrine therapy | Tamoxifen, Anastrazole, Letrozole |
| PR (low expression) | default | Chemoendocrine therapy | Tamoxifen, Anastrazole, Letrozole |
| PTEN (high expression) | Breast | | Trastuzumab |
| PTEN (low expression) | Breast | Trastuzumab | |
| PTEN (high expression) | Non-small cell Lung Cancer (NSCLC) | | Gefitinib |
| PTEN (low expression) | Non-small cell Lung Cancer (NSCLC) | Gefitinib | |
| PTEN (high expression) | Colorectal | | Cetuximab, Panitumumab |
| PTEN (low expression) | Colorectal | Cetuximab, Panitumumab | |
| PTEN (high expression) | Glioblastoma | | Erlotinib, Gefitinib |
| PTEN (low expression) | Glioblastoma | Erlotinib, Gefitinib | |
| PTEN (high expression) | default | | Cetuximab, Panitumumab, Erlotinib, Gefitinib and Trastuzumab |
| PTEN (low expression) | default | Cetuximab, Panitumumab, Erlotinib, Gefitinib and Trastuzumab | |
| RRM1 (high experssion) | Non-small cell lung cancer (NSCLC) | Gemcitabine | |
| RRM1 (low expression) | Non-small cell lung cancer (NSCLC) | | Gemcitabine |
| RRM1 (high experssion) | Pancreas | Gemcitabine | |
| RRM1 (low expression) | Pancreas | | Gemcitabine |
| RRM1 (high experssion) | default | Gemcitabine | |
| RRM1 (low expression) | default | | Gemcitabine |
| SPARC (high expression) | Breast | | nab-paclitaxel |
| SPARC (high expression) | default | | nab-paclitaxel |
| TS (high expression) | Colorectal | fluoropyrimidines | |
| TS (low expression) | Colorectal | | fluoropyrimidines |
| TS (high expression) | Pancreas | fluoropyrimidines | |
| TS (low expression) | Pancreas | | fluoropyrimidines |
| TS (high expression) | Head and Neck Cancer | fluoropyrimidines | |
| TS (low expression) | Head and Neck Cancer | | fluoropyrimidines |
| TS (high expression) | Gastric | fluoropyrimidines | |
| TS (low expression) | Gastric | | fluoropyrimidines |
| TS (high expression) | Non-small cell lung cancer (NSCLC) | fluoropyrimidines | |
| TS (low expression) | Non-small cell lung cancer (NSCLC) | | fluoropyrimidines |
| TS (high expression) | Liver | fluoropyrimidines | |

TABLE 6-continued

| Examples of Biomarkers, Lineage and Agents | | | |
|---|---|---|---|
| Biomarker | Lineage | Possibly Less Effective Agents | Possible Agents to Consider |
| TS (low expression) | Liver | | fluoropyrimidines |
| TS (high expression) | default | fluoropyrimidines | |
| TS (low expression) | default | | fluoropyrimidines |
| TOPO1 (high expression) | Colorectal | | Irinotecan |
| TOPO1 (low expression) | Colorectal | Irinotecan | |
| TOPO1 (high expression) | Ovarian | | Irinotecan |
| TOPO1 (low expression) | Ovarian | Irinotecan | |
| TOPO1 (high expression) | default | | Irinotecan |
| TOPO1 (low expression) | default | Irinotecan | |
| TopoIIa (high epxression) | Breast | | Doxorubicin, liposomal-Doxorubicin, Epirubicin |
| TopoIIa (low expression) | Breast | Doxorubicin, liposomal-Doxorubicin, Epirubicin | |
| TopoIIa (high epxression) | default | | Doxorubicin, liposomal-Doxorubicin, Epirubicin |
| TopoIIa (low expression) | default | Doxorubicin, liposomal-Doxorubicin, Epirubicin | |

Other examples of biomarkers that can be detected and the treatment agents that can be selected or possibly avoided based on the biomarker signatures are listed in Table 7. For example, for a subject suffering from cancer, detecting overexpression of ADA in vesicles from a subject is used to classify the subject as a responder to pentostatin, or pentostatin identified as an agent to use for treating the subject. In another example, for a subject suffering from cancer, detecting overexpression of BCRP in vesicles from the subject is used to classify the subject as a non-responder to cisplatin, carboplatin, irinotecan, and topotecan, meaning that cisplatin, carboplatin, irinotecan, and topotecan are identified as agents that are suboptimal for treating the subject.

TABLE 7

| Examples of Biomarkers, Agents and Resistance | | | |
|---|---|---|---|
| Gene Name | Expression Status | Candidate Agent(s) | Possible Resistance |
| ADA | Overexpressed | pentostatin | |
| ADA | Underexpressed | | cytarabine |
| AR | Overexpressed | abarelix, bicalutamide, flutamide, gonadorelin, goserelin, leuprolide | |
| ASNS | Underexpressed | asparaginase, pegaspargase | |
| BCRP (ABCG2) | Overexpressed | | cisplatin, carboplatin, irinotecan, topotecan |
| BRCA1 | Underexpressed | mitomycin | |
| BRCA2 | Underexpressed | mitomycin | |
| CD52 | Overexpressed | alemtuzumab | |
| CDA | Overexpressed | | cytarabine |
| c-erbB2 | High levels of phosphorylation in epithelial cells | Trastuzumab, c-erbB2 kinase inhibitor, lapatinib | |
| CES2 | Overexpressed | irinotecan | |
| c-kit | Overexpressed | sorafenib, sunitinib, imatinib | |
| COX-2 | Overexpressed | celecoxib | |
| DCK | Overexpressed | gemcitabine | cytarabine |
| DHFR | Underexpressed | methotrexate, pemetrexed | |
| DHFR | Overexpressed | | methotrexate |
| DNMT1 | Overexpressed | azacitidine, decitabine | |
| DNMT3A | Overexpressed | azacitidine, decitabine | |
| DNMT3B | Overexpressed | azacitidine, decitabine | |
| EGFR | Overexpressed | erlotinib, gefitinib, cetuximab, panitumumab | |
| EML4-ALK | Overexpressed (present) | crizotinib | |
| EPHA2 | Overexpressed | dasatinib | |
| ER | Overexpressed | anastrazole, exemestane, fulvestrant, letrozole, megestrol, tamoxifen, | |

TABLE 7-continued

| Examples of Biomarkers, Agents and Resistance | | | |
|---|---|---|---|
| Gene Name | Expression Status | Candidate Agent(s) | Possible Resistance |
| | | medroxyprogesterone, toremifene, aminoglutethimide | |
| ERCC1 | Overexpressed | | carboplatin, cisplatin |
| GART | Underexpressed | pemetrexed | |
| GRN (PCDGF, PGRN) | Overexpressed | | anti-oestrogen therapy, tamoxifen, faslodex, letrozole, herceptin in Her-2 overexpressing cells, doxorubicin |
| HER-2 (ERBB2) | Overexpressed | trastuzumab, lapatinib | |
| HIF-1α | Overexpressed | sorafenib, sunitinib, bevacizumab | |
| IκB-α | Overexpressed | bortezomib | |
| MGMT | Underexpressed | temozolomide | |
| MGMT | Overexpressed | | temozolomide |
| MRP1 (ABCC1) | Overexpressed | | etoposide, paclitaxel, docetaxel, vinblastine, vinorelbine, topotecan, teniposide |
| P-gp (ABCB1) | Overexpressed | | doxorubicin, etoposide, epirubicin, paclitaxel, docetaxel, vinblastine, vinorelbine, topotecan, teniposide, liposomal doxorubicin |
| PDGFR-α | Overexpressed | sorafenib, sunitinib, imatinib | |
| PDGFR-β | Overexpressed | sorafenib, sunitinib, imatinib | |
| PR | Overexpressed | exemestane, fulvestrant, gonadorelin, goserelin, medroxyprogesterone, megestrol, tamoxifen, toremifene | |
| RARA | Overexpressed | ATRA | |
| RRM1 | Underexpressed | gemcitabine, hydroxyurea | |
| RRM2 | Underexpressed | gemcitabine, hydroxyurea | |
| RRM2B | Underexpressed | gemcitabine, hydroxyurea | |
| RXR-α | Overexpressed | bexarotene | |
| RXR-β | Overexpressed | bexarotene | |
| SPARC | Overexpressed | nab-paclitaxel | |
| SRC | Overexpressed | dasatinib | |
| SSTR2 | Overexpressed | octreotide | |
| SSTR5 | Overexpressed | octreotide | |
| TOPO I | Overexpressed | irinotecan, topotecan | |
| TOPO IIα | Overexpressed | doxorubicin, epirubicin, liposomal- doxorubicin | |
| TOPO IIβ | Overexpressed | doxorubicin, epirubicin, liposomal- doxorubicin | |
| TS | Underexpressed | capecitabine, 5-fluorouracil, pemetrexed | |
| TS | Overexpressed | | capecitabine, 5-fluorouracil |
| VDR | Overexpressed | calcitriol, cholecalciferol | |
| VEGFR1 (Flt1) | Overexpressed | sorafenib, sunitinib, bevacizumab | |
| VEGFR2 | Overexpressed | sorafenib, sunitinib, bevacizumab | |
| VHL | Underexpressed | sorafenib, sunitinib | |

Further drug associations and rules that are used in embodiments of the invention are found in U.S. patent application Ser. No. 12/658,770, filed Feb. 12, 2010; International PCT Patent Application PCT/US2010/000407, filed Feb. 11, 2010; International PCT Patent Application PCMS2010/54366, filed Oct. 27, 2010; and U.S. Provisional Patent Application 61/427,788, filed Dec. 28, 2010; all of which applications are incorporated by reference herein in their entirety. See, e.g., "Table 4: Rules Summary for Treatment Selection" of PCT/US2010/54366.

Any drug-associated target can be part of a biosignature for providing a theranosis. A "druggable target" comprising a target that can be modulated with a therapeutic agent such as a small molecule or biologic, is a candidate for inclusion in the biosignature of the invention. Drug-associated targets also include biomarkers that can confer resistance to a treatment, such as shown in Tables 6 and 7. The biosignature can be based on either the gene, e.g., DNA sequence, and/or gene product, e.g., mRNA or protein, or the drug-associated target. Such nucleic acid and/or polypeptide can be profiled as applicable as to presence or absence, level or amount, activity, mutation, sequence, haplotype, rearrangement, copy number, or other measurable characteristic. The gene or gene product can be associated with a vesicle population, e.g., as a vesicle surface marker or as vesicle payload. In an embodiment, the invention provides a method of theranosing a cancer, comprising identifying a biosignature that comprises a presence or level of one or more drug-associated target, and selecting a candidate therapeutic based on the biosignature. The drug-associated target can be a circulating biomarker, a vesicle, or a vesicle associated biomarker.

The drug-associated targets assessed using the methods of the invention comprise without limitation ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKNIA, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, hENT-1, Her2/Neu, HGF, HIF1A, HIG1, HSP90, HSP9OAA1, HSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKB1A, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SRC, SSTR1, SSTR2, SSTR3, SSTR4, SSTR5, Survivin, TK1, TLE3, TNF, TOP1, TOP2A, TOP2B, TS, TXN, TXNRD1, TYMS, VDR, VEGF, VEGFA, VEGFC, VHL, YES1, ZAP70, or any combination thereof. A biosignature including one or combination of these markers can be used to characterize a phenotype according to the invention, such as providing a theranosis. These markers are known to play a role in the efficacy of various chemotherapeutic agents against proliferative diseases. Accordingly, the markers can be assessed to select a candidate treatment for the cancer independent of the origin or type of cancer. In an embodiment, the invention provides a method of selecting a candidate therapeutic for a cancer, comprising identifying a biosignature comprising a level or presence of one or more drug associated target, and selecting the candidate therapeutic based on its predicted efficacy for a patient with the biosignature. The one or more drug-associated target can be one of the targets listed above, or in Tables 6-8. In some embodiments, at least 2, 3, 4, 5, 6, 7, 8, 9, 10, 12, 15, 20, 25, 30, 35, 40, 45, or at least 50 of the one or more drug-associated targets are assessed. The one or more drug-associated target can be associated with a vesicle, e.g., as a vesicle surface marker or as vesicle payload as either nucleic acid (e.g., DNA, mRNA) or protein. In some embodiments, the presence or level of a microRNA known to interact with the one or more drug-associated target is assessed, wherein a high level of microRNA known to suppress the one or more drug-associated target can indicate a lower expression of the one or more drug-associated target and thus a lower likelihood of response to a treatment against the drug-associated target. The one or more drug-associated target can be circulating biomarkers. The one or more drug-associated target can be assessed in a tissue sample. The predicted efficacy can be determined by comparing the presence or level of the one or more drug-associated target to a reference value, wherein a higher level that the reference indicates that the subject is a likely responder. The predicted efficacy can be determined using a classifier algorithm, wherein the classifier was trained by comparing the biosignature of the one or more drug-associated target in subjects that are known to be responders or non-responders to the candidate treatment. Molecular associations of the one or more drug-associated target with appropriate candidate targets are displayed in Table 6-7 herein and U.S. patent application Ser. No. 12/658,770, filed Feb. 12, 2010; International PCT Patent Application PCT/US2010/000407, filed Feb. 11, 2010; International PCT Patent Application PCT/US2010/54366, filed Oct. 27, 2010; and U.S. Provisional Patent Application 61/427,788, filed Dec. 28, 2010; all of which applications are incorporated by reference herein in their entirety.

Table 8 provides a listing of gene and corresponding protein symbols and names of many of the theranostic targets that are analyzed according to the methods of the invention. As understood by those of skill in the art, genes and proteins have developed a number of alternative names in the scientific literature. Thus, the listing in Table 8 comprises an illustrative but not exhaustive compilation. A further listing of gene aliases and descriptions can be found using a variety of online databases, including GeneCards® (www.genecards.org), HUGO Gene Nomenclature (www.genenames.org), Entrez Gene (www.ncbi.nlm.nih.gov/entrez/query.fcgi?db=gene), UniProtKB/Swiss-Prot (www.uniprot.org), UniProtKB/TrEMBL (www.uniprot.org), OMIM (www.ncbi.nlm.nih.gov/entrez/query.fcgi?db=OMIM), GeneLoc (genecards.weizmann.ac.il/geneloc/), and Ensembl (www.ensembl.org). Generally, gene symbols and names below correspond to those approved by HUGO, and protein names are those recommended by UniProtKB/Swiss-Prot. Common alternatives are provided as well. Where a protein name indicates a precursor, the mature protein is also implied. Throughout the application, gene and protein symbols may be used interchangeably and the meaning can be derived from context as necessary.

TABLE 8

Genes and Related Proteins for Cancer Theranostics

| Gene Symbol | Gene Name | Protein Symbol | Protein Name |
|---|---|---|---|
| ABCB1, PGP | ATP-binding cassette, sub-family B (MDR/TAP), member 1 | ABCB1, MDR1, PGP | Multidrug resistance protein 1; P-glycoprotein |
| ABCC1, MRP1 | ATP-binding cassette, sub-family C (CFTR/MRP), member 1 | MRP1, ABCC1 | Multidrug resistance-associated protein 1 |
| ABCG2, BCRP | ATP-binding cassette, sub-family G (WHITE), member 2 | ABCG2 | ATP-binding cassette sub-family G member 2 |
| ACE2 | angiotensin I converting enzyme (peptidyl-dipeptidase A) 2 | ACE2 | Angiotensin-converting enzyme 2 precursor |
| ADA | adenosine deaminase | ADA | Adenosine deaminase |
| ADH1C | alcohol dehydrogenase 1C (class I), gamma polypeptide | ADH1G | Alcohol dehydrogenase 1C |

TABLE 8-continued

Genes and Related Proteins for Cancer Theranostics

| Gene Symbol | Gene Name | Protein Symbol | Protein Name |
|---|---|---|---|
| ADH4 | alcohol dehydrogenase 4 (class II), pi polypeptide | ADH4 | Alcohol dehydrogenase 4 |
| AGT | angiotensinogen (serpin peptidase inhibitor, clade A, member 8) | ANGT, AGT | Angiotensinogen precursor |
| ALK | anaplastic lymphoma receptor tyrosine kinase | ALK | ALK tyrosine kinase receptor precursor |
| AR | androgen receptor | AR | Androgen receptor |
| AREG | amphiregulin | AREG | Amphiregulin precursor |
| ASNS | asparagine synthetase | ASNS | Asparagine synthetase [glutamine-hydrolyzing] |
| BCL2 | B-cell CLL/lymphoma 2 | BCL2 | Apoptosis regulator Bcl-2 |
| BDCA1, CD1C | CD1c molecule | CD1C | T-cell surface glycoprotein CD1c precursor |
| BIRC5 | baculoviral IAP repeat-containing 5 | BIRC5, Survivin | Baculoviral IAP repeat-containing protein 5; Survivin |
| BRAF | v-raf murine sarcoma viral oncogene homolog B1 | B-RAF, BRAF | Serine/threonine-protein kinase B-raf |
| BRCA1 | breast cancer 1, early onset | BRCA1 | Breast cancer type 1 susceptibility protein |
| BRCA2 | breast cancer 2, early onset | BRCA2 | Breast cancer type 2 susceptibility protein |
| CA2 | carbonic anhydrase II | CA2 | Carbonic anhydrase 2 |
| CAV1 | caveolin 1, caveolae protein, 22 kDa | CAV1 | Caveolin-1 |
| CCND1 | cyclin D1 | CCND1, Cyclin D1, BCL-1 | G1/S-specific cyclin-D1 |
| CD20, MS4A1 | membrane-spanning 4-domains, subfamily A, member 1 | CD20 | B-lymphocyte antigen CD20 |
| CD25, IL2RA | interleukin 2 receptor, alpha | CD25 | Interleukin-2 receptor subunit alpha precursor |
| CD33 | CD33 molecule | CD33 | Myeloid cell surface antigen CD33 precursor |
| CD52, CDW52 | CD52 molecule | CD52 | CAMPATH-1 antigen precursor |
| CDA | cytidine deaminase | CDA | Cytidine deaminase |
| CDH1, ECAD | cadherin 1, type 1, E-cadherin (epithelial) | E-Cad | Cadherin-1 precursor (E-cadherin) |
| CDK2 | cyclin-dependent kinase 2 | CDK2 | Cell division protein kinase 2 |
| CDKN1A, P21 | cyclin-dependent kinase inhibitor 1A (p21, Cip1) | CDKN1A, p21 | Cyclin-dependent kinase inhibitor 1 |
| CDKN1B | cyclin-dependent kinase inhibitor 1B (p27, Kip1) | CDKN1B, p27 | Cyclin-dependent kinase inhibitor 1B |
| CDKN2A, P16 | cyclin-dependent kinase inhibitor 2A (melanoma, p16, inhibits CDK4) | CD21A, p16 | Cyclin-dependent kinase inhibitor 2A, isoforms 1/2/3 |
| CES2 | carboxylesterase 2 (intestine, liver) | CES2, EST2 | Carboxylesterase 2 precursor |
| CK 5/6 | cytokeratin 5/cytokeratin 6 | CK 5/6 | Keratin, type II cytoskeletal 5; Keratin, type II cytoskeletal 6 |
| CK14, KRT14 | keratin 14 | CK14 | Keratin, type I cytoskeletal 14 |
| CK17, KRT17 | keratin 17 | CK17 | Keratin, type I cytoskeletal 17 |
| COX2, PTGS2 | prostaglandin-endoperoxide synthase 2 (prostaglandin G/H synthase and cyclooxygenase) | COX-2, PTGS2 | Prostaglandin G/H synthase 2 precursor |
| DCK | deoxycytidine kinase | DCK | Deoxycytidine kinase |
| DHFR | dihydrofolate reductase | DHFR | Dihydrofolate reductase |
| DNMT1 | DNA (cytosine-5-)-methyltransferase 1 | DNMT1 | DNA (cytosine-5)-methyltransferase 1 |
| DNMT3A | DNA (cytosine-5-)-methyltransferase 3 alpha | DNMT3A | DNA (cytosine-5)-methyltransferase 3A |
| DNMT3B | DNA (cytosine-5-)-methyltransferase 3 beta | DNMT3B | DNA (cytosine-5)-methyltransferase 3B |
| ECGF1, TYMP | thymidine phosphorylase | TYMP, PD-ECGF, ECDF1 | Thymidine phosphorylase precursor |
| EGFR, ERBB1, HER1 | epidermal growth factor receptor (erythroblastic leukemia viral (v-erb-b) oncogene homolog, avian) | EGFR, ERBB1, HER1 | Epidermal growth factor receptor precursor |
| EML4 | echinoderm microtubule associated protein like 4 | EML4 | Echinoderm microtubule-associated protein-like 4 |
| EPHA2 | EPH receptor A2 | EPHA2 | Ephrin type-A receptor 2 precursor |
| ER, ESR1 | estrogen receptor 1 | ER, ESR1 | Estrogen receptor |
| ERBB2, HER2/NEU | v-erb-b2 erythroblastic leukemia viral oncogene homolog 2, neuro/glioblastoma derived oncogene homolog (avian) | ERBB2, HER2, HER-2/neu | Receptor tyrosine-protein kinase erbB-2 precursor |
| ERCC1 | excision repair cross-complementing rodent repair deficiency, | ERCC1 | DNA excision repair protein ERCC-1 |

TABLE 8-continued

Genes and Related Proteins for Cancer Theranostics

| Gene Symbol | Gene Name | Protein Symbol | Protein Name |
|---|---|---|---|
| | complementation group 1 (includes overlapping antisense sequence) | | |
| ERCC3 | excision repair cross-complementing rodent repair deficiency, complementation group 3 (xeroderma pigmentosum group B complementing) | ERCC3 | TFIIH basal transcription factor complex helicase XPB subunit |
| EREG | Epiregulin | EREG | Proepiregulin precursor |
| FLT1 | fms-related tyrosine kinase 1 (vascular endothelial growth factor/vascular permeability factor receptor) | FLT-1, VEGFR1 | Vascular endothelial growth factor receptor 1 precursor |
| FOLR1 | folate receptor 1 (adult) | FOLR1 | Folate receptor alpha precursor |
| FOLR2 | folate receptor 2 (fetal) | FOLR2 | Folate receptor beta precursor |
| FSHB | follicle stimulating hormone, beta polypeptide | FSHB | Follitropin subunit beta precursor |
| FSHPRH1, CENP1 | centromere protein I | FSHPRH1, CENP1 | Centromere protein I |
| FSHR | follicle stimulating hormone receptor | FSHR | Follicle-stimulating hormone receptor precursor |
| FYN | FYN oncogene related to SRC, FGR, YES | FYN | Tyrosine-protein kinase Fyn |
| GART | phosphoribosylglycinamide formyltransferase, phosphoribosylglycinamide synthetase, phosphoribosylaminoimidazole synthetase | GART, PUR2 | Trifunctional purine biosynthetic protein adenosine-3 |
| GNRH1 | gonadotropin-releasing hormone 1 (luteinizing-releasing hormone) | GNRH1, GON1 | Progonadoliberin-1 precursor |
| GNRHR1, GNRHR | gonadotropin-releasing hormone receptor | GNRHR1 | Gonadotropin-releasing hormone receptor |
| GSTP1 | glutathione S-transferase pi 1 | GSTP1 | Glutathione S-transferase P |
| HCK | hemopoietic cell kinase | HCK | Tyrosine-protein kinase HCK |
| HDAC1 | histone deacetylase 1 | HDAC1 | Histone deacetylase 1 |
| HGF | hepatocyte growth factor (hepapoietin A; scatter factor) | HGF | Hepatocyte growth factor precursor |
| HIF1A | hypoxia inducible factor 1, alpha subunit (basic helix-loop-helix transcription factor) | HIF1A | Hypoxia-inducible factor 1-alpha |
| HIG1, HIGD1A, HIG1A | HIG1 hypoxia inducible domain family, member 1A | HIG1, HIGD1A, HIG1A | HIG1 domain family member 1A |
| HSP90AA1, HSP90, HSPCA | heat shock protein 90 kDa alpha (cytosolic), class A member 1 | HSP90, HSP90A | Heat shock protein HSP 90-alpha |
| IGF1R | insulin-like growth factor 1 receptor | IGF-1R | Insulin-like growth factor 1 receptor precursor |
| IGFBP3, IGFRBP3 | insulin-like growth factor binding protein 3 | IGFBP-3, IBP-3 | Insulin-like growth factor-binding protein 3 precursor |
| IGFBP4, IGFRBP4 | insulin-like growth factor binding protein 4 | IGFBP-4, IBP-4 | Insulin-like growth factor-binding protein 4 precursor |
| IGFBP5, IGFRBP5 | insulin-like growth factor binding protein 5 | IGFBP-5, IBP-5 | Insulin-like growth factor-binding protein 5 precursor |
| IL13RA1 | interleukin 13 receptor, alpha 1 | IL-13RA1 | Interleukin-13 receptor subunit alpha-1 precursor |
| KDR | kinase insert domain receptor (a type III receptor tyrosine kinase) | KDR, VEGFR2 | Vascular endothelial growth factor receptor 2 precursor |
| KIT, c-KIT | v-kit Hardy-Zuckerman 4 feline sarcoma viral oncogene homolog | KIT, c-KIT | Mast/stem cell growth factor receptor precursor |
| KRAS | v-Ki-ras2 Kirsten rat sarcoma viral oncogene homolog | K-RAS | GTPase KRas precursor |
| LCK | lymphocyte-specific protein tyrosine kinase | LCK | Tyrosine-protein kinase Lck |
| LTB | lymphotoxin beta (TNF superfamily, member 3) | LTB, TNF3 | Lymphotoxin-beta |
| LTBR | lymphotoxin beta receptor (TNFR superfamily, member 3) | LTBR, LTBR3, TNFR | Tumor necrosis factor receptor superfamily member 3 precursor |
| LYN | v-yes-1 Yamaguchi sarcoma viral related oncogene homolog | LYN | Tyrosine-protein kinase Lyn |
| MET, c-MET | met proto-oncogene (hepatocyte growth factor receptor) | MET, c-MET | Hepatocyte growth factor receptor precursor |
| MGMT | O-6-methylguanine-DNA methyltransferase | MGMT | Methylated-DNA--protein-cysteine methyltransferase |
| MKI67, KI67 | antigen identified by monoclonal antibody Ki-67 | Ki67, Ki-67 | Antigen KI-67 |
| MLH1 | mutL homolog 1, colon cancer, nonpolyposis type 2 (*E. coli*) | MLH1 | DNA mismatch repair protein Mlh1 |

TABLE 8-continued

| Genes and Related Proteins for Cancer Theranostics | | | |
|---|---|---|---|
| Gene Symbol | Gene Name | Protein Symbol | Protein Name |
| MMR | mismatch repair (refers to MLH1, MSH2, MSH5) | | |
| MSH2 | mutS homolog 2, colon cancer, nonpolyposis type 1 (*E. coli*) | MSH2 | DNA mismatch repair protein Msh2 |
| MSH5 | mutS homolog 5 (*E. coli*) | MSH5, hMSH5 | MutS protein homolog 5 |
| MYC, c-MYC | v-myc myelocytomatosis viral oncogene homolog (avian) | MYC, c-MYC | Myc proto-oncogene protein |
| NBN, P95 | nibrin | NBN, p95 | Nibrin |
| NDGR1 | N-myc downstream regulated 1 | NDGR1 | Protein NDGR1 |
| NFKB1 | nuclear factor of kappa light polypeptide gene enhancer in B-cells 1 | NFKB1 | Nuclear factor NF-kappa-B p105 subunit |
| NFKB2 | nuclear factor of kappa light polypeptide gene enhancer in B-cells 2 (p49/p100) | NFKB2 | Nuclear factor NF-kappa-B p100 subunit |
| NFKBIA | nuclear factor of kappa light polypeptide gene enhancer in B-cells inhibitor, alpha | NFKBIA | NF-kappa-B inhibitor alpha |
| ODC1 | ornithine decarboxylase 1 | ODC | Ornithine decarboxylase |
| OGFR | opioid growth factor receptor | OGFR | Opioid growth factor receptor |
| PARP1 | poly (ADP-ribose) polymerase 1 | PARP-1 | Poly [ADP-ribose] polymerase 1 |
| PDGFC | platelet derived growth factor C | PDGF-C, VEGF-E | Platelet-derived growth factor C precursor |
| PDGFR | platelet-derived growth factor receptor | PDGFR | Platelet-derived growth factor receptor |
| PDGFRA | platelet-derived growth factor receptor, alpha polypeptide | PDGFRA, PDGFR2, CD140 A | Alpha-type platelet-derived growth factor receptor precursor |
| PDGFRB | platelet-derived growth factor receptor, beta polypeptide | PDGFRB, PDGFR, PDGFR1, CD140 B | Beta-type platelet-derived growth factor receptor precursor |
| PIK3CA | phosphoinositide-3 -kinase, catalytic, alpha polypeptide | PI3K subunit p110α | phosphoinositide-3-kinase, catalytic, alpha polypeptide |
| PSMD9, P27 | proteasome (prosome, macropain) 26S subunit, non-ATPase, 9 | p27 | 26S proteasome non-ATPase regulatory subunit 9 |
| PTEN | phosphatase and tensin homolog | | |
| RRM1 | ribonucleotide reductase M1 | RRM1, RR1 | Ribonucleoside-diphosphate reductase large subunit |
| RRM2 | ribonucleotide reductase M2 | RRM2, RR2M, RR2 | Ribonucleoside-diphosphate reductase subunit M2 |
| RRM2B | ribonucleotide reductase M2 B (TP53 inducible) | RRM2B, P53R2 | Ribonucleoside-diphosphate reductase subunit M2 B |
| RXRB | retinoid X receptor, beta | RXRB | Retinoic acid receptor RXR-beta |
| RXRG | retinoid X receptor, gamma | RXRG, RXRC | Retinoic acid receptor RXR-gamma |
| SLC29A1 | solute carrier family 29 (nucleoside transporters), member 1 | ENT-1 | Equilibrative nucleoside transporter 1 |
| SPARC | secreted protein, acidic, cysteine-rich (osteonectin) | SPARC | SPARC precursor; Osteonectin |
| SRC | v-src sarcoma (Schmidt-Ruppin A-2) viral oncogene homolog (avian) | SRC | Proto-oncogene tyrosine-protein kinase Src |
| SSTR1 | somatostatin receptor 1 | SSTR1, SSR1, SS1R | Somatostatin receptor type 1 |
| SSTR2 | somatostatin receptor 2 | SSTR2, SSR2, SS2R | Somatostatin receptor type 2 |
| SSTR3 | somatostatin receptor 3 | SSTR3, SSR3, SS3R | Somatostatin receptor type 3 |
| SSTR4 | somatostatin receptor 4 | SSTR4, SSR4, SS4R | Somatostatin receptor type 4 |
| SSTR5 | somatostatin receptor 5 | SSTR5, SSR5, SS5R | Somatostatin receptor type 5 |
| TK1 | thymidine kinase 1, soluble | TK1, KITH | Thymidine kinase, cytosolic |
| TLE3 | transducin-like enhancer of split 3 (E(sp1) homolog, *Drosophila*) | TLE3 | Transducin-like enhancer protein 3 |
| TNF | tumor necrosis factor (TNF superfamily, member 2) | TNF, TNF-alpha, TNF-a | Tumor necrosis factor precursor |
| TOP1, TOPO1 | topoisomerase (DNA) I | TOP1, TOPO1 | DNA topoisomerase 1 |
| TOP2A, TOPO2A | topoisomerase (DNA) II alpha 170 kDa | TOP2A, TOP2, TOPO2A | DNA topoisomerase 2-alpha; Topoisomerase II alpha |
| TOP2B, TOPO2B | topoisomerase (DNA) II beta 180 kDa | TOP2B, TOPO2B | DNA topoisomerase 2-beta; Topoisomerase II beta |
| TP53 | tumor protein p53 | p53 | Cellular tumor antigen p53 |
| TUBB3 | tubulin, beta 3 | Beta III tubulin, | Tubulin beta-3 chain |

TABLE 8-continued

| Genes and Related Proteins for Cancer Theranostics | | | |
|---|---|---|---|
| Gene Symbol | Gene Name | Protein Symbol | Protein Name |
| | | TUBB3, TUBB4 | |
| TXN | thioredoxin | TXN, TRX, TRX-1 | Thioredoxin |
| TXNRD1 | thioredoxin reductase 1 | TXNRD1, TXNR | Thioredoxin reductase 1, cytoplasmic; Oxidoreductase |
| TYMS, TS | thymidylate synthetase | TYMS, TS | Thymidylate synthase |
| VDR | vitamin D (1,25-dihydroxyvitamin D3) receptor | VDR | Vitamin D3 receptor |
| VEGFA, VEGF | vascular endothelial growth factor A | VEGF-A, VEGF | Vascular endothelial growth factor A precursor |
| VEGFC | vascular endothelial growth factor C | VEGF-C | Vascular endothelial growth factor C precursor |
| VHL | von Hippel-Lindau tumor suppressor | VHL | Von Hippel-Lindau disease tumor suppressor |
| YES1 | v-yes-1 Yamaguchi sarcoma viral oncogene homolog 1 | YES1, Yes, p61-Yes | Proto-oncogene tyrosine-protein kinase Yes |
| ZAP70 | zeta-chain (TCR) associated protein kinase 70 kDa | ZAP-70 | Tyrosine-protein kinase ZAP-70 |

Genes and gene products that are known to play a role in cancer and can be included in a biosignature of the invention include without limitation 2AR, A DISINTEGRIN, ACTIVATOR OF THYROID AND RETINOIC ACID RECEPTOR (ACTR), ADAM 11, ADIPOGENESIS INHIBITORY FACTOR (ADIF), ALPHA 6 INTEGRIN SUBUNIT, ALPHA V INTEGRIN SUBUNIT, ALPHA-CATENIN, AMPLIFIED IN BREAST CANCER 1 (AIB1), AMPLIFIED IN BREAST CANCER 3 (AIB3), AMPLIFIED IN BREAST CANCER 4 (AIB4), AMYLOID PRECURSOR PROTEIN SECRETASE (APPS), AP-2 GAMMA, APPS, ATP-BINDING CASSETTE TRANSPORTER (ABCT), PLACENTA-SPECIFIC (ABCP), ATP-BINDING CASSETTE SUBFAMILY C MEMBER (ABCC1), BAG-1, BASIGIN (BSG), BCEI, B-CELL DIFFERENTIATION FACTOR (BCDF), B-CELL LEUKEMIA 2 (BCL-2), B-CELL STIMULATORY FACTOR-2 (BSF-2), BCL-1, BCL-2-ASSOCIATED X PROTEIN (BAX), BCRP, BETA 1 INTEGRIN SUBUNIT, BETA 3 INTEGRIN SUBUNIT, BETA 5 INTEGRIN SUBUNIT, BETA-2 INTERFERON, BETA-CATENIN, BETA-CATENIN, BONE SIALOPROTEIN (BSP), BREAST CANCER ESTROGEN-INDUCIBLE SEQUENCE (BCEI), BREAST CANCER RESISTANCE PROTEIN (BCRP), BREAST CANCER TYPE 1 (BRCA1), BREAST CANCER TYPE 2 (BRCA2), BREAST CARCINOMA AMPLIFIED SEQUENCE 2 (BCAS2), CADHERIN, EPITHELIAL CADHERIN-11, CADHERIN-ASSOCIATED PROTEIN, CALCITONIN RECEPTOR (CTR), CALCIUM PLACENTAL PROTEIN (CAPL), CALCYCLIN, CALLA, CAMS, CAPL, CARCINOEMBRYONIC ANTIGEN (CEA), CATENIN, ALPHA 1, CATHEPSIN B, CATHEPSIN D, CATHEPSIN K, CATHEPSIN L2, CATHEPSIN 0, CATHEPSIN 01, CATHEPSIN V, CD10, CD146, CD147, CD24, CD29, CD44, CD51, CD54, CD61, CD66e, CD82, CD87, CD9, CEA, CELLULAR RETINOL-BINDING PROTEIN 1 (CRBP1), c-ERBB-2, CK7, CK8, CK18, CK19, CK20, CLAUDIN-7, c-MET, COLLAGENASE, FIBROBLAST, COLLAGENASE, INTERSTITIAL, COLLAGENASE-3, COMMON ACUTE LYMPHOCYTIC LEUKEMIA ANTIGEN (CALLA), CONNEXIN 26 (Cx26), CONNEXIN 43 (Cx43), CORTACTIN, COX-2, CTLA-8, CTR, CTSD, CYCLIN D1, CYCLOOXYGENASE-2, CYTOKERATIN 18, CYTOKERATIN 19, CYTOKERATIN 8, CYTOTOXIC T-LYMPHOCYTE-ASSOCIATED SERINE ESTERASE 8 (CTLA-8), DIFFERENTIATION-INHIBITING ACTIVITY (DIA), DNA AMPLIFIED IN MAMMARY CARCINOMA 1 (DAM1), DNA TOPO1SOMERASE II ALPHA, DR-NM23, E-CADHERIN, EMMPRIN, EMS1, ENDOTHELIAL CELL GROWTH FACTOR (ECGR), PLATELET-DERIVED (PD-ECGF), ENKEPHALINASE, EPIDERMAL GROWTH FACTOR RECEPTOR (EGFR), EPISIALIN, EPITHELIAL MEMBRANE ANTIGEN (EMA), ER-ALPHA, ERBB2, ERBB4, ER-BETA, ERF-1, ERYTHROID-POTENTIATING ACTIVITY (EPA), ESR1, ESTROGEN RECEPTOR-ALPHA, ESTROGEN RECEPTOR-BETA, ETS-1, EXTRACELLULAR MATRIX METALLOPROTEINASE INDUCER (EMMPRIN), FIBRONECTIN RECEPTOR, BETA POLYPEPTIDE (FNRB), FIBRONECTIN RECEPTOR BETA SUBUNIT (FNRB), FLK-1, GA15.3, GA733.2, GALECTIN-3, GAMMA-CATENIN, GAP JUNCTION PROTEIN (26 kDa), GAP JUNCTION PROTEIN (43 kDa), GAP JUNCTION PROTEIN ALPHA-1 (GJA1), GAP JUNCTION PROTEIN BETA-2 (GJB2), GCP1, GELATINASE A, GELATINASE B, GELATINASE (72 kDa), GELATINASE (92 kDa), GLIOSTATIN, GLUCOCORTICOID RECEPTOR INTERACTING PROTEIN 1 (GRIP1), GLUTATHIONE S-TRANSFERASE p, GM-CSF, GRANULOCYTE CHEMOTACTIC PROTEIN 1 (GCP1), GRANULOCYTE-MACROPHAGE-COLONY STIMULATING FACTOR, GROWTH FACTOR RECEPTOR BOUND-7 (GRB-7), GSTp, HAP, HEAT-SHOCK COGNATE PROTEIN 70 (HSC70), HEAT-STABLE ANTIGEN, HEPATOCYTE GROWTH FACTOR (HGF), HEPATOCYTE GROWTH FACTOR RECEPTOR (HGFR), HEPATOCYTE-STIMULATING FACTOR III (HSF III), HER-2, HER2/NEU, HERMES ANTIGEN, HET, HHM, HUMORAL HYPERCALCEMIA OF MALIGNANCY (HHM), ICERE-1, INT-1, INTERCELLULAR ADHESION MOLECULE-1 (ICAM-1), INTERFERON-GAMMA-INDUCING FACTOR (IGIF), INTERLEUKIN-1 ALPHA (IL-IA), INTERLEUKIN-1 BETA (IL-1B), INTERLEUKIN-11 (IL-11), INTERLEUKIN-17 (IL-17), INTERLEUKIN-18 (IL-18), INTERLEUKIN-6 (IL-6), INTERLEUKIN-8 (IL-8), INVERSELY CORRELATED WITH ESTROGEN RECEPTOR EXPRESSION-1 (ICERE-1), KAI1, KDR, KERATIN 8, KERATIN 18, KERATIN 19, KISS-1, LEUKEMIA INHIBITORY FACTOR (LIF), LIF, LOST IN INFLAMMATORY BREAST CANCER (LIBC), LOT ("LOST ON TRANSFORMATION"), LYMPHOCYTE HOMING RECEPTOR, MACROPHAGE-COLONY STIMULATING FACTOR, MAGE-3, MAMMAGLOBIN, MASPIN, MC56, M-CSF, MDC, MDNCF, MDR, MELANOMA CELL ADHESION MOLECULE (MCAM), MEMBRANE METALLOENDOPEPTIDASE (MME), MEMBRANE-ASSOCIATED NEUTRAL ENDOPEPTIDASE (NEP), CYSTEINE-RICH PROTEIN (MDC), METASTASIN (MTS-1), MLN64, MMP1, MMP2, MMP3, MMP1, MMP9, MMP11, MMP13, MMP14, MMP15, MMP16, MMP17, MOESIN, MONOCYTE ARGININE-SERPIN, MONOCYTE-DERIVED NEUTROPHIL CHEMOTACTIC FACTOR, MONOCYTE-DERIVED PLASMINOGEN ACTIVATOR INHIBITOR, MTS-1, MUC-1, MUC18, MUCIN LIKE CANCER ASSOCIATED ANTIGEN (MCA), MUCIN, MUC-1, MULTIDRUG RESISTANCE PROTEIN 1 (MDR, MDR1), MULTIDRUG RESISTANCE RELATED PROTEIN-1 (MRP, MRP-1), N-CADHERIN, NEP, NEU, NEUTRAL ENDOPEPTIDASE, NEUTROPHIL-ACTIVATING PEPTIDE 1 (NAP1), NM23-H1, NM23-H2, NME1, NME2, NUCLEAR RECEPTOR COACTIVATOR-1 (NCoA-1), NUCLEAR RECEPTOR COACTIVATOR-2 (NCoA-2), NUCLEAR RECEPTOR COACTIVATOR-3 (NCoA-3), NUCLEOSIDE DIPHOSPHATE KINASE A (NDPKA), NUCLEOSIDE DIPHOSPHATE KINASE B (NDPKB), ONCOSTATIN M (OSM), ORNITHINE DECARBOXYLASE (ODC), OSTEOCLAST DIFFERENTIATION FACTOR (ODF), OSTEOCLAST DIFFERENTIATION FACTOR RECEPTOR (ODFR), OSTEONECTIN (OSN, ON), OSTEOPONTIN (OPN), OXYTOCIN RECEPTOR (OXTR), p27/kipl, p300/CBP COINTEGRATOR ASSOCIATE PROTEIN (p/CIP), p53, p9Ka, PAI-1, PAI-2, PARATHYROID ADENOMATOSIS 1 (PRAD1), PARATHYROID HORMONE-LIKE HORMONE (PTHLH), PARATHYROID HORMONE-RELATED PEPTIDE (PTHrP), P-CADHERIN, PD-ECGF, PDGF, PEANUT-REACTIVE URINARY MUCIN (PUM), P-GLYCOPROTEIN (P-GP), PGP-1, PHGS-2, PHS-2, PIP, PLAKOGLOBIN, PLASMINOGEN ACTIVATOR INHIBITOR (TYPE 1), PLASMINOGEN ACTIVATOR INHIBITOR (TYPE 2), PLASMINOGEN ACTIVATOR (TISSUE-TYPE), PLASMINOGEN ACTIVATOR (UROKINASE-TYPE), PLATELET GLYCOPROTEIN IIIa (GP3A), PLAU, PLEOMORPHIC ADENOMA GENE-LIKE 1 (PLAGL1), POLYMORPHIC EPITHELIAL MUCIN (PEM), PRAD1, PROGESTERONE RECEPTOR (PgR), PROGESTERONE RESISTANCE, PROSTAGLANDIN ENDOPEROXIDE SYNTHASE-2, PROSTAGLANDIN G/H SYNTHASE-2, PROSTAGLANDIN H SYNTHASE-2, pS2, PS6K, PSORIASIN, PTHLH, PTHrP, RAD51, RAD52, RAD54, RAP46, RECEPTOR-ASSOCIATED COACTIVATOR 3 (RAC3), REPRESSOR OF ESTROGEN RECEPTOR ACTIVITY (REA), S100A4, S100A6, S100A7, S6K, SART-1, SCAFFOLD ATTACHMENT FACTOR B (SAF-B), SCATTER FACTOR (SF), SECRETED PHOSPHOPROTEIN-1 (SPP-1), SECRETED PROTEIN, ACIDIC AND RICH IN CYSTEINE (SPARC), STANNICALCIN, STEROID RECEPTOR COACTIVATOR-1 (SRC-1), STEROID RECEPTOR COACTIVATOR-2 (SRC-2), STEROID RECEPTOR COACTIVATOR-3 (SRC-3), STEROID RECEPTOR RNA ACTIVATOR (SRA), STROMELYSIN-1, STROMELYSIN-3, TENASCIN-C(TN-C), TESTES-SPECIFIC PROTEASE 50, THROMBOSPONDIN I, THROMBOSPONDIN II, THYMIDINE PHOSPHORYLASE (TP), THYROID HORMONE RECEPTOR ACTIVATOR MOLECULE 1 (TRAM-1), TIGHT JUNCTION PROTEIN 1 (TJP1), TIMP1, TIMP2, TIMP3, TIMP4, TISSUE FACTOR (TF), TISSUE-TYPE PLASMINOGEN ACTIVATOR, TN-C, TP53, tPA, TRANSCRIPTIONAL INTERMEDIARY FACTOR 2 (TIF2), TREFOIL FACTOR 1 (TFF1), TSG101, TSP-1, TSP1, TSP-2, TSP2, TSP50, TUMOR CELL COLLAGENASE STIMULATING FACTOR (TCSF), TUMOR-ASSOCIATED EPITHELIAL MUCIN, uPA, uPAR, UROKINASE, UROKINASE-TYPE PLASMINOGEN ACTIVATOR, UROKINASE-TYPE PLASMINOGEN ACTIVATOR RECEPTOR (uPAR), UVOMORULIN, VASCULAR ENDOTHELIAL GROWTH FACTOR, VASCULAR ENDOTHELIAL GROWTH FACTOR RECEPTOR-2 (VEGFR2), VASCULAR ENDOTHELIAL GROWTH FACTOR-A, VASCULAR PERMEABILITY FACTOR, VEGFR2, VERY LATE T-CELL ANTIGEN BETA (VLA-BETA), VIMENTIN, VITRONECTIN RECEPTOR ALPHA POLYPEPTIDE (VNRA), VITRONECTIN RECEPTOR, VON WILLEBRAND FACTOR, VPF, VWF, WNT-1, ZAC, ZO-1, and ZONULA OCCLUDENS-1. The genes and/or gene products can be part of a biosignature for theranosing a cancer.

As an illustration, a treatment can be selected for a subject suffering from Non-Small Cell Lung Cancer. One or more biomarkers, such as, but not limited to, EGFR, excision repair cross-complementation group 1 (ERCC1), p53, Ras, p27, class III beta tubulin, breast cancer gene 1 (BRCA1), breast cancer gene 1 (BRCA2), and ribonucleotide reductase messenger 1 (RRM I), can be assessed from a vesicle from the subject. Based on one or more characteristics of the one or more biomarkers, the subject can be determined to be a responder or non-responder for a treatment, such as, but not limited to, Erlotinib, Carboplatin, Paclitaxel, Gefitinib, or a combination thereof.

In another embodiment, a treatment can be selected for a subject suffering from Colorectal Cancer, and a biomarker, such as, but not limited to, K-ras, can be assessed from a vesicle from the subject. Based on one or more characteristics of the one or more biomarkers, the subject can be determined to be a responder or non-responder for a treatment, such as, but not limited to, Panitumumab, Cetuximab, or a combination thereof.

In another embodiment, a treatment can be selected for a subject suffering from Breast Cancer. One or more biomarkers, such as, but not limited to, HER2, toposiomerase II a, estrogen receptor, and progesterone receptor, can be assessed from a vesicle from the subject. Based on one or more characteristics of the one or more biomarkers, the subject can be determined to be a responder or non-responder for a treatment, such as, but not limited to, trastuzumab, anthracyclines, taxane, methotrexate, fluorouracil, or a combination thereof.

As described, the biosignature used to theranose a cancer can comprise analysis of one or more biomarker, which can be a protein or nucleic acid, including a mRNA or a microRNA. The biomarker can be detected in a bodily fluid and/or can be detected associated with a vesicle, e.g., as a vesicle antigen or as vesicle payload. In an illustrative example, the biosignature is used to identify a patient as a responder or non-responder to a tyrosine kinase inhibitor. The biomarkers can be one or more of those described in WO/2010/121238, entitled "METHODS AND KITS TO PREDICT THERAPEUTIC OUTCOME OF TYROSINE KINASE INHIBITORS" and filed Apr. 19, 2010; or WO/2009/105223, entitled "SYSTEMS AND METHODS OF CANCER STAGING AND TREATMENT" and filed Feb. 19, 2009; both of which applications are incorporated herein by reference in their entirety.

In an aspect, the present invention provides a method of determining whether a subject is likely to respond or not to a tyrosine kinase inhibitor, the method comprising identifying one or more biomarker in a vesicle population in a sample from the subject, wherein differential expression of the one or more biomarker in the sample as compared to a reference indicates that the subject is a responder or non-responder to the tyrosine kinase inhibitor. In an embodiment, the one or more biomarker comprises miR-497, wherein reduced expression of miR-497 indicates that the subject is a responder (i.e., sensitive to the tyrosine kinase inhibitor). In another embodiment, the one or more biomarker comprises onr or more of miR-21, miR-23a, miR-23b, and miR-29b, wherein upregulation of the microRNA indicates that the subject is a likely non-responder (i.e., resistant to the tyrosine kinase inhibitor). In some embodiments, the one or more biomarker comprises on or more of hsa-miR-029a, hsa-let-7d, hsa-miR-100, hsa-miR-1260, hsa-miR-025, hsa-let-7i, hsa-miR-146a, hsa-miR-594-Pre, hsa-miR-024, FGFR1, MET, RAB25, EGFR, KIT and VEGFR2. In another embodiment, the one or more biomarker comprises FGF1, HOXC10 or LHFP, wherein higher expression of the biomarker indicates that the subject is a non-responder (i.e., resistant to the tyrosine kinase inhibitor). The method can be used to determine the sensitivity of a cancer to the tyrosine kinase inhibitor, e.g., a non-small cell lung cancer cell, kidney cancer or GIST. The tyrosine kinase inhibitor can be erlotinib, vandetanib, sunitinib and/or sorafenib, or other inhibitors that operate by a similar mechanism of action. A tyrosine kinase inhibitor includes any agent that inhibits the action of one or more tyrosine kinases in a specific or non-specific fashion. Tyrosine kinase inhibitors include small molecules, antibodies, peptides, or any appropriate entity that directly, indirectly, allosterically, or in any other way inhibits tyrosine residue phosphorylation. Specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-643-(4-morpholinyl)propoxyl]q-uinazoline, N-(3-ethynylphenyl)-6,7-bis(2-methoxyethoxy)-4-quinazolinamine, BIBX1382, 2,3,9,10,11,12-hexahydro-10-(hydroxymethyl)-1O-hydroxy-9-methyl-9,12-epox-y-1H-dondolo[1,2,3-fg:3',2', 1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, N-[2-(diethylamino)ethyl]-5-[(Z)-(5-fluoro-1,2-dihydro-2-oxo-3H-indol-3-ylidine)methyl]-2,4-dimethyl-IH-pyrrole-3-carboxamide (commonly known as sunitinib), A-[A-[[4-chloro-3 (trifluoromethyl)phenyl]carbamoylamino]phenoxy]-N-methyl-pyridine-2-carboxamide (commonly known as sorafenib), EMD121974, and N-(3-ethynylphenyl)-6,7-bis(2-methoxyethoxy)quinazolin-4-amine (commonly known as erlotinib). In some embodiments, the tyrosine kinase inhibitor has inhibitory activity upon the epidermal growth factor receptor (EGFR), VEGFR, PDGFR beta, and/or FLT3.

Thus, a treatment can be selected for the subject suffering from a cancer, based on a biosignature identified by the methods of the invention. Accordingly, the biosignature can comprise a presence or level of a circulating biomarker, including a microRNA, a vesicle, or any useful vesicle associated biomarker.

Cardiovascular

Assessing a vesicle can be used in the theranosis of a cardiovascular condition, disorder, or disease. A cardiovascular condition includes, but is not limited to, chronic rheumatic heart disease, hypertensive disease, ischemic heart disease, pulmonary circulatory disease, heart disease, cerebrovascular disease, diseases of arteries, arterioles and capillaries and diseases of veins and lymphatics. A chronic rheumatic heart disease includes, but is not limited to diseases of mitral valve, diseases of aortic valve, diseases of mitral and aortic valves, and diseases of other endocardial structures. A hypertensive disease includes, but is not limited to essential hypertension, hypertension, malignant, hypertension, benign, hypertension, unspecified, hypertensive heart disease, hypertensive renal disease, hypertensive renal disease, unspecified, with renal failure, hypertensive heart and renal disease, hypertension, renovascular, malignant, and hypertension, renovascular benign. An ischemic heart disease includes, but is not limited to acute myocardial infarction, myocardiac infarction, acute, anterolateral, myocardiac infarction, acute, anterior, myocardiac infarction, acute, inferolateral, myocardiac infarction, acute, inferoposterior, myocardiac infarction, acute, other inferior wall, myocardiac infarction, acute, other lateral wall, myocardiac infarction, acute, true posterior, myocardiac infarction, acute, subendocardial, myocardiac infarction, acute, spec, myocardiac infarction, acute, unspecified, postmyocardial infarction syndrome, intermediate coronary syndrome, old myocardial infarction, angina pectoris, angina decubitus, prinzmetal angina, coronary atherosclerosis, aneurysm and dissection of heart, aneurysm of heart wall, aneurysm of coronary vessels, dissection of coronary artery, and unspecified chronic ischemic heart disease.

A pulmonary circulatory disease includes, but is not limited to, diseases of pulmonary circulation, acute pulmonary heart disease, pulmonary embolism, not iatrogenic, chronic pulmonary heart disease, and unspecified chronic pulmonary heart disease. A heart disease includes, but is not limited to acute pericarditis, other and unspecified acute pericarditis, acute nonspecific pericarditis, acute and subacute endocarditis, acute bacterial endocarditis acute myocarditis, other and unspecified acute myocarditis, myocarditis, idiopathic, other diseases of pericardium, other diseases of endocardium, alvular disorder, mitral, valvular disorder, aortic, valvular disorder, tricuspid, valvular disorder, pulmonic, cardiomyopathy, hypertrophic obstructive cardiomyopathy, conduction disorders, atrioventricular block, third degree, atrioventricular block, first degree, atrioventricular block, mobitz ii, atrioventricular block, wenckebach's, bundle branch block, left, bundle branch block, right, sinoatrial heart block, atrioventricular excitation, anomalous, Wolff Parkinson White syndrome, cardiac dysrhythmias, tachycardia, paroxysmal supraventricular, atrial fibrillation and flutter, atrial fibrillation, atrial flutter, ventricular fibrillation and flutter, ventricular fibrillation, cardiac arrest, premature beats, other specified cardiac dysrhythmias, sick sinus syndrome, sinus bradycardia, cardiac dysrhythmia unspecified, gallop rhythm, heart failure, heart failure, congestive, acute pulmonary edema, systolic unspecified heart failure, acute systolic heart failure, chronic systolic heart failure, diastolic unspecified heart failure, diastolic chronic heart failure, combined unspecified heart failure, and cardiomegaly.

A cerebrovascular disease includes, but is not limited to subarachnoid hemorrhage, intracerebral hemorrhage, other and unspecified intracranial hemorrhage, intracranial hemorrhage, occlusion and stenosis of precerebral arteries, occlusion and stenosis of basilar artery, occlusion and stenosis of carotid artery, occlusion and stenosis of vertebral artery, occlusion of cerebral arteries, cerebral thrombosis, cerebral thrombosis without cerebral infarction, cerebral thrombosis with cerebral infarction, cerebral embolism, cerebral embolism without cerebral infarction, cerebral embolism with cerebral infarction, transient cerebral ischemia, basilar artery syndrome, vertebral artery syndrome, subclavian steal syndrome, vertebrobasilar artery syndrome, transient ischemic attack, acute but ill defined cerebrovascular disease, ill defined cerebrovascular disease, cerebral atherosclerosis, other generalized ischemic cerebrovascular disease, hypertensive encephalopathy, cerebral aneurysm nonruptured, cerebral arteritis, moyamoya disease, nonpyogenic thrombosis of intracranial venous sinus, transient global amnesia, late effects of cerebrovascular disease, cognitive deficits, speech and language deficits, unspecified speech and language deficits, aphasia, dysphasia, other speech and language deficits, hemiplegia/hemiparesis, hemiplegia affecting unspecified side, hemiplegia affecting dominant side, hemiplegia affecting nondominant side, monoplegia of upper limb, monoplegia of lower limb, other paralytic syndrome, other late effects of cerebrovascular disease, apraxia cerebrovascular disease, dysphagia cerebrovascular disease, facial weakness, ataxia, and vertigo.

Diseases of arteries, arterioles and capillaries include, but are not limited to atherosclerosis, atherosclerosis of renal artery, atherosclerosis of native arteries of the extremities, intermittent claudication, atherosclerosis, extremities, without ulceration, atherosclerosis, not heart/brain, aortic aneurysm, dissection of aorta, abdominal ruptured aortic aneurysm, abdominal, without ruptured aortic aneurysm, unspecified aortic aneurysm, other aneurysm, other peripheral vascular disease, raynaud's syndrome, thromboangiitis obliterans, other arterial dissection, dissection of carotid artery, dissection of iliac artery, dissection of renal artery, dissection of vertebral artery, dissection of other artery, erythromelalgia, unspecified peripheral vascular disease, arterial embolism and thrombosis, polyarteritis nodosa and allied conditions, polyarteritis nodosa, kawasaki disease/acute febrile mucocutaneous lymph node syndrome, hypersensitivity angiitis, goodpasture's syndrome, lethal midline granuloma, wegener's granulomatosis, giant cell arteritis, thrombotic microangiopathy, takayasu's disease, other disorders of arteries and arterioles, arteriovenous fistula acquired, arteritis unspecified, vasculitis, and vascular non-neoplastic nevus.

Diseases of veins and lymphatics include, but are not limited to, phlebitis and thrombophlebitis, femoral deep vein thrombosis, deep vein thrombosis of other leg veins, phlebitis of other sites, superficial veins of upper extremity, unspecified thrombophlebitis, portal vein thrombosis, other venous embolism and thrombosis, unspecified deep vein thrombosis, proximal deep vein thrombosis, distal deep vein thrombosis, unspecified venous embolism, varicose veins of lower extremities, varicose veins without ulcer, varicose veins without inflammation, varicose veins withoutulcer, inflammation, varicose veins, asymptomatic, hemorrhoids, hemorrhoids, internal without complication, hemorrhoids, external without complication, hemorrhoids, external thrombosed, hemorrhoids, varicose veins of other sites, esophageal varices without bleeding, esophageal varices without bleeding, varicocele, noninfective disorders of lymphatic channels, postmastectomy lymphedema syndrome, hypotension, orthostatic hypotension, iatrogenic hypotension, other disorders of circulatory system, other specified disorders of circulatory system, and unspecified venous insufficiency.

Other examples of cardiac conditions include, without limitation, coronary artery occlusion (e.g., resulting from or associated with lipid/cholesterol deposition, macrophage/inflammatory cell recruitment, plaque rupture, thrombosis, platelet deposition, or neointimal proliferation); ischemic syndromes (e.g., resulting from or associated with myocardial infarction, stable angina, unstable angina, coronary artery restenosis or reperfusion injury); cardiomyopathy (e.g., resulting from or associated with an ischemic syndrome, a cardiotoxin, an infection, hypertension, a metabolic disease (such as uremia, beriberi, or glycogen storage disease), radiation, a neuromuscular disease, an infiltrative disease (such as sarcoidosis, hemochromatosis, amyloidosis, Fabry's disease, or Hurler's syndrome), trauma, or an idiopathic cause); arrhythmia or dysrrhythmia (e.g., resulting from or associated with an ischemic syndrome, a cardiotoxin, adriamycin, an infection, hypertension, a metabolic disease, radiation, a neuromuscular disease, an infiltrative disease, trauma, or an idiopathic cause); infection (e.g., caused by a pathogenic agent such as a bacterium, a virus, a fungus, or a parasite); and an inflammatory condition (e.g., associated with myocarditis, pericarditis, endocarditis, immune cardiac rejection, or an inflammatory conditions resulting from one of idiopathic, autoimmune, or a connective tissue disease).

Cardiovascular: Biosignature

A biosignature of a vesicle can be assessed to provide a theranosis for a subject. The biosignature of the vesicle can comprise one or more biomarkers such as, but not limited to, any one or more biomarkers as described herein, such as, but not limited to, those listed in FIG. 24, miR-21, miR-129, miR-212, miR-214, miR-134, and others such as described in US Publication No. 2010/0010073.

Cardiovascular: Standard of Care

Determining the biosignature of a vesicle, the amount of vesicles, or both, of a sample from a subject suffering from a cardiac condition, disorder, or disease, can be used select a standard of care for the subject. The standard of care may include therapeutic agents or procedures (e.g., angioplasty). Examples of therapeutic agents include, without limitation, angiogenesis promoters (e.g., vascular endothelial growth factor, nitric oxide releasing or generating agents, fibroblast growth factor, platelet derived growth factor, interleukin-6, monocyte chemotactic protein-1, granulocyte-macrophage colony stimulating factor, transforming growth factor-.beta.), anti-thrombotic agents (e.g., aspirin, heparin, PPACK, enoxaprin, hirudin), anticoagulants, antibiotics, antiplatelet agents, thrombolytics (e.g., tissue plasminogen activator), antiproliferatives, antiinflammatories, agents that inhibit hyperplasia, agents that inhibit restenosis, smooth muscle cell inhibitors, growth factors, growth factor inhibitors, cell adhesion inhibitors, chemotherapeutic agents, and combinations thereof.

For example, detection of one or more microRNAs biomarkers, such as miR-21, miR-129, miR-212, miR-214, miR-134 or a combination thereof from vesicles can be used to characterize a cardiac hypertrophy and/or heart failure, which provides a theranosis for the cardiac hypertrophy. The theranosis can include selecting a therapy such as adminstering angiogenesis promoters. Other examples of treatments include those for treating abnormal cholesterol and/or triglyceride levels in the blood, such as listed in Table 9.

TABLE 9

| Examples of Classes of Drugs for Treatment of Cardiovascular Conditions | | |
|---|---|---|
| Class | Mechanism of Action | Examples |
| Statins | Competitive inhibitors of HMG-CoA reductase | Atorvastatin, Simvastatin, Pravastatin, Fluvastatin, Rosuvastatin, Lovastatin, Pitavastatin, Cerivastatin (withdrawn) |
| Fibrates | PPARα activators | Fenofibrate, Bezafibrate, Gemfibrozil, clofibrate, ciprofibrate |
| Cholesterol Absorption Inhibitors | May inhibit NCP1L1 in gut | Ezetimibe |
| Nicotinic Acid Derivatives | Inhibits cholesterol and triglyceride synthesis, exact mechanism unknown | Niacin |
| Bile Acid Sequestrants | Interrupt the enterohepatic circulation of bile acids | Colesevelam, Cholestyramine, Colestimide, Colestipol |
| Cholesteryl Ester Transfer Protein Inhibitors | Inhibit cholesteryl ester transfer protein, a plasma protein that mediates the exchange of cholesteryl esters from antiatherogenic HDL to proatherogenic apoliprotein B-containing lipoproteins | JTT-705, CETi-1, Torcetrapib |
| Reverse Lipid Transport Pathway Activators | Stimulate reverse lipid transport, a four-step process form removing excess cholesterol and other lipids from the walls of arteries and other tissues | ETC-216, ETC-588, ETC-642, ETC-1001, ESP-1552, ESP-24232 |
| Antioxidants/ Vascular Protectants | Inhibit vascular inflammation and reduce cholesterol levels; block oxidant signals that switch on vascular cellular adhesion molecule (VCAM)-1 | AGI-1067, Probucol (withdrawn) |
| Acyl-CoA Cholesterol Acyltransferase (ACAT) Inhibitors | Inhibit ACAT, which catalyzes cholesterol esterification, regulates intracellular free cholesterol, and promotes cholesterol absorption and assemble of VLDL | Eflucimibe, Pactimibe, Avasimibe (withdrawn), SMP-797 |
| Peroxisome Proliferator Activated Receptor Agonists | Activate PPARs, e.g., PPARα, γ, and possibly δ, which have a variety of gene regulatory functions | Tesaglitazar, GW-50516, GW-590735, LY-929, LY-518674, LY-465608, LY-818 |
| Microsomal Triglyceride Transfer Protein (MTTP) Inhibitors | Inhibit MTTP, which catalyze the transport of triglycerides, cholesteryl ester, and phosphatidylcholine between membranes; required for the synthesis of ApoB. | Implitapide, CP-346086 |
| Squalene Synthase Inhibitors | Interfere with cholesterol synthesis by halting the action of liver enzymes; may also slow or stop the proliferation of several cell types that contribute to atherosclerotic plaque formation | TAK-475, ER-119884 |
| Lipoprotein Lipase Activators | Directly activate lipoprotein lipase, which promotes the breakdown of the fat portion of lipoproteins | Ibrolipim (NO-1886) |
| Liproprotein(a) Antagonists | Not yet established | Gembacene |
| Bile Acid Reabsorption Inhibitors | Inhibit intestinal epithelial uptake of bile acids. | AZD-7806, BARI-1453, S-8921 |

In one embodiment, a treatment can be selected for a subject suffering from Peripheral Arterial Disease. One or more biomarkers, such as, but not limited to, C-reactive protein (CRP), serum Amylyoid A (SAA), interleukin-6, intracellular adhesion molecule (ICAM), vascular adhesion molecule (VCAM), CD40L, fibrinogen, fibrin D-dimer, fibrinopeptide A, von Willibrand factor, tissue plasminogen activator antigen (t-PA), factor VII, prothrombin fragment 1, oxidized low density lipoprotein (oxLDL), and lipoprotein A, can be assessed from a vesicle from the subject. Based on one or more characteristics of the one or more biomarkers, the subject can be determined to be a responder or non-responder for a treatment, such as, but not limited to, Atorvastatin, Simvastatin, Rosuvastatin, Pravastatin, Fluvastatin, Lovastatin, or a combination thereof.

In another embodiment, a treatment can be selected for a subject suffering from an arrhythmia. One or more biomarkers, such as, but not limited to, SERCA, AAP, Connexin 40, Connexin 43, ATP-sensitive potassium channel, Kv1.5 channel, and acetylcholine-activated posassium channel, can be assessed from a vesicle from the subject. Based on one or more characteristics of the one or more biomarkers, the subject can be determined to be a responder or non-responder for a treatment, such as, but not limited to, Disopyramide, Flecainide, Lidocaine, Mexiletine, Moricizine, Procainamide, Propafenone, Quinidine, Tocainide, Acebutolol, Atenolol, Betaxolol, Bisoprolol, Carvedilol, Esmolol, Metoprolol, Nadolol, Propranolol, Sotalol, Timolol, Amiodarone, Azimilide, Bepridil, Dofetilide, Ibutilide, Tedisamil, Diltiazem, Verapamil, Azimilide, Dronedarone, Amiodarone, PM101, ATI-2042, Tedisamil, Nifekalant, Ambasilide, Ersentilide, Trecetilide, Almokalant, D-sotalol, BRL-32872, HMR1556, L768673, Vernakalant, AZD70009, AVE0118, S9947, NIP-141/142, XEN-D0101/2, Ranolazine, Pilsicainide, JTV519, Rotigaptide, GAP-134, or a combination thereof.

In another embodiment, a treatment can be selected for a subject suffering from abnormal coagulation. One or more biomarkers, such as, but not limited to, F1.2, TAT, FPA, beta-throboglobulin, platelet factor 4, soluble P-selectin, IL-6, and CRP can be assessed from a vesicle from the subject. Based on one or more characteristics of the one or more biomarkers, the subject can be determined to be a responder or non-responder for a treatment, such as, but not limited to, aspirin, anticoagulants, ximelagatran, Heparin, Warfarin, or a combination thereof.

In another embodiment, a treatment can be selected for a subject suffering from Premature Atherosclerosis. One or more biomarkers, such as, but not limited to, CRP, NF-kB, IL-1, IL-6, IL-18, Apo-B, Lp-PLA2, Fibrinogen, Hcy, and Hcy-thiolactone can be assessed from a vesicle from the subject. Based on one or more characteristics of the one or more biomarkers, the subject can be determined to be a responder or non-responder for a treatment.

In yet another embodiment, a treatment can be selected for a subject suffering from Hypertension. One or more biomarkers, such as, but not limited to, Brain natriuretic peptide and N-terminal prohormone BNP, can be assessed from a vesicle from the subject. Based on one or more characteristics of the one or more biomarkers, the subject can be determined to be a responder or non-responder for a treatment.

In another embodiment, a treatment can be selected for a subject suffering from Cardiovascular Disease. One or more biomarkers, such as, but not limited to, an ACE inhibitor or angiotensin can be assessed from a vesicle from the subject. Based on one or more characteristics of the one or more biomarkers, the subject can be determined to be a responder or non-responder for a treatment, such as, but not limited to, lisinopril, candesartan, enalapril, or a combination thereof.

Thus, a treatment can be selected for the subject suffering from a cardiology related condition or cardiovascular condition, based on the biosignature of the subject's vesicle.

Autoimmune

Assessing a vesicle can be used in the theranosis of an autoimmune condition, disorder, or disease. Autoimmune conditions are conditions where a mammal's immune system starts reacting against its own tissues. Such conditions include, without limitation, systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, chagas disease, chronic obstruct pulmonary disease, dermatomyositis, diabetes mellitus type 1, endometriosis, goodpasture's syndrome, graves' disease, guillain-barré syndrome (gbs), Hashimoto's disease, hidradenitis suppurat a, kawasaki disease, iga nephropathy, idiopathic thrombocytopenic purpura, interstitial cystitis, lupus erythematosus i, mixed connect e tissue disease, morphea, myasthenia gravis, narcolepsy, neuromyotonia, *pemphigus vulgaris*, pernicious anaemia, psoriasis, psoriatic arthritis, polymyositis, primary biliary cirrhosis, rheumatoid arthritis, schizophrenia, *scleroderma*, sjogren's syndrome, stiff person syndrome, temporal arteritis, ulcerat e colitis, vasculitis, vitiligo, Wegener's granulomatosis, and AID.

Autoimmune: Biosignature

A biosignature of a vesicle can be assessed to provide a theranosis for a subject. The biosignature of the vesicle can comprise one or more biomarkers such as, but not limited to, a biomarker such as listed in FIG. 1 for autoimmune disease, or for other autoimmune diseases, such as, but not limited to those listed in FIGS. 23, 34, 35, 36, 39, 41, 42, and 56.

Autoimmune: Standard of Care

Determining the biosignature of a vesicle, the amount of vesicles, or both, of a sample from a subject suffering from an autoimmune condition, disorder or disease can be used to select a standard of care for the subject. Most autoimmune diseases cannot yet be treated directly, but are treated according to symptoms associated with the condition. The standard of care includes, for example, prescribing corticosteroid drugs, non-steroidal anti-inflammatory drugs (NTHEs) or more powerful immunosuppressant drugs such as cyclophosphamide, methotrexate and azathioprine that suppress the immune response and stop the progression of the disease. Radiation of the lymph nodes and plasmapheresis (a procedure that removes the diseased cells and harmful molecules from the blood circulation) are other ways of treating an autoimmune disease.

Examples of drugs or agents for use in treating autoimmune diseases, which can be selected based on a profiling of a vesicle from a subject, include those in Table 10 for s subject suffering from diabetes, in Table 11 for those suffering from Multiple Sclerosis.

TABLE 10

Example of Classes of Drugs for Treatment of Diabetes

| Class | Mechanism of Action | Examples |
|---|---|---|
| Peroxisome Proliferator-Activated Receptor (PPAR) Agonists | Target PPAR-gamma or PPAR-gamma and -alpha (see below). PPAR are nuclear receptors that help regulate glucose and lipid metabolism. Activation of PPAR-gamma improves insulin sensitivity and thus improves glycemic control. | Rosiglitazone, Pioglitazone, Balaglitazone, see also others described herein |
| Dual-Action Peroxisome | Act on both PPAR-gamma and PPAR-alpha. PPAR-alpha activation has effects on cellular uptake of fatty acids and their | TAK-559, Muraglitazar, Tesaglitazar, Netoglitazone, |

TABLE 10-continued

| Example of Classes of Drugs for Treatment of Diabetes | | |
|---|---|---|
| Class | Mechanism of Action | Examples |
| Proliferator-Activated Receptor Agonists | oxidation, and on lipoprotein metabolism. May also act to reduce inflammatory response in vascular endothelial cells. | see also others described herein |
| Biguanidines | Complete mechanism is not known. Reduces gluconeogenesis in the liver by inhibiting glucose-6-phosphatase. | Metformin, Metformin GR |
| Sulfonylureas | Induce insulin secretion by binding to cellular receptors that cause membrane depolarization and insulin exocytosis. | Glimepride, Glyburide/glibenclamide, Glipizide, Gliclazide. Tobutamide |
| Insulin and Insulin Analogs (Injectable, Inhaled, Oral, Transdermal, Intranasal) | Supplements endogenous insulin. Insulin analogs have a variety of amino acid changes and have altered onset of action and duration of action, as well as other properties, compared to native insulin. Inhaled insulin is absorbed through the alveoli. Spray oral insulin is absorbed by the buccal mucosa and intranasal through the nasal mucosa. Transdermal insulin is absorbed through the skin. | Insulin lispro, Insulin aspart, Insulin glargine, Exubera, AERx Insulin Diabetes Management System, HIM-2, Oaralin, Insulin detemir, Insulin glulisine |
| Meglitinides | Are thought to bind to a nonsulfonylurea beta cell receptor and act to cause insulin secretion by mechanism similar to sulfonylureas | Repaglinide, Nateglinide, Mitiglinide |
| Alpha-Glucosidase Inhibitors | Inhibit carbohydrate digestion. Act at brush border of intestinal epithelium. | Acarbose, Miglitol, Voglibose |
| Glucagon-Like Peptide(GLP)-1 Analogs | Diabetic patients may lack native GLP-1, and anlalogs act as substitutes. GLP-1 is an intestinal peptide hormone that induces glucose-dependent insulin secretion, controls gastric emptying, inhibits appetite, and modulates secretion of glucagon and somatostatin. | Exenatide, Exenatide LAR, Liraglutide, ZP 10, BN51077, |
| Dipeptidyl Peptidase (DPP)-IV Inhibitors | Inhibit DPP-IV, a ubiquitous enzyme that cleaves and inactivates GLP-1, thus inhibition of DPP-IV increases GLP-1 activity | LAF-237, p-32/98, MK-431, P3298, NVP LAF 237, |
| Pancreatic Lipase Inhibitors | Inhibits lipases, thus inhibiting uptake of dietary fat. This causes weight loss, improves insulin sensitivity and lowers hyperglycemia. | Orlistat |
| Amylin Analogs | Act to augment amylin, which acts with insulin by slowing glucose absorption from the gut and slows after-meal glucose release from liver. | Pramlintide |
| Dopamine D2 receptor agonists | Thought to act to alleviate abnormal daily variations in central neuroendocrine activity that can contribute to metabolic and immune system disordered. | Bromocriptine |
| Immuno-suppressants | Suppress autoimmune response thought to be implicated in Type I and possibly Type II diabetes. Example: Humanized monoclonal antibody that recognizes and inhibits the alpha subunit of IL-2 receptors; humanized Mab that binds to T cell CDS receptor to block function of T-effector cells that attack the body and cause autoimmune disease | Daclizumab, NBI 6024, TRX-TolerRx, OKT3-gamma-1-ala-ala |
| Insulin-like growth factor-1 agonists | Recombinant protein complex of insulin-like growth factor-1 and binding protein-3; regulates the delivery of somatomedin to target tissues. Reduces insulitis severity and beta cell destruction | Somatomedin-1 binding protein 3 |
| Insulin sensitizers | Insulin sensitizers, generally orally active | S15261, Dexlipotam, CLX 0901, R 483, TAK 654 |
| Growth hormone releasing factor agonists | Mimic the action of native GHRF | TH9507, SOM 230 |
| Glucagon antagonists | Inhibit glucagon action, stimulating insulin production and secretion, resulting in lower postprandial glucose levels | Liraglutide, NN 2501 |
| Diabetes type 1 vaccine | Prevents destruction of pancreatic beta cells that occurs in type 1 diabetes | Q-Vax, Damyd vaccine |
| Sodium-glucose co-transporter inhibitor | Selectively inhibits the sodium glucose co-transporter, which mediates renal reabsorption and intestinal absorption of glucose to maintain appropriate blood glucose levels. | T 1095 |
| Glycogen phosphorylase inhibitors | Inhibit glycogen phosphorylase, thus slowing release of glucose | Ingliforib |
| Undefined mechanisms | Drugs that act in ways beneficial to those with Type I or Type II Diabetes Mellitus, e.g., by reducing blood glucose and triglyceride levels, whose mechanisms have not been elucidated. | FK 614, INGAP Peptide, R 1439 |
| Antisense oligonucleotides | Bind to RNA and cause its destruction, thereby decreasing protein production from corresponding gene. | ISIS 113715 |
| Insulinotropin agonists | Stimulate insulin release | CJC 1131 |

TABLE 10-continued

| Example of Classes of Drugs for Treatment of Diabetes | | |
|---|---|---|
| Class | Mechanism of Action | Examples |
| Gluconeogenesis inhibitors | Inhibit gluconeogenesis, thus modulating blood glucose levels | CS 917 |
| Hydroxysteroid dehydrogenase inhibitors | Inhibit hydroxysteroid dehydrogenase, which are responsible for excess glucocorticoid production and hence, visceral obesity | BVT 3498 |
| Beta 3 adrenoceptor agonist | Agonist for beta 3 adrenoceptor, decreases blood glucose and suppresses weight gain | YM 178, Solabegron, N5984, |
| Nitric oxide antagonist | Decreases effects of NO | NOX 700 |
| Carnitine palmitoyl-transferase inhibitor | Inhibits carnitine palmitoyltransferase | ST 1326 |

TABLE 11

| Classes of Drugs for Treatment of Multiple Sclerosis | | |
|---|---|---|
| Class | Mechanism of Action | Examples |
| Recombinant interferons | IFN-beta has numerous effects on the immune system. Exact mechanism of action in MS not known | Interferon-beta-1b, Interferon-beta-1a |
| Altered peptide ligands | Ligands either templated on sequence of myelin basic protein, or containing randomly arranged amino acids (e.g., ala, lys, glu, tyr) whose structure resembles myelin basic protein, which is thought to be an antigen that plays a role in MS. Bind to the T-cell receptor but do not activate the T-cell because are not presented by an antigen-presenting cell. | Glatiramer acetate, MBP-8298, Tiplimotide, AG-284 |
| Chemotherapeutic agents | Immunosuppressive. MS is thought to be an autoimmune disease, so chemotherapeutics that suppress immunity improve MS | Mitoxantrone, Methotrexate, Cyclophosphamide |
| Immuno-suppressants | Act via a variety of mechanisms to dampen immune response. | Azathioprine, Teriflunomide, Oral Cladribine |
| Corticosteroids | Induce T-cell death and may up-regulate expression of adhesion molecules in endothelial cells lining the walls of cerebral vessels, as well as decreasing CNS inflammation. | Methylprednisolone |
| Monoclonal Antibodies | Bind to specific targets in the autoimmune cascade that produces MS, e.g., bind to activated T-cells | Natalizumab, Daclizumab, Altemtuzumab, BMS-188667, E-6040, Rituximab, M1 MAbs, ABT 874, T-0047 |
| Chemokine Receptor Antagonists | Prevent chemokines from binding to specific chemokine receptors involved in the attraction of immune cells into the CNS of multiple sclerosis patients, and inhibiting immune cell migration into the CNS | BX-471, MLN-3897, MLN-1202 |
| AMPA Receptor Antagonists | AMPA receptors bind glutamate, an excitatory neurotransmitter, which is released in excessive quantities in MS. AMPA antagonists suppresses the damage caused by the glutamate | E-2007 |
| Recombinant Human Glial Growth Factor (GGF) | GGF is associated with the promotion and survival of oligodendrocytes, which myelinate neurons of the CNS. rhGGF may help myelinate oligodendrocytes and protect the myelin sheath. | Recombinant Human GGF2 |
| T-cell Receptor Vaccine | Mimic the part of the receptor in T cells that attack myelin sheath, which activates regulatory T cells to decrease pathogenic T-cells. | NeuroVax |
| Oral Immuno-modulators | Various effects on the immune response that can modulate the process of MS | Simvastatin, FTY-720, Oral Glatiramer Acetate, FTY-720, Pirfenidone, Laquinimod |

In one embodiment, detection of miR-326 from a vesicle can be used to characterize multiple sclerosis, and one or more treatments selected from Table 11 can be selected for the subject. In another embodiment, the theranosis can include selecting a therapy such as interferon β-1b and interferon β-1a.

In another embodiment, a treatment can be selected for a subject suffering from Rheumatoid arthritis. One or more biomarkers, such as, but not limited to, 677CC/1298AA MTHFR, 677CT/1298AC MTHFR, 677CT MTHFR, G80AA RFC-1, 3435TT MDRI (ABCB1), 3435TT ABCB1, AMPD1/ATIC/ITPA, IL1-RN3, HLA-DRB103, CRP, HLA-D4, HLA DRB-1, anti-citrulline epitope containing peptides, anti-A1/RA33, Erythrocyte sedimentation rate (ESR), C-reactive protein (CRP), SAA (serum amyloid-associated protein), rheumatoid factor, IL-1, TNF, IL-6, IL-8, IL-1Ra, Hyaluronic acid, Aggrecan, Glc-Gal-PYD, osteoprotegerin, RNAKL, carilage oligomeric matrix protein (COMP), and calprotecting can be assessed from a vesicle from the subject. Based on one or more characteristics of the one or more biomarkers, the subject can be determined to be a responder or non-responder for a treatment, such as, but not limited to, Methotrexate, infliximab, adalimumab'etanercept, sulfasalazine, or a combination thereof.

Thus, a treatment can be selected for the subject suffering from an autoimmune condition, based on the biosignature of the subject's vesicle Infectious Diseases Assessing a vesicle can be used in the theranosis of an infectious disease such as a bacterial, viral or other infectious condition or disease. An infectious or parasitic disease can arise from bacterial, viral, fungal, or other parasitic infection. For example, the disease or condition may be Whipple's Disease, Prion Disease, cirrhosis, methicillin-resistant *staphylococcus aureus*, HIV, hepatitis, syphilis, meningitis, malaria, tuberculosis, or influenza.

An infectious or parasitic disease includes, but is not limited to, intestinal infectious diseases, tuberculosis, zoonotic bacterial diseases, other bacterial diseases, human immunodeficiency virus hiv infection, poliomyelitis and other non arthropod borne viral diseases of central nervous system, viral diseases accompanied by exanthem, arthropod borne viral diseases, other diseases due to viruses and chlamydiae, rickettsioses and other arthropod borne diseases, syphilis and other venereal diseases, other spirochetal diseases, mycoses, helminthiases, other infectious and parasitic diseases, and late effects of infectious and parasitic diseases. Intestinal infectious diseases include, but are not limited to cholera, typhoid and paratyphoid fevers, *salmonella* gastroenteritis, shigellosis, shigellosisunspecified, staphylococcal food poisoning, amoebiasis, acute amoebic dysentery without mention of abscess, chronic intestinal amoebiasis without mention of abscess, amoebic nondysenteric colitis, amoebic liver abscess, amoebic lung abscess, amoebic brain abscess, amoebic skin ulceration, amoebic infection of other sites, unspecified amoebiasis, balantidiasis, giardiasis, coccidiosis, intestinal trichomoniasis, cryptosporidiosis, cyclosporiasisunspecifiedified protozoal intestinal disease, intestinal infections due to other organisms, enteritis due to rotavirus, enteritis due to other viral enteritis, intestinal infection due to other organism not elsewhere classified, ill defined intestinal infections, colitis enteritis and gastroenteritis of presumed infectious origin.

A human immunodeficiency virus infection includes, but is not limited to human immunodeficiency virus infection with specified conditions, human immunodeficiency virus infection causing other specified, and other human immunodeficiency virus infection.

A poliomyelitis and other non arthropod borne viral diseases of central nervous system include, but are not limited to acute poliomyelitis, slow virus infection of central nervous system, kuru, creutzfeld jakob disease, meningitis due to enterovirus, other enterovirus diseases of central nervous system, and other non arthropod borne viral diseases of central nervous system. Viral diseases accompanied by exanthem include, but are not limited to smallpox, cowpox and paravaccinia, chickenpox, herpes zoster, herpes simplex, genital herpes, herpetic gingivostomatitis, herpetic disease, uncomplicated, measles, rubella, other viral exanthemata, fifth disease, unspecified viral exanthems, roseola infantum, other human herpesvirus encephalitis, other human herpesvirus infections, other poxvirus infections, other orthopoxvirus infections, monkeypox, other parapoxvirus infections, bovine stomatitis, sealpox, yatapoxvirus infections, tanapox, yaba monkey tumor virus, other poxvirus infections, and unspecified poxvirus infections.

Arthropod borne viral diseases include, but are not limited to yellow fever, dengue fever, mosquito borne viral encephalitis, encephalitis, mosquitounspecified, tick borne viral encephalitis, viral encephalitis transmitted by other and unspecified arthropods, arthropod borne hemorrhagic fever, ebolaunspecified, other arthropod borne viral diseases, and unspecified west nile virus.

Other diseases due to viruses and chlamydiae include, but are not limited to viral hepatitis, hepatitis a with hepatic coma, hepatitis a without coma, hepatitis b with hepatic coma, hepatitis b without coma, acute, other specified viral hepatitis with mention of hepatic coma, other specified viral hepatitis without mention of hepatic coma, unspecified viral hepatitis c, viral hepatitis c without hepatic coma, viral hepatitis c with hepatic coma, hepatitis, viral, rabies, mumps, mumps, uncomplicated, ornithosis, specific diseases due to coxsackie virus, herpangina, hand, foot, mouth disease, mononucleosis, trachoma, other diseases of conjunctiva due to viruses and chlamydiae, other diseases due to viruses and chlamydiae, molluscum contagiosum, warts, all sites, condyloma acuminata, sweating fever, cat scratch disease, foot and mouth disease, cmv disease, viral infection in conditions classified elsewhere and of unspecified site, rhinovirus, hpv, and respiratory syncytial virus. Rickettsioses and other arthropod borne diseases include, but are not limited to louse borne epidemic typhus, other typhus, tick borne rickettsioses, rocky mountain spotted fever, other rickettsioses, malaria, leishmaniasis, trypa omiasis, relapsing fever, other arthropod borne diseases, other specified arthropod borne diseases, lyme disease, and babesiosis.

A viral host includes, but is not limited to Adenovirus, Astrovirus, Avian influenza virus, Coxsackievirus, Dengue virus, Ebola virus, Echovirus, Enteric adenovirus, Enterovirus, Hantaviruses, Hepatitis A virus, Hepatitis B virus, Hepatitis C virus, Hepatitis D virus, Hepatitis E virus, Herpes simplex virus (HSV), Human cytomegalovirus, Human immunodeficiency virus (HIV), Human papillomavirus (HPV), Influenza virus, Japanese encephalitis virus (JEV), Lassa virus, Marburg virus, Measles virus, Mumps virus, Norovirus, Parainfluenza virus, Poliovirus, Rabies virus, Respiratory syncytial virus, Rotavirus, Rubella virus, SARS coronavirus, Tick-borne encephalitis virus (TBEV), Variola virus, West Nile virus, and Yellow fever virus. A fungal host includes, but is not limited to *Candida albicans*. A parasitic host includes, but is not limited to *Plasmodium, Schistosoma mansoni*, and *Trichomonas vaginalis.*

A bacterial host includes, but is not limited to *Acinetobacter baumannii, Bacillus anthracis, Bartonella, Bordetella pertussis, Borrelia, Brucella, Chlamydia pneumoniae, Chlamydia trachomatis, Clostridium botulinum, Corynebacterium diphtheriae, Coxiella burnetii, Ehrlichia*, Enterococci, Enterovirulent *Escherichia coli, Francisella tularensis, Haemophilus ducreyi, Helicobacter pylori, Klebsiella pneumoniae, Legionella pneumophila*, Leptospira interrogans, *Mycobacterium tuberculosis, Mycoplasma genitalium, Mycoplasma pneumoniae, Neisseria gonorrhoeae, Neisseria meningitidis*, Orientia tsutsugamushi, *Pseudomonas aeruginosa, Rickettsia, Salmonella, Shigella, Staphylococcus aureus, Streptococcus pneumoniae, Streptococcus pyogenes, Treponema pallidum, Ureaplasma urealyticum, Vibrio cholerae, Vibrio vulnificus*, and *Yersinia pestis.*

Zoonotic bacterial diseases includes, but is not limited to plague, bubonic plague, tularemia, anthrax, brucellosis, glanders, melioidosis, rat bite fever, listeriosis, erysipelothrix infection, and pasteurellosis. Other bacterial diseases include, but are not limited to leprosy, diseases due to other mycobacteria, diphtheria, whooping cough, streptococcal sore throat and scarlatina, strep throat, scarlet fever, erysipelas, meningococcal meningitis, tetanus, septicaemia, pneumococcal septicemia, septicemia, gram negativeunspecified, septicemia, and actinomycotic infections.

Tuberculosis includes, but is not limited to primary tuberculous infection, pulmonary tuberculosis, tuberculosis of meninges and central nervous system, tuberculosis of intestines, peritoneum, and mesenteric glands, tuberculosis of bones and joints, tuberculosis of vertebral column, pott's disease, tuberculosis of genitourinary system, tuberculosis of other organs, erythema nodosum with hypersensitivity reaction in tuberculosis, bazin disease, tuberculosis of peripheral lymph nodes, scrofula, and miliary tuberculosis.

Syphilis and other venereal diseases include, but are not limited to congenital syphilis, early syphilis, symptomatic, syphilis, primary, genital, early syphilis, latent, cardiovascular syphilis, neurosyphilis, other forms of late syphilis, with symptoms, late syphilis, latent, other and unspecified syphilis, gonococcal infections, gonorrhoea, acute, lower gu tract, gonococcal conjunctivitis, and nongonococcal urethritis. Other spirochetal diseases include, but are not limited to leptospirosis, Vincent's angina, yaws, and pinta. Mycoses include, but are not limited to dermatophytosis, dermatophytosis of scalp/beard, onychomycosis, dermatophytosis of hand, tinea cruris, tinea pedis, tinea corporis, dermatomycosis, other and unspecified, tinea versicolor, dermatomycosisunspecified, candidiasis, moniliasis, oral, moniliasis, vulva/vagina, monilial balanitis, moniliasis, skin/nails, coccidioidomycosis, histoplasmosis, histoplasma infectionunspecified, blastomycotic infection, other mycoses, and opportunistic mycoses.

Helminthiases include, but are not limited to schistosomiasis bilharziasis, other trematode infections, echinococcosis, other cestode infection, trichi is, filarial infection and dracontiasis, ancylostomiasis and necatoriasis, other intestinal helminthiases, ascariasis, anisakiasis, strongyloidiasis, trichuriasis, enterobiasis, capillariasis, trichostrongyliasis, other and unspecified helminthiases, and unspecified intestinal parasitism. Other infectious and parasitic diseases include, but are not limited to toxoplasmosis, toxoplasmosisunspecified, trichomoniasis, urogenital trichomoniasis, trichomonal vaginitis, trichomoniasis, urethritis, pediculosis and phthirus infestation, pediculosis, head lice, pediculosis, body lice, pediculosis, pubic lice, pediculosisunspecified, acariasis, scabies, chiggers, sarcoidosis, ainhum, behcet's syndrome, pneumocystosis, psorospermiasis, and sarcosporidiosis. Late effects of infectious and parasitic diseases include, but are not limited to late effects of tuberculosis, and late effects of polio.

Infectious Disease: Biosignature

A biosignature of a vesicle can be assessed to provide a theranosis for a subject. The biosignature of the vesicle can comprise one or more biomarkers such as, but not limited to, any one or more biomarkers as described herein, such as, but not limited to, those listed in FIG. 1 for infection diseases, and FIGS. 24 and 43.

In some embodiments, an infectious disease can be characterized by detecting a component of a pathogen, such as a virus, bacteria, or other infectious agent, in a vesicle. For example, the component can be ABC transporters (*Candida albicans*), ABC transporters (Enterococci), AMA-1 (Apical membrane antigen 1), ATPase, Aac(6')-Aph(2") enzyme, Ace (Accessory cholera enterotoxin), Acf (Accessory colonization factor), Acr (a-crystallin) protein, AhpC and AhpD, Amyloid-β, AroC, Attachment glycoprotein (G) (Respiratory syncytial virus), Autolysin (N-acetylmuramoyl-L-alanine amidase), BacA, BmpA (P39), Botulinum neurotoxins, BvgA, —S, and —R, BvrR-BvrS, C4BP (C4b-binding protein), C5a peptidase, CAMP factor (cohemolysin), CBP (Choline binding protein), CME type β-lactamase, CSP (Circumsporozoite protein), CT (cholera toxin), CTX-M metallo-β-lactamase, CagA (cytotoxin-associated antigen), Capsid protein (C) (Dengue virus), Capsid protein (C) (Japanese encephalitis virus), Capsid protein (C) (Tick-borne encephalitis virus), Capsid protein (C) (West Nile virus), Capsid protein (C) (Yellow fever virus), Capsid protein (Astrovirus), Capsid protein (Coxsackievirus), Capsid protein (Echovirus), Capsid protein (Enterovirus), Capsid protein (Hepatitis A virus), Capsid protein (Poliovirus), Capsid protein (Rotavirus), Catechol siderophore ABC transporter, Com-1, CrmB (Cytokine response modifier), Cytolysin, D-Ala-D-Lac ligase, DHFR (Dihydrofolate reductase), DHPS (Dihydropteroate synthetase), DbpA (Decorin-binding protein A), Diphtheria toxin, Dot/Icm complex, E1 and E2 proteins (Rubella virus), E1A protein (Adenovirus), EIA protein (Enteric adenovirus), E 1B protein (Adenovirus), E1B protein (Enteric adenovirus), E2 early transcription region 2, E3 protein (Adenovirus), E4 protein (Adenovirus), E6 early transcription region 6, E7 early transcription region 7, EF (Edema factor), ESAT-6 and CFP-10, Elastase (*Vibrio vulnificus*), Env, Envelope glycoprotein (E) (Dengue virus), Envelope glycoprotein (E) (Japanese encephalitis virus), Envelope glycoprotein (E) (Tick-borne encephalitis virus), Envelope glycoprotein (E) (West Nile virus), Envelope glycoprotein (E) (Yellow fever virus), Esp (Enterococcal surface protein), Esp (Type III System-Secreted Proteins), F1 capsule (F1 antigen), FH (Factor H), FHA (Filamentous hemagglutinin), Falcipain 1/2, Fiber protein (Adenovirus), Fiber protein (Enteric adenovirus), Fibronectin binding protein II (Protein F/sfbII) (*Streptococcus pyogenes*), Fibronectin binding protein (Leptospira interrogans), Fibronetin binding protein (FBP54) (*Streptococcus pyogenes*), Fimbrial protein, Flagellin (FlaB and -A) (*H. pylori*), Flagellin (H-antigen) (*Escherichia coli*), Flagellin (H-antigen) (*Salmonella*), Flagellin (*Vibrio vulnificus*), FopA (43 kDa lipoprotein), Fusion protein (F) (Mumps virus), Fusion protein (F) (Parainfluenza virus), Fusion protein (F) (Respiratory syncytial virus), G6PD (Glucose-6-phosphate dehydrogenase), GES (Guiana extended-spectrum β-lactamase), GTP cyclohydrolase, Gag, Glycoprotein (G) (Rabies virus), Glycoprotein (GP) (Ebola virus), Glycoprotein (GP) (Lassa virus), Glycoprotein (GP) (Marburg virus), Glycoproteins (Gn/Gc) (Hantaviruses), HMW (Cytadherence accessory protein), HRP2 (Histidine-rich protein 2), Hemagglutinin (Avian influenza virus), Hemagglutinin (Influenza virus), Hemagglutinin (Measles virus), Hemagglutinin (Variola virus), Hemagglutinin-esterase glycoprotein (HE), Hemagglutinin-neuraminidase (HN) (Mumps virus), Hemagglutinin-neuraminidate (HN) (Paraninfluenza virus), Hemolysin (Vvh), Hexon protein (Adenovirus), Hexon protein (Enteric adenovirus), Hsp60 (Heat shock protein 60), Hyaluronate lyase, Hyaluronidase, IMP metallo-β-lactamase (*Acinetobacter baumannii*), IMP metallo-P-lactamase (*Klebsiella pneumoniae*), IcsA and IcsB, IgA protease (*Neisseria gonorrhoeae*), IgA 1 protease (*Streptococcus pneumoniae*), IgG and IgM for HSV 1/2, InhA, Intimin, InvA (*Rickettsia*), Invasin (*Escherichia coli*), Invasin (*Yersinia pestis*), IpaA, -B, -C, -D and -H, KPC metallo-3-lactamase, KatG, L protein (Lassa virus), L1 late transcription region 1, LF (Lethal factor), LSA1 (Liver-stage antigen 1), LT (heat labile toxin), LcrV (V antigen), LigA and LigB, Lipoprotein, M protein, MSP (Merozoite surface protein), Matrix protein (M) (Rabies virus), Matrix protein (M) (Respiratory syncytial virus), Matrix protein (Avian influenza virus), Matrix protein (Influenza virus), MexAB-OprM, MexCD-OprJ, MexEF-OprN, MexXY-OprM, Mip (Macrophage infectivity potentiator), NSE (Neuron-specific enolase), Nef, Neuraminidase (Avian influenza virus), Neuraminidase (Influenza virus), Neuraminidase (*Streptococcus pneumoniae*), Non-structural protein (NS) (Respiratory syncytial virus), Non-structural protein 1 (NS1) (Dengue virus), Non-structural protein 1 (NS1) (Japanese encephalitis virus), Non-structural protein 1 (NS1) (Tick-borne encephalitis virus), Non-structural protein 1 (NS1) (West Nile virus), Non-structural protein 1 (NS1) (Yellow fever virus), Non-structural protein 2A (NS2A) (Dengue virus), Non-structural protein 2A (NS2A) (Japanese encephalitis virus), Non-structural protein 2A (NS2A) (Tick-borne encephalitis virus), Non-structural protein 2A (NS2A) (West Nile virus), Non-structural protein 2A (NS2A) (Yellow fever virus), Non-structural protein 2B (NS2B) (Dengue virus), Non-structural protein 2B (NS2B) (Japanese encephalitis virus), Non-structural protein 2B (NS2B) (Tick-borne encephalitis virus), Non-structural protein 2B (NS2B) (West Nile virus), Non-structural protein 2B (NS2B) (Yellow fever virus), Non-structural protein 3 (NS3) (Dengue virus), Non-structural protein 3 (NS3) (Japanese encephalitis virus), Non-structural protein 3 (NS3) (Tick-borne encephalitis virus), Non-structural protein 3 (NS3) (West Nile virus), Non-structural protein 3 (NS3) (Yellow fever virus), Non-structural protein 4 (Rotavirus), Non-structural protein 4A (NS4A) (Dengue virus), Non-structural protein 4A (NS4A) (Japanese encephalitis virus), Non-structural protein 4A (NS4A) (Tick-borne encephalitis virus), Non-structural protein 4A (NS4A) (West Nile virus), Non-structural protein 4A (NS4A) (Yellow fever virus), Non-structural protein 4B (NS4B) (Dengue virus), Non-structural protein 4B (NS4B) (Japanese encephalitis virus), Non-structural protein 4B (NS4B) (Tick-borne encephalitis virus), Non-structural protein 4B (NS4B) (West Nile virus), Non-structural protein 4B (NS4B) (Yellow fever virus), Non-structural protein 5 (NS5) (Dengue virus), Non-structural protein 5 (NS5) (Japanese encephalitis virus), Non-structural protein 5 (NS5) (Tick-borne encephalitis virus), Non-structural protein 5 (NS5) (West Nile virus), Non-structural protein 5 (NS5) (Yellow fever virus), Non-structural proteins (Avian influenza virus), Non-structural proteins (Influenza virus), Nucleocapsid (Hantaviruses), Nucleocapsid (Measles virus), Nucleocapsid (Parainfluenza virus), Nucleocapsid (SARS coronavirus), Nucleoprotein (N) (Rabies virus), Nucleoprotein (NP) (Respiratory syncytial virus), Nucleoprotein (major nucleoprotein) (Marburg virus), Nucleoprotein (Avian influenza virus), Nucleoprotein (Ebola virus), Nucleoprotein (Influenza virus), Nucleoprotein (Lassa virus), ORF1 (Hepatitis E virus), ORF2 (Hepatitis E virus), ORF3 (Hepatitis E virus), OXA metallo-β-lactamase (*Acinetobacter baumannii*), OXA metallo-P-lactamase (*Klebsiella pneumoniae*), OmpA and OmpB (*Rickettsia*), OmpL1 (Leptospira interrogans), OmpQ (Outer membrane porin protein) (*Bordetella pertussis*), OmpS (*Legionella pneumophila*), Opacity factor, OprD, Osp (Outer surface protein), Outer membrane proteins (*Chlamydia pneumoniae*), Outer membrane proteins (*Ehrlichia*), P1 adhesin, P30 adhesin, PA (Protective antigen), PBP (Penicillin-binding protein), PCRMP 1-4 (Cysteine repeat modular proteins), PER metallo-P-lactamase, Patl, Peptidoglycan (murein) hydrolase, Pertactin (p69), Pertussis toxin, PfEMP1 (*Plasmodium falciparum* erythrocyte membrane protein-1), Phosphoprotein (P) (Respiratory syncytial virus), Phosphoprotein (Measles virus), Pla (plasminogen activator), Plasminogen-binding protein, Pld, Pneumolysin, Pol, Poly-D-glutamic acid capsule, Polymerase (L) (Rabies virus), Porin, Premembrane/membrane protein (PrM/M) (Dengue virus), Premembrane/membrane protein (PrM/M) (Japanese encephalitis virus), Premembrane/membrane protein (PrM/M) (Tick-borne encephalitis virus), Premembrane/membrane protein (PrM/M) (West Nile virus), Premembrane/membrane protein (PrM/M) (Yellow fever virus), Proteins for two-component regulatory systems (*Ehrlichia*), Proteins for two-component regulatory systems (*Mycobacterium tuberculosis*), Proteins of gB, gC, gD, gH, and gL, PsaA, PspA (Pneumococcal surface protein A), PurE, Pyrogenic exotoxins, RBP 1/2 (Reticulocyte binding protein 1/2), RdRp (RNA dependant RNA polymerase) (Norovirus), RdRp (RNA dependent RNA polymerase) (Astrovirus), RdRp (RNA dependent RNA polymerase) (SARS coronavirus), Rev, RfbE, RibD and RibE, Rmp, S-layer protein, S100B (S100 protein (3 chain), SHV metallo-β-lactamase, SIM metallo-β-lactamase, ST (heat stable toxin), *Salmonella* plasmid virulence (SPV) proteins, Serine protease (Astrovirus), ShET1/2, Shiga toxin (Verotoxin), SipA (*Salmonella* Invasion Protein A), SlyA, Small hydrophobic protein, Sop (*Salmonella* outer protein), Spike glycoprotein (S), Streptococcal DNase, Streptogramin A acetyltransferase, Streptokinase, Streptolysin O, StxA/B (Shiga toxin A/B), SucB (Dihydrolipoamide succinyltransferase) (*Mycobacterium tuberculosis*), SucB (dihydrolipoamide succinyltransferase) (*Coxiella burnetii*), Syc (Yop chaperones), T protein, TCP (toxin-coregulated pilus), TEM metallo-P-lactamase, TRAP (Thrombospondin-related anonymous protein), Tat, Tau-protein, TcfA (Tracheal colonization factor), Tir (Translocated intimin receptor), T1yA and TlyC, ToxR (toxin regulatory protein), Tu14 (17 kDa lipoprotein), Type IV pili, Urease (*Brucella*), Urease (*Helicobacter pylori*), VEB metallo-β-lactamase, VETF (Virus early transcription factor), VIM metallo-β-lactamase (*Acinetobacter baumannii*), VIM metallo-β-lactamase (*Klebsiella pneumoniae*), VP1 (Norovirus), VP2 (Norovirus), VP24 (Ebola virus), VP24 (Marburg virus), VP30 (minor nucleoprotein) (Ebola virus), VP30 (minor nucleoprotein) (Marburg virus), VP35 (P-like protein) (Ebola virus), VP35 (P-like protein) (Marburg virus), VP40 (Matrix Protein) (Ebola virus), VP40 (Matrix Protein) (Maburg virus), VacA (vacuolating cytotoxin), Vag8 (virulence-activated gene 8), Vif, VirB type IV secretion system, V1sE (35 kDa lipoprotein), Vpr, Vpu/Vpx, XerD, Yops (*Yersinia* outermembrane proteins), Ysc (Yop secretion apparatus), Z protein (Lassa virus), Zot (zonula occuldens toxin), gG1 (HSV-1) and gG2 (HSV-2), p41i, p83, and p100, pLDH (Plasmodium lactate dehydrogenase), α/β/γ proteins, 120 kDa gene, 16S and 5S rRNA genes (*Legionella pneumophila*), 16S rRNA (*Bartonella*), 16S rRNA (*Borrelia*), 16S rRNA (*Brucella*), 16S rRNA (*Ehrlichia*), 16S rRNA (*Klebsiella pneumoniae*), 16S rRNA (Orientia tsutsugamushi), 16S rRNA (*Rickettsia*), 16S rRNA gene (*Acinetobacter baumannii*), 16S rRNA gene (*Chlamydia pneumoniae*), 16S rRNA gene (*Clostridium botulinum*), 16S rRNA gene (*Mycoplasma pneumoniae*), 16S rRNA gene (*Neisseria gonorrhoeae*), 16S rRNA gene (*Vibrio vulnificus*), 16S-23S rRNA intergenic spacer (*Bartonella*), 16S-23S rRNA intergenic spacer (*Coxiella burnetii*), 17 kDa gene, 18S ssrRNA, 23S rRNA gene (*Acinetobacter baumannii*), 23S rRNA gene (*Neisseria gonorrhoeae*), 2C gene, 3' NCR (Dengue virus), 3' NCR (Japanese encephalitis virus), 3' NCR (Tick-borne encephalitis virus), 3' NCR (West Nile virus), 3' NCR (Yellow fever virus), 5' NCR (Coxsackievirus), 5' NCR (Dengue virus), 5' NCR (Echovirus), 5' NCR (Enterovirus), 5' NCR (Japanese encephalitis virus), 5' NCR (Polioviurs), 5' NCR (Tick-borne encephalitis virus), 5' NCR (West Nile virus), 5' NCR (Yellow fever virus), 56 kDa gene, A13L gene, ARE1 gene, ATF2 gene, B12R gene, B6R gene, B8R gene, C gene (Dengue virus), C gene (Japanese encephalitis virus), C gene (Tick-borne encephalitis virus), C gene (West Nile virus), C gene (Yellow fever virus), C3L gene, CDR 1/2 genes, E gene (Dengue virus), E gene (Japanese encephalitis virus), E gene (Tick-borne encephalitis virus), E gene (West Nile virus), E gene (Yellow fever virus), E1 and E2 genes, E1A gene (Adenovirus), E1A gene (Enteric adenovirus), E1B gene (Adenovirus), EIB gene (Enteric adenovirus), E2 gene, E3 gene (Adenovirus), E3L gene, E4 gene (Adenovirus), E6 gene, E7 gene, ERG genes, ESAT-6 and CFP-10 genes, F gene (Mumps virus), F gene (Parainfluenza virus), F gene (Respiratory syncytial virus), G gene (Rabies virus), G gene (Respiratory syncytial virus), GP gene (Ebola virus), GP gene (Lassa virus), GP gene (Marburg virus), H gene (Measles virus), HA gene (Avian influenza virus), HA gene (Influenza virus), HE gene (SARS Coronavirus), NA gene (Mumps virus), HN gene (Parainfluenza virus), IS100, IS1081, IS1533 (Leptospira interrogans), IS285, IS481 (BP0023), IS6110, IS711 (*Brucella*), ISFtu, J7R gene, L gene (Lassa virus), L gene (Rabies virus), L segment, L1 gene, LEE (locus of enterocyte effacement), Long control region (LCR), M gene (Rabies virus), M gene (Respiratory syncytial virus), M genes (Avian influenza virus), M genes (Influenza virus), M segment, MDR1 gene, MEC3 gene, N gene (Measles virus), N gene (Rabies virus), N gene (SARS coronavirus), NA gene (Avian influenza virus), NA gene (Influenza virus), NC gene (Parainfluenza virus), NP gene (Avian influenza virus), NP gene (Ebola virus), NP gene (Influenza virus), NP gene (Lassa virus), NP gene (Marburg virus), NP gene (Respiratory syncytial virus), NS gene (Avian influenza virus), NS gene (Influenza virus), NS gene (Respiratory syncytial virus), NS1 gene (Dengue virus), NS1 gene (Japanese encephalitis virus), NS1 gene (Tick-borne encephalitis virus), NS1 gene (West Nile virus), NS1 gene (Yellow fever virus), NS2A gene (Dengue virus), NS2A gene (Japanese encephalitis virus), NS2A gene (Tick-borne encephalitis virus), NS2A gene (West Nile virus), NS2A gene (Yellow fever virus), NS2B gene (Dengue virus), NS2B gene (Japanese encephalitis virus), NS2B gene (Tick-borne encephalitis virus), NS2B gene (West Nile virus), NS2B gene (Yellow fever virus), NS3 gene (Dengue virus), NS3 gene (Japanese encephalitis virus), NS3 gene (Tick-borne encephalitis virus), NS3 gene (West Nile virus), NS3 gene (Yellow fever virus), NS4 gene (Rotavirus), NS4A gene (Dengue virus), NS4A gene (Japanese encephalitis virus), NS4A gene (Tick-borne encephalitis virus), NS4A gene (West Nile virus), NS4A gene (Yellow fever virus), NS4B gene (Dengue virus), NS4B gene (Japanese encephalitis virus), NS4B gene (Tick-borne encephalitis virus), NS4B gene (West Nile virus), NS4B gene (Yellow fever virus), NS5 gene (Dengue virus), NS5 gene (Japanese encephalitis virus), NS5 gene (Tick-borne encephalitis virus), NS5 gene (West Nile virus), NS5 gene (Yellow fever virus), ORF 1a (Astrovirus), ORF 1b (Astrovirus), ORF 2 (Astrovirus), ORF1 (Hepatitis E virus), ORF1 (Norovirus), ORF2 (Hepatitis E virus), ORF2 (Norovirus), ORF3 (Hepatitis E virus), ORF3 (Norovirus), P gene (Measles virus), P gene (Respiratory syncytial virus), PDH1 gene, Peptidyltransferase mutations, Plasmids (QpH1, QpRS, QpDG, QpDV), PrM/M gene (Dengue virus), PrM/M gene (Japanese encephalitis virus), PrM/M gene (Tick-borne encephalitis virus), PrM/M gene (West Nile virus), PrM/M gene (Yellow fever virus), RdRp gene in ORF lab (SARS coronavirus), S gene (SARS coronavirus), S segment, SH gene (Mumps virus), SNP (single nucleotide polymorphism), *Salmonella* pathogenicity island (SPI), *Salmonella* plasmid virulence (SPV) operon, ShET1/2 genes, VNTR (variable number tandem repeat) (*Bacillus anthracis*), VNTR (variable number tandem repeat) (*Brucella*), VNTR (variable number tandem repeat) (*Francisella tularensis*), VNTR (variable number tandem repeat) (*Yersinia pestis*), VP24 gene (Ebola virus), VP24 gene (Marburg virus), VP30 gene (Ebola virus), VP30 gene (Marburg virus), VP35 gene (Ebola virus), VP35 gene (Marburg virus), VP40 gene (Ebola virus), VP40 gene (Marburg virus), Z gene (Lassa virus), aac(3) gene, aac(6') gene, aac(6')-aph(2") gene, aad gene, ace gene, acpA gene, agrBDCA locus, ahpC and ahpD genes, ar1RS locus, atxA gene, bc1A gene, b1aCTX-M gene, blaGES gene, blaGIM gene (*Pseudomonas aeruginosa*), blaIMP gene (*Acinetobacter baumannii*), blaIMP gene (*Klebsiella pneumoniae*), blaIMP gene (*Pseudomonas aeruginosa*), b1aKPC gene, blaOXA gene (*Acinetobacter baumannii*), bIaOXA gene (*Klebsiella pneumoniae*), blaOXA gene (*Pseudomonas aeruginosa*), bIaSHV gene, blaSIM gene (*Klebsiella pneumoniae*), blaSIM gene (*Pseudomonas aeruginosa*), bIaTEM gene, bIaVIM gene (*Acinetobacter baumannii*), blaVIM gene (*Klebsiella pneumoniae*), bIaVIM gene (*Pseudomonas aeruginosa*), bvg locus (bvgA, -S, and -R genes), cagA gene, cap locus (capB, -C, and -A genes) (*Bacillus anthracis*), cap operon (capB and -C) (*Francisella tularensis*), capsid gene (Coxsackievirus), capsid gene (Echovirus), capsid gene (Enterovirus), capsid gene (Hepatitis A virus), capsid gene (Poliovirus), capsid gene (Rotavirus), cme gene, cnt genes, com-1 gene, cppB gene, cps gene, crmB gene, ctx gene, cya gene, cyl gene, eaeA gene, east gene (*Escherichia coli*), env gene, ery gene, esp gene (Enterococci), esp genes (*Escherichia coli*), fiber gene (Adenovirus), fiber gene (Enteric adenovirus), fimbriae genes, flaB gene (*Borrelia*), flaB gene (Leptospira interrogans), flagellin genes, fljA, fljB, and fliC genes, fopA gene, ftsZ gene, gG1 and gG2 gens, gag gene, genes for two-component regulatory systems, genes of gB, gC, gD, gH, and gL, gerX locus (gerXC, -A, and -B genes), glpQ gene, gltA (citrate synthase) gene (*Bartonella*), gltA (citrate synthase) gene (*Rickettsia*), groEL gene (*Bartonella*), groEL gene (Orientia tsutsugamushi), groESL gene (*Chlamydia pneumoniae*), gyrA and gyrB genes (*Pseudomonas aeruginosa*), gyrA gene (*Neisseria gonorrhoeae*), gyrB gene (*Bacillus anthracis*), hexon gene (Adenovirus), hexon gene (Enteric adenovirus), hin gene, hlyA gene, hmw genes, hspX (Rv2031c) gene, htpAB associated repetitive element (IS1111a), hyl gene, icsA and icsB genes, ileS gene, inhA gene, inv gene (*Escherichia coli*), inv gene (*Salmonella*), ipaA, -B, -C, -D and -H genes, katG gene, lef gene, letA gene, lidA gene, 1psB gene, IrgAB locus, luxS gene, lytA gene, lytRS locus, mecA gene, mglA gene, mgrA (rat) gene, mip gene, mtgA gene, mucZ gene, multigene families, mupA gene, *nanA* and nanB genes, nef gene, omp genes (*Brucella*), omp genes (*Chlamydia* pneumonia), ompA and B gene (*Rickettsia*), ompQ gene, opa genes, osp genes, µl gene, p30 gene, pagA gene, pap31 gene, parC and parE genes (*Pseudomonas aeruginosa*), parC gene (*Neisseria gonorrhoeae*), per gene, pilQ gene, ply gene, µmm gene, pol gene, porA and porB genes, prn4 (pertactin) gene, psaA gene, pspA gene, pst1 fragment and HL-1/HR-1 primers, ptx (promoter region and complete gene), rap 1/2 genes, rev gene, rpo18 gene, rpoB gene, rpoS gene, rpsL gene, rrf(5S)-rrl(23S) intergenic spacer, rsk gene, rtx gene (*Vibrio vulnificus*), rtxA gene (*Legionella pneumophila*), sap gene (*Bacillus anthracis*), sar gene, satA (vatD) and satG (vatE) genes, sca4 gene, secY gene, stx (vt) gene, stxA/B (stxl/2) gene, sucB gene, tat gene, tcp gene, tir gene, tox gene, toxR gene, tul4 gene, urease genes, vacA gene, van A-E genes, veb gene, vif gene, viuB gene, vpr gene, vpu/vpx gene, vvh (*Vibrio vulnificus* hemolysin) gene, vvpE (*Vibrio vulnificus* elastase) gene, wboA gene, wzy (0-antigen polymerase) gene, zot gene, α/β/γ genes, C-polysaccharide (rhamnose/N-acetylglucosamine), CPS (capsular polysaccharide), Cyclic β-1,2 glucan, Hyaluronic acid capsule, LPS (lipopolysaccharide) (*Bartonella*), LPS (lipopolysaccharide) (*Brucella*), LPS (lipopolysaccharide) (*Coxiella burnetii*), LPS (lipopolysaccharide) (*Rickettsia*), LPS (lipopolysaccharide) (*Vibrio vulnificus*), O-antigen (*Escherichia coli*), 0-antigen (*Salmonella*), 0-antigen (*Vibrio cholerae*), Vi-antigen (*Salmonella*), or Catechol siderophore.

Infectious Disease: Standards of Care

Determining the biosignature of a vesicle, the amount of vesicles, or both, of a sample from a subject suffering from an infectious or parasitic disease, disorder or disease can be used to select a standard of care for the subject. An infectious or parasitic disease can be treated according to symptoms associated with the condition. The standard of care includes, for example, treating with one or more antibiotics and antiviral agents.

An antibiotic includes, but not limited to, Amikacin, Gentamicin, Kanamycin, Neomycin, Netilmicin, Streptomycin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Azithromycin, Clarithromycin, Dirithromycin, Erythromycin, Roxithromycin, Troleandomycin, Telithromycin, Spectinomycin, Aztreonam, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Bacitracin, Colistin, Polymyxin B, Ciprofloxacin, Enoxacin, Gatifloxacin, Levofloxacin, Lomefloxacin, Moxifloxacin, Norfloxacin, Ofloxacin, Trovafloxacin, Grepafloxacin, Sparfloxacin, Temafloxacin, Mafenide, Sulfonamidochrysoidine, Sulfacetamide, Sulfanilimide, Sulfasalazine, Sulflsoxazole, Trimethoprim, Trimethoprim-, Sulfamethoxazole, Demeclocycline, Doxycycline, Minocycline, Oxytetracycline, Tetracycline, Sulfadiazine, Sulfamethizole, Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin or Dalfopristin, Rifampicin, Thiamphenicol, Tinidazole, Dapsone, and Clofazimine. Examples of antibiotics are also listed in Table 12.

An antiviral agent includes, but is not limited to Abacavir, Aciclovir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Imunovir, Idoxuridine, Imiquimod, Indinavir, Inosine, Interferon type III, Interferon type II, Interferon type I, Lamivudine, Lopinavir, Loviride, Maraviroc, Moroxydine, Nelfinavir, Nevirapine, Nexavir, Oseltamivir, Peginterferon alfa-2a, Penciclovir, Peramivir, Pleconaril, Podophyllotoxin, Raltegravir, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, and Zidovudine.

TABLE 12

Examples of Antibiotic Drugs and their Structure Class

| Structure Class | Examples of Antibiotics within Structure Class |
|---|---|
| Amino Acid Derivatives | Azaserine, Bestatin, Cycloserine, 6-diazo-5-oxo-L-norleucine |
| Aminoglycosides | Armastatin, Amikacin, Gentamicin, Hygromicin, Kanamycin, Streptomycin |
| Benzochinoides | Herbimycin |
| Carbapenems | Imipenem, Meropenem |
| Coumarin-glycosides | Novobiocin |
| Fatty Acid Derivatives | Cerulenin |
| Glucosamines | 1-deoxynojirimycin |
| Glycopeptides | Bleomycin, Vancomycin |
| Imidazoles | Metroidazole |
| Penicillins | Benzylpenicillin, Benzathine penicillin, Amoxycillin, Piperacillin |
| Macrolides | Amphotericin B, Azithromycin, Erythromycin |
| Nucleosides | Cordycepin, Formycin A, Tubercidin |
| Peptides | Cyclosporin A, Echinomycin, Gramicidin |
| Peptidyl Nucleosides | Blasticidine, Nikkomycin |
| Phenicoles | Chloramphenicol, Thiamphenicol |
| Polyethers | Lasalocid A, Salinomycin |
| Quinolones | 8-quinolinol, Cinoxacin, Ofloxacin |
| Steroids | Fusidic Acid |
| Sulphonamides | Sulfamethazine, Sulfadiazine, Trimethoprim |
| Tetracyclins | Oxytetracyclin, Minocycline, Duramycin |

In one embodiment, a subject has an HIV infection. One or more biomarkers, such as, but not limited to p24 antigen, TNF-alpha, TNFR-II, CD3, CD14, CD25, CD27, Fas, FasL, beta2 microglobulin, neopterin, HIV RNA, and HLA-B*5701, can be assessed from a vesicle from the subject. Based on one or more characteristics of the one or more biomarkers, the subject can be determined to be a responder or non-responder for a treatment, such as, but not limited to, Zidovudine, Didanosine, Zalcitabine, Stavudine, Lamivudine, Saquinavir, Ritonavir, Indinavir, Nevirane, Nelfinavir, Delavirdine, Stavudine, Efavirenz, Etravirine, Enfuvirtide, Darunavir, Abacavir, Amprenavir, Lonavir/Ritonavirc, Tenofovir, Tipranavir, or a combination thereof.

Thus, a treatment can be selected for the subject suffering from an infectious disease or condition, based on the biosignature of the subject's vesicle.

Neurology

Assessing a vesicle can be used in the theranosis of a neurological disease, such as Multiple Sclerosis (MS), Parkinson's Disease (PD), Alzheimer's Disease (AD) (non-inflammatory and inflammatory), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome.

A neurological disorder includes, but is not limited to inflammatory diseases of the central nervous system, hereditary and degenerative diseases of the central nervous system, pain, other headache syndromes, other disorders of the central nervous system, and disorders of the peripheral nervous system. Inflammatory diseases of the central nervous system include, but are not limited to bacterial meningitis, meningitis, hemophilus, meningitis, bacterial, meningitis due to other organisms, cryptococcal meningitis, meningitis of unspecified cause, encephalitis, myelitis, and encephalomyelitis, postinfectious encephalitis, unspecified encephalitis, intracranial and intraspinal abscess, phlebitis and thrombophlebitis of intracranial venous sinuses, venous sinus thrombosis, intracranial, late effects of intracranial abscess or pyogenic infection, sleep disorders, unspecified organic insomnia, insomnia due to medical condition classified elsewhere, and insomnia due to mental disorder. Hereditary and degenerative diseases of the central nervous system include, but are not limited to cerebral degenerations usually manifest in childhood, leukodystrophy, krabbe disease, pelizaeus merzbacher disease, cerebral lipidoses, tay sachs disease, other cerebral degenerations, alzheimer's, pick's disease, senile degeneration of brain, communicating hydrocephalus, obstructive hydrocephalus, idiopathic normal pressure hydrocephalus, other cerebral degeneration, reye's syndrome, dementia with lewy bodies, mild cognitive impairment, so stated, Parkinson's Disease, parkinsonism, primary, other extrapyramidal disease and abnormal movement disorders, other degenerative diseases of the basal ganglia, olivopontocerebellar atrophy, shy drager syndrome, essential tremor/familial tremor, myoclonus, lafora's disease, unverricht disease, Huntington's chorea, fragments of torsion dystonia, blepharospasm, other and unspecified extrapyramidal diseases and abnormal movement disorders, other extrapyramidal diseases and abnormal movement disorders, restless legs, serotonin syndrome, spinocerebellar disease, friedreich's ataxia, spinocerebellar ataxia, hereditary spastic paraplegia, primary cerebellar degeneration, other cerebellar ataxia, cerebellar ataxia in diseases classified elsewhere, other spinocerebellar diseases, ataxia telangiectasia, corticostriatal spinal degeneration, unspecified spinocerebellar disease, anterior horn cell disease, motor neuron disease, amyotrophic lateral sclerosis, progressive muscular atrophy, progressive bulbar palsy, pseudobulbar palsy, primary lateral sclerosis, other motor neuron diseases, other diseases of spinal cord, syringomyelia and syringobulbia, disorders of the autonomic nervous system, idiopathic peripheral autonomic neuropathy, unspecified idiopathic peripheral autonomic neuropathy, carotid sinus syndrome, other idiopathic peripheral autonomic neuropathy, peripheral autonomic neuropathy in disorders classified elsewhere, reflex sympathetic dystrophy, autonomic dysreflexia, and unspecified disorder of autonomic nervous system.

Pain includes, but is not limited to, central pain syndrome, acute pain, chronic pain, neoplasm related pain acute chronic and chronic pain syndrome. Other headache syndromes include, but are not limited to cluster headaches and other trigeminal autonomic cephalgias, unspecified cluster headache syndrome, episodic cluster headache, chronic cluster headache, episodic paroxysmal hemicrania, chronic paroxysmal hemicrania, short lasting unilateral neuralgiform headache with conjunctival injection and tearing, other trigeminal autonomic cephalgias, tension type headache, unspecified tension type headache, episodic tension type headache, chronic tension type headache, post traumatic headache, unspecified post traumatic headache, acute post traumatic headache, chronic post traumatic headache, drug induced headache, not elsewhere classified, complicated headache syndromes, hemicrania continua, new daily persistent headache, primary thunderclap headache, other complicated headache syndrome, other specified headache syndromes, hypnic headache, headache associated with sexual activity, primary cough headache, primary exertional headache, and primary stabbing headache.

Other disorders of the central nervous system include, but are not limited to multiple sclerosis, other demyelinating diseases of central nervous system, neuromyelitis optica, schilder's disease, acute myelitis transverse myelitis, hemiplegia, hemiplegia, flaccid, hemiplegia, spastic, infantile cerebral palsy, cerebral palsy, paraplegic, congenital, cerebral palsy, hemiplegic, congenital, cerebral palsy, quadriplegic, other paralytic syndromes, quadraplegia and quadraparesis, paraplegia, diplegia of upper limbs, monoplegia of lower limb, monoplegia of upper limb, unspecified monoplegia, cauda equina syndrome, other specified paralytic syndromes, locked in state, epilepsy, intractable epilepsy, tonic clonic epilepsy without status, epilepsy with status, epilepsy on temporal lobe without status, unspecified epilepsy without status, migraine, classical not intractable migraine, common but not intractable migraine, not intractable cluster headache, unspecified but, not intractable migraine, cataplexy and narcolepsy, narcolepsy without cataplexy, cerebral cysts, anoxic brain damage, pseudotumor cerebri, unspecified encephalopathy, metabolic encephalopathy, compression of brain, cerebral edema, post spinal puncture, post dural puncture headache, cerebrospinal fluid rhinorrhea, and toxic encephalopathy.

Disorders of the peripheral nervous system include, but are not limited to trigeminal nerve disorders, trigeminal neuralgia, facial nerve disorders, bell's palsy, disorders of other cranial nerves, nerve root and plexus disorders, thoracic outlet syndrome, phantom limb, mononeuritis of upper limb and mononeuritis multiplex, carpal tunnel, mononeuritis of lower limb, lesion of sciatic nerve, meralgia paresthetica, other lesion of femoral nerve, lesion of lateral popliteal nerve, lesion of medial popliteal nerve, tarsal tunnel syndrome, lesion of plantar nerve, morton's neuroma, unspecified mononeuritis of lower limb, mononeuritis of unspecified site, hereditary and idiopathic peripheral neuropathy, inflammatory and toxic neuropathy, guillain bane syndrome, poly neuropathy, alcoholic poly neuropathy, myoneural disorders, myasthenia gravis with exacerbation, myasthenia gravis without exacerbation, muscular dystrophies and other myopathies, benign congenital myopathy, central core disease, centronuclear myopathy, myotubular myopathy, nemaline body disease, and hereditary muscular dyst.

A biosignature of a vesicle can be assessed to provide a theranosis for a subject. The biosignature of the vesicle can comprise one or more biomarkers such as, but not limited to, a biomarker such as those disclosed in the following table:

Neurology: Biosignature

A biosignature of a vesicle can be assessed to provide a theranosis for a subject. The biosignature of the vesicle can comprise one or more biomarkers such as, but not limited to, a biomarker such as listed in FIGS. 1, 45, 46, 47, 48, and 49. The biosignature of the vesicle can comprise one or more biomarkers including, but not limited to, amyloid β, ICAM-1 (rodent), CGRP (rodent), TIMP-1 (rodent), CLR-1 (rodent), HSP-27 (rodent), FABP (rodent), ATP5B, ATP5H, ATP6VIB, DNM1, NDUFV2, NSF, PDHB, FGF2, ALDH7A1, AGXT2L1, AQP4, PCNT2, FGFR1, FGFR2, FGFR3, AQP4, a mutation of Dysbindin, DAOA/G30, DISC1, neuregulin-1, IFITM3, SERPINA3, GLS, ALDH7A1, BASP1, OX42, ED9, apolipoprotein D (rodent), miR-7, miR-24, miR-26b, miR-29b, miR-30b, miR-30e, miR-92, miR-195, miR-181b, DISC1, dysbindin, neuregulin-1, seratonin 2a receptor, and NURR1.

Neurology: Standard of Care

Determining the biosignature of a vesicle, the amount of vesicles, or both, of a sample from a subject suffering from a neurological disorder or disease can be used to select a standard of care for the subject. An neurological disorder or disease can be treated according to symptoms associated with the condition. The standard of care can include, for example, a pharmaceutical drug. A pharmaceutical drug includes, but is not limited to aspirin, dipyridamole, naratriptan, apomorphine, donepezil, almotriptan malate, rufinamide, bromfenac, carbatrol, cenestin, tadalafil, clonazepam, entacapone, glatiramer acetate, pemoline, divalproex, difluprednate, zolpidem tartrate, rivastigmine tartrate, dexmethylphenidate, frovatriptan succinate, zinc acetate, sumatriptan, paliperidone, iontocaine, morphine, levetiracetam, lamotrigine, vardenafil, lidocaine, eszopiclone, fospropofol disodium, pregabalin, rizatriptan benzoate, meropenem, Methylphenidate, dihydroergotamine mesylate, Pramipexole, rimabotulinumtoxin B, naltrexone, memantine, rotigotine, gabapentin), hydrocodone, mitoxantrone, armodafinil, oxycodone, pramipexole, samarium 153 lexidronam, interferon beta-1a, dexfenfluramine, eletriptan hydrobromide, galantamine hydrobromide, ropinirole hydrochloride, riluzole, ramelteon, eldepryl, valproic acid, atomoxetine, tolcapone, carbamazepine, topiramate, oxcarbazepine, natalizumab, acetaminophen,tramadol, midazolam, lacosamide, iodixanol, lisdexamfetamine dimesylate, tetrabenazine, sodium oxybate, tizanidine hydrochloride, zolmitriptan, and zonisamide.

Other treatments that can be selected based on a vesicle profile of a subject includes those listed in Table 11, for a subject with Multiple Sclerosis; Table 13, for a subject with Parkinson's Disease; or Table 14, for a subject with depression.

TABLE 13

Classes of Drugs for Treatment of Parkinson's Disease

| Class | Mechanism of Action | Examples |
| --- | --- | --- |
| Dopamine Precursors | Act as precursors in the synthesis of dopamine, the neurotransmitter that is depleted in Parkinson's Disease. Usually administered in combination with an inhibitor of the carboxylase enzyme that metabolizes levodopa. Some (e.g., Duodopa) are given by infusion, e.g., intraduodenal infusion | Levodopa, Levodopa-carbidopa, Levodopa-benserazide, Etilevodopa, Duodopa |
| Dopamine Agonists | Mimic natural dopamine by directly stimulating striatal dopamine receptors. May be subclassed by which of the five known dopamine receptor subtypes the drug activates; generally most effective are those that activate receptors the in the D2 receptor family (specifically D2 and D3 receptors). Some are formulated for more controlled release or transdermal delivery. | Bromocriptine, Cabergoline, Lisuride, Pergolide, Pramipexole, Ropinirole, Talipexole, Apomorphine, Dihydroergocryptine, Lisuride, Piribedil, Talipexole, Rotigotin CDS, Sumanirole, SLV-308 |
| COMT Inhibitors | Inhibits COMT, the second major enzyme that metabolized levodopa. | Entacapone, Tolcapone, Entacapone-Levodopa-Carbidopa fixed combination, |
| MAO-B Inhibitors | MAO-B metabolizes dopamine, and inhibitors of MAO-B thus prolong dopamine's half-life | Selegiline, Rasagiline, Safinamide |
| Antiglutamatergic Agents | Block glutamate release. Reduce levodopa-induced dyskinesia | Amantadine, Budipine, Talampanel, Zonisamide |
| Anticholinergic Agents | Thought to inhibit excessive cholinergic activity that accompanies dopamine deficiency | Trihexyphenidyl, Benztropine, Biperiden |
| Mixed Dopaminergic Agents | Act on several neurotransmitter systems, both dopaminergic and nondopaminergic. | NS-2330, Sarizotan |
| Adenosine A2a antagonists | Adenosine A2 antagonize dopamine receptors and are found in conjunction with dopamine receptors. Antagonists of these receptors may enhance the activity of dopamine receptors. | Istradefylline |
| Alpha-2 Adrenergic Antagonists | Not known. | Yohimbine, Idazoxan, Fipamezole |
| Antiapoptotic Agents | Can slow the death of cells associated with the neurodegenerative process of Parkinson's disease. | CEP-1347, TCH-346 |
| Growth Factor Stimulators | Promote the survival and growth of dopaminergic cells. | GPI-1485, Glial-cell-line-derived Neurotrophic Factor, SR-57667, PYM-50028 |
| Cell Replacement Therapy | Replace damaged neurons with health neurons. | Spheramine |

TABLE 14

Classes of Drugs for Treatment of Depression

| Class | Mechanism of Action | Examples |
|---|---|---|
| Selective Serotonin Reuptake Inhibitor (SSRI) | Block presynaptic reuptake of serotonin. Exert little effect on norepinephrine or dopamine reuptake. Level of serotonin in the synaptic cleft is increased. | Escitalopram, Sertraline, Citalopram, Paroxetine, Paroxetin, controlled release, Fluoxetine, Fluoxetine weekly, Fluvoxamine, olanzapine/fluoxetine combination |
| Serotonergic/ noradrenergic agents | Inhibit both serotonin reuptake and norepinephrine reuptake. Different drugs in this class can inhibit each receptor to different degrees. Do not affect histamine, acetylcholine, and adrenergic receptors. | Venlafaxine; Reboxetine, Milnacipran, Mirtazapine, Nefazodone, Duloxetine |
| Serotonergic/ noradrenergic/ dopaminergic agents | Several different mechanisms. Block norepinephrine, serotonin, and/or dopamine reuptake. Some have addictive potential due to dopamine reuptake inhibition. | Bupropion, Maprotiline, Mianserin, Trazodone, Dexmethylphenidate, Methyphenidate, Amineptine |
| Tricyclic Antidepressants | Block synaptic reuptake of serotonin and norepinephrine. Have little effect on dopamine. Strong blockers of muscarinic, histaminergic H1, and alpha-1-adrenergic receptors. | Amitriptyline, Amoxapine, Clomipramine, Desipramine, Doxepin, Imipramine, Nortriptyline, Protriptyline, Trimipramine |
| Irreversible Monoamine Oxidase Inhibitors | Monoamine oxidase (MAO) metabolizes monoamines such as serotonin and norepinephrine. MAO inhibitors inhibit MAO, thus increasing levels of serotonin and norepinephrine. | Isocarboxazid, Phenelzine, Tranylcypromine, Transdermal Selegiline |
| Reversible Monoamine Oxidase Inhibitors | See above. Short acting, reversible inhibitor, inhibits deamination of serotonin, norepinephrine, and dopamine. | Moclobemide |
| Serotonergic/ noradenergic/ dopaminergic reuptake inhibitors | Act to block all of serotonin, norepinephrine, and dopamine reuptake. May have addictive potential due to dopamine reuptake inhibition. | DOV-216303, DOV-21947 |
| Noradrenergic/ dopaminergic agents | Block reuptake of norepinephrine and dopamine | GW-353162 |
| Serotonin Antagonists | Selective antagonist of one serotonin receptor (the 5-$HT_1$ receptor) | Agomelatine |
| Serotonin Agonists | Partial agonist of the 5-$HT_{1A}$ receptor. | Eptapirone, Vilazodone, OPC-14523, MKC-242, Gepirone ER |
| Substance P Antagonists | Modify levels of substance P, which is released during acute stress. | Aprepitant, TAK-637, CP-122721, E6006, R-763OPC-GW-597599 |
| $Beta_3$ Adrenoreceptor Agonists | Indirectly inhibit norepinephrine reuptake. Also being investigated for treatment of obesity and diabetes because they stimulate lipolysis and thermogenesis. | SR-58611 |

In one embodiment, a treatment can be selected for a subject suffering from Alzheimer's disease. One or more biomarkers, such as, but not limited to, beta-amyloid protein, amyloid precursor protein (APP), APP670/671, APP693, APP692, APP715, APP716, APP717, APP723, presenilin 1, presenilin 2, cerebrospinal fluid amyloid beta protein 42 (CSF-Abeta42), cerebrospinal fluid amyloid beta protein 40 (CSF-Abeta40), F2 isoprostane, 4-hydroxynonenal, F4 neuroprostane, and acrolein, can be assessed from a vesicle from the subject. Based on one or more characteristics of the one or more biomarkers, the subject can be determined to be a responder or non-responder for a treatment, such as, but not limited to, Donepezil, Galantamine, Memantine, Rivastigmine, Tacrine, or a combination thereof.

In another embodiment, a treatment can be selected for a subject suffering from Parkinson's Disease. One or more biomarkers, such as, but not limited to, alpha synuclein, PARK7 (DJ-1), S-phase kinase-associated protein 1A (p19A/SKP1A), Heat shock protein 70 kDa, AMP-regulated phosphoprotein (ARPP-21), vesicular monoamine member 2 (VMAT2), alcohol dehydrogenase 5 (ADH5), aldehyde dehydrogenase 1A1 (ALDH1A 1), egle nine homolog 1(EGLN1), proline hydroxylase 2 (PHD2), and hypoxia inducible factor (HIF), can be assessed from a vesicle from the subject. Based on one or more characteristics of the one or more biomarkers, the subject can be determined to be a responder or non-responder for a treatment, such as, but not limited to, those listed in Table 13.

In another embodiment, a treatment can be selected for a subject suffering from Parkinson's Disease. One or more biomarkers, such as, but not limited to, CRP, TNF, IL-6, S100B, and MMP can be assessed from a vesicle from the subject. Based on one or more characteristics of the one or more biomarkers, the subject can be determined to be a responder or non-responder for a treatment.

Thus, a treatment can be selected for the subject suffering from a neurology-related condition or neurological condition or disease, based on the biosignature of the subject's vesicle.

Biosignature Discovery

The systems and methods provided herein can be used in identifying a novel biosignature of a vesicle, such as one or more novel biomarkers for the diagnosis, prognosis or theranosis of a phenotype. In one embodiment, one or more vesicles can be isolated from a subject with a phenotype and a biosignature of the one or more vesicles determined. The biosignature can be compared to a subject without the phenotype. Differences between the two biosignatures can be determined and used to form a novel biosignature. The novel biosignature can then be used for identifying another subject as having the phenotype or not having the phenotype.

Differences between the biosignature from a subject with a particular phenotype can be compared to the biosignature from a subject without the particular phenotype. The one or more differences can be a difference in any characteristic of the vesicle. For example, the level or amount of vesicles in the sample, the half-life of the vesicle, the circulating half-life of the vesicle, the metabolic half-life of the vesicle, or the activity of the vesicle, or any combination thereof, can differ between the biosignature from the subject with a particular phenotype and the biosignature from the subject without the particular phenotype.

In some embodiments, one or more biomarkers differ between the biosignature from from the subject with a particular phenotype and the biosignature from the subject without the particular phenotype. For example, the expression level, presence, absence, mutation, variant, copy number variation, truncation, duplication, modification, molecular association of one or more biomarkers, or any combination thereof, may differ between the biosignature from from the subject with a particular phenotype and the biosignature from the subject without the particular phenotype. The biomarker can be any biomarker disclosed herein or that can be used to characterize a biological entity, including a circulating biomarker, such as protein or microRNA, a vesicle, or a component present in a vesicle or on the vesicle, such as any nucleic acid (e.g. RNA or DNA), protein, peptide, polypeptide, antigen, lipid, carbohydrate, or proteoglycan.

In an aspect, the invention provides a method of discovering a novel biosignature comprising comparing the biomarkers between two or more sample groups to identify biomarkers that show a difference between the sample groups. Multiple markers can be assessed in a panel format to potentially improve the performance of individual markers. In some embodiments, the multiple markers are assessed in a multiplex fashion. The ability of the individual markers and groups of markers to distinguish the groups can be assessed using statistical discriminate analysis or classification methods as used herein. Optimal panels of markers can be used as a biosignature to characterize the phenotype under analysis, such as to provide a diagnosis, prognosis or theranosis of a disease or condition. Optimization can be based on various criteria, including without limitation maximizing ROC AUC, accuracy, sensitivity at a certain specificity, or specificity at a certain sensitivity. The panels can include biomarkers from multiple types. For example, the biosignature can comprise vesicle antigens useful for capturing a vesicle population of interest, and the biosignature can further comprise payload markers within the vesicle population, including without limitation microRNAs, mRNAs, or soluble proteins. Optimal combinations can be identified as those vesicle antigens and payload markers with the greatest ROC AUC value when comparing two settings. As another example, the biosignature can be determined by assessing a vesicle population in addition to assessing circulating biomarkers that are not obtained by isolating exosomes, such as circulating proteins and/or microRNAs.

The phenotype can be any of those listed herein, e.g., in the "Phenotype" section above. For example, the phenotype can be a proliferative disorder such as a cancer or non-malignant growth, a perinatal or pregnancy related condition, an infectious disease, a neurological disorder, a cardiovascular disease, an inflammatory disease, an immune disease, or an autoimmune disease. The cancer includes without limitation lung cancer, non-small cell lung cancer small cell lung cancer (including small cell carcinoma (oat cell cancer), mixed small cell/large cell carcinoma, and combined small cell carcinoma), colon cancer, breast cancer, prostate cancer, liver cancer, pancreatic cancer, brain cancer, kidney cancer, ovarian cancer, stomach cancer, melanoma, bone cancer, gastric cancer, breast cancer, glioma, gliobastoma, hepatocellular carcinoma, papillary renal carcinoma, head and neck squamous cell carcinoma, leukemia, lymphoma, myeloma, or other solid tumors.

Any of the types of biomarkers or specific biomarkers described herein can be assessed to discover a novel biosignature. In an embodiment, the biomarkers selected for discovery comprise cell-specific biomarkers as listed herein, including without limitation the genes and microRNA listed in FIGS. 1-60, Tables 6-8 or Table 22. The biomarkers can comprise one or more drug associated target such as a ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, hENT-1, Her2/Neu, HGF, HIF1A, HIG1, HSP90, HSP90AA1, HSPCA, IGF-IR, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKB1A, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SRC, SSTR1, SSTR2, SSTR3, SSTR4, SSTR5, Survivin, TK1, TLE3, TNF, TOP1, TOP2A, TOP2B, TS, TXN, TXNRD1, TYMS, VDR, VEGF, VEGFA, VEGFC, VHL, YES1, and ZAP70. The biomarkers can comprise one or more general vesicle marker, one or more cell-specific vesicle marker, and/or one or more disease-specific vesicle marker.

The biomarkers used for biosignature discovery can comprise include markers commonly associated with vesicles, including without limitation one or more of HSPA8, CD63, Actb, GAPDH, CD9, CD81, ANXA2, HSP90AA1, ENO1, YWHAZ, PDCD6IP, CFL1, SDCBP, PKN2, MSN, MFGE8, EZR, YWHAG, PGK1, EEF 1A1, PPIA, GLC1F, GK, ANXA6, ANXA1, ALDOA, ACTG1, TPI1, LAMP2, HSP90AB1, DPP4, YWHAB, TSG101, PFN1, LDHB, HSPA1B, HSPA1A, GSTP1, GNAI2, GDI2, CLTC, ANXA5, YWHAQ, TUBA1A, THBS1, PRDX1, LDHA, LAMP1, CLU, and CD86. The biomarkers can further comprise one or more of CD63, GAPDH, CD9, CD81, ANXA2, ENO1, SDCBP, MSN, MFGE8, EZR, GK, ANXA1, LAMP2, DPP4, TSG101, HSPAIA, GDI2, CLTC, LAMP1, Cd86, ANPEP, TFRC, SLC3A2, RDX, RAP1B, RAB5C, RAB5B, MYH9, ICAM1, FN1, RABI1B, PIGR, LGALS3, ITGB1, EHD1, CLIC1, ATP1A1, ARF1, RAP1A, P4HB, MUC1, KRT10, HLA-A, FLOT1, CD59, Clorf58, BASP1, TACSTD1, and STOM. Other biomarkers can be selected from those disclosed in the ExoCarta database, available at exocarta.ludwig.edu.au, which discloses proteins and RNA molecules identified in exosomes. See also Mathivanan and Simpson, ExoCarta: A compendium of exosomal proteins and RNA. Proteomics. 2009 November 9(21):4997-5000.

The biomarkers used for biosignature discovery can comprise include markers commonly associated with vesicles, including without limitation one or more of A33, a33 n15, AFP, ALA, ALIX, ALP, AnnexinV, APC, ASCA, ASPH (246-260), ASPH (666-680), ASPH (A-10), ASPH (DO1P), ASPH (D03), ASPH (G-20), ASPH (H-300), AURKA, AURKB, B7H3, B7H4, BCA-225, BCNP1, BDNF, BRCA, CA125 (MUC16), CA-19-9, C-Bir, CD1.1, CD10, CD174 (Lewis y), CD24, CD44, CD46, CD59 (MEM-43), CD63, CD66e CEA, CD73, CD81, CD9, CDA, CDAC1 1a2, CEA, C-Erb2, C-erbB2, CRMP-2, CRP, CXCL12, CYFRA21-1, DLL4, DR3, EGFR, Epcam, EphA2, EphA2 (H-77), ER, ErbB4, EZH2, FASL, FRT, FRT c.f23, GDF15, GPCR, GPR30, Gro-alpha, HAP, HBD1, HBD2, HER 3 (ErbB3), HSP, HSP70, hVEGFR2, iC3b, IL 6 Unc, IL-1B, IL6 Unc, IL6R, IL8, IL-8, INSIG-2, KLK2, L1CAM, LAMN, LDH, MACC-1, MAPK4, MART-1, MCP-1, M-CSF, MFG-E8, MIC1, MIF, MIS RII, MMG, MMP26, MMP7, MMP9, MS4A1, MUC1, MUC1 seq1, MUC1 seq11A, MUC17, MUC2, Ncam, NGAL, NPGP/NPFF2, OPG, OPN, p53, p53, PA2G4, PBP, PCSA, PDGFRB, PGP9.5, PIM1, PR (B), PRL, PSA, PSMA, PSME3, PTEN, R5-CD9 Tube 1, Reg IV, RUNX2, SCRN1, seprase, SERPINB3, SPARC, SPB, SPDEF, SRVN, STAT3, STEAP1, TF (FL-295), TFF3, TGM2, TIMP-1, TIMP1, TIMP2, TMEM211, TMPRSS2, TNF-alpha, Trail-R2, Trail-R4, TrKB, TROP2, Tsg 101, TWEAK, UNC93A, VEGF A, and YPSMA-1. The biomarkers can include one or more of NSE, TRIM29, CD63, CD151, ASPH, LAMP2, TSPAN1, SNAIL, CD45, CKS1, NSE, FSHR, OPN, FTH1, PGP9, ANNEXIN 1, SPD, CD81, EPCAM, PTH1R, CEA, CYTO 7, CCL2, SPA, KRAS, TWIST1, AURKB, MMP9, P27, MMP1, HLA, HIF, CEACAM, CENPH, BTUB, INTG b4, EGFR, NACC1, CYTO 18, NAP2, CYTO 19, ANNEXIN V, TGM2, ERB2, BRCA1, B7H3, SFTPC, PNT, NCAM, MS4A1, P53, INGA3, MUC2, SPA, OPN, CD63, CD9, MUC1, UNCR3, PAN ADH, HCG, TIMP, PSMA, GPCR, RACK1, PCSA, VEGF, BMP2, CD81, CRP, PRO GRP, B7H3, MUC1, M2PK, CD9, PCSA, and PSMA. The biomarkers can also include one or more of TFF3, MS4A1, EphA2, GAL3, EGFR, N-gal, PCSA, CD63, MUC1, TGM2, CD81, DR3, MACC-1, TrKB, CD24, TIMP-1, A33, CD66 CEA, PRL, MMP9, MMP7, TMEM21 1, SCRN1, TROP2, TWEAK, CDACC1, UNC93A, APC, C-Erb, CD10, BDNF, FRT, GPR30, P53, SPR, OPN, MUC2, GRO-1, tsg 101 and GDF15. In embodiments, the biomarkers used to discover a biosignature comprise one or more of those shown in FIGS. 100A-C, 102A, and/or 103A-E.

One of skill will appreciate that any marker disclosed herein or that can be compared between two samples or sample groups of interest can be used to discover a novel biosignature for any given biological setting that can be compared.

The one or more differences can then be used to form a novel biosignature for the particular phenotype, such as the diagnosis of a condition, diagnosis of a stage of a disease or condition, prognosis of a condition, or theranosis of a condition. The novel biosignature can then be used to identify the phenotype in other subjects. The biosignature of a vesicle for a new subject can be determined and compared to the novel signature to determine if the subject has the particular phenotype for which the novel biosignature was identified from.

For example, the biosignature of a subject with cancer can be compared to another subject without cancer. Any differences can be used to form a novel biosignature for the diagnosis of the cancer. In another embodiment, the biosignature of a subject with an advanced stage of cancer can be compared to another subject with a less advanced stage of cancer. Any differences can be used to form a novel biosignature for the classification of the stage of cancer. In yet another embodiment, the biosignature of a subject with an advanced stage of cancer can be compared to another subject with a less advanced stage of cancer. Any differences can be used to form a novel biosignature for the classification of the stage of cancer.

In one embodiment, the phenotype is drug resistance or non-responsiveness to a therapeutic. One or more vesicles can be isolated from a non-responder to a particular treatment and the biosignature of the vesicle determined. The biosignature of the vesicle obtained from the non-responsder can be compared to the biosignature of a vesicle obtained from a responder. Differences between the biosignature from the non-responder can be compared to the biosignature from the responder. The one or more differences can be a difference in any characteristic of the vesicle. For example, the level or amount of vesicles in the sample, the half-life of the vesicle, the circulating half-life of the vesicle, the metabolic half-life of the vesicle, the activity of the vesicle, or any combination thereof, can differ between the biosignature from the non-responder and the biosignature from the responder.

In some embodiments, one or more biomarkers differ between the biosignature from the non-responder and the biosignature from the responder. For example, the expression level, presence, absence, mutation, variant, copy number variation, truncation, duplication, modification, molecular association of one or more biomarkers, or any combination thereof, may differ between the biosignature from the non-responder and the biosignature from the responder.

In some embodiments, the difference can be in the amount of drug or drug metabolite present in the vesicle. Both the responder and non-responder can be treated with a therapeutic. A comparison between the biosignature from the responder and the biosignature from the non-responder can be performed, the amount of drug or drug metabolite present in the vesicle from the responder differs from the amount of drug or drug metabolite present in the non-responder. The difference can also be in the half-life of the drug or drug metabolite. A difference in the amount or half-life of the drug or drug metabolite can be used to form a novel biosignature for identifying non-responders and responders.

A vesicle useful for methods and compositions described herein can be discovered by taking advantage of its physicochemical characteristics. For example, a vesicle can be discovered by its size, e.g., by filtering biological matter in a known range from 30-120 nm in diameter. Size-based discovery methods, such as differential centrifugation, sucrose gradient centrifugation, or filtration have been used for isolation of a vesicle.

A vesicle can be discovered by its molecular components. Molecular property-based discovery methods include, but are not limited to, immunological isolation using antibodies recognizing molecules associated with vesicle. For example, a surface molecule associated with a vesicle includes, but not limited to, a MHC-II molecule, CD63, CD81, LAMP-1, Rab7 or Rab5.

Various techniques known in the art are applicable for validation and characterization of a vesicle. Techniques useful for validation and characterization of a vesicle includes, but is not limited to, western blot, electron microscopy, immunohistochemistry, immunoelectron microscopy, FACS (Fluorescent activated cell sorting), electrophoresis (1 dimension, 2 dimension), liquid chromatography, mass spectrometry, MALDI-TOF (matrix assisted laser desorption/ionization-time of flight), ELISA, LC-MS-MS, and nESI (nanoelectrospray ionization). For example U.S. Pat. No. 2009/0148460 describes use of an ELISA method to characterize a vesicle. U.S. Pat. No. 2009/0258379 describes isolation of membrane vesicles from biological fluids.

Vesicles can be further analyzed for one or more nucleic acids, lipids, proteins or polypeptides, such as surface proteins or peptides, or proteins or peptides within a vesicle. Candidate peptides can be identified by various techniques including mass spectrometry coupled with purification methods such as liquid chromatography. A peptide can then be isolated and its sequence can be identified by sequencing. A computer program that predicts a sequence based on exact mass of a peptide can also be used to reveal the sequence of a peptide isolated from a vesicle. For example, LTQ-Orbitrap mass spectrometry can be used for high sensitivity and high accuracy peptide sequencing. LTQ-Orbitrap method has been described (Simpson et al, Expert Rev. Proteomics 6:267-283, 2009), which is incorporated herein by reference in its entirety.

Vesicle Compositions

Also provided herein is an isolated vesicle with a particular biosignature. The isolated vesicle can comprise one or more biomarkers or biosignatures specific for specific cell type, or for characterizing a phenotype, such as described above. For example, the isolated vesicle can comprise one or more biomarkers, such as CD63, EpCam, CD81, CD9, PCSA, PSMA, B7H3, TNFR, MFG-E8, Rab, STEAP, 5T4, or CD59.

The isolated vesicle can comprise one or more of the following biomarkers: EpCam, CD9, PCSA, CD63, CD81, PSMA, B7H3, PSCA, ICAM, STEAP, and EGFR. In one embodiment, the vesicle is EpCam+, CK+, CD45−. The isolated vesicle can have the one or more biomarkers on its surface or within the vesicle. The isolated vesicle can also comprise one or more miRNAs, such as miR-9, miR-629, miR-141, miR-671-3p, miR-491, miR-182, miR-125a-3p, miR-324-5p, miR-148B, or miR-222. In one embodiment, the vesicle comprises one or more miRNAs, such as miR-548c-5p, miR-362-3p, miR-422a, miR-597, miR-429, miR-200a, and miR-200b. In yet another embodiment, the vesicle comprises one or more miRNAs, such as miR-92a-2*, miR-147, miR-574-5p. An isolated vesicle can comprise a biomarker such as CD66, and further comprise one or more biomarkers selected from the group consisting of: EpCam, CD63, or CD9. An isolated vesicle can also comprise a fusion gene or protein, such as TMRSSG2:ERG.

An isolated vesicle can also comprise one or more biomarkers, wherein the expression level of the one or more biomarkers is higher, lower, or the same for an isolated vesicle as compared to an isolated vesicle derived from a normal cell (ie. a cell derived from a subject without a phenotype of interest). For example, an isolated vesicle can comprise one or more biomarkers selected from the group consisting of: B7H3, PSCA, MFG-E8, Rab, STEAP, PSMA, PCSA, 5T4, miR-9, miR-629, miR-141, miR-671-3p, miR-491, miR-182, miR-125a-3p, miR-324-5p, miR-148b, and miR-222, wherein the expression level of the one or more biomarkers is higher for an isolated vesicle as compared those derived from a normal cell. The isolated vesicle can comprise at least 2, 3, 4, 5, 6, 7, 8, 9, 10, 11, 13, 14, 15, 16, 17, 18, or 19 of the biomarkers selected from the group. The isolated vesicle can further comprising one or more biomarkers selected from the group consisting of: EpCam, CD63, CD59, CD81, or CD9.

An isolated vesicle can comprise the biomarkers PCSA, EpCam, CD63, and CD8; the biomarkers PCSA, EpCam, B7H3 and PSMA. An isolated vesicle can comprise the biomarkers miR-9, miR-629, miR-141, miR-671-3p, miR-491, miR-182, miR-125a-3p, miR-324-5p, miR-148b, and miR-222.

A composition comprising an isolated vesicle is also provided herein. The composition can comprise one or more isolated vesicles. For example, the composition can comprise a plurality of vesicles, or one or more populations of vesicles.

The composition can be substantially enriched for vesicles. For example, the composition can be substantially absent of cellular debris, cells, or non-exosomal proteins, peptides, or nucleic acids (such as biological molecules not contained within the vesicles). The cellular debris, cells, or non-exosomal proteins, peptides, or nucleic acids, can be present in a biological sample along with vesicles. A composition can be substantially absent of cellular debris, cells, or non-exosomal proteins, peptides, or nucleic acids (such as biological molecules not contained within the vesicles), can be obtained by any method disclosed herein, such as through the use of one or more binding agents or capture agents for one or more vesicles. The vesicles can comprise at least 30, 40, 50, 60, 70, 80, 90, 95 or 99% of the total composition, by weight or by mass. The vesicles of the composition can be a heterogeneous or homogeneous population of vesicles. For example, a homogeneous population of vesicles comprises vesicles that are homogeneous as to one or more properties or characteristics. For example, the one or more characteristics can be selected from a group consisting of: one or more of the same biomarkers, a substantially similar or identical biosignature, derived from the same cell type, vesicles of a particular size, and a combination thereof.

Thus, in some embodiments, the composition comprises a substantially enriched population of vesicles. The composition can be enriched for a population of vesicles that are at least 30, 40, 50, 60, 70, 80, 90, 95 or 99% homogeneous as to one or more properties or characteristics. For example, the one or more characteristics can be selected from a group consisting of: one or more of the same biomarkers, a substantially similar or identical biosignature, derived from the same cell type, vesicles of a particular size, and a combination thereof. For example, the population of vesicles can be homogeneous by all having a particular biosignature, having the same biomarker, having the same biomarker combination, or derived from the same cell type. In some embodients, the composition comprises a substantially homogeneous population of vesicles, such as a population with a specific biosignature, derived from a specific cell, or both.

The population of vesicles can comprise one or more of the same biomarkers. The biomarker can be any component such as any nucleic acid (e.g. RNA or DNA), protein, peptide, polypeptide, antigen, lipid, carbohydrate, or proteoglycan. For example, each vesicle in a population can comprise the same or identical one or more biomarkers. In some embodiments, each vesicle comprises the same 1, 2, 3, 4, 5, 6, 3, 4, 5, 6, 7, 8, 9, 10, 11, 12, 13, 14, 15, 16, 17, 18, 19, 20, 25, 50, 75 or 100 biomarkers. The one or more biomarkers can be selected from FIGS. 1, 3-60.

The vesicle population comprising the same or identical biomarker can refer to each vesicle in the population having the same presence or absence, expression level, mutational state, or modification of the biomarker. For example, an enriched population of vesicle can comprise vesicles wherein each vesicle has the same biomarker present, the same biomarker absent, the same expression level of a biomarker, the same modification of a biomarker, or the same mutation of a biomarker. The same expression level of a biomarker can refer to a quantitative or qualitive measurement, such as the vesicles in the population underexpress, overexpress, or have the same expression level of a biomarker as compared to a reference level.

Alternatively, the same expression level of a biomarker can be a numerical value representing the expression of a biomarker that is similar for each vesicle in a population. For example the copy number of a miRNA, the amount of protein, or the level of mRNA of each vesicle, can be quantitatively similar for each vesicle in a population, such that the numerical amount of each vesicle is ±1, 2, 3, 4, 5, 6, 7, 8, 9, 10, 15, or 20% from the amount in each other vesicle in the population, as such variations are appropriate.

In some embodiments, the composition comprises a substantially enriched population of vesicles, wherein the vesicles in the enriched population has a substantially similar or identical biosignature. The biosignature can comprise one or more characteristic of the vesicle, such as the level or amount of vesicles, temporal evaluation of the variation in vesicle half-life, circulating vesicle half-life, metabolic half-life of a vesicle, or the activity of a vesicle. The biosignature can also comprise the presence or absence, expression level, mutational state, or modification of a biomarker, such as those described herein.

The biosignature of each vesicle in the population can be at least 30, 40, 50, 60, 70, 80, 90, 95, or 99% identical. In some embodiments, the biosignature of each vesicle is 100% identical. The biosignature of each vesicle in the enriched population can have the same 1, 2, 3, 4, 5, 6, 3, 4, 5, 6, 7, 8, 9, 10, 11, 12, 13, 14, 15, 16, 17, 18, 19, 20, 25, 50, 75 or 100 characteristics. For example, a biosignature of a vesicle in an enriched population can be the presence of a first biomarker, the presence of a second biomarker, and the underexpression of a third biomarker. Another vesicle in the same population can be 100% identical, having the same first and second biomarkers present and underexpression of the third biomarker. Alternatively, a vesicle in the same population can have the same first and second biomarkers, but not have underexpression of the third biomarker.

In some embodiments, the composition comprises a substantially enriched population of vesicles, wherein the vesicles are derived from the same cell type. For example, the vesicles can all be derived from cells of a specific tissue, cells from a specific tumor of interest or a diseased tissue of interest, circulating tumor cells, or cells of maternal or fetal origin. The vesicles can all be derived from tumor cells. The vesicles can all be derived from lung, pancreas, stomach, intestine, bladder, kidney, ovary, testis, skin, colorectal, breast, prostate, brain, esophagus, liver, placenta, or fetal cells.

The composition comprising a substantially enriched population of vesicles can also comprise vesicles are of a particular size. For example, the vesicles can all a diameter of greater than about 10, 20, or 30 nm. They can all have a diameter of about 30-1000 nm, about 30-800 nm, about 30-200 nm, or about 30-100 nm. In some embodiments, the vesicles can all have a diameter of less than about 10,000 nm, 1000 nm, 800 nm, 500 nm, 200 nm, 100 nm or 50 nm.

The population of vesicles homogeneous for one or more characteristics can comprises at least about 30, 40, 50, 60, 70, 80, 90, 95, or 99% of the total vesicle population of the composition. In some embodiments, a composition comprising a substantially enriched population of vesicles comprises at least 2, 3, 4, 5, 10, 20, 25, 50, 100, 250, 500, or 1000 times the concentration of vesicle as compared to a concentration of the vesicle in a biological sample from which the composition was derived. In yet other embodiments, the composition can further comprise a second enriched population of vesicles, wherein the population of vesicles is at least 30% homogeneous as to one or more characteristics, as described herein.

Multiplex analysis can be used to obtain a composition substantially enriched for more than one population of vesicles, such as at least 2, 3, 4, 5, 6, 7, 8, 9, 10 vesicle, populations. Each substantially enriched vesicle population can comprise at least 5, 10, 15, 20, 25, 30, 35, 40, 45, 46, 47, 48, or 49% of the composition, by weight or by mass. In some embodiments, the substantially enriched vesicle population comprises at least about 30, 40, 50, 60, 70, 80, 90, 95, or 99% of the composition, by weight or by mass.

A substantially enriched population of vesicles can be obtained by using one or more methods, processes, or systems as disclosed herein. For example, isolation of a population of vesicles from a sample can be performed by using one or more binding agents for one or more biomarkers of a vesicle, such as using two or more binding agents that target two or more biomarkers of a vesicle. One or more capture agents can be used to obtain a substantially enriched population of vesicles. One or more detection agents can be used to identify a substantially enriched population of vesicles.

In one embodiment, a population of vesicles with a particular biosignature is obtained by using one or more binding agents for the biomarkers of the biosignature. The vesicles can be isolated resulting in a composition comprising a substantially enriched population of vesicles with the particular biosignature. In another embodiment, a population of vesicles with a particular biosignature of interest can be obtained by using one or more binding agents for biomarkers that are not a component of the biosignature of interest. Thus, the binding agents can be used to remove the vesicles that do not have the biosignature of interest and the resulting composition is substantially enriched for the population of vesicles with the particular biosignature of interest. The resulting composition can be substantially absent of the vesicles comprising a biomarker for the binding agent.

Detection System and Kits

Also provided is a detection system configured to determine one or more biosignatures for a vesicle. The detection system can be used to detect a heterogeneous population of vesicles or one or more homogeneous population of vesicles. The detection system can be configured to detect a plurality of vesicles, wherein at least a subset of the plurality of vesicles comprises a different biosignature from another subset of the plurality of vesicles. The detection system detect at least 2, 3, 4, 5, 6, 7, 8, 9, 10, 15, 20, 25, 30, 40, 50, 60, 70, 80, 90, or 100 different subsets of vesicles, wherein each subset of vesicles comprises a different biosignature. For example, a detection system, such as using one or more methods, processes, and compositions disclosed herein, can be used to detect at least 2, 3, 4, 5, 6, 7, 8, 9, 10, 15, 20, 25, 30, 40, 50, 60, 70, 80, 90, or 100 different populations of vesicles.

The detection system can be configured to assess at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750,000, or 1,000,000 different biomarkers for one or more vesicles. In some embodiments, the one or more biomarkers are selected from FIG. 1, 3-60, or as disclosed herein. The detection system can be configured to assess a specific population of vesicles, such as vesicles from a specific cell-of-origin, or to assess a plurality of specific populations of vesicles, wherein each population of vesicles has a specific biosignature.

The detection system can be a low density detection system or a high density detection system. For example, a low density detection system can detect up to 1, 2, 3, 4, 5, 6, 7, 8, 9, or 10 different vesicle populations, whereas a high density detection system can detect at least about 15, 20, 25, 50, or 100 different vesicle populations In another embodiment, a low density detection system can detect up to about 100, 200, 300, 400, or 500 different biomarkers, whereas a high density detection system can detect at least about 750, 1000, 2000, 3000, 4000, 5000, 6000, 7000, 8000, 9,000, 10,000, 15,000, 20,000, 25,000, 50,000, or 100,000 different biomarkers. In yet another embodiment, a low density detection system can detect up to about 100, 200, 300, 400, or 500 different biosignatures or biomarker combinations, whereas a high density detection system can detect at least about 750, 1000, 2000, 3000, 4000, 5000, 6000, 7000, 8000, 9,000, 10,000, 15,000, 20,000, 25,000, 50,000, or 100,000 biosignatures or biomarker combinations.

The detection system can comprise a probe that selectively hybridizes to a vesicle. The detection system can comprise a plurality of probes to detect a vesicle. In some embodiments, a plurality of probes is used to detect the amount of vesicles in a heterogeneous population of vesicles. In yet other embodiments, a plurality of probes is used to detect a homogeneous population of vesicles. A plurality of probes can be used to isolate or detect at least two different subsets of vesicles, wherein each subset of vesicles comprises a different biosignature.

A detection system, such as using one or more methods, processes, and compositions disclosed herein, can comprise a plurality of probes configured to detect, or isolate, such as using one or more methods, processes, and compositions disclosed herein at least 2, 3, 4, 5, 6, 7, 8, 9, 10, 15, 20, 25, 30, 40, 50, 60, 70, 80, 90, or 100 different subsets of vesicles, wherein each subset of vesicles comprises a different biosignature.

For example, a detection system can comprise a plurality of probes configured to detect at least 2, 3, 4, 5, 6, 7, 8, 9, 10, 15, 20, 25, 30, 40, 50, 60, 70, 80, 90, or 100 different populations of vesicles. The detection system can comprise a plurality of probes configured to selectively hybridize to at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250, 000, 300,000, 350,000, 400,000, 450,000, 500,000, 750,000, or 1,000,000 different biomarkers for one or more vesicles. In some embodiments, the one or more biomarkers are selected from FIG. 1, 3-60, or as disclosed herein. The plurality of probes can be configured to assess a specific population of vesicles, such as vesicles from a specific cell-of-origin, or to assess a plurality of specific populations of vesicles, wherein each population of vesicles has a specific biosignature.

The detection system can be a low density detection system or a high density detection system comprising probes to detect vesicles. For example, a low density detection system can comprise probes to detect up to 1, 2, 3, 4, 5, 6, 7, 8, 9, or 10 different vesicle populations, whereas a high density detection system can comprise probes to detect at least about 15, 20, 25, 50, or 100 different vesicle populations. In another embodiment, a low density detection system can comprise probes to detect up to about 100, 200, 300, 400, or 500 different biomarkers, whereas a high density detection system can comprise probes to detect at least about 750, 1000, 2000, 3000, 4000, 5000, 6000, 7000, 8000, 9,000, 10,000, 15,000, 20,000, 25,000, 50,000, or 100,000 different biomarkers. In yet another embodiment, a low density detection system can comprise probes to detect up to about 100, 200, 300, 400, or 500 different biosignatures or biomarker combinations, whereas a high density detection system can comprise probes to detect at least about 750, 1000, 2000, 3000, 4000, 5000, 6000, 7000, 8000, 9,000, 10,000, 15,000, 20,000, 25,000, 50,000, or 100,000 biosignatures or biomarker combinations.

The probes can be specific for detecting a specific vesicle population, for example a vesicle with a particular biosignature, and as described above. A plurality of probes for detecting prostate specific vesicles is also provided. A plurality of probes can comprise probes for detecting one or more of the following biomarkers: CD9, PSCA, TNFR, CD63, MFG-E8, EpCAM, Rab, CD81, STEAP, PCSA, 5T4, EpCAM, PSMA, CD59, CD66, CD24 and B7H3. A plurality of probes for detecting Bcl-XL, ERCC1, Keratin 15, CD81/TAPA-1, CD9, Epithelial Specific Antigen (ESA), and Mast Cell Chymase can also be provided.

A plurality of probes for detecting one or more miRNAs of a vesicle can comprise probes for detecting one or more of the following miRNAs: miR-9, miR-629, miR-141, miR-671-3p, miR-491, miR-182, miR-125a-3p, miR-324-5p, miR-148b, and miR-222. In another embodiment, the plurality of probes comprises one or more probes for detecting EpCam, CD9, PCSA, CD63, CD81, PSMA, B7H3, PSCA, ICAM, STEAP, and EGFR. In some embodiments, the plurality of probes comprises one or more probes for detecting EpCam, CD9, PCSA, CD63, CD81, PSMA, and B7H3. In other embodiments, the plurality of probes comprises one or more probes for detecting EpCam, CD9, PCSA, CD63, CD81, PSMA, B7H3, PSCA, ICAM, STEAP, and EGFR. In yet another embodiment, a subset of the plurality of probes are capture agents for one or more of EpCam, CD9, PCSA, CD63, CD81, PSMA, B7H3, PSCA, ICAM, STEAP, and EGFR, and another subset are probes for detecting one or more of CD9, CD63, and CD81. A plurality of probes can also comprises one or more probes for detecting r miR-92a-2*, miR-147, miR-574-5p, or a combination thereof. A plurality of probes can also comprise one or more probes for detecting miR-548c-5p, miR-362-3p, miR-422a, miR-597, miR-429, miR-200a, miR-200b or a combination thereof. A plurality of probes can also comprise one or more probes for detecting EpCam, CK, and CD45. In some embodiments, the one or more probes may be capture agents. In another embodiment, the probes may be detection agents. In yet another embodiment, the plurality of probes comprises capture and detection agents.

The probes, such as capture agents, may be attached to a solid substrate, such as an array or bead. Alternatively, the probes, such as detection agents, are not attached. The detection system may be an array based system, a sequencing system, a PCR-based system, or a bead-based system, such as described above. The detection system can also be a microfluidic device as described above.

The detection system may be part of a kit. Alternatively, the kit may comprise the one or more probe sets or plurality of probes, as described herein. The kit may comprise probes for detecting a vesicle or a plurality of vesicles, such as vesicles in a heterogeneous population. The kit may comprise probes for detecting a homogeneous population of vesicles. For example, the kit may comprise probes for detecting a population of specific cell-of-origin vesicles, or vesicles with the same specific biosignature.

Portfolios

Portfolios of multiplexed markers to guide clinical decisions and disease detection and management can be established such that the combination of biosignatures in the portfolio exhibit improved sensitivity and specificity relative to individual biosignatures or randomly selected combinations of biosignatures. In the context of the instant invention, the sensitivity of the portfolio can be reflected in the fold differences exhibited by a biosignature's expression in the diseased state relative to the normal state. Specificity can be reflected in statistical measurements of the correlation of the signaling of gene expression, for example, with the condition of interest (e.g. standard deviation can be a used as such a measurement). In considering a group of biosignature for inclusion in a portfolio, a small standard deviation in measurements correlates with greater specificity. Other measurements of variation such as correlation coefficients can also be used in this capacity.

When combining biomarkers or biosignatures in this invention In Vitro Diagnostic Multivariate Index Assays (IVDMIAs) guidelines and regulations may apply. IVDMIAs can apply to biosignatures as defined as a set of 2 or more markers composed of any combination of genes, gene alterations, mutations, amplifications, deletions, polymorphisms or methylations, or proteins, peptides, polypeptides or RNA molecules, miRNAs, mRNAs, snoRNAs, hnRNAs or RNA that can be grouped so that information obtained about the set of biosignatures in the group provides a sound basis for making a clinically relevant judgment such as a diagnosis, prognosis, or treatment choice. These sets of biosignatures make up various portfolios of the invention. As with most diagnostic markers, it is often desirable to use the fewest number of markers sufficient to make a correct medical judgment. This prevents a delay in treatment pending further analysis as well inappropriate use of time and resources. Preferably, portfolios are established such that the combination of biosignatures in the portfolio exhibit improved sensitivity and specificity relative to individual biosignatures or randomly selected combinations of biosignatures. In the context of the instant invention, the sensitivity of the portfolio can be reflected in the fold differences exhibited by a biosignature's expression in the diseased state relative to the normal state. Specificity can be reflected in statistical measurements of the correlation of the signaling of gene expression, for example, with the condition of interest. In considering a group of markers in a biosignature for inclusion in a portfolio, standard deviations, variances, co-variances, correlation coefficients, weighted averages, arithmetic sums, means, multiplicative values, weighted or balanced values or any mathematical manipulation of the values of 2 or more markers that can together be used to calculate a value or score that taken as a whole can be shown to produce greater sensitivity, specificity, negative predictive value, positive predictive value or accuracy can also be used in this capacity and are within the scope of this invention.

In another embodiment pattern recognition methods can be used. One example involves comparing biomarker expression profiles for various biomarkers (or biosignature portfolios) to ascribe diagnoses. The expression profiles of each of the biomarker comprising the biosignature portfolio are fixed in a medium such as a computer readable medium.

In one example, a table can be established into which the range of signals (e.g., intensity measurements) indicative of disease or physiological state is input. Actual patient data can then be compared to the values in the table to determine whether the patient samples are normal, benign, diseased, or represent a specific physiological state. In a more sophisticated embodiment, patterns of the expression signals (e.g., fluorescent intensity) are recorded digitally or graphically. In the example of RNA expression patterns from the biomarker portfolios used in conjunction with patient samples are then compared to the expression patterns. Pattern comparison software can then be used to determine whether the patient samples have a pattern indicative of the disease, a given prognosis, a pattern that indicates likeliness to respond to therapy, or a pattern that is indicative of a particular physiological state. The expression profiles of the samples are then compared to the portfolio of a control cell. If the sample expression patterns are consistent with the expression pattern(s) for disease, prognosis, or therapy-related response then (in the absence of countervailing medical considerations) the patient is diagnosed as meeting the conditions that relate to these various circumstances. If the sample expression patterns are consistent with the expression pattern derived from the normal/control vesicle population then the patient is diagnosed negative for these conditions.

In another exemplary embodiment, a method for establishing biomarker expression portfolios is through the use of optimization algorithms such as the mean variance algorithm widely used in establishing stock portfolios. This method is described in detail in the U.S. Application Publication No. 20030194734, incorporated herein by reference. Alternatively, measured DNA alterations, changes in mRNA, protein, or metabolites to phenotypic readouts of efficacy and toxicity may be modeled and analyzed using algorithms, systems and methods described in U.S. Pat. Nos. 7,089,168, 7,415,359 and U.S. Application Publication Nos. 20080208784, 20040243354, or 20040088116, each of which is herein incorporated by reference in its entirety.

An exemplary process of biosignature portfolio selection and characterization of an unknown is summarized as follows:

(1) Choose baseline class.

(2) Calculate mean, and standard deviation of each biomarker for baseline class samples.

(3) Calculate (X*Standard Deviation+Mean) for each biomarker. This is the baseline reading from which all other samples will be compared. X is a stringency variable with higher values of X being more stringent than lower.

(4) Calculate ratio between each Experimental sample versus baseline reading calculated in step 3.

(5) Transform ratios such that ratios less than 1 are negative (eg. using Log base 10). (Under expressed biomarkers now correctly have negative values necessary for MV optimization).

(6) These transformed ratios are used as inputs in place of the asset returns that are normally used in the software application.

(7) The software will plot the efficient frontier and return an optimized portfolio at any point along the efficient frontier.

(8) Choose a desired return or variance on the efficient frontier.

(9) Calculate the Portfolio's Value for each sample by summing the multiples of each gene's intensity value by the weight generated by the portfolio selection algorithm.

(10) Calculate a boundary value by adding the mean Biosignature Portfolio Value for Baseline groups to the multiple of Y and the Standard Deviation of the Baseline's Biosignature Portfolio Values. Values greater than this boundary value shall be classified as the Experimental Class.

(11) Optionally one can reiterate this process until best prediction.

The process of selecting a biosignature portfolio can also include the application of heuristic rules. Preferably, such rules are formulated based on biology and an understanding of the technology used to produce clinical results. More preferably, they are applied to output from the optimization method. For example, the mean variance method of biosignature portfolio selection can be applied to microarray data for a number of biomarkers differentially expressed in subjects with a specific disease. Output from the method would be an optimized set of biomarkers that could include those that are expressed in vesicles as well as in diseased tissue. If samples used in the testing method are obtained from vesicles and certain biomarkers differentially expressed in instances of disease or physiological state could also be differentially expressed in vesicles, then a heuristic rule can be applied in which a biosignature portfolio is selected from the efficient frontier excluding those that are differentially expressed in vesicles. Of course, the rule can be applied prior to the formation of the efficient frontier by, for example, applying the rule during data pre-selection.

Other statistical, mathematical and computational algorithms for the analysis of linear and non-linear feature subspaces, feature extraction and signal deconvolution in large scale datasets to identify vesicle-derived multiplex analyte profiles for diagnosis, prognosis and therapy selection and/or characterization of define physiological states can be done using any combination of unsupervised analysis methods, including but not limited to: principal component analysis (PCA) and linear and non-linear independent component analysis (ICA); blind source separation, nongaussinity analysis, natural gradient maximum likelihood estimation; joint-approximate diagonalization; eigenmatrices; Gaussian radical basis function, kernel and polynominal kernel analysis sequential floating forward selection.

Computer Systems

Figure 62:
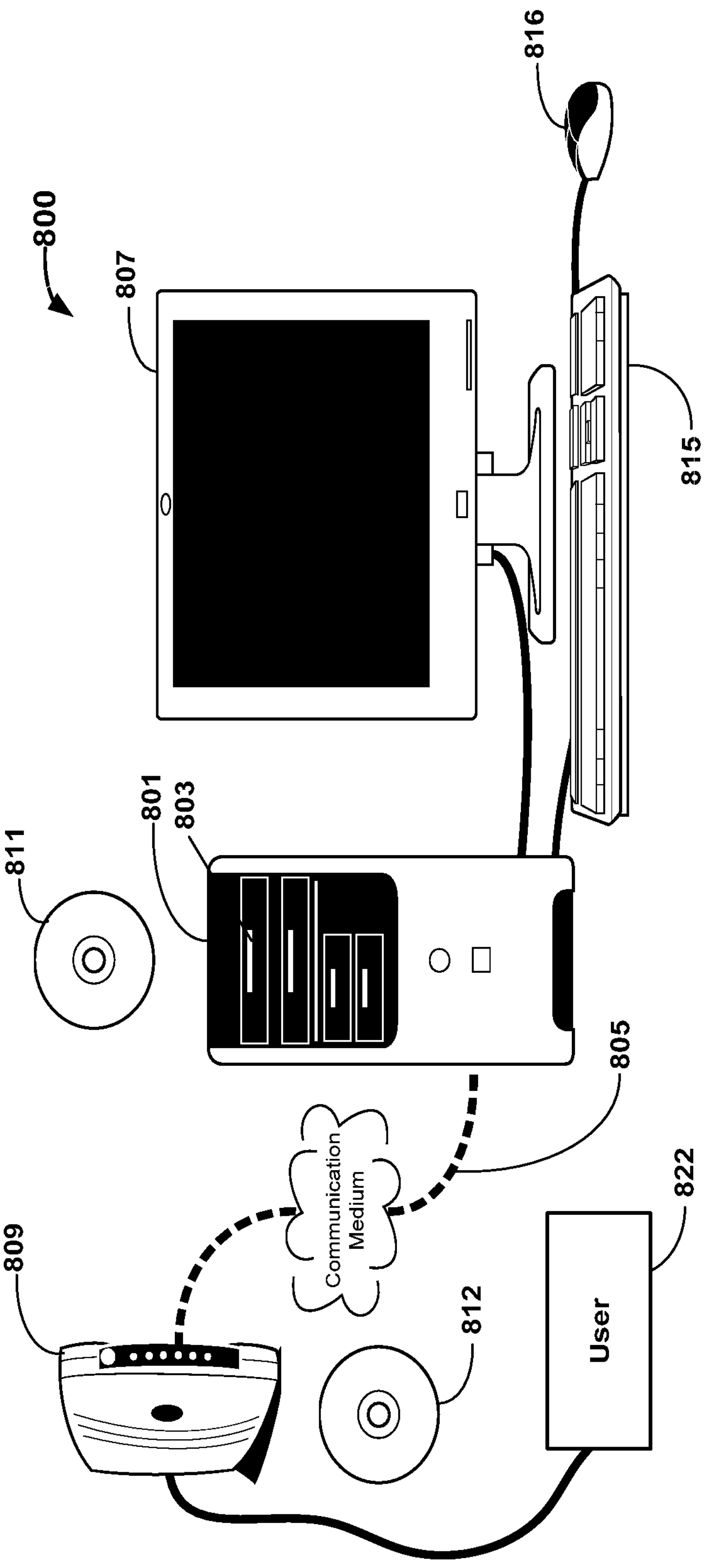
FIG. 62 illustrates a computer system that can be used in some exemplary embodiments of the invention.

A vesicle can be assayed for molecular features, for example, by determining an amount, presence or absence of one or more biomarkers such as listed FIGS. 1, 3-60. The data generated can be used to produce a biosignature, which can be stored and analyzed by a computer system, such as shown in FIG. 62. The assaying or correlating of the biosignature with one or more phenotypes can also be performed by computer systems, such as by using computer executable logic.

A computer system, such as shown in FIG. 62, can be used to transmit data and results following analysis. Accordingly, FIG. 62 is a block diagram showing a representative example logic device through which results from a vesicle can be analyzed and the analysis reported or generated. FIG. 62 shows a computer system (or digital device) 800 to receive and store data generated from a vesicle, analyze of the data to generate one or more biosignatures, and produce a report of the one or more biosignatures or phenotype characterization. The computer system can also perform comparisons and analyses of biosignatures generated, and transmit the results. Alternatively, the computer system can receive raw data of vesicle analysis, such as through transmission of the data over a network, and perform the analysis.

The computer system 800 may be understood as a logical apparatus that can read instructions from media 811 and/or network port 805, which can optionally be connected to server 809 having fixed media 812. The system shown in FIG. 62 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present invention can be transmitted over such networks or connections for reception and/or review by a party 822. The receiving party 822 can be but is not limited to an individual, a health care provider or a health care manager. Thus, the information and data on a test result can be produced anywhere in the world and transmitted to a different location. For example, when an assay is conducted in a differing building, city, state, country, continent or offshore, the information and data on a test result may be generated and cast in a transmittable form as described above. The test result in a transmittable form thus can be imported into the U.S. to receiving party 822. Accordingly, the present invention also encompasses a method for producing a transmittable form of information on the diagnosis of one or more samples from an individual. The method comprises the steps of (1) determining a diagnosis, prognosis, theranosis or the like from the samples according to methods of the invention; and (2) embodying the result of the determining step into a transmittable form. The transmittable form is the product of the production method. In one embodiment, a computer-readable medium includes a medium suitable for transmission of a result of an analysis of a biological sample, such as biosignatures. The medium can include a result regarding a vesicle, such as a biosignature of a subject, wherein such a result is derived using the methods described herein.

Ex Vivo Harvesting of Vesicles

A vesicle for analysis and determination of a phenotype can also be from ex vivo harvesting. Cells can be cultured and vesicles released from cells of interest in culture either result spontaneously or can be stimulated to release vesicles into the medium. (see for example, Zitvogel, et al. 1998. *Nat. Med.* 4: 594-600; Chaput, et al. 2004. *J. Immunol.* 172: 2137-214631: 2892-2900; Escudier, et al. 2005. *J. Transl. Med.* 3: 10; Morse, et al. 2005, *J. Transl. Med.* 3: 9; Peche, et al. 2006. *Am. J Transplant.* 6: 1541-1550; Kim, et al. 2005. J Immunol. 174: 6440-6448, all of which are herein incorporated by reference in their entireties). Cell lines or tissue samples can be grown to 80% confluence before being cultured in fresh DMEM for 72 h. Subsequent vesicle production can be stimulated (see, for example, heat shock treatment of melanoma cells as described by Dressel, et al. 2003. *Cancer Res.* 63: 8212-8220, which is herein incorporated by reference in its entirety). The supernatant can then be harvested and vesicles prepared as described herein.

A vesicle produced ex vivo can, in one example, be cultured from a cell-of-origin or cell line of interest, vesicles can be isolated from the cell culture medium and subsequently labeled with a magnetic label, a fluorescent moiety, a radioisotope, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles to be reintroduced in vivo as a label for imaging analysis. Ex vivo cultured vesicles can alternatively be used to identify novel biosignatures by setting up culturing conditions for a given cell-of-origin with characteristics of interest, for example a culture of lung cancer cells or cell line with a known EGFR mutation that confers resistant to or susceptibility to gefitinib, then exposing the cell culture to gefitinib, isolating vesicles that arise from the culture and subsequently analyzing them on a discovery array to look for novel antigens or binding agents expressed on the outside of vesicles that could be used as a biosignature to capture this species of vesicle. Additionally, it would be possible to isolate any other biomarkers or biosignatures found within these vesicles for discovery of novel signatures (including but not limited to nucleic acids, proteins, lipids, or combinations thereof) that may have clinical diagnostic, prognostic or therapy related implication.

Cells of interest can also be first isolated and cultured from tissues of interest. For example, human hair follicles in the growing phase, anagen, can be plucked individually from a patient's scalp using sterile equipment and plasticware, taking care not to damage the follicle. Each sample can be transferred to a Petri dish containing sterile PBS for tissue culture. Isolated human anagen hair follicles can be carefully transferred to an individual well of a 24-well plate containing 1 ml of William's E medium. Follicles can be maintained free-floating at 37° C. in an atmosphere of 5% $CO_2$ and 95% air in a humidified incubator. Medium can be changed every 3 days, taking care not to damage the follicles. Cells can then be collected and spun down from the media. Vesicles may then be isolated using antigens or cellular binding partners that are specific to such cell-of-origin specific vesicles using methods as previously described. Biomarkers and biosignatures can then be isolated and characterized by methods known to those skilled in the art.

Cells of interest may also be cultured under microgravity or zero-gravity conditions or under a free-fall environment. For example, NASA's bioreactor technology will allow such cells to be grown at much faster rate and in much greater quantities. Vesicles may then be isolated using antigens or cellular binding partners that are specific to such cell-of-origin specific vesicles using methods as previously described.

Rotating wall vessels or RWVersus are a class of bioreactors developed by and for NASA that are designed to grow suspension cultures of cells in a quiescent environment that simulates microgravity can also be used. (see for exapmle, U.S. Pat. Nos. 5,026,650; 5,153,131; 5,153,133; 5,437,998; 5,665,594; 5,702,941; 7,351,584, 5,523,228, 5,104,802, 6,117,674, Schwarz, R P, et al., *J. Tiss. Cult. Meth.* 14:51-58, 1992; Martin et al., *Trends in biotechnology* 2004; 22; 80-86, Li et al., *Biochemical Engineering Journal* 2004; 18; 97-104, Ashammakhi et al., *Journal Nanoscience Nanotechnology* 2006; 9-10: 2693-2711, Zhang et al., *International Journal of Medicine* 2007; 4: 623-638, Cowger, N L, et al., *Biotechnol. Bioeng* 64:14-26, 1999, Spaulding, G F, et al., *J. Cell. Biochem.* 51:249-251, 1993, Goodwin, T J, et al., *Proc. Soc. Exp. Biol. Med.* 202:181-192, 1993; Freed, L E et al., *In Vitro Cell. Dev. Biol.* 33:381-385, 1997, Clejan, S. et al, *Biotechnol. Bioeng.* 50:587-597, 1996). Khaoustov, V I, et al., *In Vitro Cell. Dev. Biol.* 35:501-509. 1999, each of which is herein incorporated by reference in its entirety).

Alternatively, cells of interest or cell-of-origin specific vesicles that have been isolated may be cultured in a stationary phase plug-flow bioreactor as generally described in U.S. Pat. No. 6,911,201, and U.S. Application Publication Nos. 20050181504, 20050180958, 20050176143 and 20050176137, each of which is herein incorporated by reference in its entirety. Alternatively, cells of interest or cell-origin specific vesicles may also be isolated and cultured as generally described in U.S. Pat. No. 5,486,359.

One embodiment can include the steps of providing a tissue specimen containing cells of interest or cell-origin specific vesicles, adding cells or vesicles from the tissue specimen to a medium which allows, when cultured, for the selective adherence of only the cells of interest or cell-origin specific vesicles to a substrate surface, culturing the specimen-medium mixture, and removing the non-adherent matter from the substrate surface is generally described in U.S. Pat. No. 5,486,359, which is herein incorporated by reference in its entirety.

EXAMPLES

Example 1

Purification of Vesicles From Prostate Cancer Cell Lines

Prostate cancer cell lines are cultured for 3-4 days in culture media containing 20% FBS (fetal bovine serum) and 1% P/S/G. The cells are then pre-spun for 10 minutes at 400×g at 4° C. The supernatant is kept and centrifuged for 20 minutes at 2000×g at 4. The supernatant containing vesicles can be concentrated using a Millipore Centricon Plus-70 (Cat # UFC710008 Fisher).

The Centricon is pre washed with 30 mls of PBS at 1000×g for 3 minutes at room temperature. Next, 15-70 mls of the pre-spun cell culture supernatant is poured into the Concentrate Cup and is centrifuged in a Swing Bucket Adapter (Fisher Cat #75-008-144) for 30 minutes at 1000×g at room temperature.

The flow through in the Collection Cup is poured off. The volume in the Concentrate Cup is brought back up to 60 mls with any additional supernatant. The Concentrate Cup is centrifuged for 30 minutes at 1000×g at room temperature to concentrate the cell supernatant.

The Concentrate Cup is washed by adding 70 mls of PBS and centrifuged for 30-60 minutes at 1000×g until approximately 2 mls remains. The vesicles are removed from the filter by inverting the concentrate into the small sample cup and centrifuge for 1 minute at 4° C. The volume is brought up to 25 mls with PBS. The vesicles are now concentrated and are added to a 30% Sucrose Cushion.

To make a cushion, 4 mls of Tris/30% Sucrose/D2O solution (30 g protease-free sucrose, 2.4g Tris base, 50 ml D2O, adjust pH to 7.4 with 10N NCL drops, adjust volume to 100 mls with D2O, sterilize by passing thru a 0.22-um filter) is loaded to the bottom of a 30 ml V bottom thin walled Ultracentrifuge tube. The diluted 25 mls of concentrated vesicles is gently added above the sucrose cushion without disturbing the interface and is centrifuged for 75 minutes at 100,000×g at 4° C. The ~25 mls above the sucrose cushion is carefully removed with a 10 ml pipet and the ~3.5 mls of vesicles is collected with a fine tip transfer pipet (SAMCO 233) and transferred to a fresh ultracentrifuge tube, where 30 mls PBS is added. The tube is centrifuged for 70 minutes at 100,000×g at 4° C. The supernatant is poured off carefully. The pellet is resuspended in 200 ul PBS and can be stored at 4° C. or used for assays. A BCA assay (1:2) can be used to determine protein content and Western blotting or electron micrography can be used to determine vesicle purification.

Example 2

Purification of Vesicles from VCaP and 22Rv1

Vesicles from Vertebral-Cancer of the Prostate (VCaP) and 22Rv1, a human prostate carcinoma cell line, derived from a human prostatic carcinoma xenograft (CWR22R) were collected by ultracentrifugation by first diluting plasma with an equal volume of PBS (1 ml). The diluted fluid was transferred to a 15 ml falcon tube and centrifuged 30 minutes at 2000×g 4° C. The supernatant (~2 mis) was transferred to an ultracentrifuge tube 5.0 ml PA thinwall tube (Sorvall #03127) and centrifuged at 12,000×g, 4° C. for 45 minutes.

The supernatant (~2 mls) was transferred to a new 5.0 ml ultracentrifuge tubes and filled to maximum volume with addition of 2.5 mls PBS and centrifuged for 90 minutes at 110,000×g, 4° C. The supernatant was poured off without disturbing the pellet and the pellet resuspended with 1 ml PBS. The tube was filled to maximum volume with addition of 4.5 ml of PBS and centrifuged at 110,000×g, 4° C. for 70 minutes.

The supernatant was poured off without disturbing the pellet and an additional 1 ml of PBS was added to wash the pellet. The volume was increased to maximum volume with the addition of 4.5 mls of PBS and centrifuged at 110,000×g for 70 minutes at 4° C. The supernatant was removed with P-1000 pipette until ~100 μl of PBS was in the bottom of the tube. The ~90 μl remaining was removed with P-200 pipette and the pellet collected with the ~10 μl of PBS remaining by gently pipetting using a P-20 pipette into the microcentrifuge tube. The residual pellet was washed from the bottom of a dry tube with an additional 5 μl of fresh PBS and collected into microcentrifuge tube and suspended in phosphate buffered saline (PBS) to a concentration of 500 μg/ml.

Example 3

Plasma Collection and Vesicle Purification

Blood is collected via standard vein puncture in a 7 ml K2-EDTA tube. The sample is spun at 400 g for 10 minutes in a 4° C. centrifuge to separate plasma from blood cells (SORVALL Legend RT+centrifuge). The supernatant (plasma) is transferred by careful pipetting to 15 ml Falcon centrifuge tubes. The plasma is spun at 2,000 g for 20 minutes and the supematant is collected.

For storage, approximately lml of the plasma (supernatant) is aliquoted to a cryovials, placed in dry ice to freeze them and stored in −80° C. Before vesicle purification, if samples were stored at −80° C., samples are thawed in a cold water bath for 5 minutes. The samples are mixed end over end by hand to dissipate insoluble material.

In a first prespin, the plasma is diluted with an equal volume of PBS (example, approximately 2 ml of plasma is diluted with 2 ml of PBS). The diluted fluid is transferred to a 15 ml Falcon tube and centrifuged for 30 minutes at 2000×g at 4° C.

For a second prespin, the supernatant (approximately 4 mls) is carefully transferred to a 50 ml Falcon tube and centrifuged at 12,000×g at 4° C. for 45 minutes in a Sorval.

In the isolation step, the supernatant (approximately 2 mls) is carefully transferred to a 5.0 ml ultracentrifuge PA thinwall tube (Sorvall #03127) using a P1000 pipette and filled to maximum volume with an additional 0.5 mls of PBS. The tube is centrifuged for 90 minutes at 110,000×g at 4° C.

In the first wash, the supernatant is poured off without disturbing the pellet. The pellet is resuspended or washed with 1 ml PBS and the tube is filled to maximum volume with an additional 4.5 ml of PBS. The tube is centrifuged at 110, 000×g at 4° C. for 70 minutes. A second wash is performed by repeating the same steps.

The vesicles are collected by removing the supernatant with P-1000 pipette until approximately 100 μl of PBS is in the bottom of the tube. Approximately 90 μl 1 of the PBS is removed and discarded with P-200 pipette. The pellet and remaining PBS is collected by gentle pipetting using a P-20 pipette. The residual pellet is washed from the bottom of the dry tube with an additional 5 μl of fresh PBS and collected into a microcentrifuge tube.

Example 4

Analysis of Vesicles Using Antibody-Coupled Microspheres and Directly Conjugated Antibodies This example demonstrates the use of particles coupled to an antibody, where the antibody captures the vesicles (see for example, FIG. 64A). An antibody, the detector antibody, is directly coupled to a label, and is used to detect a biomarker on the captured vesicle.

First, an antibody-coupled microsphere set is selected (Luminex, Austin, Tex.). The microsphere set can comprise various antibodies, and thus allows multiplexing. The microspheres are resuspended by vortex and sonication for approximately 20 seconds. A Working Microsphere Mixture is prepared by diluting the coupled microsphere stocks to a final concentration of 100 microspheres of each set/μL in Startblock (Pierce (37538)). (Note: 50 μL of Working Microsphere Mixture is required for each well.) Either PBS-1% BSA or PBS-BN (PBS, 1% BSA, 0.05% Azide, pH 7.4) may be used as Assay Buffer.

A 1.2 μm Millipore filter plate is pre-wet with 100 μl/well of PBS-1% BSA (Sigma (P3688-10PAK+0.05% NaAzide (S8032))) and aspirated by vacuum manifold. An aliquot of 500 of the Working Microsphere Mixture is dispensed into the appropriate wells of the filter plate (Millipore Multiscreen HTS (MSBVN1250)). A 50 μl aliquot of standard or sample is dispensed into to the appropriate wells. The filter plate is covered and incubated for 60 minutes at room temperature on a plate shaker. The plate is covered with a sealer, placed on the orbital shaker and set to 900 for 15-30 seconds to re-suspend the beads. Following that the speed is set to 550 for the duration of the incubation.

The supernatant is aspirated by vacuum manifold (less than 5 inches Hg in all aspiration steps). Each well is washed twice with 100 III of PBS-1% BSA (Sigma (P3688-10PAK+0.05% NaAzide (S8032))) and is aspirated by vacuum manifold. The microspheres are resuspended in 50 μL of PBS-1% BSA (Sigma (P3688-10PAK+0.05% NaAzide (S8032))). The PE conjugated detection antibody is diluted to 4 μg/mL (or appropriate concentration) in PBS-1% BSA (Sigma (P3688-10PAK+0.05% NaAzide (S8032))). (Note: 50 μL of diluted detection antibody is required for each reaction.) A 50 μl aliquot of the diluted detection antibody is added to each well. The filter plate is covered and incubated for 60 minutes at room temperature on a plate shaker. The filter plate is covered with a sealer, placed on the orbital shaker and set to 900 for 15-30 seconds to re-suspend the beads. Following that the speed is set to 550 for the duration of the incubation. The supernatant is aspirated by vacuum manifold. The wells are washed twice with 100 μl of PBS-1% BSA (Sigma (P3688-10PAK+0.05% NaAzide (S8032))) and aspirated by vacuum manifold. The microspheres are resuspended in 100 1.1.1 of PBS-1% BSA (Sigma (P3688-10PAK+0.05% NaAzide (S8032))). The microspheres are analyzed on a Luminex analyzer according to the system manual.

Example 5

Analysis of Vesicles Using Antibody-Coupled Microspheres and Biotinylated Antibody This example demonstrates the use of particles coupled to an antibody, where the antibody captures the vesicles. An antibody, the detector antibody, is biotinylated. A label coupled to streptavidin is used to detect the biomarker.

First, the appropriate antibody-coupled microsphere set is selected (Luminex, Austin, Tex.). The microspheres are resuspended by vortex and sonication for approximately 20 seconds. A Working Microsphere Mixture is prepared by diluting the coupled microsphere stocks to a final concentration of 50 microspheres of each set/μL in Startblock (Pierce (37538)). (Note: 50 μl of Working Microsphere Mixture is required for each well.) Beads in Start Block should be blocked for 30 minutes and no more than 1 hour.

A 1.2 μm Millipore filter plate is pre-wet with 100 μl/well of PBS-1% BSA+Azide (PBS-BN)((Sigma (P3688-10PAK+0.05% NaAzide (S8032))) and is aspirated by vacuum manifold. A 50 μl aliquot of the Working Microsphere Mixture is dispensed into the appropriate wells of the filter plate (Millipore Multiscreen HTS (MSBVN1250)). A 50 μl aliquot of standard or sample is dispensed to the appropriate wells. The filter plate is covered with a seal and is incubated for 60 minutes at room temperature on a plate shaker. The covered filter plate is placed on the orbital shaker and set to 900 for 15-30 seconds to re-suspend the beads. Following that, the speed is set to 550 for the duration of the incubation.

The supernatant is aspirated by a vacuum manifold (less than 5 inches Hg in all aspiration steps). Aspiration can be done with the Pall vacuum manifold. The valve is place in the full off position when the plate is placed on the manifold. To aspirate slowly, the valve is opened to draw the fluid from the wells, which takes approximately 3 seconds for the 100 μl of sample and beads to be fully aspirated from the well. Once the sample drains, the purge button on the manifold is pressed to release residual vacuum pressure from the plate.

Each well is washed twice with 100 μl of PBS-1% BSA+Azide (PBS-BN) (Sigma (P3688-10PAK+0.05% NaAzide (S8032))) and is aspirated by vacuum manifold. The microspheres are resuspended in 50 μl of PBS-1% BSA+Azide (PBS-BN) ((Sigma (P3688-10PAK+0.05% NaAzide (S8032))).

The biotinylated detection antibody is diluted to 4 μg/mL in PBS-1% BSA+Azide (PBS-BN) (Sigma (P3688-10PAK+0.05% NaAzide (S8032))). (Note: 50 μl of diluted detection antibody is required for each reaction.) A 50 μl aliquot of the diluted detection antibody is added to each well.

The filter plate is covered and incubated with shaking as described above. The supernatant is aspirated by vacuum manifold as described above. The wells are washed and resuspended with PBS-BN as described above.

The streptavidin-R-phycoerythrin reporter (Molecular Probes 1 mg/ml) is diluted to 4 μg/mL in PBS-1% BSA+Azide (PBS-BN). 50 μl of diluted streptavidin-R-phycoerythrin is required for each reaction. A 50 μl aliquot of the diluted streptavidin-R-phycoerythrin is added to each well.

The filter plate is covered and incubated with shaking as described above. The supernatant is aspirated by vacuum manifold as described above.

Each well is washed twice with 100 μl of PBS-1% BSA+Azide (PBS-BN) ((Sigma (P3688-10PAK+0.05% NaAzide (S8032))) and is aspirated by vacuum manifold. The microspheres are resuspended in 100 μl of PBS-1% BSA+Azide (PBS-BN) and analyzed on the Luminex analyzer according to the system manual.

Example 6

Determining Biosignatures for Prostate Cancer Using Multiplexing

The samples obtained using methods as described in Example 1-3 are used in multiplexing assays as described in Examples 4 and 5. The detection antibodies used are CD63, CD9, CD81, B7H3 and EpCam. The capture antibodies used are CD9, PSCA, TNFR, CD63 2X, B7H3, MFG-E8, EpCam 2X, CD63, Rab, CD81, SETAP, PCSA, PSMA, 5T4, Rab IgG (control) and IgG (control), resulting in 100 combinations to be screened (FIG. 64B).

Figure 70A:
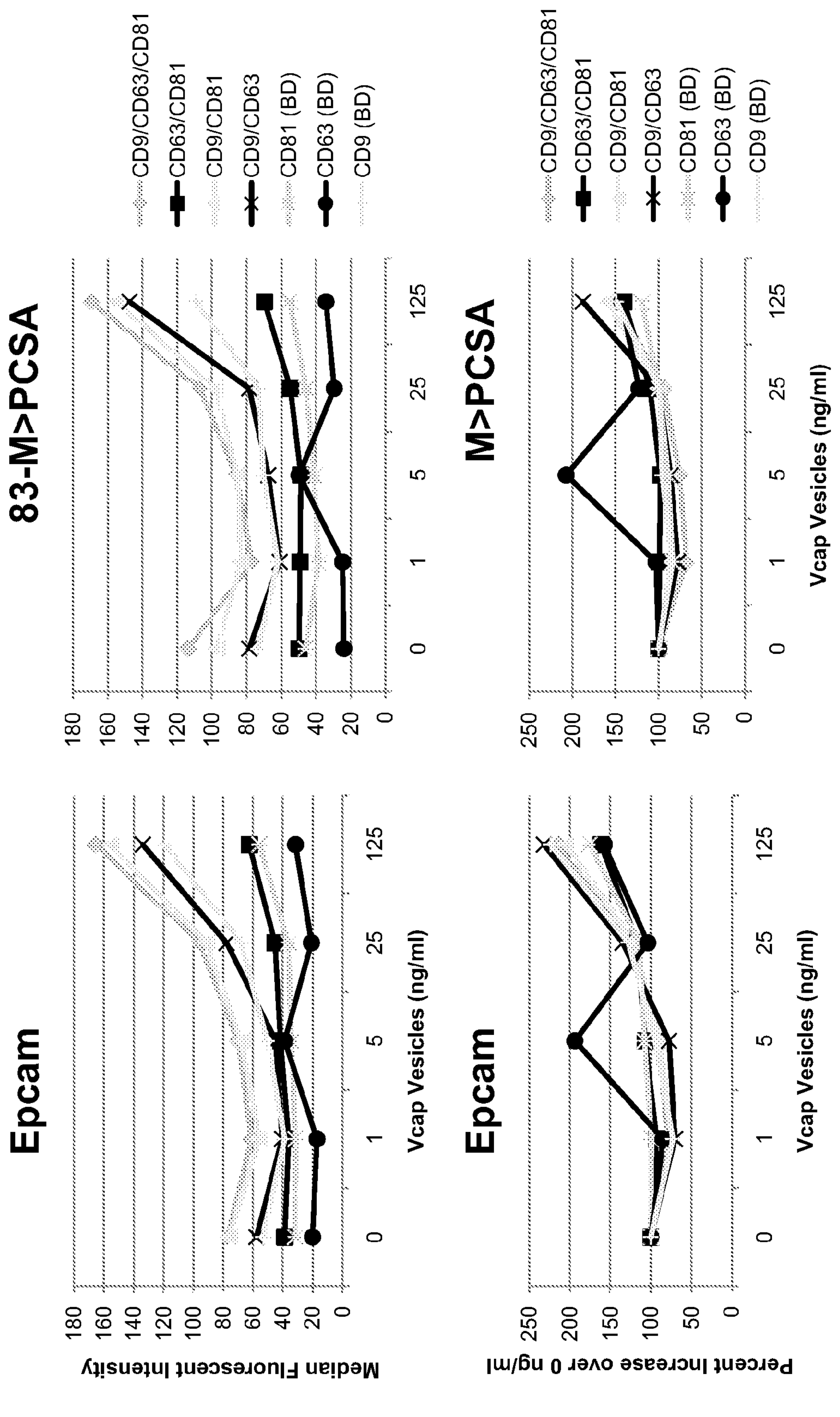
FIG. 70 illustrates multiple detectors can increase the signal. (A) Median intensity values are plotted as a function of purified concentration from the VCaP cell line when labeled with a variety of prostate specific PE conjugated antibodies. Vesicles captured with EpCam (left graphs) or PCSA (right graphs) and the various proteins detected by the detector antibody are listed to the right of each graph. In both cases the combination of CD9 and CD63 gives the best increase in signal over background (bottom graphs depicting percent increase). The combination of CD9 and CD63 gave about 200% percent increase over background. (B) further illustrates prostate cancer/prostate vesicle-specific marker multiplexing improves detection of prostate cancer cell derived vesicles. Median intensity values are plotted as a function of purified concentration from the VCaP cell line when labeled with a variety of prostate specific PE conjugated antibodies. Vesicles captured with PCSA (left) and vesicles captured with EpCam (right) are depicted. In both cases the combination of B7H3 and PSMA gives the best increase in signal over background.
Figure 70B:
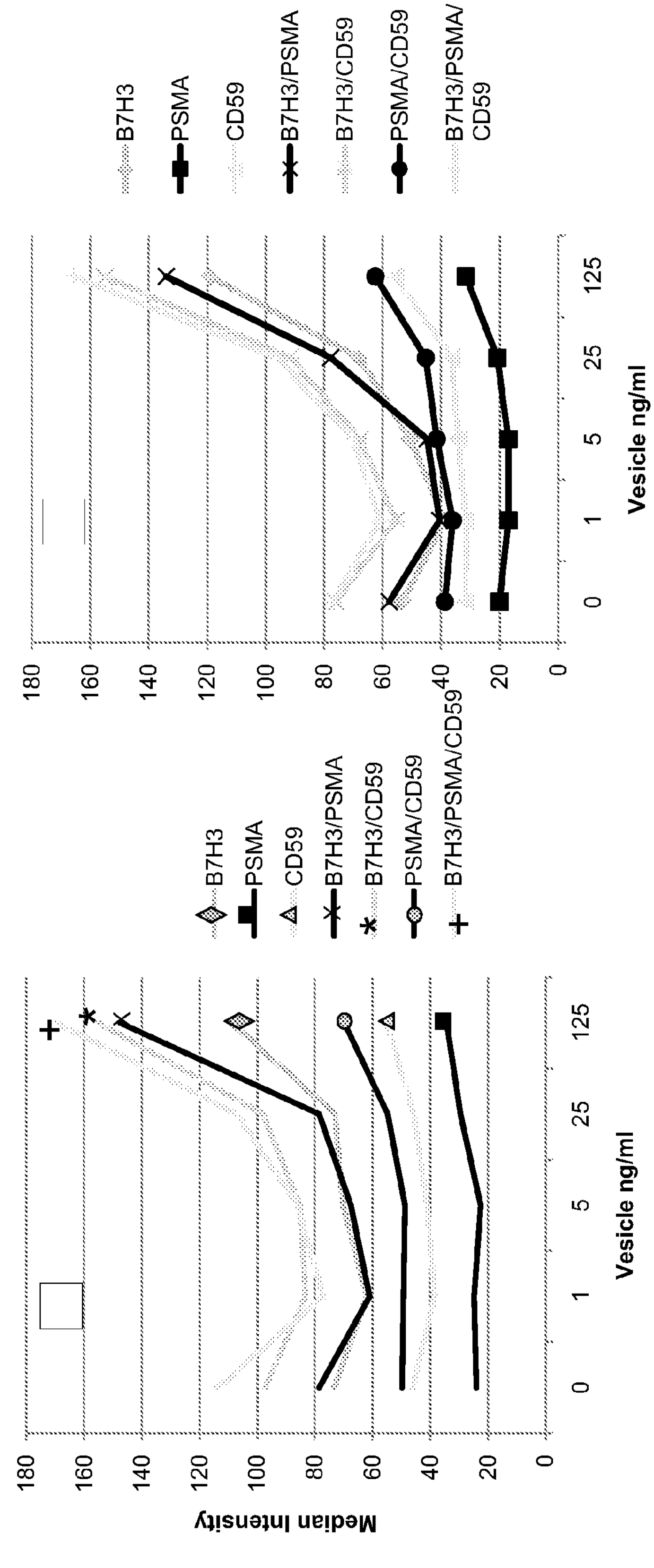
Figure 71A:
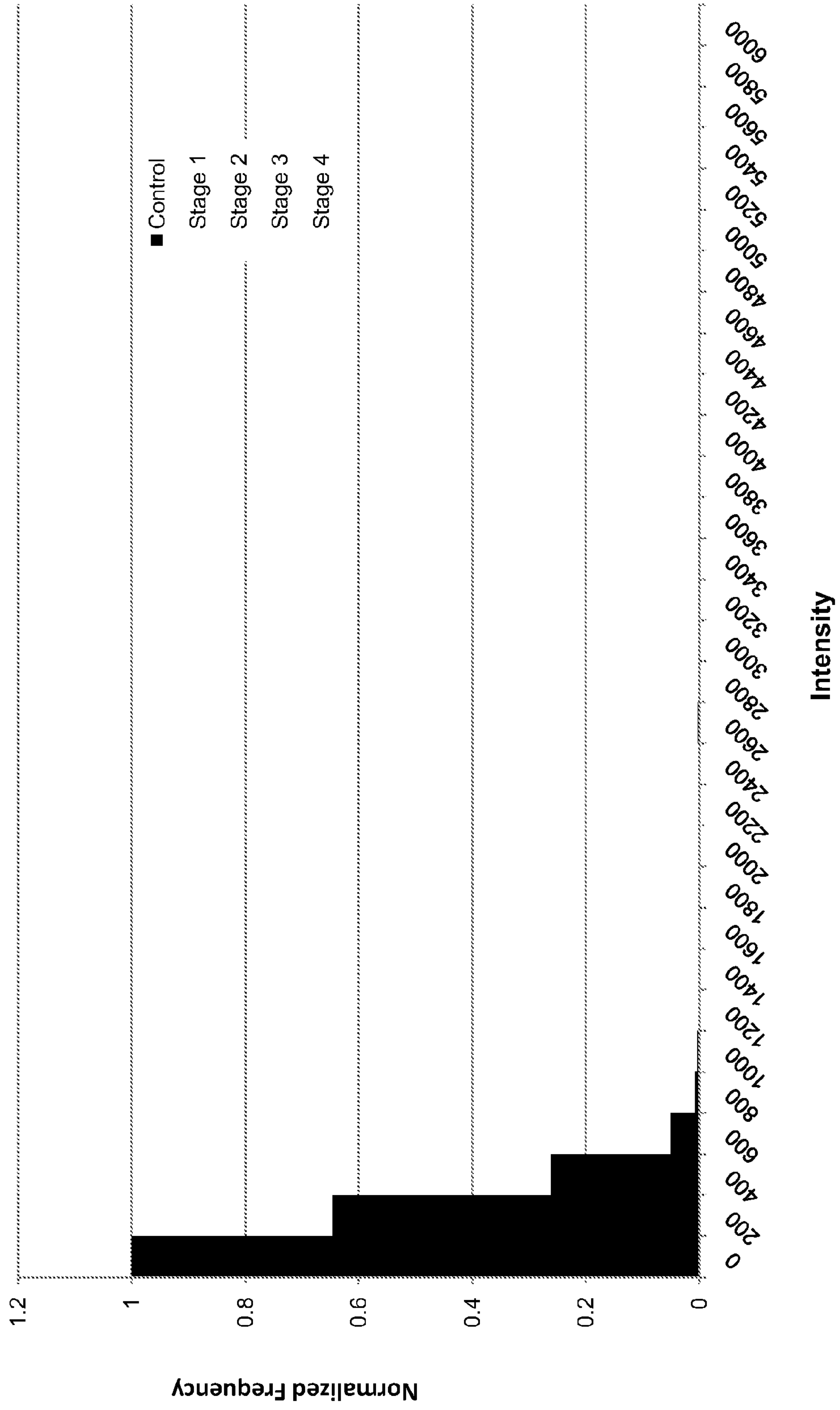
FIG. 71 illustrates a colon cancer biosignature for colon cancer by stage, using CD63 detector and CD63 capture. The histograms of intensities from vesicles captured with CD63 coated beads and labeled with CD63 conjugated PE. There are 6 patients in the control group (A), 4 in stage I (B), 5 in stage II (C), 8 in stage III (D), and 4 stage IV (E). Data from each individual was normalized to account for variation in the number of beads detected, added together, and then normalized again to account for the different number of samples in each population (F).
Figure 71B:
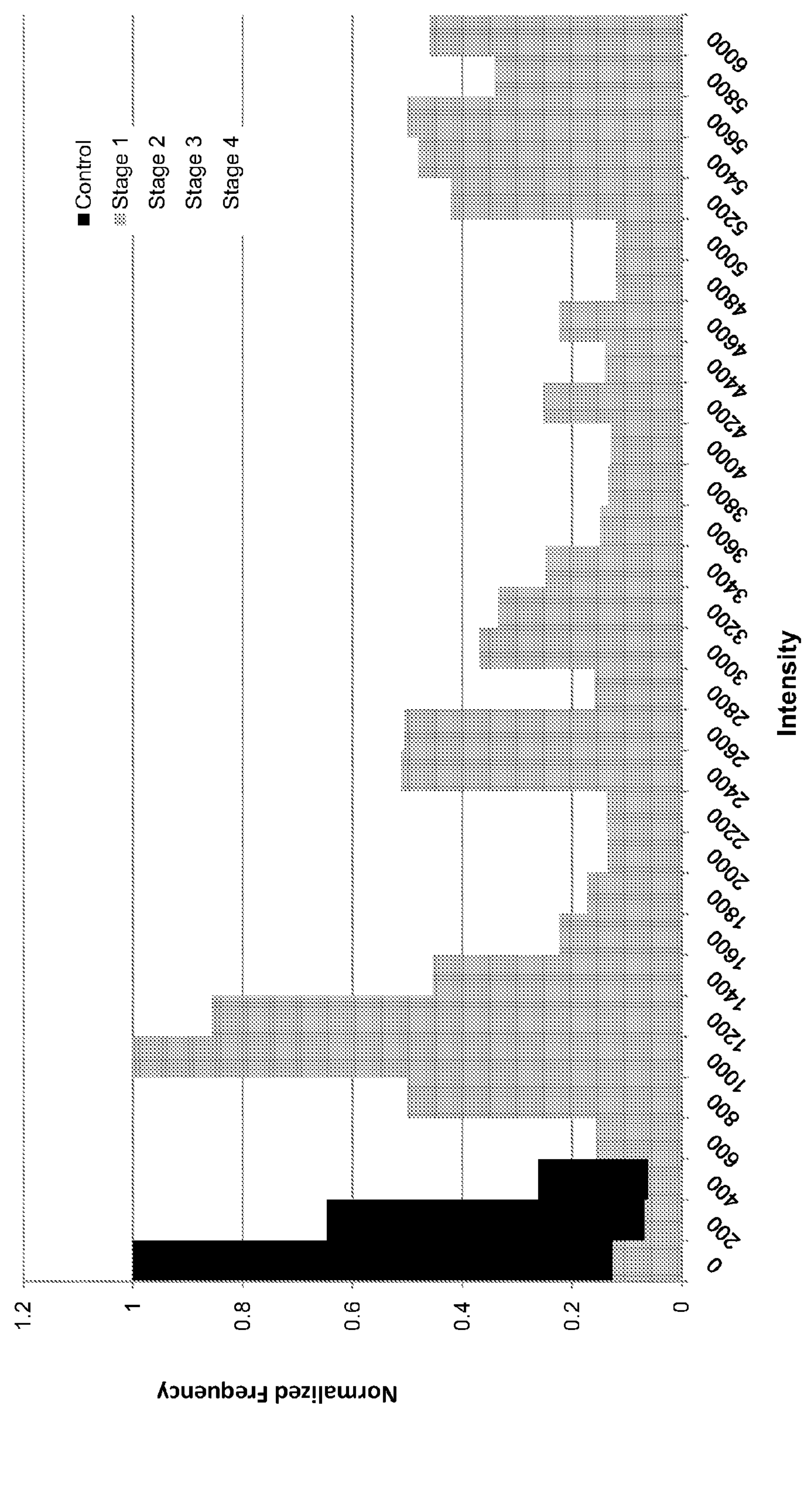
Figure 71C:
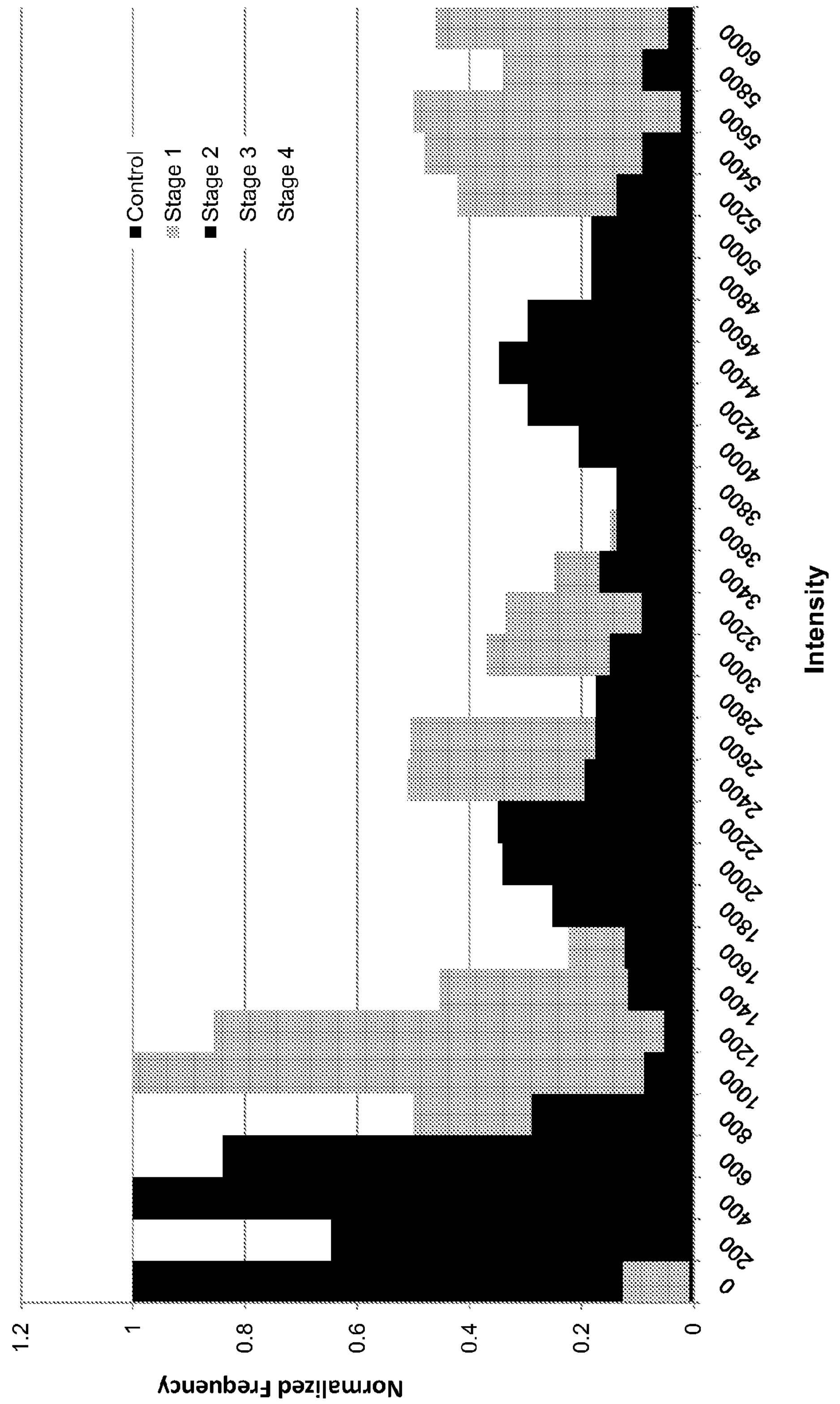
Figure 71D:
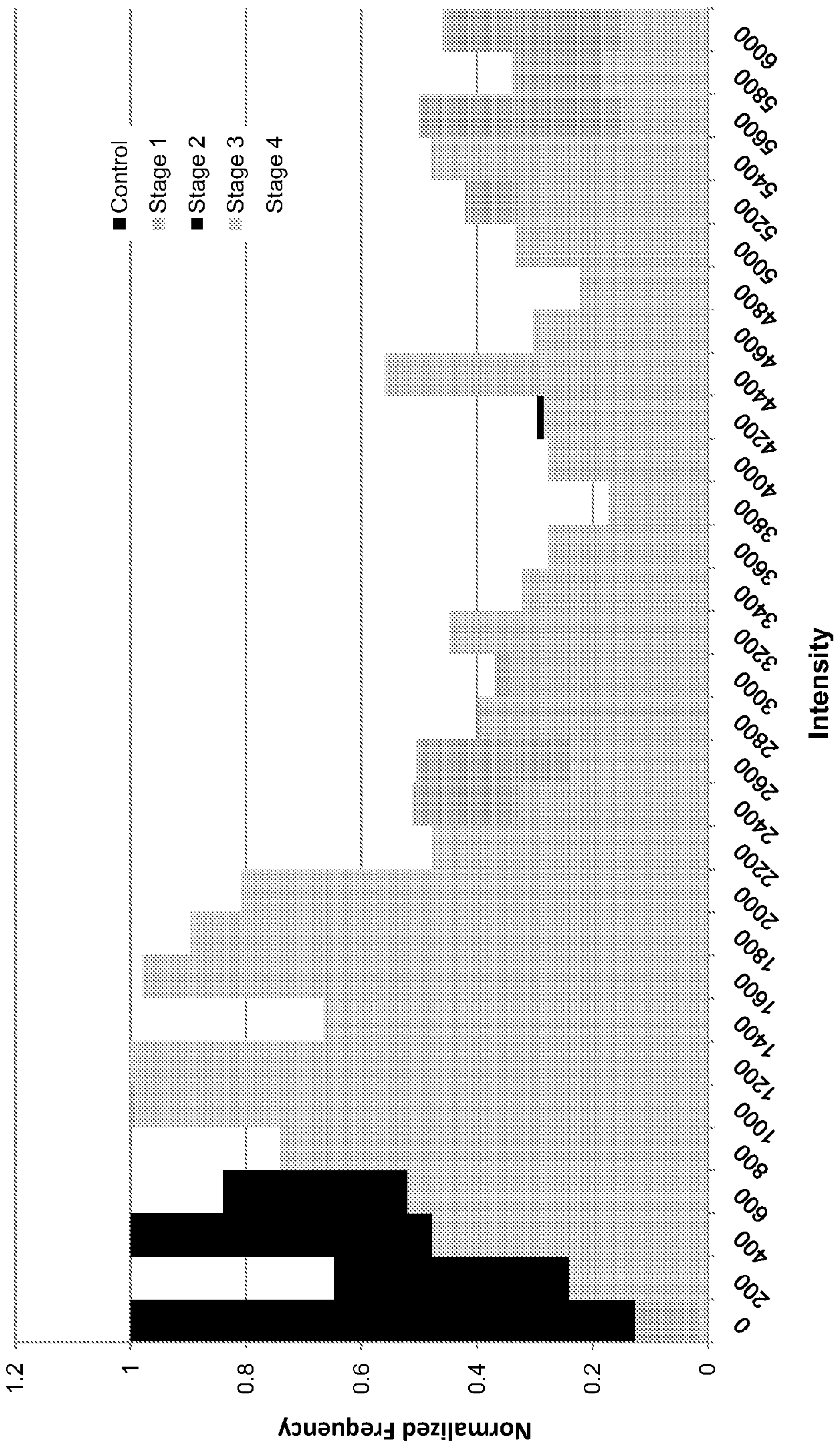
Figure 71E:
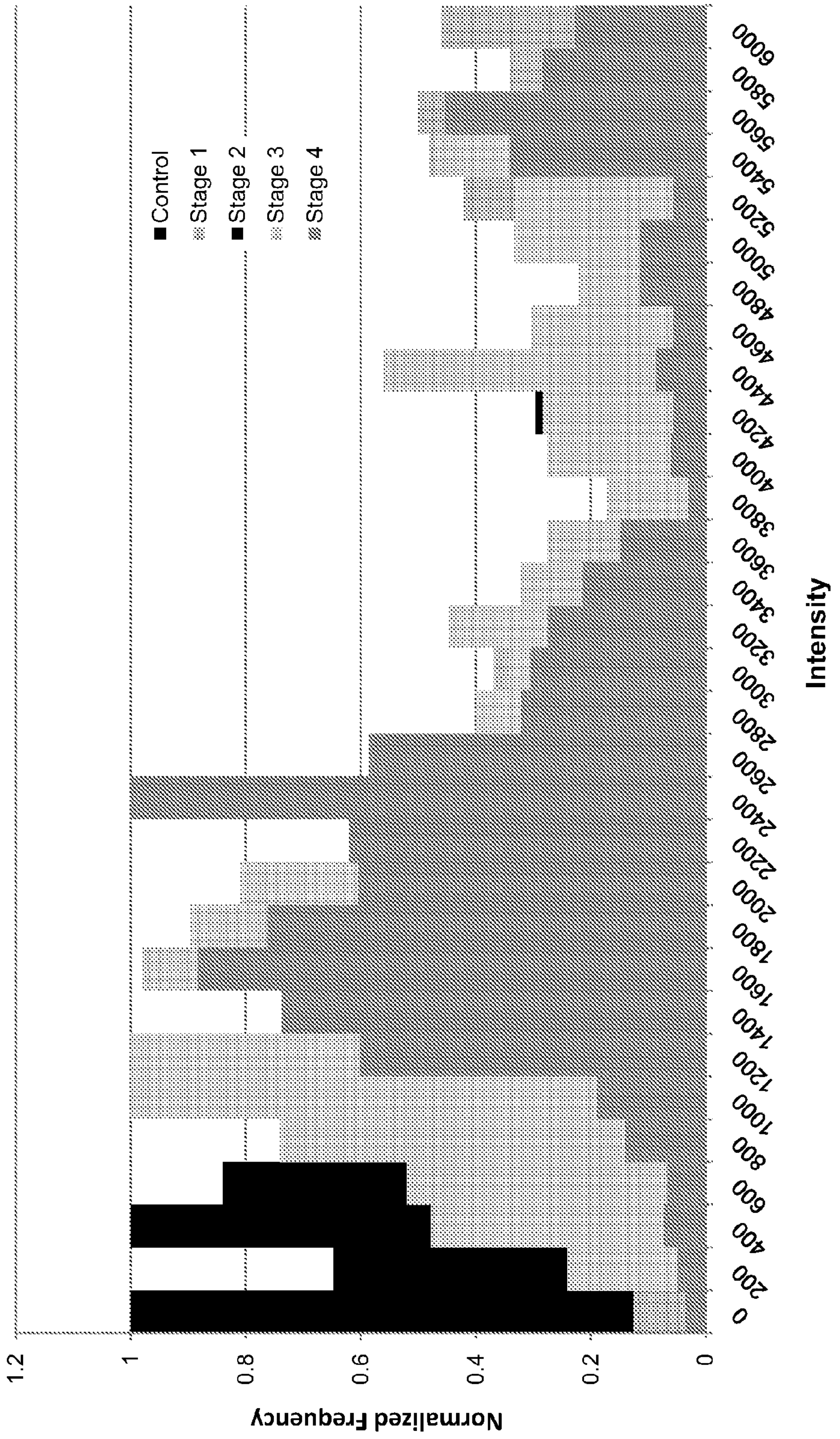
Figure 71F:
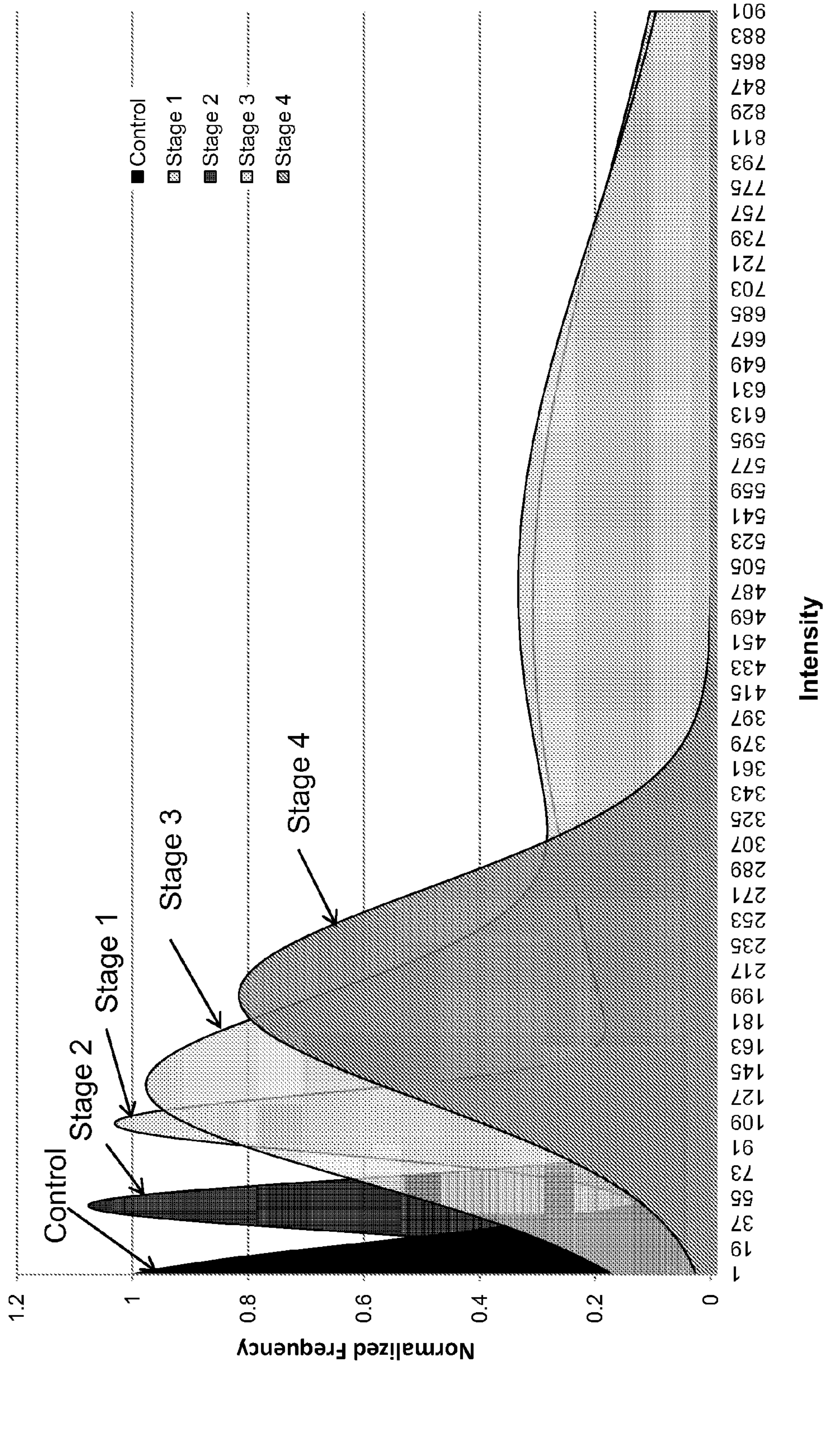
Figure 72A:
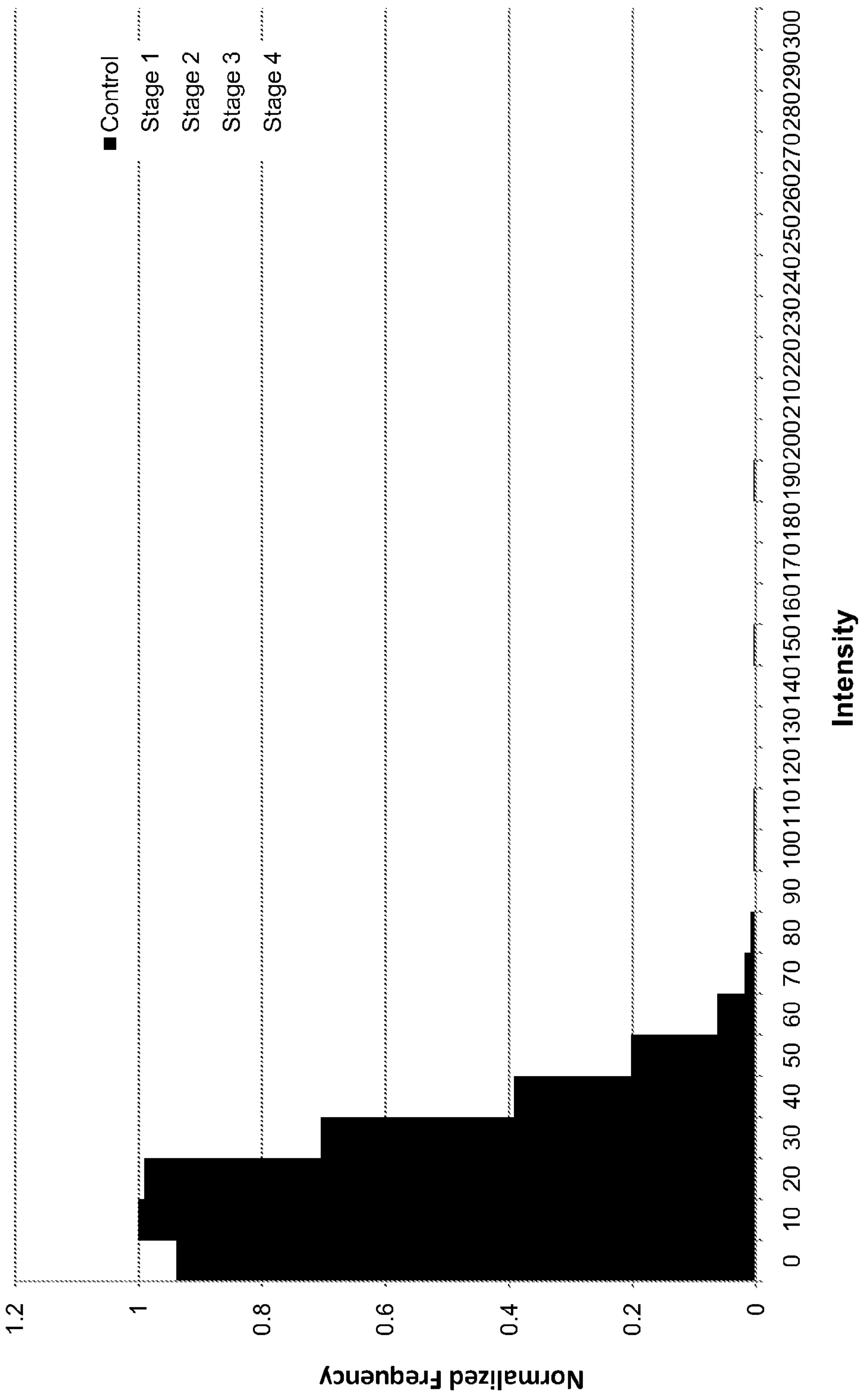
FIG. 72 illustrates colon cancer biosignature for colon cancer by stage, using EpCam detector and CD9 capture. The histograms of intensities are from vesicles captured with CD9 coated beads and labeled with EpCam. There are patients in the (A) control group, (B) stage I, (C) stage II, (D) stage III, and (E) stage IV. Data from each individual was normalized to account for variation in the number of beads detected, added together, and then normalized again to account for the different number of samples in each population (F).
Figure 72B:
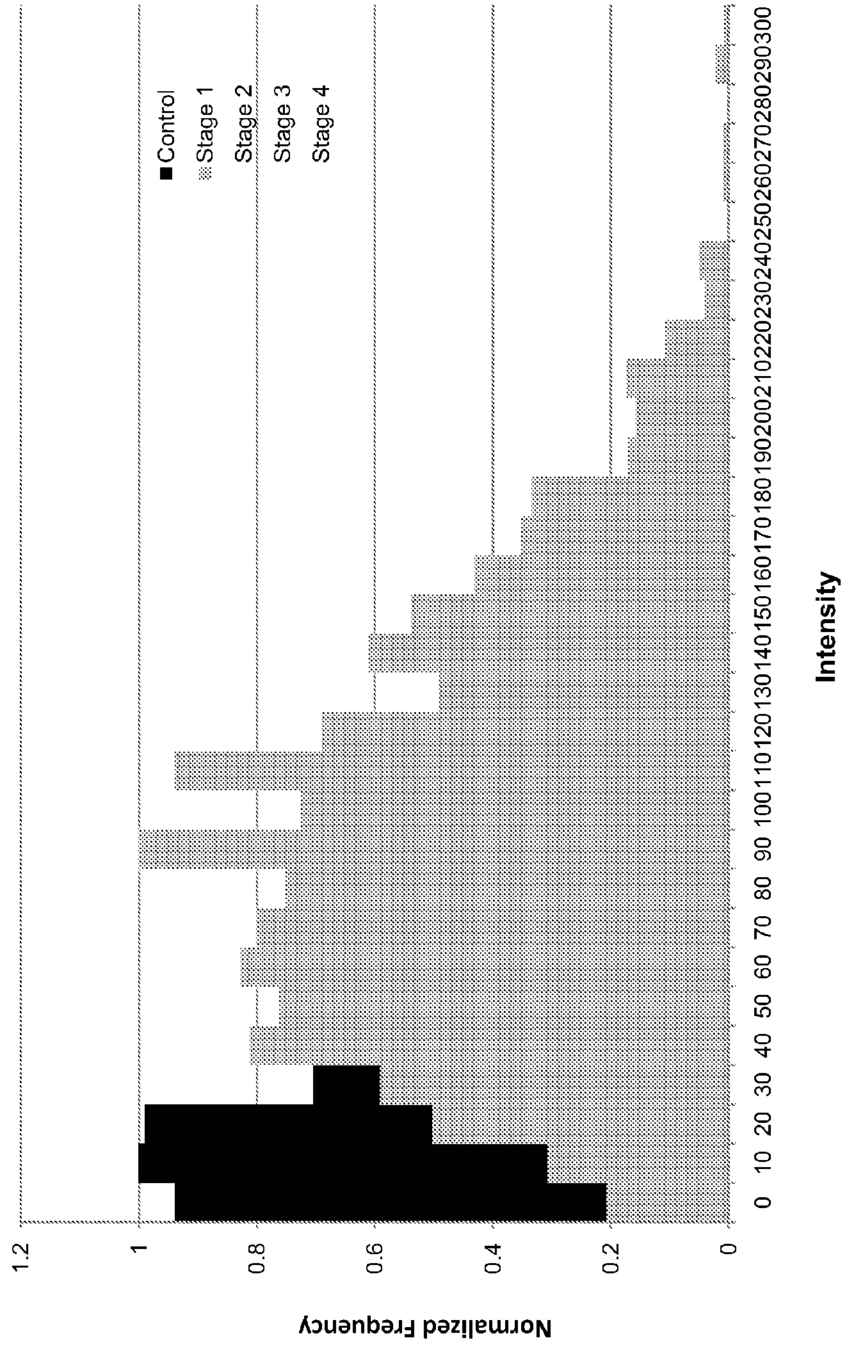
Figure 72C:
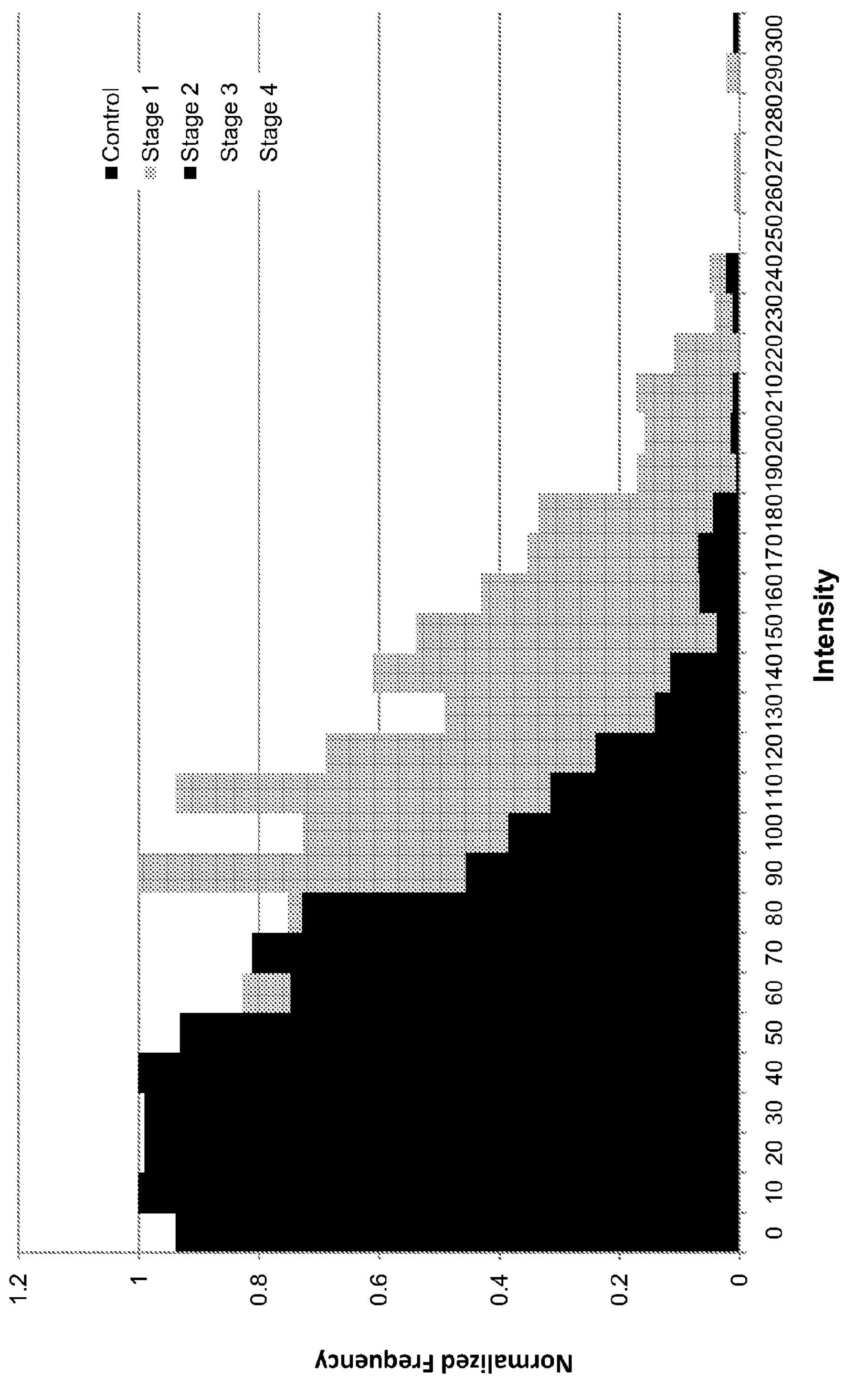
Figure 72D:
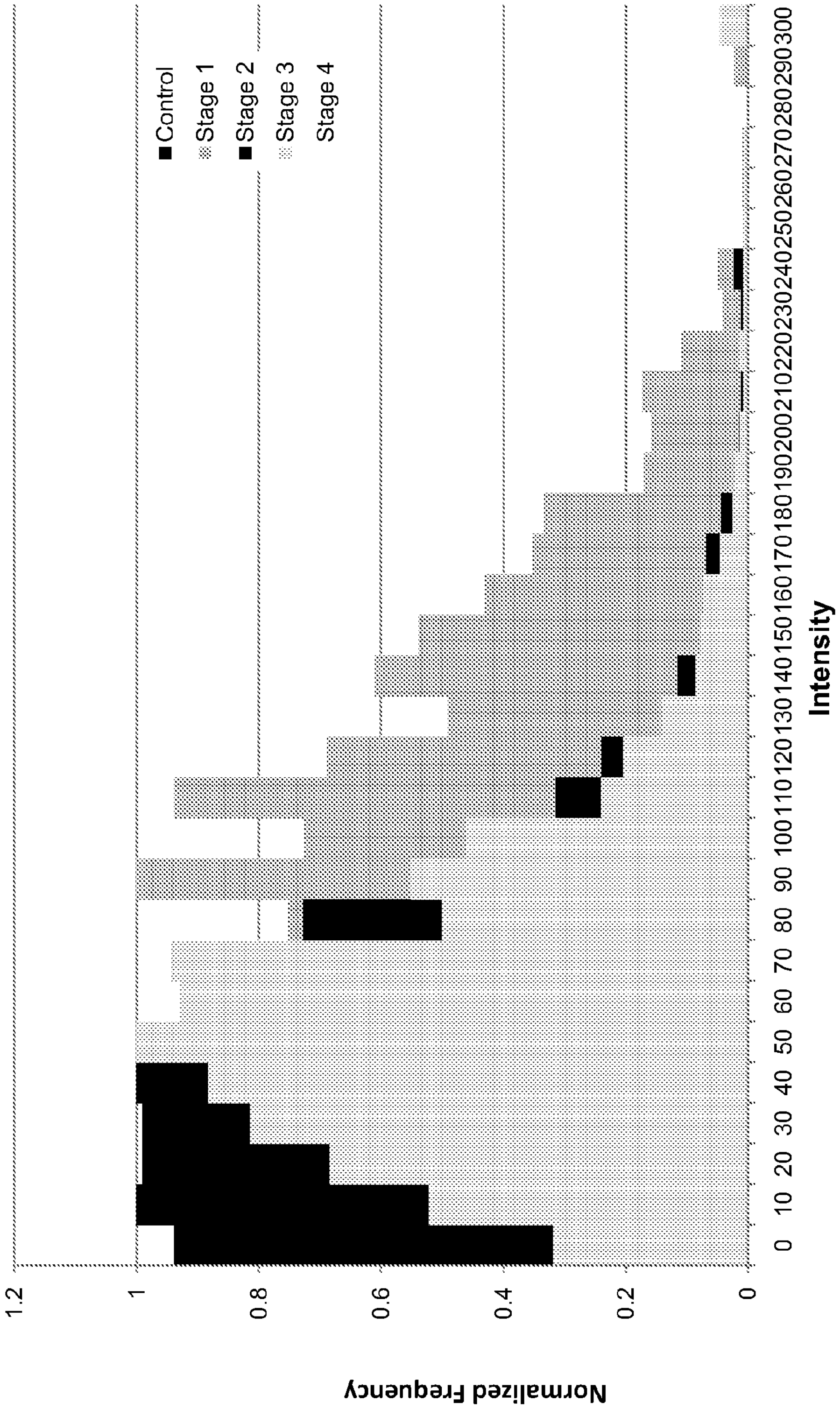
Figure 72E:
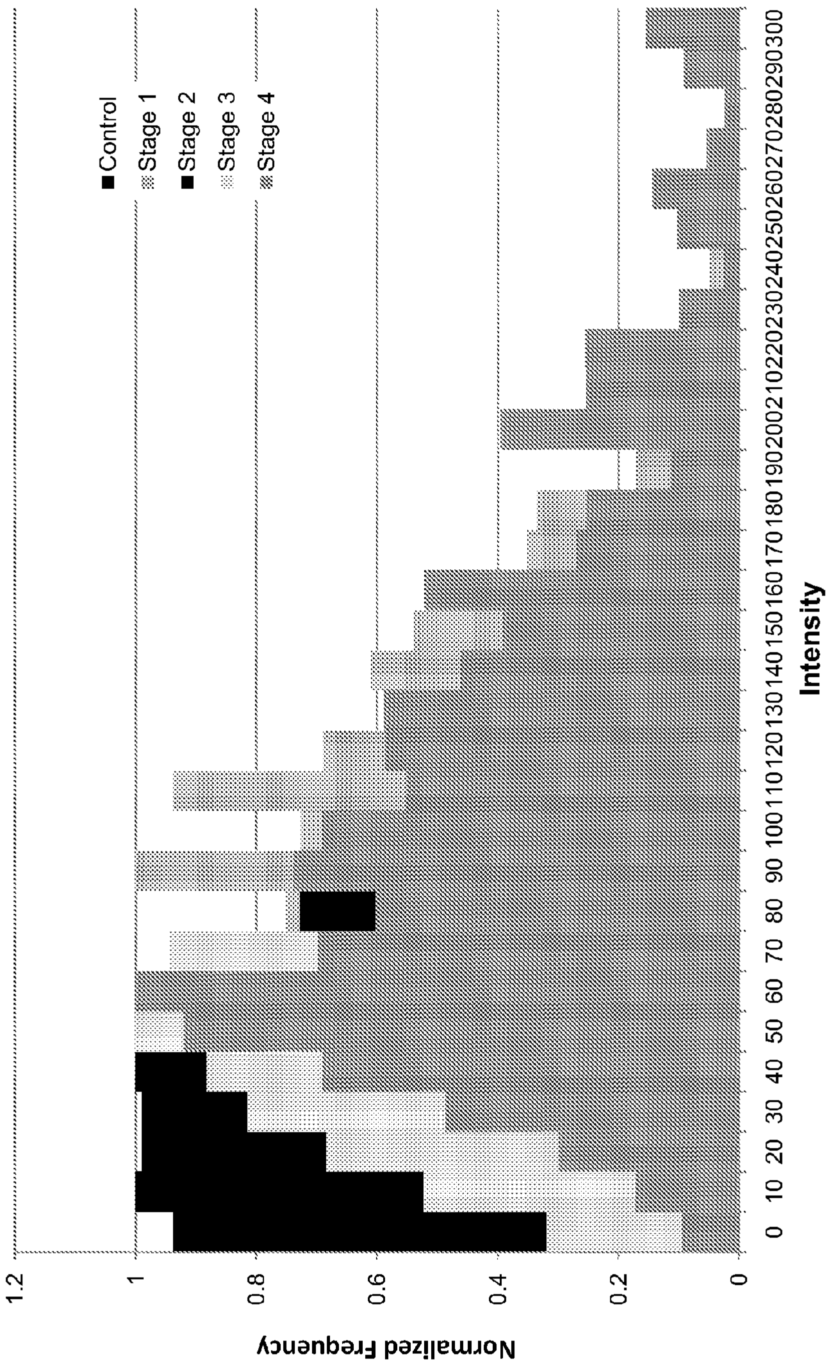
Figure 72F:
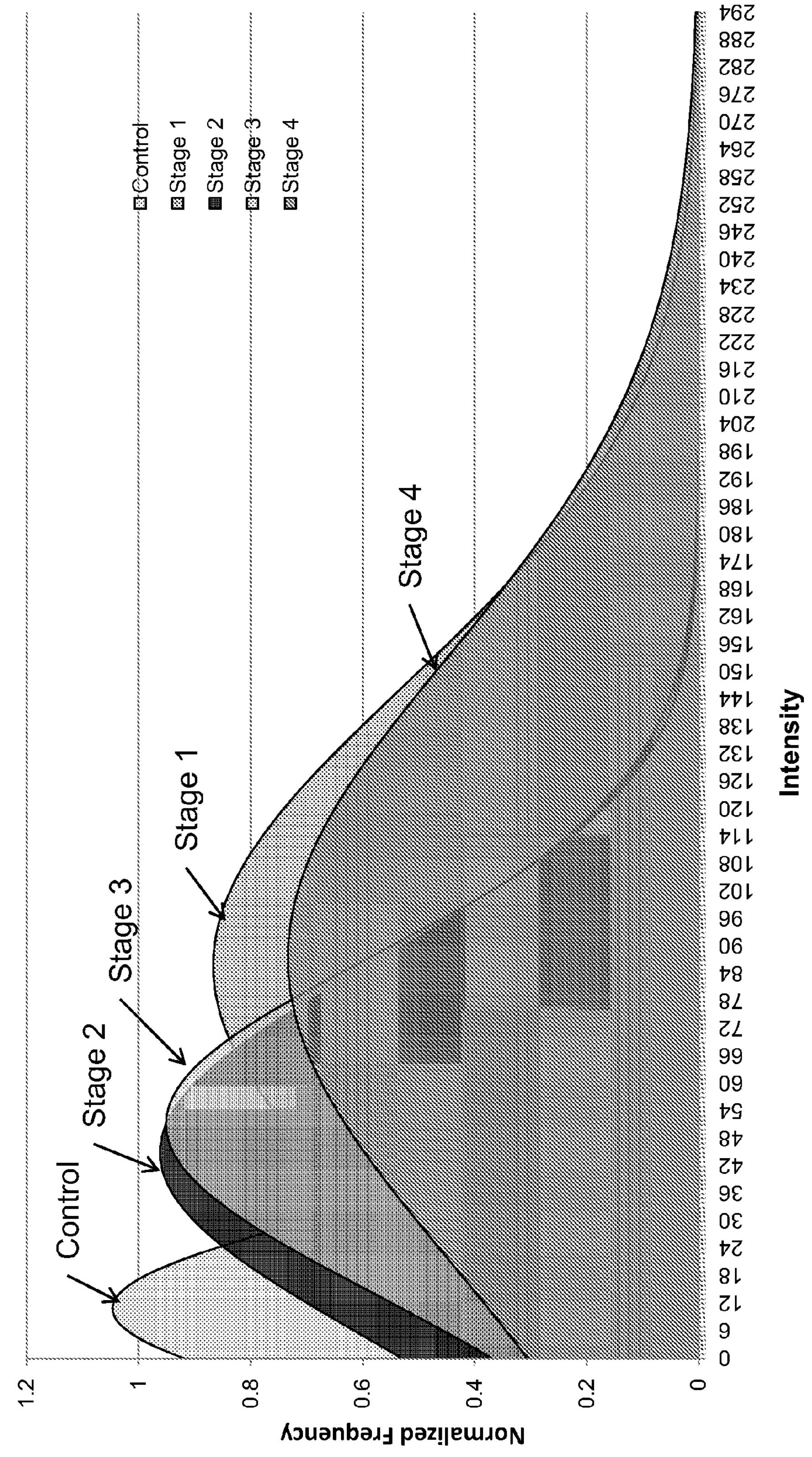

Ten prostate cancer patients and 12 normal control patients were screened. The results are depicted in FIG. 68 and FIG. 70A. FIG. 70B depicts the results of using PCSA capture antibodies (FIG. 70B, left graph) or EpCam capture antibodies (FIG. 70B, right graph), and detection using one or more detector antibodies. The sensitivity and specificity of the different combinations is depicted in FIG. 73.

Example 7

Determining Biosignatures for Colon Cancer Using Multiplexing

The vesicle samples obtained using methods as described in Example 3 is used in multiplexing assays as described in Examples 4 and 5. The detection antibodies used are CD63, CD9, CD81, B7H3 and EpCam. The capture antibodies used are CD9, PSCA, TNFR, CD63 2X, B7H3, MFG-E8, EpCam 2X, CD63, Rab, CD81, STEAP, PCSA, PSMA, 5T4, Rab IgG (control) and IgG (control), resulting in 100 combinations to be screened.

The results are depicted in FIGS. 69, 71, and 72. The sensitivity of the different combinations is depicted in FIG. 74.

Example 8

Capture of Vesicles Using Magnetic Beads

Vesicles isolated as described in Example 2 are used. Approximately 40 ul of the vesicles are incubated with approximately 5 ug (~50 μl) of EpCam antibody coated Dynal beads (Invitrogen, Carlsbad, Calif.) and 501.1.1 of Starting Block. The vesicles and beads are incubated with shaking for 2 hours at 45° C. in a shaking incubator. The tube containing the Dynal beads is placed on the magnetic separator for 1 minute and the supernatant removed. The beads are washed twice and the supernatant removed each time. Wash beads twice, discarding the supernatant each time.

Example 9

Detection of TMPRSS2:ERG in Vesicles

The RNA from the bead-bound vesicles of Example 9 was isolated using the Qiagen miRneasy™ kit, (Cat. No. 217061), according to the manufacturer's intsructions.

The vesicles are homogenized using a trizol extraction methodology (QIAzol™ Lysis Reagent (Cat. No. 79306)). After addition of chloroform, the homogenate is separated into aqueous and organic phases by centrifugation. RNA partitions to the upper, aqueous phase, while DNA partitions to the interphase and proteins to the lower, organic phase or the interphase. The upper, aqueous phase is extracted, and ethanol is added to provide appropriate binding conditions for all RNA molecules from 18 nucleotides (nt) upwards. The sample is then applied to the RNeasy™ Mini spin column, where the total RNA binds to the membrane and phenol and other contaminants are efficiently washed away. High quality RNA is then eluted in RNase-free water.

RNA from the VCAP bead captured vesicles was measured with the Taqman TMPRSS:ERG fusion transcript assay (Kirsten D. Mertz et al. *Neoplasia*. 2007 March; 9(3): 200-206.). RNA from the 22Rv1 bead captured vesicles was measured with the Taqman SPINK1 transcript assay (Scott A. Tomlins et al. *Cancer Cell* 2008 June 13(6):519-528). The GAPDH transcript (control transcript) was also measured for both sets of exosomal RNA.

Figure 75A:
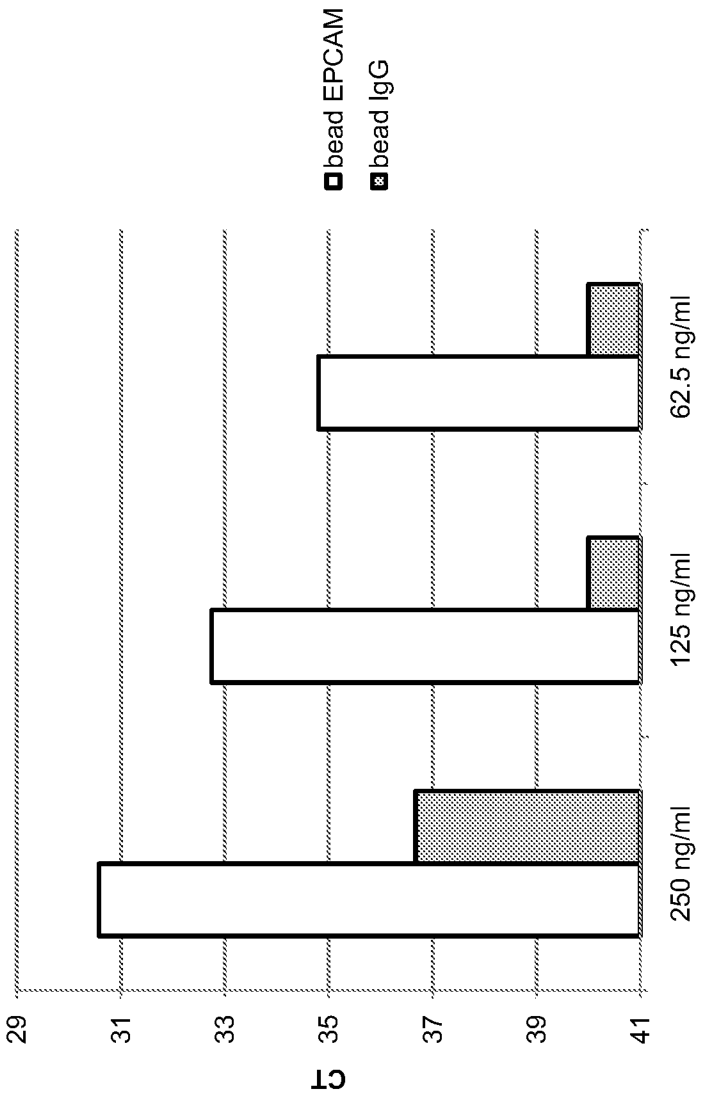
FIG. 75 illustrates the capture of prostate cancer cells-derived vesicles from plasma with EpCam by assessing TMPRSS2-ERG expression. (A) Graduated amounts of VCAP purified vesicles were spiked into normal plasma. Vesicles were isolated using Dynal beads with either EPCAM antibody or its isotype control. RNA from the vesicles was isolated and the expression of the TMPRSS2:ERG fusion transcript was measured using qRT-PCR. (B) VCaP purified vesicles were spiked into normal plasma and then incubated with Dynal magnetic beads coated with either the EpCam or isotype control antibody. RNA was isolated directly from the Dynal beads. Equal volumes of RNA from each sample were used for RT-PCR and subsequent Taqman assays. (C) Cycle threshold (CT) differences of the SPINK1 and GAPDH transcripts between 22RV1 vesicles captured with EpCam and IgG2 isotype negative control beads. Higher CT values indicate lower transcript expression.
Figure 75B:
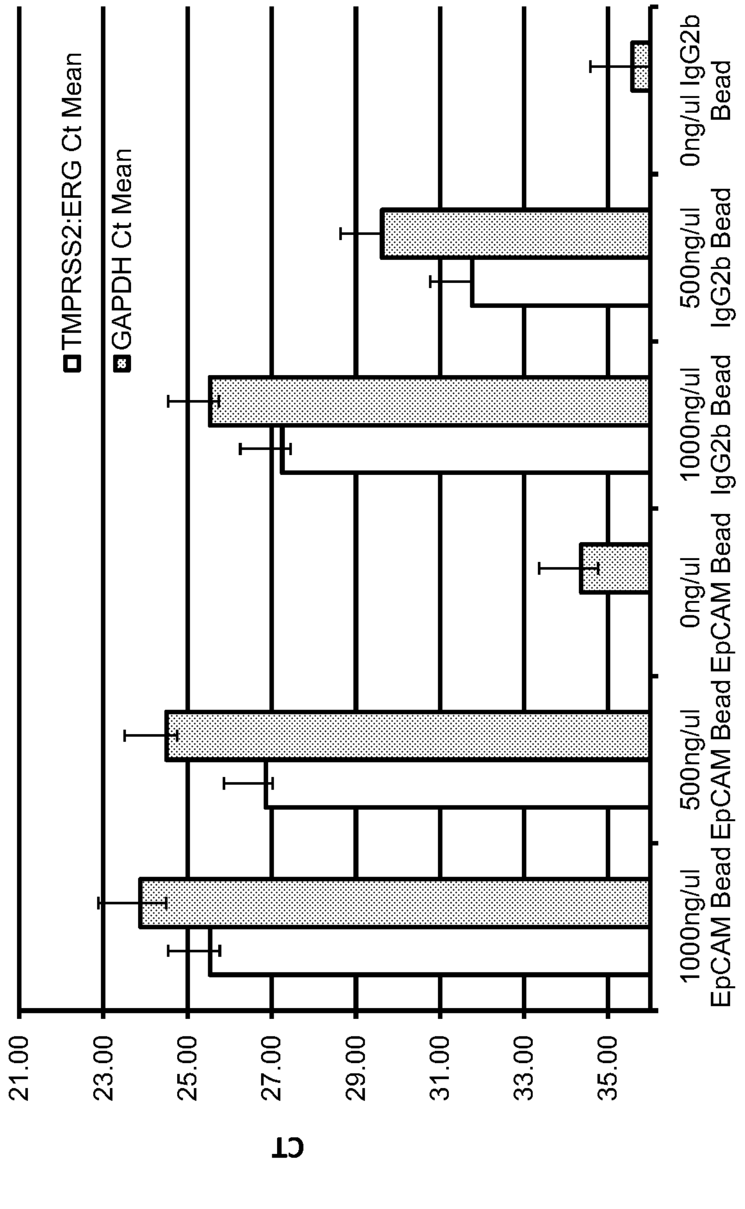
Figure 75C:
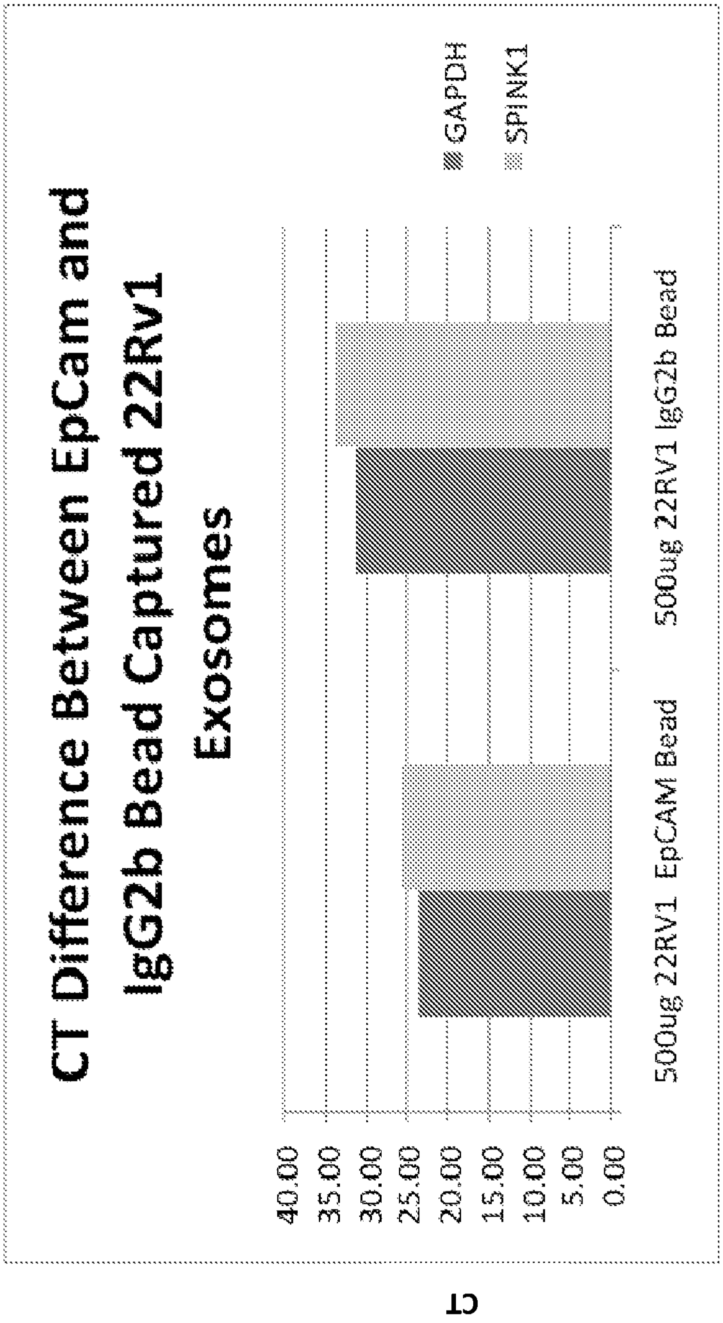

Higher CT values indicate lower transcript expression. One change in cycle threshold (CT) is equivalent to a 2 fold change, 3 CT difference to a 4 fold change, and so forth, which can be calculated with the following: $2^{\wedge CT1-CT}2$. This experiment shows a difference in CT of the expression of the fusion transcript TMPRSS:ERG and the equivalent captured with the IgG2 negative control bead (FIG. 75). The same comparison of the SPINK1 transcript in 22RV1 vesicles shows a CT difference of 6.14 for a fold change of 70.5 (FIG. 75C).

Example 10

MicroRNA Profiles in Vesicles

Vesicles were collected by ultracentrifugation from 22Rv1, LNCaP, Vcap and normal plasma (pooled from 16 donors) as described in Examples 1 and 2. RNA was extracted using the Exiqon miR isolation kit (Cat. No. 300110, 300111). Equals amounts of vesicles (30 μg) were used as determined by BCA assay.

Figure 76A:
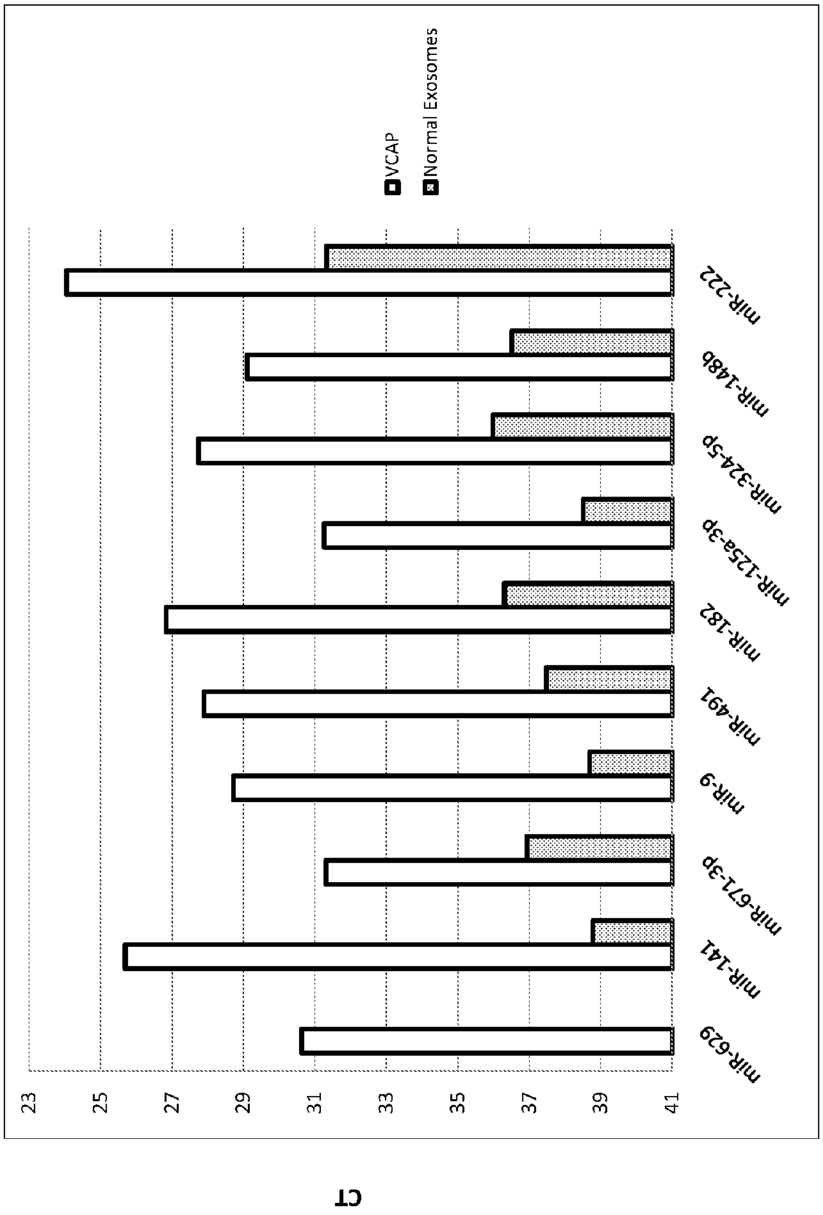
FIG. 76 illustrates the top ten differentially expressed microRNAs between VCaP prostate cancer cell derived vesicles and normal plasma vesicles. VCAP cell line vesicles and vesicles from normal plasma were isolated via ultracentrifugation followed by RNA isolation. MicroRNAs were profiled using qRT-PCR analysis. Prostate cancer cell line derived vesicles have higher levels (lower CT values) of the indicated microRNAs as depicted in the bar graph (A) and table (B).

Equal volumes (5 μl) were put into a reverse-transcription reaction for microRNA. The reverse-transcriptase reactions were diluted in 81 μl of nuclease-free water and then 9 μl of this solution was added to each individual miR assay. MiR-629 was found to only be expressed in PCa (prostate cancer) vesicles and was virtually undetectable in normal plasma vesicles. MiR-9 was found to be highly overexpressed (~704 fold increase over normal as measured by copy number) in all PCa cell lines, and has very low expression in normal plasma vesicles. The top ten differentially expressed miRNAs are depicted in FIG. 76.

Example 11

MicroRNA Profiles of Magentic EpCam-Captured Vesicles

The bead-bound vesicles of Example 9 were placed in the trizol extraction reagent (QIAzol™ Lysis Reagent (Cat. #79306)). An aliquot of 125 fmol of c. *elegans* miR-39 was added. The RNA was isolated using the Qiagen miRneasy™ kit, (Cat. #217061), according to the manufacturer's intsructions, and eluted in 30 ul RNAse free water.

10 μl of the purified RNA was placed into a pre-amplifiation reaction for miR-9, miR-141 and miR-629 using a Veriti 96-well thermocycler. A 1:5 dilution of the pre-amplification solution was used to set up a qRT-PCR reaction for miR9 (ABI 4373285), miR-141 (ABI 4373137) and miR-629 (ABI 4380969) as well as *c. elegans* miR-39 (ABI 4373455). The results were normalized to the *c. elegans* results for each sample.

Example 12

MicroRNA Profiles of CD9-Captured Vesicles

Figure 77:
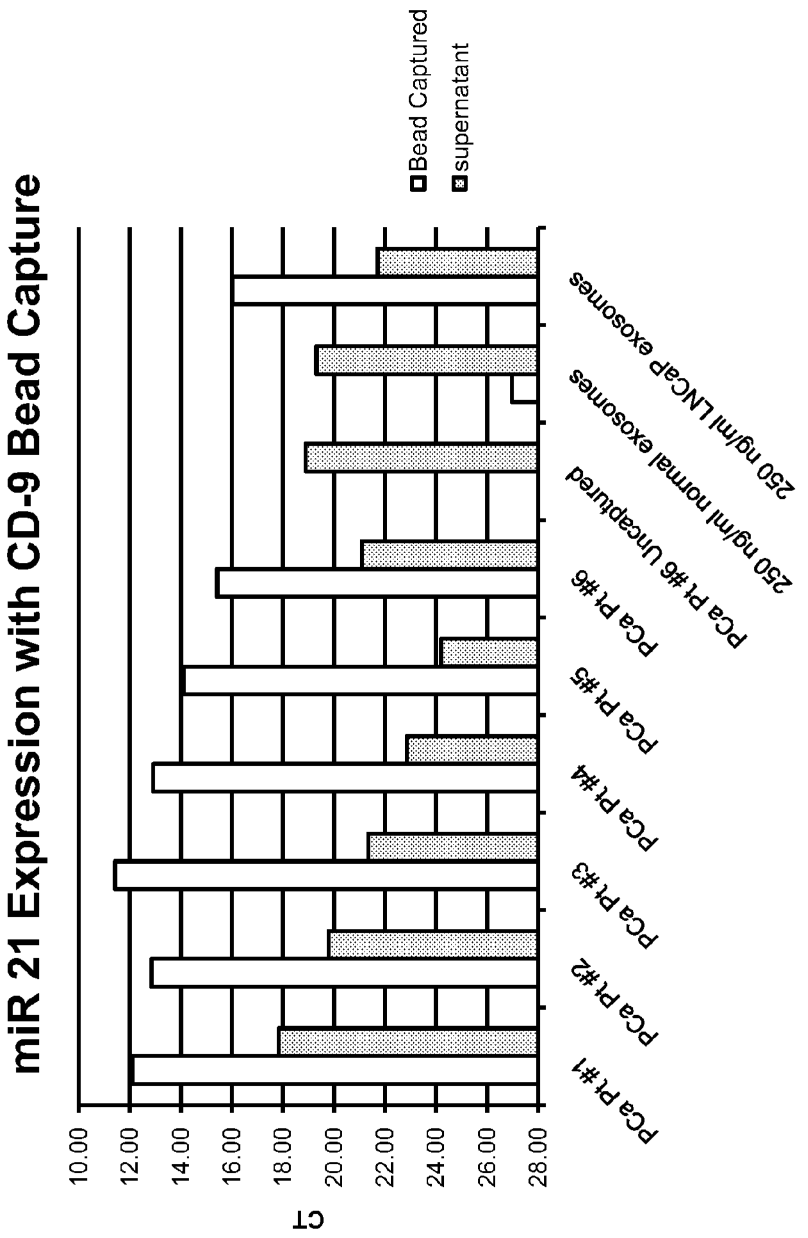
FIG. 77 depicts a bar graph of miR-21 expression with CD9 bead capture. 1 ml of plasma from prostate cancer patients, 250 ng/ml of LNCaP, or normal purified vesicles were incubated with CD9 coated Dynal beads. The RNA was isolated from the beads and the bead supernatant. One sample (#6) was also uncaptured for comparison. MiR-21 expression was measured with qRT-PCR and the mean CT values for each sample compared. CD9 capture improves the detection of miR-21 in prostate cancer samples.
Figure 78:
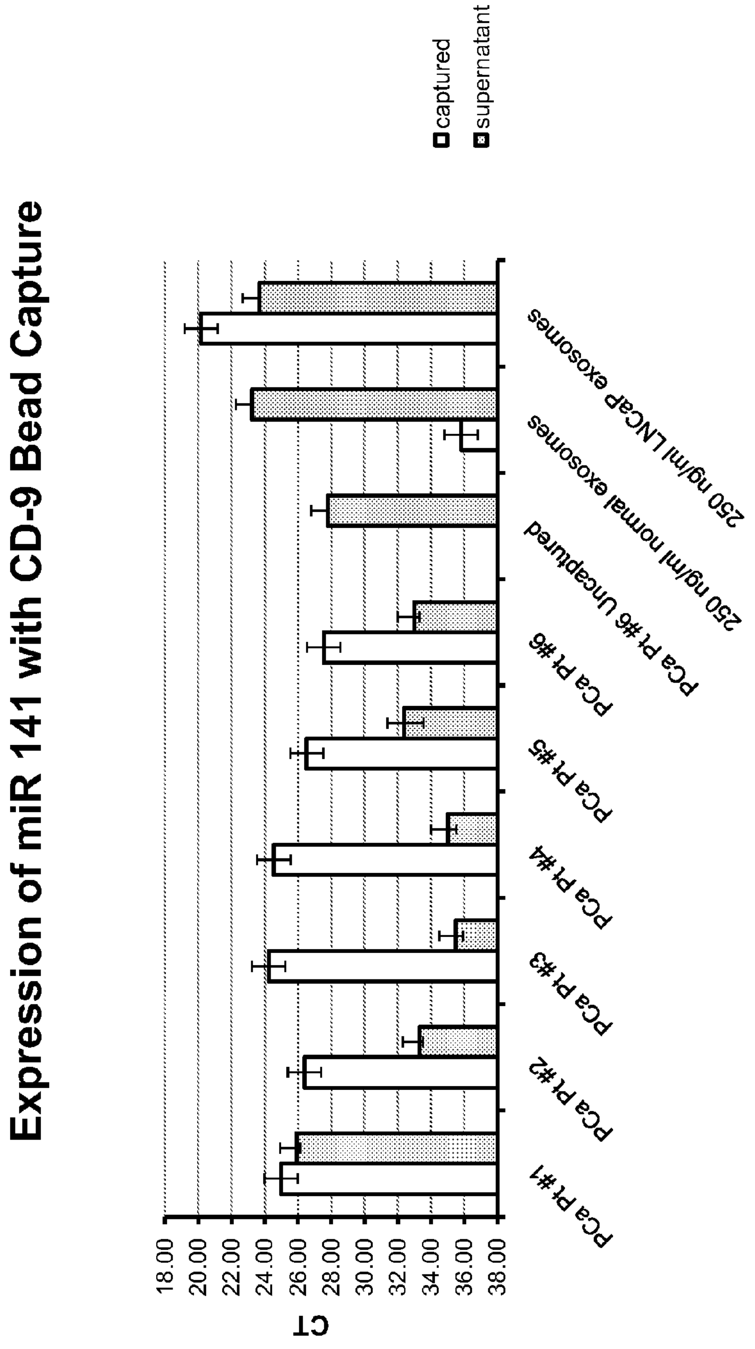
FIG. 78 depicts a bar graph of miR-141 expression with CD9 bead capture. The experiment was performed as in FIG. 77, with miR-141 expression measured with qRT-PCR instead of miR-21.

The CD9 coated Dynal beads (Invitrogen, Carlsbad, Calif.) were used instead of EpCam coated beads as in Example 12. Vesicles from prostate cancer patients, LNCaP, or normal purified exomes were incubated with the CD9 coated beads and the RNA isolated as described in Example 12. The expression of miR-21 and miR-141 was detected by qRT-PCR and the results depicted in FIGS. 77 and 78.

Example 13

Reference Values for Prostate Cancer

Fourteen stage 3 prostate cancer subjects, eleven benign prostate hyperplasia (BPH) samples, and 15 normal samples were tested. Vesicle samples were obtained using methods as described in Example 3 and used in multiplexing assays, such as described in Examples 4 and 5. The samples were analyzed to determine four criteria 1) if the sample has overexpressed vesicles, 2) if the sample has overexpressed prostate vesicles, 3) if the sample has overexpressed cancer vesicles, and 4) if the sample is reliable. If the sample met all four criteria, the categorization of the sample as positive for prostate cancer had varying sensitivities and specificities, depending on the different biosignatures present for a sample as described below (Cancer-1, Cancer-2, and Cancer-3, FIG. 79). The four criteria were as follows:

Vesicle Overexpression

The mean fluorescence intensities (MFIs) for a sample in three assays were averaged to determine a value for the sample. Each assay used a different capture antibody. The first used a CD9 capture antibody, the second a CD81 capture antibody, and the third a CD63 antibody. The same combination of detection antibodies was used for each assay, antibodies for CD9, CD81, and CD63. If the average value obtained for the three assays was greater than 3000, the sample was categorized as having overexpressed vesicles (FIG. 79, Exosome).

Prostate Vesicle Overexpression

The MFIs for a sample in two assays were averaged to determine a value for the sample.

Each assay used a different capture antibody. The first used a PCSA capture antibody and the second used a PSMA capture antibody. The same combination of detection antibodies was used for each assay, antibodies for CD9, CD81, and CD63. If the average value obtained for the two assays was greater than 100, the sample was categorized as having prostate vesicles overexpressed (FIG. 79, Prostate).

Cancer Vesicle Overexpression

Three different cancer biosignatures were used to determine if cancer vesicles were overexpressed in a sample. The first, Cancer-1, used an EpCam capture antibody and detection antibodies for CD81, CD9, and CD63. The second, Cancer-2, used a CD9 capture antibody with detection antibodies for EpCam and B7H3. If the MFI value of a sample for any two of the three cancer biosignatures was above a reference value, the sample was categorized as having overexpressed cancer (see FIG. 79, Cancer-1, Cancer-2, Cancer-3).

Reliability of Sample

Two quality control measures, QC-1 and QC-2, were determined for each sample. If the sample met one of them, the sample was categorized as reliable.

For QC-1, the sum of all the MFIs of 7 assays was determined. Each of the 7 assays used detection antibodies for CD59 and PSMA. The capture antibody used for each assay was CD63, CD81, PCSA, PSMA, STEAP, B7H3, and EpCam. If the sum was greater than 4000, the sample was not reliable and not included.

For QC-2, the sum of all the MFIs of 5 assays was determined. Each of the 5 assays used detection antibodies for CD9, CD81 and CD63. The capture antibody used for each assay was PCSA, PSMA, STEAP, B7H3, and EpCam. If the sum was greater than 8000, the sample was not reliable and not included.

The sensitivity and specificity for samples with BPH and without BPH samples after a sample met the criteria as described herein, are shown in FIG. 79.

Example 14

MicroRNA Overexpression in Colorectal Cancer Cell Lines

TaqMan Low Density Array (TLDA) miRNA cards were used to compare expression of miRNA in CRC cell lines versus normal vesicles. The miRNA was collected and analyzed using the TaqMan® MicroRNA Assays and Arrays systems from Applied Biosystems, Foster City, Calif. Applied Biosystems TaqMan® Human MicroRNA Arrays were used according to the Megaplex™ Pools Quick Reference Card protocol supplied by the manufacturer.

FIG. 80 illustrates TLDA miRNA card comparison of colorectal cancer (CRC) cell lines versus normal vesicles. The plot shows a 2-3 fold increase in expression in the CRC cell lines compared to normal controls. These miRNAs were not overexpressed in melanoma cells.

Example 15

Isolation of Vesicles Using a Filtration Module

Six mL of PBS is added to 1 mL of plasma. The sample is then put through a 1.2 micron (μm) Pall syringe filter directly into a 100 kDa MWCO (Millipore, Billerica, Mass.), 7 ml column with a 150 kDa MWCO (Pierce®, Rockford, Ill.), 15 ml column with a 100 kDa MWCO (Millipore, Billerica, Mass.), or 20 ml column with a 150 kDa MWCO (Pierce®, Rockford, Ill.).

The tube is centrifuged for between 60 to 90 minutes until the volume is about 250 μl. The retentate is collected and PBC added to bring htes ample up to 300 μl. Fifty ul of the sample is then used for further analysis, such as further described in the examples below.

Example 16

Multiplex Analysis of Vesicles Isolated with Filters

Figure 87:
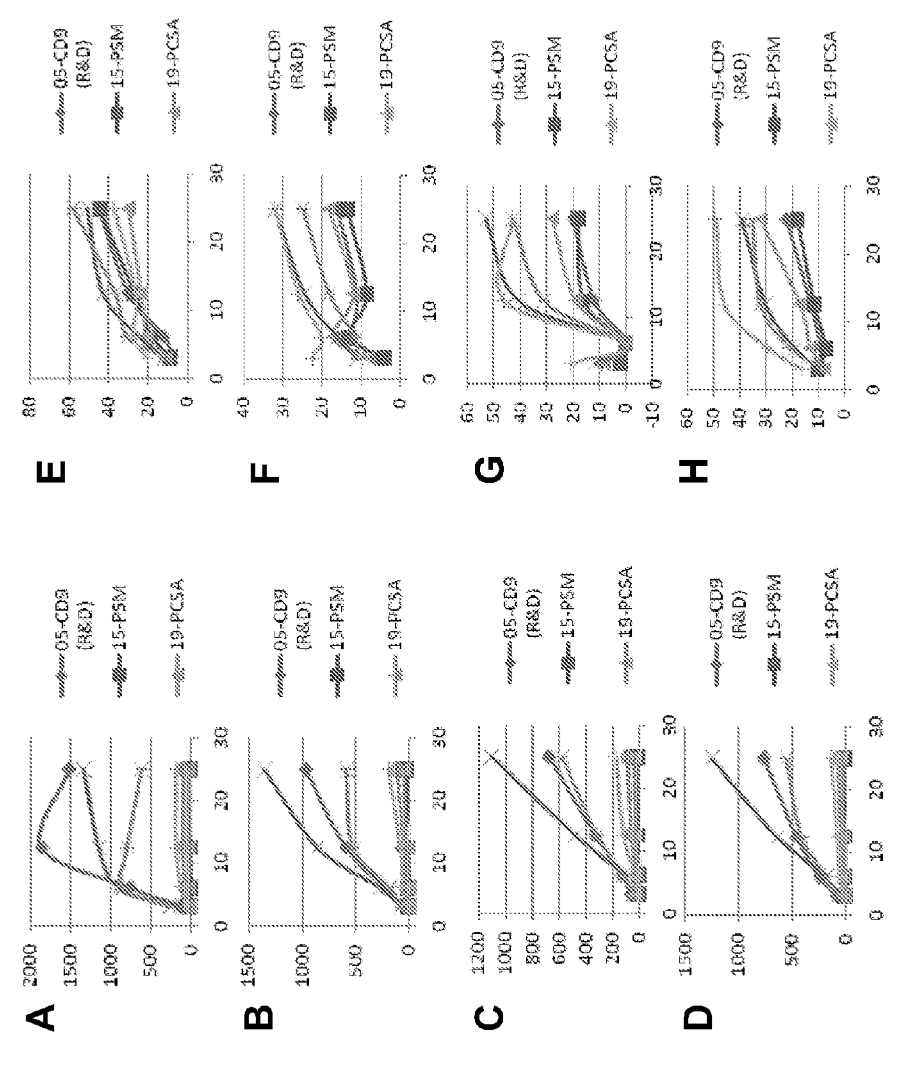
FIG. 87 represents graphs showing detection of biomarkers CD9, CD81, and CD63 (A-D) or B7H3 and EpCam (E-H) with captures agents for CD9, CD63, CD81, PSMA, PCSA, B7H3, and EpCam for vesicles isolated from a sample (#126) using a 500 μl column with a 100 kDa MWCO (Millipore, Billerica, Mass.) (A, E), 7 ml column with a 150 kDa MWCO (Pierce®, Rockford, Ill.) (B, F), 15 ml column with a 100 kDa MWCO (Millipore, Billerica, Mass.) (C, G), or 20 ml column with a 150 kDa MWCO (Pierce®, Rockford, Ill.) (D, H).
Figure 88:
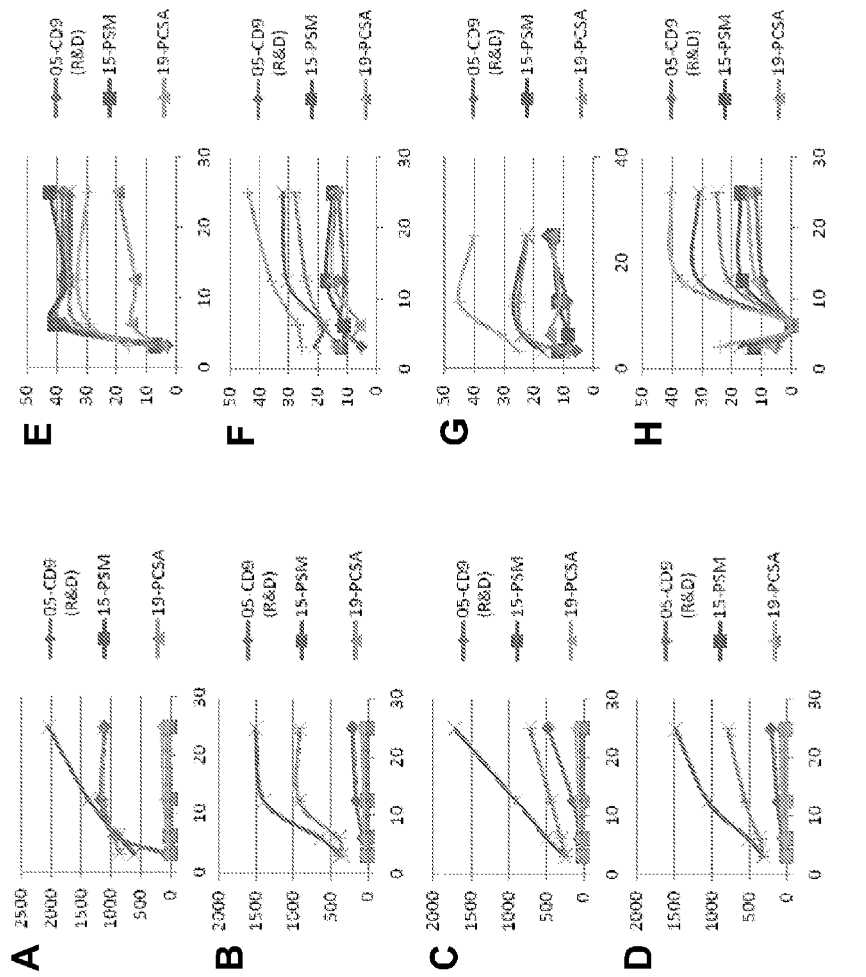
FIG. 88 represents graphs showing detection of biomarkers CD9, CD81, and CD63 (A-D) or B7H3 and EpCam (E-H) with captures agents for CD9, CD63, CD81, PSMA, PCSA, B7H3, and EpCam for vesicles isolated from a sample (#342) using a 500 μl column with a 100 kDa MWCO (Millipore, Billerica, Mass.) (A, E), 7 ml column with a 150 kDa MWCO (Pierce®, Rockford, Ill.) (B, F), 15 ml column with a 100 kDa MWCO (Millipore, Billerica, Mass.) (C, G), or 20 ml column with a 150 kDa MWCO (Pierce®, Rockford, Ill.) (D, H).
Figure 89A:
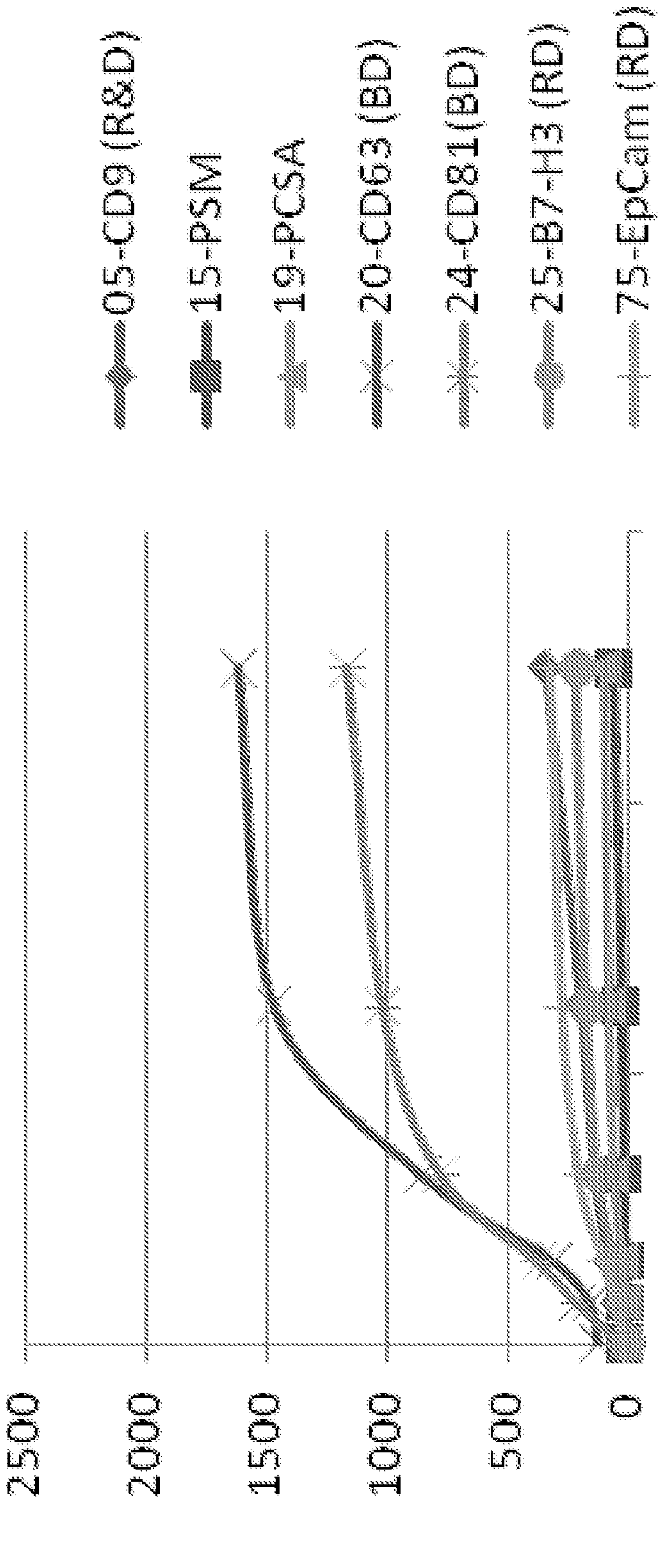
FIG. 89A-F represents graphs showing detection of biomarkers CD9, CD81, and CD63 of vesicles with captures agents for CD9, CD63, CD81, PSMA, PCSA, B7H3, and EpCam from a sample (#126) (A-C) versus another sample (#117) (D-F) using a 7 ml column with a 150 kDa MWCO (Pierce®, Rockford, Ill.) (A, D), 15 ml column with a 100 kDa MWCO (Millipore, Billerica, Mass.) (B, E), or 20 ml column with a 150 kDa MWCO (Pierce®, Rockford, Ill.) (C, F).
Figure 89B:
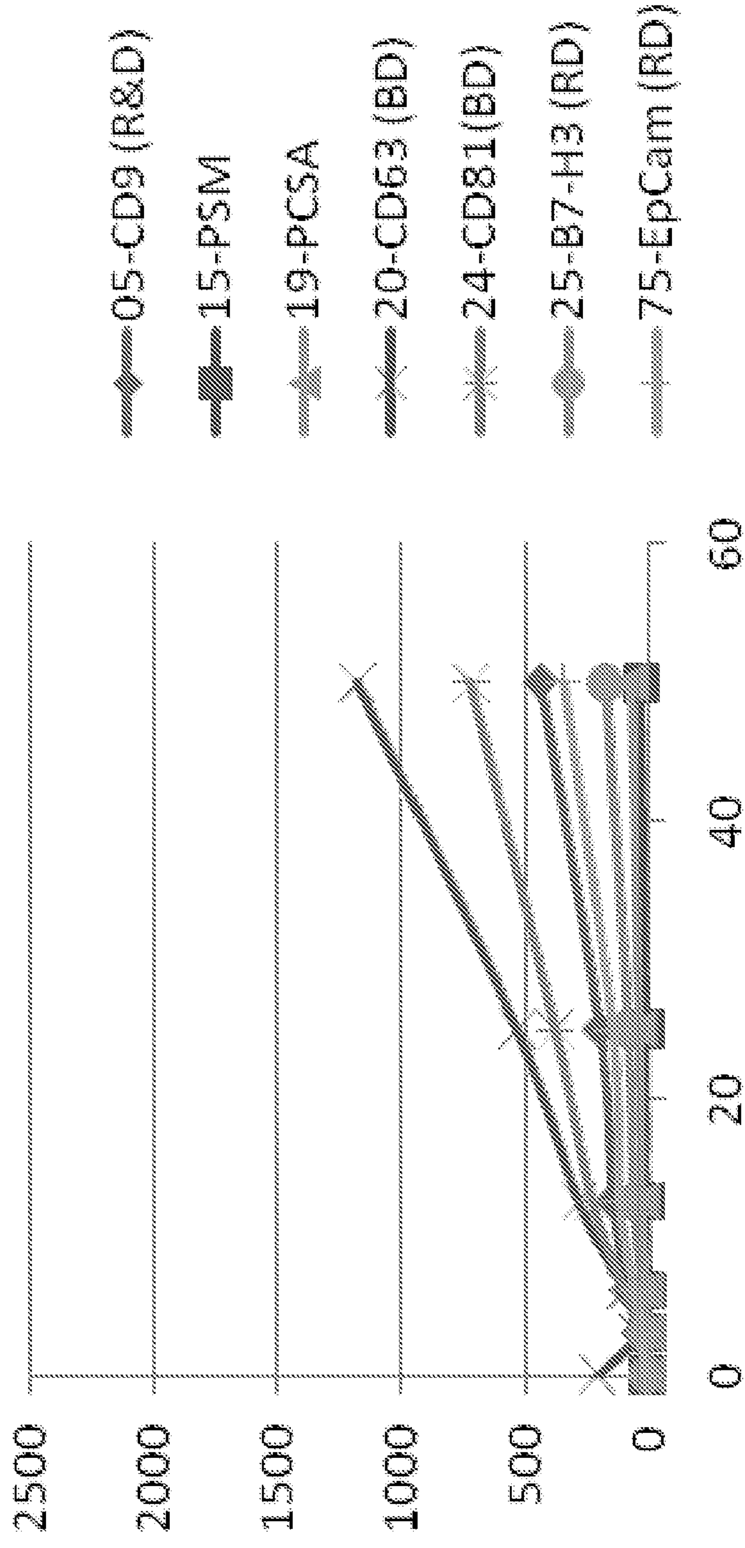
Figure 89C:
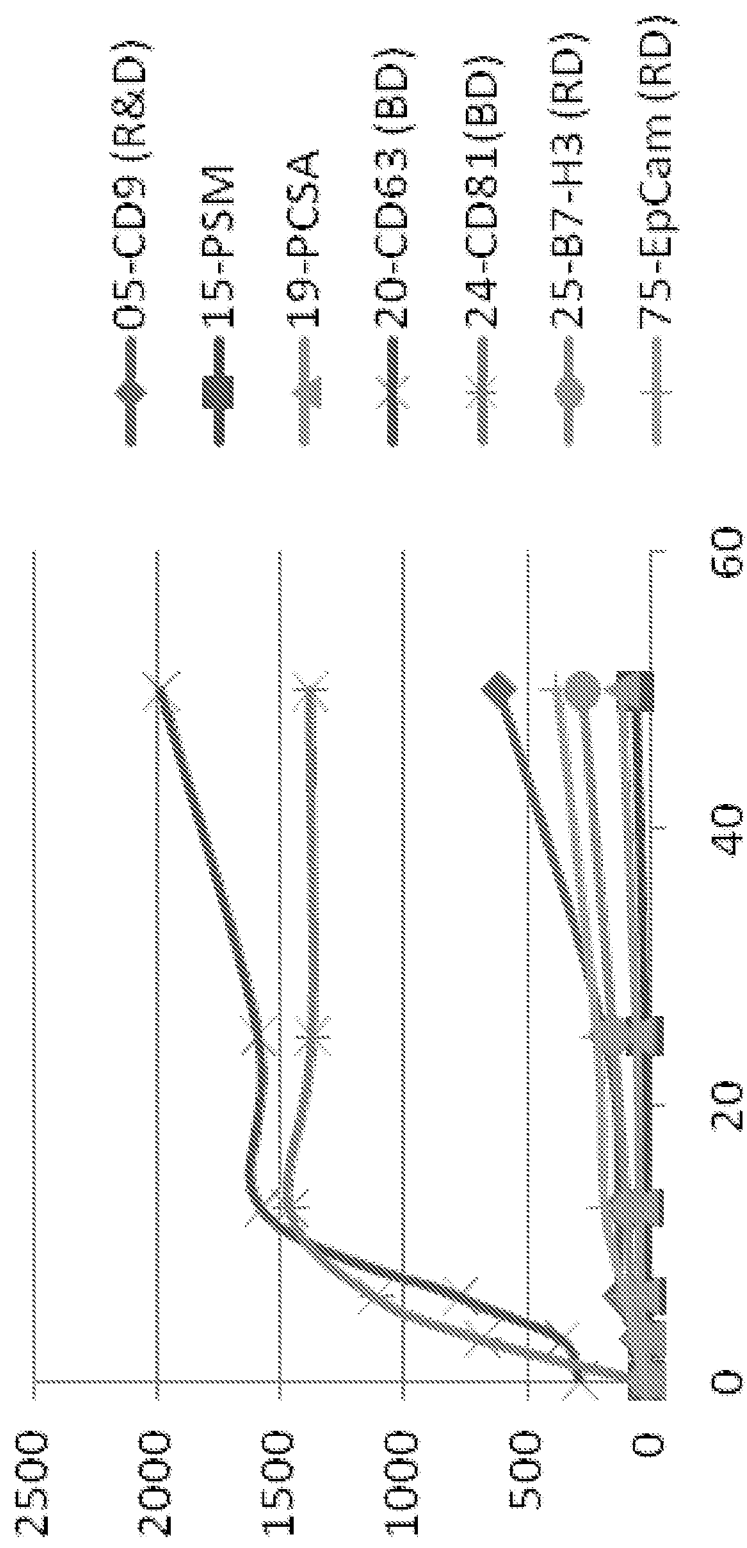
Figure 89D:
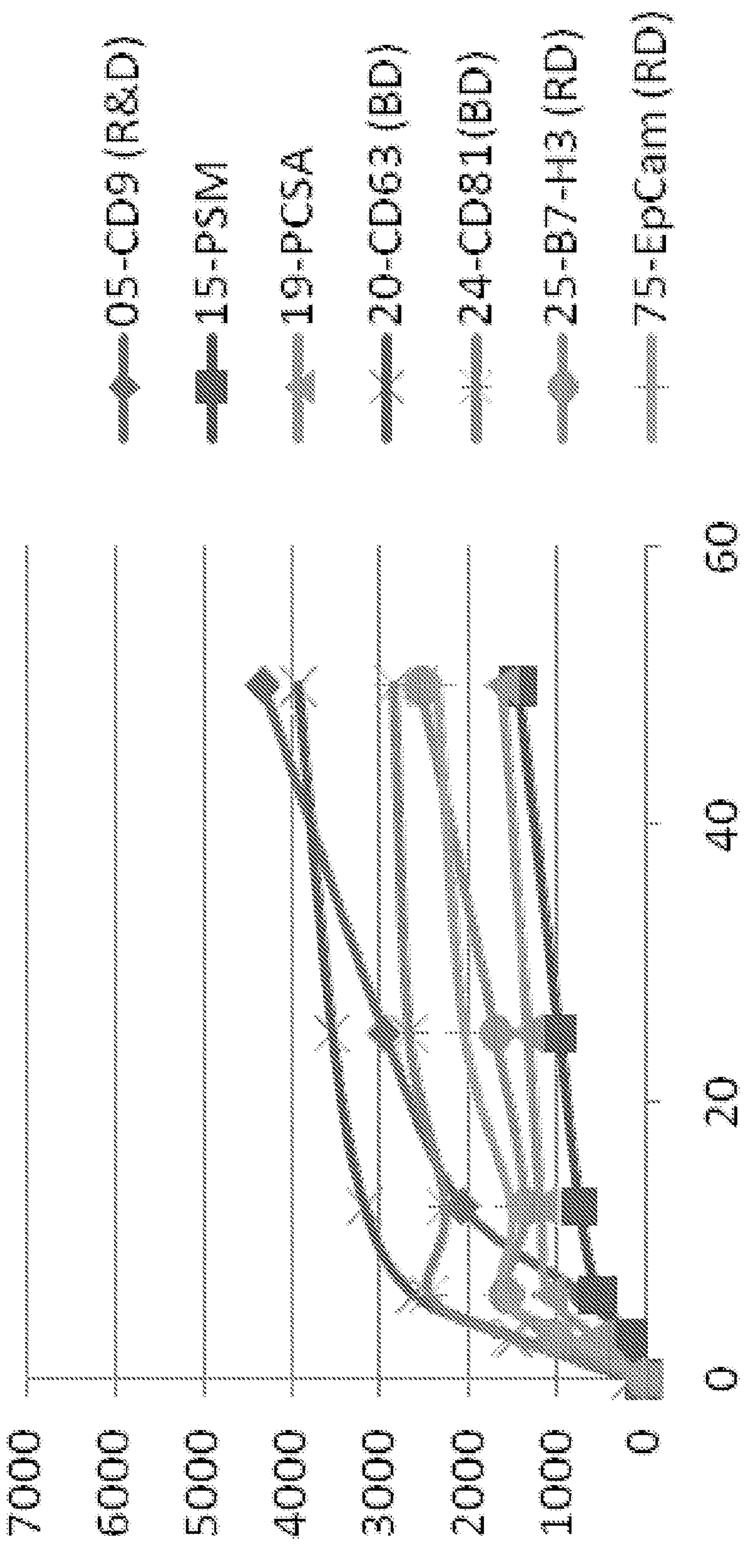
Figure 89E:
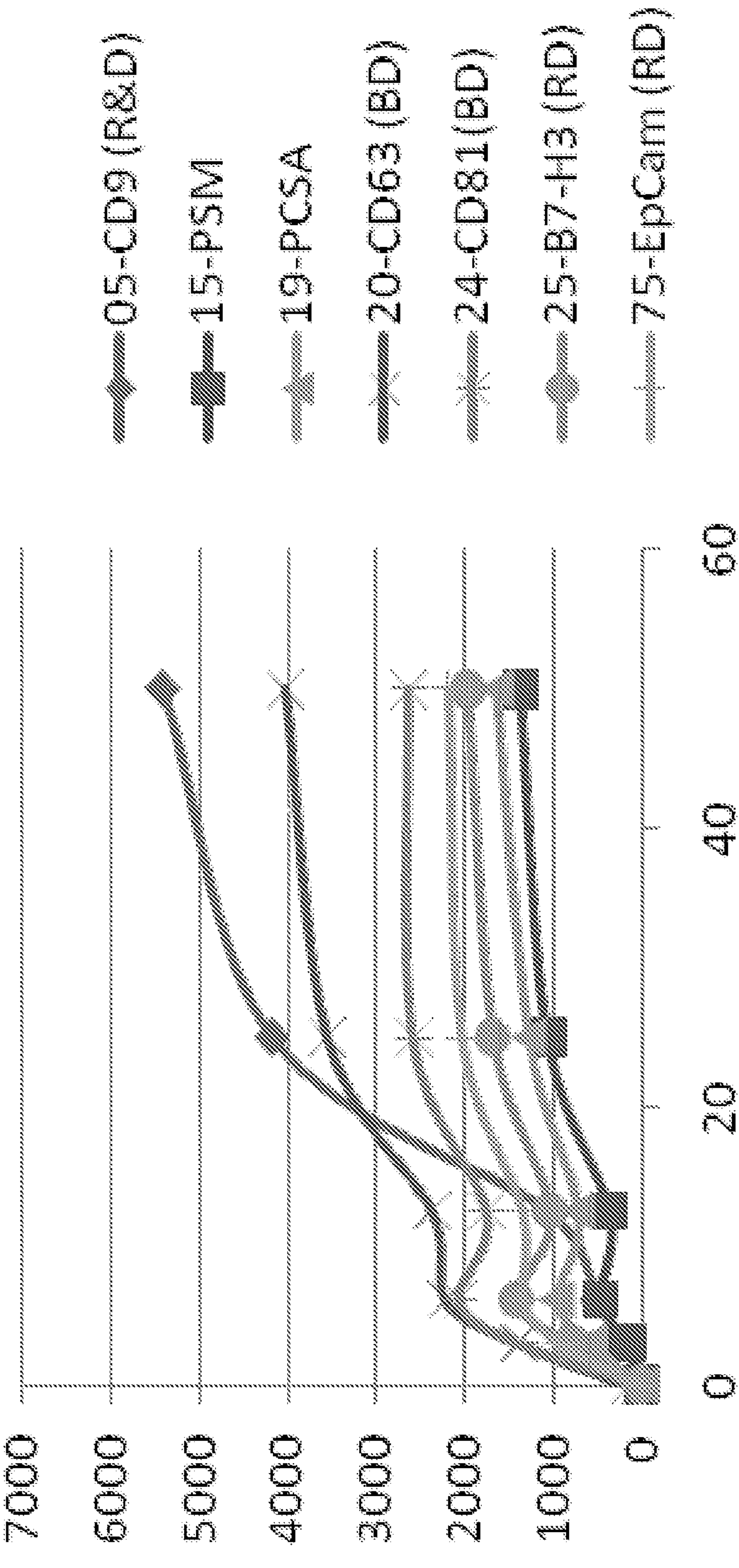
Figure 89F:
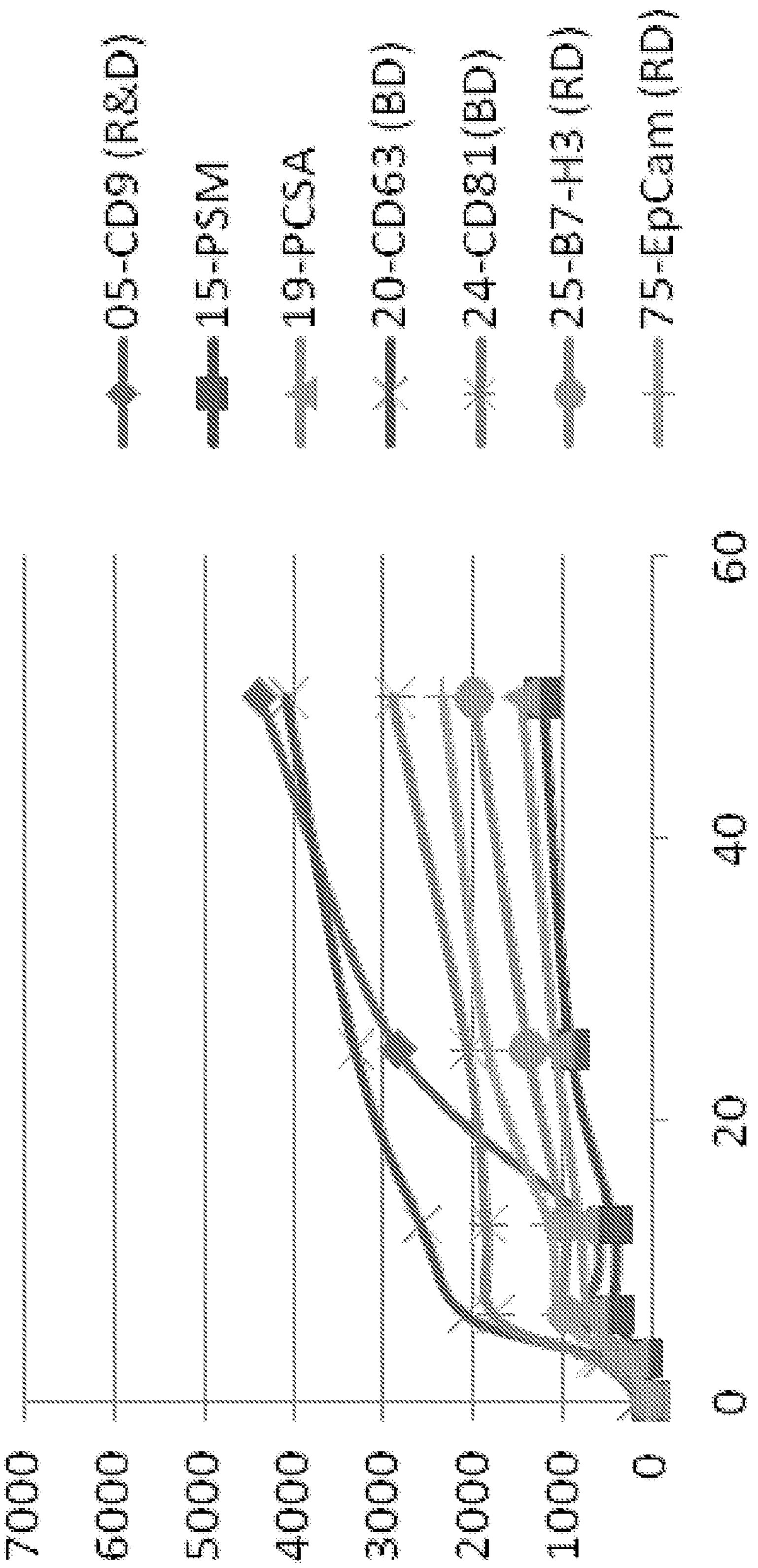

The vesicle samples obtained using methods as described in Example 15 are used in multiplexing assays as described in Example 21. The capture antibodies are CD9, CD63, CD81, PSMA, PCSA, B7H3, and EpCam. The detection antibodies are for biomarkers CD9, CD81, and CD63 or B7H3 and EpCam, as depicted in FIGS. 87, 88, and 89.

Example 17

Vesicle Isolation with Filters from Prostate Cancer Patients

Figure 83:
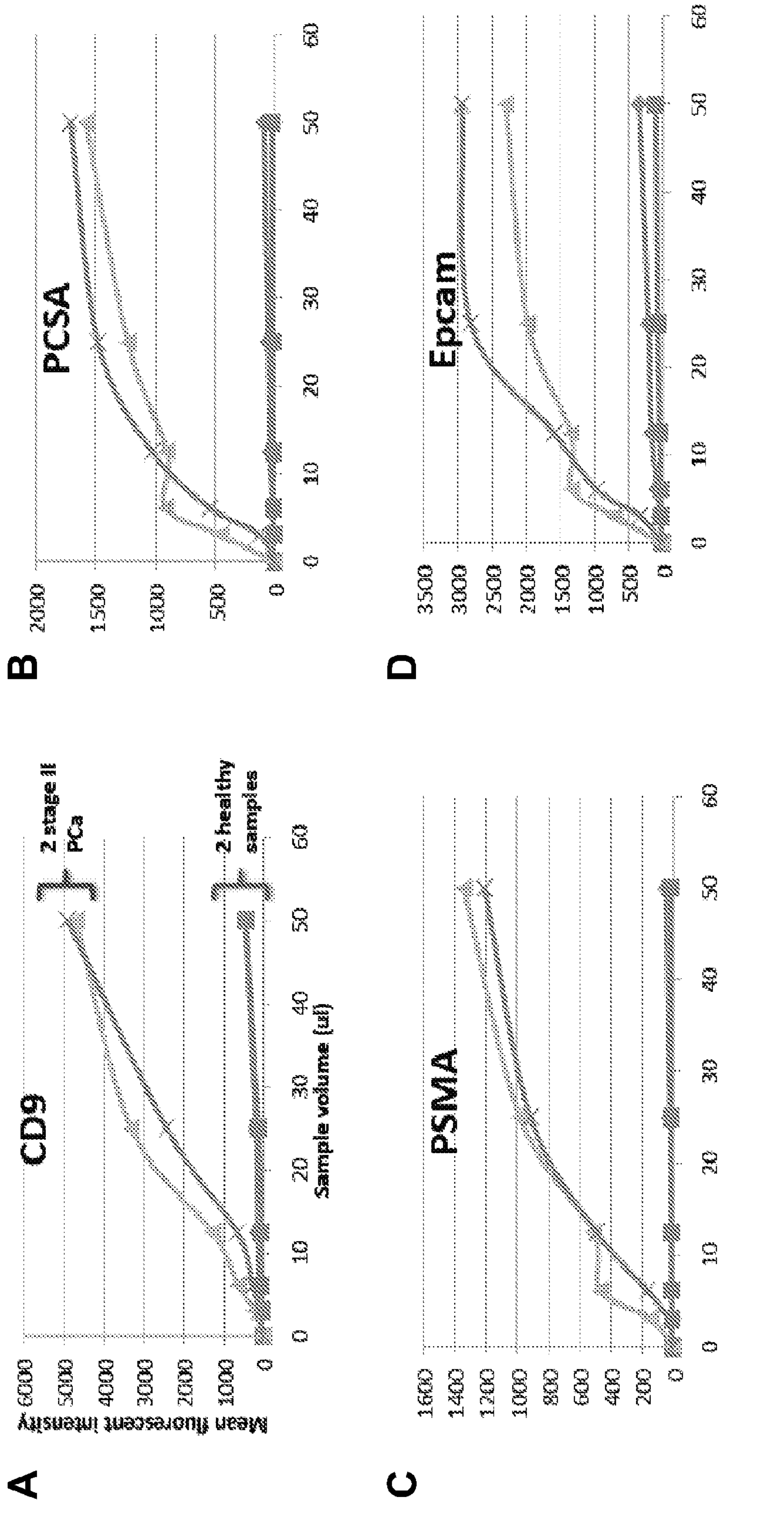
FIG. 83 represents graphs showing detection of biomarkers CD9, CD63, and CD81 with the capture agent of A) CD9, B) PCSA, C) PSMA, and D) EpCam. The vesicles were isolated from control samples (healthy samples) and prostate cancer samples, Stage II prostate cancer (PCa) samples. There is improved separation between the PCa and controls with the column-based filtration method of isolation as compared to ultracentrifugation isolation of vesicles.

The vesicle samples obtained using methods as described in Example 1, using a 7 mL Pierce® concentrator with a 150 kDa MWCO (Cat. #89920/89922) and are used in multiplexing assays as described in Example 21. The capture antibodies are CD9, CD63, CD81, PSMA, PCSA, B7H3, and EpCam. The detection antibodies used are CD63, CD9, and CD81. The results are shown in FIG. 83.

Example 18

Figure 84:
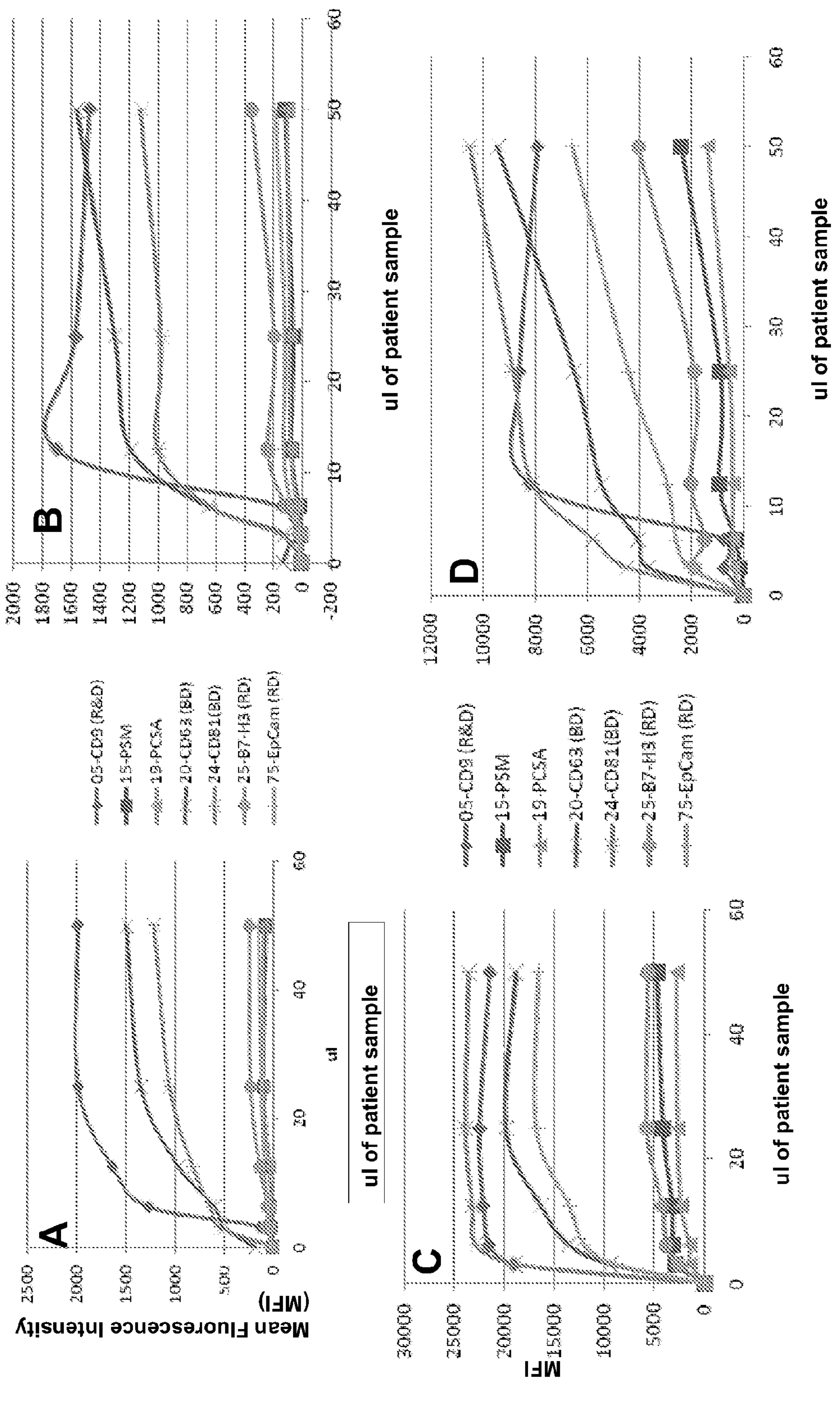
FIG. 84 depicts the comparison of the detection level of various biomarkers of vesicles isolated from a patient sample (#126) using ultracentrifugation versus a filter based method using a 500 μl column with a 100 kDa molecular weight cut off (MWCO) (Millipore, Billerica, Mass.). The graphs depict A) ultracentrifugation purified sample; B) Microcon sample C) ultracentrifugation purified sample and 10 ug Vcap and D) Microcon sample with 10 ug Vcap. The captures agents used are CD9, CD63, CD81, PSMA, PCSA, B7H3, and EpCam, and CD9, CD81, and CD63 detected.
Figure 85:
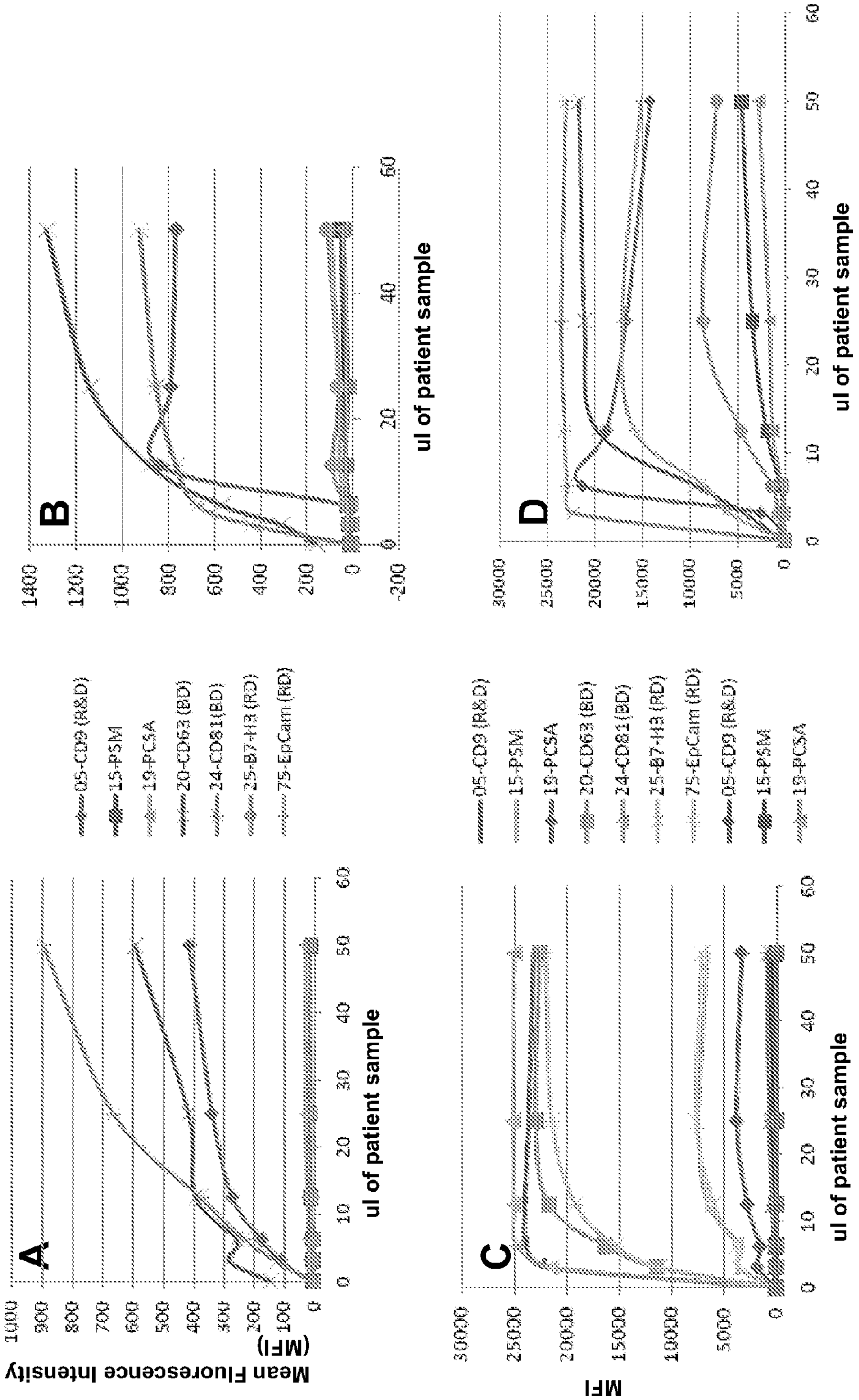
FIG. 85 depicts the comparison of the detection level of various biomarkers of vesicles isolated from a patient sample (#342) using ultracentrifugation versus a filter based method using a 500 μl column with a 100 kDa MWCO (Millipore, Billerica, Mass.). The graphs depict A) ultracentrifugation purified sample; B) Microcon sample C) ultracentrifugation purified sample and 10 ug Vcap and D) Microcon sample with 10 ug Vcap. The capture agents used are CD9, CD63, CD81, PSMA, PCSA, B7H3, and EpCam, and CD9, CD81, and CD63 detected.
Figure 86:
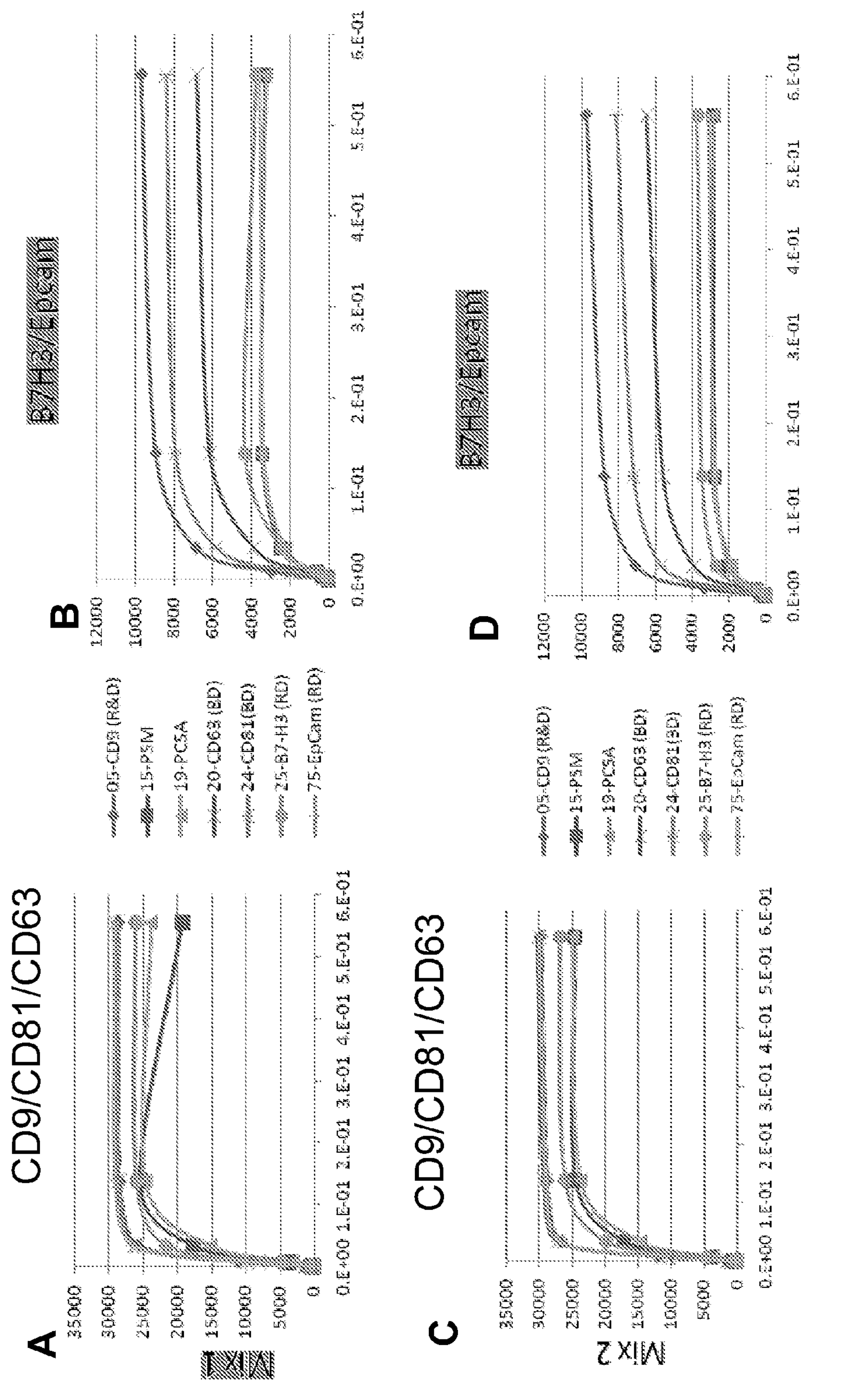
FIG. 86 represents the standard curves for using captures agents for CD9, CD63, CD81, PSMA, PCSA, B7H3, and EpCam, and detection of biomarkers CD9, CD81, and CD63 (A, C) or B7H3 and EpCam (B, D) of vesicles.

Comparison of Vesicles Isolated with Filters versus with Ultracentrifugation The vesicle samples obtained using methods as described in Example 1, using a 500 μl column with a 100 kDa MWCO and are used in multiplexing assays as described in Example 21. The capture antibodies are antibodies to CD9, CD63, CD81, PSMA, PCSA, B7H3, and EpCam. The detection antibodies are antibodies to CD63, CD9, and CD81. The results are shown in FIGS. 84 and 85.

Example 19

Detection of Prostate Cancer

High quality training set samples were obtained from commercial suppliers. The samples comprised plasma from 42 normal prostate, 42 PCa and 15 BPH patients. The PCa samples included 4 stage III and the remainder state II. The samples were blinded until all laboratory work was completed.

The vesicles from the samples were obtained by filtration to eliminate particles greater than 1.5 microns, followed by column concentration and purification using hollow fiber membrane tubes. The samples were analyzed using a multiplexed bead-based assay system.

Antibodies to the following proteins were analyzed:

a. General Vesicle (MV) markers: CD9, CD81, and CD63 b. Prostate MV markers: PCSA c. Cancer-Associated MV markers: EpCam and B7H3

Samples were required to pass a quality test as follows: if multiplexed fluorescence intensity (MFI) PSCA+MFI B7H3+MFI EpCam<200 then sample fails due to lack of signal above background. In the training set, six samples (three normals and three prostate cancers) did not achieve an adequate quality score and were excluded. An upper limit on the MFI was also established as follows: if MFI of EpCam is >6300 then test is over the upper limit score and samples are deemed not cancer (i.e., "negative" for purposes of the test).

The samples were classified according to the result of MFI scores for the six antibodies to the training set proteins, wherein the following conditions must be met to classified as PCa positive:

a. Average MFI of General MV markers>1500 b. PCSA MFI>300 c. B7H3 MFI>550 d. EpCam MFI 550-6300

Figure 90:
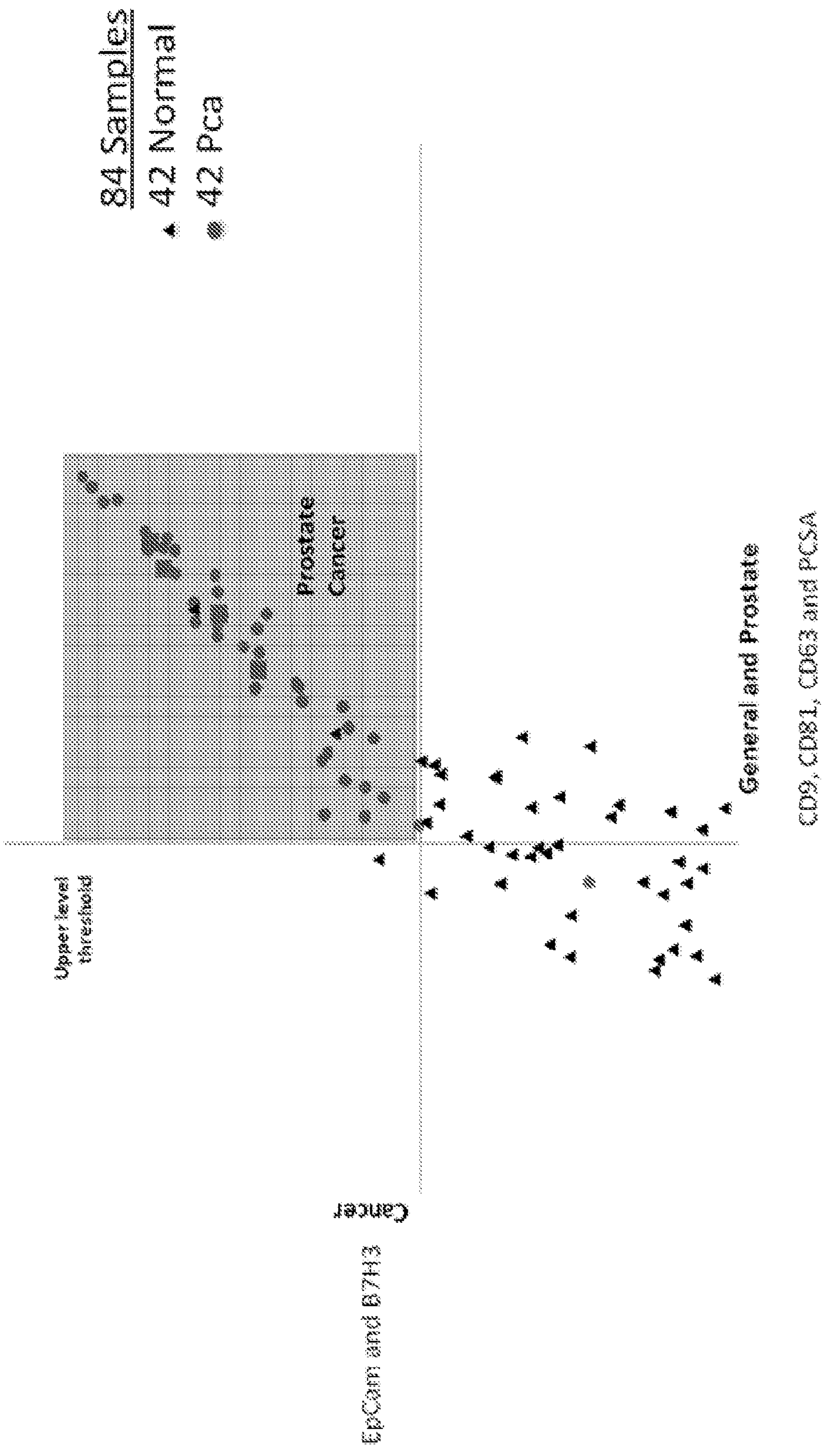
FIG. 90 illustrates the ability of a vesicle biosignature to discriminate between normal prostate and PCa samples. Cancer markers included EpCam and B7H3. General vesicle markers included CD9, CD81 and CD63. Prostate specific markers included PCSA. The test was found to be 98% sensitive and 95% specific for PCa vs normal samples.
Figure 91:
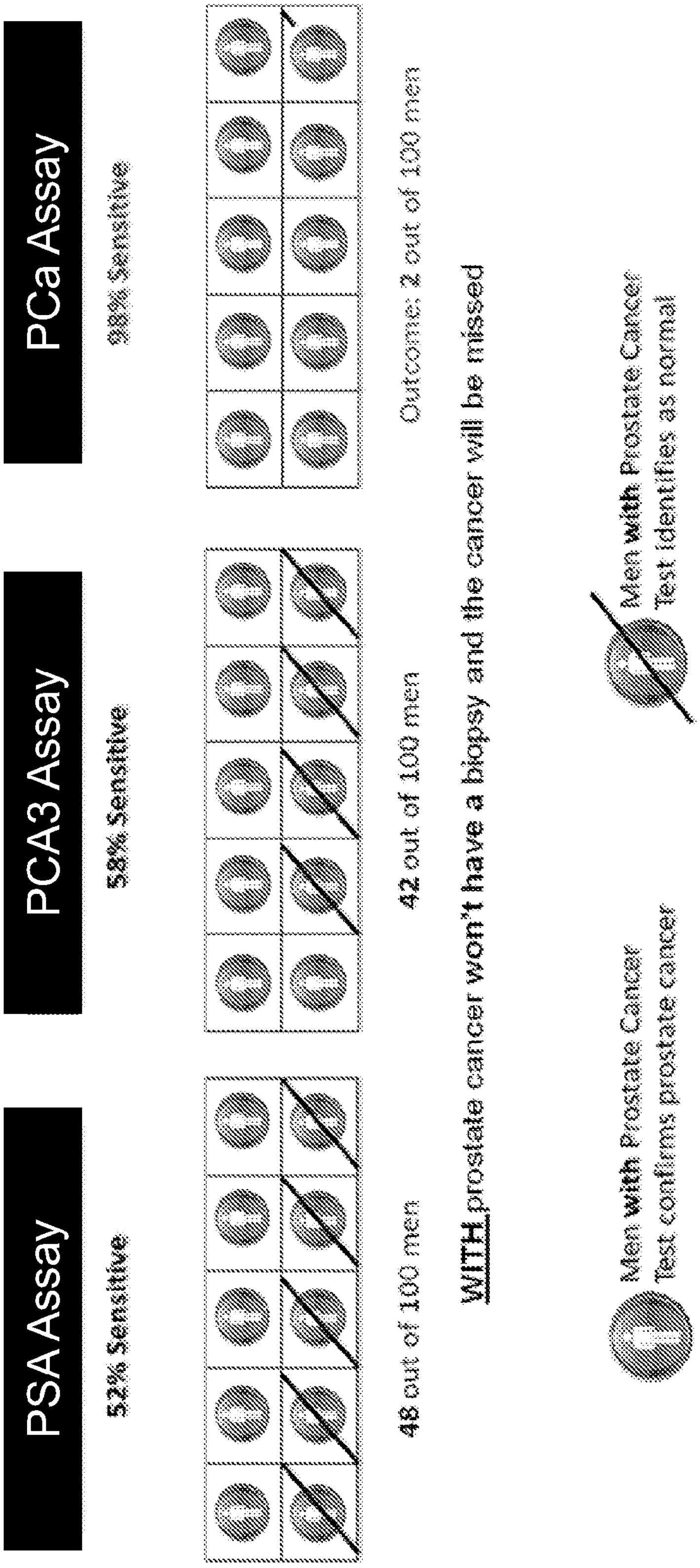
FIG. 91 illustrates improved sensitivity of the vesicle assays of the invention versus conventional PCa testing.
Figure 92:
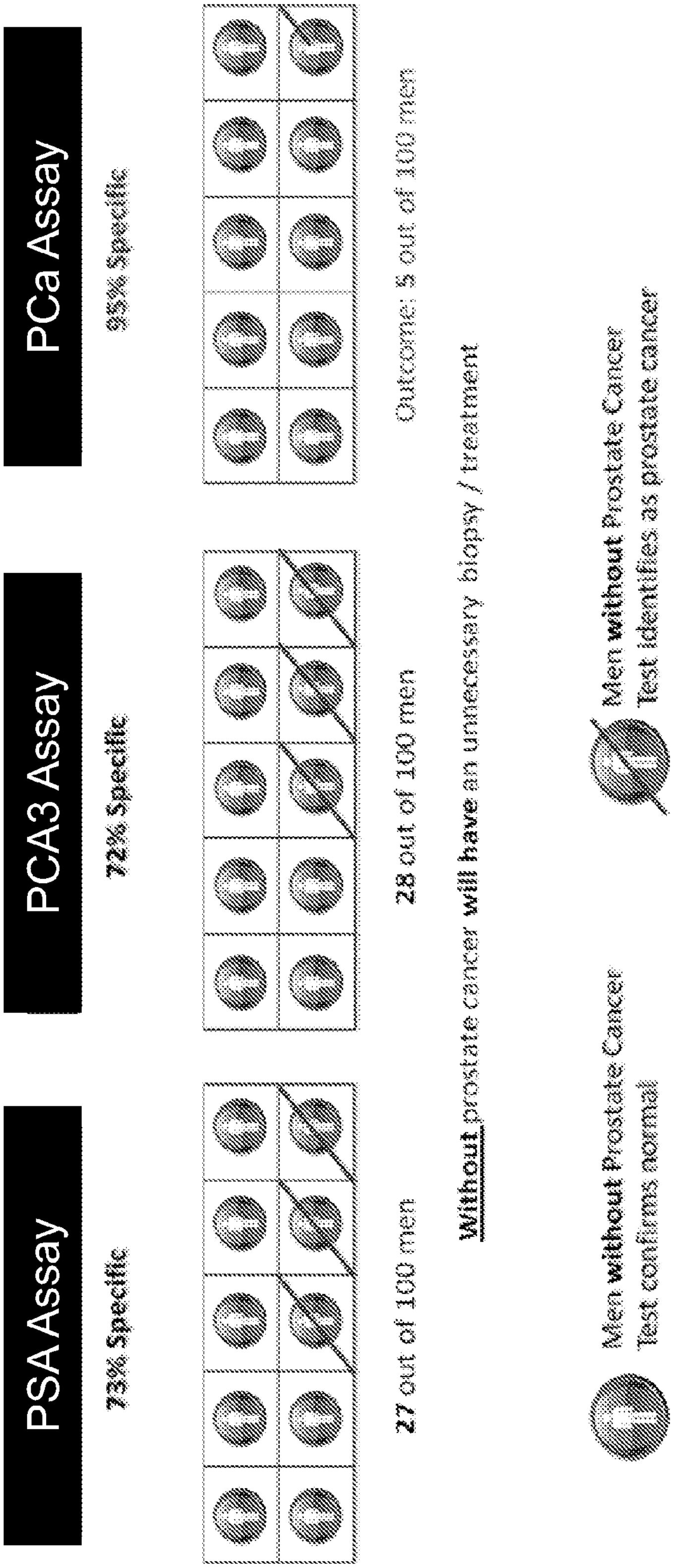
FIG. 92 illustrates improved specificity of the vesicle assays of the invention versus conventional PCa testing.

Using the 84 normal and PCa training data samples, the test was found to be 98% sensitive and 95% specific for PCa vs normal samples. See FIG. 90. The sensitivity and specificity of the test compared to conventional PSA and PCA3 are presented in FIGS. 91 and 92, respectively. Compared to PSA and PCA3 testing, the PCa Test presented in this Example can result in saving 220 men without PCa in every 1000 normal men screened from having an unnecessary biopsy.

Example 20

Differentiating BPH from PCa

BPH is a common cause of elevated PSA levels. PSA can only indicated whether there is something wrong with the prostate, but it cannot effectively differentiate between BPH and PCa. PCA3, a transcript found to be overexpressed by prostate cancer cells, is thought to be slightly more specific for PCa, but this depends on the cutoffs used for PSA and PCA3, as well as the populations studied.

Figure 93:
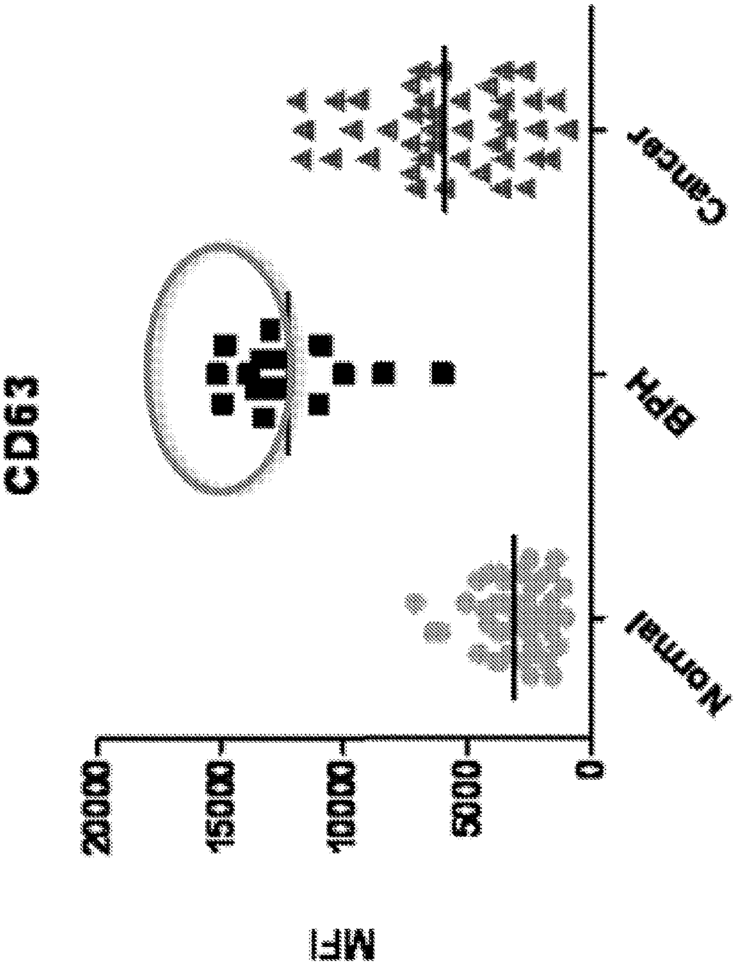
FIG. 93 illustrates discrimination of BPH samples from normals and PCa samples using CD63.

BPH can be characterized by vesicle (MV) analysis. Examining the samples described in Example 19, ten out of the 15 BPH samples (67%) have higher levels of CD63+ vesicles than the PCa samples, including the stage IIIs. See FIG. 93. Also, 14 out of 15 BPH (93%) have higher levels of CD63+ vesicles than the normals. This indicates that an inflammation-specific signature that differs from cancer may be used in differentiating BPH from PCa.

Figure 94:
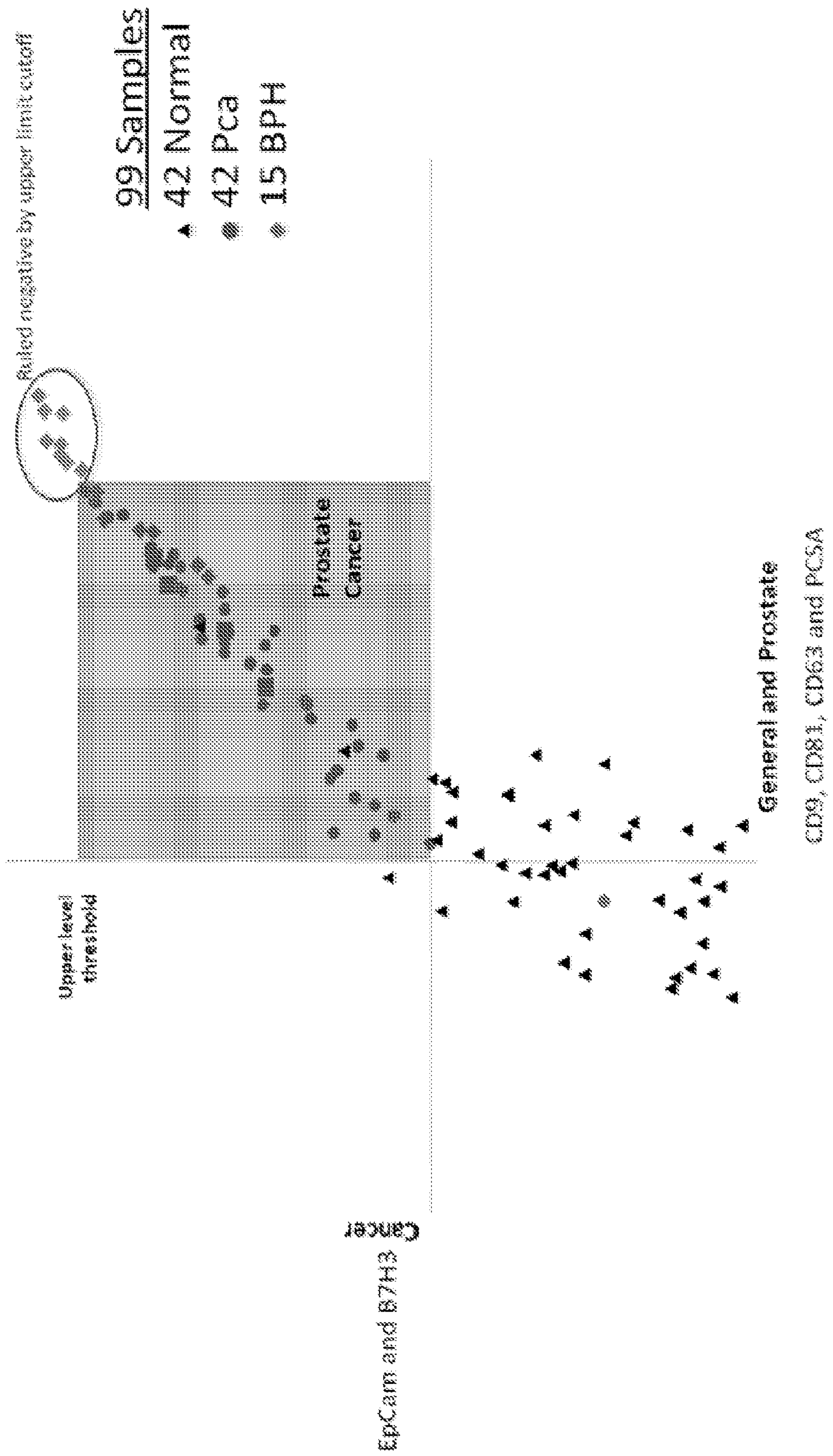
FIG. 94 illustrates the ability of a vesicle biosignature to discriminate between normal prostate and PCa samples. Cancer markers included EpCam and B7H3. General vesicle markers included CD9, CD81 and CD63. Prostate specific markers included PCSA. The test was found to be 98% sensitive and 84% specific for PCa vs normal & BPH samples.
Figure 95:
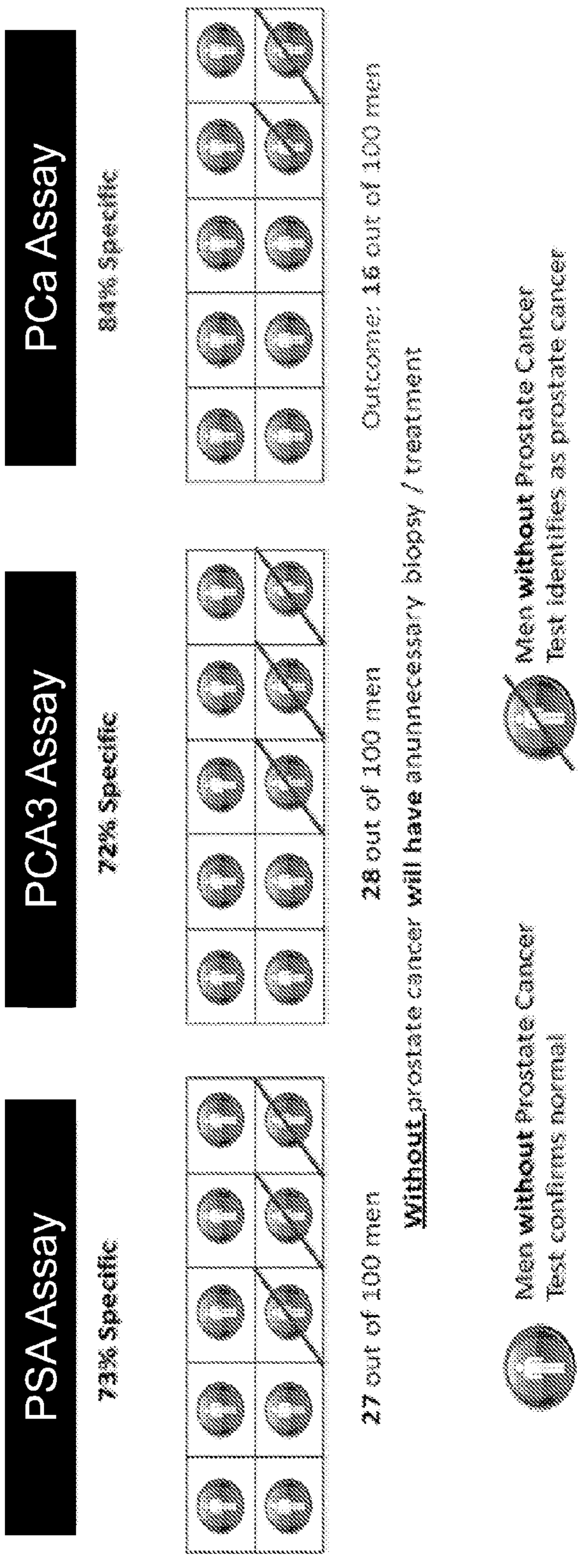
FIG. 95 illustrates improved specificity of the vesicle assays of the invention for PCa versus conventional testing even when BPH samples are included.

The PCa test from Example 19 was repeated including the 15 BPH samples. Using all 99 samples, the test was 98% sensitive and 84% specific. See FIG. 94. Thus, the test provides a 15% improvement over PSA. Performance values for PSA and PCA3 are commonly reported for settings without BPH in their cohorts, nevertheless, the vesicle test of the invention still outperforms conventional testing even when BPH was included. See FIG. 95. In this setting, the PCa test of the invention results in saving 110 men in every 1000 men without PCa screened from having an unnecessary biopsy as compared to PSA testing. And of those men biopsied due to a positive result from the assay, most will have something wrong with their prostate because the test performs well at identifying normal men (i.e., 95% specific in that population, see Example 19).

Figure 96:
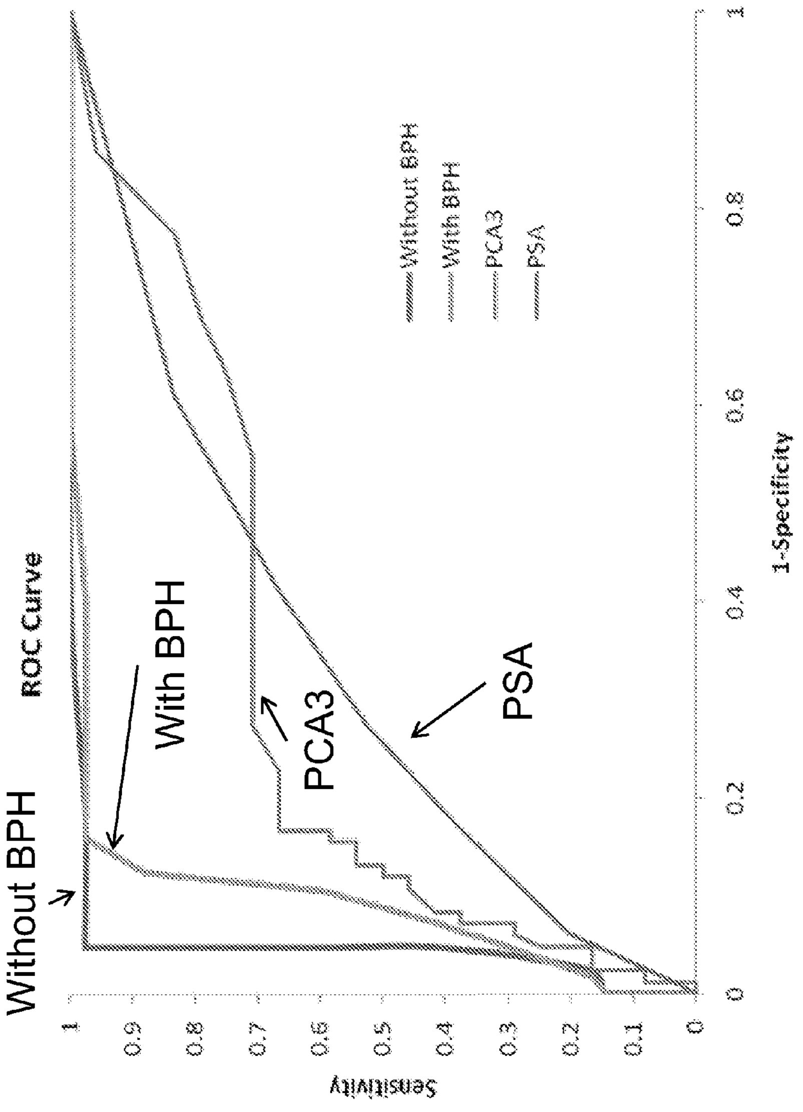
FIG. 96 illustrates ROC curve analysis of the vesicle assays of the invention versus conventional testing.

FIG. 96 presents ROC curve analysis of the vesicle assays of the invention versus conventional testing. When the ROC curve climbs rapidly towards upper left hand corner of the graph, the true positive rate is high and the false positive rate (1—specificity) is low. The AUC comparison shown in FIG. 16 shows that the test of the invention is much more likely to correctly classify a sample than conventional PSA or PCA3 testing.

Figure 97:
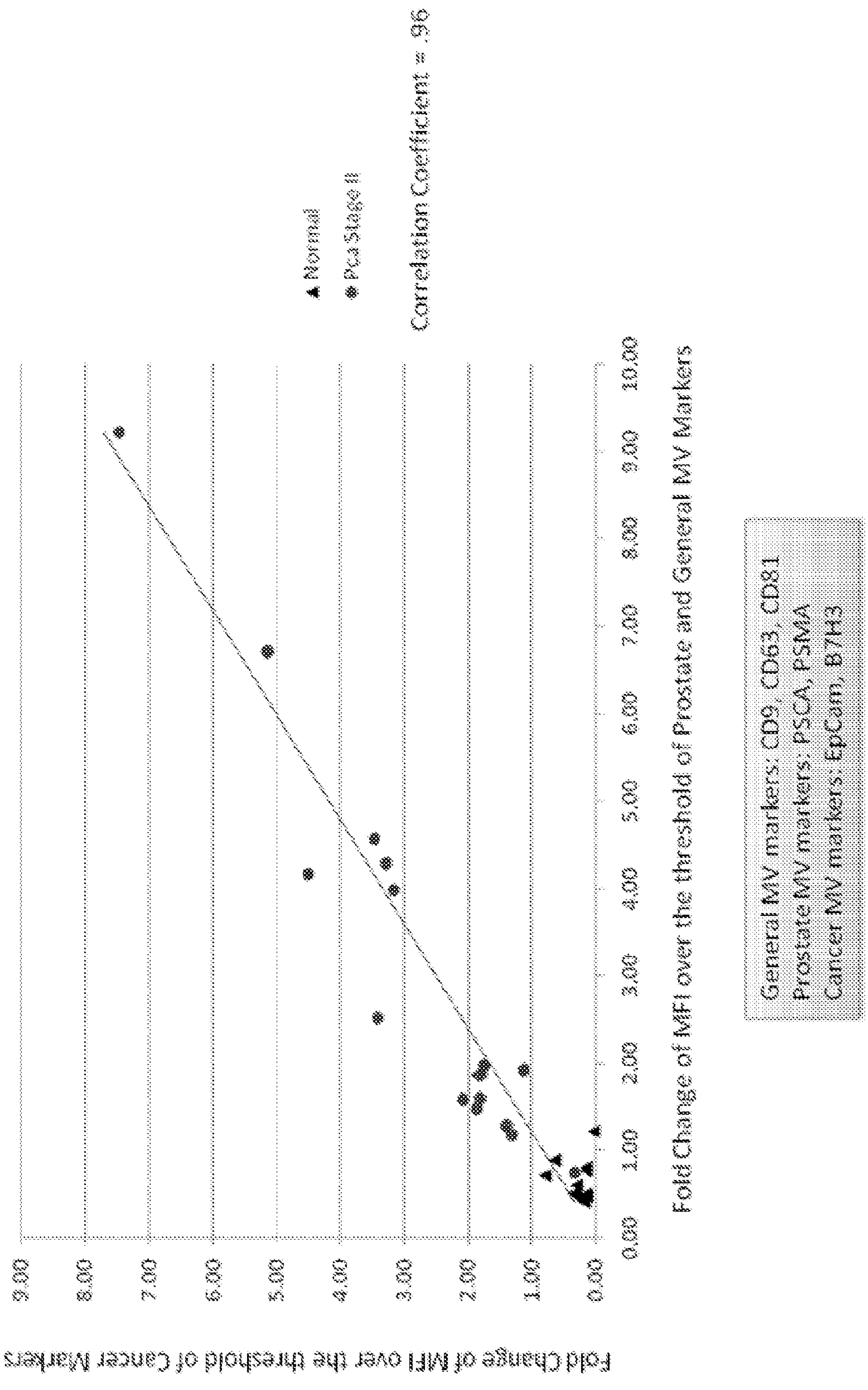
FIG. 97 illustrates a correlation between general vesicle (e.g. vesicle "MV") levels, levels of prostate-specific MVs and MVs with cancer markers.
Figure 98A:
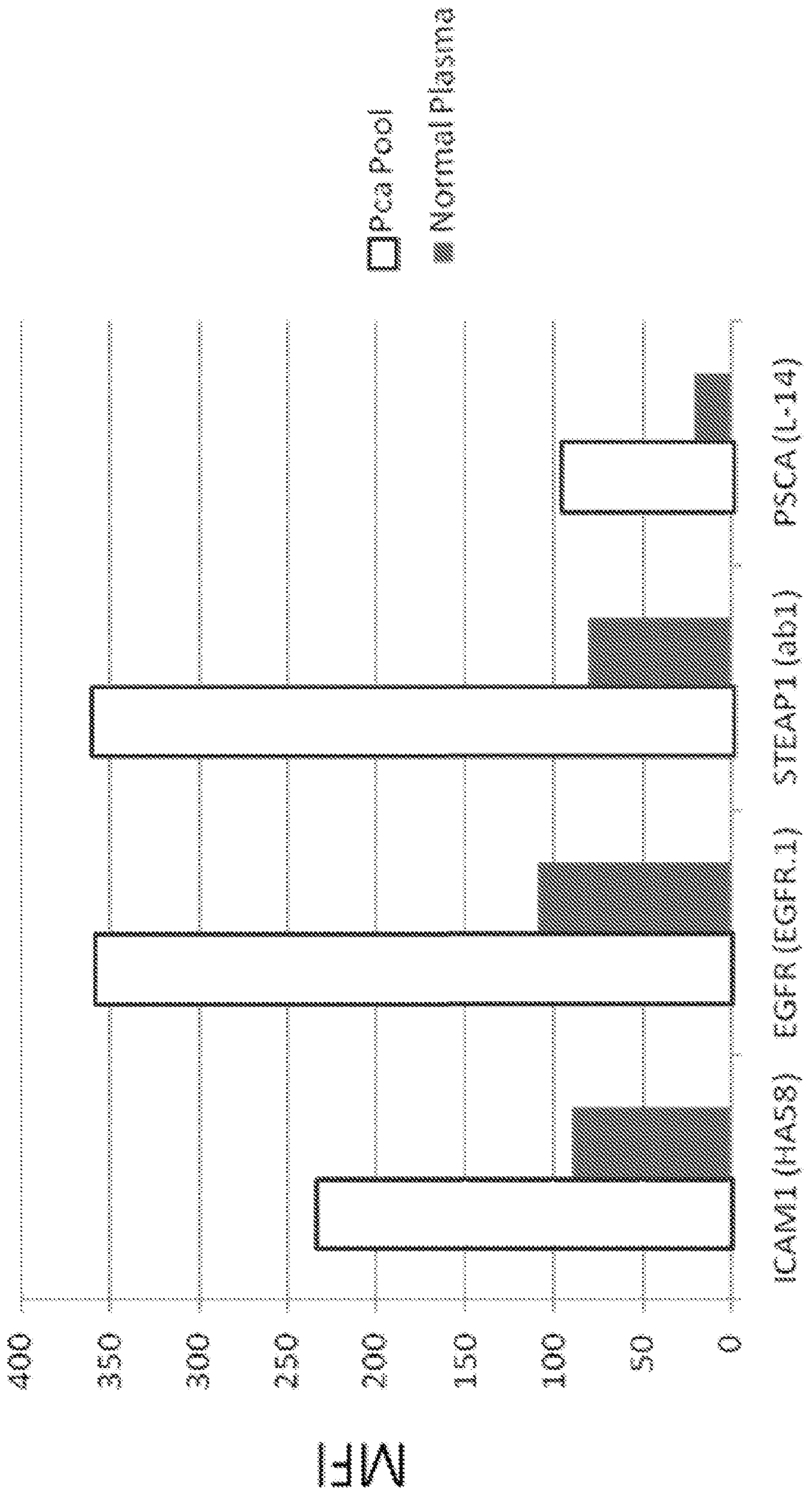
FIG. 98A illustrates vesicle markers that distinguish between PCa and normal samples.
Figure 98B:
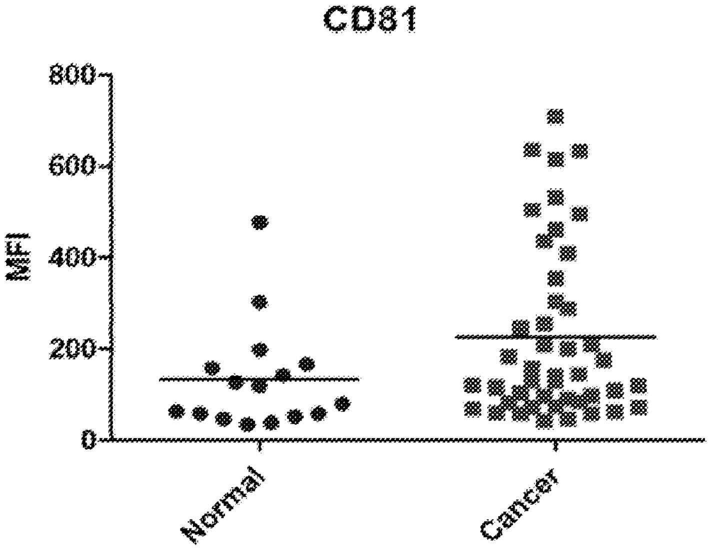
FIG. 98B-D illustrate assessing vesicles from normal and cancer subjects using a single capture agent and single detection agent. The capture agent is an antibody for EpCam and the detection agent detects B) CD81, C) EpCam, or D) CD9.
Figure 98C:
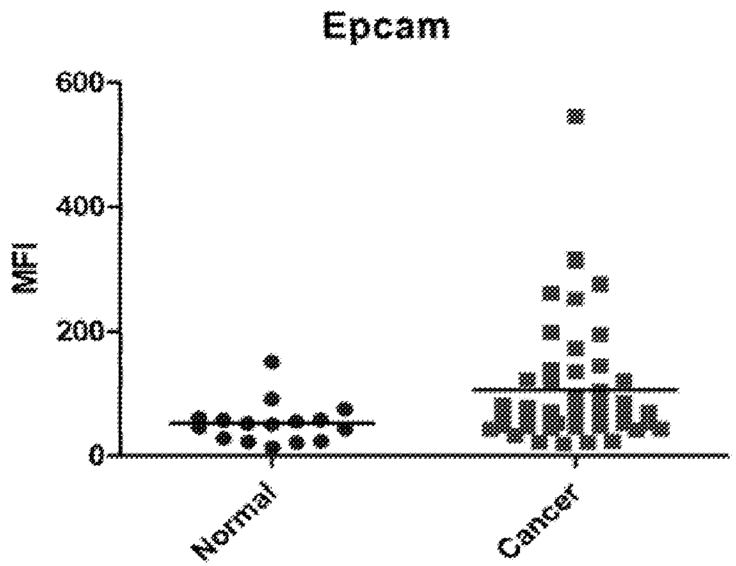
Figure 98D:
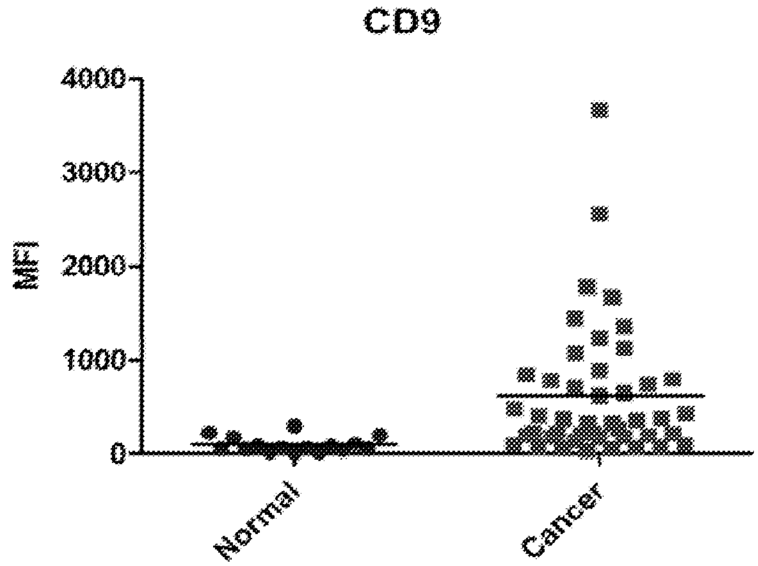

FIG. 97 shows that there is a correlation between general vesicle (MV) levels, levels of prostate-specific MVs and MVs with cancer markers, indicating these markers are correlated in the subject populations. Such cancer specific markers can be further used to differentiate between BPH and PCa. In the figure, General MV markers include CD9, CD63 and CD81; Prostate MV markers include PCSA and PSMA; and Cancer MV markers include EpCam and B7H3. Testing of PCa samples without the vesicle capture markers revealed sensitivity and specificity values nearly the same as those with the general MV markers were used. Similarly, detection of cancer without using B7H3 only leads to minimal reduction in performance. These data reveal that the markers of the invention can be substituted and tested in various configurations to still achieve optimal assay performance.

FIG. 98 shows additional markers that can distinguish between PCa and normal samples that can be added to improve test performance. FIG. 98A shows the median fluorescence intensity (MFI) levels of vesicles captured with ICAM1, EGFR, STEAP1 and PSCA and labeled with phycoerythrin-labeled antibodies to tetraspanins CD9, CD63 and CD81. FIGS. 98B-D illustrate assessing vesicles from normal and cancer subjects using a single capture agent and single detection agent. The capture agent is an antibody for EpCam and the detection agent detects CD81 (FIG. 98B), EpCam (FIG. 98C), or CD9 (FIG. 98D).

Example 21

Vesicle PCa Assay/Test

Figure 99A:
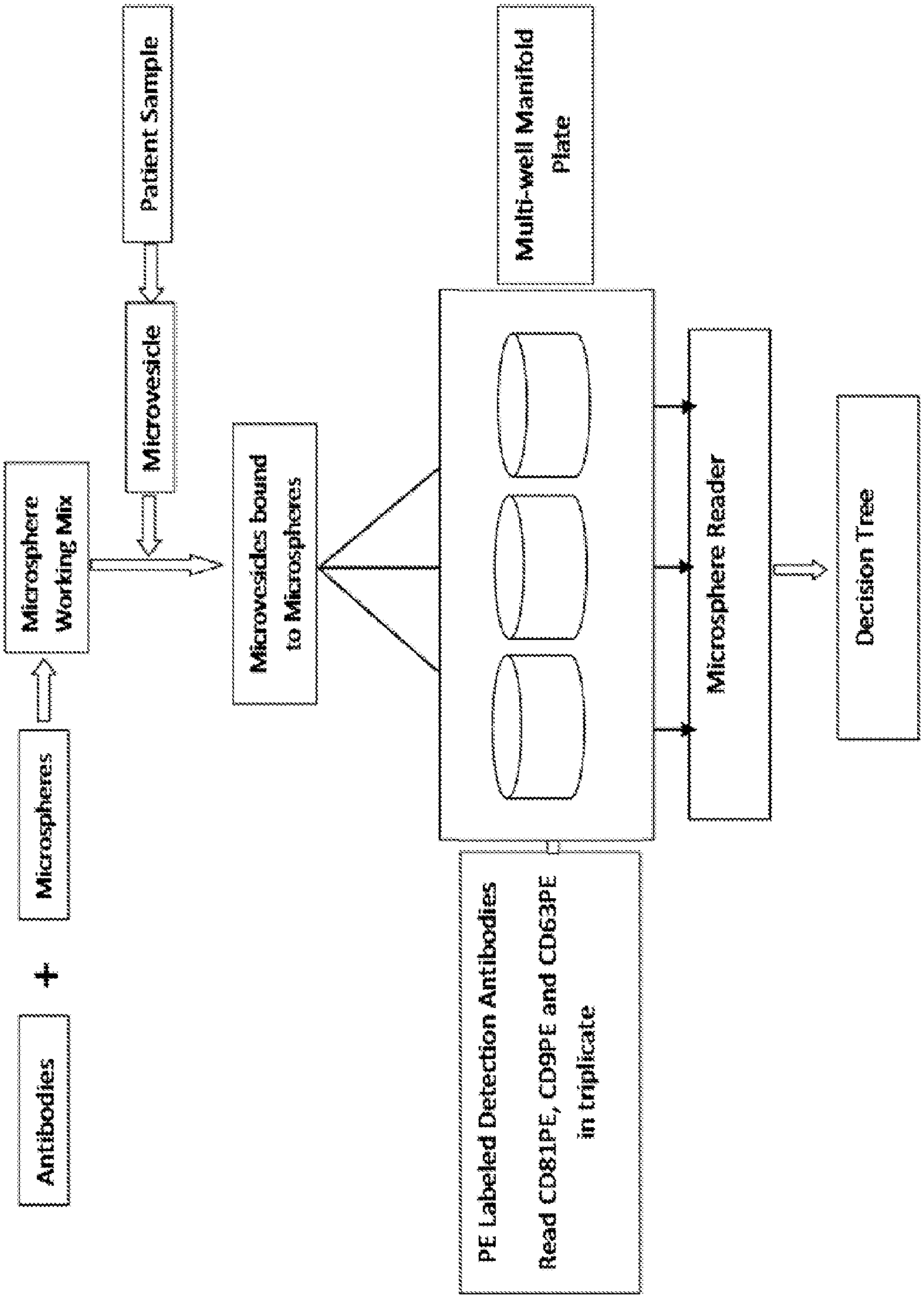
FIG. 99A-D is a schematic for A) a vesicle prostate cancer assay, which leads to a decision tree (B), C), D)) for determining whether a sample is positive for prostate cancer.

In this example, the vesicle PCa test is a microsphere based immunoassay for the detection of a set of protein biomarkers present on the vesicles from plasma of patients with prostate cancer. The test employs specific antibodies to the following protein biomarkers: CD9, CD59, CD63, CD81, PSMA, PCSA, B7H3 and EpCAM (FIG. 99A). After capture of the vesicles by antibody coated microspheres, phycoerythrin-labeled antibodies are used for the detection of vesicle specific biomarkers. Depending on the level of binding of these antibodies to the vesicles from a patient's plasma a determination of the presence or absence of prostate cancer is made.

Vesicles are isolated as described in Example 1.

Microspheres

The following microspheres are obtained from Luminex. Each microsphere is conjugated to a specific antibody after which the microspheres are combined to make a Microsphere Master Mix: L 100-C105-01; L100-C115-01; L100-C119-01; L100-C120-01; L100-C122-01; L100-C124-01; L100-C135-01; and L100-C175-01. The following microspheres (xMAP® Classification Calibration Microspheres) are obtained from Luminex and are used as instrument calibration reagents for the Luminex LX200 instrument: L100-CAL1. The following microspheres (xMAP® Reporter Calibration Microspheres) are obtained from Luminex and are used as instrument reporter calibration reagents for the Luminex LX200 instrument: L100-CAL2. The following microspheres (xMAP® Classification Control Microspheres) are obtained from Luminex and are used as instrument control reagents for the Luminex LX200 instrument: L 100-CON1. The following microspheres (xMAP Reporter Control Microspheres) are obtained from Luminex and are used as reporter control reagents for the Luminex LX200 instrument: L 1 00-CON2.

Capture Antibodies

The following antibodies are used to coat Luminex microspheres for use in capturing certain populations of vesicles by binding to their respective protein targets on the vesicles in this Example: a. Mouse anti-human CD9 monoclonal antibody is an IgG2b used to coat microsphere L100-C105 to make *EPCLMACD9-C105; b. Mouse anti-human PSMA monoclonal antibody is an IgG1 used to coat microsphere L100-C115 to make EPCLMAPSMA-C115; c. Mouse anti-human PCSA monoclonal antibody is an IgG1 used to coat microsphere L100-C119 to make EPCLMAPCSA-C119; d. Mouse anti-human CD63monoclonal antibody is an IgG1 used to coat microsphere L100-C120 to make EPCLMACD63-C120; e. Mouse anti-human CD81 monoclonal antibody is an IgG1 used to coat microsphere L100-C124 to make EPCLMACD81-C124; f. Goat anti-human B7-H3 polyclonal antibody is an IgG purified antibody used to coat microsphere L100-C125 to make EPCLGAB7-H3-C125; and g. Mouse anti-human EpCAM monoclonal antibody is an IgG2b purified antibody used to coat microsphere L100-C175 to make EPCLMAEpCAM-C175.

Detection Antibodies

The following phycoerythrin (PE) labeled antibodies are used as detection probes in this assay: a. EPCLMACD81PE: Mouse anti-human CD81 PE labeled antibody is an IgG1 antibody used to detect CD81 on captured vesicles; b. EPCLMACD9PE: Mouse anti-human CD9 PE labeled antibody is an IgG1 antibody used to detect CD9 on captured vesicles; c. EPCLMACD63PE: Mouse anti-human CD63 PE labeled antibody is an IgG1 antibody used to detect CD63 on captured vesicles; d. EPCLMAEpCAMPE: Mouse anti-human EpCAM PE labeled antibody is an IgG1 antibody used to detect EpCAM on captured vesicles; e. EPCLMAPSMAPE: Mouse anti-human PSMA PE labeled antibody is an IgG1 antibody used to detect PSMA on captured vesicles; f. EPCLMACD59PE: Mouse anti-human CD59 PE labeled antibody is an IgG1 antibody used to detect CD59 on captured vesicles; and g. EPCLMAB7-H3PE: Mouse anti-human B7-H3 PE labeled antibody is an IgG1 antibody used to detect B7-H3 on captured vesicles.

Reagent Preparation

Antibody Purification:

The following antibodies in Table 15 are received from vendors and purified and adjusted to the desired working concentrations according to the following protocol.

TABLE 15

| Antibodys for PCa Assay | |
|---|---|
| Antibody | Use |
| EPCLMACD9 | Coating of microspheres for vesicle capture |
| EPCLMACD63 | Coating of microspheres for vesicle capture |
| EPCLMACD81 | Coating of microspheres for vesicle capture |
| EPCLMAPSMA | Coating of microspheres for vesicle capture |
| EPCLGAB7-H3 | Coating of microspheres for vesicle capture |
| EPCLMAEpCAM | Coating of microspheres for vesicle capture |
| EPCLMAPCSA | Coating of microspheres for vesicle capture |
| EPCLMACD81PE | PE coated antibody for vesicle biomarker detection |
| EPCLMACD9PE | PE coated antibody for vesicle biomarker detection |
| EPCLMACD63PE | PE coated antibody for vesicle biomarker detection |
| EPCLMAEpCAMPE | PE coated antibody for vesicle biomarker detection |
| EPCLMAPSMAPE | PE coated antibody for vesicle biomarker detection |
| EPCLMACD59PE | PE coated antibody for vesicle biomarker detection |
| EPCLMAB7-H3PE | PE coated antibody for vesicle biomarker detection |

Antibody Purification Protocol:

Antibodies are purified using Protein G resin from Pierce (Protein G spin kit, prod #89979). Micro-chromatography columns made from filtered P-200 tips are used for purification.

One hundred μl of Protein G resin is loaded with 100 μl buffer from the Pierce kit to each micro column. After waiting a few minutes to allow the resin to settle down, air pressure is applied with a P-200 Pipettman to drain buffer when needed, ensuring the column is not let to dry. The column is equilibrated with 0.6 ml of Binding Buffer (pH 7.4, 100 mM Phosphate Buffer, 150 mM NaCl; (Pierce, Prod #89979). An antibody is applied to the column (<1 mg of antibody is loaded on the column). The column is washed with 1.5 ml of Binding Buffer. Five tubes (1.5 ml micro centrifuge tubes) are prepared and 10 μl of neutralization solution (Pierce, Prod #89979) is applied to each tube. The antibody is eluted with the elution buffer from the kit to each of the five tubes, 100 μl for each tube (for a total of 500 μl). The relative absorbance of each fraction is measured at 280 nm using Nanodrop (Thermo scientific, Nanodrop 1000 spectrophotometer). The fractions with highest OD reading are selected for downstream usage. The samples are dialyzed against 0.25 liters PBS buffer using Pierce Slide-A-Lyzer Dialysis Cassette (Pierce, prod 66333, 3KDa cut off). The buffer is exchanged every 2 hours for minimum three exchanges at 4° C. with continuous stirring. The dialyzed samples are then transferred to 1.5 ml microcentifuge tubes, and can be labeled and stored at 4° C. (short term) or −20° C. (long term).

Microsphere Working Mix Assembly:

A microsphere working mix MWM101 includes the first four rows of antibody, microsphere and coated microsphere of Table 16.

TABLE 16

| Antibody-Microsphere Combinations | | |
|---|---|---|
| Antibody | Microsphere | Coated Microsphere |
| EPCLMACD9 | L100-C105 | EPCLMACD9-C105 |
| EPCLMACD63 | L100-C120 | EPCLMACD63-C120 |
| EPCLMACD81 | L100-C124 | EPCLMACD81-C124 |
| EPCLMAPSMA | L100-C115 | EPCLMAPSMA-C115 |
| EPCLGAB7-H3 | L100-C125 | EPCLGAB7-H3-C125 |
| bEPCLMAEpCAM | L100-C175 | EPCLMAEpCAM-C175 |
| EPCLMAPCSA | L100-C119 | EPCLMAPCSA-C119 |

Microspheres are coated with their respective antibodies as listed above according to the following protocol.

Protocol for Two-Step Carbodiimide Coupling of Protein to Carboxylated Microspheres:

The microspheres should be protected from prolonged exposure to light throughout this procedure. The stock uncoupled microspheres are resuspended according to the instructions described in the Product Information Sheet provided with the microspheres (xMAP technologies, MicroPlex™ Microspheres). Five×106 of the stock microspheres are transferred to a USA Scientific 1.5 ml microcentrifuge tube. The stock microspheres are pelleted by microcentrifugation at ≥8000×g for 1-2 minutes at room temperature. The supernatant is removed and the pelleted microspheres are resuspended in 100 μl of dH2O by vortex and sonication for approximately 20 seconds. The microspheres are pelleted by microcentrifugation at >8000×g for 1-2 minutes at room temperature. The supernatant is removed and the washed microspheres are resuspended in 80 μl of 100 mM Monobasic Sodium Phosphate, pH 6.2 by vortex and sonication (Branson 1510, Branson ULTrasonics Corp.) for approximately 20 seconds. Ten μl of 50 mg/ml Sulfo-NHS (Thermo Scientific, Cat#24500) (diluted in dH20) is added to the microspheres and is mixed gently by vortex. Ten μl of 50 mg/ml EDC (Thermo Scientific, Cat#25952-53-8) (diluted in dH2O) is added to the microspheres and gently mixed by vortexing. The microspheres are incubated for 20 minutes at room temperature with gentle mixing by vortex at 10 minute intervals. The activated microspheres are pelleted by microcentrifugation at ≥8000×g for 1-2 minutes at room temperature. The supernatant is removed and the microspheres are resuspended in 250 μl of 50 mM MES, pH 5.0 (MES, Sigma, Cat# M2933) by vortex and sonication for approximately 20 seconds. (Only PBS-1% BSA+Azide (PBS-BN)((Sigma (P3688-10PAK+0.05% NaAzide (S8032))) should be used as assay buffer as well as wash buffer.). The microspheres are then pelleted by microcentrifugation at ≥8000×g for 1-2 minutes at room temperature.

The supernatant is removed and the microspheres are resuspended in 250 μl of 50 mM MES, pH 5.0 (MES, Sigma, Cat# M2933) by vortex and sonication for approximately 20 seconds. (Only PBS-1% BSA+Azide (PBS-BN) ((Sigma (P3688-10PAK+0.05% NaAzide (S8032))) should be used as assay buffer as well as wash buffer.). The microspheres are then pelleted by microcentrifugation at ≥8000×g for 1-2 minutes at room temperature, thus completing two washes with 50 mM MES, pH 5.0.

The supernatant is removed and the activated and washed microspheres are resuspended in 100 μl of 50 mM MES, pH 5.0 by vortex and sonication for approximately 20 seconds. Protein in the amount of 125, 25, 5 or 1 μg is added to the resuspended microspheres. (Note: Titration in the 1 to 125 μg range can be performed to determine the optimal amount of protein per specific coupling reaction.). The total volume is brought up to 500 IA with 50 mM MES, pH 5.0. The coupling reaction is mixed by vortex and is incubated for 2 hours with mixing (by rotating on Labquake rotator, Barnstead) at room temperature. The coupled microspheres are pelleted by microcentrifugation at >8000×g for 1-2 minutes at room temperature. The supernatant is removed and the pelleted microspheres are resuspended in 500 μl, of PBS-TBN by vortex and sonication for approximately 20 seconds. (Concentrations can be optimized for specific reagents, assay conditions, level of multiplexing, etc. in use.).

The microspheres are incubated for 30 minutes with mixing (by rotating on Labquake rotator, Barnstead) at room temperature. The coupled microspheres are pelleted by microcentrifugation at >8000×g for 1-2 minutes at room temperature. The supernatant is removed and the microspheres are resuspended in 1 ml of PBS-TBN by vortex and sonication for approximately 20 seconds. (Each time there is the addition of samples, detector antibody or SA-PE the plate is covered with a sealer and light blocker (such as aluminum foil), placed on the orbital shaker and set to 900 for 15-30 seconds to re-suspend the beads. Following that the speed should be set to 550 for the duration of the incubation.).

The microspheres are pelleted by microcentrifugation at >8000×g for 1-2 minutes. The supernatant is removed and the microspheres are resuspended in 1 ml of PBS-TBN by vortex and sonication for approximately 20 seconds. The microspheres are pelleted by microcentrifugation at >8000×g for 1-2 minutes (resulting in a total of two washes with 1 ml PBS-TBN).

Protocol for Microsphere Assay:

For multiple phycoerythrin detector antibody, the preparation is as described in Example 4. One hundred pi is analyzed on the Luminex analyzer (Luminex 200, xMAP technologies) according to the system manual. (High PMT setting)

Figure 99B:
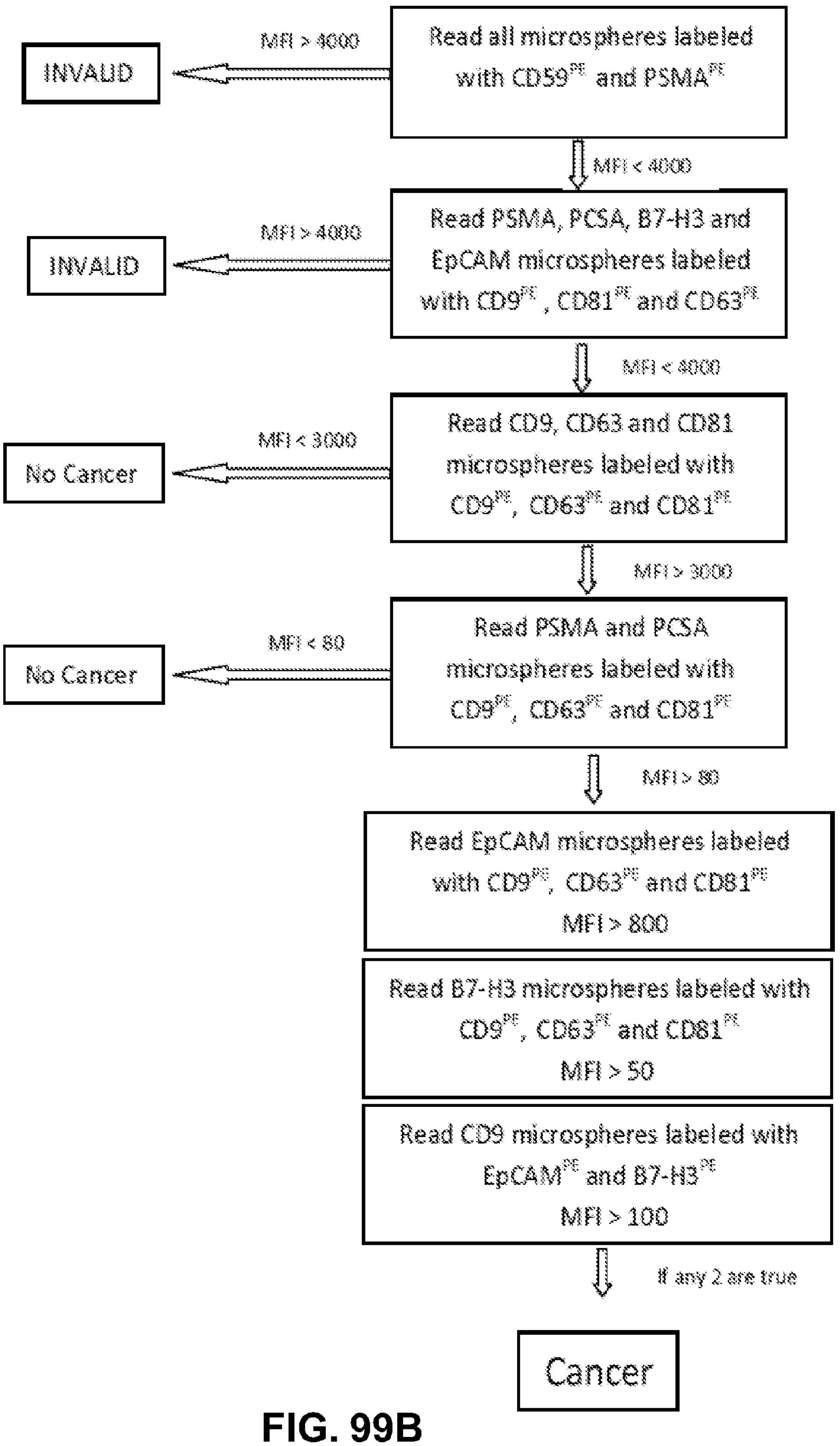
Figure 99C:
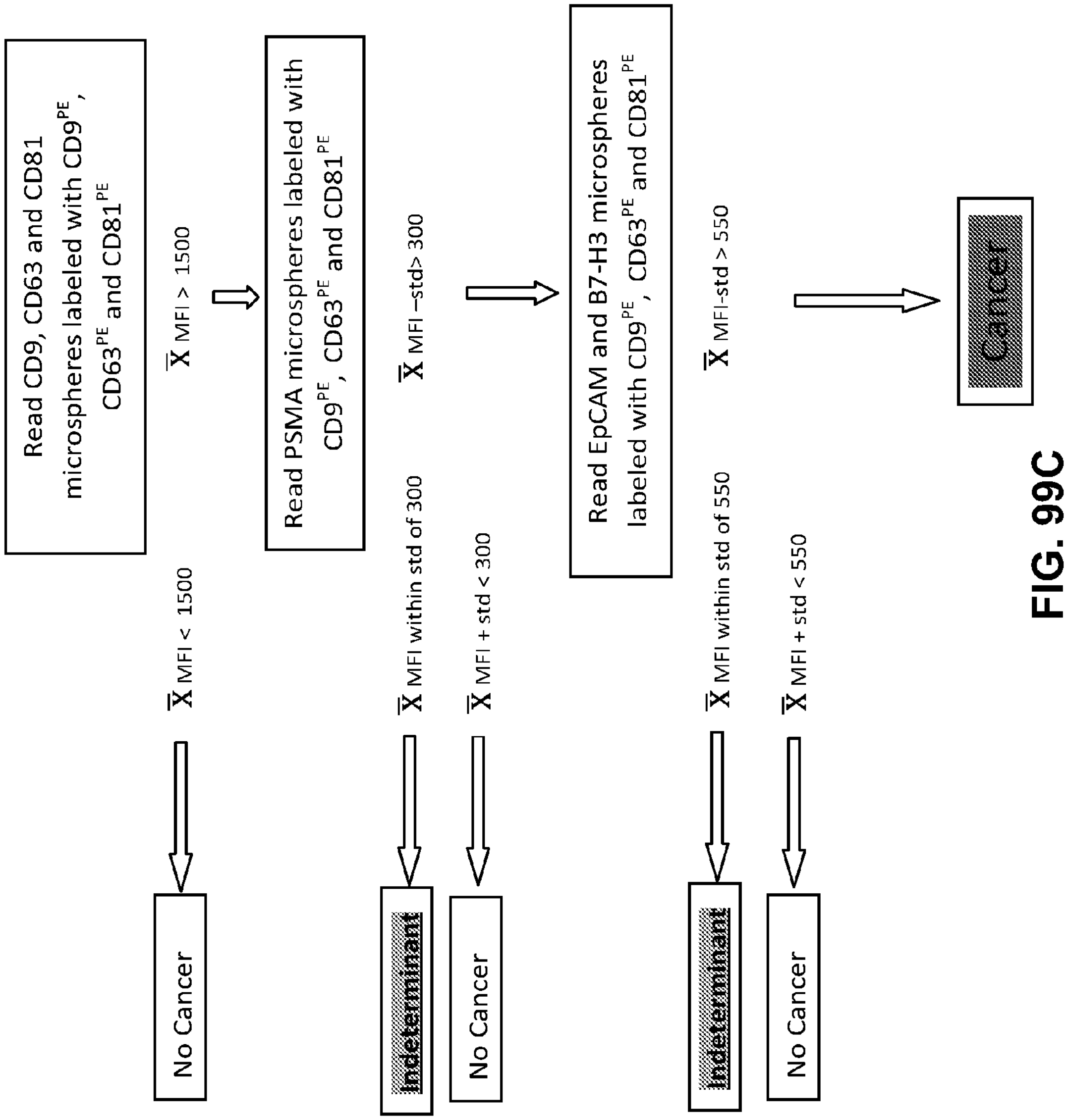
Figure 99D:
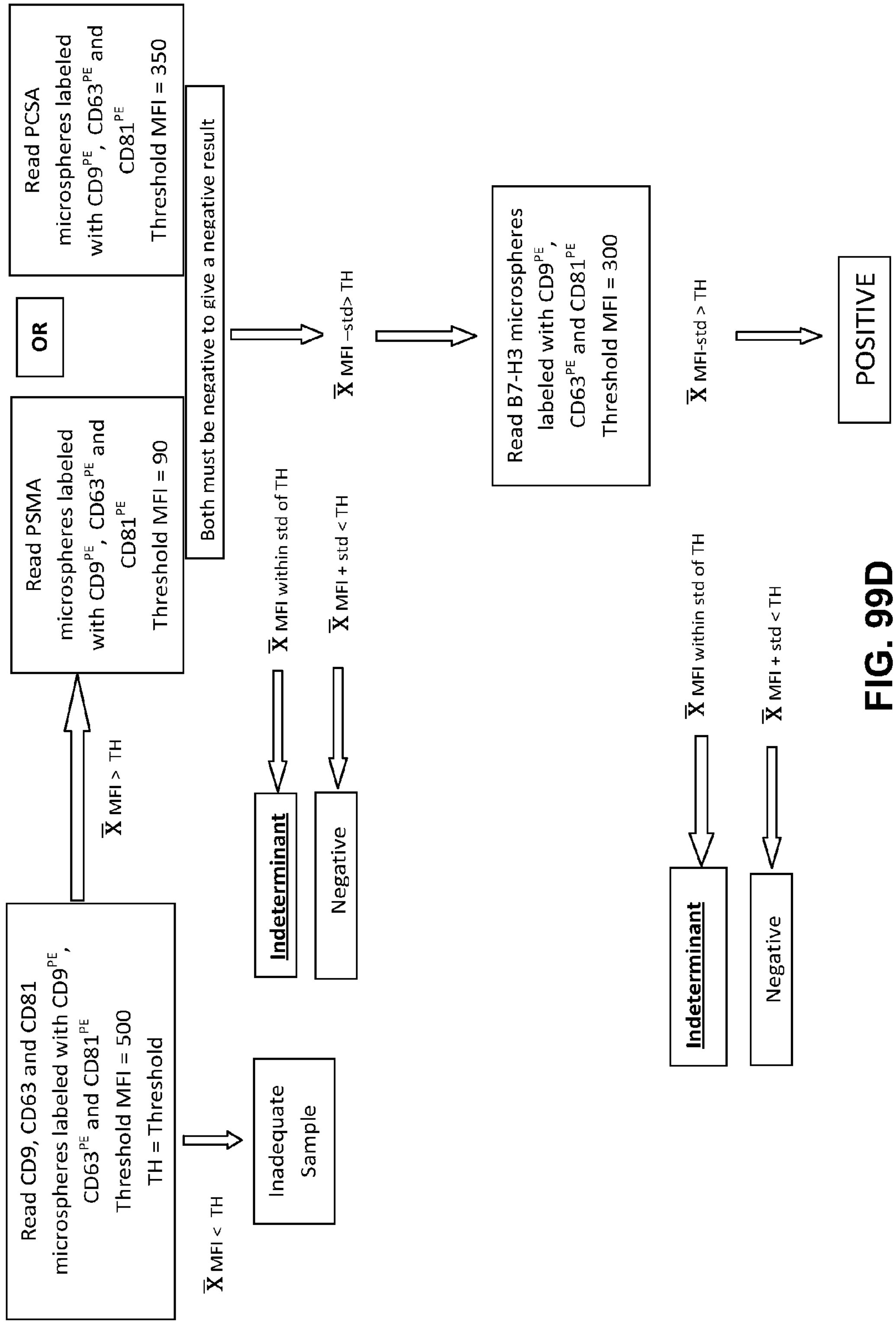

Decision Tree:

A decision tree (FIG. 99B-D) is used to assess the results from the microsphere assay to determine if a subject has cancer. Threshold limits on the MFI is established and samples classified according to the result of MFI scores for the antibodies, to determine whether a sample has sufficient signal to perform analysis (e.g., is a valid sample for analysis or an invalid sample for further analysis, in which case a second patient sample may be obtained) and whether the sample is PCa positive. FIG. 99B shows a decision tree using the MFI obtained with CD59, PSMA, PCSA, B7-H3, EpCAM, CD9, CD81 and CD63. FIG. 99C shows a decision tree using the MFI obtained with PSMA, B7-H3, EpCAM, CD9, CD81 and CD63. A sample is classified as indeterminate if the MFI is within the standard deviation of the predetermined threshold. For validation, the sample must have sufficient signal when capturing vesicles with the individual tetraspanins and labeling with all tetraspanins. A sample that passes validation is called positive if the prostate-specific marker (PSMA) is considered positive and the joint signal of the cancer markers (B7-H3 and EpCam) is also considered positive. FIG. 99D shows a decision tree using the MFI obtained with PCSA, PSMA, B7-H3, CD9, CD81 and CD63. A sample is classified as indeterminate if the MFI is within the standard deviation of the predetermined threshold (TH). In this case, a second patient sample can be obtained. For validation, the sample must have sufficient signal when capturing vesicles with the individual tetraspanins and labeling with all tetraspanins. A sample that passes validation is called positive if either of the prostate-specific markers (PSMA or PCSA) is considered positive, and the cancer marker (B7-H3) is also considered positive.

Example 22

Vesicle Protein Array

In this example, the vesicle PCa test is performed using a protein array, more specifically an antibody array, for the detection of a set of protein biomarkers present on the vesicles from plasma of patients with prostate cancer. The array comprises capture antibodies specific to the following protein biomarkers: CD9, CD59, CD63, CD81, PSMA, PCSA, B7H3 and EpCAM. Vesicles are isolated as described herein. After filtration and isolation of the vesicles from plasma of men at risk for PCa (those over the age of 50), the plasma samples are incubated with an array harboring the various capture antibodies. Depending on the level of binding of fluorescently labeled detection antibodies to general vesicle markers (CD9, CD81 and/or CD63) that bind to the vesicles from a patient's plasma that hybridize to the array, a determination of the presence or absence of prostate cancer is made. The determination of sample validation and detection of prostate cancer can be made using a decision tree as in FIG. 99. In a similar analysis, the captured antibodies are labeled with a labeling agent for membrane surface proteins. See, e.g., Alroy et al., US 2005/0158708.

In a second array format, the vesicles are isolated from plasma and hybridized to an array containing binding agents for the prostate-specific and cancer specific markers PSMA, PCSA, B7H3 and EpCAM. The captured vesicles are labeled with antibodies to general vesicle markers (CD9, CD59, CD63, CD81) labeled with Cy3 and/or Cy5. The fluorescence is detected. Depending on the pattern of binding, a determination of the presence or absence of prostate cancer is made. The determination of sample validation and detection of prostate cancer can be made using a decision tree as in FIG. 99.

In a third array format, the vesicles are isolated from plasma and hybridized to an array containing binding agents to general vesicle biomarkers including antibodies to CD9, CD59, CD63, and CD81. The captured vesicles are tagged with binding agents to prostate-specific (PSMA, PCSA) and cancer-specific (B7H3 and EpCAM) antibodies labeled with Cy3 and/or Cy5. The fluorescence is detected. Depending on the pattern of binding, a determination of the presence or absence of prostate cancer is made. The determination of sample validation and detection of prostate cancer can be made using a decision tree as in FIG. 99.

Example 23

FACS Analysis

Purified plasma vesicles are assayed using the MoFlo XDP (BC, Fort Collins, Colo., USA) and the median fluorescent intensity analyzed using the Summit 4.3 Software (BC, Fort Collins, Colo., USA). Cells are labeled directly with antibodies, or beads or microspheres (e.g., magnetic, polystyrene, including BD FACS 7-color setup, catalog no. 335775) can be incorporated. Microplex microspheres are obtained from Luminex (Austin, Tex., USA) and conjugated to the following antibodies, CD9 (Mouse anti-human CD9, MAB1880, R&D Systems, Minneapolis, Minn., USA), PSM (Mouse anti-human PSM, sc-73651, Santa Cruz, Santa Cruz, Calif., USA), PCSA (Mouse anti-human Prostate Cell Surface Antigen, MAB4089, Millipore, Mass., USA), CD63 (Mouse anti-human CD63, 556019, BD Biosciences, San Jose, Calif., USA), CD81 (Mouse anti-human CD81, 555675, BD Biosciences, San Jose, Calif., USA) B7-H3 (Goat anti-human B7-H3, AF1027, R&D Systems, Minneapolis, Minn., USA), EpCAM (Mouse anti-human EpCAM, MAB9601, R&D Systems, Minneapolis, Minn., USA) using Sulfo-NHS, and EDC obtained from Pierce Thermo (Cat. No. 24510 and 22981, respectively, Rockford, Ill., USA).

Purified membrane vesicles (1 Oug/ml) are incubated with 5,000 microspheres for one hour at room temperature with shaking. The samples ae washed in FACS buffer (0.5% FBS/PBS) for 10 minutes at 1700 rpms. The detection antibodies are incubated at the manufacturer's recommended concentrations for one hour at room temperature with shaking. Following another wash with FACS buffer for 10 minutes at 1700 rpms, the samples are resuspended in 100 μl FACS buffer and run on the FACS machine. Microspheres are sorted according to their detection antibody content into four different tubes. The first contains the population of microspheres with no detectors, the second with PE detectors, the third with FITC detectors, and the fourth with both PE and FITC detectors.

Example 24

Obtaining Serum Samples from Subjects

Blood is collected from subjects (both healthy subjects and subjects with prostate cancer) in EDTA tubes, citrate tubes or in a 10 ml Vacutainer SST plus Blood Collection Tube (BD367985 or BD366643, BD Biosciences). Blood is processed for plasma isolation within 2 h of collection.

Samples are allowed to sit at room temperature for a minimum of 30 min and a max of 2 h. Separation of the clot is accomplished by centrifugation at 1,000-1,300×g at 4° C. for 15-20 min. The serum is removed and dispensed in aliquots of 500 μl into 500 to 750 μl cryotubes. Specimens are stored at −80° C.

At a given sitting, the amount of blood drawn can range from ~20 to ~90 ml. Blood from several EDTA tubes is pooled and transferred to RNase/DNase-free 50-m1 conical tubes (Greiner), and centrifuged at 1,200×g at room temperature in a Hettich Rotanta 460R benchtop centrifuge for 10 min. Plasma is transferred to a fresh tube, leaving behind a fixed height of 0.5 cm plasma supernatant above the pellet to avoid disturbing the pellet. Plasma is aliquoted, with inversion to mix between each aliquot, and stored at −80° C.

Example 25

RNA Isolation From Human Plasma and Serum Samples

Four hundred μl of human plasma or serum is thawed on ice and lysed with an equal volume of 2× Denaturing Solution (Ambion). RNA is isolated using the mirVana PARIS kit following the manufacturer's protocol for liquid samples (Ambion), modified such that samples are extracted twice with an equal volume of acid-phenol chloroform (as supplied by the Ambion kit). RNA is eluted with 105 μl of Ambion elution solution according to the manufacturer's protocol. The average volume of eluate recovered from each column is about 80 μl.

A scaled-up version of the mirVana PARIS (Ambion) protocol is also used: 10 ml of plasma is thawed on ice, two 5-ml aliquots are transferred to 50-m1 tubes, diluted with an equal volume of mirVana PARIS 2X Denaturing Solution, mixed thoroughly by vortexing for 30 s and incubated on ice for 5 min. An equal volume (10 ml) of acid/phenol/chloroform (Ambion) is then added to each aliquot. The resulting solutions are vortexed for 1 min and spun for 5 min at 8,000 rpm, 20° C. in a JA 17 rotor. The acid/phenol/chloroform extraction is repeated three times. The resulting aqueous volume is mixed thoroughly with 1.25 volumes of 100% molecular-grade ethanol and passed through a mirVana PARIS column in sequential 700-μl aliquots. The column is washed following the manufacturer's protocol, and RNA is eluted in 105 μl of elution buffer (95° C.). A total of 1.5 μl of the eluate is quantified by Nanodrop.

Example 26

Measurement of miRNA Levels in RNA from Plasma and Serum Using qRT-PCR

A fixed volume of 1.67 μl of RNA solution from about ~80 μl-eluate from RNA isolation of a given sample is used as input into the reverse transcription (RT) reaction. For samples in which RNA is isolated from a 400-μl plasma or serum sample, for example, 1.67 μl of RNA solution represents the RNA corresponding to (1.67/80)×400=8.3 μl plasma or serum. For generation of standard curves of chemically synthesized RNA oligonucleotides corresponding to known miRNAs, varying dilutions of each oligonucleotide are made in water such that the final input into the RT reaction has a volume of 1.67 μl. Input RNA is reverse transcribed using the TaqMan miRNA Reverse Transcription Kit and miRNA-specific stem-loop primers (Applied BioSystems) in a small-scale RT reaction comprised of 1.387 μl of H2O, 0.5 μl of 10X Reverse-Transcription Buffer, 0.063 μl of RNase-Inhibitor (20 units/μl), 0.05 μl of 100 mM dNTPs with dTTP, 0.33 μl of Multiscribe Reverse-Transcriptase, and 1.67 μl of input RNA; components other than the input RNA can be prepared as a larger volume master mix, using a Tetrad2 Peltier Thermal Cycler (BioRad) at 16° C. for 30 min, 42° C. for 30 min and 85° C. for 5 min. Real-time PCR is carried out on an Applied BioSystems 7900HT thermocycler at 95° C. for 10 min, followed by 40 cycles of 95° C. for 15 s and 60° C. for 1 min. Data is analyzed with SDS Relative Quantification Software version 2.2.2 (Applied BioSystems.), with the automatic Ct setting for assigning baseline and threshold for Ct determination.

The protocol can also be modified to include a preamplification step, such as for detecting miRNA. A 1.25-μl aliquot of undiluted RT product is combined with 3.75 μl of Preamplification PCR reagents [comprised, per reaction, of 2.5 μl of TaqMan PreAmp Master Mix (2×) and 1.25 μl of 0.2× TaqMan miRNA Assay (diluted in TE)] to generate a 5.0 μl preamplification PCR, which is carried out on a Tetrad2 Peltier Thermal Cycler (BioRad) by heating to 95° C. for 10 min, followed by 14 cycles of 95° C. for 15 s and 60° C. for 4 min. The preamplification PCR product is diluted (by adding 20 μl of H2O to the 5-μl preamplification reaction product), following which 2.25 μl of the diluted material is introduced into the real-time PCR and carried forward as described.

Example 27

Generation of Standard Curves for Absolute Quantification of miRNAs

Synthetic single-stranded RNA oligonucleotides corresponding to the mature miRNA sequence (miRBase Release v.10.1) are purchased from Sigma. Synthetic miRNAs are input into the RT reaction over an empirically-derived range of copies to generate standard curves for each of the miRNA TaqMan assays listed above. In general, the lower limit of accurate quantification for each assay is designated based on the minimal number of copies input into an RT reaction that results in a Ct value within the linear range of the standard curve and that is also not equivalent to or higher than a Ct obtained from an RT input of lower copy number. A line is fit to data from each dilution series using Ct values within the linear range, from which y=m1n(x)+b equations are derived for quantification of absolute miRNA copies (x) from each sample Ct (y). Absolute copies of miRNA input into the RT reaction are converted to copies of miRNA per microliter plasma (or serum) based on the knowledge that the material input into the RT reaction corresponds to RNA from 2.1% of the total starting volume of plasma [i.e., 1.67 μl of the total RNA eluate volume (80 μl on average) is input into the RT reaction]. An example of a synthetic miRNA sequence is for miR-141 which can be obtained commercially such as from Sigma (St. Louis, Mo.).

Example 28

Extracting microRNA from Vesicles

MicroRNA is extracted from vesicles isolated from patient samples. Methods for isolation and concentration of vesicles are presented herein. The methods in the Example can be used to isolate microRNA from patient samples without first isolating vesicles as well.

Protocol Using Trizol

This protocol uses the QIAzol Lysis Reagent and RNeasy Midi Kit from Qiagen Inc., Valencia Calif. to extract microRNA from concentrated vesicles. The steps of the method comprise:

1. Add 2 μl of RNase A to 50 μl of vesicle concentrate, incubate at 37° C. for 20 min.
2. Add 700 μl of QIAzol Lysis Reagent, vortex 1 minute. Spike samples with 25 fmol/μL of *C. elegans* microRNA (1 μL) after the addition of QIAzol, making a 75 fmol/μL, spike in for each total sample (3 aliquots combined).
3. Incubate at 55° C. for 5 min.
4. Add 140 μl chloroform and shake vigorously for 15 sec.
5. Cool on ice for 2-3 min.
6. Centrifuge @ 12,000×g at 4° C. for 15 min.
7. Transfer aqueous phase (300 μL) to a new tube and add 1.5 volumes of 100% EtOH (i.e., 450 μL).
8. Pipet up to 4 ml of sample into an RNeasy Midi spin column in a 15 ml collection tube (combining lysis from 3 50 μl of concentrate)
9. Spin at 2700×g for 5 min at room temperature.
10. Discard flowthrough from the spin.
11. Add 1 ml of Buffer RWT to column and centrifuge at 2700×g for 5 min at room temperature. Do not use Buffer RW1 supplied in the Midi kit. Buffer RW1 can wash away miRNA. Buffer RWT is supplied in the Mini kit from Qiagen Inc.
12. Discard flowthrough.
13. Add 1 ml of Buffer RPE onto the column and centrifuge at 2700×g for 2 min at room temperature.
14. Repeat steps 12 and 13.
16. Place column into a new 15 ml collection tube and add 150 ul Elution Buffer. Incubate at room temperature for 3 min.
17. Centrifuge at 2700×g for 3 min at room temperature.
18. Vortex the sample and transfer to 1.7 mL tube. Store the extracted sample at −80° C.

Protocol Using MagMax

This protocol uses the MagMAX™ RNA Isolation Kit from Applied Biosystems/Ambion, Austin, Tex. to extract microRNA from concentrated vesicles. The steps of the method comprise:

1. Add 700 ml of QIAzol Lysis Reagent and vortex 1 minute.
2. Incubate on benchtop at room temperature for 5 min.
3. Add 140 μl chloroform and shake vigorously for 15 sec.
4. Incubate on benchtop for 2-3 min.
5. Centrifuge at 12,000×g at 4° C. for 15 min.
6. Transfer aqueous phase to a deep well plate and add 1.25 volumes of 100% Isopropanol.
7. Shake MagMAX™ binding beads well. Pipet 10 μl of RNA binding beads into each well.
8. Gather two elution plates and two additional deep well plates.
9. Label one elution plate "Elution" and the other "Tip Comb."
10. Label one deep well as "1st Wash 2" and the other as "2nd Wash 2."
11. Fill both Wash 2 deep well plates with 150 μl of Wash 2, being sure to add ethanol to wash beforehand. Fill in the same number of wells as there are samples.
12. Select the appropriate collection program on the MagMax Particle Processor.
13. Press start and load each appropriate plate.
14. Transfer samples to microcentrifuge tubes.
15. Vortex and store at −80° C. Residual beads will be seen in sample.

Example 29

MicroRNA Arrays

TaqMan Low Density Array

TaqMan Low Density Array (TLDA) miRNA cards are used to compare expression of miRNA in various sample groups as desired. The miRNA are collected and analyzed using the TaqMan® MicroRNA Assays and Arrays systems from Applied Biosystems, Foster City, Calif. Applied Biosystems TaqMan® Human MicroRNA Arrays are used according to the Megaplex™ Pools Quick Reference Card protocol supplied by the manufacturer.

Exiqon mIRCURY LNA microRNA

The Exiqon miRCURY LNA™ Universal RT microRNA PCR Human Panels I and II (Exiqon, Inc, Woburn, Mass.) are used to compare expression of miRNA in various sample groups as desired. The Exiqon 384 well panels include 750 miRs. Samples are normalized to control primers towards synthetic RNA spike-in from Universal cDNA synthesis kit (UniSp6 CP). Results were normalized to inter-plate calibrator probes.

With either system, quality control standards are implemented. Normalized values for each probe across three data sets for each indication are averaged. Probes with an average CV % higher than 20% are not used for analysis. Results are subjected to a paired t-test to find differentially expressed miRs between two sample groups. P-values are corrected with a Benjamini and Hochberg false-discovery rate test. Results are analyzed using using GeneSpring GX 11.0 software (Agilent Technologies, Inc., Santa Clara, Calif.).

Example 30

Vesicle Biosignature for Colorectal Cancer (CRC)

Concentrated vesicle plasma samples were run on a bead-based detection platform as described above. Antibodies to various vesicle surface antigens were attached to beads and used to capture vesicles. Several antibodies showed significant differences between samples derived from CRC and normal patients. The captured vesicles were labeled with PE-labeled antibodies to CD9, CD63, and CD81. The captured and labeled vesicles were detected using laser fluorescence.

Figure 100A:
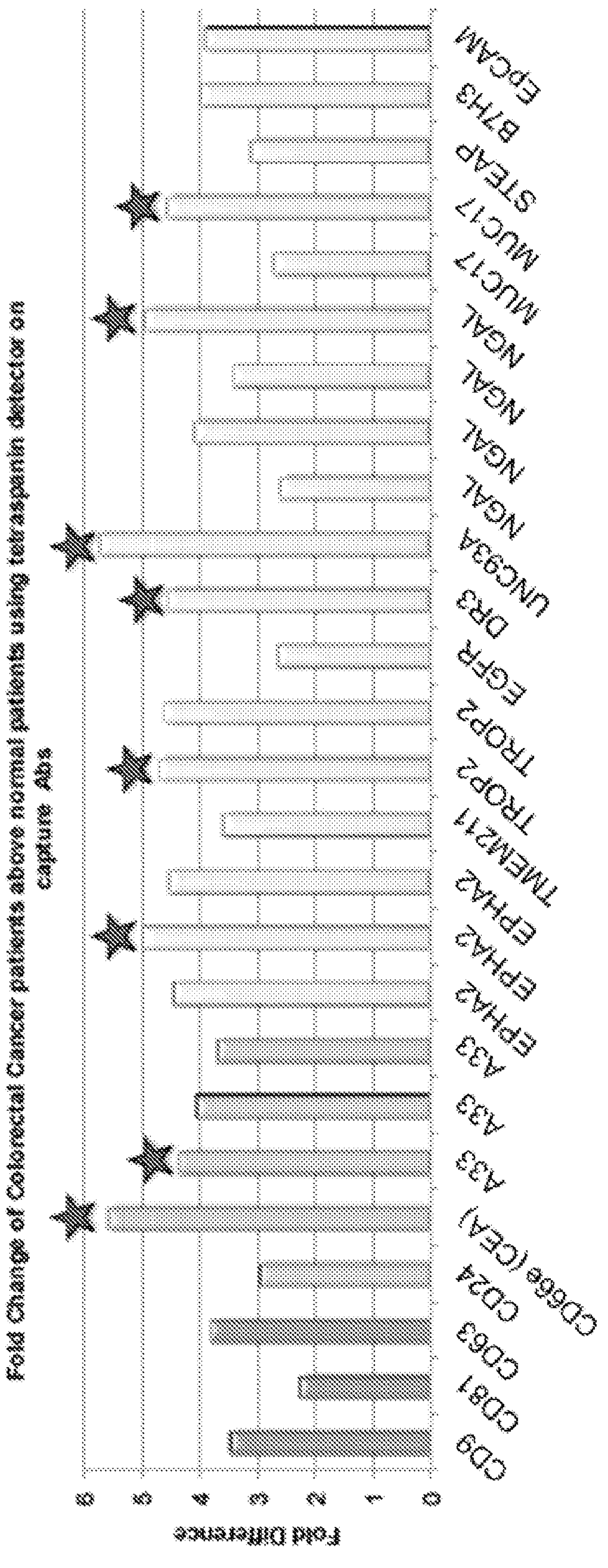
FIG. 100A-C illustrate the ability of various capture antibodies used to capture vesicles that distinguish colorectal cancer (CRC) versus normal samples.

CRC detection using antibody capture of vesicles was performed using 128 total samples consisting of vesicles isolated from plasma of 49 normals (i.e., healthy, non-CRC), 20 confounders (diseased, non-CRC), and 59 CRC. Confounder samples included those having rheumatoid arthritis, asthma, diabetes, bladder cell carcinoma, renal cell carcinoma, and chronic or acute diverticulitis. Of the CRC samples, 16 were Stage I, 19 were Stage II, and 24 were Stage III. FIG. 100A shows discrimination of Normal and CRC samples using antibodies to multiple biomarkers to capture and labeled anti-tetraspanin antibodies (CD9, CD63, and CD81) to detect vesicles. Capture antibodies are shown on the X axis and fold change in vesicles detected CRC samples as compared to normals is shown on the Y axis. The capture antibodies comprise CD9, CD81, CD63, CD24, CD66e (CEA), A33, EPHA2, TMEM211, TROP2, EGFR, DR3, UNC93A, NGAL, MUC17, STEAP, B7H3 and EpCAM. As seen in the figure, multiple capture antibodies were used to detect certain markers. Table 17 below shows sensitivity and specificity obtained with various capture antibodies:

TABLE 17

CRC Detection by Capture of Vesicles

| Marker | DR3 | STEAP | Epha2 | TMEM211 | UNC93A | A33 | CD24 | NGAL | EpCam | MUC17 | TROP2 | TETS |
|---|---|---|---|---|---|---|---|---|---|---|---|---|
| Specificity | 86% | 71% | 83% | 84% | 84% | 75% | 77% | 81% | 62% | 77% | 80% | 80% |
| Sensitivity | 82% | 100% | 90% | 100% | 86% | 100% | 98% | 94% | 90% | 86% | 96% | 86% |

The transmembrane protein 211 (TMEM211) gene encodes a transmembrane protein. Using TMEM211 as the capture antibody and detection antibodies CD9, CD63, CD81, the performance was obtained for detection of CRC as shown in Table 18:

TABLE 18

CRC Detection using TMEM211

| True Positive | 59 |
|---|---|
| True Negative | 58 |
| False Positive | 11 |
| False Negative | 0 |
| Total | 128 |

| Sensitivity | Specificity |
|---|---|
| 100.00% | 84.06% |

Figure 100B:
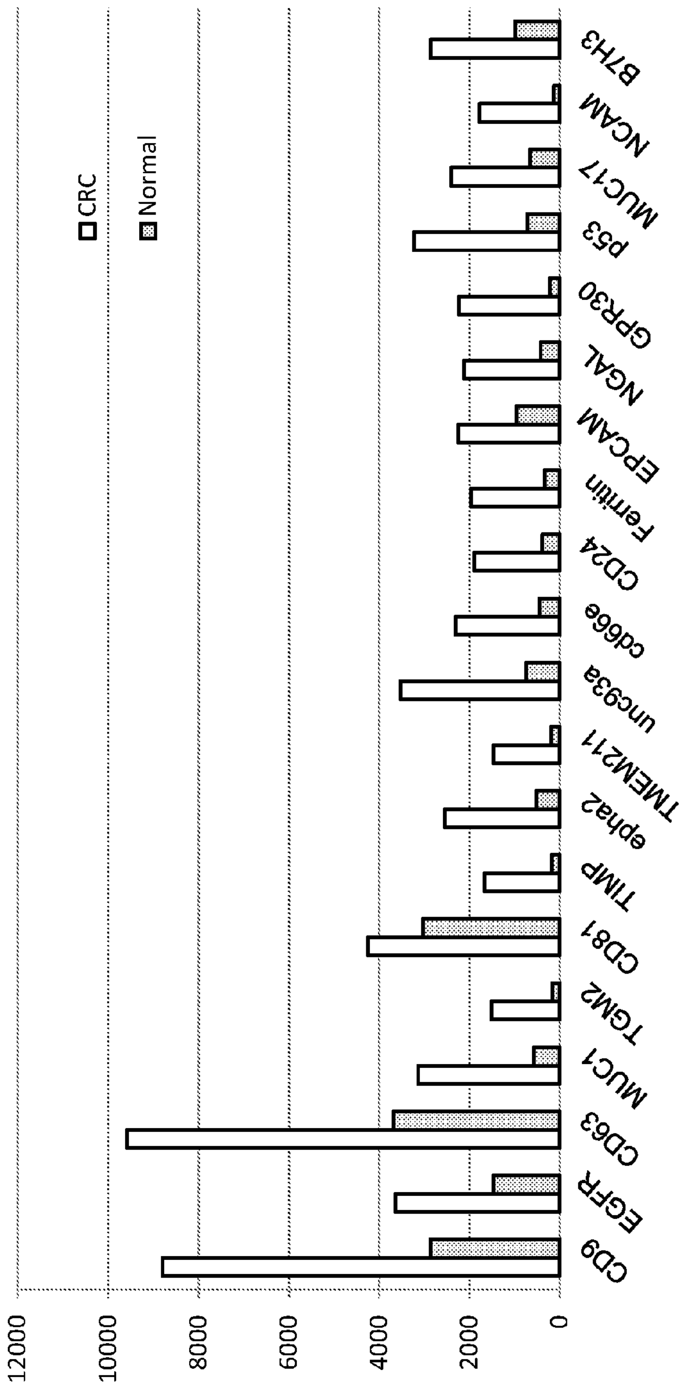
Figure 100C:
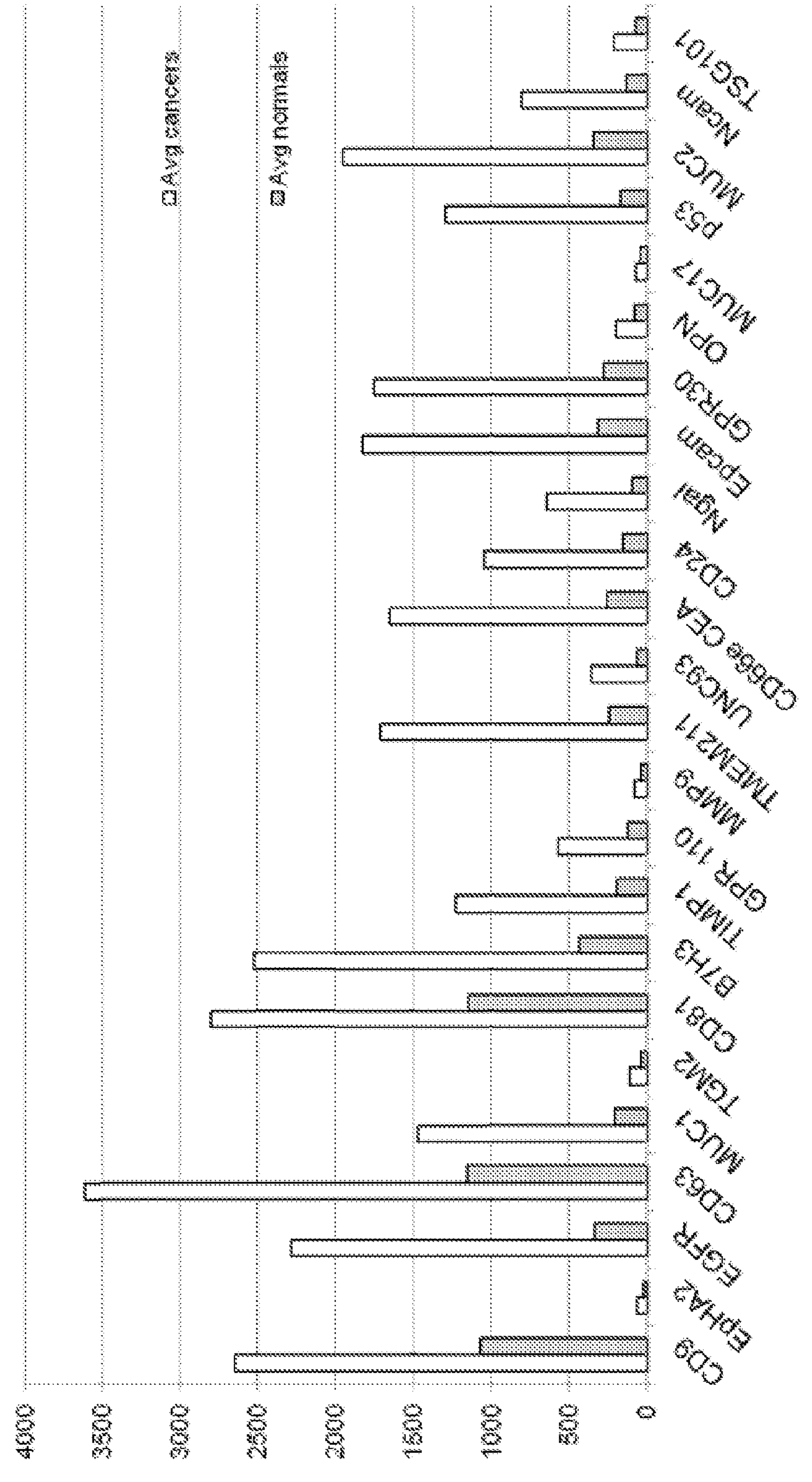

FIG. 100B shows results from similar experiments except that the Y-axis represents the median fluorescence intensity (MFI) in CRC and normal samples as indicated by the legend. The capture antibodies as shown on the X-axis are CD9, EGFR, CD63, MUC1, TGM2, CD81, TIMP, EPHA2, TMEM211, UNC93A, CD66e, CD24, Ferritin, EpCAM, NGAL, GPR30, p53, MUC17, NCAM and B7H3. The experiments as shown in FIG. 100B were repeated with a second sample set of 10 CRC samples and 10 normal. Results are shown in FIG. 100C. The capture antibodies as shown on the X-axis are CD9, EPHA2, EGFR, CD63, MUC1, TGM2, CD81, TIMP1, GPR110, MMP9, TMEM21 I, UNC93, CD66e, CD24, Nga1, EpCAM, GPR30, OPN, MUC17, p53, MUC2, Ncam and TSG101. In both cases, the capture antibodies are shown on the X axis and the detection antibodies were PE-labeled antibodies to CD9, CD63 and CD81.

The ability to assay multiple vesicle biomarkers in a single multiplexed experiment can be used to create a biosignature for colorectal cancer and for discovery of optimal target biomarkers for additional biosignatures. The same techniques can be applied in various settings (e.g., different diseases, different cancers, different target biomarkers, diagnosis, prognosis, theranosis, etc.) to identify novel biomarkers for subsequent assay development.

Example 31

KRAS Sequencing in CRC Samples

KRAS RNA was isolated from vesicles derived from CRC cell lines and sequenced. RNA was converted to cDNA prior to sequencing using standard methodology. DNA sequencing (Sanger method) was performed on the cell lines listed in Table 19:

TABLE 19

CRC cell lines and KRAS sequence

| Cell Line | DNA or Vesicle cDNA | KRAS Genotype Exon 2 | KRAS Genotype Exon 3 |
|---|---|---|---|
| Colo 205 | Vesicle cDNA | WT | WT |
| Colo 205 | DNA | WT | WT |
| HCT 116 | Vesicle cDNA | c.13G > GA | WT |
| HCT 116 | DNA | c.13G > GA | WT |
| HT29 | Vesicle cDNA | WT | WT |
| Lovo | Vesicle cDNA | c.13G > GA | WT |
| Lovo | DNA | c.13G > GA | WT |
| RKO | Vesicle cDNA | WT | WT |
| SW 620 | Vesicle cDNA | c.12G > T | WT |

Table 19 and FIG. 101 show that the mutations detected in the genomic DNA from the cell lines was also detected in RNA contained within exoxomes derived from the cell lines. FIG. 101 shows the sequence in HCT116 cells of cDNA derived from exosomal mRNA in (FIG. 101A) and genomic DNA (FIG. 101B).

Twelve CRC patient samples were sequenced for KRAS. As shown in Table 20, all were WT. All patient samples received a DNase treatment during RNA Extraction. RNA was extracted from isolated vesicles. All 12 patients amplified for GAPDH demonstrating RNA was present in their vesicles.

TABLE 20

CRC patient samples and KRAS sequence

| Sample | Sample Type | Stage | KRAS Genotype Exon 2 | KRAS Genotype Exon 3 |
|---|---|---|---|---|
| 61473a6 | Colon Ca | 1 | WT | WT |
| 62454a4 | Colon Ca | 1 | WT | WT |
| 110681a4 | Colon Ca | 1 | WT | Failed sequencing |
| 28836a7 | Colon Ca | 1 | WT | Failed sequencing |
| 62025a2 | Colon Ca | 2a | WT | WT |

TABLE 20-continued

| CRC patient samples and KRAS sequence | | | | |
|---|---|---|---|---|
| Sample | Sample Type | Stage | KRAS Genotype Exon 2 | KRAS Genotype Exon 3 |
| 62015a4 | Colon Ca | 2a | WT | WT |
| 110638a3 | Colon Ca | 2a | WT | WT |
| 110775a3 | Colon Ca | 2a | WT | WT |
| 35512a5 | Colon Ca | 3 | WT | WT |
| 73231al | Colon Ca | 2a | WT | WT |
| 85823a3 | Colon Ca | 3b | WT | WT |
| 23440a7 | Colon Ca | 3c | WT | WT |
| 145151A2/3 | Normal | | WT | WT |
| 139231A3 | Normal | | WT | Failed sequencing |
| 145155A4 | Normal | | WT | Failed sequencing |
| 145154A4 | Normal | | WT | Failed sequencing |

In another patient sample wherein the patient was found positive for the KRAS 13G>A mutation in a tumor sample, the KRAS mutation from the tumor of CRC patient samples could also be identified in plasma-derived vesicles from the same patient. FIG. 101 shows the sequence in this patient of cDNA derived from exosomal mRNA in plasma (FIG. 101C) and also genomic DNA derived from a fresh frozen paraffin embedded (FFPE) tumor sample (FIG. 101D).

Example 31

Vesicle Biosignatures for Breast Cancer (BCa)

Antibodies to a number of antigens of interest were tethered to beads and used to capture vesicles in blood samples from 10 subjects with breast cancer or 10 normals (i.e., no breast cancer) as described herein. Capture antibodies were directed to the vesicle antigens described in this Example. The bead captured vesicles were detected with fluorescently labeled antibodies against the tetraspanins CD9, CD63 and CD81. The median fluorescence intensity (MFI) of the captured and labeled vesicles was measured using laser detection.

The analysis was performed using a panel of capture antibodies. There were significant differences in the MFI of detected vesicles between breast cancer and normal plasma when analysis was performed using the following capture antibodies to the following vesicle antigens: CD9, HSP70, Ga13, MIS, EGFR, ER, ICB3, CD63, B7H4, MUC1, DLL4, CD81, ERB3, VEGF, BCA225, BRCA, CA125, CD174, CD24, ERB2, NGAL, GPR30, CYFRA21, CD31, cMET, MUC2 and ERB4.

Figure 102:
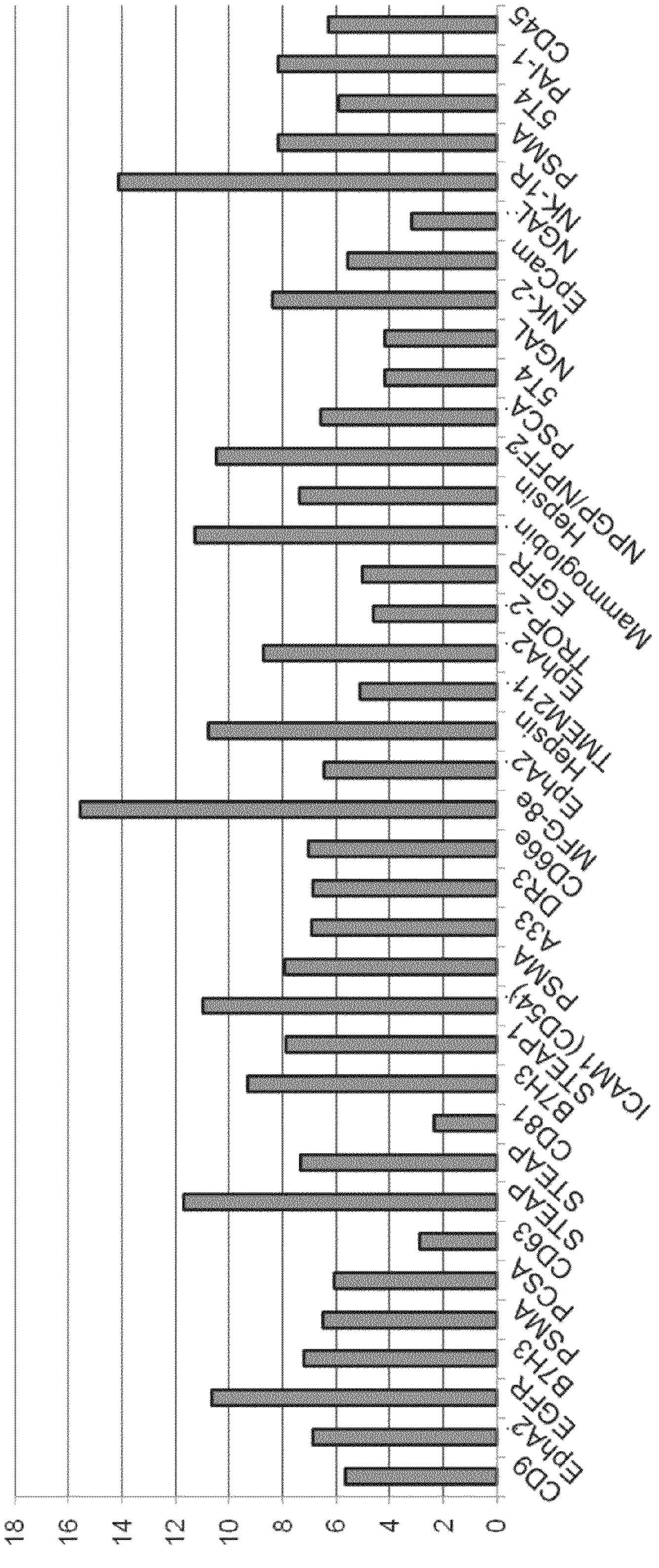
FIG. 102 illustrates a graph depicting the fold change over normal of biomarkers detected in breast cancer patient samples (n=10) or normal controls (i.e., no breast cancer). Vesicles in plasma samples were captured with antibodies to the indicated antigens tethered to beads. The captured vesicles were detected with labeled antibodies to tetraspanins CD9, CD63 and CD81. The fold change on the Y axis is the fold change median fluorescence intensity (MFI) of the vesicles detected in the breast cancer samples compared to normal.

Follow on experiments were performed using 10 breast cancer samples and 10 normal samples and additional capture antibodies. FIG. 102 illustrates a graph depicting the fold change over normal of the indicated biomarkers expressed in a breast cancer. The markers include from left to right CD9, EphA2, EGFR, B7H3, PSMA, PCSA, CD63, STEAP, STEAP, CD81, B7H3, STEAP1, ICAM1 (CD54), PSMA, A33, DR3, CD66e, MFG-8e, EphA2, Hepsin, TMEM211, EphA2, TROP-2, EGFR, Mammoglobin, Hepsin, NPGP/NPFF2, PSCA, 5T4, NGAL, NK-2, EpCam, NGAL, NK-1R, PSMA, 5T4, PAI-1, and CD45. Multiple bars for the same antigen indicate the use of different capture antibodies that may recognize different epitopes.

The ability to assay multiple vesicle biomarkers in a single multiplexed experiment can be used to create a biosignature for breast cancer and for discovery of optimal target biomarkers for additional biosignatures. The same techniques can be applied in various settings (e.g., different diseases, different cancers, different target biomarkers, diagnosis, prognosis, theranosis, etc.) to identify novel biomarkers for subsequent assay development.

Example 32

Vesicle Biosignatures for Lung Cancer (LCa)

Antibodies to a number of antigens of interest were tethered to beads and used to capture vesicles in plasma samples from subjects with lung cancer, normal controls (i.e., no lung cancer), or other diseases using methodology as described herein. Capture antibodies were directed to the vesicle antigens described in this Example. The bead captured vesicles were detected with fluorescently labeled antibodies against the tetraspanins CD9, CD63 and CD81. The median fluorescence intensity (MFI) of the captured and labeled vesicles was measured using laser detection.

In a first set of experiments, vesicles were detected following the methodology above in plasma samples from 10 normal control samples, 10 non-lung cancer samples, and 10 lung cancer samples as shown in Table 21.

TABLE 21

| Samples | |
|---|---|
| Diagnosis | Stage |
| Normal Control -male | NA |
| Normal Control -male | NA |
| Normal Control -male | NA |
| Normal Control -male | NA |
| Normal Control -male | NA |
| Normal Control - Female | NA |
| Normal Control - Female | NA |
| Normal Control - Female | NA |
| Normal Control - Female | NA |
| Normal Control - Female | NA |
| Endometrioid adenocarcinoma | Unstaged |
| Endometrioid adenocarcinoma | Unstaged |
| Infiltrating ductal carcinoma of the breast | Unstaged |
| Metastatic carcinoma of lymph node(from breast) | Unstaged |
| Metastatic carcinoma of lymph node(from breast) | Unstaged |
| Renal cell carcinoma of the kidney | Unstaged |
| Renal cell carcinoma of the kidney | Unstaged |
| Renal cell carcinoma of the kidney | Unstaged |
| Sclerosing stromal tumor of the ovary | Unstaged |
| Serous papillary cystadenoma of the ovary | Unstaged |
| Bronchioloalveolar carcinoma of the lung | IA |
| Large cell carcinoma of the lung | IIA |
| Squamous cell carcinoma of the lung | IIA |
| Squamous cell carcinoma of the lung | IA |
| Squamous cell carcinoma of the lung | IIA |
| Tubular adenocarcinoma of the lung | IB |
| Large cell carcinoma of the lung | IIB |
| Adenocarcinoma of the lung | IIB |
| Adenocarcinoma of the lung | IIIA |
| Adenocarcinoma of the lung | IB |

Figure 103A:
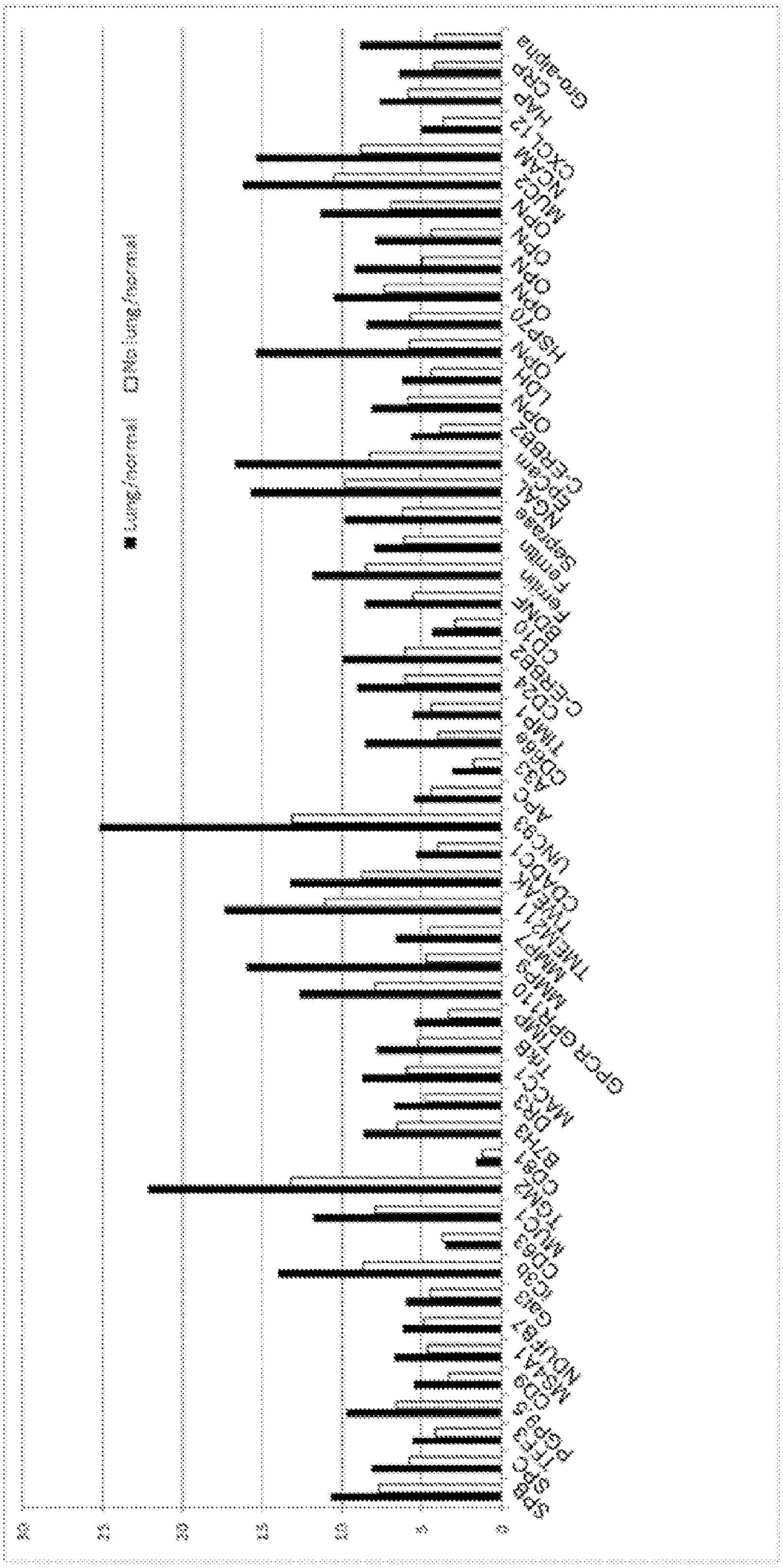
FIG. 103A illustrates a fold-change in various biomarkers in membrane vesicle from lung cancer samples as compared to normal samples detected using antibodies against the indicated vesicle antigens. Black bars are the ratios of lung cancer samples to normal samples. White bars are the ratios of non-lung cancer samples to normal samples. The underlying data is presented in FIG. 103B.
Figure 103B:
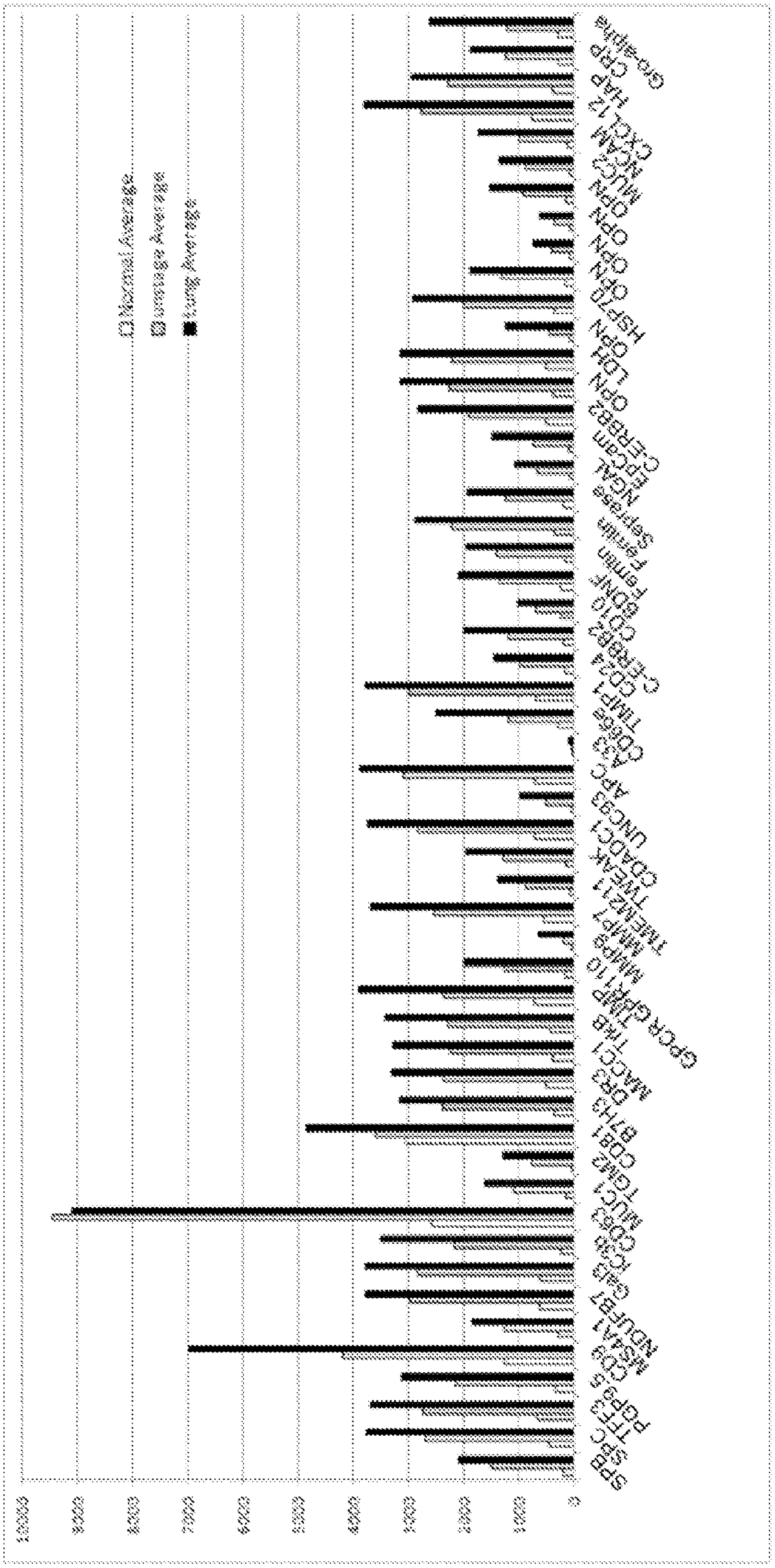
FIG. 103B illustrates fluorescence levels of membrane vesicles detected using antibodies against the indicated vesicle antigens. Fluorescence levels are averages from the following samples: normals (white), non-lung cancer samples (grey) and staged lung cancer samples (black).

Vesicles in the samples were captured using antibodies to the antigens listed in FIG. 103A and FIG. 103B using capture antibodies bound to beads. From left to right, the antigens in the figures are: SPB, SPC, TFF3, PGP9.5, CD9, MS4A1, NDUFB7, Cal3, iC3b, CD63, MUC1, TGM2, CD81, B7H3, DR3, MACC1, TrkB, TIMP1, GPCR (GPR110), MMP9, MMP1, TMEM211, TWEAK, CDADC1, UNC93, APC, A33, CD66e, TIMP1, CD24, ErbB2, CD10, BDNF, Ferritin, Ferritin, Seprase, NGAL, EpCam, ErbB2, Osteopontin (OPN), LDH, OPN, HSP70, OPN, OPN, OPN, OPN, MUC2, NCAM, CXCL12, Haptoglobin (HAP), CRP, and Gro-alpha. Different capture antibodies are used where the same antigen appears multiple times, e.g., Erbb2, Ferritin and Osteopontin. The different antibodies may recognize different epitopes of the same biomarker.

Figure 103C:
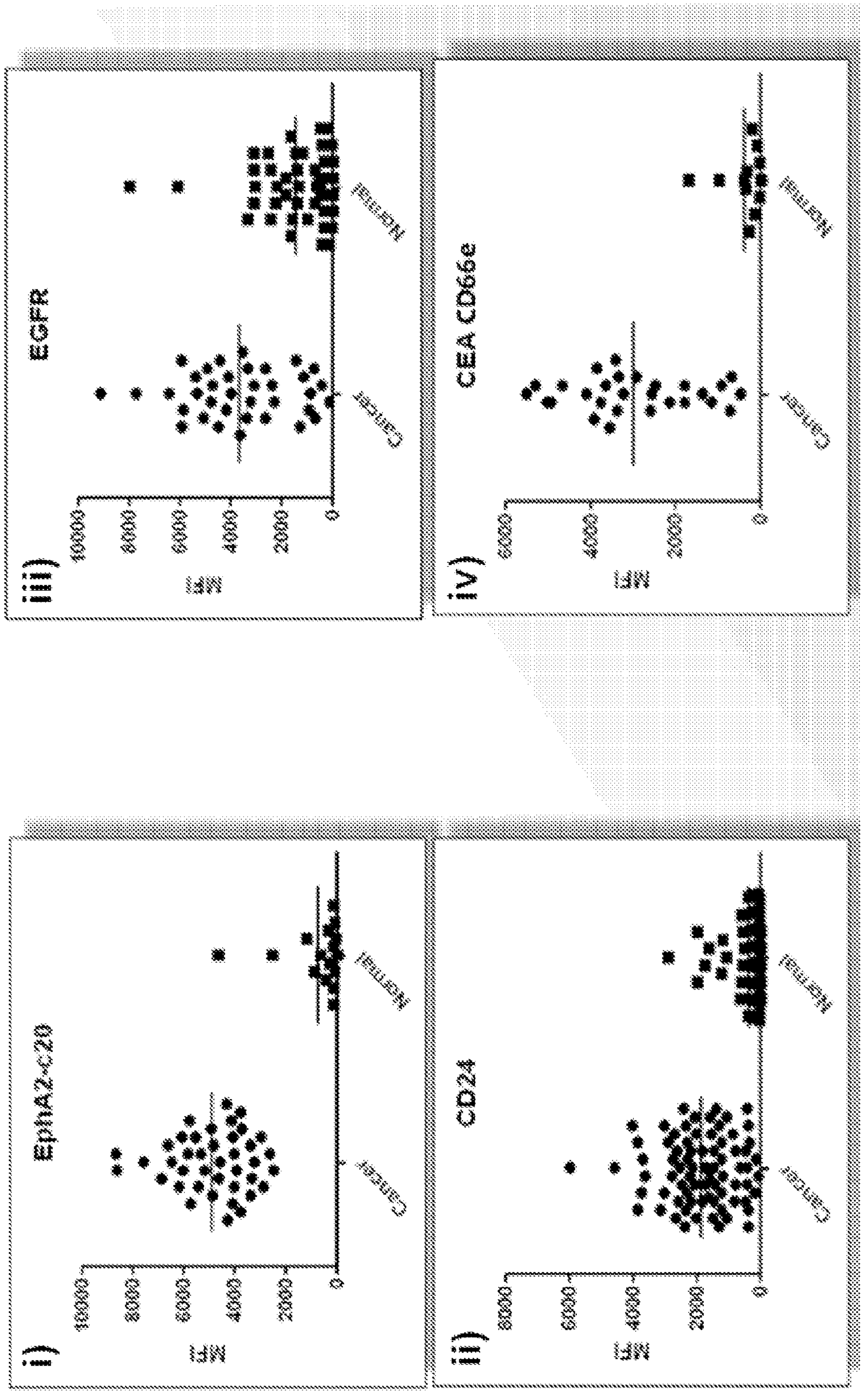
FIG. 103C shows the median fluorescence intensity (MFI) of vesicles detecting using EPHA2 (i), CD24 (ii), EGFR (iii), and CEA (iv) in samples from lung cancer patients and normal controls.

The captured vesicles were detected using fluorescently labeled antibodies to CD9, CD63 and CD81. The detected median fluorescence levels (MFI) are shown on the Y-axis in FIG. 103B. Ratios of the fluorescence in normals versus lung cancer samples, or normals versus non-lung cancer samples, are shown in FIG. 103A. FIG. 103C shows the MFI of EPHA2 (i), CD24 (ii), EGFR (iii), and CEA (iv) in samples from lung cancer patients and normal controls.

Figure 103D:
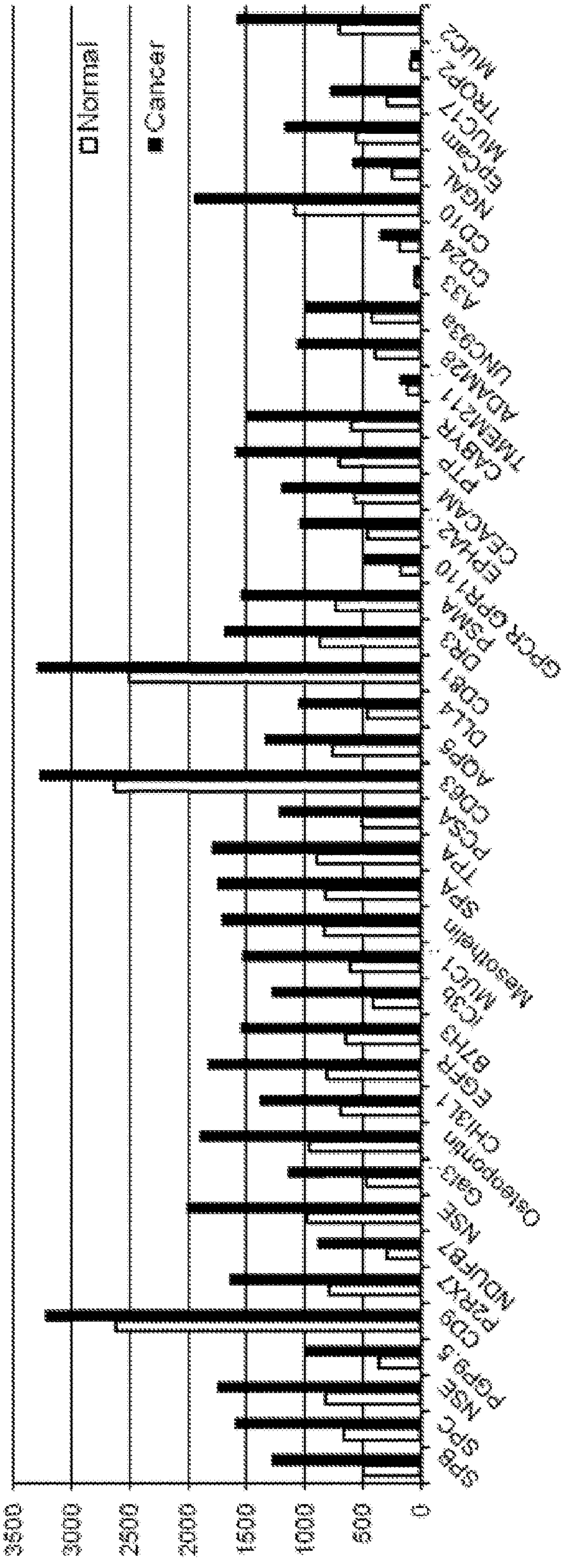
FIG. 103D and FIG. 103E present plots of mean fluorescence intensity (MFI) on the Y axis for vesicles detected in samples from lung cancer and normal (non-lung cancer) subjects. Capture antibodies are indicated along the X axis.

Concentrated microvesicle plasma samples from lung cancer and normal patients were collected and analyzed as in Examples 1 and 2. 69 patients were screened for 31 capture antibodies to vesicle surface antigens. FIG. 103D presents a graph of mean fluorescence intensity (MFI) on the Y axis for lung cancer and normal samples, with capture antibodies indicated along the X axis. The captured vesicles were detected using fluorescently labeled antibodies to CD9, CD63 and CD81. From left to right, the antigens in the figures are: SPB, SPC, NSE, PGP9.5, CD9, P2RX7, NDUFB7, NSE, Ga13, Osteopontin, CHI3L1, EGFR, B7H3, iC3b, MUC1, Mesothelin, SPA, TPA, PCSA, CD63, AQP5, DLL4, CD81, DR3, PSMA, GPCR 110 (GPR110), EPHA2, CEACAM, PTP, CABYR, TMEM211, ADAM28, UNC93a, A33, CD24, CD10, NGAL, EpCam, MUC17, TROP2 and MUC2. Antigens most able to distinguish between lung cancer and normal samples include SPB, SPC, PSP9.5, NDUFB7, Ga13, iC3b, MUC1, GPCR 110, CABYR and MUC17.

Figure 103E:
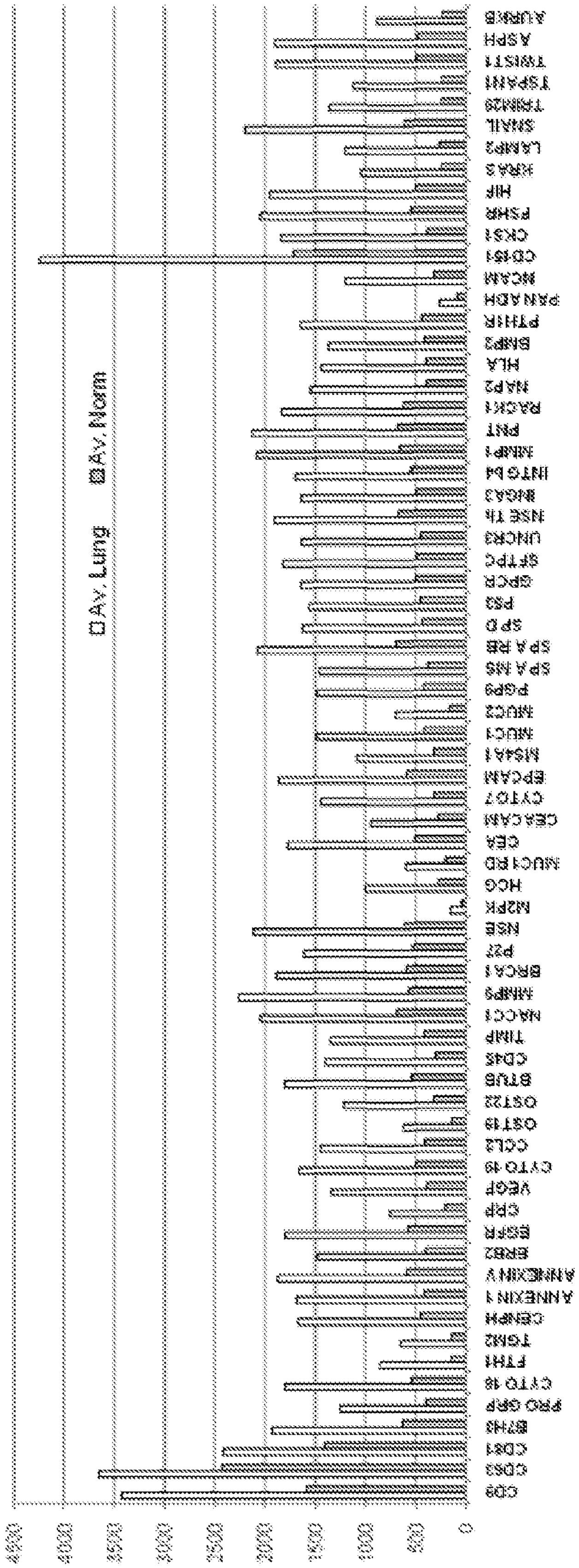

In another set of related experiments, the levels of a separate but overlapping panel of vesicle surface biomarkers was assessed in 115 lung and 78 normals samples. Of the lung cancer samples, there were 35 Stage I, 53 Stage II, and 27 Stage III lung cancers. As above, vesicles were captured in plasma samples from the cohort using capture antibodies to the indicated surface antigens, and the captured vesicles were detected with labeled detection antibodies to CD9, CD63 and CD81. Results are shown in Table 22 and FIG. 103E. From left to right, the antigens in the FIG. 103E are: CD9, CD63, CD81, B7H3, PRO GRP, CYTO 18, FTH1, TGM2, CENPH, ANNEXIN I, ANNEXIN V, ERB2, EGFR, CRP, VEGF, CYTO 19, CCL2, Osteopontin (OST19), Osteopontin (OST22), BTUB, CD45, TIMP, NACC1, MMP9, BRCA1, P27, NSE, M2PK, HCG, MUC1, CEA, CEACAM, CYTO 7, EPCAM, MS4A1, MUC1, MUC2, PGP9, SPA, SPA, SPD, P53, GPCR (GPR110), SFTPC, UNCR2, NSE, INGA3, INTG b4, MMP1, PNT, RACK1, NAP2, HLA, BMP2, PTH1R, PAN ADH, NCAM, CD151, CKS1, FSHR, HIF, KRAS, LAMP2, SNAIL, TRIM29, TSPAN1, TWIST1, ASPH and AURKB. Table 22 ranks the markers by accuracy for differentiating between cancer and non-cancer samples. As indicated in the table, not all markers were run on all samples due to sample quantity and the like.

TABLE 22

Marker Panel Results for Lung Cancer

| Marker | Sample Size | Sensitivity | Specificity | Accuracy | True Positive | True Negative | False Positive | False Negative |
|---|---|---|---|---|---|---|---|---|
| NSE | 117 | 57.38 | 96.43 | 76.07 | 35 | 54 | 2 | 26 |
| TRIM29 | 46 | 58.62 | 100 | 73.91 | 17 | 17 | 0 | 12 |
| CD63 | 76 | 74.07 | 68.18 | 72.37 | 40 | 15 | 7 | 14 |
| CD151 | 47 | 70 | 76.47 | 72.34 | 21 | 13 | 4 | 9 |
| ASPH | 47 | 60 | 94.12 | 72.34 | 18 | 16 | 1 | 12 |
| LAMP2 | 47 | 56.67 | 100 | 72.34 | 17 | 17 | 0 | 13 |
| TSPAN1 | 47 | 56.67 | 100 | 72.34 | 17 | 17 | 0 | 13 |
| SNAIL | 46 | 58.62 | 94.12 | 71.74 | 17 | 16 | 1 | 12 |
| CD45 | 164 | 50.55 | 95.89 | 70.73 | 46 | 70 | 3 | 45 |
| CKS1 | 47 | 53.33 | 100 | 70.21 | 16 | 17 | 0 | 14 |
| NSE | 77 | 43.9 | 100 | 70.13 | 18 | 36 | 0 | 23 |
| FSHR | 46 | 51.72 | 100 | 69.57 | 15 | 17 | 0 | 14 |
| OPN | 193 | 54.78 | 91.03 | 69.43 | 63 | 71 | 7 | 52 |
| FTH1 | 193 | 52.17 | 94.87 | 69.43 | 60 | 74 | 4 | 55 |
| PGP9 | 193 | 51.3 | 96.15 | 69.43 | 59 | 75 | 3 | 56 |
| ANNEXIN 1 | 193 | 50.43 | 97.44 | 69.43 | 58 | 76 | 2 | 57 |
| SPD | 193 | 48.7 | 98.72 | 68.91 | 56 | 77 | 1 | 59 |
| CD81 | 112 | 49.18 | 92.16 | 68.75 | 30 | 47 | 4 | 31 |
| EPCAM | 188 | 52.17 | 94.52 | 68.62 | 60 | 69 | 4 | 55 |
| PTH1R | 95 | 55.56 | 93.75 | 68.42 | 35 | 30 | 2 | 28 |
| CEA | 193 | 47.83 | 98.72 | 68.39 | 55 | 77 | 1 | 60 |
| CYTO 7 | 193 | 47.83 | 98.72 | 68.39 | 55 | 77 | 1 | 60 |
| CCL2 | 164 | 42.86 | 100 | 68.29 | 39 | 73 | 0 | 52 |
| SPA | 192 | 47.37 | 98.72 | 68.23 | 54 | 77 | 1 | 60 |
| KRAS | 47 | 50 | 100 | 68.09 | 15 | 17 | 0 | 15 |
| TWIST1 | 47 | 50 | 100 | 68.09 | 15 | 17 | 0 | 15 |
| AURKB | 47 | 50 | 100 | 68.09 | 15 | 17 | 0 | 15 |
| MMP9 | 191 | 47.79 | 97.44 | 68.06 | 54 | 76 | 2 | 59 |
| P27 | 169 | 56.31 | 86.36 | 68.05 | 58 | 57 | 9 | 45 |
| MMP1 | 172 | 49.04 | 97.06 | 68.02 | 51 | 66 | 2 | 53 |
| HLA | 96 | 53.12 | 96.88 | 67.71 | 34 | 31 | 1 | 30 |
| HIF | 46 | 48.28 | 100 | 67.39 | 14 | 17 | 0 | 15 |
| CEACAM | 193 | 51.3 | 91.03 | 67.36 | 59 | 71 | 7 | 56 |
| CENPH | 193 | 46.09 | 98.72 | 67.36 | 53 | 77 | 1 | 62 |
| BTUB | 193 | 46.09 | 98.72 | 67.36 | 53 | 77 | 1 | 62 |
| INTG b4 | 172 | 45.19 | 100 | 66.86 | 47 | 68 | 0 | 57 |
| EGFR | 193 | 46.09 | 97.44 | 66.84 | 53 | 76 | 2 | 62 |
| NACC1 | 193 | 45.22 | 98.72 | 66.84 | 52 | 77 | 1 | 63 |
| CYTO 18 | 193 | 44.35 | 100 | 66.84 | 51 | 78 | 0 | 64 |
| NAP2 | 96 | 50 | 100 | 66.67 | 32 | 32 | 0 | 32 |
| CYTO 19 | 192 | 45.61 | 97.44 | 66.67 | 52 | 76 | 2 | 62 |
| ANNEXIN V | 192 | 44.74 | 97.44 | 66.15 | 51 | 76 | 2 | 63 |
| TGM2 | 193 | 45.22 | 96.15 | 65.8 | 52 | 75 | 3 | 63 |

TABLE 22-continued

| Marker Panel Results for Lung Cancer | | | | | | | | |
|---|---|---|---|---|---|---|---|---|
| Marker | Sample Size | Sensitivity | Specificity | Accuracy | True Positive | True Negative | False Positive | False Negative |
| ERB2 | 193 | 43.48 | 98.72 | 65.8 | 50 | 77 | 1 | 65 |
| BRCA1 | 193 | 43.48 | 98.72 | 65.8 | 50 | 77 | 1 | 65 |
| B7H3 | 146 | 41.18 | 100 | 65.75 | 35 | 61 | 0 | 50 |
| SFTPC | 172 | 43.27 | 100 | 65.7 | 45 | 68 | 0 | 59 |
| PNT | 172 | 43.27 | 100 | 65.7 | 45 | 68 | 0 | 59 |
| NCAM | 96 | 48.44 | 100 | 65.62 | 31 | 32 | 0 | 33 |
| MS4A1 | 192 | 42.98 | 98.72 | 65.62 | 49 | 77 | 1 | 65 |
| P53 | 173 | 42.86 | 100 | 65.32 | 45 | 68 | 0 | 60 |
| INGA3 | 173 | 42.86 | 100 | 65.32 | 45 | 68 | 0 | 60 |
| MUC2 | 193 | 46.09 | 93.59 | 65.28 | 53 | 73 | 5 | 62 |
| SPA | 193 | 43.48 | 97.44 | 65.28 | 50 | 76 | 2 | 65 |
| OPN | 193 | 42.61 | 98.72 | 65.28 | 49 | 77 | 1 | 66 |
| CD63 | 112 | 45.9 | 88.24 | 65.18 | 28 | 45 | 6 | 33 |
| CD9 | 112 | 36.07 | 100 | 65.18 | 22 | 51 | 0 | 39 |
| MUC1 | 192 | 41.23 | 100 | 65.1 | 47 | 78 | 0 | 67 |
| UNCR3 | 173 | 42.86 | 98.53 | 64.74 | 45 | 67 | 1 | 60 |
| PAN ADH | 96 | 48.44 | 96.88 | 64.58 | 31 | 31 | 1 | 33 |
| HCG | 96 | 46.88 | 100 | 64.58 | 30 | 32 | 0 | 34 |
| TIMP | 193 | 41.74 | 97.44 | 64.25 | 48 | 76 | 2 | 67 |
| PSMA | 103 | 41.27 | 100 | 64.08 | 26 | 40 | 0 | 37 |
| GPCR | 173 | 40 | 100 | 63.58 | 42 | 68 | 0 | 63 |
| RACK1 | 96 | 45.31 | 100 | 63.54 | 29 | 32 | 0 | 35 |
| PCSA | 167 | 40.59 | 98.48 | 63.47 | 41 | 65 | 1 | 60 |
| VEGF | 193 | 37.39 | 100 | 62.69 | 43 | 78 | 0 | 72 |
| BMP2 | 96 | 45.31 | 96.88 | 62.5 | 29 | 31 | 1 | 35 |
| CD81 | 76 | 50 | 90.91 | 61.84 | 27 | 20 | 2 | 27 |
| CRP | 193 | 38.26 | 94.87 | 61.14 | 44 | 74 | 4 | 71 |
| PRO GRP | 193 | 33.04 | 98.72 | 59.59 | 38 | 77 | 1 | 77 |
| B7H3 | 76 | 44.44 | 95.45 | 59.21 | 24 | 21 | 1 | 30 |
| MUC1 | 92 | 33.33 | 100 | 56.52 | 20 | 32 | 0 | 40 |
| M2PK | 188 | 27.93 | 94.81 | 55.32 | 31 | 73 | 4 | 80 |
| CD9 | 76 | 38.89 | 90.91 | 53.95 | 21 | 20 | 2 | 33 |
| PCSA | 29 | 62.5 | 0 | 51.72 | 15 | 0 | 5 | 9 |
| PSMA | 76 | 24.07 | 95.45 | 44.74 | 13 | 21 | 1 | 41 |

The ability to assay multiple vesicle biomarkers in a single multiplexed experiment can be used to create a biosignature for lung cancer and for discovery of optimal target biomarkers for additional biosignatures. The same techniques can be applied in various settings (e.g., different diseases, different cancers, different target biomarkers, diagnosis, prognosis, theranosis, etc.) to identify novel biomarkers for subsequent assay development.

Example 32

Tissue Factor as a Vesicle Cancer Marker

Tissue factor is a blood clot-related protein whose expression has been noted in association with cancer. There are several biologic processes related to tumorigenesis or cancer progression that is tied to TF expression. These processes include angiogenesis, cancer cell invasion, immune evasion and circulating tumor cell survival. The fibrin clot that forms with TF expression coats cancer cells providing a protective coating for these cells. It is known that circulating TF is increased in the serum of cancer patients. Pathologic fibrotic events such as thromboembolism and stroke are major causes of cancer-associated deaths in patients and the existence of TF-expressing circulating microvesicles (cMVs).

Figure 104:
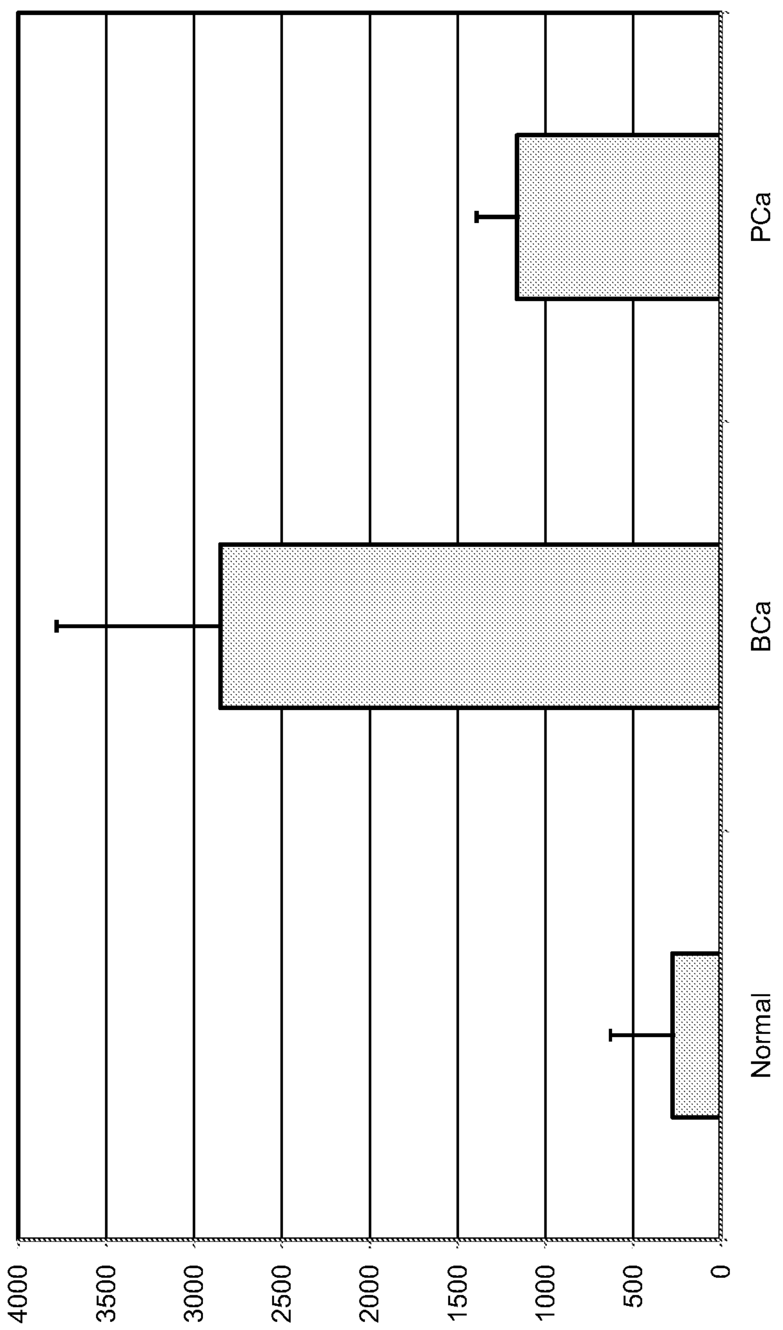
FIG. 104 illustrates detection of Tissue Factor (TF) in vesicles from normal (non-cancer) plasma samples, breast cancer (BCa) plasma samples and prostate cancer (PCa) plasma samples. Vesicles in plasma samples were captured with anti-Tissue Factor antibodies tethered to microspheres. The captured vesicles were detected with labeled antibodies to tetraspanins CD9, CD63 and CD81.

FIG. 104 illustrates detection of Tissue Factor (TF) in vesicles from 10 normal (non-cancer) plasma samples, eight breast cancer (BCa) plasma samples and two prostate cancer (PCa) plasma samples. Vesicles in plasma samples were captured with anti-Tissue Factor antibodies tethered to microspheres as described herein. See Example 21 for general methodology. The captured vesicles were detected with labeled antibodies to tetraspanins CD9, CD63 and CD81. The figure shows the median fluorescence intensity (MFI) observed by laser detection. The MFI of the BCa and PCa samples was consistently greater than the normal samples. The detection of Tissue Factor in diverse cancers indicates that TF can be used as a cancer vesicle marker.

Example 33

Selecting a Candidate Treatment for a Cancer

The methods of the invention can be used to identify a biosignature for theranosing a cancer. The biosignature can include any number of useful biomarkers, which can be assessed as described herein. The biosignature can be determined in a sample of bodily fluid, preferably a blood sample, such as plasma or serum. Vesicles are obtained from sample of bodily fluid from a patient with a cancer using methodology presented herein. See, e.g., Example 3. For determining a biosignature for different settings, the appropriate biomarkers to include in the biosignature can be discovered as described above. See, e.g., section on Biosignature Discovery. The vesicles can be isolated, captured and/or assessed for surface antigens using a binding agent bound to a microsphere, such as described in Example 21. The vesicles can also be isolated, captured and/or assessed for surface antigens using an array as in Example 22, or FACS as in Example 23. Immunoassay techniques can also be used to capture vesicles. Biomarker payload within the isolated/captured vesicles can be analyzed as desired. Examples 30-32 further describe identification of vesicle biomarkers for theranosing cancers. The vesicles can be assessed for size using laser detection techniques.

The biosignature can further comprise additional biomarkers, such as microRNA. MicroRNA can be assessed directly from a bodily fluid or can be first isolated from a vesicle population. See, e.g., Example 24 (obtaining serum); Example 25 (RNA isolation from serum or plasma); Example 28 (extracting microRNA from vesicles). The microRNA can be assessed using RT-PCR (see Examples 26, 27) and/or using array analysis (see Example 29). The microRNA can be analyzed using microfluidics to perform nucleic acid amplification.

The methods of identifying a biosignature can be performed in a single assay. For example, a number of biomarkers can be assessed using a multiplexed approach. In addition, some of the biomarkers can be assessed in a single assay while one or more other biomarkers are assessed in a different assay, which can also be a multiplexed assay. As an example, multiple vesicle surface biomarkers can be assessed in a first multiplex assay, and multiple microRNAs can be assessed in a second multiplex assay. The results of the first and second multiplex assays can be combined to identify a biosignature comprising the vesicle surface biomarkers and the microRNAs.

The biosignature can comprise any useful biomarker, including without limitation those presented herein in the context of various diseases and disorders, including without limitation markers for prostate cancer in Examples 6, 9, 19-22; markers for colorectal cancer in Examples 7, 14, 30 and 31; markers for breast cancer in Example 31 and markers for lung cancer in Example 32.

Example 34

Drug Associated Targets

The cancer is theranosed by identifying a biosignature including drug associated targets. An advantage of this approach is that the sensitivity of the cancer to a candidate therapeutic can be determined without regard to the origin of the cancer. Rather, the molecular profile of the tumor itself provides a guide to therapeutic agent selection. A panel of antibodies or aptamers are used to assess a vesicle population for the presence or level of ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, hENT-1, Her2/Neu, HGF, HIF1A, 1-HG1, HSP90, HSP9OAA1, HSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKB1A, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SRC, SSTR1, SSTR2, SSTR3, SSTR4, SSTR5, Survivin, TK1, TLE3, TNF, TOP1, TOP2A, TOP2B, TS, TXN, TXNRD1, TYMS, VDR, VEGF, VEGFA, VEGFC, VHL, YES1, and ZAP70. The antibodies or aptamers can be bound to microspheres as in Example 22 or arrayed as in Example 23. These markers are known to play a role in the efficacy of various chemotherapeutic agents against proliferative diseases. Accordingly, the markers can be assessed to select a candidate treatment for the cancer independent of the origin or type of cancer, although the treating physician can take into account any other relevant information when selecting the candidate treatment, e.g., patient history, prior treatments, other testing results, cancer characteristics (e.g., stage, origin), physician experience, and the like.

The presence or level of each marker is compared to the presence or level of the same markers observed in a group of reference samples without the cancer. Biomarkers that are overexpressed or underexpressed in the patient sample compared to the reference samples are identified. A list is assembled of candidate therapeutic agents are that known to be effective against cancers that overexpress or underexpress the biomarkers are identified using drug-target association rules as presented in Tables 6-8, and U.S. patent application Ser. No. 12/658,770, filed Feb. 12, 2010; International PCT Patent Application PCT/US2010/000407, filed Feb. 11, 2010; International PCT Patent Application PCT/US2010/54366, filed Oct. 27, 2010; and U.S. Provisional Patent Application 61/427,788, filed Dec. 28, 2010; all of which applications are incorporated by reference herein in their entirety. See, e.g., "Table 4: Rules Summary for Treatment Selection" of PCT/US2010/54366. The treating physician is presented a report comprising the expression levels of the biomarkers assessed and the list of drug indications. The physician uses the report to aid in selection of a candidate treatment.

Example 35

Monitoring Treatment Efficacy of Prostate Cancer

Methods for detecting a vesicle biosignature for prostate cancer are described in Examples 16-21. Vesicles are detected in a blood sample from a patient. The biosignature is determined by detecting the presence of the following vesicle surface antigens in the sample:

a. General Vesicle (MV) markers: CD9, CD81, and CD63 b. Prostate MV markers: PCSA, PSMA c. Cancer-Associated MV markers: B7H3, optionally EpCam The biosignature is used to monitor an efficacy of a treatment for the prostate cancer. A patient is identified with a suspicious serum PSA level (e.g., serum PSA>4.0 ng/ml) and/or a suspicious digital rectal examination (DRE). The vesicle biosignature is determined for the patient, and the results are found to be positive for prostate cancer. The treating physician determines whether to treat the prostate cancer with a therapeutic agent, hormone therapy, or a surgery (prostatectomy). After treatment, the vesicle biosignature is again determined for the patient. A positive result indicates a negative patient response to the treatment and that further treatment is required. A negative result indicates a positive patient response to the treatment and that further treatment may not be necessary.

Example 36

Selecting a Candidate Treatment for Prostate Cancer

Vesicles are obtained from sample of bodily fluid from a patient with a biopsy confirmed prostate cancer. The sample preferably comprises plasma, and urine or semen can also be assessed. A panel of capture antibodies bound to a substrate is used to assess the vesicle population for the presence or level of drug associated biomarkers using methodology as described herein. The markers comprise ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, hENT-1, Her2/Neu, HGF, HIF1A, HIG1, HSP90, HSP9OAA1, HSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKB1A, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SRC, SSTR1, SSTR2, SSTR3, SSTR4, SSTR5, Survivin, TK1, TLE3, TNF, TOP1, TOP2A, TOP2B, TS, TXN, TXNRD1, TYMS, VDR, VEGF, VEGFA, VEGFC, VHL, YES1, and ZAP70. These markers are known to play a role in the efficacy of various chemotherapeutic agents against proliferative diseases. Accordingly, the markers can be assessed to select a candidate treatment for the prostate cancer based on the molecular profile of the cancer itself independent of its origin, although the treating physician can take into account any other relevant information when selecting the candidate treatment, e.g., patient history, prior treatments, other testing results, cancer characteristics (e.g., stage, origin), physician experience, and the like.

The presence or level of each marker is compared to the presence or level of the same markers observed in a group of reference samples without the cancer. Biomarkers that are overexpressed or underexpressed in the patient sample compared to the reference samples are identified. A list is assembled of candidate therapeutic agents are that known to be effective against cancers that overexpress or underexpress the biomarkers are identified using drug-target association rules as presented in Tables 6-8, and U.S. patent application Ser. No. 12/658,770, filed Feb. 12, 2010; International PCT Patent Application PCT/US2010/000407, filed Feb. 11, 2010; International PCT Patent Application PCT/US2010/54366, filed Oct. 27, 2010; and U.S. Provisional Patent Application 61/427,788, filed Dec. 28, 2010; all of which applications are incorporated by reference herein in their entirety. See, e.g., "Table 4: Rules Summary for Treatment Selection" of PCT/US2010/54366. The treating physician is presented a report comprising the expression levels of the biomarkers assessed and the list of drug indications. The physician uses the report to aid in selection of a candidate treatment.

Example 37

Monitoring Treatment Efficacy of Colorectal Cancer

A vesicle biosignature for colorectal cancer is shown in Example 30. The biosignature comprises one or more of the biomarkers listed in Example 30 (e.g., Tables 17-18 and FIG. 100). Vesicles are detected in a plasma sample from a patient using methodology as described herein (e.g., Examples 16-21) using a CRC biosignature comprising TMEM211, CD24, CD9, CD81, and CD63; or a CRC biosignature comprising CD63, CD9, CD81, EpCam and CD66. The vesicles in the plasma are captured with labeled microspheres conjugated to anti-TMEM211 and anti-CD24 antibodies; or to anti-EpCam and anti-CD66 antibodies, respectively. The captured vesicles are further detected with PE-labeled antibodies to the general vesicle CD9, CD63, and CD81.

The biosignature is used to monitor an efficacy of a treatment for the colorectal cancer. A patient is screened using a colonoscopy and suspicious polyps are removed for biopsy. The vesicle biosignature is determined and indicates cancer. The biopsy is also positive for malignant cells. The treating physician determines to treat the patient with adjuvant therapy comprising 5-fluorouracil (5-FU) and folinic acid. The vesicle biosignature determined for the patient pre-treatment and over a time course thereafter. A positive result indicates a negative patient response to the treatment. A negative result indicates a positive patient response to the treatment.

Example 38

Selecting a Candidate Treatment for Colorectal Cancer

Vesicles are obtained from sample of bodily fluid from a patient with a colorectal cancer. The sample may comprise plasma. A panel of capture antibodies bound to a substrate is used to assess the vesicle population for the presence or level of drug associated biomarkers using methodology as described herein. The markers comprise ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, hENT-1, Her2/Neu, HGF, HIF1A, HIG1, HSP90, HSP9OAA1, RSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKB1A, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SRC, SSTR1, SSTR2, SSTR3, SSTR4, SSTR5, Survivin, TK1, TLE3, TNF, TOP1, TOP2A, TOP2B, TS, TXN, TXNRD1, TYMS, VDR, VEGF, VEGFA, VEGFC, VHL, YES1, and ZAP70. These markers are known to play a role in the efficacy of various chemotherapeutic agents against proliferative diseases. Accordingly, the markers can be assessed to select a candidate treatment for the colorectal cancer based on the molecular profile of the cancer itself independent of its origin, although the treating physician can take into account any other relevant information when selecting the candidate treatment, e.g., patient history, prior treatments, other testing results, cancer characteristics (e.g., stage, origin), physician experience, and the like. Preferably the markers comprise one or more of EGFR, EPHA2, p53, KRAS. Other markers that can be included in the biosignature comprise miR-548c-5p, miR-362-3p, miR-422a, miR-597, miR-429, miR-200a, and miR-200b.

The presence or level of each marker is compared to the presence or level of the same markers observed in a group of reference samples without the cancer. Biomarkers that are overexpressed or underexpressed in the patient sample compared to the reference samples are identified. A list is assembled of candidate therapeutic agents are that known to be effective against cancers that overexpress or underexpress the biomarkers are identified using drug-target association rules as presented in Tables 6-8, and U.S. patent application Ser. No. 12/658,770, filed Feb. 12, 2010; International PCT Patent Application PCT/US2010/000407, filed Feb. 11, 2010; International PCT Patent Application PCT/US2010/54366, filed Oct. 27, 2010; and U.S. Provisional Patent Application 61/427,788, filed Dec. 28, 2010; all of which applications are incorporated by reference herein in their entirety. See, e.g., "Table 4: Rules Summary for Treatment Selection" of PCT/US2010/54366. The treating physician is presented a report comprising the expression levels of the biomarkers assessed and the list of drug indications. The physician uses the report to aid in selection of a candidate treatment.

Example 39

Selecting a Candidate Treatment for Breast Cancer

Vesicles are obtained from sample of bodily fluid from a patient with a breast cancer. The sample may comprise plasma. A panel of capture antibodies bound to a substrate is used to assess the vesicle population for the presence or level of drug associated biomarkers using methodology as described herein. The markers comprise ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, hENT-1, Her2/Neu, HGF, HIF1A, HIG1, HSP90, HSP9OAA1, HSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKB1A, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SRC, SSTR1, SSTR2, SSTR3, SSTR4, SSTR5, Survivin, TK1, TLE3, TNF, TOP1, TOP2A, TOP2B, TS, TXN, TXNRD1, TYMS, VDR, VEGF, VEGFA, VEGFC, VHL, YES1, and ZAP70. These markers are known to play a role in the efficacy of various chemotherapeutic agents against proliferative diseases. Accordingly, the markers can be assessed to select a candidate treatment for the breast cancer based on the molecular profile of the cancer itself independent of its origin, although the treating physician can take into account any other relevant information when selecting the candidate treatment, e.g., patient history, prior treatments, other testing results, cancer characteristics (e.g., stage, origin), physician experience, and the like. Preferably the markers comprise one or more of BRCA, cMET, DLL4, EphA2, EGFR, ER, ERB2, ERB3, ERB4, and VEGF.

The presence or level of each marker is compared to the presence or level of the same markers observed in a group of reference samples without the cancer. Biomarkers that are overexpressed or underexpressed in the patient sample compared to the reference samples are identified. A list is assembled of candidate therapeutic agents are that known to be effective against cancers that overexpress or underexpress the biomarkers are identified using drug-target association rules as presented in Tables 6-8, and U.S. patent application Ser. No. 12/658,770, filed Feb. 12, 2010; International PCT Patent Application PCT/US2010/000407, filed Feb. 11, 2010; International PCT Patent Application PCT/US2010/54366, filed Oct. 27, 2010; and U.S. Provisional Patent Application 61/427,788, filed Dec. 28, 2010; all of which applications are incorporated by reference herein in their entirety. See, e.g., "Table 4: Rules Summary for Treatment Selection" of PCT/US2010/54366. The treating physician is presented a report comprising the expression levels of the biomarkers assessed and the list of drug indications. The physician uses the report to aid in selection of a candidate treatment.

Example 40

Selecting a Candidate Treatment for Lung Cancer

Vesicles are obtained from sample of bodily fluid from a patient with a lung cancer. The sample may comprise plasma. A panel of capture antibodies bound to a substrate is used to assess the vesicle population for the presence or level of drug associated biomarkers using methodology as described herein. The markers comprise ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, hENT-1, Her2/Neu, HGF, HIF1A, HIG1, HSP90, HSP9OAA1, HSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKB1A, ODC1, OGFR, p16, p21, p27, p53, p95, PARP-1, PDGFC, PDGFR, PDGFRA, PDGFRB, PGP, PGR, P13K, POLA, POLA1, PPARG, PPARGC1, PR, PTEN, PTGS2, RAF1, RARA, RRM1, RRM2, RRM2B, RXRB, RXRG, SPARC, SRC, SSTR1, SSTR2, SSTR3, SSTR4, SSTR5, Survivin, TK1, TLE3, TNF, TOP1, TOP2A, TOP2B, TS, TXN, TXNRD1, TYMS, VDR, VEGF, VEGFA, VEGFC, VHL, YES1, and ZAP70. These markers are known to play a role in the efficacy of various chemotherapeutic agents against proliferative diseases. Accordingly, the markers can be assessed to select a candidate treatment for the lung cancer based on the molecular profile of the cancer itself independent of its origin, although the treating physician can take into account any other relevant information when selecting the candidate treatment, e.g., patient history, prior treatments, other testing results, cancer characteristics (e.g., stage, origin), physician experience, and the like. Preferably the markers comprise one or more of ASPH, BRCA 1, EGFR, EPHA2, ErbB2, HIF, KRAS, MS4A1, P27, P53, ADH, PGP9, PGP9.5, and VEGF. Other markers that are included in the biosignature to assess sensitivity to a tyrosine kinase inhibitor comprise miR-497, miR-21, miR-23a, miR-23b, miR-29b, hsa-miR-029 a, hsa-let-7d, hsa-miR-100, hsa-miR-1260, hsa-miR-025, hsa-let-7i, hsa-miR-146a, hsa-miR-594-Pre, hsa-miR-024, FGFR1, MET, RAB25, EGFR, KIT, VEGFR2, FGF1, HOXC10 and/or LHFP.

The presence or level of each marker is compared to the presence or level of the same markers observed in a group of reference samples without the cancer. Biomarkers that are overexpressed or underexpressed in the patient sample compared to the reference samples are identified. A list is assembled of candidate therapeutic agents are that known to be effective against cancers that overexpress or underexpress the biomarkers are identified using drug-target association rules as presented in Tables 6-8, and U.S. patent application Ser. No. 12/658,770, filed Feb. 12, 2010; International PCT Patent Application PCT/US2010/000407, filed Feb. 11, 2010; International PCT Patent Application PCT/US2010/54366, filed Oct. 27, 2010; and U.S. Provisional Patent Application 61/427,788, filed Dec. 28, 2010; all of which applications are incorporated by reference herein in their entirety. See, e.g., "Table 4: Rules Summary for Treatment Selection" of PCT/US2010/54366. The treating physician is presented a report comprising the expression levels of the biomarkers assessed and the list of drug indications. The physician uses the report to aid in selection of a candidate treatment.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of characterizing a cancer in a subject, comprising:

a. isolating a vesicle population from a sample from the subject using a binding agent to an MMP7 polypeptide;
b. identifying a biosignature of the isolated vesicle population, wherein the biosignature comprises a presence or level of the MMP7 polypeptide; and
c. comparing the biosignature to a reference, wherein an elevated presence or level of the MMP7 polypeptide as compared to the reference indicates that the subject may be predisposed to or afflicted with cancer, thereby characterizing the cancer.

2. The method of claim 1, wherein the sample comprises a bodily fluid.

3. The method of claim 2, wherein the bodily fluid comprises peripheral blood, sera, plasma, ascites, urine, cerebrospinal fluid (CSF), sputum, saliva, bone marrow, synovial fluid, aqueous humor, amniotic fluid, breast milk, broncheoalveolar lavage fluid, semen, prostatic fluid, cowper's fluid, pre-ejaculatory fluid, female ejaculate, sweat, fecal matter, tears, cyst fluid, pleural fluid, peritoneal fluid, pericardial fluid, lymph, chyme, chyle, bile, interstitial fluid, menses, pus, vomit, vaginal secretions, mucosal secretion, stool water, pancreatic juice, lavage fluids from sinus cavities, or bronchopulmonary aspirates.

4. The method of claim 2, wherein the bodily fluid comprises serum or plasma.

5. The method of claim 1, wherein the vesicle population comprises vesicles with a diameter between 20 nm and 800 nm.

6. The method of claim 1, wherein the vesicle population comprises vesicles with a diameter between 20 nm and 200 nm.

7. The method of claim 1, wherein isolating the vesicle population further comprises size exclusion chromatography, density gradient centrifugation, differential centrifugation, nanomembrane ultrafiltration, immunoabsorbent capture, affinity purification, affinity capture, immunoassay, microfluidic separation, or combinations thereof.

8. The method of claim 1, wherein the biosignature further comprises a presence or level of at least one vesicle surface antigen selected from the group consisting of EpCAM, B7H3, CD24, Tissue Factor, and a combination thereof.

9. The method of claim 1, wherein the biosignature further comprises a presence or level of at least one vesicle surface antigen selected from the group consisting of CD63, CD9, CD81, CD82, CD37, CD53, Rab-5b, MFG-E8, Annexin V, and a combination thereof.

10. The method of claim 1, wherein the isolation step comprises contacting the sample with at least one additional binding agent specific for at least one vesicle surface antigen other than MMP7.

11. The method of claim 1, wherein the binding agent to the MMP7 polypeptide comprises, DNA molecule, RNA molecule, antibody, antibody fragment, aptamer, peptoid, zDNA, peptide nucleic acid (PNA), locked nucleic acids (LNA), lectin, peptide, dendrimer, membrane protein labeling agent, or chemical compound.

12. The method of claim 1, wherein identifying the biosignature comprises assessment of at least one nucleic acid.

13. The method of claim 12, wherein the at least one nucleic acid comprises at least one of mRNA and microRNA.

14. The method of claim 1, wherein the cancer comprises prostate cancer, colorectal cancer, lung cancer, breast cancer, ovarian cancer, kidney cancer or melanoma.

15. The method of claim 1, wherein the cancer comprises prostate cancer and the biosignature further comprises a presence or level of at least one vesicle surface antigen consisting of at least one of PCSA and PSMA; and at least one of B7H3 and EpCam.

16. The method of claim 1, wherein the cancer comprises prostate cancer and the biosignature further comprises a presence or level of the vesicle surface antigen PCSA.

17. The method of claim 1, wherein the cancer comprises breast cancer and the biosignature further comprises a presence or level of at least one vesicle surface antigen selected from the group consisting of CD9, HSP70, Ga13, MIS, EGFR, ER, ICB3, CD63, B7H4, MUC1, DLL4, CD81, ERBB3, VEGF, BCA225, BRCA, CA125, CD174, CD24, ERBB2, NGAL, GPR30, CYFRA21, CD31, cMET, MUC2, ERBB4, and a combination thereof.

18. The method of claim 1, wherein the cancer comprises breast cancer and the biosignature further comprises a presence or level of at least one vesicle surface antigen selected from the group consisting of CD9, EphA2, EGFR, B7H3, PSMA, PCSA, CD63, STEAP, CD81, B7H3, STEAP1, ICAM1 (CD54), A33, DR3, CD66e, MFG-e8, Hepsin, TMEM211, TROP-2, EGFR, Mammoglobin, Hepsin, NPGP/NPFF2, PSCA, 5T4, NGAL, NK-2, EpCam, NK-1R, 5T4, PAI-1, CD45, and a combination thereof.

19. The method of claim 1, wherein the cancer comprises breast cancer and the biosignature further comprises a presence or level of at least one vesicle surface antigen selected from the group consisting of BRCA, cMET, DLL4, EphA2, EGFR, ER, ERBB2, ERBB3, ERBB4, VEGF, and a combination thereof.

20. The method of claim 1, wherein the biosignature further comprises a presence, level or mutation in at least one of ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBB2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, hENT-1, Her2/Neu, HGF, HIF1A, HIG1, HSP90, HSP9OAA1, HSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKB1A, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SRC, SSTR1, SSTR2, SSTR3, SSTR4, SSTR5, Survivin, TK1, TLE3, TNF, TOP1, TOP2A, TOP2B, TS, TXN, TXNRD1, TYMS, VDR, VEGF, VEGFA, VEGFC, VHL, YES1, and ZAP70.

21. The method of claim 10, wherein the at least one additional binding agent comprises DNA molecule, RNA molecule, antibody, antibody fragment, aptamer, peptoid, zDNA, peptide nucleic acid (PNA), locked nucleic acids (LNA), lectin, peptide, dendrimer, membrane protein labeling agent, chemical compound, or a combination thereof.

* * * * *